US011779649B2

(12) United States Patent
Burger et al.

(10) Patent No.: US 11,779,649 B2
(45) Date of Patent: Oct. 10, 2023

(54) ANTIBODIES TO PMEL17 AND CONJUGATES THEREOF

(71) Applicant: Novartis AG, Basel (CH)

(72) Inventors: Matthew Burger, Belmont, MA (US); Joseph Anthony D'Alessio, Boston, MA (US); Tony Fleming, Stow, MA (US); Vivek Rauniyar, Cambridge, MA (US); Eusebio Manchado Robles, Basel (CH); Christian Kunz, Planegg (DE); Markus Waldhuber, Munich (DE)

(73) Assignee: Novartis AG, Basel (CH)

( * ) Notice: Subject to any disclaimer, the term of this patent is extended or adjusted under 35 U.S.C. 154(b) by 509 days.

(21) Appl. No.: 16/718,866

(22) Filed: Dec. 18, 2019

(65) Prior Publication Data

US 2020/0197528 A1 Jun. 25, 2020

Related U.S. Application Data

(60) Provisional application No. 62/803,110, filed on Feb. 8, 2019, provisional application No. 62/783,565, filed on Dec. 21, 2018.

(51) Int. Cl.
*A61K 47/68* (2017.01)
*A61P 35/00* (2006.01)
(Continued)

(52) U.S. Cl.
CPC ...... *A61K 47/6803* (2017.08); *A61K 31/4745* (2013.01); *A61P 35/00* (2018.01); *C07K 16/18* (2013.01); *A61K 45/06* (2013.01)

(58) Field of Classification Search
CPC ............ A61K 47/6803; A61K 31/4745; A61K 45/06; A61K 2039/505; A61P 35/00
See application file for complete search history.

(56) References Cited

U.S. PATENT DOCUMENTS 9,056,910 B2   6/2015   Chen et al.
9,597,411 B2   3/2017   Chen et al.
(Continued)

FOREIGN PATENT DOCUMENTS

EP      3465221 B1     7/2020
JP      S62283999 A   12/1987
(Continued)

OTHER PUBLICATIONS

Gerber et al. ("Combining antibody-drug conjugates and immune-mediated cancer therapy: What to expect?", Biochemical Pharmacology, vol. 102, 2016, pp. 1-6) (Year: 2016).*
(Continued)

*Primary Examiner* — Scarlett Y Goon
*Assistant Examiner* — Jessica Soto-Rodriguez
(74) *Attorney, Agent, or Firm* — K&L Gates LLP

(57) ABSTRACT

This application discloses anti-PMEL17 antibodies, antigen binding fragments thereof, and antibody drug conjugates comprising antibodies or antigen binding fragments conjugated to a GNAQ/GNA11 inhibitor. The application also discloses methods of treating or preventing cancer using the antibodies, antigen binding fragments, and antibody drug conjugates. Also disclosed herein are methods of making the antibodies, antigen binding fragments, and antibody drug conjugates, and methods of using the antibodies and antigen binding fragments as diagnostic reagents.

55 Claims, 16 Drawing Sheets

Specification includes a Sequence Listing.

(51) Int. Cl.
  *A61K 31/4745*   (2006.01)
  *C07K 16/18*     (2006.01)
  *A61K 45/06*     (2006.01)

(56) References Cited

U.S. PATENT DOCUMENTS

| | | | |
|---|---|---|---|
| 10,196,454 | B2 | 2/2019 | Chen et al. |
| 10,550,190 | B2 | 2/2020 | Garbaccio et al. |
| 2013/0102653 | A1 | 4/2013 | Griewank et al. |
| 2017/0252458 | A1* | 9/2017 | Albone .................. C07K 16/28 |
| 2017/0315132 | A1 | 11/2017 | Kaur et al. |
| 2017/0370906 | A1 | 12/2017 | Darwish et al. |
| 2020/0191789 | A1 | 6/2020 | Piñeiro Ces et al. |
| 2020/0282015 | A1 | 9/2020 | Blumer et al. |
| 2021/0011000 | A1 | 1/2021 | Darwish et al. |
| 2021/0123928 | A1 | 4/2021 | Kaur et al. |

FOREIGN PATENT DOCUMENTS

| | | | |
|---|---|---|---|
| JP | 2003210190 | A | 7/2003 |
| RU | 2562862 | C2 | 12/2013 |
| WO | 2011130691 | A2 | 10/2011 |
| WO | 2013165940 | A1 | 11/2013 |
| WO | 2015153401 | A1 | 10/2015 |
| WO | 2017165734 | A1 | 9/2017 |
| WO | 2017205741 | A1 | 11/2017 |
| WO | 2018229162 | A1 | 12/2018 |
| WO | 2019060781 | A1 | 3/2019 |
| WO | 2022221720 | A1 | 10/2022 |

OTHER PUBLICATIONS

Kern et al. ("Novel Phosphate Modified Cathepsin B Linkers: Improving Aqueous Solubility and Enhancing Payload Scope ADCs"; 2016, Bioconjugate Chemistry: 2-16; 27(9); 2081-2088) (Year: 2016).*

Taniguchi et al. "YM-254890, a novel platelet aggregation inhibitor produced by *Chromobacterium* sp. QS3666," The Journal of Antibiotics (2003) vol. 56, No. 4, pp. 358-363.

Nishimura et al., "Structural basis for the specific inhibition of heterotrimeric Gq protein by a small molecule," PNAS (2010) vol. 107, No. 31, pp. 13666-13671.

Shrage et al., "The experimental power of FR900359 to study Gq-regulated biological processes," Nat Commun (2015) vol. 6, Article 10156, 17 pages.

Chua et al., "Dysregulated GPCR Signaling and Therapeutic Options in Uveal Melanoma," Mol Cancer Res (2017) vol. 15, No. 5, pp. 501-506.

Matthey et al., "Targeted inhibition of Gq signaling induces airway relaxation in mouse models of asthma," Sci Transl Med (2017) vol. 9, Article eaag2288, 11 pages.

Annala et al., "Direct targeting of Galphaq and Galpha11 oncoproteins in cancer cells," Sci Signal (2019) vol. 12, Article eaau5948, 14 pages.

Damato et al., "Tebentafusp: T Cell Redirection for the Treatment of Metastatic Uveal Melanoma," Cancers (2019) vol. 11, No. 7, Article 971, 16 pages.

Valencia et al.,"Sorting of Pmel17 to melanosomes through the plasma membrane by AP1 and AP2: evidence for the polarized nature of melanocytes," J Cell Sci (2016) vol. 119, pp. 1080-1091.

Theos et al., "The Silver locus product Pmel17/gp100/Silv/ME20: controversial in name and in function," Pigment Cell Res (2005) vol. 18, No. 5, pp. 322-336.

Du et al., "MLANA/MART1 and SILV/PMEL17/GP100 are transcriptionally regulated by MITF in melanocytes and melanoma," Am J Pathol (2003) vol. 163, No. 1, pp. 333-343.

Wagner et al., "Analysis of Pmel17/gp100 expression in primary human tissue specimens: implications for melanoma immuno-and gene-therapy," Cancer Immunol Immunother (1997) vol. 44, pp. 239-247.

Chen et al., "The melanosomal protein PMEL17 as a target for antibody drug conjugate therapy in melanoma," J Biol Chem (2012) vol. 287, No. 29, pp. 24082-24091.

Lambert, "Drug-conjugated monoclonal antibodies for the treatment of cancer," Curr Opinion in Pharmacology (2005) vol. 5, pp. 543-549.

Lapadula et al., "Effects of Oncogenic G[alpha]q and G[alpha]11 Inhibition by FR900359 in Uveal Melanoma," Molecular Cancer Research (2018) vol. 17, No. 4, pp. 963-973.

International Search Report and Written Opinion issued in PCT/IB2019/001333, dated Jul. 20, 2020, 22 pages.

International Search Report and Written Opinion issued in PCT/US2022/025106, dated Sep. 19, 2022, 23 pages.

Crüsemann et al., "Heterologus Expression, Biosynthetic Studies, and Ecological Function of the Selective Gq-Signaling Inhibitor FR900359," Angewandte Chemie International Edition (2018) vol. 57, No. 3, pp. 836-840.

Hermes et al., "Thioesterase-mediated side chain transesterification generates potent Gq signaling inhibitor FR900359," Nature Communications (2021) vol. 12, No. 1, Article 144, 12 pages.

Schamari et al., "Bioinformatische und in-vitro-Analyse der frs-Biosynthesegencluster von Cand. Burkholderia crenata und Chromobacterium vaccinii," Doctoral Dissertation (2019) retrieved from bonndoc.ulb.uni-bonn.de/xmlui/handle/20.500.11811/7946, German with English Abstract.

Pistorius et al., "Genetic Engineering of Chromobacterium Vaccinii DSM 25150 for Improved Production of FR900359," retrieved from chemrxiv.org/engage/api-gateway/chemrxiv/assets/orp/resource/item/60c757b74c891947bcad4a73/original/genetic-engineering-of-chromobacterium-vaccinii-dsm-25150-for-improved-production-of-fr900359.pdf on Apr. 20, 2021, 22 pages.

Pistorius et al., "Promoter-Driven Overexpression in Chromobacterium vaccinii Facilitates Access to FR900359 and Yields Novel Low Abundance Analogs," Chemistry—a European Journal (2021) vol. 28, No. 8, Article e202103888, 6 pages.

* cited by examiner

FIG. 3A
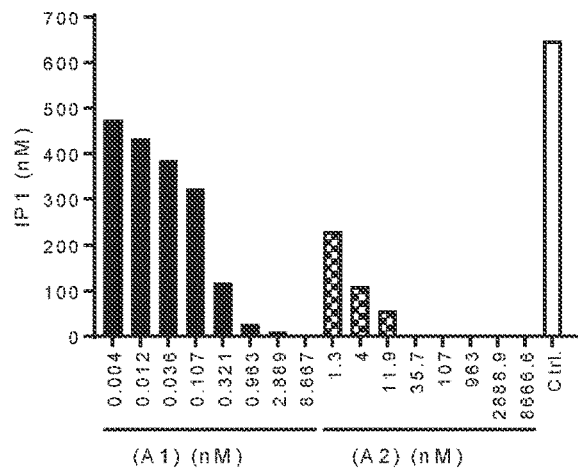
FIG. 3B
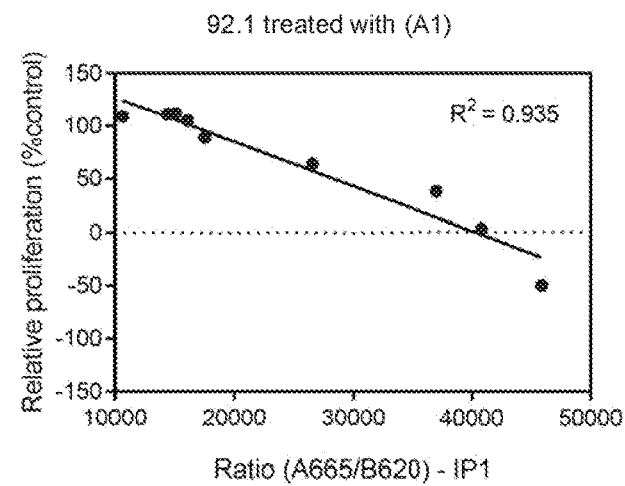
FIG. 3C
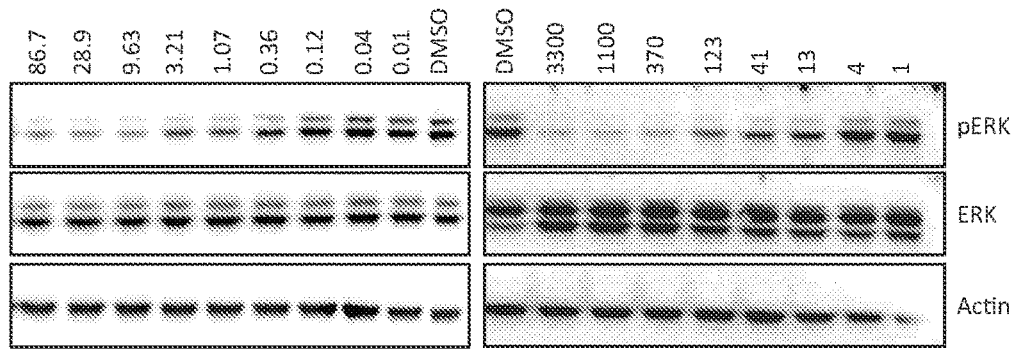
FIGURE 3

FIG. 4A
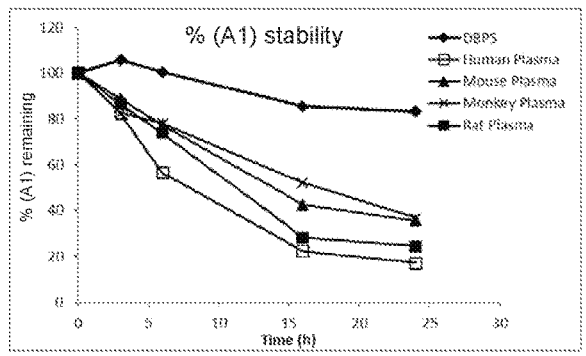
FIG. 4B
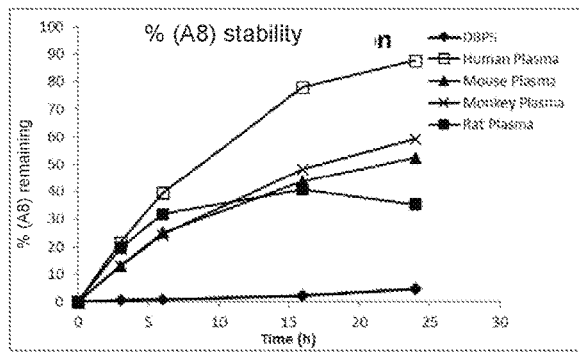
FIG. 4C
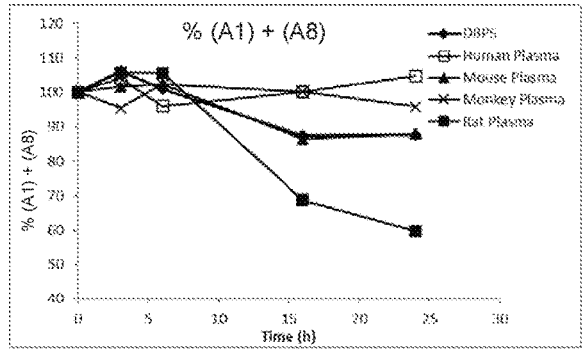
FIG. 4D
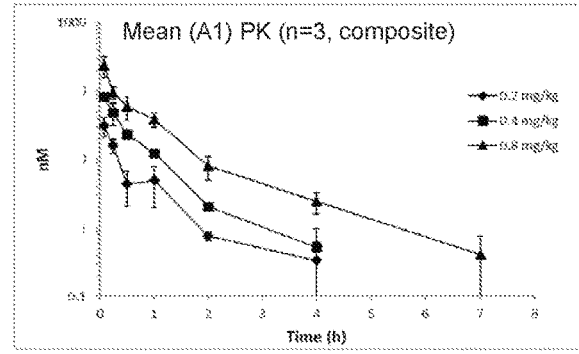
FIGURE 4

FIG. 5A
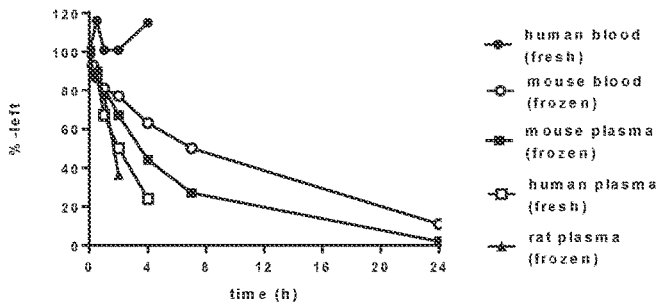
FIG. 5B
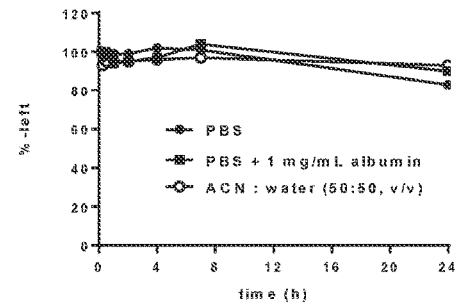
FIG. 5C
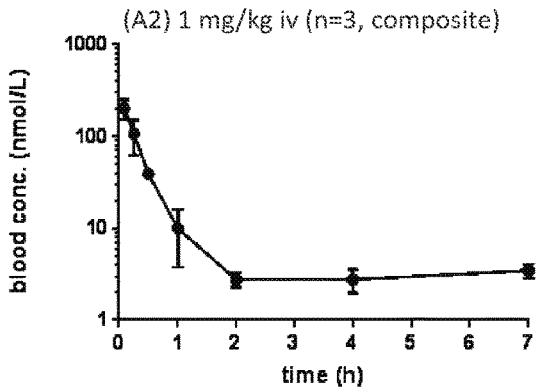
FIG. 5D
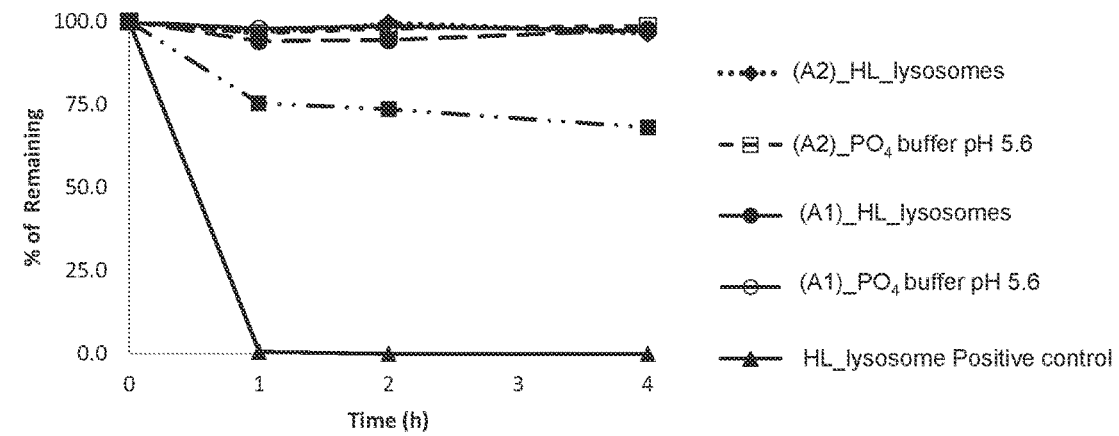
FIGURE 5

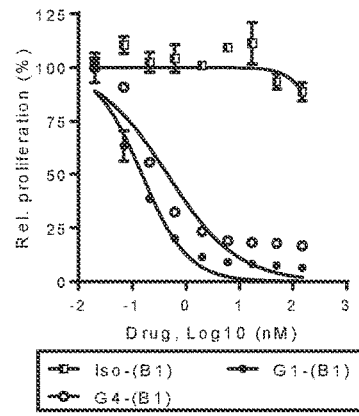
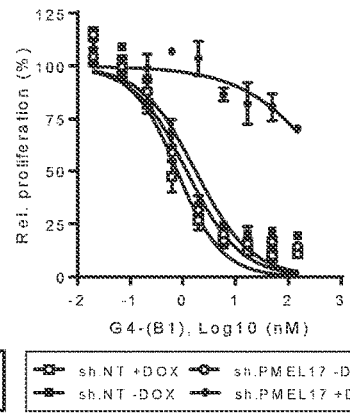
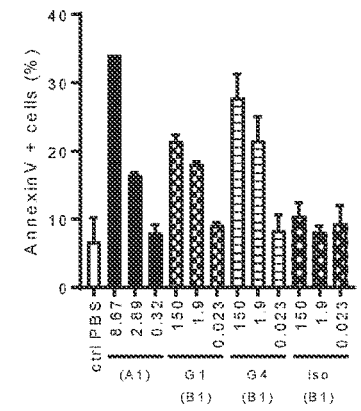
FIGURE 6
FIGURE 7
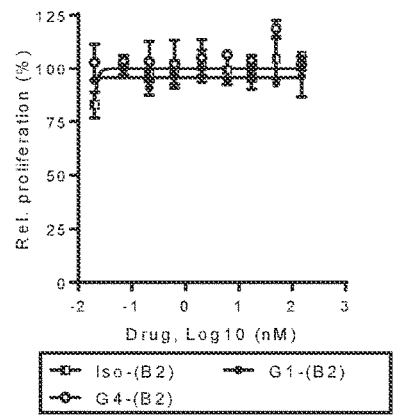
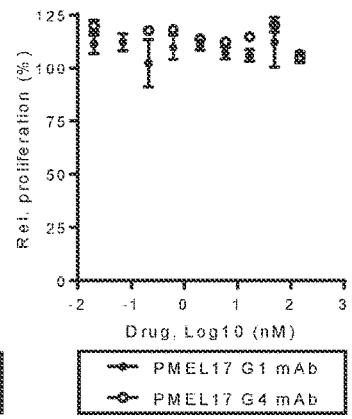
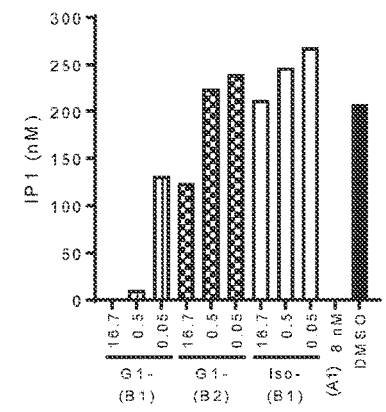
FIGURE 8
FIGURE 9

FIG. 13A
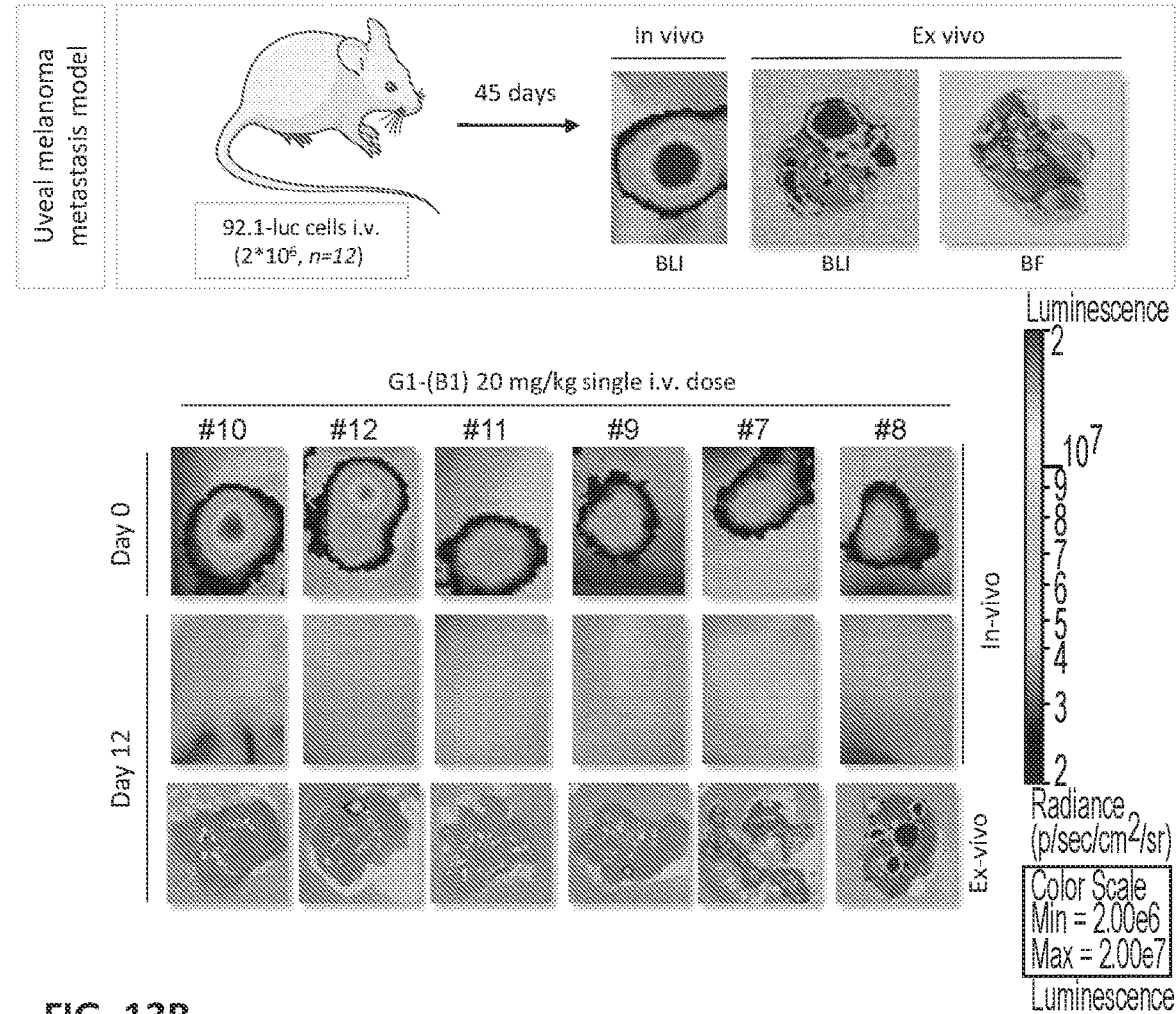
FIG. 13B
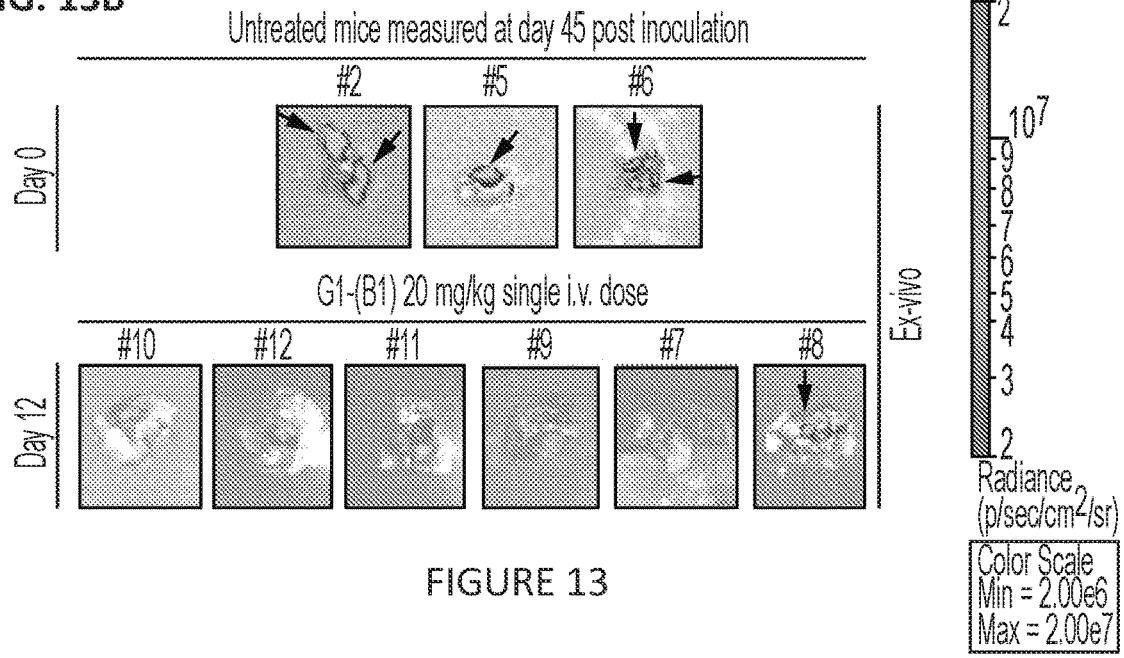
FIGURE 13

FIG. 14A
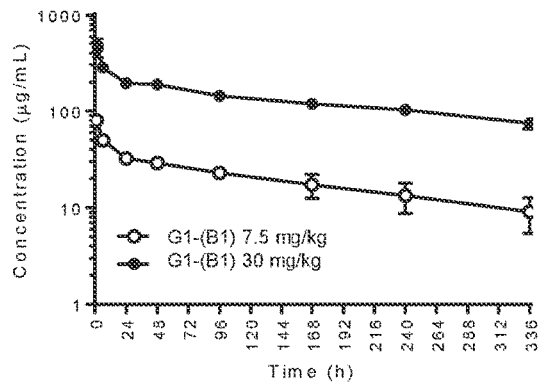
FIG. 14B
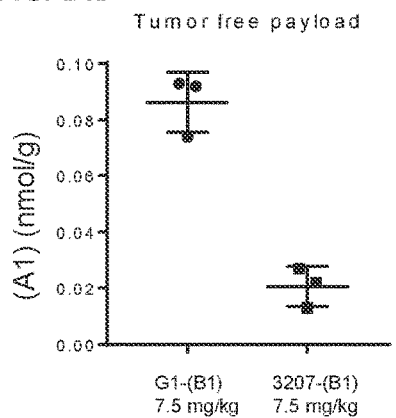
FIG. 14C
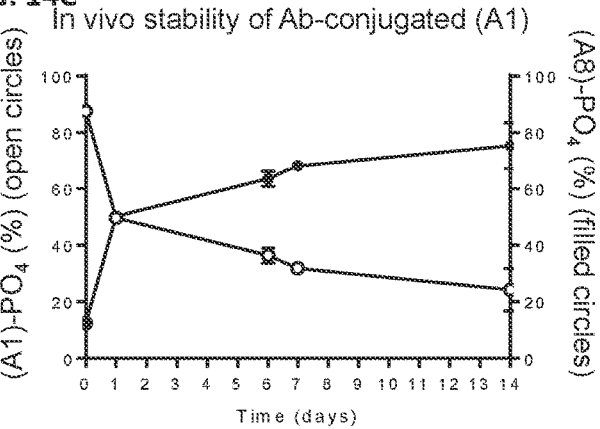
FIG. 14D
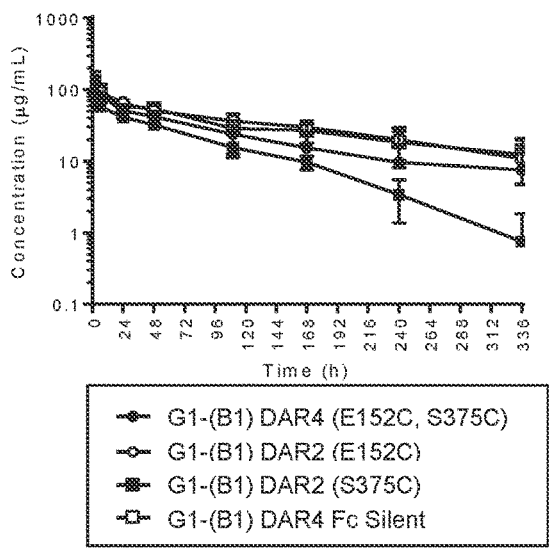
FIG. 14E
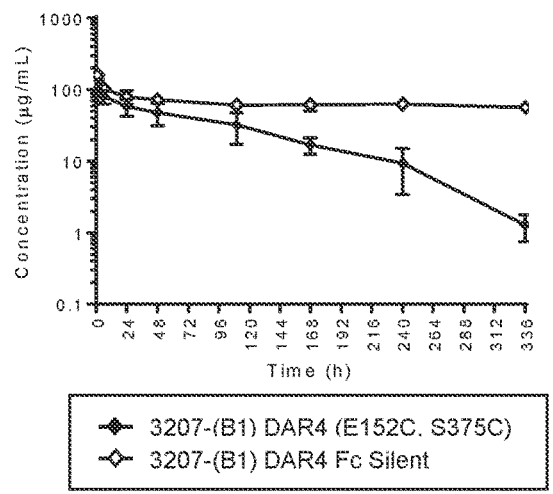
FIGURE 14

FIG. 15A
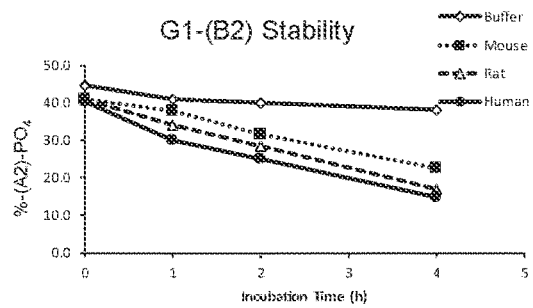
FIG. 15B
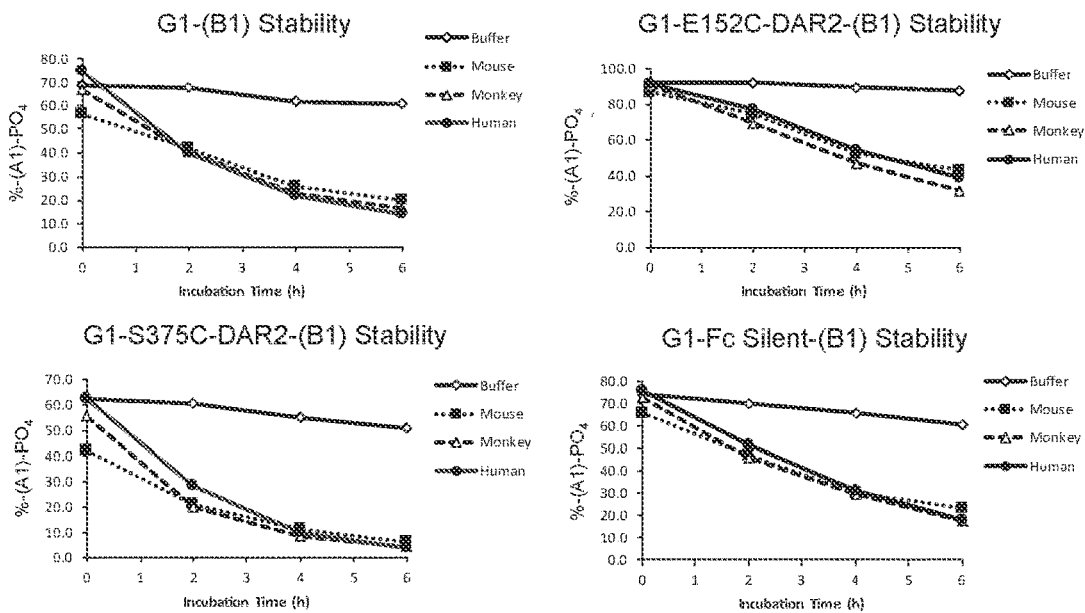
FIG. 15C
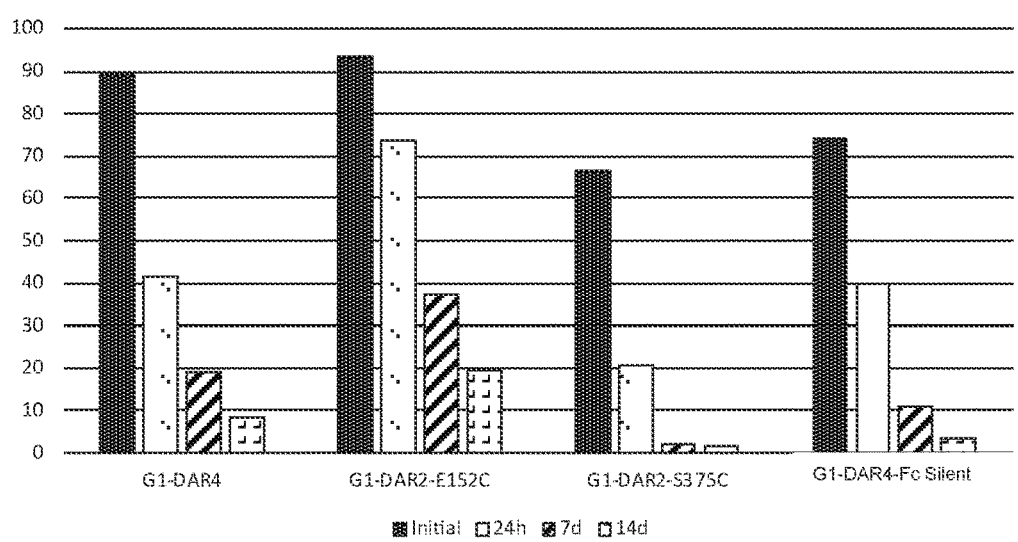
Initial values estimated based on in vitro experimental results
FIGURE 15

FIG. 16A
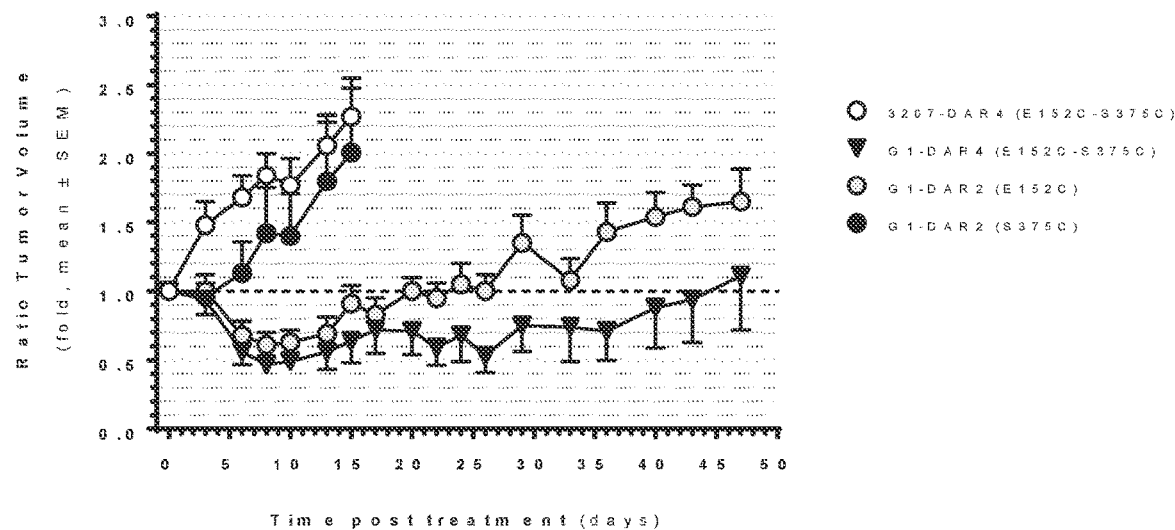
FIG. 16B
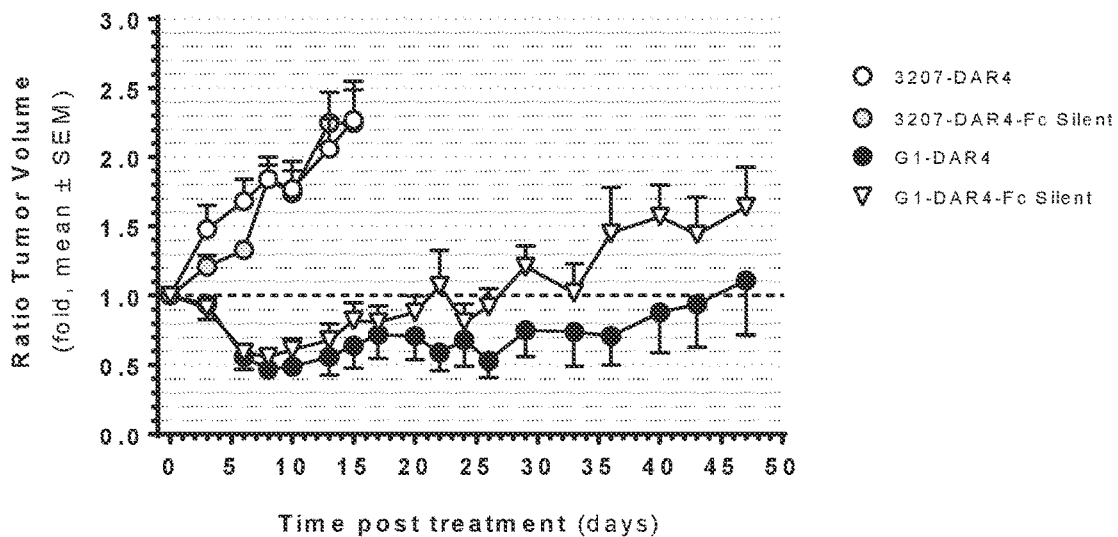
FIGURE 16

FIG. 17A
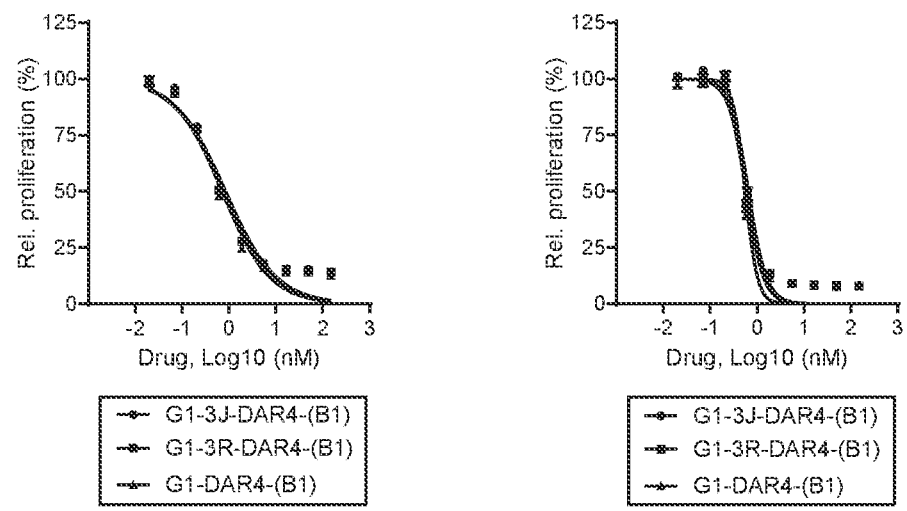
FIG. 17B
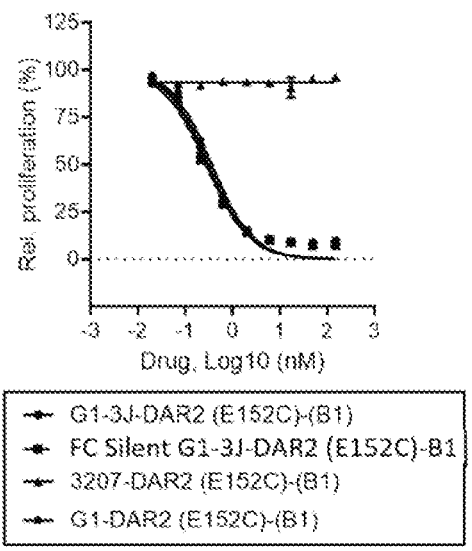
FIGURE 17

FIG. 19A
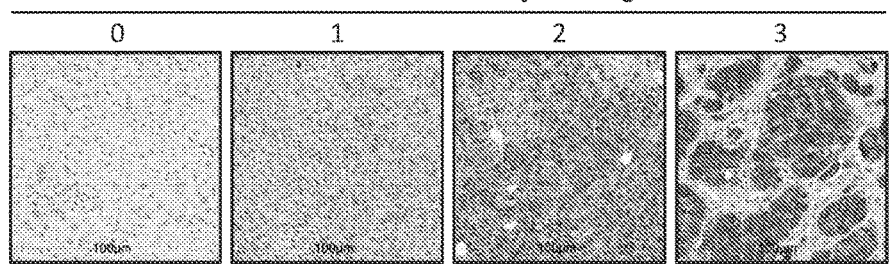
FIG. 19B
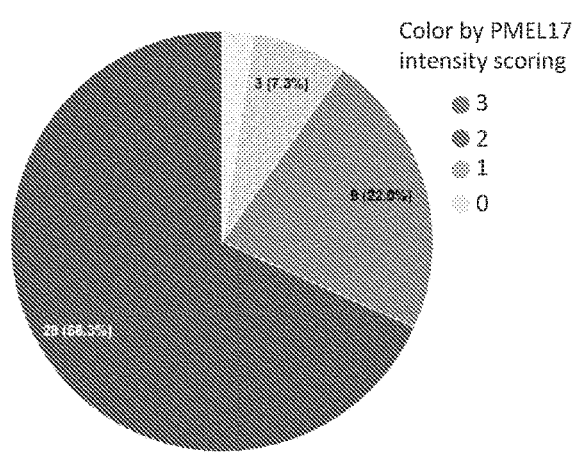
C
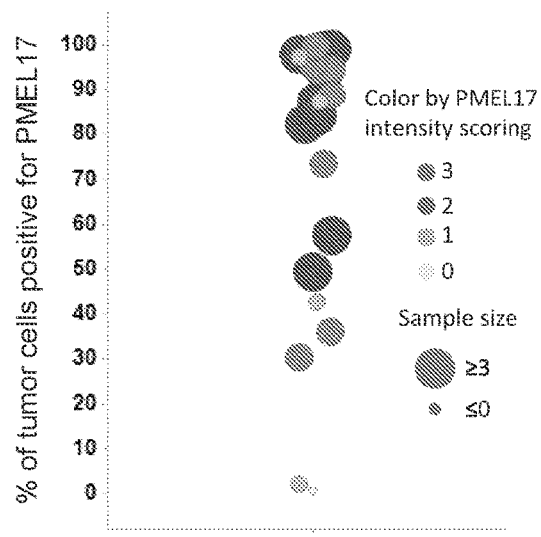
FIGURE 19

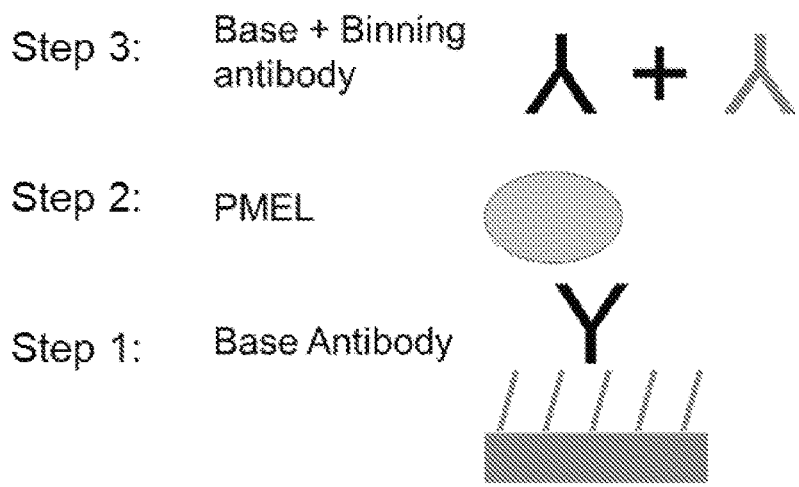
FIG. 20A
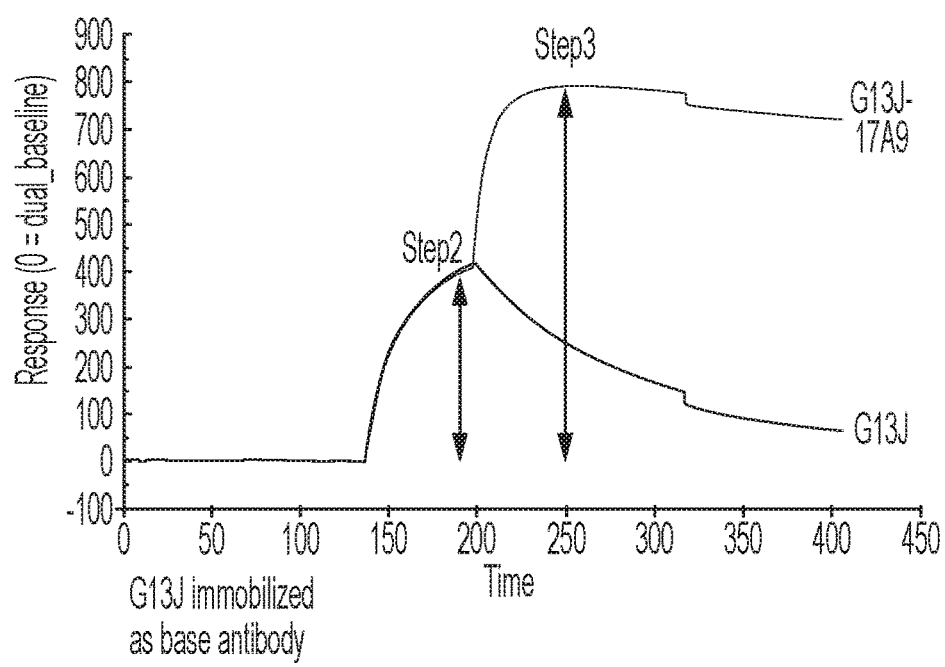
FIG. 20B
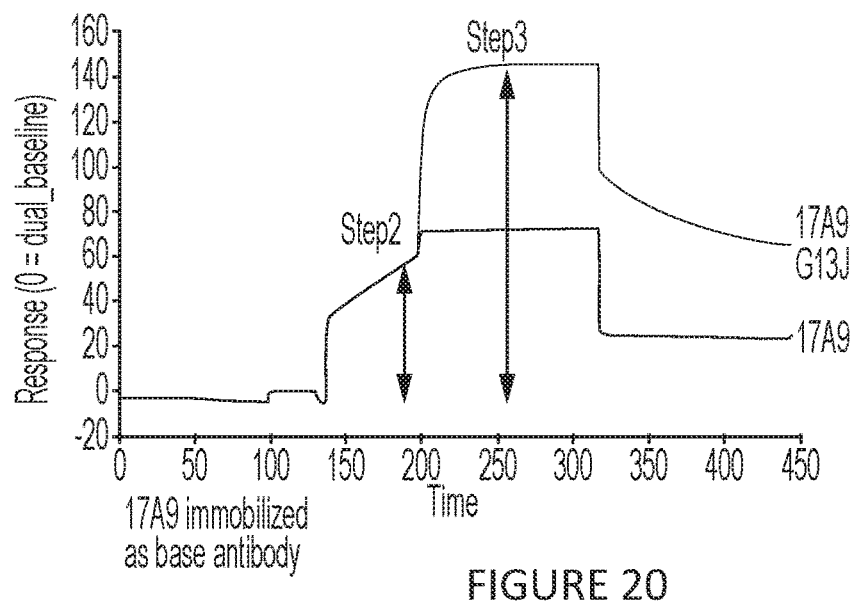
FIG. 20C
FIGURE 20

SEQUENCE LISTING

```
<160> NUMBER OF SEQ ID NOS: 282

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Gly Thr Phe Ser Asp Tyr Ala Ile Thr
1               5                   10
```

```
<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Ile Ile Pro Ile Phe Gly Thr Ala Asn Tyr Ala Gln Lys Phe Gln
1               5                   10                  15

Gly

<210> SEQ ID NO 3
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Glu Gly Gly Leu Leu Thr Asp Ile Ser Tyr Ser Arg Tyr Trp Phe Ala
1               5                   10                  15

Tyr

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Asp Tyr Ala Ile Thr
1               5

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Gly Thr Phe Ser Asp Tyr
1               5

<210> SEQ ID NO 6
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ile Pro Ile Phe Gly Thr
1               5
```

```
<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Gly Thr Phe Ser Asp Tyr Ala
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ile Ile Pro Ile Phe Gly Thr Ala
1               5

<210> SEQ ID NO 9
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ala Arg Glu Gly Gly Leu Leu Thr Asp Ile Ser Tyr Ser Arg Tyr Trp
1               5                   10                  15

Phe Ala Tyr

<210> SEQ ID NO 10
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
                20                  25                  30

Ala Ile Thr Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Leu Leu Thr Asp Ile Ser Tyr Ser Arg Tyr Trp
                100                 105                 110
```

Phe Ala Tyr Trp Gly Gln Gly Thr Leu Val Thr Val Ser Ser
            115                 120                 125

<210> SEQ ID NO 11
<211> LENGTH: 378
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11
caggtgcaat tggtgcagag cggtgccgaa gtgaaaaaac cgggcagcag cgtgaaagtt    60
agctgcaaag catccggagg gacgttttct gactacgcta tcacttgggt gcgccaggcc   120
ccgggccagg gcctcgagtg gatgggcggt atcatcccga tcttcggcac tgcgaactac   180
gcccagaaat tcagggccgg ggtgaccatt accgccgatg aaagcaccag caccgcctat   240
atggaactga gcagcctgcg cagcgaagat acggccgtgt attattgcgc gcgtgaaggt   300
ggtctgctga ctgacatctc ttactctcgt tactggttcg cttactgggg ccaaggcacc   360
ctggtgactg ttagctca                                                 378

<210> SEQ ID NO 12
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Thr Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Leu Leu Thr Asp Ile Ser Tyr Ser Arg Tyr Trp
            100                 105                 110

Phe Ala Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Cys Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
            210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Cys
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 13
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
caggtgcaat tggtgcagag cggtgccgaa gtgaaaaaac cgggcagcag cgtgaaagtt      60
agctgcaaag catccggagg gacgttttct gactacgcta tcacttgggt gcgccaggcc     120
ccgggccagg gcctcgagtg gatgggcggt atcatcccga tcttcggcac tgcgaactac     180
gcccagaaat tcagggccgg ggtgaccatt accgccgatg aaagcaccag caccgcctat     240
atggaactga gcagcctgcg cagcgaagat acggccgtgt attattgcgc gcgtgaaggt     300
ggtctgctga ctgacatctc ttactctcgt tactggttcg cttactgggg ccaaggcacc     360
ctggtgactg ttagctcagc tagcaccaag ggcccaagtg tgtttcccct ggccccccagc    420 agcaagtcta cttccggcgg aactgctgcc ctgggttgcc tggtgaagga ctacttcccc     480
tgtcccgtga cagtgtcctg gaactctggg gctctgactt ccggcgtgca caccttcccc     540

-continued

```
gccgtgctgc agagcagcgg cctgtacagc ctgagcagcg tggtgacagt gccctccagc    600
tctctgggaa cccagaccta tatctgcaac gtgaaccaca agcccagcaa caccaaggtg    660
gacaagagag tggagcccaa agctgcgac aagacccaca cctgcccccc ctgcccagct    720
ccagaactgc tggagggcc ttccgtgttc ctgttccccc caagcccaa ggacaccctg    780 atgatcagca ggaccccga ggtgacctgc gtggtggtgg acgtgtccca cgaggaccca    840
gaggtgaagt tcaactggta cgtggacggc gtggaggtgc acaacgccaa gaccaagccc    900
agagaggagc agtacaacag cacctacagg gtggtgtccg tgctgaccgt gctgcaccag    960
gactggctga acggcaaaga atacaagtgc aaagtctcca acaaggccct gccagcccca   1020
atcgaaaaga caatcagcaa ggccaagggc cagccacggg agccccaggt gtacaccctg   1080 cccccagcc gggaggagat gaccaagaac caggtgtccc tgacctgtct ggtgaagggc   1140
ttctacccct gtgatatcgc cgtggagtgg gagagcaacg gccagcccga gaacaactac   1200
aagaccaccc ccccagtgct ggacagcgac ggcagcttct tcctgtacag caagctgacc   1260
gtggacaagt ccaggtggca gcagggcaac gtgttcagct gcagcgtgat gcacgaggcc   1320
ctgcacaacc actacaccca gaagtccctg agcctgagcc ccggcaag              1368
```

<210> SEQ ID NO 14
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 14

Ser Gly Asp Ala Leu Arg Asp Lys Phe Val Tyr
1               5                   10

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 15

Asp Asp Asn Asn Arg Pro Ser
1               5

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 16

Gln Ser Trp Asp His Ser Tyr Ser Leu Val Val
1               5                   10

<210> SEQ ID NO 17
<211> LENGTH: 7
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 17

Asp Ala Leu Arg Asp Lys Phe
1               5

<210> SEQ ID NO 18
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Asp Asp Asn
1

<210> SEQ ID NO 19
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Trp Asp His Ser Tyr Ser Leu Val
1               5

<210> SEQ ID NO 20
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ala Leu Arg Asp Lys Phe
1               5

<210> SEQ ID NO 21
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Asp Ile Glu Leu Thr Gln Pro Pro Ser Val Ser Val Ser Pro Gly Gln
1               5                   10                  15

Thr Ala Ser Ile Thr Cys Ser Gly Asp Ala Leu Arg Asp Lys Phe Val
            20                  25                  30

Tyr Trp Tyr Gln Gln Lys Pro Gly Gln Ala Pro Val Leu Val Ile Tyr
        35                  40                  45

Asp Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
```

```
                65                  70                  75                  80
Asp Glu Ala Asp Tyr Tyr Cys Gln Ser Trp Asp His Ser Tyr Ser Leu
                85                  90                  95

Val Val Phe Gly Gly Gly Thr Lys Leu Thr Val Leu
            100                 105

<210> SEQ ID NO 22
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
gatatcgaac tgacccagcc gccgagcgtg agcgtgagcc cgggccagac cgcgagcatt      60
acctgtagcg gcgatgctct gcgtgacaaa ttcgtttact ggtaccagca gaaaccgggc    120
caggcgccgg tgctggtgat ctacgacgac aacaaccgtc cgagcggcat cccggaacgt    180
tttagcggat ccaacagcgg caacaccgcg accctgacca ttagcggcac ccaggcggaa    240
gacgaagcgg attattactg ccagtcttgg gaccattctt actctctggt tgtgtttggc    300
ggcggcacga agttaactgt cctg                                           324

<210> SEQ ID NO 23
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Asp Ile Glu Leu Thr Gln Pro Pro Ser Val Ser Val Ser Pro Gly Gln
1               5                   10                  15

Thr Ala Ser Ile Thr Cys Ser Gly Asp Ala Leu Arg Asp Lys Phe Val
            20                  25                  30

Tyr Trp Tyr Gln Gln Lys Pro Gly Gln Ala Pro Val Leu Val Ile Tyr
        35                  40                  45

Asp Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp His Ser Tyr Ser Leu
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190
```

Tyr Ser Cys Gln Val Thr His Glu Gly Ser Thr Val Glu Lys Thr Val
          195                 200                 205

Ala Pro Thr Glu Cys Ser
    210

<210> SEQ ID NO 24
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
gatatcgaac tgacccagcc gccgagcgtg agcgtgagcc cgggccagac cgcgagcatt      60
acctgtagcg gcgatgctct gcgtgacaaa ttcgtttact ggtaccagca gaaaccgggc     120
caggcgccgg tgctggtgat ctacgacgac aacaaccgtc cgagcggcat cccggaacgt     180
tttagcggat ccaacagcgg caacaccgcg accctgacca ttagcggcac ccaggcggaa     240
gacgaagcgg attattactg ccagtcttgg gaccattctt actctctggt tgtgtttggc     300
ggcggcacga agttaactgt cctgggacaa cctaaggccg ctccctccgt gaccctgttc     360
ccccccagct ccgaggaact gcaggccaac aaggccaccc tggtgtgcct gatcagcgac     420
ttctaccctg gcgccgtgac cgtggcctgg aaggccgaca gcagcccgt gaaggccggc     480 gtggagacaa ccaccccag caagcagagc aacaacaagt acgccgccag cagctacctg     540
agcctgaccc ccgagcagtg gaagagccac agaagctaca gctgccaggt cacccacgag     600
ggcagcaccg tggagaaaac cgtggccccc accgagtgca gc                        642

<210> SEQ ID NO 25
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Ser Tyr Glu Leu Thr Gln Pro Leu Ser Val Ser Val Ala Leu Gly Gln
1               5                   10                  15

Thr Ala Arg Ile Thr Cys Ser Gly Asp Ala Leu Arg Asp Lys Phe Val
            20                  25                  30

Tyr Trp Tyr Gln Gln Lys Pro Gly Gln Ala Pro Val Leu Val Ile Tyr
        35                  40                  45

Asp Asp Asn Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Trp Asp His Ser Tyr Ser Leu
                85                  90                  95

Val Val Phe Gly Gly Gly Thr Lys Leu Thr Val Leu
            100                 105

<210> SEQ ID NO 26
<211> LENGTH: 324
<212> TYPE: DNA
<213> ORGANISM: Artificial Sequence -continued
<220> FEATURE:
<221> NAME/KEY: source
<223> OTHER INFORMATION: /note="Description of Artificial Sequence:
      Synthetic polynucleotide"

<400> SEQUENCE: 26

```
agctacgagc tgacccagcc gctgtcggtg tcagtcgccc tgggacaaac tgccaggatc    60
acttgttccg gggacgcatt gcgggacaag ttcgtgtact ggtaccagca gaagccgggt   120
caagccccag tgctcgtgat ctacgacgac aacaaccggc cttccggtat ccccgaacgc   180
ttctccggat ccaatagcgg aaacaccgcc accctgacca tttcgagagc tcaggccggg   240
gatgaagcgg actactactg ccagtcatgg gatcactcgt actccctcgt cgtgtttgga   300
ggcggcacga agcttactgt gctg                                          324
```

<210> SEQ ID NO 27
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

```
Ser Tyr Glu Leu Thr Gln Pro Leu Ser Val Ser Val Ala Leu Gly Gln
1               5                   10                  15

Thr Ala Arg Ile Thr Cys Ser Gly Asp Ala Leu Arg Asp Lys Phe Val
            20                  25                  30

Tyr Trp Tyr Gln Gln Lys Pro Gly Gln Ala Pro Val Leu Val Ile Tyr
        35                  40                  45

Asp Asp Asn Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Trp Asp His Ser Tyr Ser Leu
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 28
<211> LENGTH: 642
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 28

```
agctacgagc tgacccagcc gctgtcggtg tcagtcgccc tgggacaaac tgccaggatc    60
acttgttccg gggacgcatt gcgggacaag ttcgtgtact ggtaccagca gaagccgggt   120
caagccccag tgctcgtgat ctacgacgac aacaaccggc cttccggtat ccccgaacgc   180
ttctccggat ccaatagcgg aaacaccgcc accctgacca tttcgagagc tcaggccggg   240
gatgaagcgg actactactg ccagtcatgg gatcactcgt actccctcgt cgtgtttgga   300
ggcggcacga agcttactgt gctgggccag cctaaggccg ctccctccgt gaccctgttc   360
cccccccagct ccgaggaact gcaggccaac aaggccaccc tggtgtgcct gatcagcgac   420
ttctaccctg gcgccgtgac cgtggcctgg aaggccgaca gcagcccgt gaaggccggc    480
gtggagacaa ccaccccag caagcagagc aacaacaagt acgccgccag cagctacctg   540
agcctgaccc ccgagcagtg gaagagccac agaagctaca gctgccaggt cacccacgag   600
ggcagcaccg tggagaaaac cgtggccccc accgagtgca gc                     642
```

<210> SEQ ID NO 29
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Ser Tyr Glu Leu Thr Gln Pro Pro Ser Val Ser Val Ser Pro Gly Gln
1               5                   10                  15

Thr Ala Ser Ile Thr Cys Ser Gly Asp Ala Leu Arg Asp Lys Phe Val
            20                  25                  30

Tyr Trp Tyr Gln Gln Lys Pro Gly Gln Ser Pro Val Leu Val Ile Tyr
        35                  40                  45

Asp Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ser Trp Asp His Ser Tyr Ser Leu
                85                  90                  95

Val Val Phe Gly Gly Gly Thr Lys Leu Thr Val Leu
            100                 105

<210> SEQ ID NO 30
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30

```
tcgtacgagc tcactcaacc gccttctgtg tccgtgtcac ccgggcagac tgcctccatt    60
acctgttcgg gagatgccct gcgcgacaag tttgtgtact ggtaccagca gaagcccgga   120
cagtcgccag tgctcgtcat ctatgacgac aacaacagac cttccggtat cccggaacgg   180
```

```
ttcagcggaa gcaattccgg caacaccgct accctgacca ttagcggcac tcaggccatg    240
gacgaagcgg attactactg ccaatcctgg gaccactcat actcccttgt ggtgttcggt    300
ggcggaacga agctgaccgt cctg                                           324
```

<210> SEQ ID NO 31
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

```
Ser Tyr Glu Leu Thr Gln Pro Pro Ser Val Ser Val Ser Pro Gly Gln
1               5                   10                  15

Thr Ala Ser Ile Thr Cys Ser Gly Asp Ala Leu Arg Asp Lys Phe Val
            20                  25                  30

Tyr Trp Tyr Gln Gln Lys Pro Gly Gln Ser Pro Val Leu Val Ile Tyr
        35                  40                  45

Asp Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ser Trp Asp His Ser Tyr Ser Leu
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 32
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 32

```
tcgtacgagc tcactcaacc gccttctgtg tccgtgtcac ccgggcagac tgcctccatt    60
acctgttcgg gagatgccct gcgcgacaag tttgtgtact ggtaccagca gaagcccgga    120
cagtcgccag tgctcgtcat ctatgacgac aacaacagac cttccggtat cccggaacgg    180
ttcagcggaa gcaattccgg caacaccgct accctgacca ttagcggcac tcaggccatg    240
```

```
gacgaagcgg attactactg ccaatcctgg gaccactcat actcccttgt ggtgttcggt    300
ggcggaacga agctgaccgt cctgggccag cctaaggccg ctccctccgt gaccctgttc    360 cccccagct ccgaggaact gcaggccaac aaggccaccc tggtgtgcct gatcagcgac     420
ttctaccctg gcgccgtgac cgtggcctgg aaggccgaca gcagcccgt gaaggccggc     480 gtggagacaa ccaccccag caagcagagc aacaacaagt acgccgccag cagctacctg     540
agcctgaccc ccgagcagtg gaagagccac agaagctaca gctgccaggt cacccacgag    600
ggcagcaccg tggagaaaac cgtggccccc accgagtgca gc                       642
```

<210> SEQ ID NO 33
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 33

```
Gly Gly Thr Phe Ser Thr Tyr Ala Ile Ser
1               5                   10
```

<210> SEQ ID NO 34
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 34

```
Arg Ile Ile Pro Ile Leu Gly Ile Ala Asn Tyr Ala Gln Lys Phe Gln
1               5                   10                  15

Gly
```

<210> SEQ ID NO 35
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 35

```
Glu Val Arg Met Ile Phe Asp Tyr
1               5
```

<210> SEQ ID NO 36
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 36

```
Thr Tyr Ala Ile Ser
1               5
```

<210> SEQ ID NO 37

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gly Gly Thr Phe Ser Thr Tyr
1               5

<210> SEQ ID NO 38
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ile Pro Ile Leu Gly Ile
1               5

<210> SEQ ID NO 39
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gly Gly Thr Phe Ser Thr Tyr Ala
1               5

<210> SEQ ID NO 40
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Ile Ile Pro Ile Leu Gly Ile Ala
1               5

<210> SEQ ID NO 41
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Ala Arg Glu Val Arg Met Ile Phe Asp Tyr
1               5                   10

<210> SEQ ID NO 42
<211> LENGTH: 117
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Arg Met Ile Phe Asp Tyr Trp Gly Gln Gly Thr Leu
            100                 105                 110

Val Thr Val Ser Ser
        115

<210> SEQ ID NO 43
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 43
caggtgcaat tggtgcagag cggtgccgaa gtgaaaaaac cgggcagcag cgtgaaagtt      60
agctgcaaag catccggagg gacgtttttct acttacgcta tctcttgggt gcgccaggcc    120
ccgggccagg gcctcgagtg gatgggccgt atcatcccga tcctgggcat cgcgaactac    180
gcccagaaat ttcagggccg ggtgaccatt accgccgatg aaagcaccag caccgcctat    240
atggaactga gcagcctgcg cagcgaagat acggccgtgt attattgcgc gcgtgaagtt    300
cgtatgatct tcgattactg gggccaaggc accctggtga ctgttagctc a              351

<210> SEQ ID NO 44
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
```

```
                65                  70                  75                  80
Met Glu Leu Ser Ser Leu Arg Ser Glu Asp Thr Ala Val Tyr Tyr Cys
                    85                  90                  95

Ala Arg Glu Val Arg Met Ile Phe Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
            130                 135                 140

Leu Val Lys Asp Tyr Phe Pro Cys Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Cys Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 45
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 45

```
caggtgcaat tggtgcagag cggtgccgaa gtgaaaaaac cgggcagcag cgtgaaagtt      60
agctgcaaag catccggagg gacgttttct acttacgcta tctcttgggt gcgccaggcc     120
ccgggccagg gcctcgagtg gatgggccgt atcatcccga tcctgggcat cgcgaactac     180
gcccagaaat ttcagggccg ggtgaccatt accgccgatg aaagcaccag caccgcctat     240
atggaactga gcagcctgcg cagcgaagat acggccgtgt attattgcgc gcgtgaagtt     300
cgtatgatct tcgattactg gggccaaggc accctggtga ctgttagctc agcctctacg     360
aaaggcccaa gcgtatttcc cctggctcct tctagtaaat caacctcagg tggtacagca     420
gcccttggct gcctggtcaa agactatttc ccctgtccgg tgaccgtctc atggaactca     480
ggtgctttga catctggtgt gcatacattc ccagctgtgt gcaaagtag tggactgtac     540
agcctttcca gcgtggtcac ggtgccaagt agctccttgg gtactcagac ttatatctgc     600
aatgtgaacc acaagccctc taacacgaag gtggacaagc gcgtggagcc caaatcttgc     660
gataagacgc atacttgtcc cccatgccct gctcctgagc tgttgggagg cccgtcagtg     720
ttcttgttcc ctccgaagcc taaggacact ttgatgataa gtaggacacc agaggtgact     780
tgcgtggtgg ttgatgtgtc ccatgaagat cccgaggtca aatttaattg gtacgtagat     840
ggtgtcgaag ttcacaatgc taagactaag ccaagggaag agcagtacaa cagtacatat     900
agggtagtct ccgtgctgac agtcctccac caggactggt tgaacggcaa ggaatacaaa     960
tgtaaggtgt caaacaaagc tctgcctgct cccattgaga aaacaatctc taaagccaaa    1020
ggccagccga gagagcccca agtctacact ttgccccga gcagggagga atgaccaag     1080
aatcaggtga gtctgacgtg cctcgtcaaa ggatttttatc catgcgatat tgcagttgaa    1140
tgggagagca atggccagcc agagaacaac tataaaacca caccaccgt gctcgactct    1200
gatggcagct tcttcctcta tagcaagctg acagtcgata atctcgctg gcagcaaggc    1260
aatgtgttct cctgctccgt catgcacgag gctttgcata accattatac tcaaaaatct    1320
ctgtccctgt cacctggtaa a                                              1341
```

<210> SEQ ID NO 46
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 46

Arg Ala Ser Gln Ser Ile Ser Ser Tyr Leu Ala
1               5                   10

<210> SEQ ID NO 47
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 47

Ala Ala Ser Ser Leu Gln Ser
1               5

```
<210> SEQ ID NO 48
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gln Gln Ser Tyr Asp Tyr Tyr Thr
1               5

<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ser Gln Ser Ile Ser Ser Tyr
1               5

<210> SEQ ID NO 50
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ala Ala Ser
1

<210> SEQ ID NO 51
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ser Tyr Asp Tyr Tyr
1               5

<210> SEQ ID NO 52
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Gln Ser Ile Ser Ser Tyr
1               5

<210> SEQ ID NO 53
<211> LENGTH: 106
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Tyr Tyr Thr
                85                  90                  95

Phe Gly Gln Gly Thr Lys Val Glu Ile Lys
            100                 105

<210> SEQ ID NO 54
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54
gatatccaga tgacccagag cccgagcagc ctgagcgcca gcgtgggcga tcgcgtgacc      60
attacctgca gagccagcca gtctatttct tcttacctgg cttggtacca gcagaaaccg     120
ggcaaagcgc cgaaactatt aatctacgct gcttcttctc tgcaaagcgg cgtgccgagc     180
cgctttagcg gcagcggatc cggcaccgat ttcaccctga ccattagctc tctgcaaccg     240
gaagactttg cgacctatta ttgccagcag tcttacgact actacacctt tggccagggc     300
acgaaagttg aaattaaa                                                   318

<210> SEQ ID NO 55
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Tyr Asp Tyr Thr
                    85                  90                  95
Phe Gly Gln Gly Thr Lys Val Glu Ile Lys Arg Thr Val Ala Ala Pro
                100                 105                 110
Ser Val Phe Ile Phe Pro Pro Ser Asp Glu Gln Leu Lys Ser Gly Thr
            115                 120                 125
Ala Ser Val Val Cys Leu Leu Asn Asn Phe Tyr Pro Arg Glu Ala Lys
        130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 56
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56
gatatccaga tgacccagag cccgagcagc ctgagcgcca gcgtgggcga tcgcgtgacc      60
attacctgca gagccagcca gtctatttct tcttacctgg cttggtacca gcagaaaccg    120
ggcaaagcgc cgaaactatt aatctacgct gcttcttctc tgcaaagcgg cgtgccgagc    180
cgctttagcg gcagcggatc cggcaccgat ttcaccctga ccattagctc tctgcaaccg    240
gaagactttg cgacctatta ttgccagcag tcttacgact actacacctt tggccagggc    300
acgaaagttg aaattaaacg tacggtggca gctccgtctg ttttcatctt cccacctagc    360
gacgagcaac tcaaaagtgg tacagcatcc gtggtttgtc tgctgaacaa ttttacccc    420 agggaggcta aggtccagtg gaaagtcgat aacgctcttc agtctggcaa cagtcaggag    480
agcgtcacag agcaggactc taaggatagc acttatagtc tgtcctccac gctgacactg    540
tctaaagcgg attatgagaa gcacaaggtt tacgcctgtg aggtaacgca ccaaggactc    600
tcctccccag ttaccaaatc tttcaacaga ggagaatgt                           639

<210> SEQ ID NO 57
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gly Gly Thr Phe Ser Asp Tyr Ala Ile Ser
1               5                   10
```

-continued

```
<210> SEQ ID NO 58
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Ile Ile Pro Ile Phe Gly Asp Ala Asn Tyr Ala Gln Lys Phe Gln
1               5                   10                  15

Gly

<210> SEQ ID NO 59
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Glu Gly Ser Ser Tyr Phe Tyr Met Ala Tyr
1               5                   10

<210> SEQ ID NO 60
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Asp Tyr Ala Ile Ser
1               5

<210> SEQ ID NO 61
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ile Pro Ile Phe Gly Asp
1               5

<210> SEQ ID NO 62
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ile Ile Pro Ile Phe Gly Asp Ala
1               5

<210> SEQ ID NO 63
<211> LENGTH: 12
```

<210> SEQ ID NO 63
<211> LENGTH: 12 (implied)
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 63

Ala Arg Glu Gly Ser Ser Tyr Phe Tyr Met Ala Tyr
1               5                   10

<210> SEQ ID NO 64
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Asp Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ser Ser Tyr Phe Tyr Met Ala Tyr Trp Gly Gln Gly
            100                 105                 110

Thr Leu Val Thr Val Ser Ser
        115

<210> SEQ ID NO 65
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 65
caggttcagc tggtgcagtc tggcgccgaa gtgaagaaac ctggcagcag cgtgaaggtg      60
tcctgcaaag caagcggcgg caccttcagc gattacgcca tctcttgggt ccgacaggcc     120
cctggacaag cttggaatg gatgggcggc atcatcccca tcttcggcga cgccaattac     180
gcccagaaat tccagggcag agtgaccatc accgccacg agtctacaag caccgcctac     240
atggaactga gcagcctgag aagcgaggac accgccgtgt actactgtgc cagagagggc     300
agcagctact tctacatggc ctattggggc caggcaccc tggtcacagt tagctct        357

<210> SEQ ID NO 66
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 66

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Gly | Thr | Phe | Ser | Asp | Tyr |
| | | | 20 | | | | | 25 | | | | | 30 | | |
| Ala | Ile | Ser | Trp | Val | Arg | Gln | Ala | Pro | Gly | Gln | Gly | Leu | Glu | Trp | Met |
| | | 35 | | | | | 40 | | | | | 45 | | | |
| Gly | Gly | Ile | Ile | Pro | Ile | Phe | Gly | Asp | Ala | Asn | Tyr | Ala | Gln | Lys | Phe |
| 50 | | | | | 55 | | | | | 60 | | | | | |
| Gln | Gly | Arg | Val | Thr | Ile | Thr | Ala | Asp | Glu | Ser | Thr | Ser | Thr | Ala | Tyr |
| 65 | | | | 70 | | | | | 75 | | | | | 80 | |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Glu | Gly | Ser | Ser | Tyr | Phe | Tyr | Met | Ala | Tyr | Trp | Gly | Gln | Gly |
| | | | 100 | | | | | 105 | | | | | 110 | | |
| Thr | Leu | Val | Thr | Val | Ser | Ser | Ala | Ser | Thr | Lys | Gly | Pro | Ser | Val | Phe |
| | | 115 | | | | | 120 | | | | | 125 | | | |
| Pro | Leu | Ala | Pro | Ser | Ser | Lys | Ser | Thr | Ser | Gly | Gly | Thr | Ala | Ala | Leu |
| 130 | | | | | 135 | | | | | 140 | | | | | |
| Gly | Cys | Leu | Val | Lys | Asp | Tyr | Phe | Pro | Cys | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | | 195 | | | | | 200 | | | | | 205 | | |
| Ser | Asn | Thr | Lys | Val | Asp | Lys | Arg | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Tyr | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Glu | Glu | Met | Thr | Lys | Asn | Gln | Val | Ser | Leu | Thr |
| | | 355 | | | | | 360 | | | | | 365 | | | |
| Cys | Leu | Val | Lys | Gly | Phe | Tyr | Pro | Cys | Asp | Ile | Ala | Val | Glu | Trp | Glu |
| | 370 | | | | | 375 | | | | | 380 | | | | |
| Ser | Asn | Gly | Gln | Pro | Glu | Asn | Asn | Tyr | Lys | Thr | Thr | Pro | Pro | Val | Leu |
| 385 | | | | | 390 | | | | | 395 | | | | | 400 |

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 67
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67
caggttcagc tggtgcagtc tggcgccgaa gtgaagaaac tggcagcag cgtgaaggtg      60 tcctgcaaag caagcggcgg caccttcagc gattacgcca tctcttgggt ccgacaggcc     120
cctggacaag gcttggaatg gatgggcggc atcatcccca tcttcggcga cgccaattac     180
gcccagaaat tccagggcag agtgaccatc accgccgacg agtctacaag caccgcctac     240
atggaactga gcagcctgag aagcgaggac accgccgtgt actactgtgc cagagagggc     300
agcagctact tctacatggc ctattggggc cagggcaccc tggtcacagt tagctctgct     360
agcaccaagg gcccaagtgt gtttcccctg gcccccagca gcaagtctac ttccggcgga     420
actgctgccc tgggttgcct ggtgaaggac tacttcccct gtcccgtgac agtgtcctgg     480
aactctgggg ctctgacttc cggcgtgcac accttcccg ccgtgctgca gagcagcggc     540
ctgtacagcc tgagcagcgt ggtgacagtg ccctccagct ctctgggaac ccagacctat     600
atctgcaacg tgaaccacaa gcccagcaac accaaggtgg acaagagagt ggagcccaag     660
agctgcgaca gacccacac ctgccccccc tgcccagctc cagaactgct gggagggcct     720
tccgtgttcc tgttccccc caagcccaag gacaccctga tgatcagcag gaccccgag     780 gtgacctgcg tggtggtgga cgtgtcccac gaggacccag aggtgaagtt caactggtac     840
gtggacggcg tggaggtgca caacgccaag accaagccca gagaggagca gtacaacagc     900
acctacaggg tggtgtccgt gctgaccgtg ctgcaccagg actggctgaa cggcaaagaa     960
tacaagtgca aagtctccaa caaggccctg ccagccccaa tcgaaaagac aatcagcaag    1020
gccaagggcc agccacggga gccccaggtg tacaccctgc cccccagccg ggaggagatg    1080
accaagaacc aggtgtccct gacctgtctg gtgaagggct tctaccctg tgatatcgcc    1140 gtggagtggg agagcaacgg ccagcccgag aacaactaca gaccaccccc ccagtgctg    1200 gacagcgacg gcagcttctt cctgtacagc aagctgaccg tggacaagtc caggtggcag    1260
cagggcaacg tgttcagctg cagcgtgatg cacgaggccc tgcacaacca ctacacccag    1320
aagtccctga gcctgagccc cggcaag                                       1347

<210> SEQ ID NO 68
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 68

Ser Gly Asp Asn Ile Gly Ser Lys Leu Ala Ser
1               5                   10

<210> SEQ ID NO 69
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Asp Asp Ser Asn Arg Pro Ser
1               5

<210> SEQ ID NO 70
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Ala Ala Thr Ala Gly Asp Arg Trp Ala Tyr Val
1               5                   10

<210> SEQ ID NO 71
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Asp Asn Ile Gly Ser Lys Leu
1               5

<210> SEQ ID NO 72
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Asp Asp Ser
1

<210> SEQ ID NO 73
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Thr Ala Gly Asp Arg Trp Ala Tyr
```

<210> SEQ ID NO 74
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 74

Asn Ile Gly Ser Lys Leu
1               5

<210> SEQ ID NO 75
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 75

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Gly Ser Lys Leu Ala
            20                  25                  30

Ser Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Ala Ala Thr Ala Gly Asp Arg Trp Ala
                85                  90                  95

Tyr Val Phe Gly Gly Gly Thr Lys Leu Thr Val Leu
            100                 105

<210> SEQ ID NO 76
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 76
agctatgagc tgacacagcc tctgtccgtg tctgtggctc tgggacagac cgccagaatc      60
acctgtagcg gcgacaacat cggcagcaag ctggcctctt ggtatcagca gaagcctgga     120
caggcccctg tgctggtcat ctacgacgac agcaatagac ccagcggcat ccccgagaga     180
ttcagcggca gcaatagcgg caataccgcc acactgacca tcagcagagc acaggctggc     240
gacgaggccg attactattg tgctgccaca gccggcgaca gatgggccta tgttttggc      300 ggcggaacaa agctgaccgt gctg                                            324

<210> SEQ ID NO 77
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Gly Ser Lys Leu Ala
            20                  25                  30

Ser Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Ala Ala Thr Ala Gly Asp Arg Trp Ala
                85                  90                  95

Tyr Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 78
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
agctatgagc tgacacagcc tctgtccgtg tctgtggctc tgggacagac cgccagaatc      60
acctgtagcg gcgacaacat cggcagcaag ctggcctctt ggtatcagca gaagcctgga     120
caggcccctg tgctggtcat ctacgacgac agcaatagac cagcggcat ccccgagaga      180 ttcagcggca gcaatagcgg caataccgcc acactgacca tcagcagagc acaggctggc     240
gacgaggccg attactattg tgctgccaca gccggcgaca gatgggccta tgttttggc      300 ggcggaacaa agctgaccgt gctgggacag cctaaggccg ctccctccgt gaccctgttc     360 cccccccagct ccgaggaact gcaggccaac aaggccaccc tggtgtgcct gatcagcgac    420
ttctaccctg gcgccgtgac cgtggcctgg aaggccgaca gcagcccgt gaaggccggc      480 gtggagacaa ccaccccag caagcagagc aacaacaagt acgccgccag cagctacctg     540

```
agcctgaccc ccgagcagtg gaagagccac agaagctaca gctgccaggt cacccacgag      600
ggcagcaccg tggagaaaac cgtggccccc accgagtgca gc                        642
```

<210> SEQ ID NO 79
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 79

```
Gly Phe Thr Phe Ser Ser Phe Gly Met Ser
1               5                   10
```

<210> SEQ ID NO 80
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 80

```
Ala Ile Ser Tyr Ser Gly Ser Asp Thr Tyr Tyr Ala Asp Ser Val Lys
1               5                   10                  15

Gly
```

<210> SEQ ID NO 81
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 81

```
Asp Val Gly Val Met Asp Tyr
1               5
```

<210> SEQ ID NO 82
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 82

```
Ser Phe Gly Met Ser
1               5
```

<210> SEQ ID NO 83
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 83

Gly Phe Thr Phe Ser Ser Phe

```
<210> SEQ ID NO 84
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Ser Tyr Ser Gly Ser Asp
1               5

<210> SEQ ID NO 85
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Gly Phe Thr Phe Ser Ser Phe Gly
1               5

<210> SEQ ID NO 86
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Ile Ser Tyr Ser Gly Ser Asp Thr
1               5

<210> SEQ ID NO 87
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Ala Arg Asp Val Gly Val Met Asp Tyr
1               5

<210> SEQ ID NO 88
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30
```

Gly Met Ser Trp Val Arg Gln Ala Pro Gly Lys Gly Leu Glu Trp Val
            35                  40                  45

Ser Ala Ile Ser Tyr Ser Gly Ser Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly Val Met Asp Tyr Trp Gly Gln Gly Thr Leu Val
            100                 105                 110

Thr Val Ser Ser
        115

<210> SEQ ID NO 89
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89
caggttcagc tgctggaatc tggcggagga ctggttcaac ctggcggctc tctgagactg      60
tcttgtgccg ccagcggctt caccttcagc agctttggca tgagctgggt ccgacaggcc    120
cctggcaaag gacttgaatg ggtgtccgcc atcagctaca gcggcagcga tacctactac    180
gccgacagcg tgaagggcag attcaccatc tccagagaca acagcaagaa caccctgtac    240
ctgcagatga acagcctgag agccgaggac accgccgtgt actactgtgc cagagatgtg    300
ggcgtgatgg actattgggg ccagggcaca ctggtcaccg ttagctct                 348

<210> SEQ ID NO 90
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ala Ile Ser Tyr Ser Gly Ser Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly Val Met Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Cys Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Cys Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 91
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91
caggttcagc tgctggaatc tggcggagga ctggttcaac tggcggctc tctgagactg      60 tcttgtgccg ccagcggctt caccttcagc agctttggca tgagctgggt ccgacaggcc    120
cctggcaaag gacttgaatg ggtgtccgcc atcagctaca gcggcagcga tacctactac    180
gccgacagcg tgaagggcag attcaccatc tccagagaca acagcaagaa caccctgtac    240

```
ctgcagatga acagcctgag agccgaggac accgccgtgt actactgtgc cagagatgtg    300
ggcgtgatgg actattgggg ccagggcaca ctggtcaccg ttagctctgc tagcaccaag    360
ggcccaagtg tgtttcccct ggccccagc agcaagtcta cttccggcgg aactgctgcc    420
ctgggttgcc tggtgaagga ctacttcccc tgtcccgtga cagtgtcctg gaactctggg    480
gctctgactt ccggcgtgca caccttcccc gccgtgctgc agagcagcgg cctgtacagc    540
ctgagcagcg tggtgacagt gccctccagc tctctgggaa cccagaccta tatctgcaac    600
gtgaaccaca gcccagcaa caccaaggtg acaagagag tggagcccaa agctgcgac     660 aagacccaca cctgcccccc ctgcccagct ccagaactgc tgggagggcc ttccgtgttc    720 ctgttcccc ccaagcccaa ggacaccctg atgatcagca ggaccccga ggtgacctgc     780 gtggtggtgg acgtgtccca cgaggaccca gaggtgaagt tcaactggta cgtggacggc    840
gtggaggtgc acaacgccaa gaccaagccc agagaggagc agtacaacag cacctacagg    900
gtggtgtccg tgctgaccgt gctgcaccag gactggctga acggcaaaga atacaagtgc    960
aaagtctcca acaaggccct gccagcccca atcgaaaaga caatcagcaa ggccaagggc   1020
cagccacggg agccccaggt gtacaccctg ccccccagcc gggaggagat gaccaagaac   1080
caggtgtccc tgacctgtct ggtgaagggc ttctacccct gtgatatcgc cgtggagtgg   1140
gagagcaacg gccagcccga gaacaactac aagaccaccc ccccagtgct ggacagcgac   1200
ggcagcttct tcctgtacag caagctgacc gtggacaagt ccaggtggca gcagggcaac   1260
gtgttcagct gcagcgtgat gcacgaggcc ctgcacaacc actacaccca gaagtccctg   1320
agcctgagcc ccggcaag                                                 1338
```

<210> SEQ ID NO 92
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 92

Ser Gly Asp Asn Leu Gly Thr Tyr Tyr Ala His
1               5                   10

<210> SEQ ID NO 93
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 93

Ser Gln Ser His Arg Pro Ser
1               5

<210> SEQ ID NO 94
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 94

Gly Ala Trp Asp Ala Pro Ser Pro Glu Leu Val
1               5                   10

<210> SEQ ID NO 95
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Asp Asn Leu Gly Thr Tyr Tyr
1               5

<210> SEQ ID NO 96
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Ser Gln Ser
1

<210> SEQ ID NO 97
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Trp Asp Ala Pro Ser Pro Glu Leu
1               5

<210> SEQ ID NO 98
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Asn Leu Gly Thr Tyr Tyr
1               5

<210> SEQ ID NO 99
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Ser Tyr Glu Leu Thr Gln Pro Leu Ser Val Ser Val Ala Leu Gly Gln
1               5                   10                  15
```

```
Thr Ala Arg Ile Thr Cys Ser Gly Asp Asn Leu Gly Thr Tyr Tyr Ala
            20                  25                  30

His Trp Tyr Gln Gln Lys Pro Gly Gln Ala Pro Val Leu Val Ile Tyr
        35                  40                  45

Ser Gln Ser His Arg Pro Ser Gly Ile Pro Glu Arg Phe Ser Gly Ser
50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gly Ala Trp Asp Ala Pro Ser Pro Glu
                85                  90                  95

Leu Val Phe Gly Gly Gly Thr Lys Leu Thr Val Leu
            100                 105
```

```
<210> SEQ ID NO 100
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 100
agctatgagc tgacacagcc tctgtccgtg tctgtggctc tgggacagac cgccagaatc      60
acctgtagcg gcgataacct gggcacctac tacgcccact ggtatcagca gaagcctgga     120
caggctcccg tgctggtcat ctacagccag tctcacagac ccagcggcat ccccgagaga     180
ttcagcggca gcaatagcgg caataccgcc acactgacca tcagcagagc acaggctggc     240
gacgaggccg attactattg tggcgcttgg gacgccccat ctcctgagct tgttttggc      300 ggaggcacca agctgacagt gctg                                           324
```

```
<210> SEQ ID NO 101
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Leu Gly Thr Tyr Tyr Ala
            20                  25                  30

His Trp Tyr Gln Gln Lys Pro Gly Gln Ala Pro Val Leu Val Ile Tyr
        35                  40                  45

Ser Gln Ser His Arg Pro Ser Gly Ile Pro Glu Arg Phe Ser Gly Ser
50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gly Ala Trp Asp Ala Pro Ser Pro Glu
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125
```

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 102
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 102
agctatgagc tgacacagcc tctgtccgtg tctgtggctc tgggacagac cgccagaatc      60
acctgtagcg gcgataacct gggcacctac tacgcccact ggtatcagca gaagcctgga     120
caggctcccg tgctggtcat ctacagccag tctcacagac ccagcggcat ccccgagaga     180
ttcagcggca gcaatagcgg caataccgcc acactgacca tcagcagagc acaggctggc     240
gacgaggccg attactattg tggcgcttgg gacgccccat ctcctgagct tgttttttggc     300 ggaggcacca gctgacagt gctgggacag cctaaggccg ctccctccgt gaccctgttc     360
ccccccagct ccgaggaact gcaggccaac aaggccaccc tggtgtgcct gatcagcgac     420
ttctaccctg gcgccgtgac cgtggcctgg aaggccgaca gcagccccgt gaaggccggc     480
gtggagacaa ccaccccag caagcagagc aacaacaagt acgccgccag cagctacctg     540
agcctgaccc ccgagcagtg gaagagccac agaagctaca gctgccaggt cacccacgag     600
ggcagcaccg tggagaaaac cgtggccccc accgagtgca gc                       642

<210> SEQ ID NO 103
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Gly Phe Thr Phe Ser Ser Tyr Ala Met Ser
1               5                   10

<210> SEQ ID NO 104
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Ala Ile Ser Gly Ser Gly Gly Ser Thr Tyr Tyr Ala Asp Ser Val Lys
1               5                   10                  15
Gly

<210> SEQ ID NO 105
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Ala Phe Arg Leu Tyr Trp Leu Asp Val
1               5

<210> SEQ ID NO 106
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Ser Tyr Ala Met Ser
1               5

<210> SEQ ID NO 107
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Gly Phe Thr Phe Ser Ser Tyr
1               5

<210> SEQ ID NO 108
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Ser Gly Ser Gly Gly Ser
1               5

<210> SEQ ID NO 109
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Gly Phe Thr Phe Ser Ser Tyr Ala
1               5

<210> SEQ ID NO 110
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Ile Ser Gly Ser Gly Gly Ser Thr
1               5

<210> SEQ ID NO 111
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Ala Arg Ala Phe Arg Leu Tyr Trp Leu Asp Val
1               5                   10

<210> SEQ ID NO 112
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Phe Arg Leu Tyr Trp Leu Asp Val Trp Gly Gln Gly Thr
            100                 105                 110

Leu Val Thr Val Ser Ser
        115

<210> SEQ ID NO 113
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 113

```
gaagttcagc tgctggaatc tggcggagga ctggttcaac ctggcggctc tctgagactg        60
tcttgtgccg ccagcggctt cacctttagc agctacgcca tgagctgggt ccgacaggct       120
cctggcaaag gccttgaatg ggtgtccgcc atctctggct ctggcggcag cacatattac       180
gccgactctg tgaagggcag attcaccatc agccgggaca acagcaagaa cacccctgtac      240 ctgcagatga acagcctgag agccgaggac accgccgtgt actattgtgc cagagccttc      300
cggctgtact ggctggatgt ttggggacag ggcaccctgg tcacagtgtc atct             354
```

<210> SEQ ID NO 114
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 114

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Phe Arg Leu Tyr Trp Leu Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Cys Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
```

```
                290                 295                 300
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Cys Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 115
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 115
gaagttcagc tgctggaatc tggcggagga ctggttcaac tggcggctc tctgagactg        60 tcttgtgccg ccagcggctt cacctttagc agctacgcca tgagctgggt ccgacaggct      120
cctggcaaag gccttgaatg ggtgtccgcc atctctggct ctggcggcag cacatattac      180
gccgactctg tgaagggcag attcaccatc agccgggaca acagcaagaa caccctgtac      240
ctgcagatga acagcctgag agccgaggac accgccgtgt actattgtgc cagagccttc      300
cggctgtact ggctggatgt ttggggacag ggcaccctgg tcacagtgtc atctgctagc      360
accaagggcc caagtgtgtt tcccctggcc ccagcagca gtctacttc cggcggaact       420 gctgccctgg gttgcctggt gaaggactac ttccctgtc cgtgacagt gtcctggaac        480 tctgggctc tgacttccgg cgtgcacacc ttccccgccg tgctgcagag cagcggcctg      540
tacagcctga gcagcgtggt gacagtgccc tccagctctc tgggaaccca gacctatatc     600
tgcaacgtga accacaagcc cagcaacacc aaggtggaca gagagtgga gcccaagagc      660 tgcgacaaga cccacacctg ccccccctgc ccagctccag aactgctggg agggccttcc     720
gtgttcctgt tccccccaa gcccaaggac ccctgatga tcagcaggac ccccgaggtg       780
acctgcgtgg tggtggacgt gtcccacgag acccagaggt gaagttcaa ctggtacgtg     840 gacggcgtgg aggtgcacaa cgccaagacc aagcccagag aggagcagta caacagcacc      900
tacagggtgg tgtccgtgct gaccgtgctg caccaggact ggctgaacgg caaagaatac     960
aagtgcaaag tctccaacaa ggccctgcca gccccaatcg aaaagacaat cagcaaggcc    1020
aagggccagc cacgggagcc ccaggtgtac accctgcccc ccagccggga ggagatgacc    1080
aagaaccagg tgtccctgac ctgtctggtg aagggcttct acccctgtga tatcgccgtg    1140
```

```
gagtgggaga gcaacggcca gcccgagaac aactacaaga ccaccccccc agtgctggac    1200
agcgacggca gcttcttcct gtacagcaag ctgaccgtgg acaagtccag gtggcagcag    1260
ggcaacgtgt tcagctgcag cgtgatgcac gaggccctgc acaaccacta cacccagaag    1320
tccctgagcc tgagccccgg caag                                           1344
```

```
<210> SEQ ID NO 116
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Arg Ala Ser Gln Ser Ile Ser Ser Tyr Leu Asn
1               5                   10

<210> SEQ ID NO 117
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Gln Gln Val Tyr Ser Ala Pro Val Thr
1               5

<210> SEQ ID NO 118
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Val Tyr Ser Ala Pro Val
1               5

<210> SEQ ID NO 119
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Val Tyr Ser Ala Pro Val
                85                  90                  95

Thr Phe Gly Gln Gly Thr Lys Val Glu Ile Lys
           100                 105

<210> SEQ ID NO 120
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 120
gacatccaga tgacacagag ccctagcagc ctgtctgcca gcgtgggaga cagagtgacc      60
atcacctgta gagccagcca gagcatcagc agctacctga actggtatca gcagaagccc     120
ggcaaggccc ctaaactgct gatctatgcc gccagctctc tgcagtctgg cgtgccaagc     180
agattttctg gcagcggctc tggcaccgac ttcaccctga ccatatctag cctgcagcca     240
gaggacttcg ccacctacta ctgccagcag gtctacagcg cccctgtgac atttggccag     300
ggcaccaagg tggaaatcaa g                                                321

<210> SEQ ID NO 121
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Ser Ala Pro Val
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 122
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 122

```
gacatccaga tgacacagag ccctagcagc ctgtctgcca gcgtgggaga cagagtgacc      60
atcacctgta gagccagcca gagcatcagc agctacctga actggtatca gcagaagccc     120
ggcaaggccc ctaaactgct gatctatgcc gccagctctc tgcagtctgg cgtgccaagc     180 agatttctg gcagcggctc tggcaccgac ttcaccctga ccatatctag cctgcagcca      240
gaggacttcg ccacctacta ctgccagcag gtctacagcg cccctgtgac atttggccag     300
ggcaccaagg tggaaatcaa gcgtacggtg gccgctccca gcgtgttcat cttccccccc     360
agcgacgagc agctgaagag tggcaccgcc agcgtggtgt gcctgctgaa caacttctac     420 cccgggagg ccaaggtgca gtggaaggtg acaacgccc tgcagagcgg caacagccag       480
gagagcgtca ccgagcagga cagcaaggac tccacctaca gcctgagcag caccctgacc     540
ctgagcaagg ccgactacga gaagcataag gtgtacgcct gcgaggtgac ccaccagggc     600
ctgtccagcc ccgtgaccaa gagcttcaac aggggcgagt gc                        642
```

<210> SEQ ID NO 123
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

```
Gly Phe Thr Phe Ser Asn Tyr Trp Ile Ser
1               5                   10
```

<210> SEQ ID NO 124
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

```
Arg Ile Lys Ser Lys Thr Tyr Gly Gly Thr Thr Asp Tyr Ala Glu Pro
1               5                   10                  15

Val Lys Gly
```

<210> SEQ ID NO 125
<211> LENGTH: 10
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 125

Thr Ser Arg Arg Ser Tyr Ala Phe Asp Tyr
1               5                   10

<210> SEQ ID NO 126
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Asn Tyr Trp Ile Ser
1               5

<210> SEQ ID NO 127
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Gly Phe Thr Phe Ser Asn Tyr
1               5

<210> SEQ ID NO 128
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Lys Ser Lys Thr Tyr Gly Gly Thr
1               5

<210> SEQ ID NO 129
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Gly Phe Thr Phe Ser Asn Tyr Trp
1               5

<210> SEQ ID NO 130
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130
```

```
Ile Lys Ser Lys Thr Tyr Gly Gly Thr Thr
1               5                   10
```

<210> SEQ ID NO 131
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

```
Ala Arg Thr Ser Arg Arg Ser Tyr Ala Phe Asp Tyr
1               5                   10
```

<210> SEQ ID NO 132
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
                20                  25                  30

Trp Ile Ser Trp Val Arg Gln Ala Pro Gly Lys Gly Leu Glu Trp Val
            35                  40                  45

Gly Arg Ile Lys Ser Lys Thr Tyr Gly Gly Thr Thr Asp Tyr Ala Glu
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Thr Ser Arg Arg Ser Tyr Ala Phe Asp Tyr Trp Gly
            100                 105                 110

Gln Gly Thr Leu Val Thr Val Ser Ser
        115                 120
```

<210> SEQ ID NO 133
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 133

```
gaagtgcagc tggtggaatc tggcggcgga cttgtgaaac tggcggctc tctgagactg      60 agctgtgccg cttccggctt caccttcagc aactactgga tcagctgggt ccgacaggcc    120
cctggcaaag gacttgagtg gtcggacgg atcaagagca agacctacgg cggcaccacc    180
gattatgccg agcctgtgaa gggcagattc accatcagcc gggacgacag caagaacacc    240
ctgtacctgc agatgaacag cctgaaaacc gaggacaccg ccgtgtacta ctgcgccaga    300
accagcagaa gaagctacgc cttcgactac tggggccagg gcacactggt taccgttagc    360
``` tct                                                                  363

<210> SEQ ID NO 134
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Gly Arg Ile Lys Ser Lys Thr Tyr Gly Gly Thr Thr Asp Tyr Ala Glu
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Thr Ser Arg Arg Ser Tyr Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Cys Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

```
Tyr Thr Leu Pro Pro Ser Arg Glu Glu Met Thr Lys Asn Gln Val Ser
        355                 360                 365
Leu Thr Cys Leu Val Lys Gly Phe Tyr Pro Cys Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys
    450

<210> SEQ ID NO 135
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 135
gaagtgcagc tggtggaatc tggcggcgga cttgtgaaac ctggcggctc tctgagactg        60
agctgtgccg cttccggctt caccttcagc aactactgga tcagctgggt ccgacaggcc       120
cctggcaaag acttgagtg gtcggacgg atcaagagca agacctacgg cggcaccacc         180
gattatgccg agcctgtgaa gggcagattc accatcagcc gggacgacag caagaacacc       240
ctgtacctgc agatgaacag cctgaaaacc gaggacaccg ccgtgtacta ctgcgccaga       300
accagcagaa gaagctacgc cttcgactac tggggccagg gcacactggt taccgttagc       360
tctgctagca ccaagggccc aagtgtgttt cccctggccc cagcagcaa gtctacttcc        420 ggcggaactg ctgccctggg ttgcctggtg aaggactact cccctgtcc cgtgacagtg        480 tcctggaact ctggggctct gacttccggc gtgcacacct tccccgccgt gctgcagagc       540
agcggcctgt acagcctgag cagcgtggtg acagtgccct ccagctctct gggaacccag       600
acctatatct gcaacgtgaa ccacaagccc agcaacacca aggtggacaa gagagtggag       660
cccaagagct gcgacaagac ccacacctgc ccccccctgcc cagctccaga actgctggga      720
gggccttccg tgttcctgtt ccccccaaag cccaaggaca cctgatgat cagcaggacc        780 cccgaggtga cctgcgtggt ggtggacgtg tcccacgagg acccagaggt gaagttcaac       840
tggtacgtgg acggcgtgga ggtgcacaac gccaagacca gcccagaga ggagcagtac       900 aacagcaccc tacagggtgg tgtccgtgctg accgtgctgc accaggactg gctgaacggc      960
aaagaataca agtgcaaagt ctccaacaag gccctgccag ccccaatcga aaagacaatc       1020
agcaaggcca agggccagcc acgggagccc caggtgtaca ccctgccccc cagccgggag       1080
gagatgacca gaaccaggt gtccctgacc tgtctggtga agggcttcta ccctgtgat        1140 atcgccgtgg agtgggagag caacggccag cccgagaaca actacaagac cacccccccca      1200 gtgctggaca gcgacggcag cttcttcctg tacagcaagc tgaccgtgga caagtccagg       1260
tggcagcagg gcaacgtgtt cagctgcagc gtgatgcacg aggccctgca caaccactac       1320
acccagaagt ccctgagcct gagccccggc aag                                   1353
```

```
<210> SEQ ID NO 136
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Arg Ala Ser Gln Ser Ile Ser Ser Trp Leu Ala
1               5                   10

<210> SEQ ID NO 137
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Asp Ala Ser Ser Leu Glu Ser
1               5

<210> SEQ ID NO 138
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Gln Gln Ile Thr Arg Tyr Pro Val Thr
1               5

<210> SEQ ID NO 139
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Ser Gln Ser Ile Ser Ser Trp
1               5

<210> SEQ ID NO 140
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Asp Ala Ser
1

<210> SEQ ID NO 141
<211> LENGTH: 6
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Ile Thr Arg Tyr Pro Val
1               5

<210> SEQ ID NO 142
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Gln Ser Ile Ser Ser Trp
1               5

<210> SEQ ID NO 143
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ile Thr Arg Tyr Pro Val
                85                  90                  95

Thr Phe Gly Gln Gly Thr Lys Val Glu Ile Lys
            100                 105

<210> SEQ ID NO 144
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 144
gacatccaga tgacacagag cccccagcaca ctgtctgcca gcgtgggaga cagagtgacc      60
atcacctgta gagccagcca gagcatctcc tcttggctgg cctggtatca gcagaagcct     120
ggcaaggccc ctaagctgct gatctacgat gccagcagcc tggaaagcgg cgtgccaagc     180 agatttctg gcagcggctc tggcaccgag ttcaccctga ccatatctag cctgcagcca     240
```
gaggacttcg ccacctacta ctgccagcag atcacaagat accccgtgac ctttggccag    300
ggcaccaagg tggaaatcaa g                                              321

<210> SEQ ID NO 145
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ile Thr Arg Tyr Pro Val
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 146
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 146
gacatccaga tgacacagag ccccagcaca ctgtctgcca gcgtgggaga cagagtgacc    60
atcacctgta gagccagcca gagcatctcc tcttggctgg cctggtatca gcagaagcct   120
ggcaaggccc ctaagctgct gatctacgat gccagcagcc tggaaagcgg cgtgccaagc   180
agattttctg gcagcggctc tggcaccgag ttcaccctga ccatatctag cctgcagcca   240

```
gaggacttcg ccacctacta ctgccagcag atcacaagat accccgtgac ctttggccag    300
ggcaccaagg tggaaatcaa gcgtacggtg gccgctccca gcgtgttcat cttccccccc    360
agcgacgagc agctgaagag tggcaccgcc agcgtggtgt gcctgctgaa caacttctac    420 ccccggggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga aagcataag gtgtacgcct gcgaggtgac ccaccagggc    600
ctgtccagcc ccgtgaccaa gagcttcaac agggcgagt gc                       642
```

<210> SEQ ID NO 147
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 147

Val Ser Gly Tyr Tyr Ser His Ser Gly Gly Phe Asp Val
1               5                   10

<210> SEQ ID NO 148
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 148

Ala Arg Val Ser Gly Tyr Tyr Ser His Ser Gly Gly Phe Asp Val
1               5                   10                  15

<210> SEQ ID NO 149
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 149

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Gly Arg Ile Lys Ser Lys Thr Tyr Gly Gly Thr Thr Asp Tyr Ala Glu
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Val Ser Gly Tyr Tyr Ser His Ser Gly Gly Phe Asp
            100                 105                 110

Val Trp Gly Gln Gly Thr Leu Val Thr Val Ser Ser
        115                 120

<210> SEQ ID NO 150
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 150

```
gaagtgcagc tggtggaatc tggcggcgga cttgtgaaac ctggcggctc tctgagactg      60
agctgtgccg cttccggctt caccttcagc aactactgga tcagctgggt ccgacaggcc     120
cctggcaaag gacttgagtg ggtcggacgg atcaagagca agacctacgg cggcaccacc     180
gattatgccg agcctgtgaa gggcagattc accatcagcc gggacgacag caagaacacc     240
ctgtacctgc agatgaacag cctgaaaacc gaggacaccg ccgtgtacta ctgcgccaga     300
gtgtctggct actactctca cagcggcggc tttgatgtgt ggggccaggg aacactggtc     360
accgttagtt ct                                                         372
```

<210> SEQ ID NO 151
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 151

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Gly Arg Ile Lys Ser Lys Thr Tyr Gly Gly Thr Thr Asp Tyr Ala Glu
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Val Ser Gly Tyr Tyr Ser His Ser Gly Gly Phe Asp
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Cys Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
```

```
                210                 215                 220
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Cys Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
        450

<210> SEQ ID NO 152
<211> LENGTH: 1362
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 152
gaagtgcagc tggtggaatc tggcggcgga cttgtgaaac tggcggctc tctgagactg      60 agctgtgccg cttccggctt caccttcagc aactactgga tcagctgggt ccgacaggcc    120
cctggcaaag acttgagtg ggtcggacgg atcaagagca agacctacgg cggcaccacc     180
gattatgccg agcctgtgaa gggcagattc accatcagcc gggacgacag caagaacacc    240
ctgtacctgc agatgaacag cctgaaaacc gaggacaccg ccgtgtacta ctgcgccaga    300
gtgtctggct actactctca cagcggcggc tttgatgtgt ggggccaggg aacactggtc    360
accgttagtt ctgctagcac caagggccca agtgtgtttc ccctggcccc cagcagcaag    420
tctacttccg gcggaactgc tgccctgggt gcctggtga aggactactt ccctgtccc     480 gtgacagtgt cctggaactc tggggctctg acttccggcg tgcacacctt ccccgccgtg    540
ctgcagagca gcggcctgta cagcctgagc agcgtggtga cagtgccctc cagctctctg    600
```

```
ggaacccaga cctatatctg caacgtgaac cacaagccca gcaacaccaa ggtggacaag    660
agagtggagc ccaagagctg cgacaagacc cacacctgcc cccctgccc agctccagaa     720 ctgctgggag ggccttccgt gttcctgttc cccccaagc caaggacac cctgatgatc     780 agcaggaccc ccgaggtgac ctgcgtggtg gtggacgtgt cccacgagga cccagaggtg    840
aagttcaact ggtacgtgga cggcgtggag gtgcacaacg ccaagaccaa gcccagagag    900
gagcagtaca acagcaccta cagggtggtg tccgtgctga ccgtgctgca ccaggactgg    960
ctgaacggca agaatacaa gtgcaaagtc tccaacaagg ccctgccagc cccaatcgaa    1020
aagacaatca gcaaggccaa gggccagcca cgggagcccc aggtgtacac cctgccccc     1080 agccgggagg agatgaccaa gaaccaggtg tccctgacct gtctggtgaa gggcttctac    1140
ccctgtgata tcgccgtgga gtgggagagc aacggccagc ccgagaacaa ctacaagacc    1200 accccccag tgctggacag cgacggcagc ttcttcctgt acagcaagct gaccgtggac     1260
aagtccaggt ggcagcaggg caacgtgttc agctgcagcg tgatgcacga ggccctgcac    1320
aaccactaca cccagaagtc cctgagcctg agccccggca ag                      1362

<210> SEQ ID NO 153
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Arg Ala Ser Gln Gly Ile Ser Asn Tyr Leu Ala
1               5                   10

<210> SEQ ID NO 154
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Ala Ala Ser Thr Leu Gln Ser
1               5

<210> SEQ ID NO 155
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Gln Lys Thr Trp Arg Thr Pro Gly Thr
1               5

<210> SEQ ID NO 156
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 156

Ser Gln Gly Ile Ser Asn Tyr
1               5

<210> SEQ ID NO 157
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Thr Trp Arg Thr Pro Gly
1               5

<210> SEQ ID NO 158
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Gln Gly Ile Ser Asn Tyr
1               5

<210> SEQ ID NO 159
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Thr Trp Arg Thr Pro Gly
                85                  90                  95

Thr Phe Gly Gln Gly Thr Lys Val Glu Ile Lys
            100                 105

<210> SEQ ID NO 160
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 160

```
gacatccaga tgacacagag ccctagcagc ctgtctgcca gcgtgggaga cagagtgacc      60
atcacctgta gagccagcca gggcatcagc aactacctgg cctggtatca gcagaaaccc     120
ggcaaggtgc ccaagctgct gatctacgct gccagcacac tgcagagcgg agtgcctagc     180
agatttctg gcagcggctc cggcaccgat ttcaccctga ccatatctag cctgcagcca     240
gaggacgtgg ccacctacta ctgtcagaaa acctggcgga cccctggcac atttggccag     300
ggaacaaagg tggaaatcaa g                                               321
```

<210> SEQ ID NO 161
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 161

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Thr Trp Arg Thr Pro Gly
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 162
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

-continued

<400> SEQUENCE: 162

```
gacatccaga tgacacagag ccctagcagc ctgtctgcca gcgtgggaga cagagtgacc    60
atcacctgta gagccagcca gggcatcagc aactacctgg cctggtatca gcagaaaccc   120
ggcaaggtgc ccaagctgct gatctacgct gccagcacac tgcagagcgg agtgcctagc   180
agattttctg gcagcggctc cggcaccgat ttcaccctga ccatatctag cctgcagcca   240
gaggacgtgg ccacctacta ctgtcagaaa acctggcgga cccctggcac atttggccag   300
ggaacaaagg tggaaatcaa gcgtacggtg gccgctccca gcgtgttcat cttccccccc   360
agcgacgagc agctgaagag tggcaccgcc agcgtggtgt gcctgctgaa caacttctac   420
ccccgggagg ccaaggtgca gtggaaggtg acaacgccc tgcagagcgg caacagccag    480
gagagcgtca ccgagcagga cagcaaggac tccacctaca gcctgagcag caccctgacc   540
ctgagcaagg ccgactacga aagcataag gtgtacgcct gcgaggtgac ccaccagggc    600
ctgtccagcc ccgtgaccaa gagcttcaac aggggcgagt gc                      642
```

<210> SEQ ID NO 163
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

```
Ser Arg Leu Ile Ala Pro Trp Leu Asp Tyr
1               5                   10
```

<210> SEQ ID NO 164
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

```
Ala Arg Ser Arg Leu Ile Ala Pro Trp Leu Asp Tyr
1               5                   10
```

<210> SEQ ID NO 165
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Arg Ser Arg Leu Ile Ala Pro Trp Leu Asp Tyr Trp Gly Gln Gly
                100                 105                 110

Thr Leu Val Thr Val Ser Ser
        115
```

```
<210> SEQ ID NO 166
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 166
```

```
gaagttcagc tgctggaatc tggcggagga ctggttcaac ctggcggctc tctgagactg      60
tcttgtgccg ccagcggctt cacctttagc agctacgcca tgagctgggt ccgacaggct     120
cctggcaaag ccttgaatg ggtgtccgcc atctctggct ctggcggcag cacatattac     180
gccgactctg tgaagggcag attcaccatc agccgggaca acagcaagaa caccctgtac     240
ctgcagatga acagcctgag agccgaggac accgccgtgt actactgtgc cagaagcaga     300
ctgatcgccc cttggctgga ttattgggc cagggcacac tggtcaccgt gtcatct         357
```

```
<210> SEQ ID NO 167
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Ser Arg Leu Ile Ala Pro Trp Leu Asp Tyr Trp Gly Gln Gly
                100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Cys Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
        355                 360                 365

Cys Leu Val Lys Gly Phe Tyr Pro Cys Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 168
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 168
gaagttcagc tgctggaatc tggcggagga ctggttcaac tggcggctc tctgagactg      60 tcttgtgccg ccagcggctt cacctttagc agctacgcca tgagctgggt ccgacaggct    120
cctggcaaag gccttgaatg ggtgtccgcc atctctggct ctggcggcag cacatattac    180
gccgactctg tgaagggcag attcaccatc agccgggaca cagcaagaa caccctgtac    240 ctgcagatga acagcctgag agccgaggac accgccgtgt actactgtgc cagaagcaga    300
ctgatcgccc ttggctgga ttattggggc cagggcacac tggtcaccgt gtcatctgct    360
agcaccaagg gcccaagtgt gtttcccctg gccccagca gcaagtctac ttccggcgga    420

```
actgctgccc tgggttgcct ggtgaaggac tacttcccct gtcccgtgac agtgtcctgg    480
aactctgggg ctctgacttc cggcgtgcac accttccccg ccgtgctgca gagcagcggc    540
ctgtacagcc tgagcagcgt ggtgacagtg ccctccagct ctctgggaac ccagacctat    600
atctgcaacg tgaaccacaa gcccagcaac accaaggtgg acaagagagt ggagcccaag    660
agctgcgaca agacccacac ctgccccccc tgcccagctc cagaactgct gggagggcct    720
tccgtgttcc tgttcccccc caagcccaag gacaccctga tgatcagcag gacccccgag    780
gtgacctgcg tggtggtgga cgtgtcccac gaggacccag aggtgaagtt caactggtac    840
gtggacggcg tggaggtgca caacgccaag accaagccca gagaggagca gtacaacagc    900
acctacaggg tggtgtccgt gctgaccgtg ctgcaccagg actggctgaa cggcaaagaa    960
tacaagtgca aagtctccaa caaggccctg ccagccccaa tcgaaaagac aatcagcaag   1020
gccaagggcc agccacggga gccccaggtg tacaccctgc cccccagccg ggaggagatg   1080
accaagaacc aggtgtccct gacctgtctg gtgaagggct tctacccctg tgatatcgcc   1140
gtggagtggg agagcaacgg ccagcccgag aacaactaca agaccacccc cccagtgctg   1200
gacagcgacg gcagcttctt cctgtacagc aagctgaccg tggacaagtc caggtggcag   1260
cagggcaacg tgttcagctg cagcgtgatg cacgaggccc tgcacaacca ctacacccag   1320
aagtccctga gcctgagccc cggcaag                                       1347
```

```
<210> SEQ ID NO 169
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Gln Gln Val Tyr Gly Ser Pro Pro Thr
1               5

<210> SEQ ID NO 170
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Val Tyr Gly Ser Pro Pro
1               5

<210> SEQ ID NO 171
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
```

```
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Gly Ser Pro Pro
                85                  90                  95

Thr Phe Gly Gln Gly Thr Lys Val Glu Ile Lys
            100                 105
```

<210> SEQ ID NO 172
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 172

```
gacatccaga tgacacagag ccctagcagc ctgtctgcca gcgtgggaga cagagtgacc    60
atcacctgta gagccagcca gagcatcagc agctacctga actggtatca gcagaagccc   120
ggcaaggccc ctaaactgct gatctatgcc gccagctctc tgcagtctgg cgtgccaagc   180
agattttctg gcagcggctc tggcaccgac ttcaccctga ccatatctag cctgcagcca   240
gaggacttcg ccacctacta ctgccagcag gtctacggca gccctcctac atttggccag   300
ggcaccaagg tggaaatcaa g                                             321
```

<210> SEQ ID NO 173
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 173

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Gly Ser Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 174
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 174
gacatccaga tgacacagag ccctagcagc ctgtctgcca gcgtgggaga cagagtgacc    60
atcacctgta gagccagcca gagcatcagc agctacctga actggtatca gcagaagccc   120
ggcaaggccc ctaaactgct gatctatgcc gccagctctc tgcagtctgg cgtgccaagc   180
agattttctg gcagcggctc tggcaccgac ttcaccctga ccatatctag cctgcagcca   240
gaggacttcg ccacctacta ctgccagcag gtctacggca ccctcctac atttggccag   300 ggcaccaagg tggaaatcaa gcgtacggtg gccgctccca gcgtgttcat cttccccccc   360
agcgacgagc agctgaagag tggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag caccctgacc   540
ctgagcaagg ccgactacga aagcataag gtgtacgcct gcgaggtgac ccaccaggc    600 ctgtccagcc ccgtgaccaa gagcttcaac agggcgagt gc                      642

<210> SEQ ID NO 175
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 175

Gly Tyr Ser Phe Thr Ser Tyr Trp Ile Gly
1               5                   10

<210> SEQ ID NO 176
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 176

Ile Ile Tyr Pro Gly Asp Ser Asp Thr Arg Tyr Ser Pro Ser Phe Gln
1               5                   10                  15

Gly

<210> SEQ ID NO 177
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Gly Ser Ser Ala Ala Ser Gly Leu Ser Gly Asp Leu
1               5                   10

<210> SEQ ID NO 178
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Ser Tyr Trp Ile Gly
1               5

<210> SEQ ID NO 179
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Gly Tyr Ser Phe Thr Ser Tyr
1               5

<210> SEQ ID NO 180
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Tyr Pro Gly Asp Ser Asp
1               5

<210> SEQ ID NO 181
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Gly Tyr Ser Phe Thr Ser Tyr Trp
1               5

<210> SEQ ID NO 182
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 182

Ile Tyr Pro Gly Asp Ser Asp Thr
1               5

<210> SEQ ID NO 183
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 183

Ala Arg Gly Ser Ser Ala Ala Ser Gly Leu Ser Gly Asp Leu
1               5                   10

<210> SEQ ID NO 184
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 184

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ser Ser Ala Ala Ser Gly Leu Ser Gly Asp Leu Trp Gly
            100                 105                 110

Gln Gly Thr Leu Val Thr Val Ser Ser
        115                 120

<210> SEQ ID NO 185
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 185
gaagttcagc tggtgcagtc tggcgccgaa gtgaagaagc ctggcgagag cctgaagatc      60

```
tcctgcaaag gcagcggcta cagcttcacc agctactgga tcggctgggt ccgacagatg    120
cctggcaaag gccttgagtg gatgggcatc atctacccccg gcgacagcga caccagatac    180
agccctagct ttcagggcca agtgaccatc agcgccgaca gagcatcag cacagcctac     240 ctgcagtggt ccagcctgaa ggcctctgac accgccatgt actactgtgc cagaggaagc    300
tctgccgcct ctggactgtc tggcgatctt tggggacagg gcacactggt cacagtgtct    360
agt                                                                  363
```

```
<210> SEQ ID NO 186
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 186
```

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ser Ser Ala Ala Ser Gly Leu Ser Gly Asp Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Cys Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
                  290                 295                 300

Arg Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Cys Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 187
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 187
gaagttcagc tggtgcagtc tggcgccgaa gtgaagaagc tggcgagag cctgaagatc        60 tcctgcaaag gcagcggcta cagcttcacc agctactgga tcggctgggt ccgacagatg      120
cctggcaaag gccttgagtg gatgggcatc atctaccccg cgacagcga caccagatac       180 agccctagct ttcagggcca agtgaccatc agcgccgaca gagcatcag cacagcctac       240 ctgcagtggt ccagcctgaa ggcctctgac accgccatgt actactgtgc agaggaagc       300 tctgccgcct ctggactgtc tggcgatctt tggggacagg gcacactggt cacagtgtct      360
agtgctagca ccaagggccc aagtgtgttt cccctggccc ccagcagcaa gtctacttcc      420
ggcggaactg ctgccctggg ttgcctggtg aaggactact cccctgtcc cgtgacagtg       480 tcctggaact ctggggctct gacttccggc gtgcacacct ccccgccgt gctgcagagc       540 agcggcctgt acagcctgag cagcgtggtg acagtgccct ccagctctct gggaacccag      600
acctatatct gcaacgtgaa ccacaagccc agcaacacca aggtggacaa gagagtggag      660
cccaagagct gcgacaagac ccacacctgc ccccctgcc cagctccaga actgctggga       720
gggccttccg tgttcctgtt ccccccaag cccaaggaca cctgatgat cagcaggacc        780 cccgaggtga cctgcgtggt ggtggacgtg tcccacgagg acccagaggt gaagttcaac      840
tggtacgtgg acggcgtgga ggtgcacaac gccaagacca gcccagaga ggagcagtac       900 aacagcacct acagggtggt gtccgtgctg accgtgctgc accaggactg gctgaacggc      960
aaagaataca agtgcaaagt ctccaacaag gccctgccag ccccaatcga aaagacaatc    1020
agcaaggcca agggccagcc acgggagccc caggtgtaca ccctgccccc cagccgggag    1080
```

```
gagatgacca agaaccaggt gtccctgacc tgtctggtga agggcttcta cccctgtgat   1140
atcgccgtgg agtgggagag caacggccag cccgagaaca actacaagac cacccccca    1200 gtgctggaca gcgacggcag cttcttcctg tacagcaagc tgaccgtgga caagtccagg   1260
tggcagcagg gcaacgtgtt cagctgcagc gtgatgcacg aggccctgca caaccactac   1320
acccagaagt ccctgagcct gagccccggc aag                                1353
```

<210> SEQ ID NO 188
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 188

Gln Gln Asp Tyr Tyr Ser Pro Phe Thr
1               5

<210> SEQ ID NO 189
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 189

Asp Tyr Tyr Ser Pro Phe
1               5

<210> SEQ ID NO 190
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Tyr Ser Pro Phe
                85                  90                  95

Thr Phe Gly Gln Gly Thr Lys Val Glu Ile Lys
            100                 105

<210> SEQ ID NO 191
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 191

```
gacatccaga tgacacagag ccctagcagc ctgtctgcca gcgtgggaga cagagtgacc    60
atcacctgta gagccagcca gagcatcagc agctacctga actggtatca gcagaagccc   120
ggcaaggccc ctaaactgct gatctatgcc gccagctctc tgcagtctgg cgtgccaagc   180
agatttctg gcagcggctc tggcaccgac ttcaccctga ccatatctag cctgcagcca   240
gaggacttcg ccacctacta ctgccagcag gactactaca gccccttcac ctttggccag   300
ggcaccaagg tggaaatcaa g                                              321
```

<210> SEQ ID NO 192
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 192

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Tyr Ser Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 193
<211> LENGTH: 642
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 193

```
gacatccaga tgacacagag ccctagcagc ctgtctgcca gcgtgggaga cagagtgacc      60
atcacctgta gagccagcca gagcatcagc agctacctga actggtatca gcagaagccc     120
ggcaaggccc ctaaactgct gatctatgcc gccagctctc tgcagtctgg cgtgccaagc     180
agattttctg gcagcggctc tggcaccgac ttcaccctga ccatatctag cctgcagcca     240
gaggacttcg ccacctacta ctgccagcag gactactaca gccccttcac ctttggccag     300
ggcaccaagg tggaaatcaa gcgtacggtg gccgctccca gcgtgttcat cttcccccc     360
agcgacgagc agctgaagag tggcaccgcc agcgtggtgt gcctgctgaa caacttctac     420
ccccgggagg ccaaggtgca gtggaaggtg acaacgccc tgcagagcgg caacagccag     480
gagagcgtca ccgagcagga cagcaaggac tccacctaca gcctgagcag caccctgacc     540
ctgagcaagg ccgactacga aagcataag gtgtacgcct gcgaggtgac caccagggc      600
ctgtccagcc ccgtgaccaa gagcttcaac aggggcgagt gc                        642
```

<210> SEQ ID NO 194
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Ala Tyr Lys Leu Ser Trp Leu Asp Leu
1               5

<210> SEQ ID NO 195
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Ala Arg Ala Tyr Lys Leu Ser Trp Leu Asp Leu
1               5                   10

<210> SEQ ID NO 196
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 196

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Tyr Lys Leu Ser Trp Leu Asp Leu Trp Gly Gln Gly Thr
            100                 105                 110

Leu Val Thr Val Ser Ser
            115
```

<210> SEQ ID NO 197
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 197

```
gaagttcagc tgctggaatc tggcggagga ctggttcaac ctggcggctc tctgagactg      60
tcttgtgccg ccagcggctt cacctttagc agctacgcca tgagctgggt ccgacaggct     120
cctggcaaag ccttgaatg ggtgtccgcc atctctggct ctggcggcag cacatattac     180
gccgactctg tgaagggcag attcaccatc agccgggaca acagcaagaa caccctgtac     240
ctgcagatga acagcctgag agccgaggac accgccgtgt actattgtgc cagagcctac     300
aagctgagct ggctggatct ttggggccag ggcacactgg tcacagtgtc atct           354
```

<210> SEQ ID NO 198
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 198

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Tyr Lys Leu Ser Trp Leu Asp Leu Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Cys Pro Val Thr Val Ser Trp Asn
```

```
                145                 150                 155                 160
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Cys Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 199
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 199
gaagttcagc tgctggaatc tggcggagga ctggttcaac ctggcggctc tctgagactg      60
tcttgtgccg ccagcggctt cacctttagc agctacgcca tgagctgggt ccgacaggct     120
cctggcaaag gccttgaatg gtgtccgcc atctctggct ctggcggcag cacatattac      180
gccgactctg tgaagggcag attcaccatc agccgggaca acagcaagaa caccctgtac     240
ctgcagatga acagcctgag agccgaggac accgccgtgt actattgtgc cagagcctac     300
aagctgagct ggctggatct ttggggccag ggcacactgg tcacagtgtc atctgctagc     360
```

```
accaagggcc caagtgtgtt tcccctggcc cccagcagca agtctacttc cggcggaact    420
gctgccctgg gttgcctggt gaaggactac ttccctgtc ccgtgacagt gtcctggaac    480
tctgggctc tgacttccgg cgtgcacacc ttccccgccg tgctgcagag cagcggcctg    540
tacagcctga gcagcgtggt gacagtgccc tccagctctc tgggaaccca gacctatatc    600
tgcaacgtga accacaagcc cagcaacacc aaggtggaca agagagtgga gcccaagagc    660
tgcgacaaga cccacacctg cccccccgc ccagctccag aactgctggg agggccttcc    720
gtgttcctgt tcccccccaa gcccaaggac accctgatga tcagcaggac cccgaggtg    780
acctgcgtga tggtggacgt gtcccacgag gacccagagg tgaagttcaa ctggtacgtg    840
gacggcgtgg aggtgcacaa cgccaagacc aagcccagag aggagcagta caacagcacc    900
tacagggtgg tgtccgtgct gaccgtgctg caccaggact ggctgaacgg caaagaatac    960
aagtgcaaag tctccaacaa ggccctgcca gccccaatcg aaaagacaat cagcaaggcc   1020
aagggccagc cacgggagcc ccaggtgtac accctgcccc ccagccggga ggagatgacc   1080
aagaaccagg tgtccctgac ctgtctggtg aagggcttct accctgtga tatcgccgtg   1140
gagtgggaga gcaacggcca gcccgagaac aactacaaga ccaccccccc agtgctggac   1200
agcgacggca gcttcttcct gtacagcaag ctgaccgtgg acaagtccag gtggcagcag   1260
ggcaacgtgt tcagctgcag cgtgatgcac gaggccctgc acaaccacta cacccagaag   1320
tccctgagcc tgagccccgg caag                                         1344
```

<210> SEQ ID NO 200
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 200

Gln Gln Val Trp Tyr Ala Pro Val Thr
1               5

<210> SEQ ID NO 201
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 201

Val Trp Tyr Ala Pro Val
1               5

<210> SEQ ID NO 202
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 202

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Trp Tyr Ala Pro Val
                85                  90                  95

Thr Phe Gly Gln Gly Thr Lys Val Glu Ile Lys
            100                 105
```

<210> SEQ ID NO 203
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 203

```
gacatccaga tgacacagag ccctagcagc ctgtctgcca gcgtgggaga cagagtgacc    60
atcacctgta gagccagcca gagcatcagc agctacctga actggtatca gcagaagccc   120
ggcaaggccc ctaaactgct gatctatgcc gccagctctc tgcagtctgg cgtgccaagc   180
agatttctg gcagcggctc tggcaccgac ttcaccctga ccatatctag cctgcagcca   240
gaggacttcg ccacctacta ctgccagcaa gtttggtacg cccctgtgac ctttggccag   300
ggcaccaagg tggaaatcaa g                                              321
```

<210> SEQ ID NO 204
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 204

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Trp Tyr Ala Pro Val
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 205
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 205
gacatccaga tgacacagag ccctagcagc ctgtctgcca gcgtgggaga cagagtgacc      60
atcacctgta gagccagcca gagcatcagc agctacctga actggtatca gcagaagccc     120
ggcaaggccc ctaaactgct gatctatgcc gccagctctc tgcagtctgg cgtgccaagc     180 agatttctg gcagcggctc tggcaccgac ttcaccctga ccatatctag cctgcagcca     240
gaggacttcg ccacctacta ctgccagcaa gtttggtacg cccctgtgac ctttggccag     300
ggcaccaagg tggaaatcaa gcgtacggtg gccgctccca gcgtgttcat cttccccccc     360
agcgacgagc agctgaagag tggcaccgcc agcgtggtgt gcctgctgaa caacttctac     420
ccccgggagg ccaaggtgca gtggaaggtg acaacgccc tgcagagcgg caacagccag     480
gagagcgtca ccgagcagga cagcaaggac tccacctaca gcctgagcag caccctgacc     540
ctgagcaagg ccgactacga aagcataag gtgtacgcct gcgaggtgac ccaccagggc     600
ctgtccagcc ccgtgaccaa gagcttcaac aggggcgagt gc                        642

<210> SEQ ID NO 206
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Gly Phe Thr Phe Ser Asn Ala Trp Met Ser
1               5                   10

<210> SEQ ID NO 207
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

```
Arg Ile Lys Ser Lys Thr Asp Ala Gly Thr Thr Asp Tyr Ala Ala Pro
1               5                   10                  15
Val Lys Gly

<210> SEQ ID NO 208
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Thr Ile Tyr Pro Ser Ala Pro Ser Ser Ser Leu Asp Tyr
1               5                   10

<210> SEQ ID NO 209
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Asn Ala Trp Met Ser
1               5

<210> SEQ ID NO 210
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Gly Phe Thr Phe Ser Asn Ala
1               5

<210> SEQ ID NO 211
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Lys Ser Lys Thr Asp Ala Gly Thr
1               5

<210> SEQ ID NO 212
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 212

Gly Phe Thr Phe Ser Asn Ala Trp
1               5
```

```
<210> SEQ ID NO 213
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Ile Lys Ser Lys Thr Asp Ala Gly Thr Thr
1               5                   10

<210> SEQ ID NO 214
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Ala Arg Thr Ile Tyr Pro Ser Ala Pro Ser Ser Ser Leu Asp Tyr
1               5                   10                  15

<210> SEQ ID NO 215
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 215

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Ala Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Thr Ile Tyr Pro Ser Ala Pro Ser Ser Ser Leu Asp
            100                 105                 110

Tyr Trp Gly Gln Gly Thr Leu Val Thr Val Ser Ser
        115                 120

<210> SEQ ID NO 216
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 216
```

-continued

```
gaagtgcagc tggtggaatc tggcggcgga cttgtgaaac ctggcggctc tctgagactg    60
agctgtgccg cttccggctt caccttcagc aatgcctgga tgagctgggt ccgacaggcc   120
cctggaaaag gccttgagtg ggtcggacgg atcaagagca agaccgatgc cggcaccacc   180
gattatgctg cccctgtgaa gggcagattc accatcagca gggacgacag caagaacacc   240
ctgtacctgc agatgaacag cctgaaaacc gaggacaccg ccgtgtacta ctgcgccaga   300
acaatctacc ccagcgctcc tagcagcagc ctggattatt ggggccaggg cacactggtc   360
accgtgtcat ct                                                      372
```

```
<210> SEQ ID NO 217
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 217
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Ala Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Thr Ile Tyr Pro Ser Ala Pro Ser Ser Ser Leu Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Cys Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

```
Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Cys Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 218
<211> LENGTH: 1362
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 218
gaagtgcagc tggtggaatc tggcggcgga cttgtgaaac ctggcggctc tctgagactg     60
agctgtgccg cttccggctt caccttcagc aatgcctgga tgagctgggt ccgacaggcc    120
cctggaaaag gccttgagtg ggtcggacgg atcaagagca agaccgatgc cggcaccacc    180
gattatgctg cccctgtgaa gggcagattc accatcagca gggacgacag caagaacacc    240
ctgtacctgc agatgaacag cctgaaaacc gaggacaccg ccgtgtacta ctgcgccaga    300
acaatctacc ccagcgctcc tagcagcagc tggattattg ggggccaggg cacactggtc    360
accgtgtcat ctgctagcac caagggccca agtgtgtttc ccctggcccc cagcagcaag    420
tctacttccg gcggaactgc tgccctgggt tgcctggtga aggactactt ccctgtgccc    480
gtgacagtgt cctggaactc tggggctctg acttccggcg tgcacacctt ccccgccgtg    540
ctgcagagca cggcctgtaa cagcctgagc agcgtggtga cagtgccctc cagctctctg    600
ggaacccaga cctatatctg caacgtgaac cacaagccca gcaacaccaa ggtggacaag    660
agagtggagc ccaagagctg cgacaagacc cacacctgcc ccccctgccc agctccagaa    720
ctgctgggag gccttccgt gttcctgttc ccccccaagc ccaaggacac cctgatgatc    780
agcaggaccc ccgaggtgac ctgcgtggtg gtggacgtgt cccacgagga cccagaggtg    840
aagttcaact ggtacgtgga cggcgtggag gtgcacaacg ccaagaccaa gccagagag    900 gagcagtaca acagcaccta cagggtggtg tccgtgctga ccgtgctgca ccaggactgg    960
ctgaacggca agaatacaa gtgcaaagtc tccaacaagg ccctgccagc cccaatcgaa    1020
```

-continued

```
aagacaatca gcaaggccaa gggccagcca cgggagcccc aggtgtacac cctgcccccc      1080
agccgggagg agatgaccaa gaaccaggtg tccctgacct gtctggtgaa gggcttctac      1140
ccctgtgata tcgccgtgga gtgggagagc aacggccagc ccgagaacaa ctacaagacc      1200 accccccag tgctggacag cgacggcagc ttcttcctgt acagcaagct gaccgtggac       1260
aagtccaggt ggcagcaggg caacgtgttc agctgcagcg tgatgcacga ggccctgcac      1320
aaccactaca cccagaagtc cctgagcctg agccccggca ag                         1362

<210> SEQ ID NO 219
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Gln Gln Leu Ile Phe Phe Pro Leu Thr
1               5

<210> SEQ ID NO 220
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Leu Ile Phe Phe Pro Leu
1               5

<210> SEQ ID NO 221
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 221

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Leu Ile Phe Phe Pro Leu
                85                  90                  95

Thr Phe Gly Gln Gly Thr Lys Val Glu Ile Lys
            100                 105

<210> SEQ ID NO 222
<211> LENGTH: 321
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 222
gacatccaga tgacacagag ccctagcagc ctgtctgcca gcgtgggaga cagagtgacc    60
atcacctgta gagccagcca gggcatcagc aactacctgg cctggtatca gcagaaaccc   120
ggcaaggtgc ccaagctgct gatctacgct gccagcacac tgcagagcgg agtgcctagc   180 agatttctg gcagcggctc cggcaccgat tcaccctga ccatatctag cctgcagcca     240
gaggacgtgg ccacctacta ttgccagcag ctgatcttct tccctctgac ctttggccag   300
ggcaccaagg tggaaatcaa g                                             321

<210> SEQ ID NO 223
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 223

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Leu Ile Phe Phe Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 224
<211> LENGTH: 642
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 224

```
gacatccaga tgacacagag ccctagcagc ctgtctgcca gcgtgggaga cagagtgacc      60
atcacctgta gagccagcca gggcatcagc aactacctgg cctggtatca gcagaaaccc     120
ggcaaggtgc ccaagctgct gatctacgct gccagcacac tgcagagcgg agtgcctagc     180
agattttctg gcagcggctc cggcaccgat tcacccctga ccatatctag cctgcagcca     240
gaggacgtgg ccacctacta ttgccagcag ctgatcttct ccctctctgac ctttggccag     300
ggcaccaagg tggaaatcaa gcgtacggtg gccgctccca gcgtgttcat cttcccccc       360
agcgacgagc agctgaagag tggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag cacccctgacc    540
ctgagcaagg ccgactacga gaagcataag gtgtacgcct gcgaggtgac ccaccagggc     600
ctgtccagcc ccgtgaccaa gagcttcaac aggggcgagt gc                        642
```

<210> SEQ ID NO 225
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Ala Ser His Arg Leu His Ser Leu Phe Asp Val
1               5                   10

<210> SEQ ID NO 226
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Ala Arg Ala Ser His Arg Leu His Ser Leu Phe Asp Val
1               5                   10

<210> SEQ ID NO 227
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 227

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val 35                  40                  45
Gly Arg Ile Lys Ser Lys Thr Asp Ala Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Ser His Arg Leu His Ser Leu Phe Asp Val Trp
            100                 105                 110

Gly Gln Gly Thr Leu Val Thr Val Ser Ser
        115                 120

<210> SEQ ID NO 228
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 228
gaagtgcagc tggtggaatc tggcggcgga cttgtgaaac tggcggctc tctgagactg      60 agctgtgccg cttccggctt caccttcagc aatgcctgga tgagctgggt ccgacaggcc    120
cctggaaaag gccttgagtg gtcggacgg atcaagagca gaccgatgc cggcaccacc      180 gattatgctg cccctgtgaa gggcagattc accatcagca gggacgacag caagaacacc    240
ctgtacctgc agatgaacag cctgaaaacc gaggacaccg ccgtgtacta ctgtgccaga    300
gcctctcaca gactgcacag cctgtttgac gtgtggggcc agggaacact ggtcaccgtt    360
agttct                                                                366

<210> SEQ ID NO 229
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 229

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Ala Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Ser His Arg Leu His Ser Leu Phe Asp Val Trp
            100                 105                 110

Gly Gln Gly Thr Leu Val Thr Val Ser Ser Ala Ser Thr Lys Gly Pro
        115                 120                 125

```
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Cys Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Arg Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Cys Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 230
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 230
gaagtgcagc tggtggaatc tggcggcgga cttgtgaaac tggcggctc tctgagactg      60 agctgtgccg cttccggctt caccttcagc aatgcctgga tgagctgggt ccgacaggcc    120
```

-continued

```
cctggaaaag gccttgagtg ggtcggacgg atcaagagca agaccgatgc cggcaccacc    180
gattatgctg cccctgtgaa gggcagattc accatcagca gggacgacag caagaacacc    240
ctgtacctgc agatgaacag cctgaaaacc gaggacaccg ccgtgtacta ctgtgccaga    300
gcctctcaca gactgcacag cctgtttgac gtgtggggcc agggaacact ggtcaccgtt    360
agttctgcta gcaccaaggg cccaagtgtg tttcccctgg cccccagcag caagtctact    420
tccggcggaa ctgctgccct gggttgcctg gtgaaggact acttccctg tcccgtgaca    480 gtgtcctgga actctggggc tctgacttcc ggcgtgcaca ccttccccgc cgtgctgcag    540
agcagcggcc tgtacagcct gagcagcgtg gtgacagtgc cctccagctc tctgggaacc    600
cagacctata tctgcaacgt gaaccacaag cccagcaaca ccaaggtgga caagagagtg    660
gagcccaaga gctgcgacaa gacccacacc tgcccccct gcccagctcc agaactgctg    720
ggagggcctt ccgtgttcct gttccccccc aagcccaagg acaccctgat gatcagcagg    780 accccgagg tgacctgcgt ggtggtggac gtgtcccacg aggacccaga ggtgaagttc    840
aactggtacg tggacggcgt ggaggtgcac aacgccaaga ccaagcccag agaggagcag    900
tacaacagca cctacagggt ggtgtccgtg ctgaccgtgc tgcaccagga ctggctgaac    960
ggcaaagaat acaagtgcaa agtctccaac aaggccctgc cagcccccaat cgaaaagaca   1020 atcagcaagg ccaagggcca gccacgggag ccccaggtgt acaccctgcc ccccagccgg   1080
gaggagatga ccaagaacca ggtgtccctg acctgtctgg tgaagggctt ctaccccctgt   1140 gatatcgccg tggagtggga gagcaacggc cagcccgaga caactacaa gaccacccccc   1200 ccagtgctgg acagcgacgg cagcttcttc ctgtacagca gctgaccgt ggacaagtcc    1260 aggtggcagc agggcaacgt gttcagctgc agcgtgatgc acgaggccct gcacaaccac   1320
tacacccaga agtccctgag cctgagcccc ggcaag                             1356
```

<210> SEQ ID NO 231
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Gln Gln Gly Leu Phe Tyr Pro His Thr
1               5

<210> SEQ ID NO 232
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Gly Leu Phe Tyr Pro His
1               5

<210> SEQ ID NO 233
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 233

| Asp | Ile | Gln | Met | Thr | Gln | Ser | Pro | Ser | Thr | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Ser | Ile | Ser | Ser | Trp |
|---|---|---|---|---|---|---|---|---|---|---|---|---|---|---|---|
| | | | 20 | | | | | 25 | | | | | 30 | | |

| Leu | Ala | Trp | Tyr | Gln | Gln | Lys | Pro | Gly | Lys | Ala | Pro | Lys | Leu | Leu | Ile |
|---|---|---|---|---|---|---|---|---|---|---|---|---|---|---|---|
| | | | 35 | | | | | 40 | | | | | 45 | | |

| Tyr | Asp | Ala | Ser | Ser | Leu | Glu | Ser | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | Glu | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Glu | Asp | Phe | Ala | Thr | Tyr | Tyr | Cys | Gln | Gln | Gly | Leu | Phe | Tyr | Pro | His |
|---|---|---|---|---|---|---|---|---|---|---|---|---|---|---|---|
| | | | | 85 | | | | | 90 | | | | | 95 | |

| Thr | Phe | Gly | Gln | Gly | Thr | Lys | Val | Glu | Ile | Lys |
|---|---|---|---|---|---|---|---|---|---|---|
| | | | 100 | | | | | 105 | | |

<210> SEQ ID NO 234
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 234

```
gacatccaga tgacacagag ccccagcaca ctgtctgcca gcgtgggaga cagagtgacc      60
atcacctgta gagccagcca gagcatctcc tcttggctgg cctggtatca gcagaagcct     120
ggcaaggccc ctaagctgct gatctacgat gccagcagcc tggaaagcgg cgtgccaagc     180
agatttctg gcagcggctc tggcaccgag ttcaccctga ccatatctag cctgcagcca     240
gaggacttcg ccacctacta ttgtcagcag ggcctgttct accctcacac ctttggccag     300
ggcaccaagg tggaaatcaa g                                               321
```

<210> SEQ ID NO 235
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 235

| Asp | Ile | Gln | Met | Thr | Gln | Ser | Pro | Ser | Thr | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Ser | Ile | Ser | Ser | Trp |
|---|---|---|---|---|---|---|---|---|---|---|---|---|---|---|---|
| | | | 20 | | | | | 25 | | | | | 30 | | |

| Leu | Ala | Trp | Tyr | Gln | Gln | Lys | Pro | Gly | Lys | Ala | Pro | Lys | Leu | Leu | Ile |
|---|---|---|---|---|---|---|---|---|---|---|---|---|---|---|---|
| | | | 35 | | | | | 40 | | | | | 45 | | |

| Tyr | Asp | Ala | Ser | Ser | Leu | Glu | Ser | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | Glu | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Glu | Asp | Phe | Ala | Thr | Tyr | Tyr | Cys | Gln | Gln | Gly | Leu | Phe | Tyr | Pro | His |
|---|---|---|---|---|---|---|---|---|---|---|---|---|---|---|---|
| | | | | 85 | | | | | 90 | | | | | 95 | |

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 236
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 236

```
gacatccaga tgacacagag ccccagcaca ctgtctgcca gcgtgggaga cagagtgacc      60
atcacctgta gagccagcca gagcatctcc tcttggctgg cctggtatca gcagaagcct     120
ggcaaggccc ctaagctgct gatctacgat gccagcagcc tggaaagcgg cgtgccaagc     180
agatttctg gcagcggctc tggcaccgag ttcaccctga ccatatctag cctgcagcca     240
gaggacttcg ccacctacta ttgtcagcag ggcctgttct accctcacac ctttggccag     300
ggcaccaagg tggaaatcaa gctacggtg gccgctccca gcgtgttcat cttccccccc     360
agcgacgagc agctgaagag tggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag caccctgacc     540
ctgagcaagg ccgactacga gaagcataag gtgtacgcct gcgaggtgac ccaccagggc     600
ctgtccagcc ccgtgaccaa gagcttcaac agggcgagt gc                        642
```

<210> SEQ ID NO 237
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 237

Asp Glu Tyr Pro Trp Gly Trp Phe Asp Val
1               5                   10

<210> SEQ ID NO 238
<211> LENGTH: 12
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 238

Ala Arg Asp Glu Tyr Pro Trp Gly Trp Phe Asp Val
1               5                   10

<210> SEQ ID NO 239
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 239

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Ala Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Glu Tyr Pro Trp Gly Trp Phe Asp Val Trp Gly
            100                 105                 110

Gln Gly Thr Leu Val Thr Val Ser Ser
        115                 120

<210> SEQ ID NO 240
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 240
gaagtgcagc tggtggaatc tggcggcgga cttgtgaaac ctggcggctc tctgagactg     60
agctgtgccg cttccggctt caccttcagc aatgcctgga tgagctgggt ccgacaggcc    120
cctggaaaag gccttgagtg ggtcggacgg atcaagagca gaccgatgc cggcaccacc     180 gattatgctg cccctgtgaa gggcagattc accatcagca gggacgacag caagaacacc    240
ctgtacctgc agatgaacag cctgaaaacc gaggacaccg ccgtgtacta ctgcgccaga    300
gatgagtacc cctggggatg gttcgatgtg tggggacagg gaaccctggt caccgttagt    360
tct                                                                  363

<210> SEQ ID NO 241
<211> LENGTH: 451
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 241

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Lys | Pro | Gly |
| 1 | | | | 5 | | | | | 10 | | | | | 15 |
| Gly | Ser | Leu | Arg | Leu | Ser | Cys | Ala | Ala | Ser | Gly | Phe | Thr | Phe | Ser |
| | | | 20 | | | | | 25 | | | | | 30 | |
| Asn | Ala | Trp | Met | Ser | Trp | Val | Arg | Gln | Ala | Pro | Gly | Lys | Gly | Leu |
| | | | 35 | | | | | 40 | | | | | 45 | |
| Glu | Trp | Val | Gly | Arg | Ile | Lys | Ser | Lys | Thr | Asp | Ala | Gly | Thr | Thr |
| | | | 50 | | | | | 55 | | | | | 60 | |
| Asp | Tyr | Ala | Ala | Pro | Val | Lys | Gly | Arg | Phe | Thr | Ile | Ser | Arg | Asp |
| 65 | | | | | 70 | | | | | 75 | | | | 80 |
| Asp | Ser | Lys | Asn | Thr | Leu | Tyr | Leu | Gln | Met | Asn | Ser | Leu | Lys | Thr |
| | | | | 85 | | | | | 90 | | | | | 95 |
| Glu | Asp | Thr | Ala | Val | Tyr | Tyr | Cys | Ala | Arg | Asp | Glu | Tyr | Pro | Trp |
| | | | 100 | | | | | 105 | | | | | 110 | |
| Gly | Trp | Phe | Asp | Val | Trp | Gly | Gln | Gly | Thr | Leu | Val | Thr | Val | Ser |
| | | | 115 | | | | | 120 | | | | | 125 | |
| Ser | Ala | Ser | Thr | Lys | Gly | Pro | Ser | Val | Phe | Pro | Leu | Ala | Pro | Ser |
| 130 | | | | | 135 | | | | | 140 | | | | |
| Ser | Lys | Ser | Thr | Ser | Gly | Gly | Thr | Ala | Ala | Leu | Gly | Cys | Leu | Val |
| 145 | | | | | 150 | | | | | 155 | | | | 160 |
| Lys | Asp | Tyr | Phe | Pro | Cys | Pro | Val | Thr | Val | Ser | Trp | Asn | Ser | Gly |
| | | | | 165 | | | | | 170 | | | | | 175 |
| Ala | Leu | Thr | Ser | Gly | Val | His | Thr | Phe | Pro | Ala | Val | Leu | Gln | Ser |
| | | | | 180 | | | | | 185 | | | | | 190 |
| Ser | Gly | Leu | Tyr | Ser | Leu | Ser | Ser | Val | Val | Thr | Val | Pro | Ser | Ser |
| | | | | 195 | | | | | 200 | | | | | 205 |
| Ser | Leu | Gly | Thr | Gln | Thr | Tyr | Ile | Cys | Asn | Val | Asn | His | Lys | Pro |
| | | 210 | | | | | 215 | | | | | 220 | | |
| Ser | Asn | Thr | Lys | Val | Asp | Lys | Arg | Val | Glu | Pro | Lys | Ser | Cys | Asp |
| 225 | | | | | 230 | | | | | 235 | | | | 240 |
| Lys | Thr | His | Thr | Cys | Pro | Pro | Cys | Pro | Ala | Pro | Glu | Leu | Leu | Gly |
| | | | | 245 | | | | | 250 | | | | | 255 |
| Gly | Pro | Ser | Val | Phe | Leu | Phe | Pro | Pro | Lys | Pro | Lys | Asp | Thr | Leu |
| | | | | 260 | | | | | 265 | | | | | 270 |
| Met | Ile | Ser | Arg | Thr | Pro | Glu | Val | Thr | Cys | Val | Val | Val | Asp | Val |
| | | | | 275 | | | | | 280 | | | | | 285 |
| Ser | His | Glu | Asp | Pro | Glu | Val | Lys | Phe | Asn | Trp | Tyr | Val | Asp | Gly |
| | | 290 | | | | | 295 | | | | | 300 | | |
| Val | Glu | Val | His | Asn | Ala | Lys | Thr | Lys | Pro | Arg | Glu | Glu | Gln | Tyr |
| 305 | | | | | 310 | | | | | 315 | | | | 320 |
| Asn | Ser | Thr | Tyr | Arg | Val | Val | Ser | Val | Leu | Thr | Val | Leu | His | Gln |
| | | | | 325 | | | | | 330 | | | | | 335 |
| Asp | Trp | Leu | Asn | Gly | Lys | Glu | Tyr | Lys | Cys | Lys | Val | Ser | Asn | Lys |
| | | | | 340 | | | | | 345 | | | | | 350 |
| Ala | Leu | Pro | Ala | Pro | Ile | Glu | Lys | Thr | Ile | Ser | Lys | Ala | Lys | Gly |
| | | | | 355 | | | | | 360 | | | | | 365 |
| Gln | Pro | Arg | Glu | Pro | Gln | Val | Tyr | Thr | Leu | Pro | Pro | Ser | Arg | Glu |
| | | 370 | | | | | 375 | | | | | 380 | | |
| Glu | Met | Thr | Lys | Asn | Gln | Val | Ser | Leu | Thr | Cys | Leu | Val | Lys | Gly |
| 385 | | | | | 390 | | | | | 395 | | | | 400 |

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
        435                 440                 445

Pro Gly Lys
    450

<210> SEQ ID NO 242
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 242
gaagtgcagc tggtggaatc tggcggcgga cttgtgaaac tggcggctc tctgagactg        60 agctgtgccg cttccggctt caccttcagc aatgcctgga tgagctgggt ccgacaggcc      120
cctggaaaag gccttgagtg gtcggacgg atcaagagca agaccgatgc cggcaccacc       180
gattatgctg cccctgtgaa gggcagattc accatcagca gggacgacag caagaacacc      240
ctgtacctgc agatgaacag cctgaaaacc gaggacaccg ccgtgtacta ctgcgccaga      300
gatgagtacc ctggggatg gttcgatgtg tggggacagg gaaccctggt caccgttagt      360
tctgctagca ccaagggccc aagtgtgttt ccctggccc ccagcagcaa gtctacttcc       420
ggcggaactg ctgccctggg ttgcctggtg aaggactact ccccctgtcc cgtgacagtg      480
tcctggaact ctggggctct gacttccggc gtgcacacct ccccgccgt gctgcagagc       540 agcggcctgt acagcctgag cagcgtggtg acagtgccct ccagctctct gggaacccag      600
acctatatct gcaacgtgaa ccacaagccc agcaacacca aggtggacaa gagagtggag      660
cccaagagct gcgacaagac ccacacctgc cccccctgcc cagctccaga actgctggga      720
gggccttccg tgttcctgtt ccccccaag cccaaggaca cctgatgat cagcaggacc       780 cccgaggtga cctgcgtggt ggtggacgtg tcccacgagg acccagaggt gaagttcaac      840
tggtacgtgg acggcgtgga ggtgcacaac gccaagacca gcccagaga ggagcagtac      900 aacagcacct acagggtggt gtccgtgctg accgtgctgc accaggactg gctgaacggc      960
aaagaataca agtgcaaagt ctccaacaag gccctgccag ccccaatcga aaagacaatc     1020
agcaaggcca agggccagcc acgggagccc caggtgtaca ccctgccccc cagccgggag     1080
gagatgacca gaaccaggt gtccctgacc tgtctggtga agggcttcta cccctgtgat      1140
atcgccgtgg agtgggagag caacggccag cccgagaaca actacaagac cacccccca      1200 gtgctggaca gcgacggcag cttcttcctg tacagcaagc tgaccgtgga caagtccagg     1260
tggcagcagg gcaacgtgtt cagctgcagc gtgatgcacg aggccctgca caaccactac     1320
acccagaagt ccctgagcct gagccccggc aag                                   1353

<210> SEQ ID NO 243
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 243

Arg Ala Ser Gln Gly Ile Ser Ser Trp Leu Ala
1               5                   10

<210> SEQ ID NO 244
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Gln Gln Tyr Ile Phe Tyr Pro Leu Thr
1               5

<210> SEQ ID NO 245
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 245

Ser Gln Gly Ile Ser Ser Trp
1               5

<210> SEQ ID NO 246
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Tyr Ile Phe Tyr Pro Leu
1               5

<210> SEQ ID NO 247
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 247

Gln Gly Ile Ser Ser Trp
1               5

<210> SEQ ID NO 248
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 248

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Phe Tyr Pro Leu
                85                  90                  95

Thr Phe Gly Gln Gly Thr Lys Val Glu Ile Lys
            100                 105

<210> SEQ ID NO 249
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 249
gacatccaga tgacacagag ccctagctcc gtgtctgcca gcgtgggaga cagagtgacc      60
atcacctgta gagccagcca gggcatctct tcttggctgg cctggtatca gcagaagcct    120
ggcaaggccc ctaagctgct gatctatgcc gcttccagtc tgcagagcgg cgtgccaagc    180 agatttctg gcagcggctc tggcaccgac ttcaccctga ccatatctag cctgcagcca    240
gaggacttcg ccacctacta ctgccagcag tacatcttct accctctgac cttcggccag    300
ggcaccaagg tggaaatcaa g                                              321

<210> SEQ ID NO 250
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 250

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Phe Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly

```
                115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 251
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 251
gacatccaga tgacacagag ccctagctcc gtgtctgcca gcgtgggaga cagagtgacc      60
atcacctgta gagccagcca gggcatctct tcttggctgg cctggtatca gcagaagcct     120
ggcaaggccc ctaagctgct gatctatgcc gcttccagtc tgcagagcgg cgtgccaagc     180 agatttctg gcagcggctc tggcaccgac ttcaccctga ccatatctag cctgcagcca     240
gaggacttcg ccacctacta ctgccagcag tacatcttct accctctgac cttcggccag     300
ggcaccaagg tggaaatcaa gcgtacggtg gccgctccca gcgtgttcat cttcccccc     360 agcgacgagc agctgaagag tggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag caccctgacc     540
ctgagcaagg ccgactacga gaagcataag gtgtacgcct gcgaggtgac ccaccagggc     600
ctgtccagcc ccgtgaccaa gagcttcaac aggggcgagt gc                       642

<210> SEQ ID NO 252
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Val Ala Ser Pro Ser Ala Pro Gly Gly Phe Asp Tyr
1               5                   10

<210> SEQ ID NO 253
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 253

Ala Arg Val Ala Ser Pro Ser Ala Pro Gly Gly Phe Asp Tyr
1               5                   10

<210> SEQ ID NO 254
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 254

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Ala Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Val Ala Ser Pro Ser Ala Pro Gly Gly Phe Asp Tyr
            100                 105                 110

Trp Gly Gln Gly Thr Leu Val Thr Val Ser Ser
        115                 120

<210> SEQ ID NO 255
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 255
gaagtgcagc tggtggaatc tggcggcgga cttgtgaaac ctggcggctc tctgagactg      60
agctgtgccg cttccggctt caccttcagc aatgcctgga tgagctgggt ccgacaggcc     120
cctggaaaag gccttgagtg gatcggacgg atcaagagca gaccgatgc cggcaccacc      180 gattatgctg cccctgtgaa gggcagattc accatcagca gggacgacag caagaacacc     240
ctgtacctgc agatgaacag cctgaaaacc gaggacaccg ccgtgtacta ctgcgccaga     300
gtggcttctc cttctgctcc cggcggattc gattattggg gccagggaac actggtcacc     360
gtgtctagt                                                             369

<210> SEQ ID NO 256
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 256

-continued

```
Glu Val Gln Leu Val Glu Ser Gly Gly Gly Leu Val Lys Pro Gly Gly
 1               5                  10                  15
Ser Leu Arg Leu Ser Cys Ala Ala Ser Gly Phe Thr Phe Ser Asn Ala
             20                  25                  30
Trp Met Ser Trp Val Arg Gln Ala Pro Gly Lys Gly Leu Glu Trp Val
         35                  40                  45
Gly Arg Ile Lys Ser Lys Thr Asp Ala Gly Thr Thr Asp Tyr Ala Ala
     50                  55                  60
Pro Val Lys Gly Arg Phe Thr Ile Ser Arg Asp Asp Ser Lys Asn Thr
 65                  70                  75                  80
Leu Tyr Leu Gln Met Asn Ser Leu Lys Thr Glu Asp Thr Ala Val Tyr
             85                  90                  95
Tyr Cys Ala Arg Val Ala Ser Pro Ser Ala Pro Gly Gly Phe Asp Tyr
         100                 105                 110
Trp Gly Gln Gly Thr Leu Val Thr Val Ser Ser Ala Ser Thr Lys Gly
     115                 120                 125
Pro Ser Val Phe Pro Leu Ala Pro Ser Ser Lys Ser Thr Ser Gly Gly
 130                 135                 140
Thr Ala Ala Leu Gly Cys Leu Val Lys Asp Tyr Phe Pro Cys Pro Val
145                 150                 155                 160
Thr Val Ser Trp Asn Ser Gly Ala Leu Thr Ser Gly Val His Thr Phe
             165                 170                 175
Pro Ala Val Leu Gln Ser Ser Gly Leu Tyr Ser Leu Ser Ser Val Val
         180                 185                 190
Thr Val Pro Ser Ser Ser Leu Gly Thr Gln Thr Tyr Ile Cys Asn Val
     195                 200                 205
Asn His Lys Pro Ser Asn Thr Lys Val Asp Lys Arg Val Glu Pro Lys
 210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
             245                 250                 255
Leu Met Ile Ser Arg Thr Pro Glu Val Thr Cys Val Val Val Asp Val
         260                 265                 270
Ser His Glu Asp Pro Glu Val Lys Phe Asn Trp Tyr Val Asp Gly Val
     275                 280                 285
Glu Val His Asn Ala Lys Thr Lys Pro Arg Glu Glu Gln Tyr Asn Ser
 290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
             325                 330                 335
Pro Ile Glu Lys Thr Ile Ser Lys Ala Lys Gly Gln Pro Arg Glu Pro
         340                 345                 350
Gln Val Tyr Thr Leu Pro Pro Ser Arg Glu Glu Met Thr Lys Asn Gln
     355                 360                 365
Val Ser Leu Thr Cys Leu Val Lys Gly Phe Tyr Pro Cys Asp Ile Ala
 370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
             405                 410                 415
Thr Val Asp Lys Ser Arg Trp Gln Gln Gly Asn Val Phe Ser Cys Ser
```

```
            420                 425                 430
Val Met His Glu Ala Leu His Asn His Tyr Thr Gln Lys Ser Leu Ser
        435                 440                 445

Leu Ser Pro Gly Lys
    450

<210> SEQ ID NO 257
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 257
gaagtgcagc tggtggaatc tggcggcgga cttgtgaaac tggcggctc tctgagactg      60 agctgtgccg cttccggctt caccttcagc aatgcctgga tgagctgggt ccgacaggcc    120
cctggaaaag gccttgagtg ggtcggacgg atcaagagca gaccgatgc ggcaccacc     180 gattatgctg cccctgtgaa gggcagattc accatcagca gggacgacag caagaacacc   240
ctgtacctgc agatgaacag cctgaaaacc gaggacaccg ccgtgtacta ctgcgccaga   300
gtggcttctc cttctgctcc cggcggattc gattattggg ccagggaac actggtcacc   360 gtgtctagtg ctagcaccaa gggcccaagt gtgtttcccc tggcccccag cagcaagtct   420
acttccggcg gaactgctgc cctgggttgc ctggtgaagg actacttccc ctgtcccgtg   480
acagtgtcct ggaactctgg ggctctgact tccggcgtgc acaccttccc cgccgtgctg   540
cagagcagcg gcctgtacag cctgagcagc gtggtgacag tgccctccag ctctctggga   600
acccagacct atatctgcaa cgtgaaccac aagcccagca caccaaggt ggacaagaga   660 gtggagccca gagctgcga caagacccac acctgccccc cctgcccagc tccagaactg   720
ctgggagggc cttccgtgtt cctgttcccc ccaagcccca ggacaccct gatgatcagc   780 aggaccccg aggtgacctg cgtggtggtg gacgtgtccc acgaggaccc agaggtgaag   840
ttcaactggt acgtggacgg cgtggaggtg cacaacgcca agaccaagcc agagaggag   900 cagtacaaca gcacctacag ggtggtgtcc gtgctgaccg tgctgcacca ggactggctg   960
aacggcaaaa atacaagtg caaagtctcc aacaaggccc tgccagcccc aatcgaaaag  1020
acaatcagca aggccaaggg ccagccacgg gagccccagg tgtacaccct gccccccagc  1080
cgggaggaga tgaccaagaa ccaggtgtcc ctgacctgtc tggtgaaggg cttctacccc  1140
tgtgatatcg ccgtggagtg ggagagcaac ggccagcccg agaacaacta caagaccacc  1200
cccccagtgc tggacagcga cggcagcttc ttcctgtaca gcaagctgac cgtgacaag  1260 tccaggtggc agcagggcaa cgtgttcagc tgcagcgtga tgcacgaggc cctgcacaac  1320
cactacaccc agaagtccct gagcctgagc cccggcaag                         1359

<210> SEQ ID NO 258
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 258

Gln Gln Ser Leu Phe Ala Pro Phe Thr
```

<210> SEQ ID NO 259
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 259

Ser Leu Phe Ala Pro Phe
1               5

<210> SEQ ID NO 260
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Ser Leu Phe Ala Pro Phe
                85                  90                  95

Thr Phe Gly Gln Gly Thr Lys Val Glu Ile Lys
            100                 105

<210> SEQ ID NO 261
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 261
gacatccaga tgacacagag ccctagcagc ctgtctgcca gcgtgggaga cagagtgacc    60
atcacctgta gagccagcca gggcatcagc aactacctgg cctggtatca gcagaaaccc   120
ggcaaggtgc ccaagctgct gatctacgct gccagcacac tgcagagcgg agtgcctagc   180 agatttctg gcagcggctc cggcaccgat ttcaccctga ccatatctag cctgcagcca   240
gaggacgtgg ccacctacta ctgtcagcag agcctgttcg ccccttt cac ctttggccag   300 ggcaccaagg tggaaatcaa g                                             321

<210> SEQ ID NO 262
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 262

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Ser Leu Phe Ala Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 263
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 263
gacatccaga tgacacagag ccctagcagc ctgtctgcca gcgtgggaga cagagtgacc      60
atcacctgta gagccagcca gggcatcagc aactacctgg cctggtatca gcagaaaccc     120
ggcaaggtgc ccaagctgct gatctacgct gccagcacac tgcagagcgg agtgcctagc     180 agatttctg gcagcggctc cggcaccgat ttcaccctga ccatatctag cctgcagcca     240
gaggacgtgg ccacctacta ctgtcagcag agcctgttcg ccccttttac ctttggccag     300
ggcaccaagg tggaaatcaa gcgtacggtg gccgctccca gcgtgttcat cttccccccc     360
agcgacgagc agctgaagag tggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag caccctgacc     540

```
ctgagcaagg ccgactacga gaagcataag gtgtacgcct gcgaggtgac ccaccagggc        600
ctgtccagcc ccgtgaccaa gagcttcaac aggggcgagt gc                          642
```

<210> SEQ ID NO 264
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264

```
ctctagcgcc accatgaaac a                                                  21
```

<210> SEQ ID NO 265
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265

```
agcccagcaa caccaagg                                                      18
```

<210> SEQ ID NO 266
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266

```
taatacgact cactataggg                                                    20
```

<210> SEQ ID NO 267
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 267

```
His His His His His His
1               5
```

<210> SEQ ID NO 268
<211> LENGTH: 359
<212> TYPE: PRT
<213> ORGANISM: Homo sapiens

<400> SEQUENCE: 268

```
Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
                20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
```

```
                50                  55                  60
Ser Gly Tyr Ser Asp Glu Asp Lys Arg Gly Phe Thr Lys Leu Val Tyr
 65                  70                  75                  80

Gln Asn Ile Phe Thr Ala Met Gln Ala Met Ile Arg Ala Met Asp Thr
                 85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
            115                 120                 125

Val Asp Ala Ile Lys Ser Leu Trp Asn Asp Pro Gly Ile Gln Glu Cys
        130                 135                 140

Tyr Asp Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
            195                 200                 205

Gln Arg Ser Glu Arg Arg Lys Trp Ile His Cys Phe Glu Asn Val Thr
        210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
            275                 280                 285

Val Asp Tyr Phe Pro Glu Tyr Asp Gly Pro Gln Arg Asp Ala Gln Ala
        290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355

<210> SEQ ID NO 269
<211> LENGTH: 6343
<212> TYPE: DNA
<213> ORGANISM: Homo sapiens

<400> SEQUENCE: 269
agactatccg ctcccaccgc gcccccggcc cacctggtgg ccccggccct ggccgccgcc      60
cccgcggcgg ttcccggagc tcgtcccgga cgcgcgcccg ggcggcgggg gctcggcggc     120
caccgctgcc tcggggagc gagggcggga gggtgtgtgt gcgcgctgtg agcagggggt     180
gccggcgggg ctgcagcgga ggcactttgg aagaatgact ctggagtcca tcatggcgtg     240
ctgcctgagc gaggaggcca aggaagcccg gcggatcaac gacgagatcg agcggcagct     300
ccgcagggac aagcgggacg cccgccggga gctcaagctg ctgctgctcg ggacaggaga     360
```

```
gagtggcaag agtacgttta tcaagcagat gagaatcatc catgggtcag gatactctga    420
tgaagataaa aggggcttca ccaagctggt gtatcagaac atcttcacgg ccatgcaggc    480
catgatcaga gccatggaca cactcaagat cccatacaag tatgagcaca ataaggctca    540
tgcacaatta gttcgagaag ttgatgtgga aaggtgtct gcttttgaga atccatatgt    600
agatgcaata aagagtttat ggaatgatcc tggaatccag gaatgctatg atagacgacg    660
agaatatcaa ttatctgact ctaccaaata ctatcttaat gacttggacc gcgtagctga    720
ccctgcctac ctgcctacgc aacaagatgt gcttagagtt cgagtcccca ccacagggat    780
catcgaatac ccctttgact tacaaagtgt cattttcaga atggtcgatg taggggccca    840
aaggtcagag agaagaaaat ggatacactg ctttgaaaat gtcacctcta tcatgtttct    900
agtagcgctt agtgaatatg atcaagttct cgtggagtca gacaatgaga accgaatgga    960
ggaaagcaag gctctctttta gaacaattat cacatacccc tggttccaga actcctcggt   1020
tattctgttc ttaaacaaga aagatcttct agaggagaaa atcatgtatt cccatctagt   1080
cgactacttc ccagaatatg atggacccca gagagatgcc caggcagccc gagaattcat   1140
tctgaagatg ttcgtggacc tgaacccaga cagtgacaaa attatctact cccacttcac   1200
gtgcgccaca gacaccgaga atatccgctt tgtctttgct gccgtcaagg acaccatcct   1260
ccagttgaac ctgaaggagt acaatctggt ctaattgtgc ctcctagaca cccgccctgc   1320
ccttccctgg tgggctattg aagatacaca agagggactg tatttctgtg aaaacaatt    1380 tgcataatac taatttattg ccgtcctgga ctctgtgtga gcgtgtccac agagtttgta   1440
gtaaatatta tgatttttatt taaactattc agaggaaaaa cagaggatgc tgaagtacag   1500
tcccagcaca tttcctctct atcttttttt taggcaaaac cttgtgactc agtgtatttt   1560
aaattctcag tcatgcactc acaaagataa gacttgtttc tttctgtctc tctctctttt   1620
tcttttctat ggagcaaaac aaagctgatt tcccttttttt cttccccgc taattcatac   1680 ctccctcctg atgtttttcc caggttacaa tggcctttat cctagttcca ttcttggtca   1740 agttttctc tcaaatgata cagtcaggac acatcgttcg atttaagcca tcatcagctt   1800
aatttaagtt tgtagttttt gctgaaggat tatatgtatt aatacttacg gttttaaatg   1860
tgttgctttg gatacacaca tagtttcttt tttaatagaa tatactgtct tgtctcactt   1920
tggactggga cagtggatgc ccatctaaaa gttaagtgtc atttcttttta gatgtttacc   1980 ttcagccata gcttgattgc tcagagaaat atgcagaagg caggatcaaa gacacacagg   2040
agtcctttct tttgaaatgc cacgtgccat tgtctttcct cccttctttg cttctttttc   2100
ttaccctctc tttcaattgc agatgccaaa aaagatgcca acagacacta cattacccta   2160
atggctgcta cccagaacct tttataggt tgttcttaat ttttttgttg ttgttgttca   2220 agctttttcct ttcttttttt tcttggtgtt tgggccacga ttttaaaatg acttttatta   2280
tgggtatgtg ttgccaaagc tggcttttttg tcaaataaaa tgaatacgaa cttaaaaaat   2340
aaaagctggt atcttaaaat gtaagagagt aagactgtga agcctaaaat gactggctga   2400
gaatgaacca gaaatgccat ttgccaaaca gttgtaacta gaaatttgat tctcacggtc   2460
cattcttttc tttgtcctta agatgacatt gttagtgttc acgtcccatg ttcagtgtcc   2520
aaaccggcaa tgtaaaaagt atcctgtgtg gtttaacagg aaatctgttt atgtctcttt   2580
atttgaaacc agttttactc tcagtggttc tttaagttca atgaagtctg ccaggaacat   2640
tggttggtag tattattccg acacctttaa tttccaaaat ctgaagttcc tgctagttta   2700
ccaccttcat gatcttcttg aactggtaac tgattaggtt gaacttatgg aagatttgtg   2760
```

```
gacttaactc aaaagtaacc tctcagtgtt ctatagaaca tgtatttgtg taactgaacc    2820
taccaggaga aatgtttgga attctatatg tgcaattttt caacaaatgc aaaaaaaata    2880
cagcacatgt attgacaagc ttctgtcaag cagcttgagt tgaaatttga tttaagaaaa    2940
taaatcatga ttgttcaaag ctgctgggac gttagaatta ggccatgata ctggtctcat    3000
tttaactaca gtggtatttg gcactagtgt aaacttccat ataaatcact cttttggaac    3060
aacaaagggg gagggagaaa atcacggcc tgttaaatga gtaccaaagc cgcccaacag    3120
taatgagatg ttctcatcct tgattctccc agcctcaaac aacacagctt actttttttt    3180
tcccttgctc agaaagtacc tgtaatttaa caaacagact gcctgtaggt atagtgcaat    3240
tacaaatgct ctaatcattg tacatacatc tctcttgata ttgcagcatc catactggct    3300
ttgtaatcat taatttttg gcagattgaa tgtgctgtat tgatatgtat ctatgtaatt    3360
gtattgtatg tctatagcta attcacgttt tgaataatgt tattttattt acttttttaa    3420
gagaggagaa tgtaaatttg tcagtttatt tctgactagg gatattttct ttccatttag    3480
aaaagaagaa aaaaaaaaaa ccttactgtc atacagagcg gtactagcgt cgtgctgtat    3540
aaaatcattt gcacattcct gagtagaggt atactgatta taagacccaa aggtaatttc    3600
atagcaaaat acataaaatc agtcggagct tttatacaaa catggaaacc aactttgtag    3660
aacttttgcc atttgatcta ggattggaat atgagctttt atacaattca tattcttatt    3720
tggcaaatgc acagtttagt attacctctc tgatggcctt tactagaaag gcagttttag    3780
aagctattgt gatccactaa ggaaatgttt taacagctag agaccactgc ttgcctgaaa    3840
gggcgttctt aaatttggtg cagcaaaaaa aaaaaaaaa aaaaaaaaaa ttaaacaaca    3900
acatttgaag gcctacagtg tgtatagaga aaacctcatc acaagatcat aagtgttaca    3960
gttttaggga atcaagatat tctatttaat agagctatag taaatgtagt caattaaacc    4020
tgatctcaaa gcttgaagaa gctgagcaaa acagggaaag attgttatat ttgtctttat    4080
gaaattggga tggaatttgc tatgcagaat tgaggtttgt ggcttcgctg ttcctgtagg    4140
gtgcatgaca agatcccttc tcttgagaaa ggaaaaaatt gatcaccta gcagcagtga    4200 tgcatagaaa cctaattta gccacaccag tcaatcgaag ctaaaggatt ttctttttttg    4260 tttcttcggg gttttattga aggggctagg ggcgggacgg gattctttc agttttgtat    4320 aaaaacaaag tttactcatg ctttatatta tattgtgatt gcaagcgtta taagcgtgtg    4380
ccactggcct cctattgttg atgcttaggt aatggaggcc tgtggtgagt tttatggtga    4440
cttgggcatg tcttattcaa aaacaaaaac ataaacaca gaaaccttc ttcagcatac    4500 caaggcaagc agccatttca tgactcactt aacacattgc agtgtaccag tttacagatg    4560
atttttccct ttttgcgtga catggcagtt ctaacccca gagaattcct tatttgtaaa    4620
ttggaagttt ctactatgcc ttacagagct taaattcaga agtttgtgcc tcatatctga    4680
aacaaaggga aataacacac ccattcaaaa gtaaataaat ctcctagaag tttttgtttt    4740
taacatttcc atataaagag ctctgttgaa tgtcatgaat agactggaaa aaaaaatttt    4800
aagaacctgc atatgttgtt tactagcaga tgacaactac aaaaggaatc tgaagaacac    4860
gtaaaacttg tattttttttt tttttggtag attaactagc aggcctattt taaaaggta    4920 attcagctaa agggcaattt acttttttgt acttcagact atcttgattg tcaaagtgta    4980
cgaactgtaa ttttaaaatt tatactgcca catgattgta aatttagtt gtcttaagtt    5040 aggaattggt gaaaagctat ttatgctgga tttgggtcaa aatgacttat ttgcaaaaaa    5100
```

```
ataaataatg ggaagaaagg gctgtataat gaaatactgc aagactcaca tattggttgg    5160
aaatttccct caaatcacct accgattacc cttgatttcc ctttgttttc agtttctcaa    5220
aacgaatgaa atgaaatata gcagaatgtt aacccatata aaataaagt gtacccaaat     5280 attgtaatgt atattgctgc tcttcttcaa attaaataag ggtttaaaac cacttaattg    5340
gtaatcaaca tctcaattga tacaaataag gtgtgcttgg tatacattaa tattttcttc    5400
caaagatata tctttggtta gaaacacaaa aaaataaaac tagtaatatt gtatgtttat    5460
ctatctctac atatttccag catatgtagc gttaatagat ctgtcctggt aactgtgtct    5520
ttgggatttc attttggttc catcaaatta ggaaaagaaa tggcttagtt gtatatgatt    5580
agctagagat ttttggagcc agacacctgc tgtttagtag ataacttagt acagaccta     5640 aacttgtcat tgttttttct cacagaatag ccatttcctg ctgtcttccc aatgatcact    5700
gccctttcaa taacactctt gcctctagaa tcatatgttc aaagtatgaa tacacaccta    5760
gcacatagta ggtgctcaaa tattaatttc ctccttgcct tccttatcta ccctgtgtcc    5820
tccatttccc cgtatgattc caacccaata tagcaaatga catttacatg ttatgaaaac    5880
atctattggg taaaatcaga tcttggataa agaaattctg acttttatat aagcttttgg    5940
tagacagaaa aaacagaaag gtattcgttg gtagaacatt tttaagttca ggaaagaaag    6000
ctggaataat actacgtaac tttgtccagg ttactttgac tgaaacacgt ttttggtgga    6060
tttcttttcc tcaaagaact ctctaaatgc aactccttgc tggattcctc acccatcatc    6120
ctgttggaaa cccttactag acctatgtat ttagggagtt ttgtcagaaa acatttttaa    6180
cttgcagtat ttaaaagaat atttactgtt cctaaaatgt cattcaaatg catgtactgt    6240
ctattgtttg gggatgggaa ctagttttgc aaaaaacacc taatgttgta taataatgcc    6300
ccaatgatct tgctggttaa aaatacagta tttttggcca taa                      6343
```

<210> SEQ ID NO 270
<211> LENGTH: 359
<212> TYPE: PRT
<213> ORGANISM: Homo sapiens

<400> SEQUENCE: 270

Met Thr Leu Glu Ser Met Met Ala Cys Cys Leu Ser Asp Glu Val Lys
1               5                   10                  15

Glu Ser Lys Arg Ile Asn Ala Glu Ile Glu Lys Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ala Gly Tyr Ser Glu Glu Asp Lys Arg Gly Phe Thr Lys Leu Val Tyr
65                  70                  75                  80

Gln Asn Ile Phe Thr Ala Met Gln Ala Met Ile Arg Ala Met Glu Thr
                85                  90                  95

Leu Lys Ile Leu Tyr Lys Tyr Glu Gln Asn Lys Ala Asn Ala Leu Leu
            100                 105                 110

Ile Arg Glu Val Asp Val Glu Lys Val Thr Thr Phe Glu His Gln Tyr
        115                 120                 125

Val Ser Ala Ile Lys Thr Leu Trp Glu Asp Pro Gly Ile Gln Glu Cys
    130                 135                 140

Tyr Asp Arg Arg Arg Glu Tyr Gln Leu Ser Asp Ser Ala Lys Tyr Tyr
145                 150                 155                 160

Leu Thr Asp Val Asp Arg Ile Ala Thr Leu Gly Tyr Leu Pro Thr Gln
            165                 170                 175

Gln Asp Val Leu Arg Val Arg Val Pro Thr Thr Gly Ile Ile Glu Tyr
        180                 185                 190

Pro Phe Asp Leu Glu Asn Ile Ile Phe Arg Met Val Asp Val Gly Gly
        195                 200                 205

Gln Arg Ser Glu Arg Arg Lys Trp Ile His Cys Phe Glu Asn Val Thr
        210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Asp Lys Ile Leu Tyr Ser His Leu
        275                 280                 285

Val Asp Tyr Phe Pro Glu Phe Asp Gly Pro Gln Arg Asp Ala Gln Ala
        290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355

<210> SEQ ID NO 271
<211> LENGTH: 4190
<212> TYPE: DNA
<213> ORGANISM: Homo sapiens

<400> SEQUENCE: 271
aggttgtccg gcgctgtcgc tcggttgcgg cggctgcggt tggcggtggc tgcggcggcg      60
gcgcgggctg agtgcggccg cgcgggagtc cgcggctggc gcggcccgag cggggacccg     120
gcggctcgcc aggcggcggc cgaggcgggg cgggccggcc cggggccgag ggccggtggc     180
cgaggccgga gggccgcggc gggcggcggc cgaggcggct ccggccaggg ccgggccggg     240
ggccgggggg cggcggcggg caggcggccg cgtcggccgg ggccgggacg atgactctgg     300
agtccatgat ggcgtgttgc ctgagcgatg aggtgaagga gtccaagcgg atcaacgccg     360
agatcgagaa gcagctgcgg cgggacaagc gcgacgcccg cgcgagctc aagctgctgc      420 tgctcggcac gggcgagagc gggaagagca cgttcatcaa gcagatgcgc atcatccacg     480
gcgccggcta ctcggaggag acaagcgcg gcttcaccaa gctcgtctac agaacatct       540 tcaccgccat gcaggccatg atccgggcca tggacgcgct caagatcctc tacaagtacg     600
agcagaacaa ggccaatgcg ctcctgatcc gggaggtgga cgtggagaag gtgaccacct     660
tcgagcatca gtacgtcagt gccatcaaga ccctgtggga ggacccgggc atccaggaat     720
gctacgaccg caggcgcgag taccagctct ccgactctgc caagtactac ctgaccgacg     780
ttgaccgcat cgccaccttg ggctacctgc cacccagca ggacgtgctg cgggtccgcg      840
tgcccaccac cggcatcatc gagtacccct tcgacctgga gaacatcatc ttccggatgg     900
tggatgtggg gggccagcgg tcggagcgga ggaagtggat ccactgcttt gagaacgtga     960

```
catccatcat gtttctcgtc gccctcagcg aatacgacca agtcctggtg gagtcggaca    1020
acgagaaccg gatggaggag agcaaagccc tgttccggac catcatcacc tacccctggt    1080
tccagaactc ctccgtcatc ctcttcctca acaagaagga cctgctggag gacaagatcc    1140
tgtactcgca cctggtggac tacttccccg agttcgatgg tccccagcgg gacgcccagg    1200
cggcgcggga gttcatcctg aagatgttcg tggacctgaa ccccgacagc gacaagatca    1260
tctactcaca cttcacgtgt gccaccgaca cggagaacat ccgcttcgtg ttcgcggccg    1320
tgaaggacac catcctgcag ctcaacctca aggagtacaa cctggtctga gcgcccaggc    1380
ccagggagac gggatggaga cacggggcag gaccttcctt ccacggagcc tgcggctgcc    1440
gggcgggtgg cgctgccgag tccgggccgg ggcctctgcc cgcgggagga gattttttt    1500 tttcatattt ttaacaaatg gttttattt cacagttatc aggggatgta catctctccc    1560
tccgtacact tcgcgcacct tctcacccttt tgtcaacggc aaaggcagcc ttttctggc    1620 cttgacttat ggctcgcttt tttctaaaaa aaaaaaaaa agaaagaaag aaaaaaagca    1680
acgaaacata aaacacacaa gcgccccgtg cccccagtga ctctgggcct cacagagccc    1740
ccgccagcca gcatggggcc ccgccctgca gccagtcacg cgcccccaca ccgcagcccc    1800
ccgtggctgt ccttccaacc ccacgtgctt tttctttctc ctgcccgctt cttttcttca    1860
tcacaaaagg cgtggagact cggagacgga cgttttccc cttttttaag ttattgacgc    1920
ccagcgcgcc tcgcctcttc acccatcaac gctgtgcttt gcccactgga ctcctgaaga    1980
gggggtgggg ggctccctcg gtcgcccacc ctgggaagtg cctaacctttt tattttattt    2040 tatttttttg aggaaaaaga acgcctgact cacaggttga agaaacaccc tgggccctct    2100
ctcatggccg ggttccccgt ccctctgcag aggctgggaa gggtccccgg gctggagcca    2160
cgggggcttc tctgggctgt gcctccgggg ccaacactgg ctgcttgggg ctgcccgggg    2220
actccagagg gctgcacggc caccctgccc tggctagagc gcaccccacc ggagcccacg    2280
tgggctgggc ggctggaggg atggtccccc ggtgacactg ggagaaaggc cacttggatg    2340
ggggcgtttc tgttttgttc cgctttgtga tgtcaccaat ttggaaacag cgagggtggg    2400
tggggacttt tacagaatat tctcaggtgt gtacccgaga ggcagagaga gggacgtggc    2460
cggcagctct gtgcgtggcc ttgtcccaag cacttgcgcc cgcccccgag cgccgccccc    2520
ggggagcggg aagccagcac tcgcactttg gccaggggcg cgtggaaggt ggtggcaggc    2580
accggcctgg gcagcttcca ggcctggctg gccacgacca cggcccgagg gggagcccgc    2640
caggccacgc cgcactgagc cacagccccg ggggccgcct cccggggccc cttgaggcac    2700
tgaggcaccg agactggttc tccccgagag actcggaagg tggggaacga ggggactgtg    2760
tttggggagg tggcttttc gtctgctgtt gactgaacac tacagcgccc tgtggttccg    2820
ggcttcgcac agctgtccca gggatggatc gcctgtgctg ccttcgcccg ccgccacacc    2880
gggaccctgc acggctgctt ctggcctcga cagatgacaa agaaacagc cccaaaatac    2940 gaccactcca accagcagtt cccgcctgcc tgcccgccac tgtcaggcct gccctggcct    3000
cctcgtccgc agggctgtct gctgcttct gggggcagaa gagcggggag ccccgtggaa    3060
gggtcagggg agaccaggtc agggcagcta catttctggt gatcagcccc atggggagac    3120
ggggctggcg ggatacccc cccccggctt ccccacacca cttctgtctc acccggaagc    3180 gtccttttt tgtgccaggt gtctacctaa gagggttggt gccagaagcc cccatggcg    3240 agtgctgggg cccggcggtg ccctggggga gcagatgggg ccacccctgg cagggccgct    3300
```

-continued

```
acaaccttttt ccagcagcgg agccctctgg ggggcctgtg cttgtggcat ctctgagggc    3360
ctagattgca caaggtgacc tggccgtggc ctgagggtgg agtcgcccag cacgcaggcc    3420
ggggcgctgc ggggctaagt attaggcctt cccagggagg gggcgtgcca agcatcccag    3480
agccgggctg ggaccgccaa aacgtcgtgg cctggatcct ctgggtctga gtgcctgatc    3540
ccctgccccc caaaaaagca gaggtaggtg ttgcaggccc agggcagggg tgcctgcccc    3600
aggagagtcc caggcagtgg ttctcgtgcc agtggcaccc aggggcaagg acagccaacc    3660
cccacccttg ccacgtgtgg ggccacgtgg gcatgtgggg tgtgtgtttt taccttggtg    3720
aatctcacct gccaacgatt tctcgtgagt gccgaccacc ttctccgacc atgttacgcc    3780
cgggcggcag cagcccccgg ccactgcaaa cccatgccct gggtccccg gctcccccag     3840
ggaggcatcc ccgtgccaat gtcccccagt ggtggcagca gatcctgtgg ccggcctggc    3900
ggacgggacc cagtgatact tgtatattac acagtcctga tttcagacaa tttcaacctt    3960
aatctattta aaaagaata ttctatacaa gctgttttta agcctttttac catttgaaat    4020
gcatgtgttg tgcgcgttgg ggatgggagg aggggctgag gagcggctca gtgtcacctc    4080
ccacagccac cggccctgac ccttaatcca gacaccgatg gaagtcgact tttcatatct    4140
ttctcctgaa atgaactctg tttttaaattg gaataaattt tgttcctaaa              4190
```

<210> SEQ ID NO 272
<211> LENGTH: 661
<212> TYPE: PRT
<213> ORGANISM: Homo sapiens

<400> SEQUENCE: 272

```
Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
        195                 200                 205

Ile Thr Asp Gln Val Pro Phe Ser Val Ser Val Ser Gln Leu Arg Ala
    210                 215                 220
```

-continued

```
Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
            245                 250                 255

Ser Tyr Thr Trp Asp Phe Gly Asp Ser Ser Gly Thr Leu Ile Ser Arg
        260                 265                 270

Ala Leu Val Val Thr His Thr Tyr Leu Glu Pro Gly Pro Val Thr Ala
    275                 280                 285

Gln Val Val Leu Gln Ala Ala Ile Pro Leu Thr Ser Cys Gly Ser Ser
290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
            325                 330                 335

Pro Gly Gln Ala Pro Thr Ala Glu Pro Ser Gly Thr Thr Ser Val Gln
        340                 345                 350

Val Pro Thr Thr Glu Val Ile Ser Thr Ala Pro Val Gln Met Pro Thr
    355                 360                 365

Ala Glu Ser Thr Gly Met Thr Pro Glu Lys Val Pro Val Ser Glu Val
370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
            405                 410                 415

Gln Val Thr Thr Thr Glu Trp Val Glu Thr Thr Ala Arg Glu Leu Pro
        420                 425                 430

Ile Pro Glu Pro Glu Gly Pro Asp Ala Ser Ser Ile Met Ser Thr Glu
    435                 440                 445

Ser Ile Thr Gly Ser Leu Gly Pro Leu Leu Asp Gly Thr Ala Thr Leu
450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
            485                 490                 495

Glu Ile Leu Gln Ala Val Pro Ser Gly Glu Gly Asp Ala Phe Glu Leu
        500                 505                 510

Thr Val Ser Cys Gln Gly Gly Leu Pro Lys Glu Ala Cys Met Glu Ile
    515                 520                 525

Ser Ser Pro Gly Cys Gln Pro Pro Ala Gln Arg Leu Cys Gln Pro Val
530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
            565                 570                 575

Leu Ala Val Val Ser Thr Gln Leu Ile Met Pro Gly Gln Glu Ala Gly
        580                 585                 590

Leu Gly Gln Val Pro Leu Ile Val Gly Ile Leu Leu Val Leu Met Ala
    595                 600                 605

Val Val Leu Ala Ser Leu Ile Tyr Arg Arg Arg Leu Met Lys Gln Asp
610                 615                 620

Phe Ser Val Pro Gln Leu Pro His Ser Ser His Trp Leu Arg Leu
625                 630                 635                 640
```

```
Pro Arg Ile Phe Cys Ser Cys Pro Ile Gly Glu Asn Ser Pro Leu Leu
                645                 650                 655

Ser Gly Gln Gln Val
            660

<210> SEQ ID NO 273
<211> LENGTH: 626
<212> TYPE: PRT
<213> ORGANISM: Homo sapiens

<400> SEQUENCE: 273

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
        195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
        275                 280                 285

Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350
```

Val Pro Thr Thr Glu Val Ile Ser Thr Ala Pro Val Gln Met Pro Thr
        355                 360                 365

Ala Glu Ser Thr Ala Ala Gln Val Thr Thr Thr Glu Trp Val Glu Thr
370                 375                 380

Thr Ala Arg Glu Leu Pro Ile Pro Glu Pro Gly Pro Asp Ala Ser
385                 390                 395                 400

Ser Ile Met Ser Thr Glu Ser Ile Thr Gly Ser Leu Gly Pro Leu Leu
                405                 410                 415

Asp Gly Thr Ala Thr Leu Arg Leu Val Lys Arg Gln Val Pro Leu Asp
                420                 425                 430

Cys Val Leu Tyr Arg Tyr Gly Ser Phe Ser Val Thr Leu Asp Ile Val
                435                 440                 445

Gln Gly Ile Glu Ser Ala Glu Ile Leu Gln Ala Val Pro Ser Gly Glu
        450                 455                 460

Gly Asp Ala Phe Glu Leu Thr Val Ser Cys Gln Gly Gly Leu Pro Lys
465                 470                 475                 480

Glu Ala Cys Met Glu Ile Ser Ser Pro Gly Cys Gln Pro Pro Ala Gln
                485                 490                 495

Arg Leu Cys Gln Pro Val Leu Pro Ser Pro Ala Cys Gln Leu Val Leu
                500                 505                 510

His Gln Ile Leu Lys Gly Gly Ser Gly Thr Tyr Cys Leu Asn Val Ser
                515                 520                 525

Leu Ala Asp Thr Asn Ser Leu Ala Val Val Ser Thr Gln Leu Ile Met
        530                 535                 540

Pro Val Pro Gly Ile Leu Leu Thr Gly Gln Glu Ala Gly Leu Gly Gln
545                 550                 555                 560

Val Pro Leu Ile Val Gly Ile Leu Leu Val Leu Met Ala Val Val Leu
                565                 570                 575

Ala Ser Leu Ile Tyr Arg Arg Arg Leu Met Lys Gln Asp Phe Ser Val
                580                 585                 590

Pro Gln Leu Pro His Ser Ser Ser His Trp Leu Arg Leu Pro Arg Ile
                595                 600                 605

Phe Cys Ser Cys Pro Ile Gly Glu Asn Ser Pro Leu Leu Ser Gly Gln
        610                 615                 620

Gln Val
625

<210> SEQ ID NO 274
<211> LENGTH: 619
<212> TYPE: PRT
<213> ORGANISM: Homo sapiens

<400> SEQUENCE: 274

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
                20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
        50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val

```
                        85                  90                  95
Leu Pro Asp Gly Gln Val Ile Trp Val Asn Asn Thr Ile Ile Asn Gly
                100                 105                 110

Ser Gln Val Trp Gly Gly Gln Pro Val Tyr Pro Gln Glu Thr Asp Asp
                115                 120                 125

Ala Cys Ile Phe Pro Asp Gly Pro Cys Pro Ser Gly Ser Trp Ser
            130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
                180                 185                 190

Gly Ser Arg Ser Tyr Val Pro Leu Ala His Ser Ser Ala Phe Thr
            195                 200                 205

Ile Thr Asp Gln Val Pro Phe Ser Val Ser Val Ser Gln Leu Arg Ala
            210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
                260                 265                 270

Ala Leu Val Val Thr His Thr Tyr Leu Glu Pro Gly Pro Val Thr Ala
                275                 280                 285

Gln Val Val Leu Gln Ala Ala Ile Pro Leu Thr Ser Cys Gly Ser Ser
                290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
                340                 345                 350

Val Pro Thr Thr Glu Val Ile Ser Thr Ala Pro Val Gln Met Pro Thr
                355                 360                 365

Ala Glu Ser Thr Ala Ala Gln Val Thr Thr Glu Trp Val Glu Thr
                370                 375                 380

Thr Ala Arg Glu Leu Pro Ile Pro Glu Pro Glu Gly Pro Asp Ala Ser
385                 390                 395                 400

Ser Ile Met Ser Thr Glu Ser Ile Thr Gly Ser Leu Gly Pro Leu Leu
                405                 410                 415

Asp Gly Thr Ala Thr Leu Arg Leu Val Lys Arg Gln Val Pro Leu Asp
                420                 425                 430

Cys Val Leu Tyr Arg Tyr Gly Ser Phe Ser Val Thr Leu Asp Ile Val
                435                 440                 445

Gln Gly Ile Glu Ser Ala Glu Ile Leu Gln Ala Val Pro Ser Gly Glu
            450                 455                 460

Gly Asp Ala Phe Glu Leu Thr Val Ser Cys Gln Gly Gly Leu Pro Lys
465                 470                 475                 480

Glu Ala Cys Met Glu Ile Ser Ser Pro Gly Cys Gln Pro Pro Ala Gln
                485                 490                 495

Arg Leu Cys Gln Pro Val Leu Pro Ser Pro Ala Cys Gln Leu Val Leu
                500                 505                 510
```

-continued

His Gln Ile Leu Lys Gly Gly Ser Gly Thr Tyr Cys Leu Asn Val Ser
              515                 520                 525

Leu Ala Asp Thr Asn Ser Leu Ala Val Val Ser Thr Gln Leu Ile Met
        530                 535                 540

Pro Gly Gln Glu Ala Gly Leu Gly Gln Val Pro Leu Ile Val Gly Ile
545                 550                 555                 560

Leu Leu Val Leu Met Ala Val Val Leu Ala Ser Leu Ile Tyr Arg Arg
                565                 570                 575

Arg Leu Met Lys Gln Asp Phe Ser Val Pro Gln Leu Pro His Ser Ser
            580                 585                 590

Ser His Trp Leu Arg Leu Pro Arg Ile Phe Cys Ser Cys Pro Ile Gly
        595                 600                 605

Glu Asn Ser Pro Leu Leu Ser Gly Gln Gln Val
            610                 615

<210> SEQ ID NO 275
<211> LENGTH: 575
<212> TYPE: PRT
<213> ORGANISM: Homo sapiens

<400> SEQUENCE: 275

Met Asp Leu Val Leu Lys Arg Cys Leu Leu His Leu Ala Val Ile Gly
1               5                   10                  15

Ala Leu Leu Ala Val Gly Ala Thr Lys Gly Ser Gln Val Trp Gly Gly
            20                  25                  30

Gln Pro Val Tyr Pro Gln Glu Thr Asp Asp Ala Cys Ile Phe Pro Asp
        35                  40                  45

Gly Gly Pro Cys Pro Ser Gly Ser Trp Ser Gln Lys Arg Ser Phe Val
    50                  55                  60

Tyr Val Trp Lys Thr Trp Gly Gln Tyr Trp Gln Val Leu Gly Gly Pro
65                  70                  75                  80

Val Ser Gly Leu Ser Ile Gly Thr Gly Arg Ala Met Leu Gly Thr His
                85                  90                  95

Thr Met Glu Val Thr Val Tyr His Arg Arg Gly Ser Arg Ser Tyr Val
            100                 105                 110

Pro Leu Ala His Ser Ser Ser Ala Phe Thr Ile Thr Asp Gln Val Pro
        115                 120                 125

Phe Ser Val Ser Val Ser Gln Leu Arg Ala Leu Asp Gly Gly Asn Lys
130                 135                 140

His Phe Leu Arg Asn Gln Pro Leu Thr Phe Ala Leu Gln Leu His Asp
145                 150                 155                 160

Pro Ser Gly Tyr Leu Ala Glu Ala Asp Leu Ser Tyr Thr Trp Asp Phe
                165                 170                 175

Gly Asp Ser Ser Gly Thr Leu Ile Ser Arg Ala Leu Val Val Thr His
            180                 185                 190

Thr Tyr Leu Glu Pro Gly Pro Val Thr Ala Gln Val Val Leu Gln Ala
        195                 200                 205

Ala Ile Pro Leu Thr Ser Cys Gly Ser Ser Pro Val Pro Gly Thr Thr
    210                 215                 220

Asp Gly His Arg Pro Thr Ala Glu Ala Pro Asn Thr Thr Ala Gly Gln
225                 230                 235                 240

Val Pro Thr Thr Glu Val Val Gly Thr Thr Pro Gly Gln Ala Pro Thr
                245                 250                 255

Ala Glu Pro Ser Gly Thr Thr Ser Val Gln Val Pro Thr Thr Glu Val

```
            260                 265                 270
Ile Ser Thr Ala Pro Val Gln Met Pro Thr Ala Glu Ser Thr Gly Met
        275                 280                 285

Thr Pro Glu Lys Val Pro Val Ser Glu Val Met Gly Thr Thr Leu Ala
    290                 295                 300

Glu Met Ser Thr Pro Glu Ala Thr Gly Met Thr Pro Ala Glu Val Ser
305                 310                 315                 320

Ile Val Val Leu Ser Gly Thr Thr Ala Ala Gln Val Thr Thr Thr Glu
                325                 330                 335

Trp Val Glu Thr Thr Ala Arg Glu Leu Pro Ile Pro Glu Pro Glu Gly
                340                 345                 350

Pro Asp Ala Ser Ser Ile Met Ser Thr Glu Ser Ile Thr Gly Ser Leu
            355                 360                 365

Gly Pro Leu Leu Asp Gly Thr Ala Thr Leu Arg Leu Val Lys Arg Gln
        370                 375                 380

Val Pro Leu Asp Cys Val Leu Tyr Arg Tyr Gly Ser Phe Ser Val Thr
385                 390                 395                 400

Leu Asp Ile Val Gln Gly Ile Glu Ser Ala Glu Ile Leu Gln Ala Val
                405                 410                 415

Pro Ser Gly Glu Gly Asp Ala Phe Glu Leu Thr Val Ser Cys Gln Gly
            420                 425                 430

Gly Leu Pro Lys Glu Ala Cys Met Glu Ile Ser Ser Pro Gly Cys Gln
        435                 440                 445

Pro Pro Ala Gln Arg Leu Cys Gln Pro Val Leu Pro Ser Pro Ala Cys
    450                 455                 460

Gln Leu Val Leu His Gln Ile Leu Lys Gly Gly Ser Gly Thr Tyr Cys
465                 470                 475                 480

Leu Asn Val Ser Leu Ala Asp Thr Asn Ser Leu Ala Val Val Ser Thr
                485                 490                 495

Gln Leu Ile Met Pro Gly Gln Glu Ala Gly Leu Gly Gln Val Pro Leu
            500                 505                 510

Ile Val Gly Ile Leu Leu Val Leu Met Ala Val Val Leu Ala Ser Leu
        515                 520                 525

Ile Tyr Arg Arg Arg Leu Met Lys Gln Asp Phe Ser Val Pro Gln Leu
    530                 535                 540

Pro His Ser Ser Ser His Trp Leu Arg Leu Pro Arg Ile Phe Cys Ser
545                 550                 555                 560

Cys Pro Ile Gly Glu Asn Ser Pro Leu Leu Ser Gly Gln Gln Val
                565                 570                 575

<210> SEQ ID NO 276
<211> LENGTH: 668
<212> TYPE: PRT
<213> ORGANISM: Homo sapiens

<400> SEQUENCE: 276

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60
```

```
Gln Val Ser Leu Lys Val Ser Asn Asp Gly Pro Thr Leu Ile Gly Ala
 65                  70                  75                  80

Asn Ala Ser Phe Ser Ile Ala Leu Asn Phe Pro Gly Ser Gln Lys Val
             85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
            115                 120                 125

Ala Cys Ile Phe Pro Asp Gly Pro Cys Pro Ser Gly Ser Trp Ser
130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
            165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ala Phe Thr
            195                 200                 205

Ile Thr Asp Gln Val Pro Phe Ser Val Ser Val Ser Gln Leu Arg Ala
            210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
            245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
            275                 280                 285

Gln Val Val Leu Gln Ala Ala Ile Pro Leu Thr Ser Cys Gly Ser Ser
            290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
            325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
            355                 360                 365

Ala Glu Ser Thr Gly Met Thr Pro Glu Lys Val Pro Val Ser Glu Val
370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
            405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
            435                 440                 445

Ser Ile Thr Gly Ser Leu Gly Pro Leu Leu Asp Gly Thr Ala Thr Leu
            450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
```

```
                485                 490                 495
Glu Ile Leu Gln Ala Val Pro Ser Gly Glu Gly Asp Ala Phe Glu Leu
                500                 505                 510

Thr Val Ser Cys Gln Gly Gly Leu Pro Lys Glu Ala Cys Met Glu Ile
            515                 520                 525

Ser Ser Pro Gly Cys Gln Pro Ala Gln Arg Leu Cys Gln Pro Val
        530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Val Pro Gly Ile Leu
            580                 585                 590

Leu Thr Gly Gln Glu Ala Gly Leu Gly Gln Val Pro Leu Ile Val Gly
        595                 600                 605

Ile Leu Leu Val Leu Met Ala Val Val Leu Ala Ser Leu Ile Tyr Arg
    610                 615                 620

Arg Arg Leu Met Lys Gln Asp Phe Ser Val Pro Gln Leu Pro His Ser
625                 630                 635                 640

Ser Ser His Trp Leu Arg Leu Pro Arg Ile Phe Cys Ser Cys Pro Ile
                645                 650                 655

Gly Glu Asn Ser Pro Leu Leu Ser Gly Gln Gln Val
            660                 665
```

<210> SEQ ID NO 277
<211> LENGTH: 2195
<212> TYPE: DNA
<213> ORGANISM: Homo sapiens

<400> SEQUENCE: 277

```
cccagcgctc ctccccgcaa atgatcccgc cccaggggcc tatcccagtc cccccagtgc    60
cctttggttgc tggagggaag aacacaatgg atctggtgct aaaaagatgc cttcttcatt   120
tggctgtgat aggtgctttg ctggctgtgg gggctacaaa agtacccaga accaggact    180
ggcttggtgt ctcaaggcaa ctcagaacca aagcctggaa caggcagctg tatccagagt   240
ggacagaagc ccagagactt gactgctgga gaggtggtca gtgtccctc aaggtcagta    300
atgatgggcc tacactgatt ggtgcaaatg cctccttctc tattgccttg aacttccctg   360
gaagccaaaa ggtattgcca gatgggcagg ttatctgggt caacaatacc atcatcaatg   420
ggagccaggt gtggggagga cagccagtgt atccccagga aactgacgat gcctgcatct   480
tccctgatgg tggaccttgc ccatctggct cttggtctca aagagaagc tttgtttatg    540
tctgaagac ctgggccaa tactggcaag ttctaggggg cccagtgtct gggctgagca    600
ttgggacagg caggcaatg ctgggcacac accatggaa agtgactgtc taccatcgcc    660
ggggatcccg gagctatgtg cctcttgctc attccagctc agccttcacc attactgacc    720
aggtgccttt ctccgtgagc gtgtcccagt tgcgggcctt ggatggaggg aacaagcact   780
tcctgagaaa tcagcctctg acctttgccc tccagctcca tgaccccagt ggctatctgg    840
ctgaagctga cctctcctac acctgggact ttggagacag tagtggaacc ctgatctctc    900
gggcacttgt ggtcactcat acttacctgg agcctggccc agtcactgcc caggtggtcc    960
tgcaggctgc cattcctctc acctcctgtg gctcctcccc agttccaggc accacagatt   1020
ggcacaggcc aactgcagag gcccctaaca ccacagctgg ccaagtgcct actacagaag   1080
```

| | |
|---|---|
| ttgtgggtac tacacctggt caggcgccaa ctgcagagcc ctctggaacc acatctgtgc | 1140 |
| aggtgccaac cactgaagtc ataagcactg cacctgtgca gatgccaact gcagagagca | 1200 |
| caggtatgac acctgagaag gtgccagttt cagaggtcat gggtaccaca ctggcagaga | 1260 |
| tgtcaactcc agaggctaca ggtatgacac ctgcagaggt atcaattgtg gtgctttctg | 1320 |
| gaaccacagc tgcacaggta caactacag agtgggtgga gaccacagct agagagctac | 1380 |
| ctatccctga gcctgaaggt ccagatgcca gctcaatcat gtctacggaa agtattacag | 1440 |
| gttccctggg ccccctgctg gatggtacag ccaccttaag gctggtgaag agacaagtcc | 1500 |
| ccctggattg tgttctgtat cgatatggtt ccttttccgt caccctggac attgtccagg | 1560 |
| gtattgaaag tgccgagatc ctgcaggctg tgccgtccgg tgaggggat gcatttgagc | 1620 |
| tgactgtgtc ctgccaaggc gggctgccca aggaagcctg catggagatc tcatcgccag | 1680 |
| ggtgccagcc ccctgcccag cggctgtgcc agcctgtgct acccagccca gcctgccagc | 1740 |
| tggttctgca ccagatactg aagggtggct cggggacata ctgcctcaat gtgtctctgg | 1800 |
| ctgataccaa cagcctggca gtggtcagca cccagcttat catgcctggt caagaagcag | 1860 |
| gccttgggca ggttccgctg atcgtgggca tcttgctggt gttgatggct gtggtccttg | 1920 |
| catctctgat atataggcgc agactatga agcaagactt ctccgtaccc cagttgccac | 1980 |
| atagcagcag tcactggctg cgtctacccc gcatcttctg ctcttgtccc attggtgaga | 2040 |
| acagccccct cctcagtggg cagcaggtct gagtactctc atatgatgct gtgattttcc | 2100 |
| tggagttgac agaaacacct atatttcccc cagtcttccc tgggagacta ctattaactg | 2160 |
| aaataaatac tcagagcctg aaaaaaaaaa aaaaa | 2195 |

<210> SEQ ID NO 278
<211> LENGTH: 1902
<212> TYPE: DNA
<213> ORGANISM: Homo sapiens

<400> SEQUENCE: 278

| | |
|---|---|
| gggcctatcc cagtcccccc agtgcctttg gttgctggag ggaagaacac aatggatctg | 60 |
| gtgctaaaaa gatgccttct tcatttggct gtgataggtg ctttgctggc tgtgggggct | 120 |
| acaaaaggga gccaggtgtg gggaggacag ccagtgtatc cccaggaaac tgacgatgcc | 180 |
| tgcatcttcc ctgatggtgg accttgccca tctggctctt ggtctcagaa agagaagcttt | 240 |
| gtttatgtct ggaagacctg gggccaatac tggcaagttc taggggggccc agtgtctggg | 300 |
| ctgagcattg ggacaggcag ggcaatgctg gcacacaca ccatggaagt gactgtctac | 360 |
| catcgccggg gatcccggag ctatgtgcct cttgctcatt ccagctcagc cttcaccatt | 420 |
| actgaccagg tgcctttctc cgtgagcgtg tcccagttgc gggccttgga tggagggaac | 480 |
| aagcacttcc tgagaaatca gcctctgacc tttgccctcc agctccatga ccccagtggc | 540 |
| tatctggctg aagctgacct ctcctacacc tgggactttg agacagtag tggaaccctg | 600 |
| atctctcggg cacttgtggt cactcatact tacctggagc ctggcccagt cactgcccag | 660 |
| gtggtcctgc aggctgccat tcctctcacc tcctgtggct cctccccagt tccaggcacc | 720 |
| acagatgggc acaggccaac tgcagaggcc cctaacacca cagctggcca agtgcctact | 780 |
| acagaagttg tgggtactac acctggtcag gcgccaactg cagagccctc tggaaccaca | 840 |
| tctgtgcagg tgccaaccac tgaagtcata agcactgcac ctgtgcagat gccaactgca | 900 |
| gagagcacag gtatgacacc tgagaaggtg ccagtttcag aggtcatggg taccacactg | 960 |
| gcagagatgt caactccaga ggctacaggt atgacacctg cagaggtatc aattgtggtg | 1020 |

```
ctttctggaa ccacagctgc acaggtaaca actacagagt gggtggagac cacagctaga    1080
gagctaccta tccctgagcc tgaaggtcca gatgccagct caatcatgtc tacggaaagt    1140
attacaggtt ccctgggccc cctgctggat ggtacagcca ccttaaggct ggtgaagaga    1200
caagtccccc tggattgtgt tctgtatcga tatggttcct tttccgtcac cctggacatt    1260
gtccagggta ttgaaagtgc cgagatcctg caggctgtgc cgtccggtga ggggatgca    1320 tttgagctga ctgtgtcctg ccaaggcggg ctgcccaagg aagcctgcat ggagatctca    1380
tcgccagggt gccagccccc tgcccagcgg ctgtgccagc ctgtgctacc cagcccagcc    1440
tgccagctgg ttctgcacca gatactgaag ggtggctcgg gacatactg cctcaatgtg    1500 tctctggctg ataccaacag cctggcagtg gtcagcaccc agcttatcat gcctggtcaa    1560
gaagcaggcc ttgggcaggt tccgctgatc gtgggcatct tgctggtgtt gatgctgtg    1620 gtccttgcat ctctgatata taggcgcaga cttatgaagc aagacttctc cgtaccccag    1680
ttgccacata gcagcagtca ctggctgcgt ctaccccgca tcttctgctc ttgtcccatt    1740
ggtgagaaca gcccctcct cagtgggcag caggtctgag tactctcata tgatgctgtg    1800
attttcctgg agttgacaga aacacctata tttccccag tcttccctgg gagactacta    1860
ttaactgaaa taaatactca gagcctgaaa aaaaaaaaa aa                        1902
```

<210> SEQ ID NO 279
<211> LENGTH: 2181
<212> TYPE: DNA
<213> ORGANISM: Homo sapiens

<400> SEQUENCE: 279

```
gggcctatcc cagtcccccc agtgcctttg gttgctggag ggaagaacac aatggatctg      60
gtgctaaaaa gatgccttct tcatttggct gtgataggtg ctttgctggc tgtgggggct     120
acaaaagtac ccagaaacca ggactggctt ggtgtctcaa ggcaactcag aaccaaagcc     180
tggaacaggc agctgtatcc agagtggaca gaagcccaga gacttgactg ctggagaggt     240
ggtcaagtgt ccctcaaggt cagtaatgat gggcctacac tgattggtgc aaatgcctcc     300
ttctctattg ccttgaactt ccctggaagc caaaaggtat tgccagatgg gcaggttatc     360
tgggtcaaca ataccatcat caatgggagc caggtgtggg aggacagcc agtgtatccc     420 caggaaactg acgatgcctg catcttccct gatggtggac cttgcccatc tggctcttgg     480
tctcagaaga gaagctttgt ttatgtctgg aagacctggg ccaatactg gcaagttcta     540 gggggcccag tgtctgggct gagcattggg acaggcaggg caatgctggg cacacacacc     600
atggaagtga ctgtctacca tcgccgggga tcccggagct atgtgcctct gctcattcc     660 agctcagcct tcaccattac tgaccaggtg ccttttctccg tgagcgtgtc ccagttgcgg    720
gccttggatg gagggaacaa gcacttcctg agaaatcagc ctctgacctt tgccctccag    780
ctccatgacc ccagtggcta tctggctgaa gctgacctct cctacacctg gactttgga    840 gacagtagtg gaaccctgat ctctcgggca cttgtggtca ctcatactta cctggagcct    900
ggcccagtca ctgcccaggt ggtcctgcag gctgccattc ctctcacctc ctgtggctcc    960 tcccagttc aggcaccac agatgggcac aggccaactg cagaggcccc taacaccaca   1020
gctggccaag tgcctactac agaagttgtg ggtactacac ctggtcaggc gccaactgca   1080
gagccctctg gaaccacatc tgtgcaggtg ccaaccactg aagtcataag cactgcacct   1140
gtgcagatgc caactgcaga gagcacaggt atgacacctg agaaggtgcc agtttcagag   1200
```

```
gtcatgggta ccacactggc agagatgtca actccagagg ctacaggtat gacacctgca    1260
gaggtatcaa ttgtggtgct ttctggaacc acagctgcac aggtaacaac tacagagtgg    1320
gtggagacca cagctagaga gctacctatc cctgagcctg aaggtccaga tgccagctca    1380
atcatgtcta cggaaagtat tacaggttcc ctgggccccc tgctggatgg tacagccacc    1440
ttaaggctgg tgaagagaca agtcccctg gattgtgttc tgtatcgata tggttccttt    1500
tccgtcaccc tggacattgt ccagggtatt gaaagtgccg agatcctgca ggctgtgccg    1560
tccggtgagg gggatgcatt tgagctgact gtgtcctgcc aaggcgggct gcccaaggaa    1620
gcctgcatgg agatctcatc gccagggtgc cagcccctg cccagcggct gtgccagcct    1680
gtgctaccca gcccagcctg ccagctggtt ctgcaccaga tactgaaggg tggctcgggg    1740
acatactgcc tcaatgtgtc tctggctgat accaacagcc tggcagtggt cagcacccag    1800
cttatcatgc ctgtgcctgg gattcttctc acaggtcaag aagcaggcct tgggcaggtt    1860
ccgctgatcg tgggcatctt gctggtgttg atggctgtgg tccttgcatc tctgatatat    1920
aggcgcagac ttatgaagca agacttctcc gtaccccagt tgccacatag cagcagtcac    1980
tggctgcgtc taccccgcat cttctgctct tgtcccattg gtgagaacag ccccctcctc    2040
agtgggcagc aggtctgagt actctcatat gatgctgtga ttttcctgga gttgacagaa    2100
acacctatat ttcccccagt cttccctggg agactactat taactgaaat aaatactcag    2160
agcctgaaaa aaaaaaaaa a                                               2181

<210> SEQ ID NO 280
<211> LENGTH: 2041
<212> TYPE: DNA
<213> ORGANISM: Homo sapiens

<400> SEQUENCE: 280
gggcctatcc cagtcccccc agtgcctttg gttgctggag ggaagaacac aatggatctg      60
gtgctaaaaa gatgccttct tcatttggct gtgataggtg ctttgctggc tgtgggggct     120
acaaaagtac ccagaaacca ggactggctt ggtgtctcaa ggcaactcag aaccaaagcc     180
tggaacaggc agctgtatcc agagtggaca gaagcccaga gacttgactg ctggagaggt     240
ggtcaagtgt ccctcaaggt cagtaatgat gggcctacac tgattggtgc aaatgcctcc     300
ttctctattg ccttgaactt ccctggaagc caaaaggtat tgccagatgg gcaggttatc     360
tgggtcaaca ataccatcat caatgggagc caggtgtggg aggacagcc agtgtatccc     420 caggaaactg acgatgcctg catcttccct gatggtggac cttgcccatc tggctcttgg     480
tctcagaaga gaagctttgt ttatgtctgg aagacctggg gccaatactg gcaagttcta    540
gggggcccag tgtctgggct gagcattggg acaggcaggg caatgctggg cacacacacc    600
atggaagtga ctgtctacca tcgccgggga tcccggagct atgtgcctct tgctcattcc    660
agctcagcct tcaccattac tgaccaggtg ccttttctccg tgagcgtgtc ccagttgcgg    720
gccttggatg gagggaacaa gcacttcctg agaaatcagc ctctgacctt tgccctccag    780
ctccatgacc ccagtggcta tctggctgaa gctgacctct cctacacctg gactttgga    840 gacagtagtg gaaccctgat ctctcgggca cttgtggtca ctcatactta cctggagcct    900
ggcccagtca ctgcccaggt ggtcctgcag gctgccattc ctctcacctc ctgtggctcc    960
tccccagttc caggcaccac agatgggcac aggccaactg cagaggcccc taacaccaca   1020
gctggccaag tgcctactac agaagttgtg ggtactacac ctggtcaggc gccaactgca   1080
gagccctctg gaaccacatc tgtgcaggtg ccaaccactg aagtcataag cactgcacct   1140
```

```
gtgcagatgc caactgcaga gagcacagct gcacaggtaa caactacaga gtgggtggag      1200
accacagcta gagagctacc tatccctgag cctgaaggtc cagatgccag ctcaatcatg      1260
tctacggaaa gtattacagg ttccctgggc cccctgctgg atggtacagc caccttaagg      1320
ctggtgaaga gacaagtccc cctggattgt gttctgtatc gatatggttc cttttccgtc      1380
accctggaca ttgtccaggg tattgaaagt gccgagatcc tgcaggctgt gccgtccggt      1440 gaggggatg catttgagct gactgtgtcc tgccaaggcg gctgcccaa ggaagcctgc        1500 atggagatct catcgccagg gtgccagccc cctgcccagc ggctgtgcca gcctgtgcta     1560
cccagcccag cctgccagct ggttctgcac cagatactga agggtggctc ggggacatac      1620
tgcctcaatg tgtctctggc tgataccaac agcctggcag tggtcagcac ccagcttatc      1680
atgcctgtgc ctgggattct tctcacaggt caagaagcag gccttgggca ggttccgctg      1740
atcgtgggca tcttgctggt gttgatggct gtggtccttg catctctgat atataggcgc      1800
agacttatga agcaagactt ctccgtaccc cagttgccac atagcagcag tcactggctg      1860
cgtctacccc gcatcttctg ctcttgtccc attggtgaga acagccccct cctcagtggg     1920
cagcaggtct gagtactctc atatgatgct gtgattttcc tggagttgac agaaacacct      1980
atatttcccc cagtcttccc tgggagacta ctattaactg aaataaatac tcagagcctg     2040
a                                                                      2041

<210> SEQ ID NO 281
<211> LENGTH: 2020
<212> TYPE: DNA
<213> ORGANISM: Homo sapiens

<400> SEQUENCE: 281
gggcctatcc cagtcccccc agtgcctttg gttgctggag ggaagaacac aatggatctg       60
gtgctaaaaa gatgccttct tcatttggct gtgataggtg ctttgctggc tgtgggggct      120
acaaaagtac ccagaaacca ggactggctt ggtgtctcaa ggcaactcag aaccaaagcc      180
tggaacaggc agctgtatcc agagtggaca gaagcccaga gacttgactg ctggagaggt      240
ggtcaagtgt ccctcaaggt cagtaatgat gggcctacac tgattggtgc aaatgcctcc      300
ttctctattg ccttgaactt ccctggaagc caaaaggtat gccagatgg gcaggttatc       360 tgggtcaaca ataccatcat caatgggagc caggtgtggg gaggacagcc agtgtatccc      420
caggaaactg acgatgcctg catcttccct gatggtggac cttgcccatc tggctcttgg      480
tctcagaaga gaagctttgt ttatgtctgg aagacctggg gccaatactg gcaagttcta      540
gggggcccag tgtctgggct gagcattggg acaggcaggg caatgctggg cacacacacc      600
atggaagtga ctgtctacca tcgccgggga tcccggagct atgtgcctct tgctcattcc      660
agctcagcct tcaccattac tgaccaggtg cctttctccg tgagcgtgtc ccagttgcgg      720
gccttggatg gagggaacaa gcacttcctg agaaatcagc ctctgacctt tgccctccag      780
ctccatgacc ccagtggcta tctggctgaa gctgacctct cctacacctg ggactttgga      840
```

```
gacagtagtg gaaccctgat ctctcgggca cttgtggtca ctcatactta cctggagcct    900
ggcccagtca ctgcccaggt ggtcctgcag gctgccattc ctctcacctc ctgtggctcc    960
tccccagttc caggcaccac agatgggcac aggccaactg cagaggcccc taacaccaca   1020
gctggccaag tgcctactac agaagttgtg ggtactacac ctggtcaggc gccaactgca   1080
gagccctctg gaaccacatc tgtgcaggtg ccaaccactg aagtcataag cactgcacct   1140
gtgcagatgc caactgcaga gagcacagct gcacaggtaa caactacaga gtgggtggag   1200
accacagcta gagagctacc tatccctgag cctgaaggtc cagatgccag ctcaatcatg   1260
tctacggaaa gtattacagg ttccctgggc cccctgctgg atggtacagc caccttaagg   1320
ctggtgaaga gacaagtccc cctggattgt gttctgtatc gatatggttc cttttccgtc   1380
accctggaca ttgtccaggg tattgaaagt gccgagatcc tgcaggctgt gccgtccggt   1440 gaggggatg catttgagct gactgtgtcc tgccaaggcg ggctgcccaa ggaagcctgc   1500
atggagatct catcgccagg gtgccagccc cctgcccagc ggctgtgcca gcctgtgcta   1560
cccagcccag cctgccagct ggttctgcac cagatactga agggtggctc ggggacatac   1620
tgcctcaatg tgtctctggc tgataccaac agcctggcag tggtcagcac ccagcttatc   1680
atgcctggtc aagaagcagg ccttgggcag gttccgctga tcgtgggcat cttgctggtg   1740
ttgatggctg tggtccttgc atctctgata taggcgca gacttatgaa gcaagacttc   1800
tccgtacccc agttgccaca tagcagcagt cactggctgc gtctaccccg catcttctgc   1860
tcttgtccca ttggtgagaa cagcccctc ctcagtgggc agcaggtctg agtactctca   1920
tatgatgctg tgatttcct ggagttgaca gaaacaccta tatttccccc agtcttccct   1980
gggagactac tattaactga aataaatact cagagcctga                         2020

<210> SEQ ID NO 282
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Tyr Gly Arg Lys Lys Arg Arg Gln Arg Arg Leu Tyr Arg Ser Pro
1               5                   10                  15

Ala Met Pro Glu Asn Leu
            20
```

ANTIBODIES TO PMEL17 AND CONJUGATES THEREOF

CROSS-REFERENCE TO RELATED APPLICATIONS

This is application is a nonprovisional application of U.S. Provisional Patent Application No. 62/783,565, filed Dec. 21, 2018 and U.S. Provisional Patent Application No. 62/803,110 filed Feb. 8, 2019, each of which are herein incorporated by reference in their entireties.

SEQUENCE LISTING

The instant application contains a Sequence Listing which has been submitted electronically in ASCII format and is hereby incorporated by reference in its entirety. Said ASCII copy, created on Dec. 6, 2019, is named PAT058359-US-NP_SL.txt and is 285,253 bytes in size

FIELD OF THE INVENTION

The present invention generally relates to anti-PMEL17 antibodies, or fragments thereof, conjugates thereof, including GNAQ/GNA11 inhibitor conjugates thereof, and their uses for the treatment or prevention of cancer.

BACKGROUND OF THE INVENTION

PMEL17 (also referred to as gp100 and SILV) is a single-pass Type I transmembrane protein produced by melanocytes and involved in melanin synthesis. Along its maturation, PMEL17 is transiently expressed at the cell surface before trafficked to melanosomes where PMEL17 is degraded into various domains that multimerizes to form fibrillar sheets. Such pattern then serves as a support for trapping melanin. The melanosomes PMEL17 expression is regulated by MITF, a lineage oncogene, and was found to be up-regulated in a variety of primary and metastatic subcutaneous and uveal melanomas. The transient cell surface expression and subsequent internalization of PMEL17 makes it a suitable target for developing antibody drug conjugate (ADC) for the treatment of melanoma.

PMEL17 and Cancer

Along its maturation, PMEL17 is heavily processed by pro-protein convertases. The protein is cleaved between V467/K468 forming two subdomains, Mα at the N-term and M3 at the C-term, supposedly maintained via a disulphide bridge. After leaving the golgi apparatus, some PMEL17 molecules are transiently expressed at the cell surface. Most PMEL17 is then redirected to a melanocyte for further maturation while some PMEL17 appears to be shed. Following additional enzymatic cleavages, PMEL17 is degraded into various domains which reorganize and form fibrillar sheets where melanin polymerizes (Valencia J C, et al. *Sorting of Pmel17 to melanosomes through the plasma membrane by AP1 and AP2: evidence for the polarized nature of melanocytes*. J Cell Sci. 2006 Mar. 15; 119(Pt 6):1080-91; Theos A C, et al. *The Silver locus product Pmel17/gp100/Silv/ME20: controversial in name and in function*. Pigment Cell Res. 2005 October; 18(5):322-36).

PMEL17 constitutes a potential therapeutic target for the treatment of melanoma. PMEL17 is a direct transcriptional target of MITF, a lineage oncogene in melanoma, as observed by mRNA expression studies (Du J, et al. *MLANA/MART1 and SILV/PMEL17/GP100 are transcriptionally regulated by MITF in melanocytes and melanoma*. Am J Pathol. 2003 July; 163(1):333-43). PMEL17 expression is restricted to the melanocyte lineage which includes skin melanocytes, hair bulb melanocytes, retinal pigment epithelium, pigmented cilliary epithelium, and possibly the choroid melanocytes in the retina. PMEL17 is also highly expressed in melanocyte lineage tumors such as subcutaneous and uveal melanoma. In contrast, mRNA studies have demonstrated that PMEL17 expression is limited on other tumor types and normal tissues (Wagner S N, Wagner C, Schultewolter T, Goos M. *Analysis of Pmel17/gp100 expression in primary human tissue specimens: implications for melanoma immuno-and gene-therapy*. Cancer Immunol Immunother. 1997 June; 44(4):239-47). Besides, ADC and ImmTAC compounds targeting PMEL17 have previously been described to specifically induce killing of melanoma in vivo and in vitro and are currently evaluated in clinical trials (Chen Y, et al. *The melanosomal protein PMEL17 as a target for antibody drug conjugate therapy in melanoma*. J Biol Chem. 2012 Jul. 13; 287(29):24082-91. doi:10.1074/jbc.M112.361485. Epub 2012 May 21).

GNAQ/GNA11 and Cancer

GNAQ and GNA11 genes encode for the alpha subunit of the heterotrimeric G proteins Gq/11, which are almost ubiquitously expressed and act as binary molecular switches that cycle between active guanosine triphosphate (GTP)-bound and inactive guanosine diphosphate (GDP)-bound states. GTP-bound Gαq and Gα11 activate β-isoforms of phospholipase C, which triggers a number of signal transduction pathways through the generation of second messengers IP3 and DAG. Signaling termination is triggered by GTP hydrolysis mediated by intrinsic GTPase activity of these Gα proteins. Gq and G11 have been shown to be involved in a vast array of physiological functions including platelet activation, myocardial hypertrophy, and smooth muscle tone.

Oncogenic mutations in either GNAQ or GNA11 occur in up to 90% of cases of uveal melanoma (UM) and in ~2-3% of cutaneous melanoma. Approximately 95% of these mutations affect codons 209 (Q209) in the Ras-like domain, resulting in complete or partial loss of GTPase activity and thereby locking GNAQ/11 into its active state. Q209 GNAQ/11 are dominant acting oncogenes that transform melanocytes by triggering the activation of multiple pathways including PKC/MAPK, Rho/Rac, β-catenin, and YAP. Although the PKC/MAPK pathway has been shown as one contributing factor to GNAQ-mediated oncogenesis, multiple lines of evidence suggest that mutant GNAQ/11 govern additional pathways that are also likely to play a role in UM tumorigenesis (i.e. YAP, β-catenin). Interestingly, another somatic activating mutation in GNAQ (R183Q) was recently described to be the cause of the Sturge-Weber syndrome (SWS), a neurocutaneous disorder characterized by capillary malformation (port-wine stains), and choroidal and leptomeningeal vascular malformations. Thus, GNAQ and GNA11 constitutes potential therapeutic targets for the treatment of uveal and cutaneous melanoma.

Antibody Drug Conjugates

Antibody drug conjugates ("ADCs") have been used for the local delivery of cytotoxic agents in the treatment of cancer (see, e.g., Lambert, Curr. Opinion In Pharmacology 5:543-549, 2005). ADCs allow targeted delivery of the drug moiety where maximum efficacy with minimal toxicity may be achieved. ADCs include an antibody selected for its ability to bind to a cell targeted for therapeutic intervention, linked to a drug selected for its cytostatic or cytotoxic activity. Binding of the antibody to the targeted cell thereby delivers the drug to the site where its therapeutic effect is needed.

Many antibodies that recognize and selectively bind to targeted cells, e.g., cancer cells, have been disclosed for use in ADCs. In spite of the extensive work on ADCs, antibody binding to a particular target of interest is not sufficient to predict success in ADC applications. Examples of factors that can effect therapeutic effectiveness of ADCs (besides target-intrinsic features) include various aspects that need customized fine-tuning, such as the optimal antibody affinity as a balance between target-mediated disposition (TMDD) and efficacy-driving exposure, evaluation of Fc-mediated functions (antibody-dependent cell-mediated cytotoxicity, ADCC), method of conjugation (site-specific or not), the ratio of the drug/payload molecules that conjugate to each antibody ("DAR" or "drug antibody ratio"), the cleavability or stability of the linker, stability of the ADC, and the tendency of an ADC to aggregate.

There remains a need for antibodies, attachment methods, and cytotoxic payloads with improved properties for use as effective ADC therapeutic compositions and methods.

SUMMARY OF THE INVENTION

In one embodiment, the present application discloses an antibody or antigen binding fragment thereof that binds PMEL17 comprising:

a. a heavy chain variable region that comprises a heavy chain CDR1 (Complementarity Determining Region 1) of SEQ ID NO:1, 4, 5 or 7, a heavy chain CDR2 (Complementarity Determining Region 2) of SEQ ID NO:2, 6 or 8, and a heavy chain CDR3 (Complementarity Determining Region 3) of SEQ ID NO:3 or 9; and a light chain variable region that comprises a light chain CDR1 (Complementarity Determining Region 1) of SEQ ID NO:14, 17 or 20, a light chain CDR2 (Complementarity Determining Region 2) of SEQ ID NO:15 or 18, and a light chain CDR3 (Complementarity Determining Region 3) of SEQ ID NO:16 or 19;

b. a heavy chain variable region that comprises a heavy chain CDR1 of SEQ ID NO:33, 36, 37 or 39, a heavy chain CDR2 of SEQ ID NO:34, 38 or 40; a heavy chain CDR3 of SEQ ID NO:35 or 41; a light chain CDR1 of SEQ ID NO:46, 49 or 52; a light chain CDR2 of SEQ ID NO:47 or 50; and a light chain CDR3 of SEQ ID NO:48 or 51;

c. a heavy chain variable region that comprises a heavy chain CDR1 of SEQ ID NO:5, 7, 57 or 60, a heavy chain CDR2 of SEQ ID NO:58, 61 or 62; a heavy chain CDR3 of SEQ ID NO:59 or 63; a light chain CDR1 of SEQ ID NO:68, 71 or 74; a light chain CDR2 of SEQ ID NO:69 or 72; and a light chain CDR3 of SEQ ID NO:70 or 73;

d. a heavy chain variable region that comprises a heavy chain CDR1 of SEQ ID NO:79, 82, 83 or 85, a heavy chain CDR2 of SEQ ID NO:80, 84 or 86; a heavy chain CDR3 of SEQ ID NO:81 or 87; a light chain CDR1 of SEQ ID NO:92, 95 or 98; a light chain CDR2 of SEQ ID NO:93 or 96; and a light chain CDR3 of SEQ ID NO:94 or 97;

e. a heavy chain variable region that comprises a heavy chain CDR1 of SEQ ID NO:103, 106, 107 or 109, a heavy chain CDR2 of SEQ ID NO:104, 108 or 110; a heavy chain CDR3 of SEQ ID NO: 105 or 111; a light chain CDR1 of SEQ ID NO:49, 52 or 116; a light chain CDR2 of SEQ ID NO:47 or 50; and a light chain CDR3 of SEQ ID NO:117 or 118;

f. a heavy chain variable region that comprises a heavy chain CDR1 of SEQ ID NO:123, 126, 127 or 129, a heavy chain CDR2 of SEQ ID NO:124, 128 or 130; a heavy chain CDR3 of SEQ ID NO:125 or 131; a light chain CDR1 of SEQ ID NO:136, 139 or 142; a light chain CDR2 of SEQ ID NO:137 or 140; and a light chain CDR3 of SEQ ID NO:138 or 141;

g. a heavy chain variable region that comprises a heavy chain CDR1 of SEQ ID NO:123, 126, 127 or 129, a heavy chain CDR2 of SEQ ID NO:124, 128 or 130; a heavy chain CDR3 of SEQ ID NO:147 or 148; a light chain CDR1 of SEQ ID NO:153, 156 or 158; a light chain CDR2 of SEQ ID NO:50 or 154; and a light chain CDR3 of SEQ ID NO:155 or 157;

h. a heavy chain variable region that comprises a heavy chain CDR1 of SEQ ID NO:103, 106, 107 or 109, a heavy chain CDR2 of SEQ ID NO:104, 108 or 110; a heavy chain CDR3 of SEQ ID NO:163 or 164; a light chain CDR1 of SEQ ID NO:49, 52 or 116; a light chain CDR2 of SEQ ID NO:47 or 50; and a light chain CDR3 of SEQ ID NO:169 or 170;

i. a heavy chain variable region that comprises a heavy chain CDR1 of SEQ ID NO:175, 178, 179 or 181, a heavy chain CDR2 of SEQ ID NO:176, 180 or 182; a heavy chain CDR3 of SEQ ID NO:177 or 183; a light chain CDR1 of SEQ ID NO:49, 52 or 116; a light chain CDR2 of SEQ ID NO:47 or 50; and a light chain CDR3 of SEQ ID NO:188 or 189;

j. a heavy chain variable region that comprises a heavy chain CDR1 of SEQ ID NO: 103, 106, 107 or 109, a heavy chain CDR2 of SEQ ID NO: 104, 108 or 110; a heavy chain CDR3 of SEQ ID NO:194 or 195; a light chain CDR1 of SEQ ID NO: 49, 52 or 116; a light chain CDR2 of SEQ ID NO: 47 or 50; and a light chain CDR3 of SEQ ID NO:200 or 201;

k. a heavy chain variable region that comprises a heavy chain CDR1 of SEQ ID NO:206, 209, 210 or 212, a heavy chain CDR2 of SEQ ID NO:207, 211 or 213; a heavy chain CDR3 of SEQ ID NO:208 or 214; a light chain CDR1 of SEQ ID NO:153, 156 or 158; a light chain CDR2 of SEQ ID NO:50 or 154; and a light chain CDR3 of SEQ ID NO:219 or 220;

l. a heavy chain variable region that comprises a heavy chain CDR1 of SEQ ID NO: 206, 209, 210 or 212, a heavy chain CDR2 of SEQ ID NO: 207, 211 or 213; a heavy chain CDR3 of SEQ ID NO:225 or 226; a light chain CDR1 of SEQ ID NO:136, 139 or 142; a light chain CDR2 of SEQ ID NO:137 or 140; and a light chain CDR3 of SEQ ID NO:231 or 232;

m. a heavy chain variable region that comprises a heavy chain variable region that comprises an HCDR1 of SEQ ID NO: 206, 209, 210 or 212, an HCDR2 of SEQ ID NO: 207, 211 or 213, and an HCDR3 of SEQ ID NO:237 or 238; and a light chain variable region that comprises an LCDR1 of SEQ ID NO:243, 245 or 247, an LCDR2 of SEQ ID NO:47 or 50, and an LCDR3 of SEQ ID NO:244 or 246;

n. a heavy chain variable region that comprises a heavy chain variable region that comprises an HCDR1 of SEQ ID NO: 206, 209, 210 or 212, an HCDR2 of SEQ ID NO: 207, 211 or 213, and an HCDR3 of SEQ ID NO:252 or 253; and a light chain variable region that comprises an LCDR1 of SEQ ID NO:153, 156 or 158, an LCDR2 of SEQ ID NO:50 or 154, and an LCDR3 of SEQ ID NO:258 or 259;

o. a heavy chain CDR1 of SEQ ID NO:1, a heavy chain CDR2 of SEQ ID NO:2, a heavy chain CDR3 of SEQ ID NO:3, a light chain CDR1 of SEQ ID NO:14, a light chain CDR2 of SEQ ID NO:15, and a light chain CDR3 of SEQ ID NO:16;
p. a heavy chain CDR1 of SEQ ID NO: 4, a heavy chain CDR2 of SEQ ID NO:2, a heavy chain CDR3 of SEQ ID NO:3, a light chain CDR1 of SEQ ID NO:14, a light chain CDR2 of SEQ ID NO:15, and a light chain CDR3 of SEQ ID NO:16;
q. a heavy chain CDR1 of SEQ ID NO:5, a heavy chain CDR2 of SEQ ID NO:6, a heavy chain CDR3 of SEQ ID NO:3, a light chain CDR1 of SEQ ID NO:17, a light chain CDR2 of SEQ ID NO: 18, and a light chain CDR3 of SEQ ID NO: 19;
r. a heavy chain CDR1 of SEQ ID NO:7, a heavy chain CDR2 of SEQ ID NO:8, a heavy chain CDR3 of SEQ ID NO:9, a light chain CDR1 of SEQ ID NO:20, a light chain CDR2 of SEQ ID NO:18, and a light chain CDR3 of SEQ ID NO:16;
s. a heavy chain CDR1 of SEQ ID NO:33, a heavy chain CDR2 of SEQ ID NO:34, a heavy chain CDR3 of SEQ ID NO:35, a light chain CDR1 of SEQ ID NO:46, a light chain CDR2 of SEQ ID NO:47, and a light chain CDR3 of SEQ ID NO:48;
t. a heavy chain CDR1 of SEQ ID NO:36, a heavy chain CDR2 of SEQ ID NO:34, a heavy chain CDR3 of SEQ ID NO:35, a light chain CDR1 of SEQ ID NO:46, a light chain CDR2 of SEQ ID NO:47, and a light chain CDR3 of SEQ ID NO:48;
u. a heavy chain CDR1 of SEQ ID NO:37, a heavy chain CDR2 of SEQ ID NO:38, a heavy chain CDR3 of SEQ ID NO:35, a light chain CDR1 of SEQ ID NO:49, a light chain CDR2 of SEQ ID NO:50, and a light chain CDR3 of SEQ ID NO:51;
v. a heavy chain CDR1 of SEQ ID NO: 39, a heavy chain CDR2 of SEQ ID NO:40, a heavy chain CDR3 of SEQ ID NO:41, a light chain CDR1 of SEQ ID NO:52, a light chain CDR2 of SEQ ID NO:50, and a light chain CDR3 of SEQ ID NO:48;
w. a heavy chain CDR1 of SEQ ID NO:57, a heavy chain CDR2 of SEQ ID NO:58, a heavy chain CDR3 of SEQ ID NO:59, a light chain CDR1 of SEQ ID NO:68, a light chain CDR2 of SEQ ID NO:69, and a light chain CDR3 of SEQ ID NO:70;
x. a heavy chain CDR1 of SEQ ID NO:60, a heavy chain CDR2 of SEQ ID NO:58, a heavy chain CDR3 of SEQ ID NO:59, a light chain CDR1 of SEQ ID NO:68, a light chain CDR2 of SEQ ID NO:69, and a light chain CDR3 of SEQ ID NO:70;
y. a heavy chain CDR1 of SEQ ID NO:5, a heavy chain CDR2 of SEQ ID NO:61, a heavy chain CDR3 of SEQ ID NO:59, a light chain CDR1 of SEQ ID NO:71, a light chain CDR2 of SEQ ID NO:72, and a light chain CDR3 of SEQ ID NO:73;
z. a heavy chain CDR1 of SEQ ID NO:7, a heavy chain CDR2 of SEQ ID NO:62, a heavy chain CDR3 of SEQ ID NO:63, a light chain CDR1 of SEQ ID NO:74, a light chain CDR2 of SEQ ID NO:72, and a light chain CDR3 of SEQ ID NO:70;
aa. a heavy chain CDR1 of SEQ ID NO:79, a heavy chain CDR2 of SEQ ID NO:80, a heavy chain CDR3 of SEQ ID NO:81, a light chain CDR1 of SEQ ID NO:92, a light chain CDR2 of SEQ ID NO:93, and a light chain CDR3 of SEQ ID NO:94;
bb. a heavy chain CDR1 of SEQ ID NO:82, a heavy chain CDR2 of SEQ ID NO:80, a heavy chain CDR3 of SEQ ID NO:81, a light chain CDR1 of SEQ ID NO:92, a light chain CDR2 of SEQ ID NO:93, and a light chain CDR3 of SEQ ID NO:94;
cc. a heavy chain CDR1 of SEQ ID NO:83, a heavy chain CDR2 of SEQ ID NO:84, a heavy chain CDR3 of SEQ ID NO:81, a light chain CDR1 of SEQ ID NO:95, a light chain CDR2 of SEQ ID NO:96, and a light chain CDR3 of SEQ ID NO: 97;
dd. a heavy chain CDR1 of SEQ ID NO: 85, a heavy chain CDR2 of SEQ ID NO:86, a heavy chain CDR3 of SEQ ID NO:87, a light chain CDR1 of SEQ ID NO:98, a light chain CDR2 of SEQ ID NO:96, and a light chain CDR3 of SEQ ID NO:94;
ee. a heavy chain CDR1 of SEQ ID NO:103, a heavy chain CDR2 of SEQ ID NO:104, a heavy chain CDR3 of SEQ ID NO:105, a light chain CDR1 of SEQ ID NO: 116; a light chain CDR2 of SEQ ID NO:47; and a light chain CDR3 of SEQ ID NO:117;
ff. a heavy chain CDR1 of SEQ ID NO:106, a heavy chain CDR2 of SEQ ID NO:104, a heavy chain CDR3 of SEQ ID NO:105, a light chain CDR1 of SEQ ID NO: 116, a light chain CDR2 of SEQ ID NO:47, and a light chain CDR3 of SEQ ID NO:117;
gg. a heavy chain CDR1 of SEQ ID NO:107, a heavy chain CDR2 of SEQ ID NO:108, a heavy chain CDR3 of SEQ ID NO:105, a light chain CDR1 of SEQ ID NO:49, a light chain CDR2 of SEQ ID NO:50, and a light chain CDR3 of SEQ ID NO:118;
hh. a heavy chain CDR1 of SEQ ID NO:109, a heavy chain CDR2 of SEQ ID NO:110, a heavy chain CDR3 of SEQ ID NO:111, a light chain CDR1 of SEQ ID NO:52 a light chain CDR2 of SEQ ID NO:50, and a light chain CDR3 of SEQ ID NO:117;
ii. a heavy chain CDR1 of SEQ ID NO:123, a heavy chain CDR2 of SEQ ID NO:124, a heavy chain CDR3 of SEQ ID NO:125, a light chain CDR1 of SEQ ID NO:136, a light chain CDR2 of SEQ ID NO:137, and a light chain CDR3 of SEQ ID NO:138;
jj. a heavy chain CDR1 of SEQ ID NO:126, a heavy chain CDR2 of SEQ ID NO:124, a heavy chain CDR3 of SEQ ID NO:125, a light chain CDR1 of SEQ ID NO:136, a light chain CDR2 of SEQ ID NO:137, and a light chain CDR3 of SEQ ID NO:138;
kk. a heavy chain CDR1 of SEQ ID NO:127, a heavy chain CDR2 of SEQ ID NO:128, a heavy chain CDR3 of SEQ ID NO:125, a light chain CDR1 of SEQ ID NO:139, a light chain CDR2 of SEQ ID NO:140, and a light chain CDR3 of SEQ ID NO: 141;
ll. a heavy chain CDR1 of SEQ ID NO: 129, a heavy chain CDR2 of SEQ ID NO:130, a heavy chain CDR3 of SEQ ID NO:131, a light chain CDR1 of SEQ ID NO:142, a light chain CDR2 of SEQ ID NO:140, and a light chain CDR3 of SEQ ID NO:138;
mm. a heavy chain CDR1 of SEQ ID NO:123, a heavy chain CDR2 of SEQ ID NO:124, a heavy chain CDR3 of SEQ ID NO:147, a light chain CDR1 of SEQ ID NO:153, a light chain CDR2 of SEQ ID NO:154, and a light chain CDR3 of SEQ ID NO:155;
nn. a heavy chain CDR1 of SEQ ID NO:126, a heavy chain CDR2 of SEQ ID NO:124, a heavy chain CDR3 of SEQ ID NO:147, a light chain CDR1 of SEQ ID NO:153, a light chain CDR2 of SEQ ID NO: 154, and a light chain CDR3 of SEQ ID NO:155;
oo. a heavy chain CDR1 of SEQ ID NO:127, a heavy chain CDR2 of SEQ ID NO:128, a heavy chain CDR3 of SEQ ID NO:147, a light chain CDR1 of SEQ ID NO:156, a light chain CDR2 of SEQ ID NO:50, and a light chain CDR3 of SEQ ID NO:157;

pp. a heavy chain CDR1 of SEQ ID NO: 129, a heavy chain CDR2 of SEQ ID NO:130, a heavy chain CDR3 of SEQ ID NO:148, a light chain CDR1 of SEQ ID NO:158, a light chain CDR2 of SEQ ID NO:50, and a light chain CDR3 of SEQ ID NO:155;

qq. a heavy chain CDR1 of SEQ ID NO:103, a heavy chain CDR2 of SEQ ID NO:104, a heavy chain CDR3 of SEQ ID NO:163, a light chain CDR1 of SEQ ID NO: 116, a light chain CDR2 of SEQ ID NO:47, and a light chain CDR3 of SEQ ID NO:169;

rr. a heavy chain CDR1 of SEQ ID NO:106, a heavy chain CDR2 of SEQ ID NO:104, a heavy chain CDR3 of SEQ ID NO:163, a light chain CDR1 of SEQ ID NO:116, a light chain CDR2 of SEQ ID NO:47, and a light chain CDR3 of SEQ ID NO:169;

ss. a heavy chain CDR1 of SEQ ID NO:107, a heavy chain CDR2 of SEQ ID NO:108, a heavy chain CDR3 of SEQ ID NO:163, a light chain CDR1 of SEQ ID NO:49, a light chain CDR2 of SEQ ID NO:50, and a light chain CDR3 of SEQ ID NO:170;

tt. a heavy chain CDR1 of SEQ ID NO: 109, a heavy chain CDR2 of SEQ ID NO:110, a heavy chain CDR3 of SEQ ID NO:164, a light chain CDR1 of SEQ ID NO:52, a light chain CDR2 of SEQ ID NO:50, and a light chain CDR3 of SEQ ID NO:169;

uu. a heavy chain CDR1 of SEQ ID NO:175, a heavy chain CDR2 of SEQ ID NO:176, a heavy chain CDR3 of SEQ ID NO:177, a light chain CDR1 of SEQ ID NO:116, a light chain CDR2 of SEQ ID NO:47, and a light chain CDR3 of SEQ ID NO:188;

vv. a heavy chain CDR1 of SEQ ID NO:178, a heavy chain CDR2 of SEQ ID NO:176, a heavy chain CDR3 of SEQ ID NO:177, a light chain CDR1 of SEQ ID NO:116, a light chain CDR2 of SEQ ID NO:47, and a light chain CDR3 of SEQ ID NO:188;

ww. a heavy chain CDR1 of SEQ ID NO:179, a heavy chain CDR2 of SEQ ID NO:180, a heavy chain CDR3 of SEQ ID NO:177, a light chain CDR1 of SEQ ID NO:49, a light chain CDR2 of SEQ ID NO:50, and a light chain CDR3 of SEQ ID NO:189;

xx. a heavy chain CDR1 of SEQ ID NO: 181, a heavy chain CDR2 of SEQ ID NO:182; a heavy chain CDR3 of SEQ ID NO:183, a light chain CDR1 of SEQ ID NO:52, a light chain CDR2 of SEQ ID NO:50, and a light chain CDR3 of SEQ ID NO:188;

yy. a heavy chain CDR1 of SEQ ID NO: 103, a heavy chain CDR2 of SEQ ID NO: 104, a heavy chain CDR3 of SEQ ID NO:194, a light chain CDR1 of SEQ ID NO: 116, a light chain CDR2 of SEQ ID NO: 47, and a light chain CDR3 of SEQ ID NO:200;

zz. a heavy chain CDR1 of SEQ ID NO: 106, a heavy chain CDR2 of SEQ ID NO: 104, a heavy chain CDR3 of SEQ ID NO:194, a light chain CDR1 of SEQ ID NO: 116, a light chain CDR2 of SEQ ID NO: 47, and a light chain CDR3 of SEQ ID NO:200;

aaa. a heavy chain CDR1 of SEQ ID NO: 107, a heavy chain CDR2 of SEQ ID NO: 108, a heavy chain CDR3 of SEQ ID NO:194, a light chain CDR1 of SEQ ID NO: 49, a light chain CDR2 of SEQ ID NO: 50, and a light chain CDR3 of SEQ ID NO: 201;

bbb. a heavy chain CDR1 of SEQ ID NO: 109, a heavy chain CDR2 of SEQ ID NO: 110, a heavy chain CDR3 of SEQ ID NO:195, a light chain CDR1 of SEQ ID NO: 52, a light chain CDR2 of SEQ ID NO: 50, and a light chain CDR3 of SEQ ID NO:200;

ccc. a heavy chain CDR1 of SEQ ID NO:206, a heavy chain CDR2 of SEQ ID NO:207, a heavy chain CDR3 of SEQ ID NO:208, a light chain CDR1 of SEQ ID NO:153, a light chain CDR2 of SEQ ID NO:154, and a light chain CDR3 of SEQ ID NO:219;

ddd. a heavy chain CDR1 of SEQ ID NO:209, a heavy chain CDR2 of SEQ ID NO:207, a heavy chain CDR3 of SEQ ID NO:208, a light chain CDR1 of SEQ ID NO:153, a light chain CDR2 of SEQ ID NO: 154, and a light chain CDR3 of SEQ ID NO:219;

eee. a heavy chain CDR1 of SEQ ID NO:210, a heavy chain CDR2 of SEQ ID NO:211, a heavy chain CDR3 of SEQ ID NO:208, a light chain CDR1 of SEQ ID NO:156, a light chain CDR2 of SEQ ID NO:50, and a light chain CDR3 of SEQ ID NO:220;

fff. a heavy chain CDR1 of SEQ ID NO: 212, a heavy chain CDR2 of SEQ ID NO:213, a heavy chain CDR3 of SEQ ID NO:214, a light chain CDR1 of SEQ ID NO:158, a light chain CDR2 of SEQ ID NO:50, and a light chain CDR3 of SEQ ID NO:219;

ggg. a heavy chain CDR1 of SEQ ID NO: 206, a heavy chain CDR2 of SEQ ID NO: 207, a heavy chain CDR3 of SEQ ID NO:225, a light chain CDR1 of SEQ ID NO:136, a light chain CDR2 of SEQ ID NO:137, and a light chain CDR3 of SEQ ID NO:231;

hhh. a heavy chain CDR1 of SEQ ID NO: 209, a heavy chain CDR2 of SEQ ID NO: 207, a heavy chain CDR3 of SEQ ID NO:225, a light chain CDR1 of SEQ ID NO:136, a light chain CDR2 of SEQ ID NO:137, and a light chain CDR3 of SEQ ID NO:231;

iii. a heavy chain CDR1 of SEQ ID NO: 210, a heavy chain CDR2 of SEQ ID NO: 211, a heavy chain CDR3 of SEQ ID NO:225, a light chain CDR1 of SEQ ID NO:139, a light chain CDR2 of SEQ ID NO:140, and a light chain CDR3 of SEQ ID NO: 232;

jjj. a heavy chain CDR1 of SEQ ID NO: 212, a heavy chain CDR2 of SEQ ID NO: 213, a heavy chain CDR3 of SEQ ID NO: 226, a light chain CDR1 of SEQ ID NO:142; a light chain CDR2 of SEQ ID NO: 140; and a light chain CDR3 of SEQ ID NO:231;

kkk. a heavy chain variable region that comprises an HCDR1 of SEQ ID NO: 206, an HCDR2 of SEQ ID NO: 207, and an HCDR3 of SEQ ID NO:237, and a light chain variable region that comprises an LCDR1 of SEQ ID NO:243, an LCDR2 of SEQ ID NO:47, and an LCDR3 of SEQ ID NO:244;

lll. a heavy chain variable region that comprises an HCDR1 of SEQ ID NO: 209, an HCDR2 of SEQ ID NO: 207, and an HCDR3 of SEQ ID NO:237, and a light chain variable region that comprises an LCDR1 of SEQ ID NO:243, an LCDR2 of SEQ ID NO:47, and an LCDR3 of SEQ ID NO:244;

mmm. a heavy chain variable region that comprises an HCDR1 of SEQ ID NO: 210, an HCDR2 of SEQ ID NO: 211, and an HCDR3 of SEQ ID NO:237, and a light chain variable region that comprises an LCDR1 of SEQ ID NO:245, an LCDR2 of SEQ ID NO:50, and an LCDR3 of SEQ ID NO:246;

nnn. a heavy chain variable region that comprises an HCDR1 of SEQ ID NO: 212, an HCDR2 of SEQ ID NO: 213, and an HCDR3 of SEQ ID NO:238; and a light chain variable region that comprises an LCDR1 of SEQ ID NO:247, an LCDR2 of SEQ ID NO: 50, and an LCDR3 of SEQ ID NO:244;

ooo. a heavy chain variable region that comprises an HCDR1 of SEQ ID NO: 206, an HCDR2 of SEQ ID NO: 207, and an HCDR3 of SEQ ID NO:252, and a light chain variable region that comprises an LCDR1 of SEQ ID NO:153, an LCDR2 of SEQ ID NO: 154, and an LCDR3 of SEQ ID NO:258;
ppp. a heavy chain variable region that comprises an HCDR1 of SEQ ID NO: 209, an HCDR2 of SEQ ID NO: 207, and an HCDR3 of SEQ ID NO:252, and a light chain variable region that comprises an LCDR1 of SEQ ID NO:153, an LCDR2 of SEQ ID NO:154, and an LCDR3 of SEQ ID NO:258;
qqq. a heavy chain variable region that comprises an HCDR1 of SEQ ID NO: 210, an HCDR2 of SEQ ID NO: 211, and an HCDR3 of SEQ ID NO:252, and a light chain variable region that comprises an LCDR1 of SEQ ID NO:156, an LCDR2 of SEQ ID NO:50, and an LCDR3 of SEQ ID NO:259; or
rrr. a heavy chain variable region that comprises an HCDR1 of SEQ ID NO: 212, an HCDR2 of SEQ ID NO: 213, and an HCDR3 of SEQ ID NO: 253; and a light chain variable region that comprises an LCDR1 of SEQ ID NO:158, an LCDR2 of SEQ ID NO:50, and an LCDR3 of SEQ ID NO:258.

An antibody or antigen binding fragment thereof that binds PMEL17 of the present application may also comprise:
  a. A heavy chain variable region (VH) comprising the amino acid sequence of SEQ ID NO:10, and a light chain variable region (VL) comprising the amino acid sequence of SEQ ID NO:21;
  b. A heavy chain variable region (VH) comprising the amino acid sequence of SEQ ID NO:10, and a light chain variable region (VL) comprising the amino acid sequence of SEQ ID NO:25;
  c. A heavy chain variable region (VH) comprising the amino acid sequence of SEQ ID NO:10, and a light chain variable region (VL) comprising the amino acid sequence of SEQ ID NO:29;
  d. A heavy chain variable region (VH) comprising the amino acid sequence of SEQ ID NO:42, and a light chain variable region (VL) comprising the amino acid sequence of SEQ ID NO:53;
  e. A heavy chain variable region (VH) comprising the amino acid sequence of SEQ ID NO:64, and a light chain variable region (VL) comprising the amino acid sequence of SEQ ID NO:75;
  f. A heavy chain variable region (VH) comprising the amino acid sequence of SEQ ID NO:88, and a light chain variable region (VL) comprising the amino acid sequence of SEQ ID NO:99;
  g. A heavy chain variable region (VH) comprising the amino acid sequence of SEQ ID NO:112, and a light chain variable region (VL) comprising the amino acid sequence of SEQ ID NO:119;
  h. A heavy chain variable region (VH) comprising the amino acid sequence of SEQ ID NO:132, and a light chain variable region (VL) comprising the amino acid sequence of SEQ ID NO:143;
  i. A heavy chain variable region (VH) comprising the amino acid sequence of SEQ ID NO:149, and a light chain variable region (VL) comprising the amino acid sequence of SEQ ID NO:159;
  j. A heavy chain variable region (VH) comprising the amino acid sequence of SEQ ID NO:165, and a light chain variable region (VL) comprising the amino acid sequence of SEQ ID NO:171;
  k. A heavy chain variable region (VH) comprising the amino acid sequence of SEQ ID NO:184, and a light chain variable region (VL) comprising the amino acid sequence of SEQ ID NO:190;
  l. A heavy chain variable region (VH) comprising the amino acid sequence of SEQ ID NO:196, and a light chain variable region (VL) comprising the amino acid sequence of SEQ ID NO:202;
  m. A heavy chain variable region (VH) comprising the amino acid sequence of SEQ ID NO:215, and a light chain variable region (VL) comprising the amino acid sequence of SEQ ID NO:221;
  n. A heavy chain variable region (VH) comprising the amino acid sequence of SEQ ID NO:227, and a light chain variable region (VL) comprising the amino acid sequence of SEQ ID NO:233;
  o. A heavy chain variable region (VH) comprising the amino acid sequence of SEQ ID NO:239, and a light chain variable region (VL) comprising the amino acid sequence of SEQ ID NO:248; or
  p. A heavy chain variable region (VH) comprising the amino acid sequence of SEQ ID NO:254, and a light chain variable region (VL) comprising the amino acid sequence of SEQ ID NO:260.

In another embodiment, the antibody or antigen binding fragment thereof that binds PMEL17 comprises:
  a. A heavy chain comprising the amino acid sequence of SEQ ID NO:12, and a light chain comprising the amino acid sequence of SEQ ID NO:23;
  b. A heavy chain comprising the amino acid sequence of SEQ ID NO:12, and a light chain comprising the amino acid sequence of SEQ ID NO:27;
  c. A heavy chain comprising the amino acid sequence of SEQ ID NO:12, and a light chain comprising the amino acid sequence of SEQ ID NO:31;
  d. A heavy chain comprising the amino acid sequence of SEQ ID NO:44, and a light chain comprising the amino acid sequence of SEQ ID NO:55;
  e. A heavy chain comprising the amino acid sequence of SEQ ID NO:66, and a light chain comprising the amino acid sequence of SEQ ID NO:77;
  f. A heavy chain comprising the amino acid sequence of SEQ ID NO:90, and a light chain comprising the amino acid sequence of SEQ ID NO:101;
  g. A heavy chain comprising the amino acid sequence of SEQ ID NO:114, and a light chain comprising the amino acid sequence of SEQ ID NO:121;
  h. A heavy chain comprising the amino acid sequence of SEQ ID NO:134, and a light chain comprising the amino acid sequence of SEQ ID NO:145;
  i. A heavy chain comprising the amino acid sequence of SEQ ID NO:151, and a light chain comprising the amino acid sequence of SEQ ID NO:161;
  j. A heavy chain comprising the amino acid sequence of SEQ ID NO:167, and a light chain comprising the amino acid sequence of SEQ ID NO:173;
  k. A heavy chain comprising the amino acid sequence of SEQ ID NO:186, and a light chain comprising the amino acid sequence of SEQ ID NO:192;
  l. A heavy chain comprising the amino acid sequence of SEQ ID NO:198, and a light chain comprising the amino acid sequence of SEQ ID NO:204;
  m. A heavy chain comprising the amino acid sequence of SEQ ID NO:217, and a light chain comprising the amino acid sequence of SEQ ID NO:223;
  n. A heavy chain comprising the amino acid sequence of SEQ ID NO:229, and a light chain comprising the amino acid sequence of SEQ ID NO:235;

o. A heavy chain comprising the amino acid sequence of SEQ ID NO:241, and a light chain comprising the amino acid sequence of SEQ ID NO:250; or p. A heavy chain comprising the amino acid sequence of SEQ ID NO:256, and a light chain comprising the amino acid sequence of SEQ ID NO:262.

The antibody or antigen binding fragment thereof as described herein may comprise one or more cysteine substitutions. In one embodiment, the antibody or antigen binding fragment thereof comprises one or more cysteine substitutions selected from S152C, S375C, or both S152C and S375C of the heavy chain of the antibody or antigen binding fragment thereof, wherein the position is numbered according to the EU system. An antibody as disclosed herein can be a monoclonal antibody.

In one aspect, the Antibody Drug Conjugate of the invention is a conjugate of Formula (C):

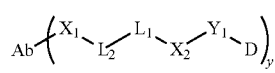     (C)

wherein:
D is a GNAQ inhibitor, a GNA11 inhibitor or an inhibitor of GNAQ and GNA11;
Ab is an antibody or antigen binding fragment thereof that binds to human PMEL17 protein;
$L_A$ is a linker;
n is 1, 2, 3 or 4, and
y is 1, 2, 3 or 4,
where the Linker-Drug moiety -($L_A$-(D)$_n$) is covalently attached to the antibody or antigen binding fragment thereof.

In another aspect of the Antibody Drug Conjugates of Formula (C), $L_A$ is a cleavable linker comprising one or more linker components selected from a self-immolative spacer, a phosphate group, a carbonate group and a bivalent peptide linker.

In another aspect, the Antibody Drug Conjugate of Formula (C) is a conjugate of Formula (C-1):

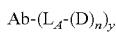     (C-1)

wherein:
D is a GNAQ inhibitor, a GNA11 inhibitor or an inhibitor of GNAQ and GNA11;
Ab is an antibody or antigen binding fragment thereof that binds to human PMEL17 protein;
$X_1$ is a bivalent coupling group;
$X_2$ is a self-immolative spacer;
$Y_1$ is

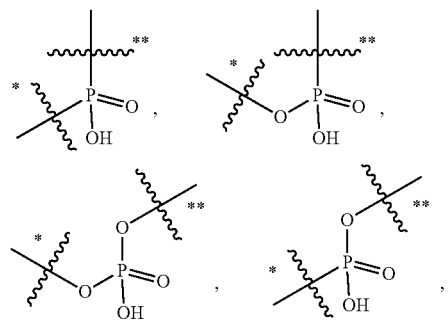

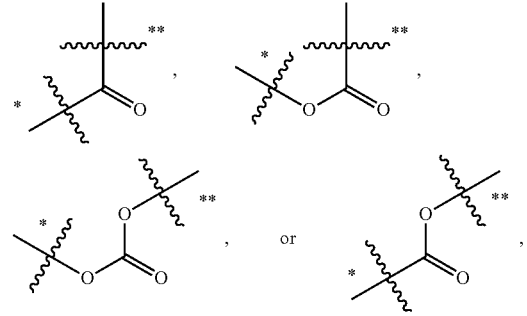

where the * of $Y_1$ indicates the point of attachment to $X_2$ and the ** of $Y_1$ indicates the point of attachment to D;
$L_1$ is a bivalent peptide linker;
$L_2$ is a bond or a linker, and
y is 1, 2, 3 or 4.

The present application also discloses pharmaceutical compositions comprising the antibodies, or antigen binding fragments thereof, disclosed herein and a pharmaceutically acceptable carrier. The present application also discloses pharmaceutical compositions comprising the antibody drug conjugates as disclosed herein and a pharmaceutically acceptable carrier.

The present application also discloses methods of treating or preventing cancer in a patient in need thereof, comprising administering to said patient the antibody drug conjugates or the pharmaceutical compositions disclosed herein, wherein the cancer expresses PMEL17, contains a mutation of the GNAQ or GNA11 gene, or the cancer expresses PMEL17 and contains a mutation of GNAQ, GNA11, or both.

In some embodiments of the methods of treatment or preventing cancer, the antibody drug conjugate or pharmaceutical composition are administered to the patient in combination with one or more additional therapeutic compounds. In one embodiment, the one or more additional therapeutic compounds is selected from a standard of care chemotherapeutic, an MDM2 inhibitor, an MRC2 inhibitor, a PKC inhibitor, a MAPK inhibitor, a costimulatory molecule, or a checkpoint inhibitor. In one embodiment, the costimulatory molecule is selected from an agonist of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, STING, or CD83 ligand. In another embodiment, the checkpoint inhibitor is selected from an inhibitor of PD-1, PD-L1, PD-L2, CTLA4, TIM3, LAG3, VISTA, BTLA, TIGIT, LAIR1, CD160, 2B4 and/or TGFR beta.

The present application also discloses the antibody drug conjugates or the pharmaceutical compositions disclosed herein, for use as a medicament. In one embodiment, the antibody drug conjugates or the pharmaceutical compositions disclosed herein, are for use in the treatment or prevention of a PMEL17 expressing cancer or a cancer that contains a mutation of the GNAQ or GNA11 gene in a patient in need thereof.

In one embodiment, the application discloses use of the antibodies or antigen binding fragments thereof, the antibody drug conjugates, or the pharmaceutical composition as disclosed herein, to treat or prevent a PMEL17 expressing cancer in a patient in need thereof.

In one embodiment, the application discloses use of the antibodies or antigen binding fragments thereof, the antibody drug conjugates, or the pharmaceutical compositions as disclosed herein, to treat or prevent a PMEL17 expressing cancer or a cancer that contains a mutation of the GNAQ or GNA11 gene in a patient in need thereof. In one embodiment, the application discloses use of the antibodies or antigen binding fragments thereof, the antibody drug conjugates, or the pharmaceutical compositions as disclosed herein, in the manufacture of a medicament.

In one embodiment, the cancer expresses PMEL17 or contains a mutation of the GNAQ or GNA11 gene. In one embodiment, the cancer is uveal melanoma, subcutaneous melanoma, hepatocellular carcinoma, or a metastatic cancer thereof.

The present application also discloses nucleic acids that encodes the antibodies or antigen binding fragments as disclosed herein. In one embodiment, the nucleic acid comprises the nucleotide sequence of SEQ ID NOs: 13, 24, 28, 32, 45, 56, 67, 78, 91, 102, 115, 122, 135, 146, 152, 162, 168, 174, 187, 193, 199, 205, 218, 224, 230, 236, 242, 251, 257, or 26. This application also discloses vectors comprising the nucleic acids, and host cells comprising the vectors or nucleic acids. This application also discloses a process for producing the antibodies or antigen binding fragments disclosed herein comprising cultivating the host cell and recovering the antibody from cell culture. In one embodiment, the process of recovering the antibody from cell culture comprises the steps of:
 a) removing cells and filtering the culture;
 b) purifying the culture by affinity chromatography;
 c) inactivating any viruses in the culture by adjusting the pH to 3.4-3.6, then readjusting the pH to 5.8-6.2 and filtering the culture;
 d) purifying the culture by cation exchange chromatography and performing on-column reduction of the culture;
 e) performing anion exchange chromatography on the culture;
 f) removing viruses by nanofiltration;
 g) filtering the culture containing the antibody; and
 h) obtaining purified antibody.

The present application also discloses a process for producing an anti-PMEL17 antibody drug conjugate comprising:
 (a) pre-forming a linker-drug moiety of the following Formula (B):

wherein:
  D is a GNAQ inhibitor, a GNA11 inhibitor or an inhibitor of GNAQ and GNA11;
  $R^8$ is a reactive group;
  $L_B$ is a cleavable or non-cleavable linker, and
  n is 1, 2, 3 or 4;
 (b) conjugating said linker-drug moiety to the antibody recovered from the cell culture using the process for producing an antibody or antigen binding fragment disclosed herein to produce an antibody drug conjugate; and
 (c) purifying the antibody drug conjugate.

The present application also discloses a diagnostic reagent comprising an antibody or antigen binding fragment thereof as disclosed herein. In some embodiments, the antibody or antigen binding fragment thereof is labeled with a radiolabel, a fluorophore, a chromophore, an imaging agent, or a metal ion.

BRIEF DESCRIPTION OF THE DRAWINGS

FIGS. 3A-3C show exemplary data on GNAQ/11 inhibition by Compound (A1) and Compound (A2). Compound (A1) and Compound (A2) reduced IP1 levels (FIG. 3A) and relative proliferation (FIG. 3B) in 92.1 cells. Immunoblots of 92.1 cells treated with Compound (A1) and Compound (A2) showed reduced ERK signaling (FIG. 3C).

FIGS. 4A-4D show exemplary data on metabolic stability and PK properties of Compound (A1). Both disappearance of Compound (A1) (FIG. 4A) as well as appearance of the ring-opened form Compound (A8) (FIG. 4B) was monitored over 24 h. With the exception of the rat, adding the % remaining Compound (A1) and % formed Compound (A8) shows stoichiometry over 24 h (FIG. 4C). The PK of Compound (A1) after intravenous dosing in mouse is characterized by a very high clearance and moderate to high volume of distribution (FIG. 4D).

FIGS. 5A-5D show exemplary data on metabolic stability and PK properties of Compound (A1) and Compound (A2). In vitro stability of Compound (A2) was tested in plasma and blood from different species (FIG. 5A). Compound (A2) showed good chemical stability in three different systems (FIG. 5B). PK of Compound (A2) in female balb/c mice showed high clearance and a short elimination half-life (FIG. 5C). Compound (A1) and Compound (A2) were stable in buffer at pH 5.6 and in lysosomes over 4 h (FIG. 5D).

FIGS. 6A-6B show exemplary data on in vitro anti-uveal melanoma activity of anti-PMEL17-(B1) ADCs. Data presented as mean of 3 independent replicates and relative to PBS-treated cells (control).

FIG. 7 shows exemplary data on anti-PMEL17-(B1) ADCs inducing apoptosis in uveal melanoma cells. Data presented as mean of 3 independent replicates.

FIGS. 8A-8B show exemplary data on in vitro anti-uveal melanoma activity of anti-PMEL17-(B2) ADCs and anti-PMEL17 mAbs. Data presented as mean of 3 independent replicates and relative to PBS-treated cells (control).

FIG. 9 shows exemplary data on GNAQ/11 inhibition by anti-PMEL17-(B1) and anti-PMEL17-(B2) ADCs in uveal melanoma cells. IP1 levels (nM) are presented as mean of 3 independent replicates.

FIGS. 14A-14E show exemplary data on PK properties of G1-(B1) ADCs. The pharmacokinetic profile (total IgG levels) of G1-(B1) showed a slightly over-proportional increase of exposure with dose between 7.5 and 30 mg/kg in nude mice (FIG. 14A). In tumor bearing mice, free payload concentrations were measured after dosing either target binding G1-(B1) or isotype control 3207-(B1). A clear (>4-fold) increase in tumor delivery of Compound (A1) payload could be observed using the targeted ADC (FIG. 14B). The conversion of Compound (A1) (open circles) into its ring-opened form Compound (A8) (filled circles) while being conjugated to the antibody was shown in vivo in mice (FIG. 14C). The exposures in an in vivo efficacy study, comparing two different DAR2 formats with the DAR4 format of G1-(B1) and with the DAR4 Fc-silent format, showed lowest clearance for the DAR2 (E152C) and the DAR4 Fc-silent ADCs, whereas the DAR2 (S375C) exposure decreases faster (FIG. 14D). FIG. 14E shows the concentration of 3207 (isotype control antibody)-(B1) DAR4 (E152C, S375C) and 3207 (isotype control antibody)-(B1) DAR4 Fc-silent conjugates over time.

FIGS. 15A-15C show exemplary data on in vitro stability of anti-PMEL17-GNAQ/11i ADCs in buffer, mouse, rat, and human plasma, and in vivo stability of anti-PMEL17-GNAQ/11i ADCs in mouse.

FIGS. 16A-16B show exemplary data on in vivo efficacy of G1-E152C-DAR2-(B1), G1-S375C-DAR2-(B1), Fc-silent G1-(B1) in a xenograft model of uveal melanoma. Values represent mean±SEM; sample size, (n=5-6 mice per group). Initial tumor volume at day 0 was approximately 300-325 mm$^3$.

FIGS. 17A-17B show exemplary data on in vitro anti-uveal melanoma activity of anti-PMEL17-(B1) ADCs. Data presented as mean of 3 independent replicates and relative to PBS-treated cells (control).

FIG. 19A-19B shows exemplary data on an immunohistochemical analysis of tumor biopsies from metastatic uveal melanoma patients.

FIGS. 20A-20C shows exemplary sensorgram data to assess epitope binning of anti-PMEL antibodies. FIG. 20A illustrates the binding steps. FIG. 20B shows the sensorgram when antibody G1 3J LC is immobilized first and 17A9 is flowed over. FIG. 20C shows the sensorgram when 17A9 is immobilized first and G1 3J LC is flowed over. In both cases, binding is observed when the second antibody is flowed over, suggesting that G1 3J LC and 17A9 bind to different epitopes of human PMEL.

DETAILED DESCRIPTION OF THE INVENTION

Definitions

Figure 1:
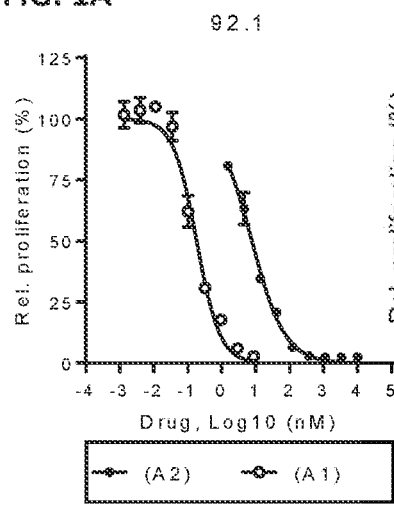
FIGS. 1A-1B show exemplary data on in vitro anti-UM activity of GNAQ/11 inhibitors Compound (A1) and Compound (A2).
Figure 1:
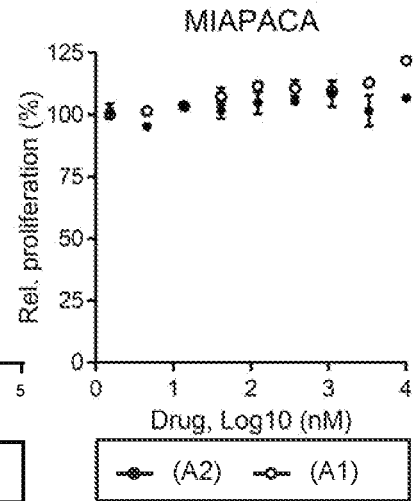

Unless stated otherwise, the following terms and phrases as used herein are intended to have the following meanings:

The term "alkyl" refers to a monovalent saturated hydrocarbon chain having the specified number of carbon atoms. For example, $C_1$-$C_6$alkyl refers to an alkyl group having from 1 to 6 carbon atoms. Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

"Cleavable" as used herein refers to a linking group or linker component that connects two moieties by covalent connections, but breaks down to sever the covalent connection between the moieties under physiologically relevant conditions, typically a cleavable linking group is severed in vivo more rapidly in an intracellular environment than when outside a cell, causing release of the payload to preferentially occur inside a targeted cell. Cleavage may be enzymatic or non-enzymatic, but generally releases a payload from an antibody without degrading the antibody. Cleavage may leave some portion of a linking group or linker component attached to the payload, or it may release the payload without any residue of the linking group.

"Non-cleavable" as used herein refers to a linking group or linker component that is not especially susceptible to breaking down under physiological conditions, e.g., it is at least as stable as the antibody or antigen binding fragment portion of the conjugate. Such linking groups are sometimes referred to as 'stable', meaning they are sufficiently resistant to degradation to keep the payload connected to antibody or antigen binding fragment until the antibody or antigen binding fragment is itself at least partially degraded, i.e., the degradation of the antibody or antigen binding fragment precedes cleavage of the linking group in vivo. Degradation of the antibody portion of an ADC having a stable or non-cleavable linking group may leave some or all of the linking group, e.g., one or more amino acid groups from an antibody, attached to the payload or drug moiety that is delivered in vivo.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody" includes, but is not limited to, monoclonal antibodies, human antibodies, humanized antibodies, chimeric antibodies, and anti-idiotypic (anti-Id) antibodies (including, e.g., anti-Id antibodies to antibodies of the invention). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementary-determining regions ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting about 15-20% of the variable domains. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, international ImMunoGeneTics database (IMGT) (on the worldwide web at www.imgt.org/), and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), camelid antibodies, disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, single domain antibodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000). Also included are antibodies derived from human sequences wherein one or more CDRs has been mutated for affinity maturation or for manufacturing/payload conjugation purposes. See Kilpatrick et al., "Rapid development of affinity matured monoclonal antibodies using RIMMS," *Hybridoma*. 1997 August; 16(4):381-9.

The human antibodies of the invention may include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the invention specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)).

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementarity determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91, 92%, 93%, 94%, 95%, 96%, 97%, 98%, 99%, or 100% sequence identity with the reference variable region nucleic acid or amino acid sequence. Corresponding human germline sequences can be determined, for example, through the publicly available international ImMunoGeneTics database (IMGT) (on the worldwide web at www.imgt.org/) and V-base (on the worldwide web at vbase.mrc-cpe.cam.ac.uk).

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one embodiment, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some embodiments, antibodies or antibody fragments are selected that cross-react with certain desired molecules.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least 10 to 100 times over the background.

The term "equilibrium dissociation constant (KD, M)" refers to the dissociation rate constant (kd, time-1) divided by the association rate constant (ka, time-1, M-1). Equilibrium dissociation constants can be measured using any known method in the art. The antibodies of the present invention generally will have an equilibrium dissociation constant of less than about $10^{-7}$ or $10^{-8}$ M, for example, less than about $10^{-9}$ M or $10^{-10}$ M, in some embodiments, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than an antibody drug conjugate of the invention. In some embodiments, the phrase "consisting essentially of" expressly excludes the inclusion of one or more additional active agents other than an antibody drug conjugate of the invention and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4:11-17 (1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453 (1970) algorithm which has been incorporated into the GAP program in the GCG software package (available at www.gcg.com), using either a BLOSUM62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "antibody drug conjugate" or "immunoconjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the antibody drug conjugate. Additionally, the antibody drug conjugate can be provided in the form of a fusion protein that may be expressed from a polynucleotide encoding the immunoconjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "cytotoxin", or "cytotoxic agent" as used herein, refers to any agent that is detrimental to the growth and proliferation of cells and may act to reduce, inhibit, or destroy a cell or malignancy.

The term "anti-cancer agent" as used herein refers to any agent that can be used to treat or prevent a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein refers to a chemical moiety that is conjugated to an antibody or antigen binding fragment of the invention, and can include any therapeutic or diagnostic agent, for example, an anti-cancer, anti-inflammatory, anti-infective (e.g., anti-fungal, antibacterial, anti-parasitic, anti-viral), or an anesthetic agent. For example, the drug moiety can be an anti-cancer agent, such as a cytotoxin. In certain embodiments, a drug moiety is a target inhibitor compound. In addition, a payload can be a biophysical probe, a fluorophore, a spin label, an infrared probe, an affinity probe, a chelator, a spectroscopic probe, a radioactive probe, a lipid molecule, a polyethylene glycol, a polymer, a spin label, DNA, RNA, a protein, a peptide, a surface, an antibody, an antibody fragment, a nanoparticle, a quantum dot, a liposome, a PLGA particle, a saccharide or a polysaccharide.

In some embodiments, the drug moiety or payload is a GNAQ inhibitor, a GNA11 inhibitor or an inhibitor of GNAQ and GNA11 (GNAQ/GNA11 inhibitor). In some embodiments, a GNAQ/11 inhibitor is a molecule that inhibits GNAQ/11-mediated production of IP3 and/or exhibits a dose-response antiproliferative effect in cells dependent on GNAQ/11 signaling (i.e., GNAQ/11 mutant uveal melanoma cells). In some embodiments, a GNAQ/11 inhibitor is a compound that stabilizes GNAQ/11 in the inactive GDP-bound state and prevents GDP release, or binds to the active GTP-bound state and prevents GNAQ/11 interaction with downstream effectors. In some embodiments, a GNAQ/11 inhibitor functions by inhibiting a mutant GNAQ and/or GNA11, such as one comprising a Q209L/P mutation. Methods for attaching such drug moieties to a linker compatible with the targeting moiety are given in the present disclosure, along with the methods known in the art. See, e.g., Singh et al., (2009) Therapeutic Antibodies: Methods and Protocols, vol. 525, 445-457.

GNAQ (Guanine nucleotide-binding protein G(q) subunit alpha, also known as CMC1, G-ALPHA-q, GAQ, SWS, and G protein subunit alpha q) and GNA11 (Guanine nucleotide-binding protein subunit alpha-11, also known as FBH, FBH2, FHH2, GNA-11, HHC2, HYPOC2, and G protein subunit alpha 11) are closely related GTPases that constitute a subunits of heterotrimeric G proteins acting downstream of G protein-coupled receptors (GPCRs). The a subunits act as a switch for activation of G proteins by exchanging the guanosine diphosphate (GDP) for guanosine triphosphate (GTP), leading to the activation of distinct downstream effectors. The activation is terminated by the intrinsic GTPase activity, as GTP is hydrolyzed to GDP (Van Raamsdonk et al., 2010, N Engl J Med.; 363(23):2191-9). The classical activation of Gq protein cascade occurs via phospholipase C-β (PLC-β), which hydrolyses phospholipid phosphatidylinositol 4,5-biphosphate to release two potent second messengers: D-myo-inositol 1,4,5-triphosphate (IP3) and diacylglycerol (DAG). Following the transient increase of intracellular $Ca^{2+}$, IP3 is rapidly transformed into IP2, IP1, and myo-inositol. On the other hand, DAG activates protein kinase C (PKC), leading to a cascade of phosphorylation of RAF, MEK, and ERK, which translocates to the nucleus to regulate cell proliferation and survival (Krantz et al., 2017, Clin Ophthalmol.; 11:279-289).

The nucleic acid and amino acid sequences of human GNAQ have been published in GenBank with the following Accession Nos.:

```
NP_002063
                                                          (SEQ ID NO: 268)
   1 mtlesimacc lseeakearr indeierqlr rdkrdarrel kllllgtges gkstfikqmr 61 iihgsgysde dkrgftklvy qniftamqam iramdtlkip ykyehnkaha qlvrevdvek 121 vsafenpyvd aikslwndpg iqecydrrre yqlsdstkyy lndldrvadp aylptqqdvl 181 rvrvpttgii eypfdlqsvi frmvdvggqr serrkwihcf envtsimflv alseydqvlv 241 esdnenrmee skalfrtiit ypwfqnssvi lflnkkdlle ekimyshlvd yfpeydgpqr 301 daqaarefil kmfvdlnpds dkiiyshftc atdtenirfv faavkdtilq lnlkeynlv NM_002072
                                                          (SEQ ID NO: 269)
   1 agactatccg ctcccaccgc gccccggcc cacctggtgg ccccggcct ggccgccgcc 61 cccgcggcgg ttcccggagc tcgtcccgga cgcgcgcccg ggcggcgggg gctcggcggc 121 caccgctgcc tcggggagc gagggcggga gggtgtgtgt gcgcgctgtg agcaggggt 181 gccggcgggg ctgcagcgga ggcactttgg aagaatgact ctggagtcca tcatggcgtg 241 ctgcctgagc gaggaggcca aggaagcccg gcggatcaac gacgagatcg agcggcagct 301 ccgcagggac aagcgggacg cccgccggga gctcaagctg ctgctgctcg ggacaggaga 361 gagtggcaag agtacgttta tcaagcagat gagaatcatc catgggtcag gatactctga 421 tgaagataaa aggggcttca ccaagctggt gtatcagaac atcttcacgg ccatgcaggc
```

-continued

```
 481 catgatcaga gccatggaca cactcaagat cccatacaag tatgagcaca ataaggctca
 541 tgcacaatta gttcgagaag ttgatgtgga gaaggtgtct gcttttgaga atccatatgt
 601 agatgcaata aagagtttat ggaatgatcc tggaatccag gaatgctatg atagacgacg
 661 agaatatcaa ttatctgact ctaccaaata ctatcttaat gacttggacc gcgtagctga
 721 ccctgcctac ctgcctacgc aacaagatgt gcttagagtt cgagtcccca ccacagggat
 781 catcgaatac ccctttgact tacaaagtgt cattttcaga atggtcgatg taggggggcca
 841 aaggtcagag agaagaaaat ggatacactg ctttgaaaat gtcacctcta tcatgtttct
 901 agtagcgctt agtgaatatg atcaagttct cgtggagtca gacaatgaga accgaatgga
 961 ggaaagcaag gctctcttta gaacaattat cacatacccc tggttccaga actcctcggt
1021 tattctgttc ttaaacaaga aagatcttct agaggagaaa atcatgtatt cccatctagt
1081 cgactacttc ccagaatatg atggacccca gagagatgcc caggcagccc gagaattcat
1141 tctgaagatg ttcgtggacc tgaacccaga cagtgacaaa attatctact cccacttcac
1201 gtgcgccaca gacaccgaga atatccgctt tgtctttgct gccgtcaagg acaccatcct
1261 ccagttgaac ctgaaggagt acaatctggt ctaattgtgc ctcctagaca ccgccctgc
1321 ccttccctgg tgggctattg aagatacaca agagggactg tatttctgtg gaaaacaatt
1381 tgcataatac taattattg ccgtcctgga ctctgtgtga gcgtgtccac agagtttgta
1441 gtaaatatta tgattttatt taaactattc agaggaaaaa cagaggatgc tgaagtacag
1501 tcccagcaca tttcctctct atcttttttt taggcaaaac cttgtgactc agtgtatttt
1561 aaattctcag tcatgcactc acaaagataa gacttgtttc tttctgtctc tctctctttt
1621 tcttttctat ggagcaaaac aaagctgatt tccctttttt cttccccgc taattcatac
1681 ctccctcctg atgttttttcc caggttacaa tggcctttat cctagttcca ttcttggtca
1741 agttttctc tcaaatgata cagtcaggac acatcgttcg atttaagcca tcatcagctt
1801 aatttaagtt tgtagtttt gctgaaggat tatatgtatt aatacttacg gttttaaatg
1861 tgttgctttg gatacacaca tagtttcttt tttaatagaa tatactgtct tgtctcactt
1921 tggactggga cagtggatgc ccatctaaaa gttaagtgtc atttcttta gatgtttacc
1981 ttcagccata gcttgattgc tcagagaaat atgcagaagg caggatcaaa gacacacagg
2041 agtcctttct tttgaaatgc cacgtgccat tgtctttcct cccttctttg cttcttttt
2101 ttaccctctc tttcaattgc agatgccaaa aaagatgcca acagacacta cattacccta
2161 atggctgcta cccagaacct ttttataggt tgttcttaat ttttttgttg ttgttgttca
2221 agcttttcct ttcttttttt tcttggtgtt tgggccacga ttttaaaatg acttttatta
2281 tgggtatgtg ttgccaaagc tggcttttg tcaaataaaa tgaatacgaa cttaaaaaat
2341 aaaagctggt atcttaaaat gtaagagagt aagactgtga agcctaaaat gactggctga
2401 gaatgaacca gaaatgccat ttgccaaaca gttgtaacta gaaatttgat tctcacggtc
2461 cattctttc tttgtcctta agatgacatt gttagtgttc acgtcccatg ttcagtgtcc
2521 aaaccggcaa tgtaaaaagt atcctgtgtg gtttaacagg aaatctgttt atgtctcttt
2581 atttgaaacc agttttactc tcagtggttc tttaagttca atgaagtctg ccaggaacat
2641 tggttggtag tattattccg acacctttaa tttccaaaat ctgaagttcc tgctagttta
2701 ccaccttcat gatcttcttg aactggtaac tgattaggtt gaacttatgg aagatttgtg
2761 gacttaactc aaaagtaacc tctcagtgtt ctatagaaca tgtatttgtg taactgaacc
2821 taccaggaga aatgtttgga attctatatg tgcaattttt caacaaatgc aaaaaaaata
```

-continued

```
2881 cagcacatgt attgacaagc ttctgtcaag cagcttgagt tgaaatttga tttaagaaaa 2941 taaatcatga ttgttcaaag ctgctgggac gttagaatta ggccatgata ctggtctcat 3001 tttaactaca gtggtatttg gcactagtgt aaacttccat ataaatcact cttttggaac 3061 aacaaagggg gagggagaaa aatcacggcc tgttaaatga gtaccaaagc cgcccaacag 3121 taatgagatg ttctcatcct tgattctccc agcctcaaac aacacagctt actttttttt 3181 tcccttgctc agaaagtacc tgtaatttaa caaacagact gcctgtaggt atagtgcaat 3241 tacaaatgct ctaatcattg tacatacatc tctcttgata ttgcagcatc catactggct 3301 ttgtaatcat taatttttg gcagattgaa tgtgctgtat tgatatgtat ctatgtaatt 3361 gtattgtatg tctatagcta attcacgttt tgaataatgt tattttattt acttttttaa 3421 gagaggagaa tgtaaatttg tcagtttatt tctgactagg gatattttct ttccatttag 3481 aaagaagaa aaaaaaaaaa ccttactgtc atacagagcg gtactagcgt cgtgctgtat 3541 aaaatcattt gcacattcct gagtagaggt atactgatta taagacccaa aggtaatttc 3601 atagcaaaat acataaaatc agtcggagct tttatacaaa catggaaacc aactttgtag 3661 aacttttgcc atttgatcta ggattggaat atgagctttt atacaattca tattcttatt 3721 tggcaaatgc acagtttagt attacctctc tgatggcctt tactagaaag gcagttttag 3781 aagctattgt gatccactaa ggaaatgttt taacagctag agaccactgc ttgcctgaaa 3841 gggcgttctt aaatttggtg cagcaaaaaa aaaaaaaaaa aaaaaaaaaa ttaaacaaca 3901 acatttgaag gcctacagtg tgtatagaga aaacctcatc acaagatcat aagtgttaca 3961 gttttaggga atcaagatat tctatttaat agagctatag taaatgtagt caattaaacc 4021 tgatctcaaa gcttgaagaa gctgagcaaa acagggaaag attgttatat ttgtctttat 4081 gaaatttggga tggaatttgc tatgcagaat tgaggtttgt ggcttcgctg ttcctgtagg 4141 gtgcatgaca agatcccttc tcttgagaaa ggaaaaaatt gatcacccta gcagcagtga 4201 tgcatagaaa cctaatttta gccacaccag tcaatcgaag ctaaaggatt ttcttttttg 4261 tttcttcggg gttttattga aggggctagg ggcgggacgg gattcttttc agttttgtat 4321 aaaaacaaag tttactcatg ctttatatta tattgtgatt gcaagcgtta taagcgtgtg 4381 ccactggcct cctattgttg atgcttaggt aatggaggcc tgtggtgagt tttatggtga 4441 cttgggcatg tcttattcaa aaacaaaaac ataaaacaca gaaacctttc ttcagcatac 4501 caaggcaagc agccatttca tgactcactt aacacattgc agtgtaccag tttacagatg 4561 attttttccct ttttgcgtga catggcagtt ctaaccccca gagaattcct tatttgtaaa 4621 ttggaagttt ctactatgcc ttacagagct taaattcaga agtttgtgcc tcatatctga 4681 aacaagggga ataacacac ccattcaaaa gtaaataaat ctcctagaag ttttttgtttt 4741 taacatttcc atataaagag ctctgttgaa tgtcatgaat agactggaaa aaaaaatttt 4801 aagaacctgc atatgttgtt tactagcaga tgacaactac aaaaggaatc tgaagaacac 4861 gtaaaacttg tatttttttt tttttggtag attaactagc aggcctattt taaaaaggta 4921 attcagctaa agggcaattt acttttttgt acttcagact atcttgattc tcaaagtgta 4981 cgaactgtaa ttttaaaatt tatactgcca catgattgta aattttagtt gtcttaagtt 5041 aggaattggt gaaaagctat ttatgctgga tttgggtcaa aatgacttat ttgcaaaaaa 5101 ataaataatg ggaagaaagg gctgtataat gaaatactgc aagactcaca tattggttgg 5161 aaatttccct caaatcacct accgattacc cttgatttcc ctttgttttc agtttctcaa 5221 aacgaatgaa atgaaatata gcagaatgtt aacccatata aaataaagt gtacccaaat 5281 attgtaatgt atattgctgc tcttcttcaa attaaataag ggtttaaaac cacttaattg
```

-continued

```
5341 gtaatcaaca tctcaattga tacaaataag gtgtgcttgg tatacattaa tattttcttc 5401 caaagatata tctttggtta gaaacacaaa aaaataaaac tagtaatatt gtatgtttat 5461 ctatctctac atatttccag catatgtagc gttaatagat ctgtcctggt aactgtgtct 5521 ttgggatttc attttggttc catcaaatta ggaaaagaaa tggcttagtt gtatatgatt 5581 agctagagat ttttggagcc agacacctgc tgtttagtag ataacttagt acagacccta

5641 aacttgtcat ttgttttct cacagaatag ccatttcctg ctgtcttccc aatgatcact 5701 gcccttttcaa taacactctt gcctctagaa tcatatgttc aaagtatgaa tacacaccta 5761 gcacatagta ggtgctcaaa tattaatttc ctccttgcct tccttatcta ccctgtgtcc 5821 tccatttccc cgtatgattc caacccaata tagcaaatga catttacatg ttatgaaaac 5881 atctattggg taaaatcaga tcttggataa agaaattctg acttttatat aagcttttgg 5941 tagacagaaa aaacagaaag gtattcgttg gtagaacatt tttaagttca ggaaagaaag 6001 ctggaataat actacgtaac tttgtccagg ttactttgac tgaaacacgt ttttggtgga 6061 tttcttttcc tcaaagaact ctctaaatgc aactccttgc tggattcctc acccatcatc 6121 ctgttggaaa cccttactag acctatgtat ttagggagtt ttgtcagaaa acatttttaa 6181 cttgcagtat ttaaaagaat atttactgtt cctaaaatgt cattcaaatg catgtactgt 6241 ctattgtttg gggatgggaa ctagttttgc aaaaaacacc taatgttgta taataatgcc 6301 ccaatgatct tgctggttaa aaatacagta tttttggcca taa
```

The nucleic acid and amino acid sequence of human GNA11 have been published in GenBank with the following Accession Nos.:

NP_002058

(SEQ ID NO: 270)

```
  1 mtlesmmacc lsdevkeskr inaeiekqlr rdkrdarrel kllllgtges gkstfikqmr 61 iihgagysee dkrgftklvy qniftamqam irametlkil ykyeqnkana llirevdvek 121 vttfehqyvs aiktlwedpg iqecydrrre yqlsdsakyy ltdvdriatl gylptqqdvl 181 rvrvpttgii eypfdlenii frmvdvggqr serrkwihcf envtsimflv alseydqvlv 241 esdnenrmee skalfrtiit ypwfqnssvi lflnkkdlle dkilyshlvd yfpefdgpqr 301 daqaarefil kmfvdlnpds dkiiyshftc atdtenirfv faavkdtilq lnlkeynlv
```

NM_002067

(SEQ ID NO: 271)

```
  1 aggttgtccg gcgctgtcgc tcggttgcgg cggctgcggt tggcggtggc tgcggcggcg 61 gcgcgggctg agtgcggccg cgcgggagtc cgcggctggc gcggcccgag cggggacccg 121 gcggctcgcc aggcggcggc cgaggcgggg cgggccggcc cggggccgag ggccggtggc 181 cgaggccgga gggccgcggc gggcggcggc cgaggcggct ccggccaggc ccgggccggg 241 ggccgggggg cggcggcggg caggcggccg cgtcggccgg gccgggacg atgactctgg 301 agtccatgat ggcgtgttgc ctgagcgatg aggtgaagga gtccaagcgg atcaacgccg 361 agatcgagaa gcagctgcgg cgggacaagc gcgacgcccg cgcgagctc aagctgctgc 421 tgctcggcac gggcgagagc gggaagagca cgttcatcaa gcagatgcgc atcatccacg 481 gcgccggcta ctcggaggag acaagcgcg gcttcaccaa gctcgtctac cagaacatct 541 tcaccgccat gcaggccatg atccggggca tggagacgct caagatcctc tacaagtacg 601 agcagaacaa ggccaatgcg ctcctgatcc gggaggtgga cgtggagaag gtgaccacct 661 tcgagcatca gtacgtcagt gccatcaaga cccgtgggga ggacccgggc atccaggaat
```

-continued

```
 721 gctacgaccg caggcgcgag taccagctct ccgactctgc caagtactac ctgaccgacg
 781 ttgaccgcat cgccaccttg ggctacctgc ccacccagca ggacgtgctg cgggtccgcg
 841 tgcccaccac cggcatcatc gagtacccct tcgacctgga aacatcatc ttccggatgg
 901 tggatgtggg gggccagcgg tcggagcgga ggaagtggat ccactgcttt gagaacgtga
 961 catccatcat gtttctcgtc gccctcagcg aatacgacca agtcctggtg gagtcggaca
1021 acgagaaccg gatggaggag agcaaagccc tgttccggac catcatcacc taccccctggt
1081 tccagaactc ctccgtcatc ctcttcctca acaagaagga cctgctggag acaagatcc
1141 tgtactcgca cctggtggac tacttccccg agttcgatgg tccccagcgg gacgcccagg
1201 cggcgcggga gttcatcctg aagatgttcg tggacctgaa ccccgacagc gacaagatca
1261 tctactcaca cttcacgtgt gccaccgaca cggagaacat ccgcttcgtg ttcgcggccg
1321 tgaaggacac catcctgcag ctcaacctca aggagtacaa cctggtctga gcgcccaggc
1381 ccagggagac gggatggaga cacggggcag gaccttcctt ccacggagcc tgcggctgcc
1441 gggcgggtgg cgctgccgag tccgggccgg ggcctctgcc cgcgggagga gattttttttt
1501 tttcatattt ttaacaaatg gttttattt cacagttatc agggggatgta catctctccc
1561 tccgtacact tcgcgcacct tctcacctttt gtcaacggc aaaggcagcc ttttttctggc
1621 cttgacttat ggctcgcttt tttctaaaaa aaaaaaaaa agaaagaaag aaaaaaagca
1681 acgaaacata aaacacacaa gcgccccgtg cccccagtga ctctgggcct cacagagccc
1741 ccgccagcca gcatggggcc ccgccctgca gccagtcacg cgccccccaca ccgcagcccc
1801 ccgtggctgt ccttccaacc ccacgtgctt tttctttctc ctgcccgctt cttttcttca
1861 tcacaaaagg cgtggagact cggagacgga cgttttttccc cttttttaag ttattgacgc
1921 ccagcgcgcc tcgcctcttc acccatcaac gctgtgcttt gcccactgga ctcctgaaga
1981 gggggtgggg ggctccctcg gtcgcccacc ctgggaagtg cctaaccttt tattttattt
2041 tatttttttg aggaaaaaga acgcctgact cacaggttga agaaacaccc tgggccctct
2101 ctcatggccg ggttccccgt ccctctgcag aggctgggaa gggtccccgg gctggagcca
2161 cgggggcttc tctgggctgt gcctccgggg ccaacactgg ctgcttgggg ctgcccgggg
2221 actccagagg gctgcacggc caccctgccc tggctagagc gcaccccacc ggagcccacg
2281 tgggctgggc ggctggaggg atggtccccc ggtgacactg ggagaaaggc cacttggatg
2341 ggggcgtttc tgttttgttc cgctttgtga tgtcaccaat ttggaaacag cgagggtggg
2401 tggggacttt tacagaatat tctcaggtgt gtacccgaga ggcagagaga ggacgtggc
2461 cggcagctct gtgcgtggcc ttgtcccaag cacttgcgcc cgccccgag cgccgccccc
2521 gggagcggg aagccagcac tcgcactttg gccaggggcg cgtggaaggt ggtggcaggc
2581 accggcctgg gcagcttcca ggcctggctg gccacgacca cggcccgagg gggagcccgc
2641 caggccacgc cgcactgagc cacagccccg ggggccgcct cccggggccc cttgaggcac
2701 tgaggcaccg agactggttc tccccgagag actcggaagg tggggaacga ggggactgtg
2761 tttggggagg tggcttttttc gtctgctgtt gactgaacac tacagcgccc tgtggttccg
2821 ggcttcgcac agctgtccca gggatggatc gcctgtgctg ccttcgcccg ccgccacacc
2881 gggaccctgc acggctgctt ctggcctcga cagatgacaa agaaacagc cccaaaatac
2941 gaccactcca accagcagtt cccgcctgcc tgcccgccac tgtcaggcct gccctggcct
3001 cctcgtccgc agggctgtct gctggcttct gggggcagaa gagcggggag cccgtggaa
3061 gggtcagggg agaccaggtc agggcagcta catttctggt gatcagcccc atggggagac
```

```
-continued
3121 ggggctggcg ggatacccccc ccccggctt ccccacacca cttctgtctc acccggaagc 3181 gtccttttt tgtgccaggt gtctacctaa gagggttggt gccagaagcc ccccatggcg 3241 agtgctgggg cccggcggtg ccctggggga gcagatgggg ccacccctgg cagggccgct 3301 acaaccttt ccagcagcgg agccctctgg ggggcctgtg cttgtggcat ctctgagggc 3361 ctagattgca caaggtgacc tggccgtggc ctgagggtgg agtcgcccag cacgcaggcc 3421 ggggcgctgc ggggctaagt attaggcctt cccagggagg gggcgtgcca agcatcccag 3481 agccgggctg ggaccgccaa aacgtcgtgg cctggatcct ctgggtctga gtgcctgatc 3541 ccctgccccc caaaaaagca gaggtaggtg ttgcaggccc agggcagggg tgcctgcccc 3601 aggagagtcc caggcagtgg ttctcgtgcc agtggcaccc aggggcaagg acagccaacc 3661 cccaccttg ccacgtgtgg ggccacgtgg gcatgtgggg tgtgtgtttt taccttggtg 3721 aatctcacct gccaacgatt tctcgtgagt gccgaccacc ttctccgacc atgttacgcc 3781 cgggcggcag cagcccccgg ccactgcaaa cccatgccct gggtccccccg gctcccccag 3841 ggaggcatcc ccgtgccaat gtccccccagt ggtggcagca gatcctgtgg ccggcctggc 3901 ggacgggacc cagtgatact tgtatattac acagtcctga tttcagacaa tttcaacctt 3961 aatctattta aaaagaata ttctatacaa gctgtttta agccttttac catttgaaat 4021 gcatgtgttg tgcgcgttgg ggatgggagg aggggctgag gagcggctca gtgtcacctc 4081 ccacagccac cggccctgac ccttaatcca gacaccgatg gaagtcgact tttcatatct 4141 ttctcctgaa atgaactctg ttttaaattg gaataaattt tgttcctaaa
```

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. For example, anti-tumor activity can be shown by a decline in growth rate of abnormal cells that arises during therapy or tumor size stability or reduction, or longer survival due to therapy as compared to control without therapy. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

The term "PMEL17" (also referred to as premelanosome protein (PMEL), D12S53E, ME20, ME20-M, ME20M, P1, P100, gp100, SI, SIL, and silver locus protein homolog (SILV)) refers to a single-pass Type I transmembrane protein produced by melanocytes and involved in melanin synthesis. The nucleic acid and amino acid sequence of human PMEL17 have been published in GenBank with the following Accession Nos.: NP_008859, NP_001307050, NP_001307051, NP_001186982, NP_001186983 (amino acid sequences), and NM_006928, NM_001200053, NM_001200054, NM_001320121, NM_001320122 (nucleotide sequences). As used herein, the term "PMEL17" is used to refer collectively to all naturally occurring isoforms of PMEL17 protein, or a variant thereof.

```
NP_008859
                                                               (SEQ ID NO: 272)
  1 mdlvlkrcll hlavigalla vgatkvprnq dwlgvsrqlr tkawnrqlyp ewteaqrldc 61 wrggqvslkv sndgptliga nasfsialnf pgsqkvlpdg qviwvnntii ngsqvwggqp 121 vypqetddac ifpdggpcps gswsqkrsfv yvwktwgqyw qvlggpvsgl sigtgramlg 181 thtmevtvyh rrgsrsyvpl ahsssaftit dqvpfsysys qlraldggnk hflrnqpltf 241 alqlhdpsgy laeadlsytw dfgdssgtli sralvvthty lepgpvtaqv vlqaaiplts 301 cgsspvpgtt dghrptaeap nttagqvptt evvgttpgqa ptaepsgtts vqvpttevis 361 tapvqmptae stgmtpekvp vsevmgttla emstpeatgm tpaevsivvl sgttaaqvtt 421 tewvettare lpipepegpd assimstesi tgslgplldg tatlrlykrq vpldcvlyry
```

-continued

```
481 gsfsvtldiv qgiesaeilq avpsgegdaf eltvscqggl pkeacmeiss pgcqppaqrl 541 cqpvlpspac qlvlhqilkg gsgtyclnvs ladtnslavv stqlimpgqe aglgqvpliv 601 gillvlmavv lasliyrrrl mkqdfsvpql phssshwlrl prifcscpig enspllsgqq 661 v
```

NP_001307050

(SEQ ID NO: 273)
```
  1 mdlvlkrcll hlavigalla vgatkvprnq dwlgvsrqlr tkawnrqlyp ewteaqrldc 61 wrggqvslkv sndgptliga nasfsialnf pgsqkvlpdg qviwvnntii ngsqvwggqp 121 vypqetddac ifpdggpcps gswsqkrsfv yvwktwgqyw qvlggpvsgl sigtgramlg 181 thtmevtvyh rrgsrsyvpl ahsssaftit dqvpfsvsvs qlraldggnk hflrnqpltf 241 alqlhdpsgy laeadlsytw dfgdssgtli sralvvthty lepgpvtaqv vlqaaiplts 301 cgsspvpgtt dghrptaeap nttagqvptt evvgttpgqa ptaepsgtts vqvpttevis 361 tapvqmptae staaqvttte wvettarelp ipepegpdas simstesitg slgplldgta 421 tlrlvkrqvp ldcvlyrygs fsvtldivqg iesaeilqav psgegdafel tvscqgglpk 481 eacmeisspg cqppaqrlcq pvlpspacql vlhqilkggs gtyclnvsla dtnslavvst 541 qlimpvpgil ltgqeaglgq vplivgillv lmavvlasli yrrrlmkqdf svpqlphsss 601 hwlrlprifc scpigenspl lsgqqv
```

NP_001307051

(SEQ ID NO: 274)
```
  1 mdlvlkrcll hlavigalla vgatkvprnq dwlgvsrqlr tkawnrqlyp ewteaqrldc 61 wrggqvslkv sndgptliga nasfsialnf pgsqkvlpdg qviwvnntii ngsqvwggqp 121 vypqetddac ifpdggpcps gswsqkrsfv yvwktwgqyw qvlggpvsgl sigtgramlg 181 thtmevtvyh rrgsrsyvpl ahsssaftit dqvpfsvsvs qlraldggnk hflrnqpltf 241 alqlhdpsgy laeadlsytw dfgdssgtli sralvvthty lepgpvtaqv vlqaaiplts 301 cgsspvpgtt dghrptaeap nttagqvptt evvgttpgqa ptaepsgtts vqvpttevis 361 tapvqmptae staaqvttte wvettarelp ipepegpdas simstesitg slgplldgta 421 tlrlvkrqvp ldcvlyrygs fsvtldivqg iesaeilqav psgegdafel tvscqgglpk 481 eacmeisspg cqppaqrlcq pvlpspacql vlhqilkggs gtyclnvsla dtnslavvst 541 qlimpgqeag lgqvplivgi llvlmavvla sliyrrrlmk qdfsvpqlph ssshwlrlpr 601 ifcscpigen spllsgqqv
```

NP_001186982

(SEQ ID NO: 275)
```
  1 mdlvlkrcll hlavigalla vgatkgsqvw ggqpvypqet ddacifpdgg pcpsgswsqk 61 rsfvyvwktw gqywqvlggp vsglsigtgr amlgthtmev tvyhrrgsrs yvplahsssa 121 ftitdqvpfs vsvsqlrald ggnkhflrnq pltfalqlhd psgylaeadl sytwdfgdss 181 gtlisralvv thtylepgpv taqvvlqaai pltscgsspv pgttdghrpt aeapnttagq 241 vpttevvgtt pgqaptaeps gttsvqvptt evistapvqm ptaestgmtp ekvpvsevmg 301 ttlaemstpe atgmtpaevs ivvlsgttaa qvtttewvet tarelpipep egpdassims 361 tesitgslgp lldgtatlrl vkrqvpldcv lyrygsfsvt ldivqgiesa eilqavpsge 421 gdafeltvsc qgglpkeacm eisspgcqpp aqrlcqpvlp spacqlvlhq ilkggsgtyc 481 lnvsladtns lavvstqlim pgqeaglgqv plivgillvl mavvlasliy rrrlmkqdfs 541 vpqlphsssh wlrlprifcs cpigensplI sgqqv
```

NP_001186983

(SEQ ID NO: 276)

```
  1 mdlvlkrcll hlavigalla vgatkvprnq dwlgvsrqlr tkawnrqlyp ewteaqrldc
 61 wrggqvslkv sndgptliga nasfsialnf pgsqkvlpdg qviwvnntii ngsqvwggqp
121 vypqetddac ifpdggpcps gswsqkrsfv yvwktwgqyw qvlggpvsgl sigtgramlg
181 thtmevtvyh rrgsrsyvpl ahsssaftit dqvpfsvsvs qlraldggnk hflrnqpltf
241 alqlhdpsgy laeadlsytw dfgdssgtli sralvvthty lepgpvtaqv vlqaaiplts
301 cgsspvpgtt dghrptaeap nttagqvptt evvgttpgqa ptaepsgtts vqvpttevis
361 tapvqmptae stgmtpekvp vsevmgttla emstpeatgm tpaevsivvl sgttaaqvtt
421 tewvettare lpipepegpd assimstesi tgslgplldg tatlrlvkrq vpldcvlyry
481 gsfsvtldiv qgiesaeilq avpsgegdaf eltvscqggl pkeacmeiss pgcqppaqrl
541 cqpvlpspac qlvlhqilkg gsgtyclnvs ladtnslavv stqlimpvpg illtgqeagl
601 gqvplivgil lvlmavvlas liyrrrlmkq dfsvpqlphs sshwlrlpri fcscpigens
661 pllsgqqv
```

NM_006928

(SEQ ID NO: 277)

```
   1 cccagcgctc ctccccgcaa atgatcccgc cccaggggcc tatcccagtc cccccagtgc
  61 ctttggttgc tggagggaag aacacaatgg atctggtgct aaaaagatgc cttcttcatt
 121 tggctgtgat aggtgctttg ctggctgtgg ggctacaaa agtacccaga accaggact
 181 ggcttggtgt ctcaaggcaa ctcagaacca aagcctggaa caggcagctg tatccagagt
 241 ggacagaagc ccagagactt gactgctgga gaggtggtca agtgtccctc aaggtcagta
 301 atgatgggcc tacactgatt ggtgcaaatg cctccttctc tattgccttg aacttccctg
 361 gaagccaaaa ggtattgcca gatgggcagg ttatctgggt caacaatacc atcatcaatg
 421 ggagccaggt gtggggagga cagccagtgt atccccagga aactgacgat gcctgcatct
 481 tccctgatgg tggacctttgc ccatctggct cttggtctca aagagaagc tttgtttatg
 541 tctggaagac ctggggccaa tactggcaag ttctagggg cccagtgtct gggctgagca
 601 ttgggacagg cagggcaatg ctgggcacac acaccatgga agtgactgtc taccatcgcc
 661 ggggatcccg gagctatgtg cctcttgctc attccagctc agccttcacc attactgacc
 721 aggtgccttt ctccgtgagc gtgtcccagt tgcgggcctt ggatggaggg aacaagcact
 781 tcctgagaaa tcagcctctg acctttgccc tccagctcca tgaccccagt ggctatctgg
 841 ctgaagctga cctctcctac acctgggact tggagacag tagtggaacc ctgatctctc
 901 gggcacttgt ggtcactcat acttacctgg agcctggccc agtcactgcc caggtggtcc
 961 tgcaggctgc cattcctctc acctcctgtg ctcctcccc agttccaggc accacagatg
1021 ggcacaggcc aactgcagag gcccctaaca ccacagctgg ccaagtgcct actacagaag
1081 ttgtgggtac tacacctggt caggcgccaa ctgcagagcc ctctggaacc acatctgtgc
1141 aggtgccaac cactgaagtc ataagcactg cacctgtgca gatgccaact gcagagagca
1201 caggtatgac acctgagaag gtgccagttt cagaggtcat gggtaccaca ctggcagaga
1261 tgtcaactcc agaggctaca ggtatgacac tgcagaggt atcaattgtg gtgctttctg
1321 gaaccacagc tgcacaggta acaactacag agtgggtgga gaccacagct agagagctac
1381 ctatccctga gcctgaaggt ccagatgcca gctcaatcat gtctacgaa agtattacag
1441 gttccctggg cccctgctg gatggtacag ccaccttaag gctggtgaag agacaagtcc
1501 ccctggattg tgttctgtat cgatatggtt ccttttccgt cacccctgac attgtccagg
1561 gtattgaaag tgccgagatc ctgcaggctg tgccgtccgg tgagggggat gcatttgagc
```

-continued

```
1621 tgactgtgtc ctgccaaggc gggctgccca aggaagcctg catgagatc tcatcgccag 1681 ggtgccagcc ccctgcccag cggctgtgcc agcctgtgct acccagccca gcctgccagc 1741 tggttctgca ccagatactg aagggtggct cggggacata ctgcctcaat gtgtctctgg 1801 ctgataccaa cagcctggca gtggtcagca cccagcttat catgcctggt caagaagcag 1861 gccttgggca ggttccgctg atcgtgggca tcttgctggt gttgatggct gtggtccttg 1921 catctctgat ataggcgc agacttatga agcaagactt ctccgtaccc cagttgccac 1981 atagcagcag tcactggctg cgtctacccc gcatcttctg ctcttgtccc attggtgaga 2041 acagccccct cctcagtggg cagcaggtct gagtactctc atatgatgct gtgatttcc 2101 tggagttgac agaaacacct atatttcccc cagtcttccc tgggagacta ctattaactg 2161 aaataaatac tcagagcctg aaaaaaaaaa aaaaa
```

NM_001200053

(SEQ ID NO: 278)

```
  1 gggcctatcc cagtcccccc agtgcctttg gttgctggag ggaagaacac aatggatctg 61 gtgctaaaaa gatgccttct tcatttggct gtgataggtg ctttgctggc tgtgggggct 121 acaaaaggga gccaggtgtg gggaggacag ccagtgtatc cccaggaaac tgacgatgcc 181 tgcatcttcc ctgatggtgg accttgccca tctggctctt ggtctcagaa gagaagcttt 241 gtttatgtct ggaagacctg gggccaatac tggcaagttc taggggccc agtgtctggg 301 ctgagcattg ggacaggcag ggcaatgctg ggcacacaca ccatggaagt gactgtctac 361 catcgccggg gatcccggag ctatgtgcct cttgctcatt ccagctcagc cttcaccatt 421 actgaccagg tgcctttctc cgtgagcgtg tcccagttgc gggccttgga tggagggaac 481 aagcacttcc tgagaaatca gcctctgacc tttgccctcc agctccatga cccagtggc 541 tatctggctg aagctgacct ctcctacacc tgggactttg agacagtag tggaaccctg 601 atctctcggg cacttgtggt cactcatact tacctggagc ctggcccagt cactgcccag 661 gtggtcctgc aggctgccat tcctctcacc tcctgtggct cctccccagt tccaggcacc 721 acagatgggc acaggccaac tgcagaggcc cctaacacca cagctggcca agtgcctact 781 acagaagttg tgggtactac acctggtcag cgccaactg cagagccctc tggaaccaca 841 tctgtgcagg tgccaaccac tgaagtcata agcactgcac ctgtgcagat gccaactgca 901 gagagcacag gtatgacacc tgagaaggtg ccagtttcag aggtcatggg taccacactg 961 gcagagatgt caactccaga ggctacaggt atgacacctg cagaggtatc aattgtggtg 1021 ctttctggaa ccacagctgc acaggtaaca actacagagt gggtggagac cacagctaga 1081 gagctaccta tccctgagcc tgaaggtcca gatgccagct caatcatgtc tacggaaagt 1141 attacaggtt ccctgggccc cctgctggat ggtacagcca ccttaaggct ggtgaagaga 1201 caagtccccc tggattgtgt tctgtatcga tatggttcct tttccgtcac cctggacatt 1261 gtccagggta ttgaaagtgc cgagatcctg caggctgtgc cgtccggtga gggggatgca 1321 tttgagctga ctgtgtcctg ccaaggcggg ctgcccaagg aagcctgcat ggagatctca 1381 tcgccagggt gccagccccc tgcccagcgg ctgtgccagc ctgtgctacc cagcccagcc 1441 tgccagctgg ttctgcacca gatactgaag ggtggctcgg ggacatactg cctcaatgtg 1501 tctctggctg ataccaacag cctggcagtg tcagcaccc agcttatcat gcctggtcaa 1561 gaagcaggcc ttgggcaggt tccgctgatc gtgggcatct tgctggtgtt gatggctgtg 1621 gtccttgcat ctctgatata taggcgcaga cttatgaagc aagacttctc cgtaccccag 1681 ttgccacata gcagcagtca ctggctgcgt ctaccccgca tcttctgctc ttgtcccatt
```

-continued

```
1741 ggtgagaaca gcccctcct cagtgggcag caggtctgag tactctcata tgatgctgtg
1801 attttcctgg agttgacaga aacacctata tttcccccag tcttccctgg gagactacta
1861 ttaactgaaa taaatactca gagcctgaaa aaaaaaaaaa aa
```

NM_001200054
(SEQ ID NO: 279)
```
   1 gggcctatcc cagtcccccc agtgcctttg gttgctggag ggaagaacac aatggatctg
  61 gtgctaaaaa gatgccttct tcatttggct gtgataggtg ctttgctggc tgtgggggct
 121 acaaaagtac ccagaaacca ggactggctt ggtgtctcaa ggcaactcag aaccaaagcc
 181 tggaacaggc agctgtatcc agagtggaca gaagcccaga gacttgactc tggagaggt
 241 ggtcaagtgt ccctcaaggt cagtaatgat gggcctacac tgattggtgc aaatgcctcc
 301 ttctctattg ccttgaactt ccctggaagc caaaaggtat tgccagatgg gcaggttatc
 361 tgggtcaaca ataccatcat caatgggagc caggtgtggg gaggacagcc agtgtatccc
 421 caggaaactg acgatgcctg catcttccct gatggtggac cttgcccatc tggctcttgg
 481 tctcagaaga gaagctttgt ttatgtctgg aagacctggg gccaatactg caagttcta
 541 gggggcccag tgtctgggct gagcattggg acaggcaggg caatgctggg cacacacacc
 601 atggaagtga ctgtctacca tcgccgggga tcccgagct atgtgcctct tgctcattcc
 661 agctcagcct tcaccattac tgaccaggtg cctttctccg tgagcgtgtc ccagttgcgg
 721 gccttggatg gagggaacaa gcacttcctg agaaatcagc ctctgacctt tgccctccag
 781 ctccatgacc ccagtggcta tctggctgaa gctgacctct cctacacctg ggactttgga
 841 gacagtagtg gaaccctgat ctctcgggca cttgtggtca ctcatactta cctggagcct
 901 ggcccagtca ctgcccaggt ggtcctgcag gctgccattc ctctcacctc ctgtggctcc
 961 tccccagttc caggcaccac agatgggcac aggccaactg cagaggcccc taacaccaca
1021 gctggccaag tgcctactac agaagttgtg ggtactacac tggtcaggc gccaactgca
1081 gagccctctg aaccacatc tgtgcaggtg ccaaccactg aagtcataag cactgcacct
1141 gtgcagatgc caactgcaga gagcacaggt atgacacctg agaaggtgcc agtttcagag
1201 gtcatgggta ccacactggc agagatgtca actccagagg ctacaggtat gacacctgca
1261 gaggtatcaa ttgtggtgct ttctggaacc acagctgcac aggtaacaac tacagagtgg
1321 gtggagacca cagctagaga gctacctatc cctgagcctg aaggtccaga tgccagctca
1381 atcatgtcta cggaaagtat tacaggttcc ctgggccccc tgctggatgg tacagccacc
1441 ttaaggctgg tgaagagaca agtcccctg gattgtgttc tgtatcgata tggttccttt
1501 tccgtcaccc tggacattgt ccagggtatt gaaagtgccg agatcctgca ggctgtgccg
1561 tccggtgagg gggatgcatt tgagctgact gtgtcctgcc aaggcgggct gcccaaggaa
1621 gcctgcatgg agatctcatc gccagggtgc cagccccctg cccagcggct gtgccagcct
1681 gtgctacccca gcccagcctg ccagctggtt ctgcaccaga tactgaaggg tggctcgggg
1741 acatactgcc tcaatgtgtc tctggctgat accaacagcc tggcagtggt cagcacccag
1801 cttatcatgc ctgtgcctag gattcttctc acaggtcaag aagcaggcct tgggcaggtt
1861 ccgctgatcg tgggcatctt gctggtgttg atggctgtgg tccttgcatc tctgatatat
1921 aggcgcagac ttatgaagca agacttctcc gtaccccagt tgccacatag cagcagtcac
1981 tggctgcgtc tacccgcat cttctgctct tgtcccattg gtgagaacag ccccctcctc
2041 agtgggcagc aggtctgagt actctcatat gatgctgtga ttttcctgga gttgacagaa
2101 acacctatat ttcccccagt cttccctggg agactactat taactgaaat aaatactcag
2161 agcctgaaaa aaaaaaaaaa a
```

-continued

NM_001320121
(SEQ ID NO: 280)
```
   1 gggcctatcc cagtcccccc agtgcctttg gttgctggag ggaagaacac aatggatctg
  61 gtgctaaaaa gatgccttct tcatttggct gtgataggtg ctttgctggc tgtgggggct
 121 acaaaagtac ccagaaacca ggactggctt ggtgtctcaa ggcaactcag aaccaaagcc
 181 tggaacaggc agctgtatcc agagtggaca gaagcccaga gacttgactg ctggagaggt
 241 ggtcaagtgt ccctcaaggt cagtaatgat gggcctacac tgattggtgc aaatgcctcc
 301 ttctctattg ccttgaactt ccctggaagc caaaaggtat tgccagatgg gcaggttatc
 361 tgggtcaaca ataccatcat caatgggagc caggtgtggg gaggacagcc agtgtatccc
 421 caggaaactg acgatgcctg catcttccct gatggtggac cttgcccatc tggctcttgg
 481 tctcagaaga gaagctttgt ttatgtctgg aagacctggg gccaatactg caagttcta
 541 gggggcccag tgtctgggct gagcattggg acaggcaggg caatgctggg cacacacacc
 601 atggaagtga ctgtctacca tcgccgggga tcccggagct atgtgcctct tgctcattcc
 661 agctcagcct tcaccattac tgaccaggtg cctttctccg tgagcgtgtc ccagttgcgg
 721 gccttggatg gagggaacaa gcacttcctg agaaatcagc ctctgacctt tgccctccag
 781 ctccatgacc ccagtggcta tctggctgaa gctgacctct cctacacctg ggactttgga
 841 gacagtagtg gaaccctgat ctctcgggca cttgtggtca ctcatactta cctggagcct
 901 ggcccagtca ctgcccaggt ggtcctgcag gctgccattc ctctcacctc ctgtggctcc
 961 tccccagttc caggcaccac agatgggcac aggccaactg cagaggcccc taacaccaca
1021 gctggccaag tgcctactac agaagttgtg ggtactacac ctggtcaggc gccaactgca
1081 gagccctctg gaaccacatc tgtgcaggtg ccaaccactg aagtcataag cactgcacct
1141 gtgcagatgc caactgcaga gagcacagct gcacaggtaa caactacaga gtgggtggag
1201 accacagcta gagagctacc tatccctgag cctgaaggtc cagatgccac ctcaatcatg
1261 tctacggaaa gtattacagg ttccctgggc cccctgctgg atggtacagc caccttaagg
1321 ctggtgaaga gacaagtccc cctggattgt gttctgtatc gatatggttc cttttccgtc
1381 accctggaca ttgtccaggg tattgaaagt gccgagatcc tgcaggctgt gccgtccggt
1441 gagggggatg catttgagct gactgtgtcc tgccaaggcg ggctgcccaa ggaagcctgc
1501 atggagatct catcgccagg gtgccagccc cctgcccagc ggctgtgcca gcctgtgcta
1561 cccagcccag cctgccagct ggttctgcac cagatactga agggtggctc ggggacatac
1621 tgcctcaatg tgtctctggc tgataccaac agcctggcag tggtcagcac ccagccttatc
1681 atgcctgtgc ctgggattct tctcacaggt caagaagcag gccttgggca ggttccgctg
1741 atcgtgggca tcttgctggt gttgatggct gtggtccttg catctctgat atataggcgc
1801 agacttatga agcaagactt ctccgtaccc cagttgccac atagcagcag tcactggctg
1861 cgtctacccc gcatcttctg ctcttgtccc attggtgaga acagccccct cctcagtggg
1921 cagcaggtct gagtactctc atatgatgct gtgattttcc tggagttgac agaaacacct
1981 atatttcccc cagtcttccc tgggagacta ctattaactg aaataaatac tcagagcctg
2041 a
```

NM_001320122
(SEQ ID NO: 281)
```
   1 gggcctatcc cagtcccccc agtgcctttg gttgctggag ggaagaacac aatggatctg
  61 gtgctaaaaa gatgccttct tcatttggct gtgataggtg ctttgctggc tgtgggggct
 121 acaaaagtac ccagaaacca ggactggctt ggtgtctcaa ggcaactcag aaccaaagcc
```

-continued

```
 181 tggaacaggc agctgtatcc agagtggaca gaagcccaga gacttgactg ctggagaggt 241 ggtcaagtgt ccctcaaggt cagtaatgat gggcctacac tgattggtgc aaatgcctcc 301 ttctctattg ccttgaactt ccctggaagc caaaaggtat tgccagatgg caggttatc 361 tgggtcaaca ataccatcat caatgggagc caggtgtggg gaggacagcc agtgtatccc 421 caggaaactg acgatgcctg catcttccct gatggtggac cttgcccatc tggctcttgg 481 tctcagaaga gaagctttgt ttatgtctgg aagacctggg gccaatactg gcaagttcta 541 gggggcccag tgtctgggct gagcattggg acaggcaggg caatgctggg cacacacacc 601 atggaagtga ctgtctacca tcgccgggga tcccggagct atgtgcctct tgctcattcc 661 agctcagcct tcaccattac tgaccaggtg cctttctccg tgagcgtgtc ccagttgcgg 721 gccttggatg gagggaacaa gcacttcctg agaaatcagc ctctgacctt tgccctccag 781 ctccatgacc ccagtggcta tctggctgaa gctgacctct cctacacctg ggactttgga 841 gacagtagtg gaaccctgat ctctcgggca cttgtggtca ctcatactta cctggagcct 901 ggcccagtca ctgcccaggt ggtcctgcag gctgccattc ctctcacctc ctgtggctcc 961 tccccagttc caggcaccac agatgggcac aggccaactg cagaggcccc taacaccaca 1021 gctggccaag tgcctactac agaagttgtg ggtactacac ctggtcaggc gccaactgca 1081 gagccctctg gaaccacatc tgtgcaggtg ccaaccactg aagtcataag cactgcacct 1141 gtgcagatgc caactgcaga gagcacagct gcacaggtaa caactacaga gtgggtggag 1201 accacagcta gagagctacc tatccctgag cctgaaggtc cagatgccag ctcaatcatg 1261 tctacggaaa gtattacagg ttccctgggc cccctgctgg atggtacagc caccttaagg 1321 ctggtgaaga gacaagtccc cctggattgt gttctgtatc gatatggttc cttttccgtc 1381 accctggaca ttgtccaggg tattgaaagt gccgagatcc tgcaggctgt gccgtccggt 1441 gaggggatg catttgagct gactgtgtcc tgccaaggcg ggctgcccaa ggaagcctgc 1501 atggagatct catcgccagg gtgccagccc cctgcccagc ggctgtgcca gcctgtgcta 1561 cccagcccag cctgccagct ggttctgcac cagatactga agggtggctc ggggacatac 1621 tgcctcaatg tgtctctggc tgataccaac agcctggcag tggtcagcac ccagcttatc 1681 atgcctggtc aagaagcagg ccttgggcag gttccgctga tcgtgggcat cttgctggtg 1741 ttgatggctg tggtccttgc atctctgata tataggcgca gacttatgaa gcaagacttc 1801 tccgtacccc agttgccaca tagcagcagt cactggctgc gtctaccccg catcttctgc 1861 tcttgtccca ttggtgagaa cagccccctc ctcagtgggc agcaggtctg agtactctca 1921 tatgatgctg tgattttcct ggagttgaca gaaacaccta tatttccccc agtcttccct 1981 gggagactac tattaactga aataaatact cagagcctga
```

The term "variant" refers to a polypeptide that has a substantially identical amino acid sequence to a reference polypeptide, or is encoded by a substantially identical nucleotide sequence, and is capable of having one or more activities of the reference polypeptide. For example, a variant can have about 85%, 90%, 91%, 92%, 93%, 94%, 95%, 96%, 97%, 98%, 99% or higher sequence identity to a reference polypeptide, while retain one or more activities of the reference polypeptide.

As used herein, the terms "treat," "treating," or "treatment" of any disease or disorder refers in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both.

As used herein, the term "prevent", "preventing" or "prevention" of any disease or disorder refers to the prophylactic treatment of the disease or disorder; or delaying the onset or progression of the disease or disorder The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some embodiments, a therapeutically acceptable amount does not induce or cause undesirable side effects. In some embodiments, a therapeutically acceptable amount induces or causes side effects but only those that are acceptable by the healthcare providers in view of a patient's condition. A therapeutically acceptable amount can be determined by first administering a low dose, and then incrementally increasing that dose until the desired effect is achieved. A "prophylactically effective dosage," and a "therapeutically effective dosage," of the molecules of the invention can prevent the onset of, or result in a decrease in severity of, respectively, disease symptoms, including symptoms associated with cancer.

The term "co-administer" refers to the presence of two active agents in the blood of an individual. Active agents that are co-administered can be concurrently or sequentially delivered.

The present invention provides antibodies, antibody fragments (e.g., antigen binding fragments), and drug conjugates thereof, i.e., antibody drug conjugates or ADCs, that bind to PMEL17. In particular, the present invention provides antibodies and antibody fragments (e.g., antigen binding fragments) that bind to PMEL17, and internalize upon such binding. The antibodies and antibody fragments (e.g., antigen binding fragments) of the present invention can be used for producing antibody drug conjugates. Furthermore, the present invention provides antibody drug conjugates that have desirable pharmacokinetic characteristics and other desirable attributes, and thus can be used for treating or preventing a cancer expressing PMEL17. The present invention further provides pharmaceutical compositions comprising the antibody drug conjugates of the invention, and methods of making and using such pharmaceutical compositions for the treatment or prevention of cancer.

Drug Moiety (D)

In one aspect, the Drug moiety (D) of the Antibody Drug Conjugate of the invention is a GNAQ inhibitor, a GNA11 inhibitor, or an inhibitor of GNAQ and GNA11 (GNAQ/GNA11 inhibitor).

In another aspect, the Drug moiety (D) of the Antibody Drug Conjugate of the invention is a GNAQ inhibitor.

In another aspect, the Drug moiety (D) of the Antibody Drug Conjugate of the invention is a GNA11 inhibitor.

In another aspect, the Drug moiety (D) of the Antibody Drug Conjugate of the invention is an inhibitor of GNAQ and GNA11 (GNAQ/GNA11 inhibitor).

In another aspect, the Drug moiety of the Antibody Drug Conjugate of the invention is a compound having the structure of Formula (A):

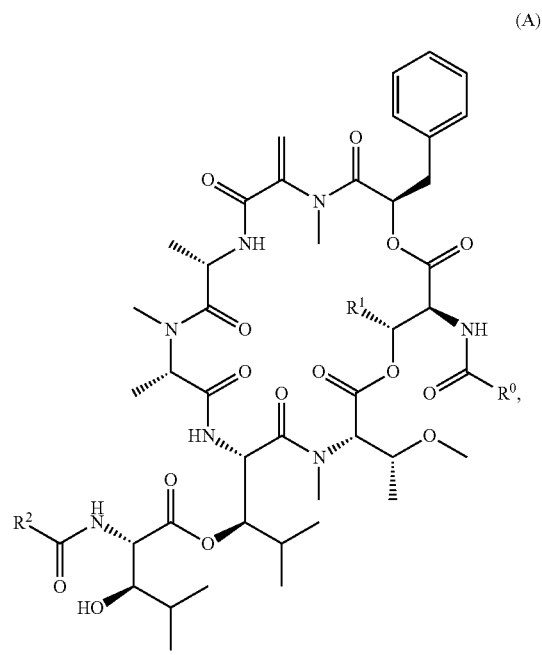

(A)

wherein $R_0$ is methyl or ethyl, $R_1$ is methyl or i-propyl, and $R_2$ is methyl or ethyl.

In another aspect, Drug moiety of the Antibody Drug Conjugate of the invention is compound (A1) having the following structure:

(A1)

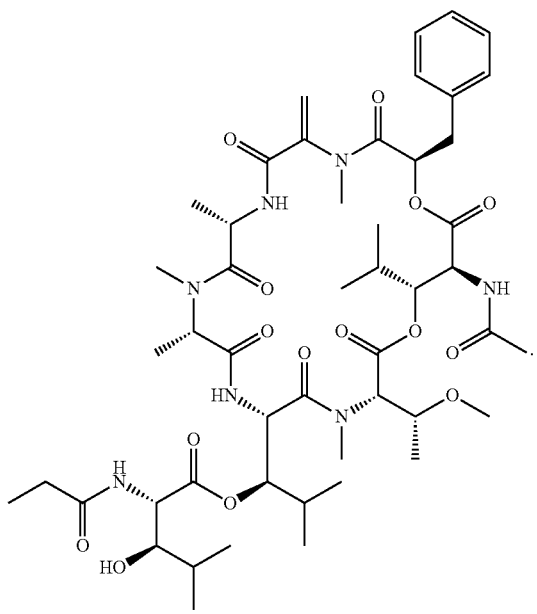

(A3)

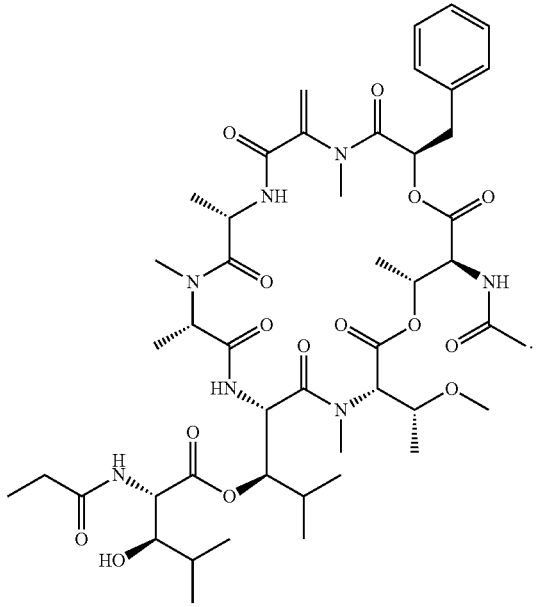

Table 1 gives the inhibitory activity of compounds (A1), (A2) and (A3) obtained using the assay described in Example 5.

In another aspect, Drug moiety of the Antibody Drug Conjugate of the invention is compound (A2) having the following structure:

TABLE 1

| Compound | $GI_{50}$ (nM) 92.1GNAQ$^{Q209L}$ |
|---|---|
| A1 | 0.467 |
| A2 | 22.1 |
| A3 | 9.3 |

(A2)

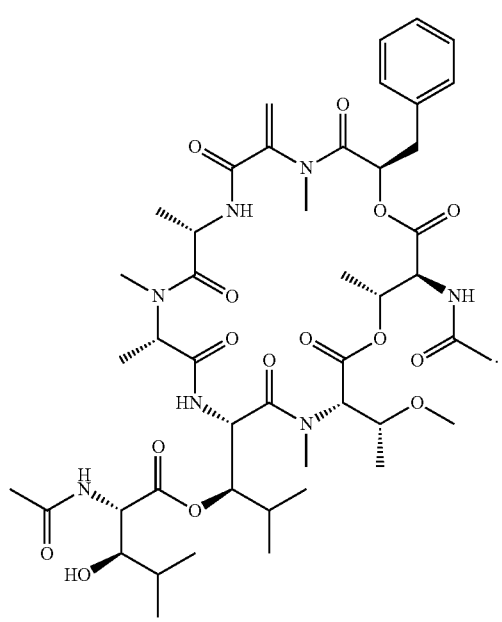

In another aspect, Drug moiety of the Antibody Drug Conjugate of the invention is compound (A3) having the following structure:

Linker-Drug Moiety ($L_A$-(D)$_n$)

In a second aspect, the Linker-Drug moiety, (($L_A$-(D)$_n$)), of the Antibody Drug Conjugate of the invention comprises one or more Drug moieties covalently attached to a linker ($L_A$), wherein the one or more Drug moieties are each independently selected from a GNAQ inhibitor, a GNA11 inhibitor or an inhibitor of GNAQ and GNA11 (GNAQ/GNA11 inhibitor).

In another aspect, the Linker-Drug moiety, (($L_A$-(D)$_n$)), of the Antibody Drug Conjugate of the invention comprises one or more Drug moieties covalently attached to a linker ($L_A$), wherein the one or more Drug moieties are each independently selected from a GNAQ inhibitor.

In another aspect, the Linker-Drug moiety, (($L_A$-(D)$_n$)), of the Antibody Drug Conjugate of the invention comprises one or more Drug moieties attached to a linker ($L_A$), wherein the one or more Drug moieties are each independently selected from a GNA11 inhibitor.

In another aspect, the Linker-Drug moiety, (($L_A$-(D)$_n$)), of the Antibody Drug Conjugate of the invention comprises one or more Drug moieties covalently attached to a linker ($L_A$), wherein the one or more Drug moieties are each independently selected from an inhibitor of GNAQ and GNA11 (GNAQ/GNA11 inhibitor).

In another aspect, the Linker-Drug moiety, (($L_A$-(D)$_n$)), of the Antibody Drug Conjugate of the invention comprises one or more Drug moieties covalently attached to a linker ($L_A$), wherein the linker ($L_A$) is a cleavable linker and the one or more Drug moieties are each independently selected from a GNAQ inhibitor, a GNA11 inhibitor or an inhibitor of GNAQ and GNA11 (GNAQ/GNA11 inhibitor).

In another aspect, the Linker-Drug moiety, $((L_A\text{-}(D)_n)))$, of the Antibody Drug Conjugate of the invention comprises one or more Drug moieties covalently attached to a linker $(L_A)$, wherein the linker $(L_A)$ is a cleavable linker and the one or more Drug moieties are each independently selected from a GNAQ inhibitor.

In another aspect, the Linker-Drug moiety, $((L_A\text{-}(D)_n)))$, of the Antibody Drug Conjugate of the invention comprises one or more Drug moieties covalently attached to a linker $(L_A)$, wherein the linker $(L_A)$ is a cleavable linker and the one or more Drug moieties are each independently selected from a GNA11 inhibitor.

In another aspect, the Linker-Drug moiety, $((L_A\text{-}(D)_n)))$, of the Antibody Drug Conjugate of the invention comprises one or more Drug moieties covalently attached to a linker $(L_A)$, wherein the linker $(L_A)$ is a cleavable linker and the one or more Drug moieties are each independently selected from an inhibitor of GNAQ and GNA11 (GNAQ/GNA11 inhibitor).

In another aspect, the Linker-Drug moiety, $((L_A\text{-}(D)_n)))$, of the Antibody Drug Conjugate of the invention comprises one or more Drug moieties covalently attached to a linker $(L_A)$, wherein the linker $(L_A)$ is a non-cleavable linker and the one or more Drug moieties are each independently selected from a GNAQ inhibitor, a GNA11 inhibitor or an inhibitor of GNAQ and GNA11 (GNAQ/GNA11 inhibitor).

In another aspect, the Linker-Drug moiety, $((L_A\text{-}(D)_n)))$, of the Antibody Drug Conjugate of the invention comprises one or more Drug moieties covalently attached to a linker $(L_A)$, wherein the linker $(L_A)$ is a non-cleavable linker and the one or more Drug moieties are each independently selected from a GNAQ inhibitor.

In another aspect, the Linker-Drug moiety, $((L_A\text{-}(D)_n)))$, of the Antibody Drug Conjugate of the invention comprises one or more Drug moieties covalently attached to a linker $(L_A)$, wherein the linker $(L_A)$ is a non-cleavable linker and the one or more Drug moieties are each independently selected from a GNA11 inhibitor.

In another aspect, the Linker-Drug moiety, $((L_A\text{-}(D)_n)))$, of the Antibody Drug Conjugate of the invention comprises one or more Drug moieties covalently attached to a linker $(L_A)$, wherein the linker $(L_A)$ is a non-cleavable linker and the one or more Drug moieties are each independently selected from an inhibitor of GNAQ and GNA11 (GNAQ/GNA11 inhibitor).

In another aspect, the linker $(L_A)$ of the Linker-Drug moiety, $((L_A\text{-}(D)_n)))$, of the Antibody Drug Conjugate of the invention has the following formula:

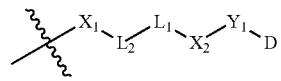

wherein:
   $X_1$ is a bivalent coupling group;
   $X_2$ is a self-immolative spacer;
   $Y_1$ is

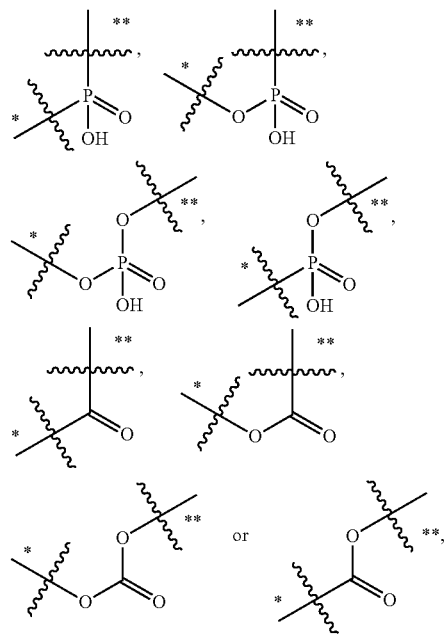

where the * of $Y_1$ indicates the point of attachment to $X_2$ and the ** of $Y_1$ indicates the other point of attachment;
   $L_1$ is a bivalent peptide linker, and
   $L_2$ is a bond or a linker.

In another aspect, the Linker-Drug moiety, $((L_A\text{-}(D)_n)))$, of the Antibody Drug Conjugate of the invention has the following formula:

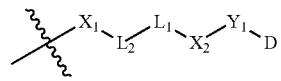

wherein:
   D is a GNAQ inhibitor, a GNA11 inhibitor or an inhibitor of GNAQ and GNA11;
   $X_1$ is a bivalent coupling group;
   $X_2$ is a self-immolative spacer;
   $Y_1$ is

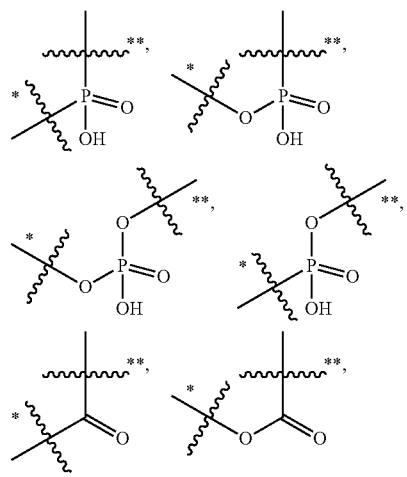

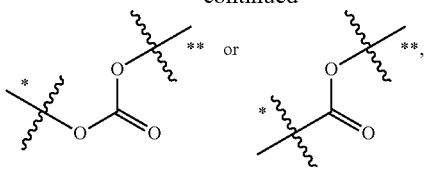

where the * of $Y_1$ indicates the point of attachment to $X_2$ and the ** of Y, indicates the point of attachment to D;

$L_1$ is a bivalent peptide linker, and $L_2$ is a bond or a linker.

Linker-Drug Compounds ($L_B$-(D)$_n$)

In one aspect the Linker-Drug of the invention is a compound having the structure of Formula (B), or stereoisomers or pharmaceutically acceptable salts thereof, $$R^8\text{-}L_B\text{-}(D)_n \quad (B)$$

wherein:

D is a GNAQ inhibitor, a GNA11 inhibitor or an inhibitor of GNAQ and GNA11;

$R^8$ is a reactive group;

$L_B$ is a cleavable linker or non-cleavable linker, and n is 1, 2, 3 or 4.

In one aspect the Linker-Drug of the invention having the structure of Formula (B), or stereoisomers or pharmaceutically acceptable salts thereof, wherein D is a GNAQ inhibitor, a GNA11 inhibitor or an inhibitor of GNAQ and GNA11;

$R^8$ is a reactive group;

$L_B$ is a cleavable linker comprising one or more linker components selected from a self-immolative spacer, a phosphate group, a carbonate group and a bivalent peptide linker, and n is 1, 2, 3 or 4.

In one aspect the Linker-Drug of the invention is a compound having the structure of Formula (B-1), or stereoisomers or pharmaceutically acceptable salts thereof,

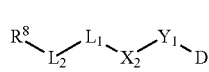
(B-1)

wherein:

D is a GNAQ inhibitor, a GNA11 inhibitor or an inhibitor of GNAQ and GNA11;

$R^8$ is a reactive group;

$X_2$ is a self-immolative spacer;

$Y_1$ is

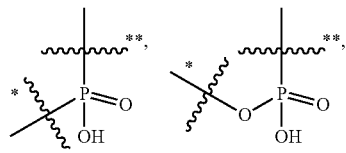

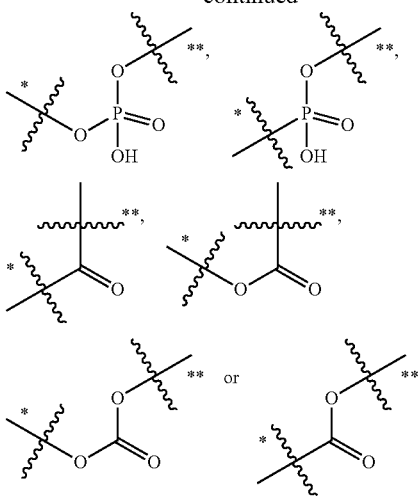

where the * of $Y_1$ indicates the point of attachment to $X_2$ and the ** of Y, indicates the point of attachment to D;

$L_1$ is a bivalent peptide linker, and $L_2$ is a bond or a linker.

Certain aspects and examples of the Linker-Drug compounds of the invention are provided in the following listing of additional, enumerated embodiments. It will be recognized that features specified in each embodiment may be combined with other specified features to provide further embodiments of the present invention.

Embodiment 1

The compound of Formula (B) or Formula (B-1), or stereoisomers or a pharmaceutically acceptable salt thereof, wherein D is a GNAQ inhibitor.

Embodiment 2

The compound of Formula (B) or Formula (B-1), or stereoisomers or a pharmaceutically acceptable salt thereof, wherein D is a GNA11 inhibitor.

Embodiment 3

The compound of Formula (B) or Formula (B-1), or stereoisomers or a pharmaceutically acceptable salt thereof, wherein D is an inhibitor of GNAQ and GNA11.

Embodiment 4

The compound of Formula (B) or Formula (B-1), or stereoisomers or a pharmaceutically acceptable salt thereof, wherein D is

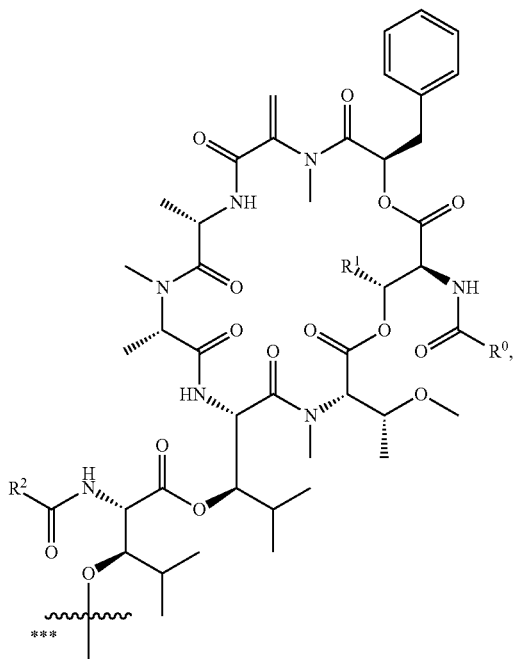

wherein $R^0$ is methyl or ethyl, $R^1$ is methyl or isopropyl, $R^2$ is methyl or ethyl, and the *** indicates the point of attachment to $L_B$ or $Y_1$.

Embodiment 5

The compound of Formula (B) or Formula (B-1), or stereoisomers or a pharmaceutically acceptable salt thereof, wherein D is

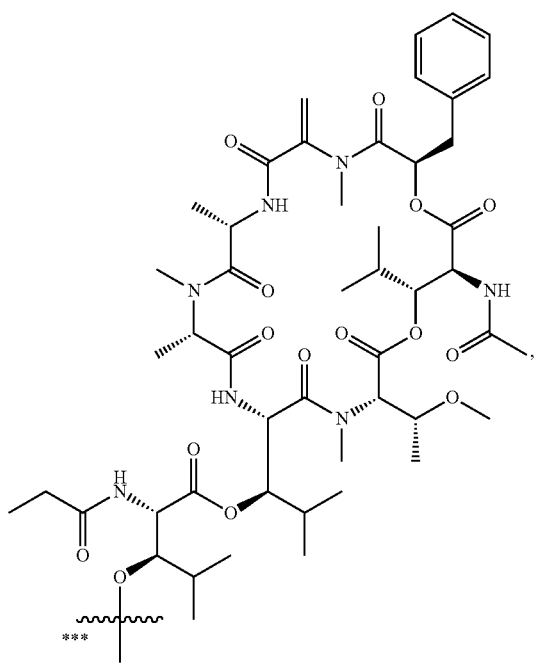 [SMILES: *O[C@H](C(C)C)[C@H](NC(=O)CC)C(=O)O[C@H](C(C)C)[C@@H]1NC(=O)[C@H](C)N(C)C(=O)[C@H](C)NC(=O)C(=C)N(C)C(=O)[C@@H](Cc2ccccc2)OC(=O)[C@@H](NC(C)=O)[C@@H](C(C)C)OC(=O)[C@H]([C@@H](C)OC)N(C)C1=O]

where the *** indicates the point of attachment to $L_B$ or $Y_1$.

Embodiment 6

The compound of Formula (B) or Formula (B-1), or stereoisomers or a pharmaceutically acceptable salt thereof, wherein D is

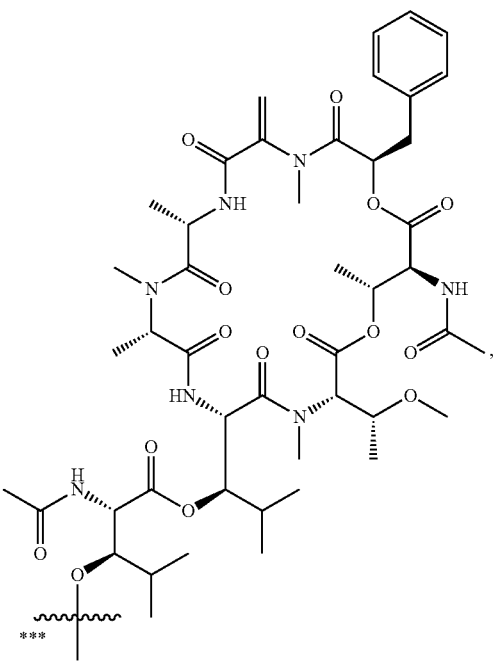 [SMILES: *O[C@H](C(C)C)[C@H](NC(C)=O)C(=O)O[C@H](C(C)C)[C@@H]1NC(=O)[C@H](C)N(C)C(=O)[C@H](C)NC(=O)C(=C)N(C)C(=O)[C@@H](Cc2ccccc2)OC(=O)[C@@H](NC(C)=O)[C@@H](C)OC(=O)[C@H]([C@@H](C)OC)N(C)C1=O]

where the *** indicates the point of attachment to $L_B$ or $Y_1$.

Embodiment 7

The compound of Formula (B) or Formula (B-1), or stereoisomers or a pharmaceutically acceptable salt thereof, wherein D is

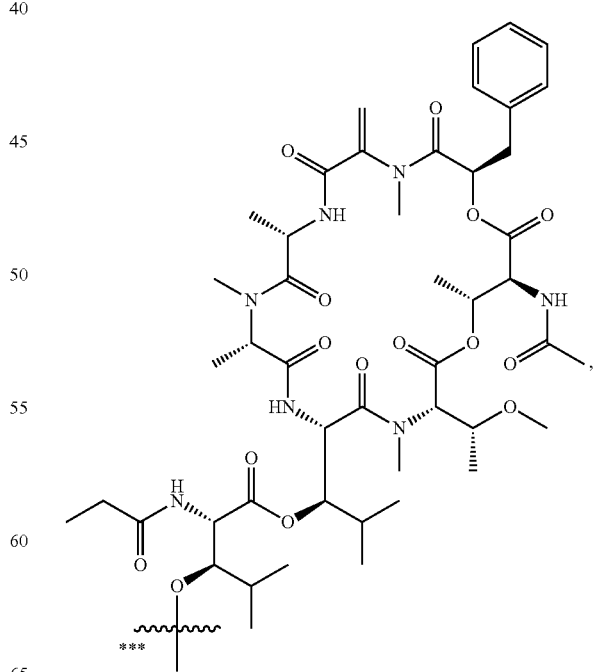

where the *** indicates the point of attachment to $L_B$ or $Y_1$.

Embodiment 8

The compound of Formula (B) or Formula (B-1), or stereoisomers or a pharmaceutically acceptable salt thereof, having the structure of Formula (B-2), or a pharmaceutically acceptable salt thereof:

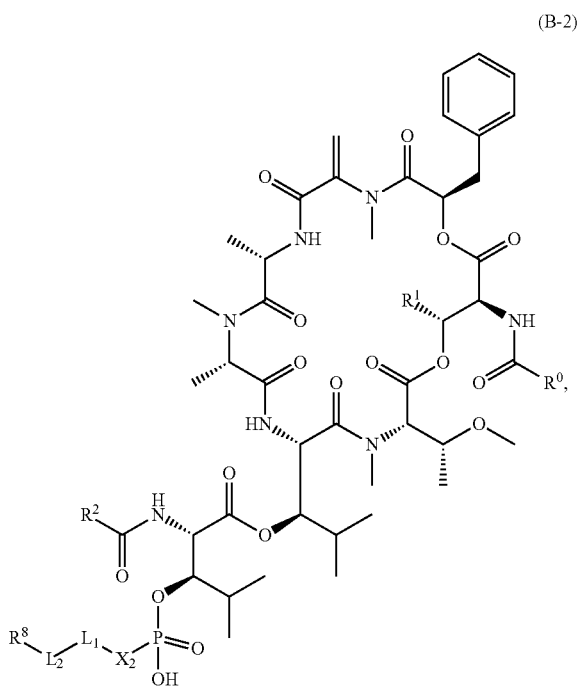

(B-2)

wherein:
- $R^0$ is methyl or ethyl;
- $R^1$ is methyl or isopropyl;
- $R^2$ is methyl or ethyl, and
- $X_2$, $L_1$, $L_2$ and $R^8$ are as define in compounds of Formula (B-1) above.

Embodiment 9

The compound of Formula (B), Formula (B-1) or Formula (B-2), or stereoisomers or a pharmaceutically acceptable salt thereof, having the structure of Formula (B-2a), or a pharmaceutically acceptable salt thereof:

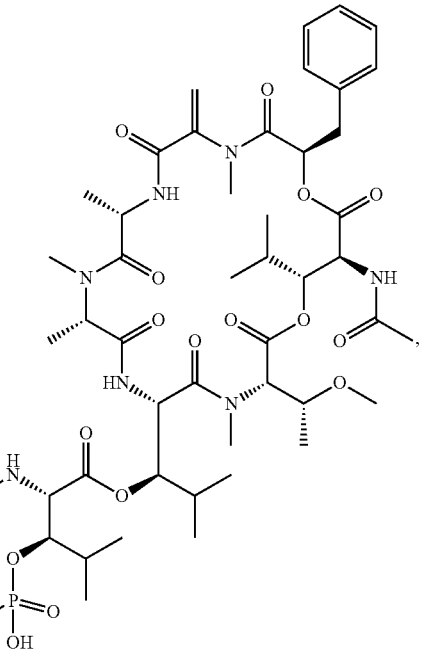

(B-2a)

wherein:
- $X_2$, $L_1$, $L_2$ and $R^8$ are as define in compounds of Formula (B-1) above.

Embodiment 10

The compound of Formula (B), Formula (B-1) or Formula (B-2), or stereoisomers or a pharmaceutically acceptable salt thereof, having the structure of Formula (B-2b), or a pharmaceutically acceptable salt thereof:

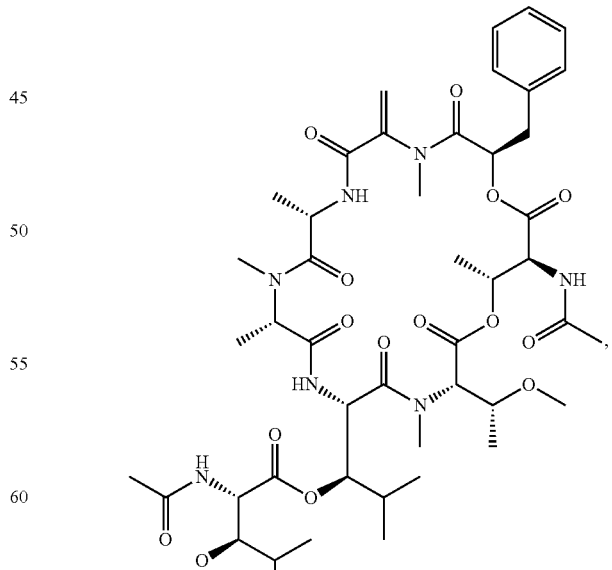

(B-2b)

wherein:

X$_2$, L$_1$, L$_2$ and R$^8$ are as define in compounds of Formula (B-1) above.

Embodiment 11

The compound of Formula (B), Formula (B-1) or Formula (B-2), or stereoisomers or a pharmaceutically acceptable salt thereof, having the structure of Formula (B-2c), or a pharmaceutically acceptable salt thereof:

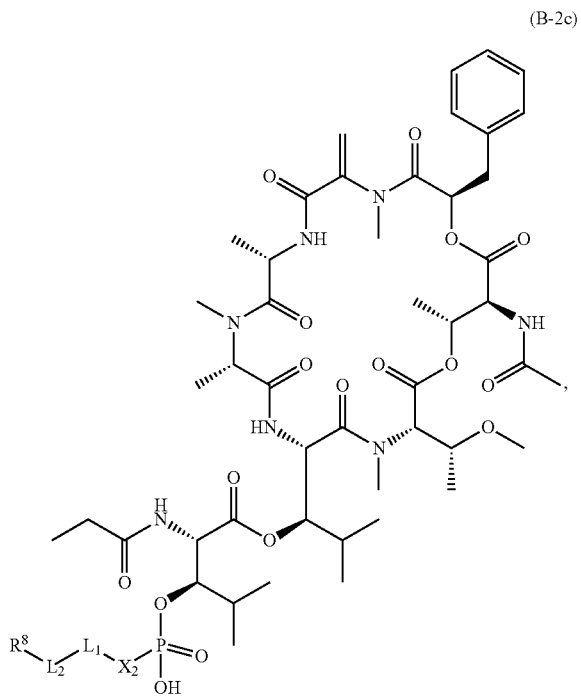

(B-2c)

wherein:

X$_2$, L$_1$, L$_2$ and R$^8$ are as define in compounds of Formula (B-1) above.

Embodiment 12

The compound of Formula (B) or Formula (B-1), or stereoisomers or a pharmaceutically acceptable salt thereof, having the structure of Formula (B-3), or a pharmaceutically acceptable salt thereof:

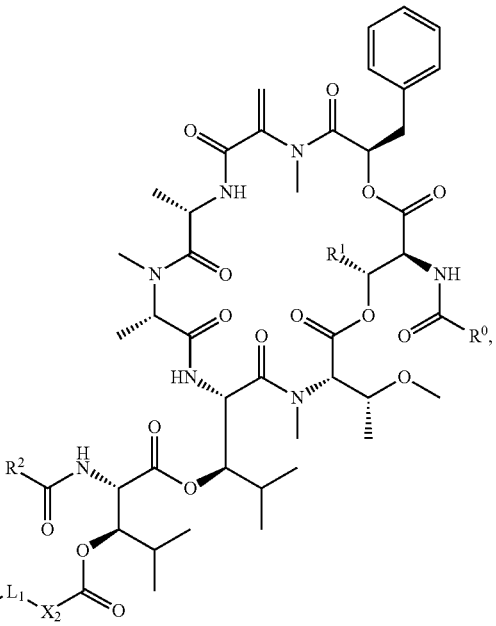

(B-3)

wherein:

R$^0$ is methyl or ethyl;

R$^1$ is methyl or isopropyl;

R$^2$ is methyl or ethyl, and

X$_2$, L$_1$, L$_2$ and R$^8$ are as define in compounds of Formula (B-1) above.

Embodiment 13

The compound of Formula (B), Formula (B-1) or Formula (B-3), or stereoisomers or a pharmaceutically acceptable salt thereof, having the structure of Formula (B-3a), or a pharmaceutically acceptable salt thereof:

(B-3a)

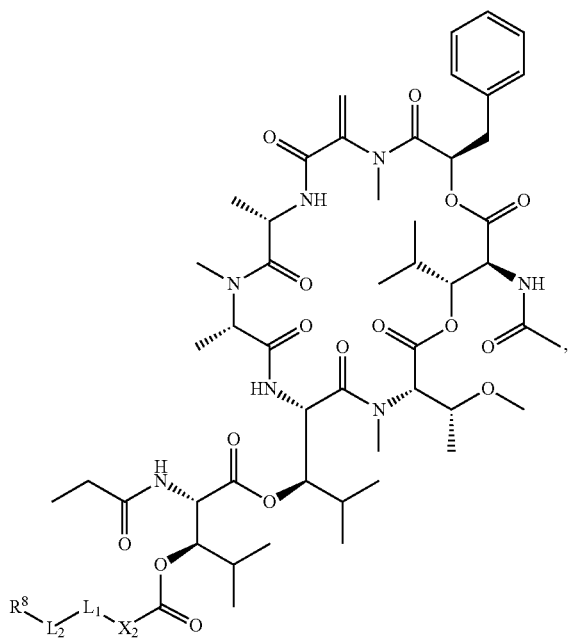

wherein:
X$_2$, L$_1$, L$_2$ and R$^8$ are as define in compounds of Formula (B-1) above.

Embodiment 14

The compound of Formula (B), Formula (B-1) or Formula (B-3), or stereoisomers or a pharmaceutically acceptable salt thereof, having the structure of Formula (B-3b), or a pharmaceutically acceptable salt thereof:

(B-3b)

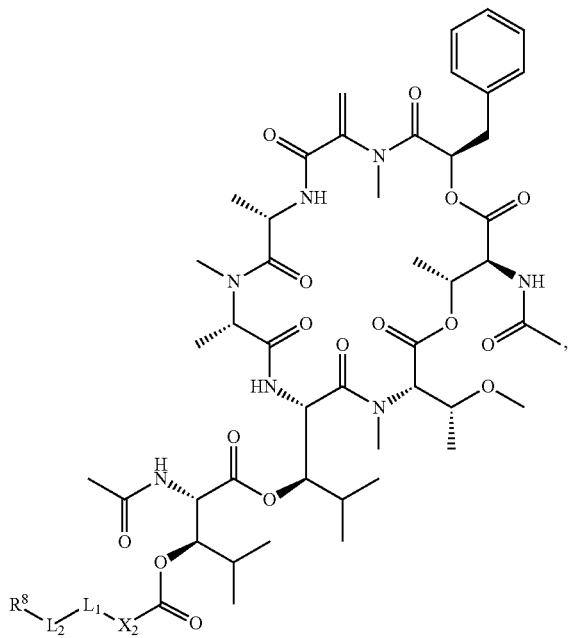

wherein:
X$_2$, L$_1$, L$_2$ and R$^8$ are as define in compounds of Formula (B-1) above.

Embodiment 15

The compound of Formula (B), Formula (B-1) or Formula (B-3), or stereoisomers or a pharmaceutically acceptable salt thereof, having the structure of Formula (B-3c), or a pharmaceutically acceptable salt thereof:

(B-3c)

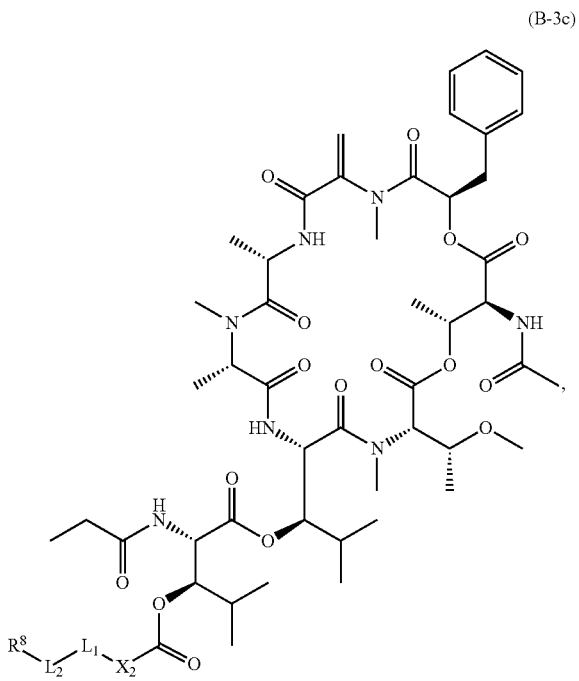

wherein:
X$_2$, L$_1$, L$_2$ and R$^8$ are as define in compounds of Formula (B-1) above.

Embodiment 16

The compound of Formula (B-2) of Embodiment 8, Formula (B-3) of Embodiment 12, or a pharmaceutically acceptable salt thereof:
wherein:
R$^0$ is methyl or ethyl;
R$^1$ is methyl or isopropyl;
R$^2$ is methyl or ethyl;
X$_2$ is a self-immolative spacer selected from

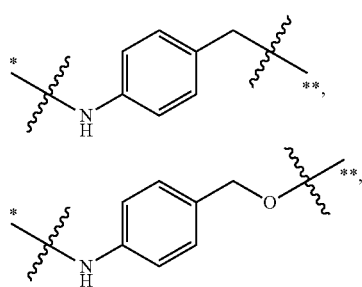

-continued

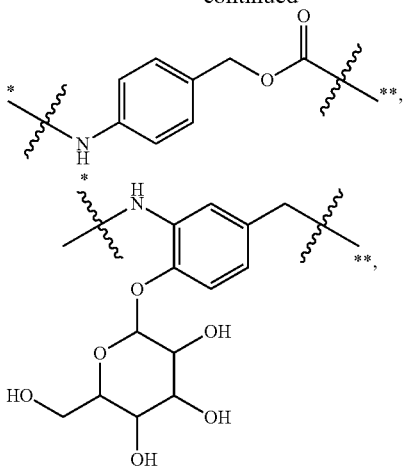

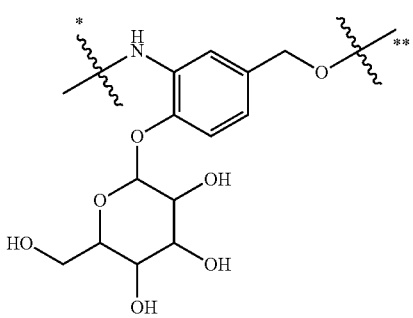

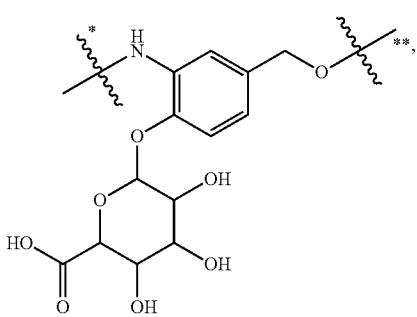

where the * of $X_2$ indicates the point of attachment to $L_1$ and the ** of $X_2$ indicates the point of attachment to the

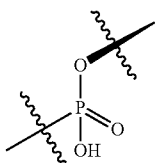

group or the point of attachment to

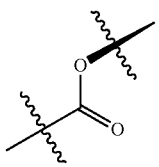

group;
$L_1$ is a bivalent peptide linker comprising 2 to 4 amino acid residues;
$L_2$ is a linker,
$R^8$ is selected from

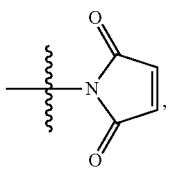 [SMILES: *N1C(=O)C=CC1=O]

—$N_3$, —$ONH_2$, —$NR^4C(=O)CH=CH_2$, SH, —$SSR^{13}$, —$S(=O)_2(CH=CH_2)$, —$NR^4S(=O)_2(CH=CH_2)$, —$NR^4C(=O)CH_2Br$, —$NR^4C(=O)CH_2I$, —$NHC(=O)CH_2Br$, —$NHC(=O)CH_2I$, —$C(=O)NHNH_2$,

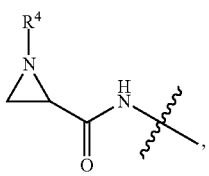

—$CO_2H$, —$NH_2$,

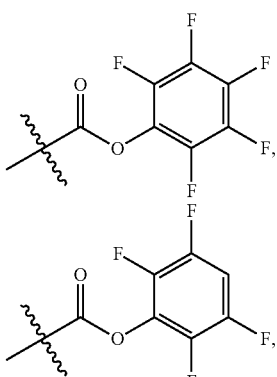

67

-continued

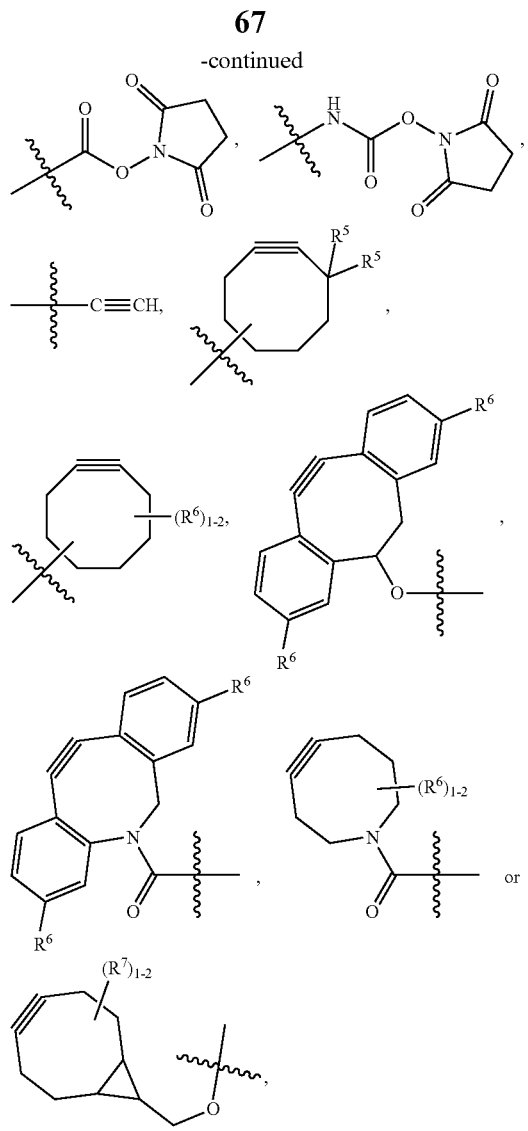

wherein:
each $R^4$ is independently selected from H and $C_1$-$C_6$alkyl;
each $R^5$ is independently selected from H, $C_1$-$C_6$alkyl, F, Cl, and —OH;
each $R^6$ is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH, and
each $R^7$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH.

Embodiment 17

The compound of any one of Embodiments 1 to 16, wherein $X_2$ is a self-immolative spacer selected from

68

-continued

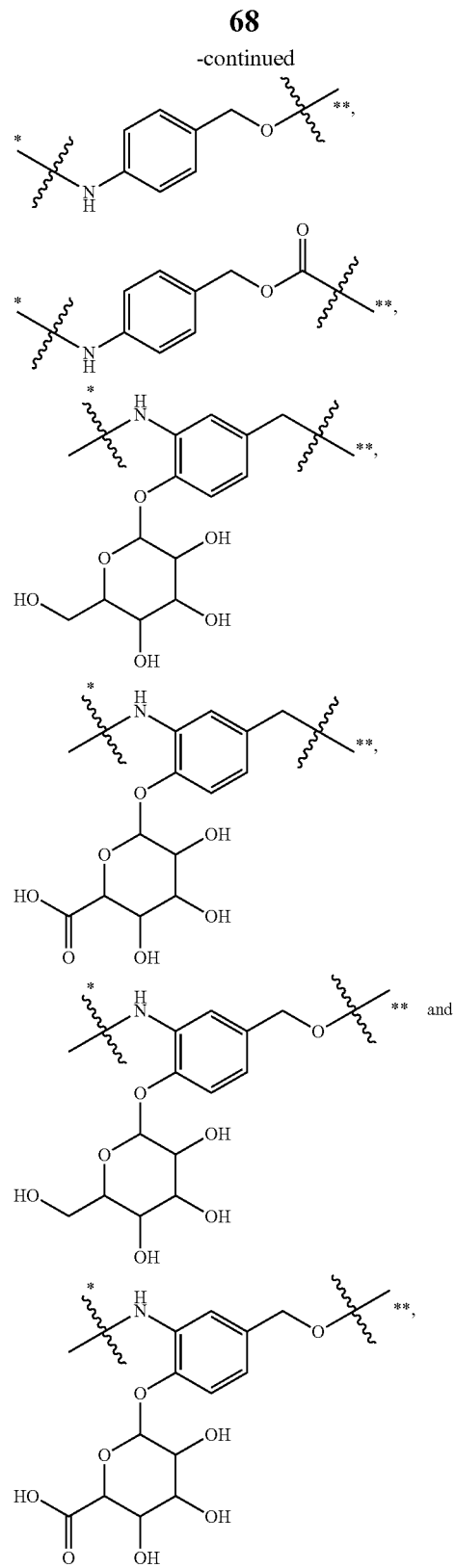

where the * of $X_2$ indicates the point of attachment to $L_1$ and the ** of $X_2$ indicates the point of attachment to $Y_1$, the point of attachment to the

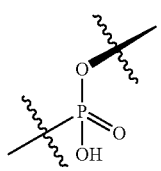

group or the point of attachment to

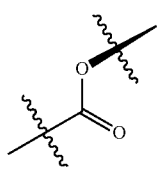

group.

Embodiment 18

The compound of any one of Embodiments 1 to 17, wherein $X_2$ is

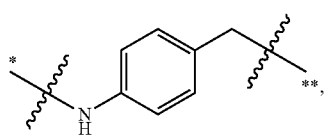 [SMILES: *Cc1ccc(N*)cc1]

where the * of $X_2$ indicates the point of attachment to $L_1$ and the ** of $X_2$ indicates the point of attachment to $Y_1$, the point of attachment to the

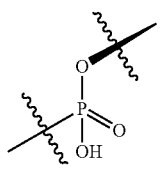

group or the point of attachment to

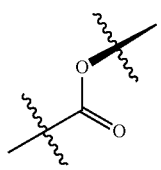

group.

Embodiment 19

The compound of any one of Embodiments 1 to 18, wherein $L_1$ is a bivalent peptide linker comprising 2 to 4 amino acid residues.

Embodiment 20

The compound of any one of Embodiments 1 to 18, wherein $L_1$ is a is a bivalent peptide linker comprising an amino acid residue selected from valine, citrulline, lysine, isoleucine, phenylalanine, methionine, asparagine, proline, alanine, leucine, tryptophan, and tyrosine.

Embodiment 21

The compound of any one of Embodiments 1 to 18, wherein $L_1$ is a bivalent peptide linker comprising at least one valine (Val) or citrulline (Cit) residue.

Embodiment 22

The compound of any one of Embodiments 1 to 18, wherein $L_1$ is a bivalent dipeptide linker selected from ValCit, PheLys, ValAla and ValLys.

Embodiment 23

The compound of any one of Embodiments 1 to 18, wherein $L_1$ is a bivalent dipeptide linker selected from

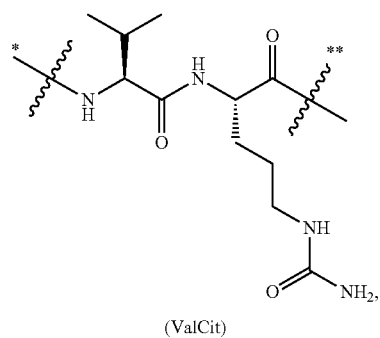 [SMILES: *N[C@H](C(=O)N[C@@H](CCCNC(N)=O)C(*)=O)C(C)C]

(ValCit)

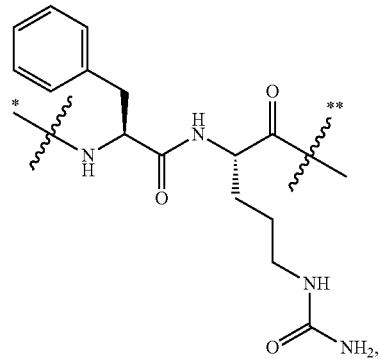

(PheLys)

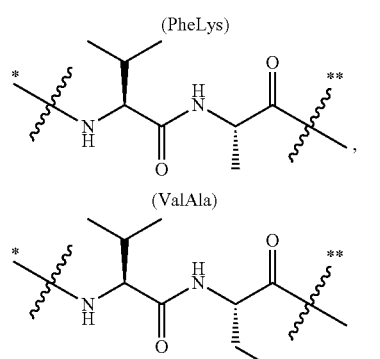

(ValAla),

(ValLys) and

-continued

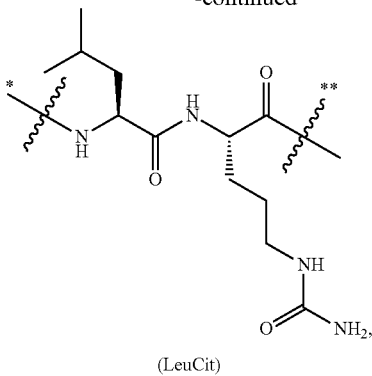

(LeuCit)

where the * of L₁ indicates the attachment point to L₂ and the ** of L₁ indicates the attachment point to X₂.

Embodiment 24

The compound of any one of Embodiments 1 to 18, wherein L₁ is ValCit.

Embodiment 25

The compound of any one of Embodiments 1 to 18, wherein L₁ is

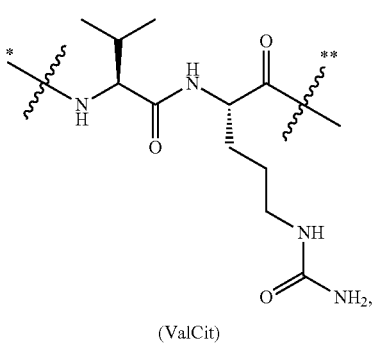

(ValCit)

where the * of L₁ indicates the attachment point to L₂ and the ** of L₁ indicates the attachment point to X₂.

Embodiment 26

The compound of any one of Embodiments 1 to 25, wherein L₂ is a linker.

Embodiment 27

The compound of any one of Embodiments 1 to 25, wherein L₂ is a linker selected from:
—*C(=O)((CH₂)$_m$O)$_p$(CH₂)$_m$**—, —*C(=O)(CH₂)$_m$**—, —*C(=O)(CH₂)$_n$NHC(=O)(CH₂)$_m$**—, —*C(=O)(CH₂)$_m$NHC(=O)((CH₂)$_m$O)(CH₂)$_m$**—, —*((CH₂)$_m$O)$_p$(CH₂)$_m$**—, —*((CH₂)$_m$O)$_p$(CH₂)$_m$**—, —(CH₂)$_m$—, —*(CH₂)$_m$NHC(=O)(CH₂)$_m$**—, —*(CH₂)$_m$NHC(=O)(CH₂)$_m$C(=O)NH(CH₂)$_m$**—, —*((CH₂)$_m$O)$_p$(CH₂)$_m$NHC(=O)(CH₂)$_m$**—, —*((CH₂)$_m$O)$_p$CH₂)$_m$C(=O)NH(CH₂)$_m$**—, —*(CH₂)$_m$C(R₃)₂**—, and —*(CH₂)$_m$C(R₃)₂SS(CH₂)$_m$NHC(=O)(CH₂)$_m$**—, where the * of L₂ indicates the attachment point to L₁ and the ** of L₂ indicates the point of attachment to R₈;

and wherein:
each R₃ is independently selected from H and C₁-C₆alkyl;
each m is independently selected from 1, 2, 3, 4, 5, 6, 7, 8, 9 and 10, and
each p is independently selected from 1, 2, 3, 4, 5, 6, 7, 8, 9, 10, 11, 12, 13 and 14.

Embodiment 28

The compound of any one of Embodiments 1 to 25, wherein L₂ is —*C(=O)((CH₂)$_m$O)$_p$(CH₂)$_m$**— or —*C(=O)(CH₂)$_m$**—, where the * of L₂ indicates the point of attachment to L₁ and the ** of L₂ indicates the point of attachment to R₈, and wherein each m is independently selected from 1, 2, 3, 4, 5, 6, 7, 8, 9 or 10 and p is 1, 2, 3, 4, 5, 6, 7, 8, 9, 10, 11, 12, 13 or 14.

Embodiment 29

The compound of any one of Embodiments 1 to 25, wherein L₂ is

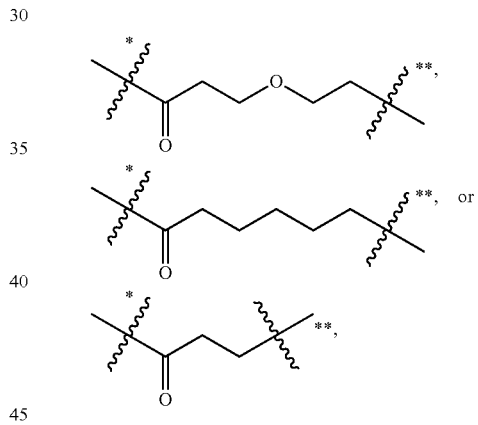

where the * of L₂ indicates the point of attachment to L₁ and the ** of L₂ indicates the point of attachment to R₈.

Embodiment 30

The compound of any one of Embodiments 1 to 29, wherein R⁸ is

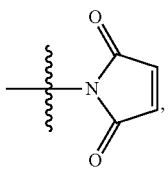 [SMILES: *N1C(=O)C=CC1=O]

—N₃, —ONH₂, —NR⁴C(=O)CH=CH₂, SH, —SSR¹³, —S(=O)₂(CH=CH₂), —NR⁴S(=O)₂(CH=CH₂), —NR⁴C(=O)CH₂Br, —NR⁴C(=O)CH₂I, —NHC(=O)CH₂Br, —NHC(=O)CH₂I, —C(=O)NHNH₂,

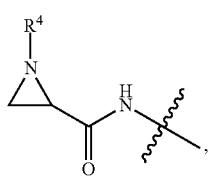

—CO₂H, —NH₂,

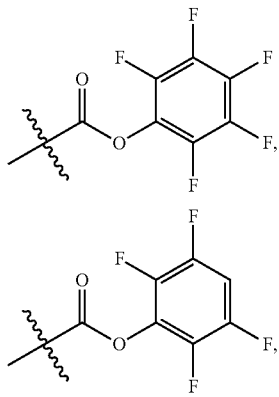

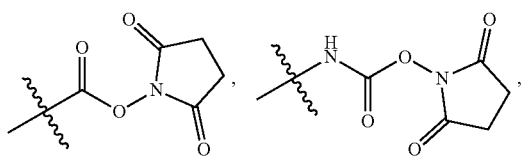

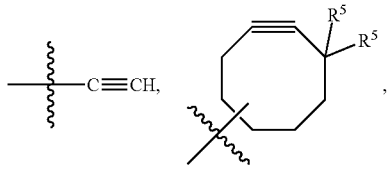

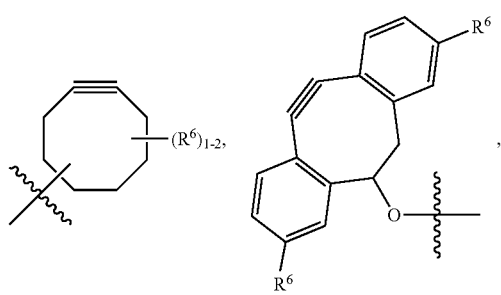

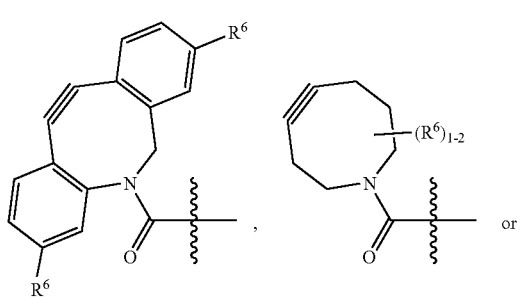

or

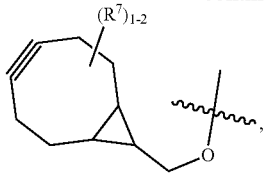

wherein:
each $R^4$ is independently selected from H and $C_1$-$C_6$alkyl;
each $R^5$ is independently selected from H, $C_1$-$C_6$alkyl, F, Cl, and —OH;
each $R^6$ is independently selected from H, $C_1$-$C_6$alkyl, F, Cl, —NH₂, —OCH₃, —OCH₂CH₃, —N(CH₃)₂, —CN, —NO₂ and —OH, and
each $R^7$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH.

Embodiment 31

The compound of any one of Embodiments 1 to 29, wherein $R^8$ is

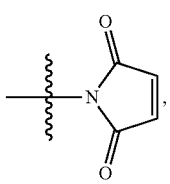

—ONH₂,

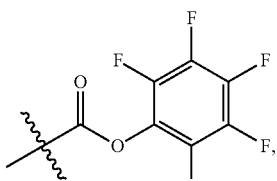

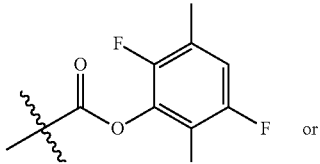

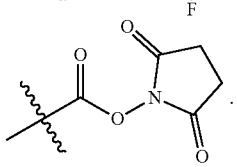

Embodiment 32

The compound of any one of Embodiments 1 to 29, wherein $R^8$ is

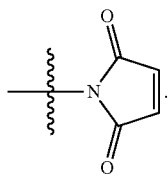 [SMILES: *N1C(=O)C=CC1=O]

Embodiment 33

The compound of Formula (B-2) of Embodiment 8, or a pharmaceutically acceptable salt thereof:
wherein:
R⁰ is methyl or ethyl;
R¹ is methyl or isopropyl;
R² is methyl or ethyl;
X₂ is

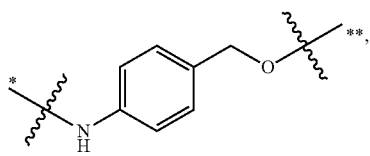 [SMILES: *Nc1ccc(CO*)cc1]

where the * of X₂ indicates the point of attachment to L₁ and the ** of X₂ indicates the point of attachment to the

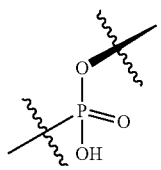

group;
L₁ is

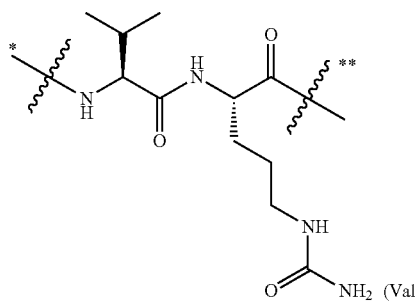

where the * of L₁ indicates the attachment point to L₂ and the ** of L₁ indicates the attachment point to X₂;
L₂ is

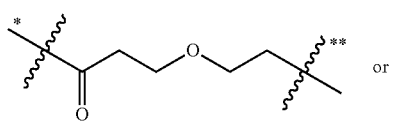 or

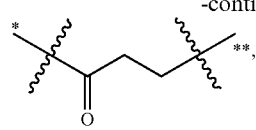

where the * of L₂ indicates the point of attachment to L₁ and the ** of L₂ indicates the point of attachment to R₈, and
R⁸ is

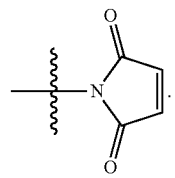 [SMILES: *N1C(=O)C=CC1=O]

Embodiment 34

The compound of Formula (B-3) of Embodiment 12, or a pharmaceutically acceptable salt thereof:
wherein:
R⁰ is methyl or ethyl;
R¹ is methyl or isopropyl;
R² is methyl or ethyl;
X₂ is

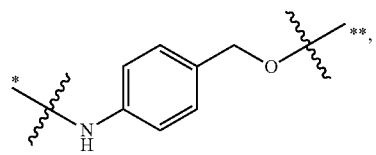 [SMILES: *Nc1ccc(CO*)cc1]

where the * of X₂ indicates the point of attachment to L₁ and the ** of X₂ indicates the point of attachment to the

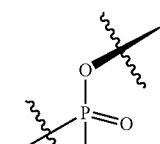

group;
L₁ is

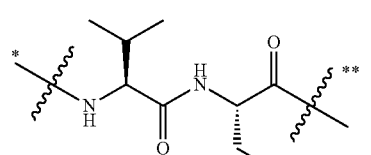

where the * of $L_1$ indicates the attachment point to $L_2$ and the ** of $L_1$ indicates the attachment point to $X_2$;

$L_2$ is

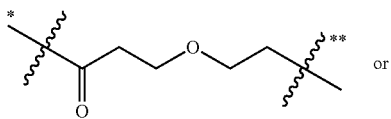 or

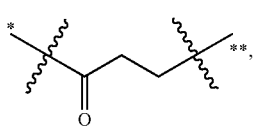

where the * of $L_2$ indicates the point of attachment to $L_1$ and the ** of $L_2$ indicates the point of attachment to $R_8$, and $R^8$ is

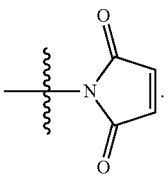 [SMILES: *N1C(=O)C=CC1=O]

Embodiment 35

The compound of Formula (B), Formula (B-1) or Formula (B-2), wherein the compound is

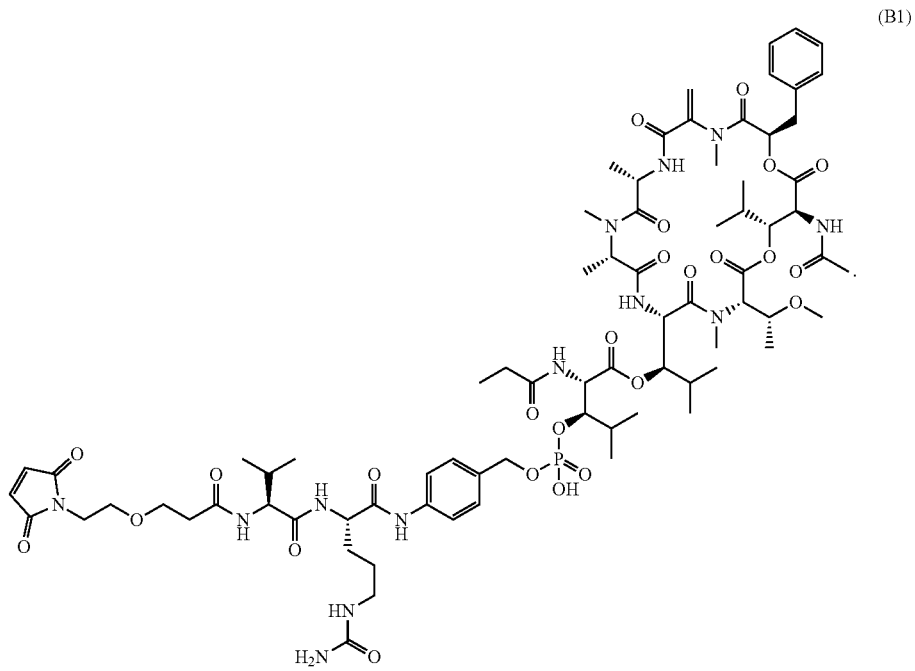 [SMILES: C=C1C(=O)N[C@@H](C)C(=O)N(C)[C@@H](C)C(=O)N[C@@H]([C@H](OC(=O)[C@@H](NC(=O)CC)[C@H](OP(=O)(O)OCc2ccc(NC(=O)[C@H](CCCNC(N)=O)NC(=O)[C@@H](NC(=O)CCOCCN3C(=O)C=CC3=O)C(C)C)cc2)C(C)C)C(C)C)C(=O)N(C)[C@@H]([C@@H](C)OC)C(=O)O[C@H](C(C)C)[C@H](NC(C)=O)C(=O)O[C@H](Cc2ccccc2)C(=O)N1C]

(B1)

Embodiment 36

The compound of Formula (B), Formula (B-1) or Formula (B-2), wherein the compound is

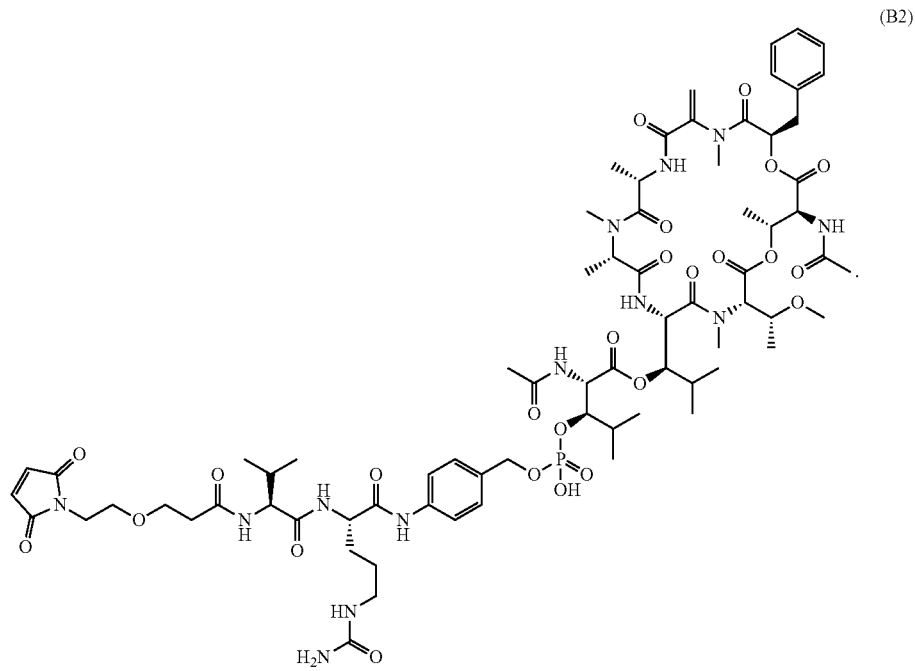 [SMILES: C=C1C(=O)N[C@@H](C)C(=O)N(C)[C@@H](C)C(=O)N[C@@H]([C@H](OC(=O)[C@@H](NC(C)=O)[C@H](OP(=O)(O)OCc2ccc(NC(=O)[C@H](CCCNC(N)=O)NC(=O)[C@@H](NC(=O)CCOCCN3C(=O)C=CC3=O)C(C)C)cc2)C(C)C)C(C)C)C(=O)N(C)[C@@H]([C@@H](C)OC)C(=O)O[C@H](C)[C@H](NC(C)=O)C(=O)O[C@H](Cc2ccccc2)C(=O)N1C]
(B2)
Embodiment 37
The compound of Formula (B), Formula (B-1) or Formula (B-2), wherein the compound is
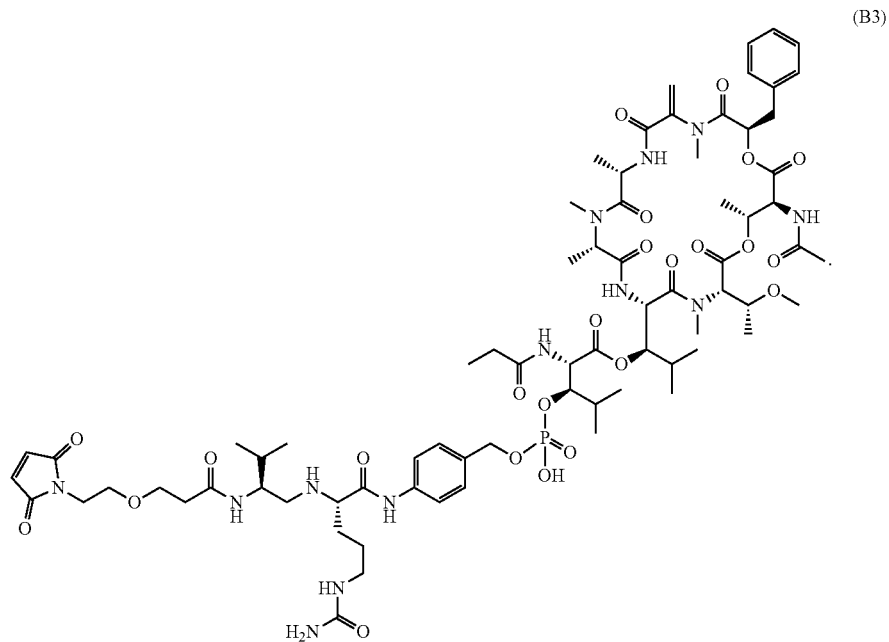 [SMILES: C=C1C(=O)N[C@@H](C)C(=O)N(C)[C@@H](C)C(=O)N[C@@H]([C@H](OC(=O)[C@@H](NC(=O)CC)[C@H](OP(=O)(O)OCc2ccc(NC(=O)[C@H](CCCNC(N)=O)NC[C@@H](NC(=O)CCOCCN3C(=O)C=CC3=O)C(C)C)cc2)C(C)C)C(C)C)C(=O)N(C)[C@@H]([C@@H](C)OC)C(=O)O[C@H](C)[C@H](NC(C)=O)C(=O)O[C@H](Cc2ccccc2)C(=O)N1C]
(B3)
Embodiment 38
The compound of Formula (B), Formula (B-1) or Formula (B-2), wherein the compound is (B4)
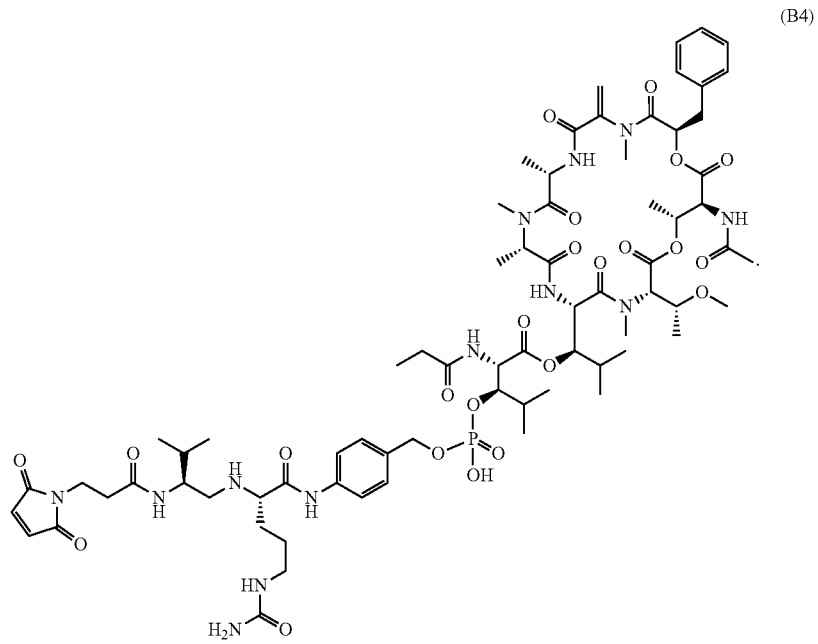 [SMILES: C=C1C(=O)N[C@@H](C)C(=O)N(C)[C@@H](C)C(=O)N[C@@H]([C@H](OC(=O)[C@@H](NC(=O)CC)[C@H](OP(=O)(O)OCc2ccc(NC(=O)[C@H](CCCNC(N)=O)NC[C@@H](NC(=O)CCN3C(=O)C=CC3=O)C(C)C)cc2)C(C)C)C(C)C)C(=O)N(C)[C@@H]([C@@H](C)OC)C(=O)O[C@H](C)[C@H](NC(C)=O)C(=O)O[C@H](Cc2ccccc2)C(=O)N1C]
Embodiment 39
The compound of Formula (B), Formula (B-1) or Formula (B-2), wherein the compound is
(B5)
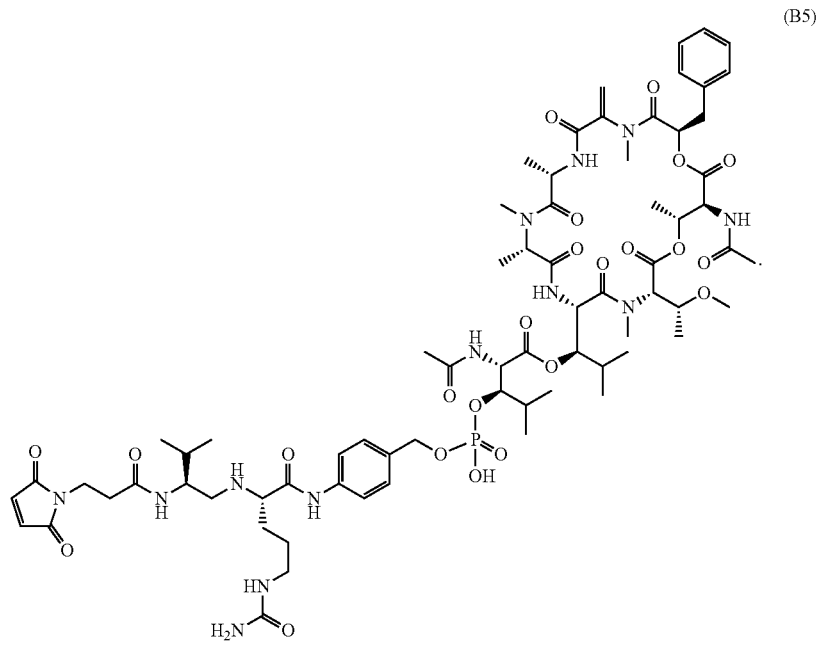 [SMILES: C=C1C(=O)N[C@@H](C)C(=O)N(C)[C@@H](C)C(=O)N[C@@H]([C@H](OC(=O)[C@@H](NC(C)=O)[C@H](OP(=O)(O)OCc2ccc(NC(=O)[C@H](CCCNC(N)=O)NC[C@@H](NC(=O)CCN3C(=O)C=CC3=O)C(C)C)cc2)C(C)C)C(C)C)C(=O)N(C)[C@@H]([C@@H](C)OC)C(=O)O[C@H](C)[C@H](NC(C)=O)C(=O)O[C@H](Cc2ccccc2)C(=O)N1C]
Embodiment 40
The compound of Formula (B), Formula (B-1) or Formula (B-2), wherein the compound is

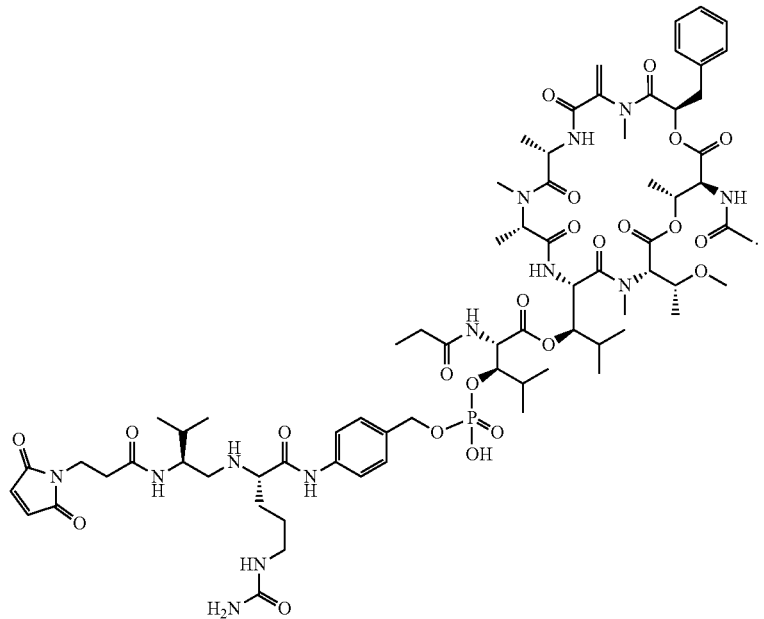
(B6)
Embodiment 41
The compound of Formula (B), Formula (B-1) or Formula (B-3), wherein the compound is
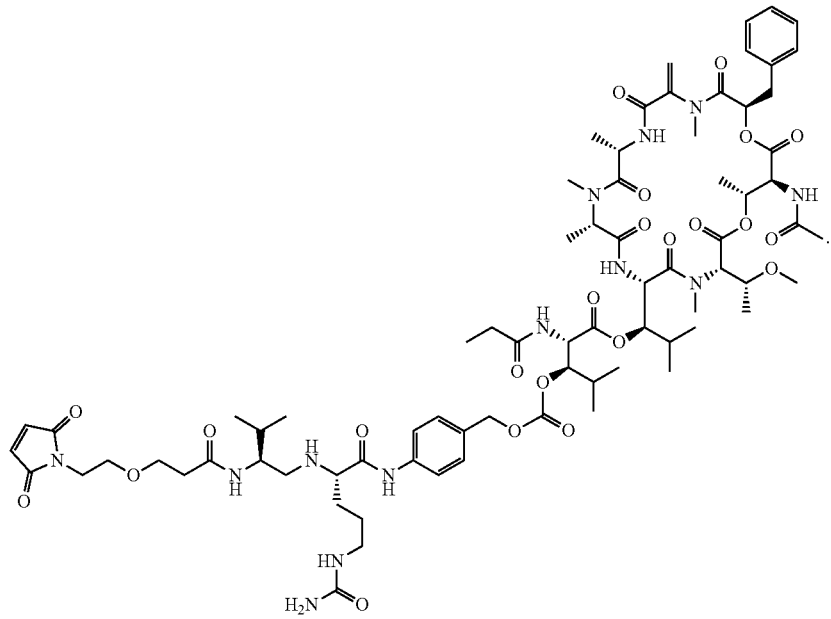
(B7)
Embodiment 42
The compound of Formula (B), Formula (B-1) or Formula (B-3), wherein the compound is

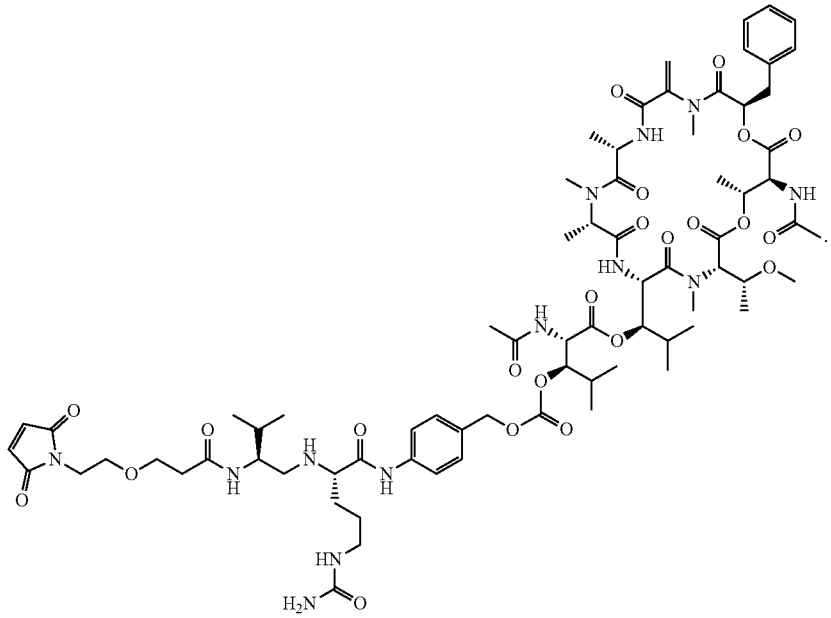
(B8)
Embodiment 43
The compound of Formula (B), Formula (B-1) or Formula (B-3), wherein the compound is
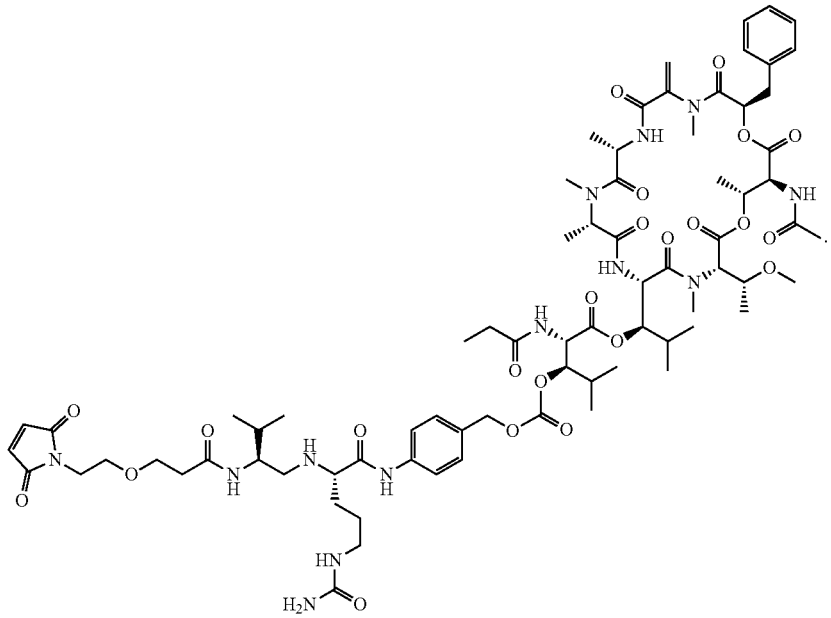
(B9)
Embodiment 44
The compound of Formula (B), Formula (B-1) or Formula (B-3), wherein the compound is (B10)
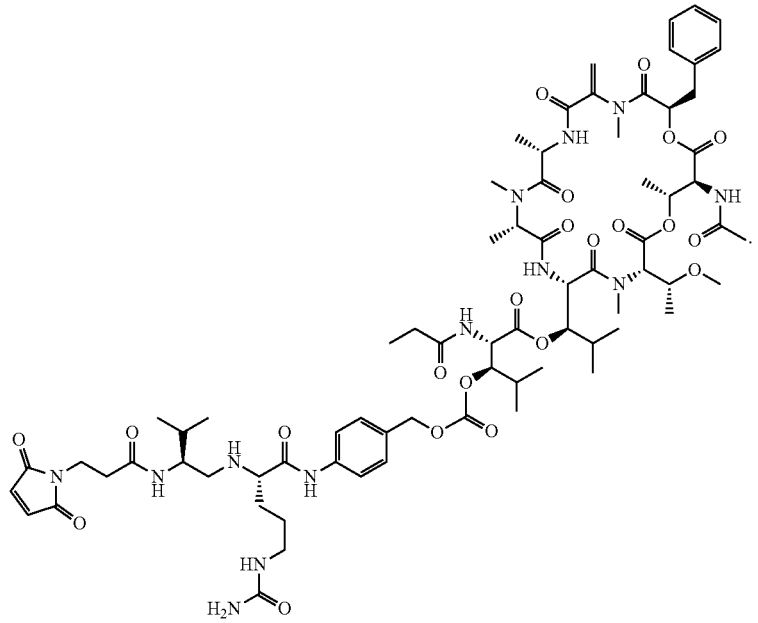
Embodiment 45
The compound of Formula (B), Formula (B-1) or Formula (B-3), wherein the compound is
(B11)
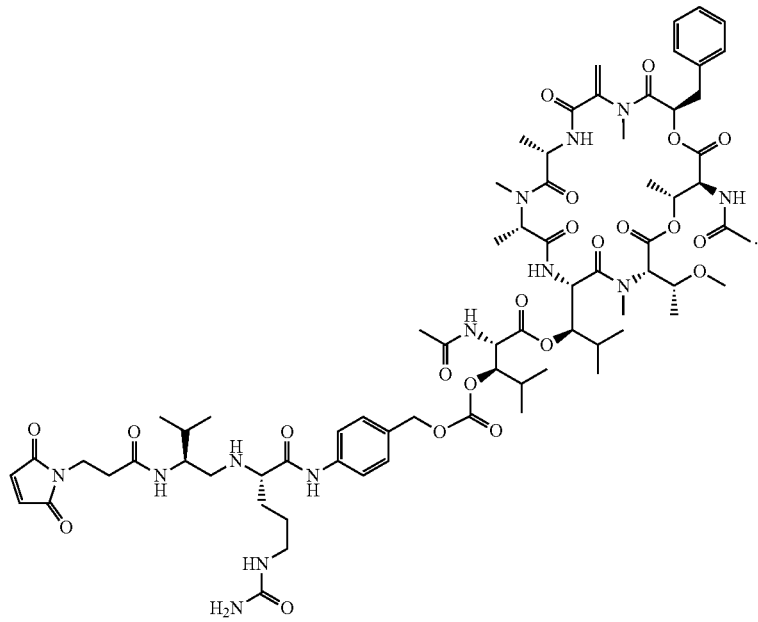
Embodiment 46
The compound of Formula (B), Formula (B-1) or Formula (B-3), wherein the compound is (B12)

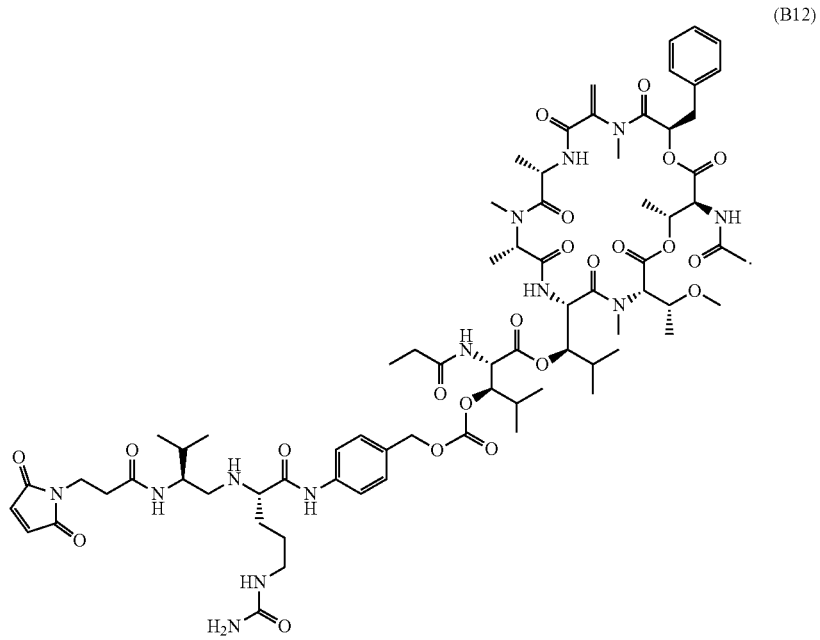 [SMILES: C=C1C(=O)N[C@@H](C)C(=O)N(C)[C@@H](C)C(=O)N[C@@H]([C@H](OC(=O)[C@@H](NC(=O)CC)[C@H](OC(=O)OCc2ccc(NC(=O)[C@H](CCCNC(N)=O)NC[C@@H](NC(=O)CCN3C(=O)C=CC3=O)C(C)C)cc2)C(C)C)C(C)C)C(=O)N(C)[C@@H]([C@@H](C)OC)C(=O)O[C@H](C)[C@H](NC(C)=O)C(=O)O[C@H](Cc2ccccc2)C(=O)N1C]

Antibody Drug Conjugates

In one aspect, the Antibody Drug Conjugate of the invention is a conjugate of Formula (C):

Ab-(L$_A$-(D)$_n$)$_y$      (C)

wherein:
D is a drug moiety;
Ab is an antibody or antigen binding fragment thereof that binds to human PMEL17 protein;
L$_A$ is a linker;
n is 1, 2, 3 or 4, and
y is 1, 2, 3 or 4,
where the Linker-Drug moiety (L$_A$-(D)$_n$) is covalently attached to the antibody or antigen binding fragment thereof.

In one aspect, the Antibody Drug Conjugate of the invention having the structure of Formula (C), wherein:
D is a GNAQ inhibitor, a GNA11 inhibitor or an inhibitor of GNAQ and GNA11;
Ab is an antibody or antigen binding fragment thereof that binds to human PMEL17 protein;
L$_A$ is a cleavable linker comprising one or more linker components selected from a self-immolative spacer, a phosphate group, a carbonate group and a bivalent peptide linker;
n is 1, 2, 3 or 4, and
y is 1, 2, 3 or 4,
where the Linker-Drug moiety (L$_A$-(D)$_n$) is covalently attached to the antibody or antigen binding fragment thereof.

In one aspect, the Antibody Drug Conjugate of Formula (C) is a conjugate of Formula (C-1):

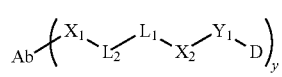      (C-1)

wherein:
D is a GNAQ inhibitor, a GNA11 inhibitor or an inhibitor of GNAQ and GNA11;
Ab is an antibody or antigen binding fragment thereof that binds to human PMEL17 protein;
X$_1$ is a bivalent coupling group;
X$_2$ is a self-immolative spacer;
Y$_1$ is

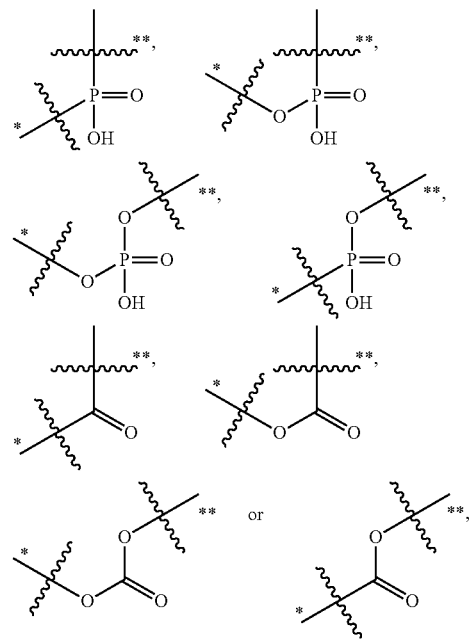

where the * of Y$_1$ indicates the point of attachment to X$_2$ and the ** of Y$_1$ indicates the point of attachment to D;
L$_1$ is a bivalent peptide linker;
L$_2$ is a bond or a linker, and
y is 1, 2, 3 or 4.

In the conjugates of Formula (C), one or more Linker-Drug moiety ($L_B$-$(D)_n$) can be covalently attached to the antibody or antigen binding fragment thereof, Ab, thereby covalently attaching one or more drug moieties, D, to the antibody or antigen binding fragment thereof, Ab, through linker, $L_A$. $L_A$ is any chemical moiety that is capable of linking the antibody or antigen binding fragment thereof, Ab, to one or more drug moieties, D. The conjugates of Formula (C), wherein one or more drug moieties, D, are covalently linked to an antibody or antigen binding fragment thereof, Ab, can be formed using a bifunctional or multifunctional linker reagent having one or more reactive functional groups that are the same or different. One of the reactive functional groups of the bifunctional or multifunctional linker reagent is used to react with a group on the antibody or antigen binding fragment thereof, Ab, by way of example, a thiol or an amine (e.g. a cysteine, an N-terminus or amino acid side chain such as lysine) to form a covalent linkage with one end of the linker $L_A$. Such reactive functional groups of the bifunctional or multifunctional linker reagent include, but are not limited to, a maleimide, a thiol and an NHS ester. The other reactive functional group or groups of the bifunctional or multifunctional linker reagent are used to covalently attached one or more drug moieties, D, to linker $L_A$.

In one aspect, $L_A$ is a cleavable linker. In another aspect, $L_A$ is a non-cleavable linker. In some aspects, $L_A$ is an acid-labile linker, photo-labile linker, peptidase cleavable linker, esterase cleavable linker, glycosidase cleavable linker, phosphodiesterase cleavable linker, a disulfide bond reducible linker, a hydrophilic linker, or a dicarboxylic acid based linker.

In one aspect, $L_A$ is a cleavable linker comprising one or more linker components selected from a self-immolative spacer, a phosphate group, a carbonate group and a bivalent peptide linker.

In one aspect, $L_A$ is a cleavable linker comprising one or more linker components selected from a self-immolative spacer, a phosphate group, a carbonate group, a bivalent peptide linker and a bivalent coupling group.

In one aspect, $L_A$ is a cleavable linker comprising one or more linker components selected from a self-immolative spacer, a phosphate group and a bivalent peptide linker.

In one aspect, $L_A$ is a cleavable linker comprising one or more linker components selected from a self-immolative spacer, a phosphate group, a bivalent peptide linker and a bivalent coupling group.

In another aspect, the linker ($L_A$) has the following formula:

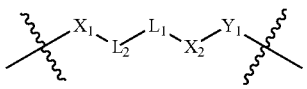

wherein:
$X_1$ is a bivalent coupling group;
$X_2$ is a self-immolative spacer;
$Y_1$ is

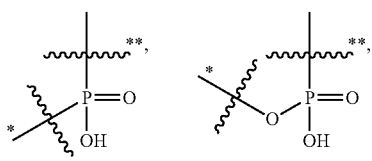

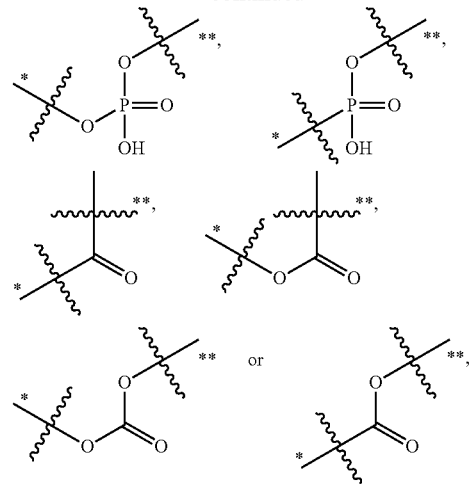

where the * of $Y_1$ indicates the point of attachment to $X_2$, and the ** of $Y_1$ indicates the other point of attachment;
$L_1$ is a bivalent peptide linker, and
$L_2$ is a bond or a linker.

In another aspect, the linker ($L_A$) has the following formula:

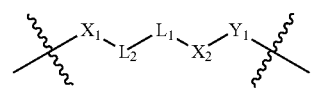

wherein:
$X_1$ is a bivalent coupling group;
$X_2$ is a self-immolative spacer;
$Y_1$ is

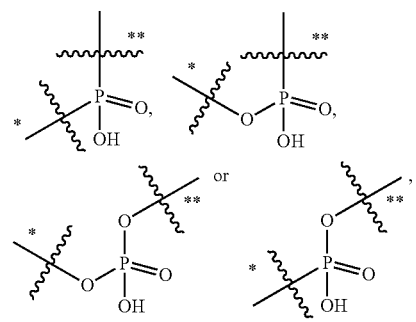

where the * of Y, indicates the point of attachment to $X_2$;
$L_1$ is a bivalent peptide linker, and
$L_2$ is a bond or a linker.

In another aspect, the linker ($L_A$) has the following formula:

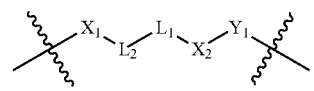

wherein:
X$_1$ is a bivalent coupling group;
X$_2$ is a self-immolative spacer;
Y$_1$ is

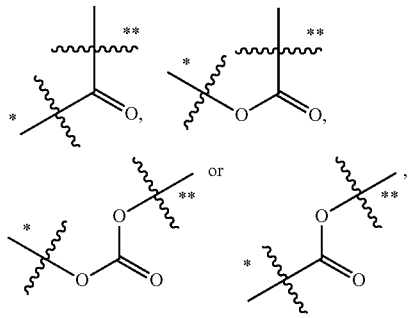

where the * of Y, indicates the point of attachment to X$_2$;
L$_1$ is a bivalent peptide linker, and
L$_2$ is a bond or a linker.

While the drug to antibody ratio has an exact integer value for a specific conjugate molecule (e.g., the product of n and y in Formula (C), it is understood that the value will often be an average value when used to describe a sample containing many molecules, due to some degree of heterogeneity, typically associated with the conjugation step. The average loading for a sample of a conjugate is referred to herein as the drug to antibody ratio, or "DAR." In some aspects, the DAR is between about 1 and about 5, and typically is about 1, 2, 3, or 4. In some aspects, at least 50% of a sample by weight is compound having the average DAR plus or minus 2, and preferably at least 50% of the sample is a conjugate that contains the average DAR plus or minus 1. Other aspects include conjugates wherein the DAR is about 2. In some aspects, a DAR of 'about y' means the measured value for DAR is within 20% of the product of n and y in Formula (I). In some aspects, a DAR of 'about n' means the measured value for DAR is within 20% of n in Formula (11).

In one aspect, the average molar ratio of the drug to the antibody in the conjugates of Formula (C) (i.e., average value of the product of n and y, also known as drug to antibody ratio (DAR)) is about 1 to about 10, about 1 to about 6 (e.g., 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0), about 1 to about 5, about 1.5 to about 4.5, or about 2 to about 4.

In one aspect provided by the disclosure, the conjugate has substantially high purity and has one or more of the following features: (a) greater than about 90% (e.g., greater than or equal to about 91%, 92%, 93%, 94%, 95%, 96%, 97%, 98%, 99%, or 100%), preferably greater than about 95%, of conjugate species are monomeric, (b) unconjugated linker level in the conjugate preparation is less than about 10% (e.g., less than or equal to about 9%, 8%, 7%, 6%, 5%, 4%, 3%, 2%, 1%, or 0%) (relative to total linker), (c) less than 10% of conjugate species are crosslinked (e.g., less than or equal to about 9%, 8%, 7%, 6%, 5%, 4%, 3%, 2%, 1%, or 0%), (d) free drug (ADP-induced platelet aggregation inhibitor, e.g., a GNAQ inhibitor, a GNA11 inhibitor, or a GNAQ and a GNA11 inhibitor) level in the conjugate preparation is less than about 2% (e.g., less than or equal to about 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (mol/mol relative to total drug).

Certain aspects and examples of the Antibody Drug Conjugates of the invention are provided in the following listing of additional, enumerated embodiments. It will be recognized that features specified in each embodiment may be combined with other specified features to provide further embodiments of the present invention.

Embodiment 47

The conjugate of Formula (C) or Formula (C-1), wherein D is a GNAQ inhibitor.

Embodiment 48

The conjugate of Formula (C) or Formula (C-1), wherein D is a GNA11 inhibitor.

Embodiment 49

The conjugate of Formula (C) or Formula (C-1), wherein D is an inhibitor of GNAQ and GNA11.

Embodiment 50

The conjugate of Formula (C) or Formula (C-1), wherein D is

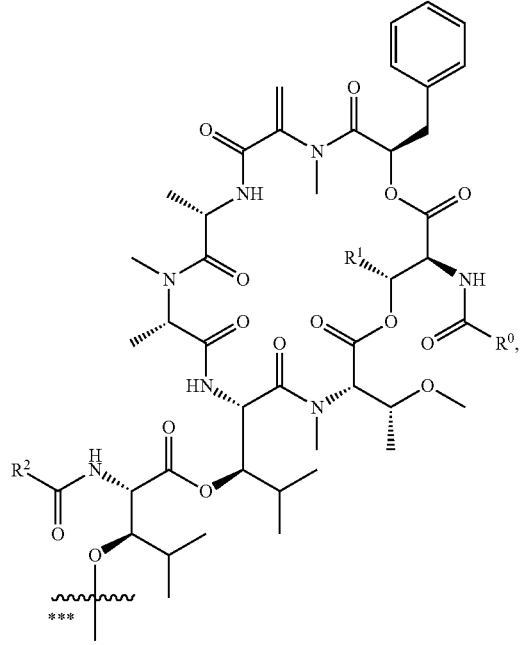

wherein R$^0$ is methyl or ethyl, R$_1$ is methyl or isopropyl, R$_2$ is methyl or ethyl, and the *** indicates the point of attachment to L$_A$ or Y$_1$.

Embodiment 51

The conjugate of Formula (C) or Formula (C-1), wherein D is

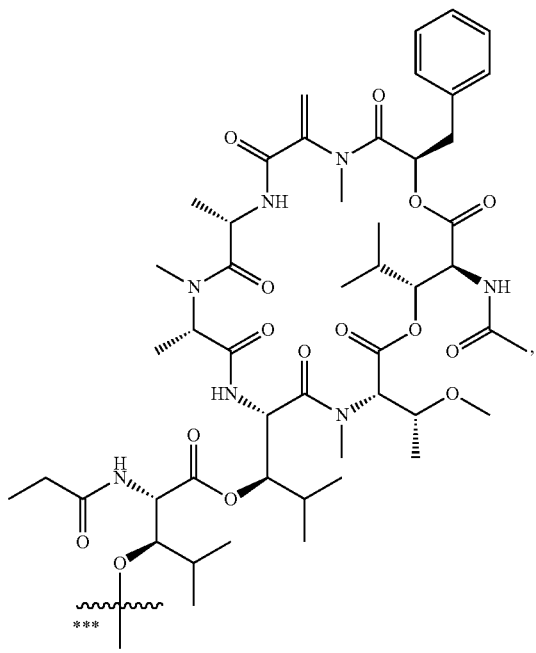 [SMILES: *O[C@H](C(C)C)[C@H](NC(=O)CC)C(=O)O[C@H](C(C)C)[C@@H]1NC(=O)[C@H](C)N(C)C(=O)[C@H](C)NC(=O)C(=C)N(C)C(=O)[C@@H](Cc2ccccc2)OC(=O)[C@@H](NC(C)=O)[C@@H](C(C)C)OC(=O)[C@H]([C@@H](C)OC)N(C)C1=O]

where the *** indicates the point of attachment to $L_A$ or $Y_1$.

Embodiment 52

The conjugate of Formula (C) or Formula (C-1), wherein D is

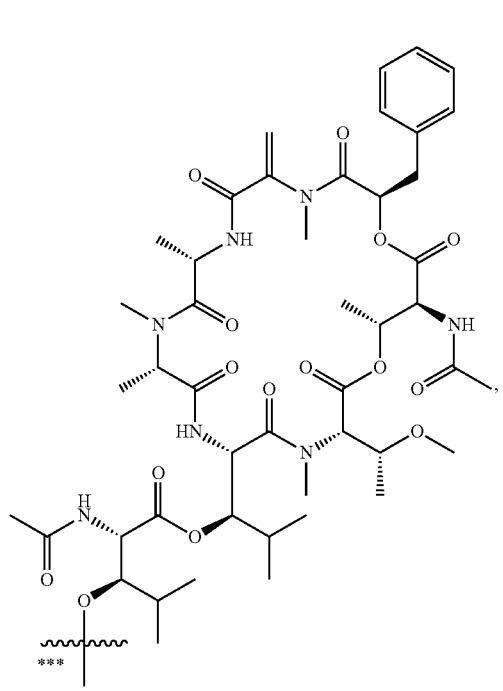 [SMILES: *O[C@H](C(C)C)[C@H](NC(C)=O)C(=O)O[C@H](C(C)C)[C@@H]1NC(=O)[C@H](C)N(C)C(=O)[C@H](C)NC(=O)C(=C)N(C)C(=O)[C@@H](Cc2ccccc2)OC(=O)[C@@H](NC(C)=O)[C@@H](C)OC(=O)[C@H]([C@@H](C)OC)N(C)C1=O]

where the *** indicates the point of attachment to $L_A$ or $Y_1$.

Embodiment 53

The conjugate of Formula (C) or Formula (C-1), wherein D is

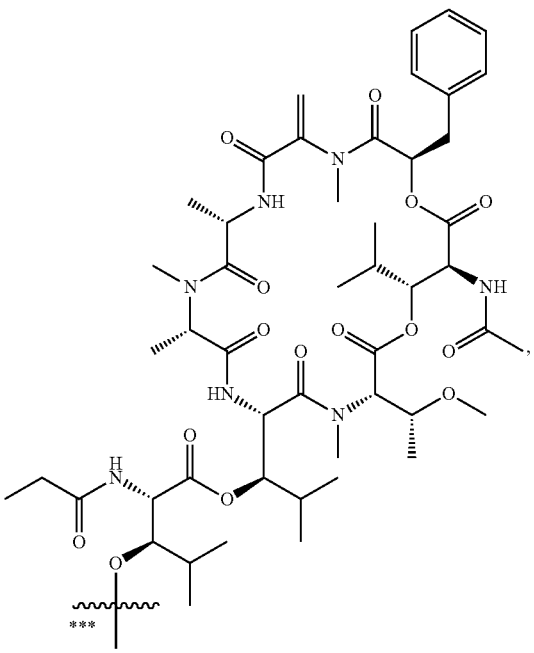 [SMILES: *O[C@H](C(C)C)[C@H](NC(=O)CC)C(=O)O[C@H](C(C)C)[C@@H]1NC(=O)[C@H](C)N(C)C(=O)[C@H](C)NC(=O)C(=C)N(C)C(=O)[C@@H](Cc2ccccc2)OC(=O)[C@@H](NC(C)=O)[C@@H](C(C)C)OC(=O)[C@H]([C@@H](C)OC)N(C)C1=O]

where the *** indicates the point of attachment to $L_A$ or $Y_1$.

Embodiment 54

The conjugate of Formula (C) or Formula (C-1), having the structure of Formula (C-2):

(C-2)

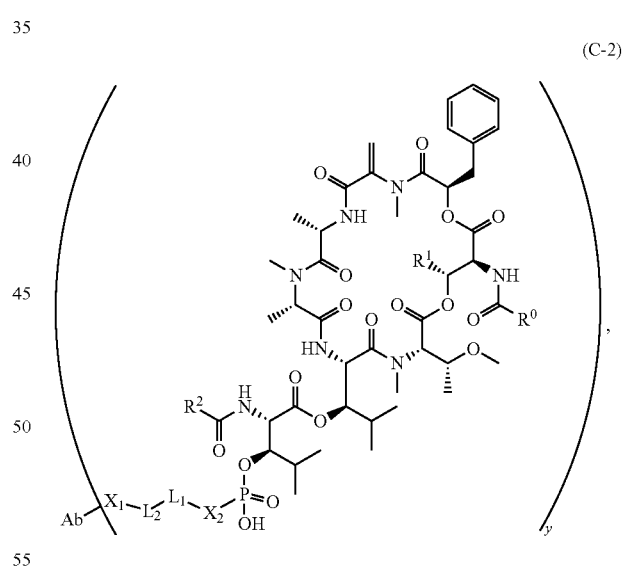

wherein:
$R^0$ is methyl or ethyl;
$R^1$ is methyl or isopropyl;
$R^2$ is methyl or ethyl;
Ab is an antibody or antigen binding fragment thereof that binds to human PMEL17 protein;
$X_1$ is a bivalent coupling group;
$X_2$ is a self-immolative spacer;
$L_1$ is a bivalent peptide linker;
$L_2$ is a bond or a linker, and
y is 1, 2, 3 or 4.

Embodiment 55

The conjugate of Formula (C) or Formula (C-1), having the structure of Formula (C-2a):

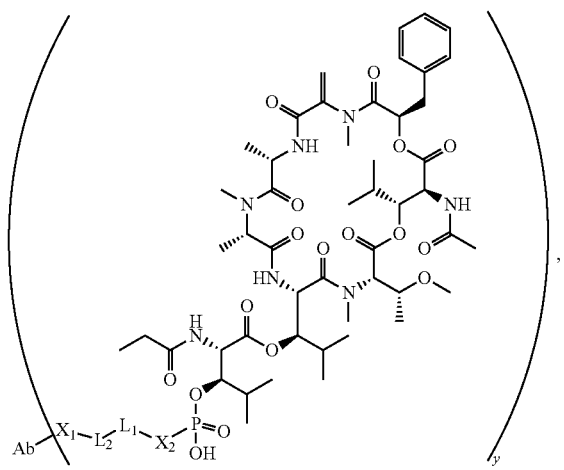

(C-2a)

wherein:
- Ab is an antibody or antigen binding fragment thereof that binds to human PMEL17 protein;
- $X_1$ is a bivalent coupling group;
- $X_2$ is a self-immolative spacer;
- $L_1$ is a bivalent peptide linker;
- $L_2$ is a bond or a linker, and
- y is 1, 2, 3 or 4.

Embodiment 56

The conjugate of Formula (C) or Formula (C-1), having the structure of Formula (C-2b):

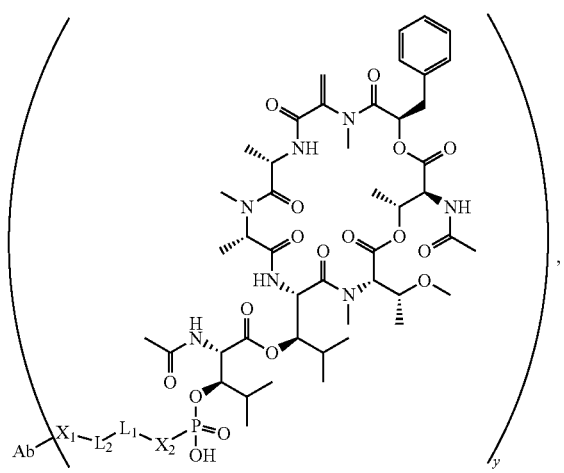

(C-2b)

wherein:
- Ab is an antibody or antigen binding fragment thereof that binds to human PMEL17 protein;
- $X_1$ is a bivalent coupling group;
- $X_2$ is a self-immolative spacer;
- $L_1$ is a bivalent peptide linker;
- $L_2$ is a bond or a linker, and
- y is 1, 2, 3 or 4.

Embodiment 57

The conjugate of Formula (C) or Formula (C-1), having the structure of Formula (C-2c):

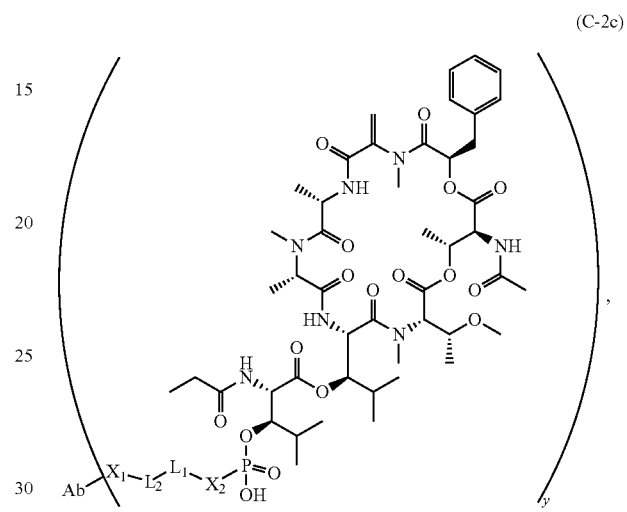

(C-2c)

wherein:
- Ab is an antibody or antigen binding fragment thereof that binds to human PMEL17 protein;
- $X_1$ is a bivalent coupling group;
- $X_2$ is a self-immolative spacer;
- $L_1$ is a bivalent peptide linker;
- $L_2$ is a bond or a linker, and
- y is 1, 2, 3 or 4.

Embodiment 58

The conjugate of Formula (C) or Formula (C-1), having the structure of Formula (C-3):

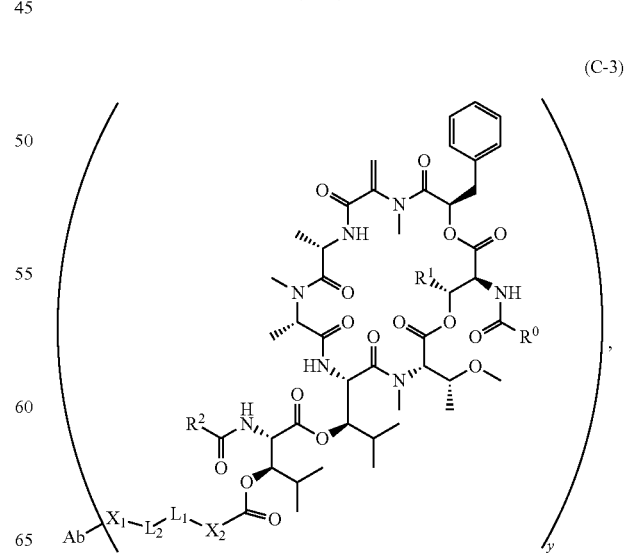

(C-3)

wherein:
- $R^0$ is methyl or ethyl;
- $R^1$ is methyl or isopropyl;
- $R^2$ is methyl or ethyl;
- Ab is an antibody or antigen binding fragment thereof that binds to human PMEL17 protein;
- $X_1$ is a bivalent coupling group;
- $X_2$ is a self-immolative spacer;
- $L_1$ is a bivalent peptide linker;
- $L_2$ is a bond or a linker, and
- y is 1, 2, 3 or 4.

Embodiment 59

The conjugate of Formula (C) or Formula (C-1), having the structure of Formula (C-3a):

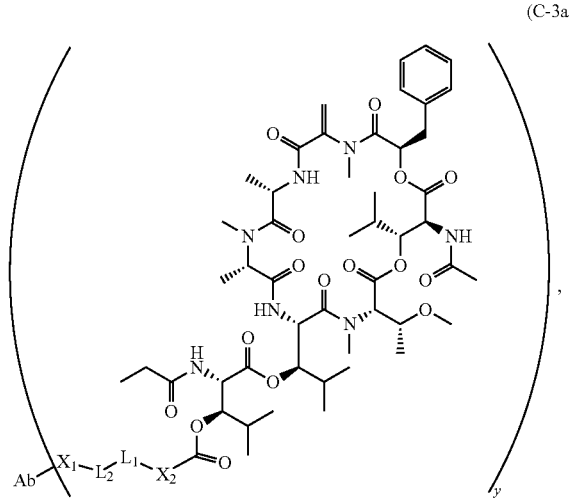

(C-3a)

wherein:
- Ab is an antibody or antigen binding fragment thereof that binds to human PMEL17 protein;
- $X_1$ is a bivalent coupling group;
- $X_2$ is a self-immolative spacer;
- $L_1$ is a bivalent peptide linker;
- $L_2$ is a bond or a linker, and
- y is 1, 2, 3 or 4.

Embodiment 60

The conjugate of Formula (C) or Formula (C-1), having the structure of Formula (C-3b):

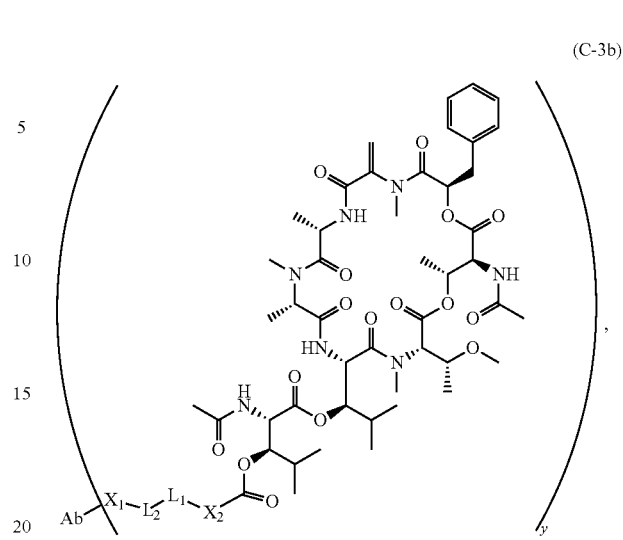

(C-3b)

wherein:
- Ab is an antibody or antigen binding fragment thereof that binds to human PMEL17 protein;
- $X_1$ is a bivalent coupling group;
- $X_2$ is a self-immolative spacer;
- $L_1$ is a bivalent peptide linker;
- $L_2$ is a bond or a linker, and
- y is 1, 2, 3 or 4.

Embodiment 61

The conjugate of Formula (C) or Formula (C-1), having the structure of Formula (C-3c):

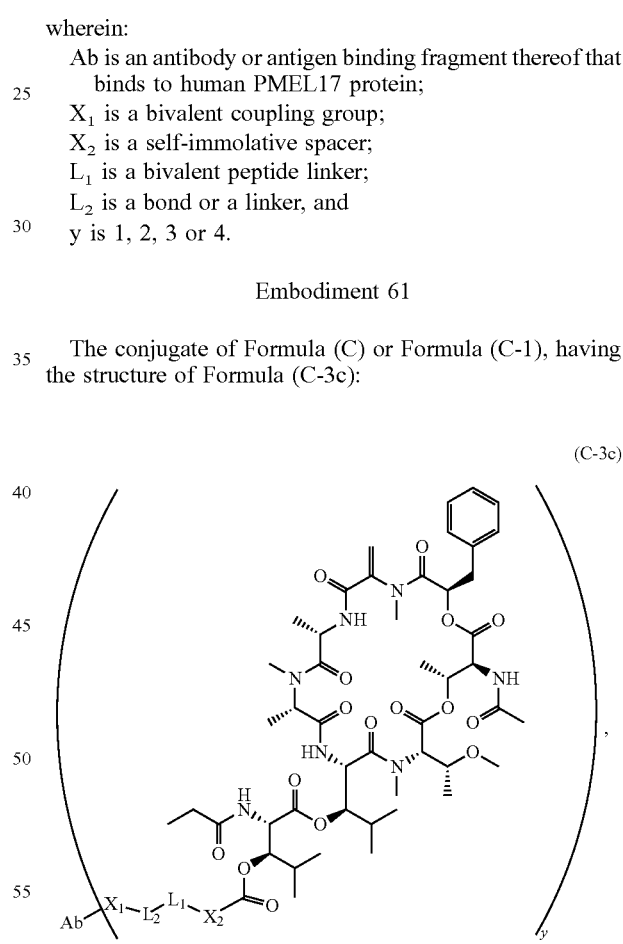

(C-3c)

wherein:
- Ab is an antibody or antigen binding fragment thereof that binds to human PMEL17 protein;
- $X_1$ is a bivalent coupling group;
- $X_2$ is a self-immolative spacer;
- $L_1$ is a bivalent peptide linker;
- $L_2$ is a bond or a linker, and
- y is 1, 2, 3 or 4.

101

Embodiment 62

The conjugate of Formula (C-2) of Embodiment 54 or the conjugate of Formula (C-3) of Embodiment 58:
wherein:
  R⁰ is methyl or ethyl;
  R¹ is methyl or isopropyl;
  R² is methyl or ethyl;
  Ab is an antibody or antigen binding fragment thereof that binds to human PMEL17 protein;
  X₂ is a self-immolative spacer selected from

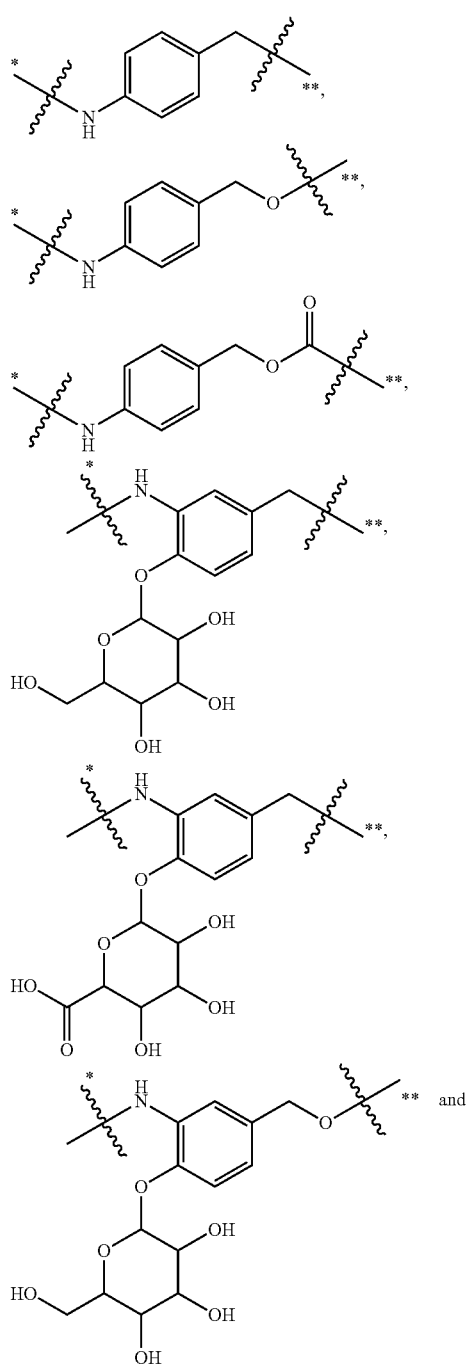

102

-continued

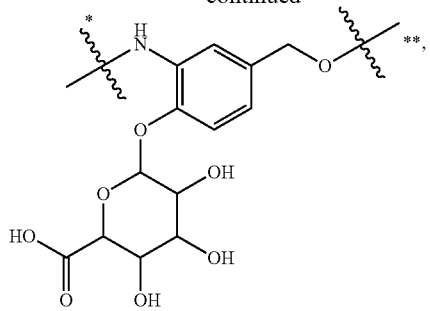

where the * of X₂ indicates the point of attachment to L₁ and the ** of X₂ indicates the point of attachment to the

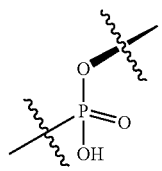

group or the point of attachment to

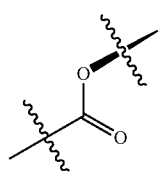

group;
L₁ is a bivalent peptide linker comprising 2 to 4 amino acid residues;
L₂ is a linker;
X₁ is a bivalent coupling group selected from

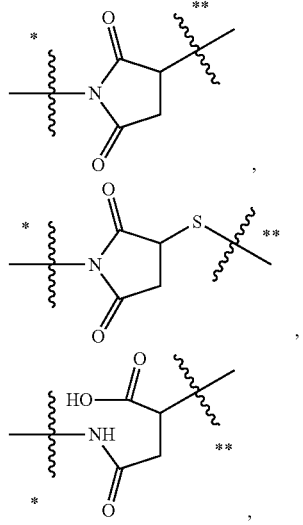

103

-continued

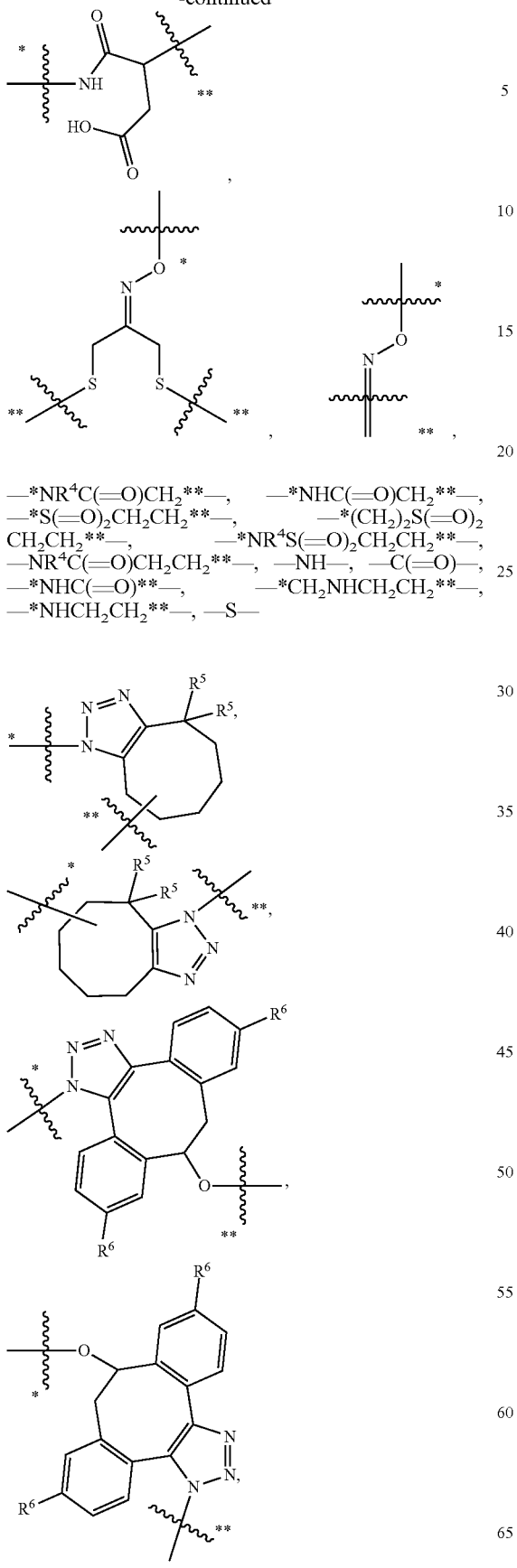

—*NR⁴C(=O)CH₂**—, —*NHC(=O)CH₂**—,
—*S(=O)₂CH₂CH₂**—, —*(CH₂)₂S(=O)₂
CH₂CH₂**—, —*NR⁴S(=O)₂CH₂CH₂**—,
—NR⁴C(=O)CH₂CH₂**—, —NH—, —C(=O)—
—*NHC(=O)**—, —*CH₂NHCH₂CH₂**—,
—*NHCH₂CH₂**—, —S—

104

-continued

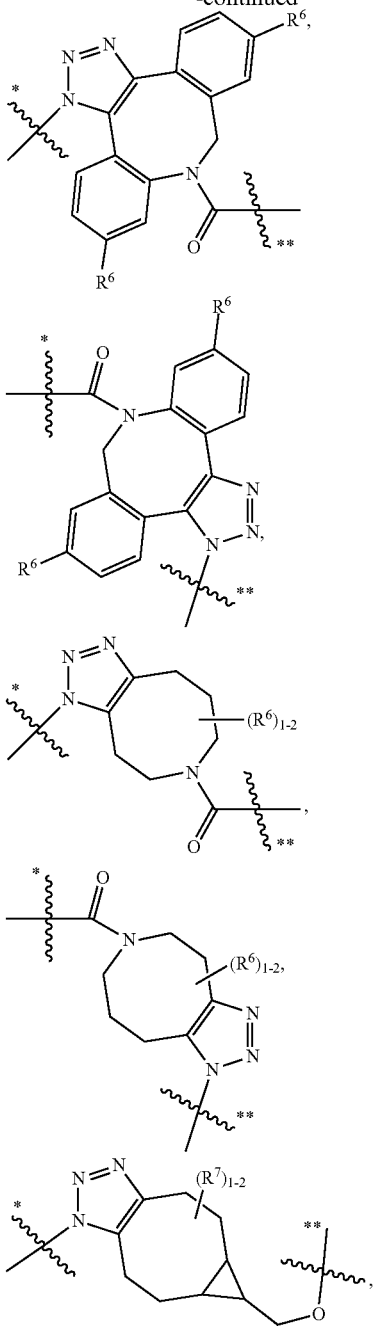

**—, where the * of $X_1$ indicates the point of attachment to $L_2$ and the ** of $X_1$ indicates the point of attachment to Ab; and wherein:

each $R^4$ is independently selected from H and $C_1$-$C_6$alkyl;

each $R^5$ is independently selected from H, $C_1$-$C_6$alkyl, F, Cl, and —OH;

each $R^6$ is independently selected from H, $C_1$-$C_6$alkyl, F, Cl, —NH₂, —OCH₃, —OCH₂CH₃, —N(CH₃)₂, —CN, —NO₂ and —OH, and each $R^7$ is independently selected from H, $C_{1-6}$alkyl, fluoro, benzyloxy substituted with —C(=O)OH, benzyl substituted with —C(=O)OH, C$_{1-4}$alkoxy substituted with —C(=O)OH and C$_{1-4}$alkyl substituted with —C(=O)OH, and y is 1, 2, 3 or 4.

Embodiment 63

The conjugate of any one of Embodiments 54 to 62, wherein X$_2$ is a self-immolative spacer selected from

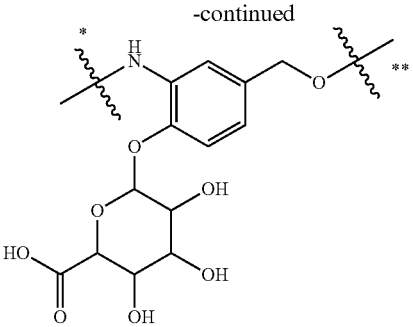

where the * of X$_2$ indicates the point of attachment to L$_1$ and the ** of X$_2$ indicates the point of attachment to Y, or the point of attachment to the

group or the point of attachment to

group.

Embodiment 64

The conjugate of any one of Embodiments 54 to 63, wherein X$_2$ is where the * of X$_2$ indicates the point of attachment to L$_1$ and the ** of X$_2$ indicates the point of attachment to Y, or the point of attachment to the

group or the point of attachment to

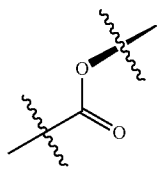

group.

Embodiment 65

The conjugate of any one of Embodiments 54 to 64, wherein L is a bivalent peptide linker comprising 2 to 4 amino acid residues.

Embodiment 66

The conjugate of any one of Embodiments 54 to 65, wherein L is a is a bivalent peptide linker comprising an amino acid residue selected from valine, citrulline, lysine, isoleucine, phenylalanine, methionine, asparagine, proline, alanine, leucine, tryptophan, and tyrosine.

Embodiment 67

The conjugate of any one of Embodiments 54-64, wherein $L_1$ is a bivalent peptide linker comprising at least one valine (Val) or citrulline (Cit) residue.

Embodiment 68

The conjugate of any one of Embodiments 54 to 64, wherein L is a bivalent dipeptide linker selected from ValCit, PheLys, ValAla and ValLys.

Embodiment 69

The conjugate of any one of Embodiments 54 to 64, wherein $L_1$ is a bivalent dipeptide linker selected from

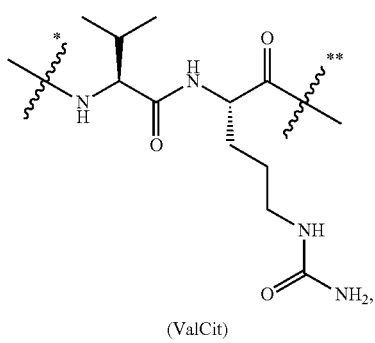

(ValCit)

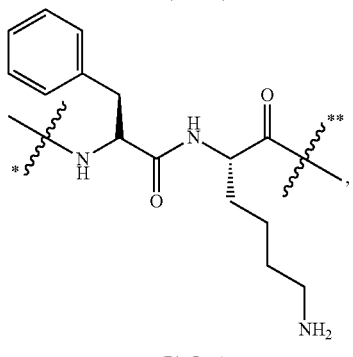

(PheLys)

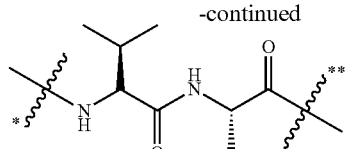

(ValAla)

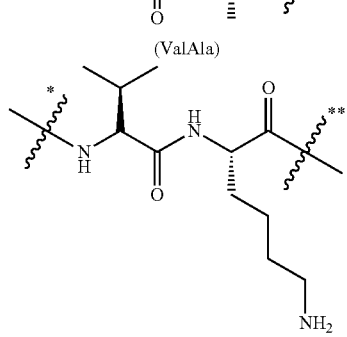

(ValLys) and

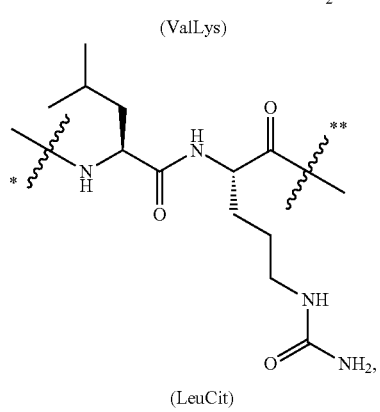

(LeuCit)

where the * of $L_1$ indicates the attachment point to $L_2$ and the ** of $L_1$ indicates the attachment point to $X_2$.

Embodiment 70

The conjugate of any one of Embodiments 54 to 64, wherein $L_1$ is ValCit.

Embodiment 71

The conjugate of any one of Embodiments 54 to 64, wherein $L_1$ is

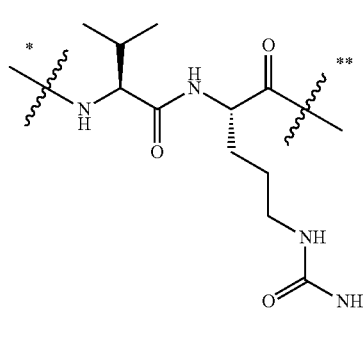

(ValCit)

where the * of $L_1$ indicates the attachment point to $L_2$ and the ** of $L_1$ indicates the attachment point to $X_2$.

Embodiment 72

The conjugate of any one of Embodiments 54 to 71, wherein $L_2$ is a linker.

Embodiment 73

The conjugate of any one of Embodiments 54 to 71, wherein $L_2$ is a linker selected from:
—*C(=O)((CH$_2$)$_m$O)$_p$(CH$_2$)$_m$**—, —*C(=O)(CH$_2$)$_m$**—, —*C(=O)(CH$_2$)$_n$NHC(=O)(CH$_2$)$_m$**—, —*C(=O)(CH$_2$)$_m$NHC(=O)((CH$_2$)$_m$O)(CH$_2$)$_m$**—, —*((CH$_2$)$_m$O)$_p$(CH$_2$)$_m$**—, —*((CH$_2$)$_m$O)$_p$(CH$_2$)$_m$**—, —(CH$_2$)$_m$—, —*(CH$_2$)$_m$NHC(=O)(CH$_2$)$_m$**—, —*(CH$_2$)$_m$NHC(=O)(CH$_2$)$_m$C(=O)NH(CH$_2$)$_m$**—, —*((CH$_2$)$_m$O)$_p$(CH$_2$)$_m$NHC(=O)(CH$_2$)$_m$—, —((CH$_2$)$_m$O)$_p$CH$_2$)$_m$C(=O)NH(CH$_2$)$_m$**—, —*(CH$_2$)$_m$C(R$_3$)$_2$**—, and —*(CH$_2$)$_m$C(R$_3$)$_2$SS(CH$_2$)$_m$NHC(=O)(CH$_2$)$_m$**—, where the * of $L_2$ indicates the attachment point to $L_1$ and the ** of $L_2$ indicates the point of attachment to $X_1$;

and wherein:
each $R_3$ is independently selected from H and $C_1$-$C_6$alkyl;
each m is independently selected from 1, 2, 3, 4, 5, 6, 7, 8, 9 and 10, and
each p is independently selected from 1, 2, 3, 4, 5, 6, 7, 8, 9, 10, 11, 12, 13 and 14.

Embodiment 74

The conjugate of any one of Embodiments 54 to 71, wherein $L_2$ is —*C(=O)((CH$_2$)$_m$O)$_p$(CH$_2$)$_m$**— or —*C(=O)(CH$_2$)$_m$**—, where the * of $L_2$ indicates the point of attachment to $L_1$ and the ** of $L_2$ indicates the point of attachment to $X_1$, and wherein each m is independently selected from 1, 2, 3, 4, 5, 6, 7, 8, 9 or 10 and p is 1, 2, 3, 4, 5, 6, 7, 8, 9, 10, 11, 12, 13 or 14.

Embodiment 75

The conjugate of any one of Embodiments 54 to 71, wherein $L_2$ is

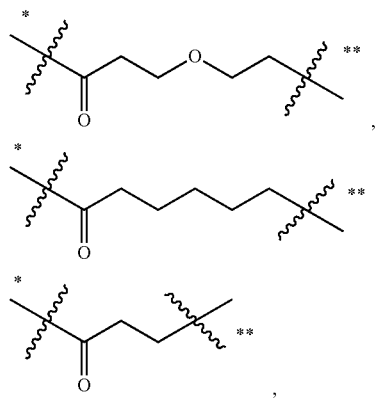

where the * of $L_2$ indicates the point of attachment to $L_1$ and the ** of $L_2$ indicates the point of attachment to $X_1$.

Embodiment 76

The conjugate of any one of Embodiments 54 to 75, wherein $X_1$ is a bivalent coupling group selected from

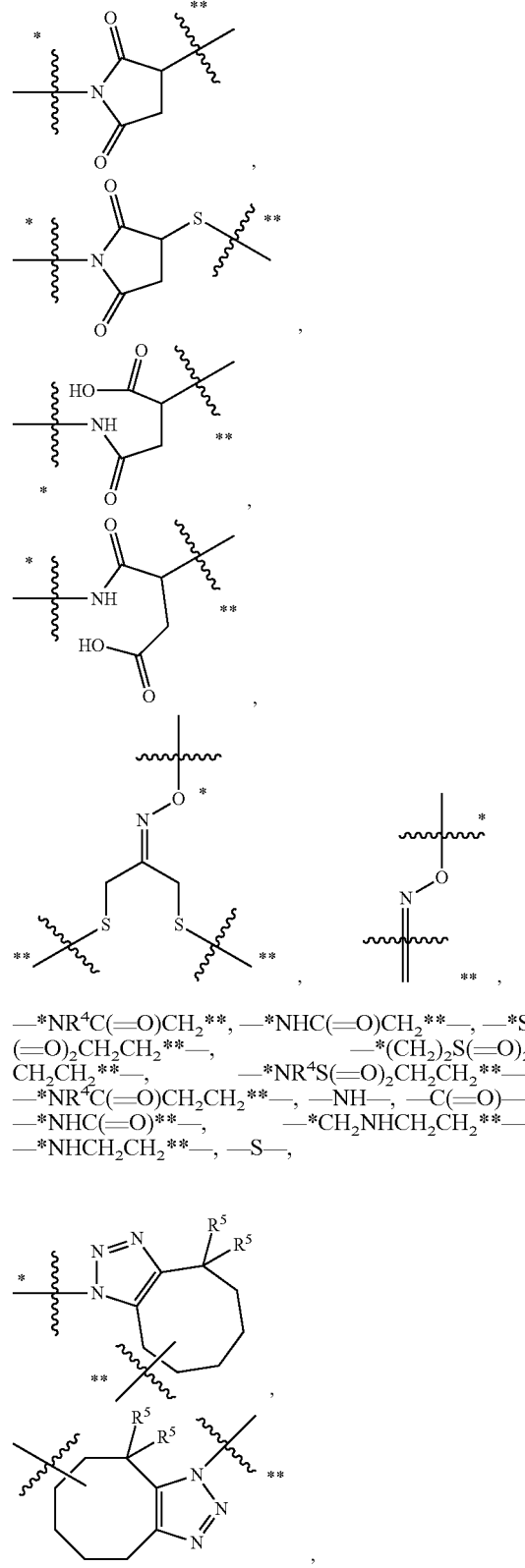

—*NR$^4$C(=O)CH$_2$**—, —*NHC(=O)CH$_2$**—, —*S(=O)$_2$CH$_2$CH$_2$**—, —*(CH$_2$)$_2$S(=O)$_2$CH$_2$CH$_2$**—, —*NR$^4$S(=O)$_2$CH$_2$CH$_2$**—, —*NR$^4$C(=O)CH$_2$CH$_2$**—, —NH—, —C(=O)—, —*NHC(=O)**—, —*CH$_2$NHCH$_2$CH$_2$**—, —*NHCH$_2$CH$_2$**—, —S—,

111
-continued

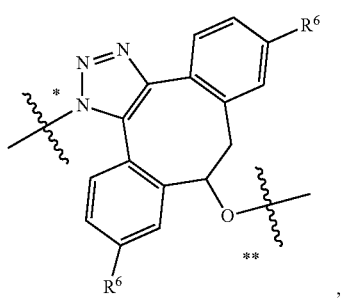
,

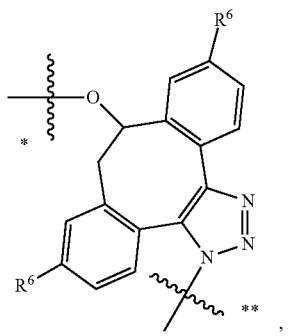
,

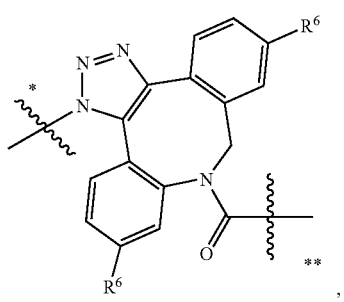
,

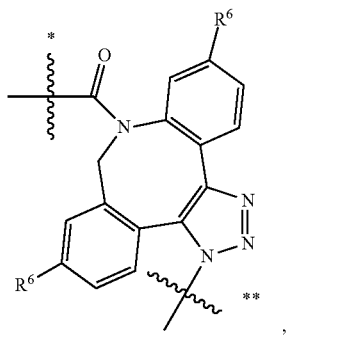
,

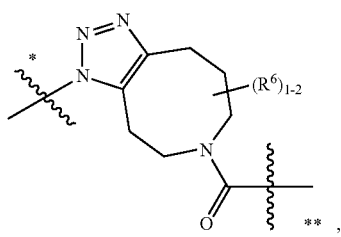
,

112
-continued

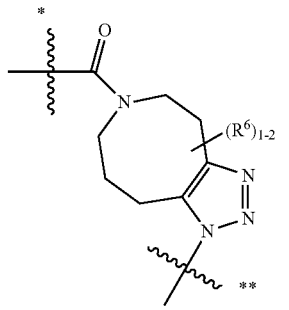
,

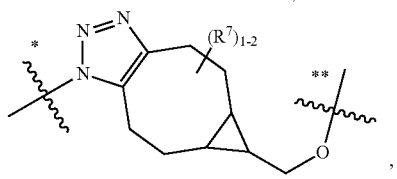
,

**—, where the * of $X_1$ indicates the point of attachment to $L_2$ and the ** of $X_1$ indicates the point of attachment to Ab;

and wherein:
  each $R^4$ is independently selected from H and $C_1$-$C_6$alkyl;
  each $R^5$ is independently selected from H, $C_1$-$C_6$alkyl, F, Cl, and —OH;
  each $R^6$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH, and
  each $R^7$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH.

Embodiment 77

The conjugate of any one of Embodiments 54 to 75, wherein $X_1$ is a bivalent coupling group selected from

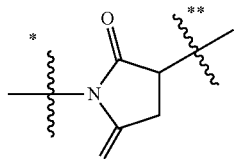
,

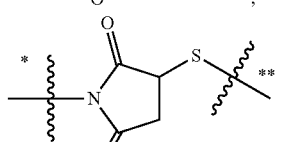
,

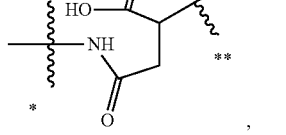
,

113

-continued

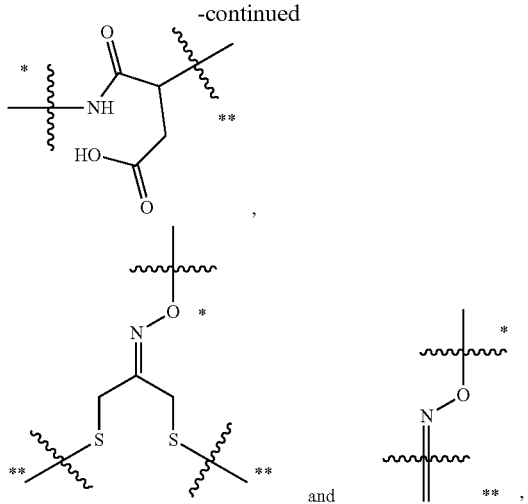

where the * of X₁ indicates the point of attachment to L₂ and the ** of X₁ indicates the point of attachment to Ab.

Embodiment 78

The conjugate of any one of Embodiments 54 to 75, wherein X₁ is a bivalent coupling group selected from

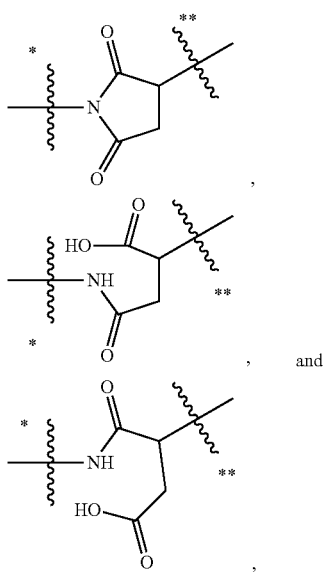

where the * of X indicates the point of attachment to L₂ and the ** of X indicates the point of attachment to Ab.

Embodiment 79

The conjugate of Formula (C-2) of Embodiment 54 wherein:
Ab is an antibody or antigen binding fragment thereof that binds to human PMEL17 protein;
$R^0$ is methyl or ethyl;
$R^1$ is methyl or isopropyl;
$R^2$ is methyl or ethyl;

114

$X_1$ is is a bivalent coupling group selected from

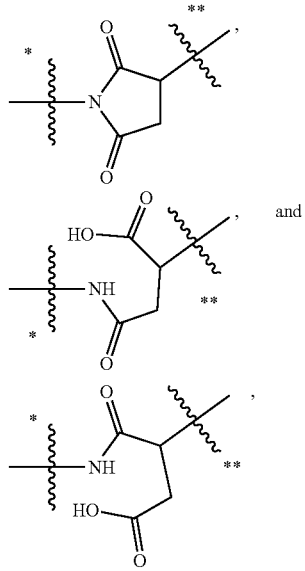

where the * of $X_1$ indicates the point of attachment to $L_2$ and the ** of $X_1$ indicates the point of attachment to Ab $X_2$ is

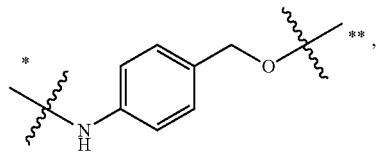 [SMILES: *Nc1ccc(CO*)cc1]

where the * of $X_2$ indicates the point of attachment to $L_1$ and the ** of $X_2$ indicates the point of attachment to the

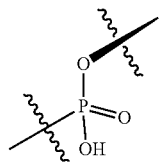

group;

$L_1$ is

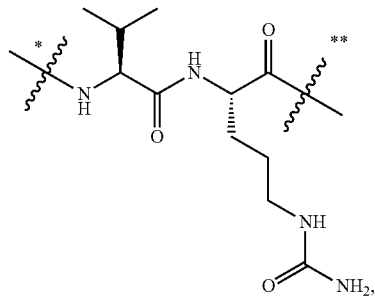

(ValCit)

where the * of $L_1$ indicates the attachment point to $L_2$ and the ** of $L_1$ indicates the attachment point to $X_2$;

$L_2$ is

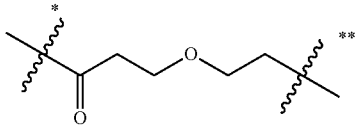 or

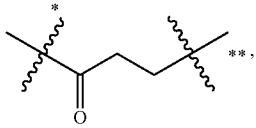, where the * of $L_2$ indicates the point of attachment to $L_1$ and the ** of $L_2$ indicates the point of attachment to $R_8$, and y is 1, 2, 3 or 4.

Embodiment 80

The conjugate of Formula (C-3) of Embodiment 58 wherein:

Ab is an antibody or antigen binding fragment thereof that binds to human PMEL17 protein;

$R^0$ is methyl or ethyl;

$R_1$ is methyl or isopropyl;

$R^2$ is methyl or ethyl;

$X_1$ is is a bivalent coupling group selected from

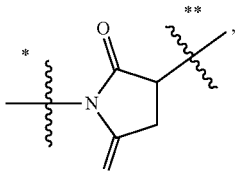

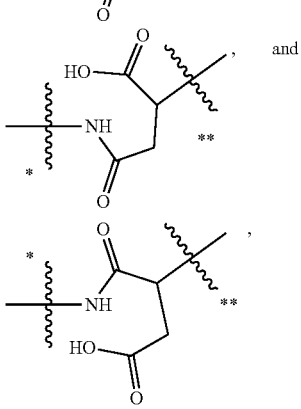

where the * of $X_1$ indicates the point of attachment to $L_2$ and the ** of $X_1$ indicates the point of attachment to Ab $X_2$ is

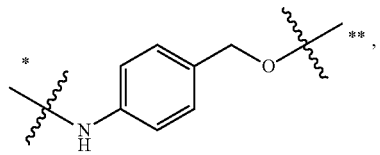 [SMILES: *Nc1ccc(CO*)cc1], where the * of $X_2$ indicates the point of attachment to $L_1$ and the ** of $X_2$ indicates the point of attachment to the

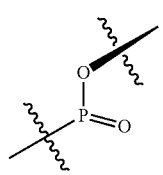

group;

$L_1$ is

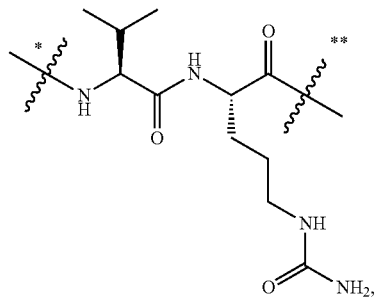

(ValCit)

where the * of $L_1$ indicates the attachment point to $L_2$ and the ** of $L_1$ indicates the attachment point to $X_2$;

$L_2$ is

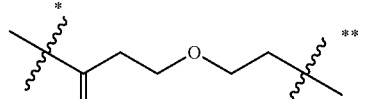 or

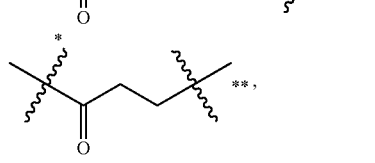, where the * of $L_2$ indicates the point of attachment to $L_1$ and the ** of $L_2$ indicates the point of attachment to $R_8$, and y is 1, 2, 3 or 4.

Embodiment 81

The conjugate of Formula (C), Formula (C-1) or Formula (C-2) having the structure:

wherein:

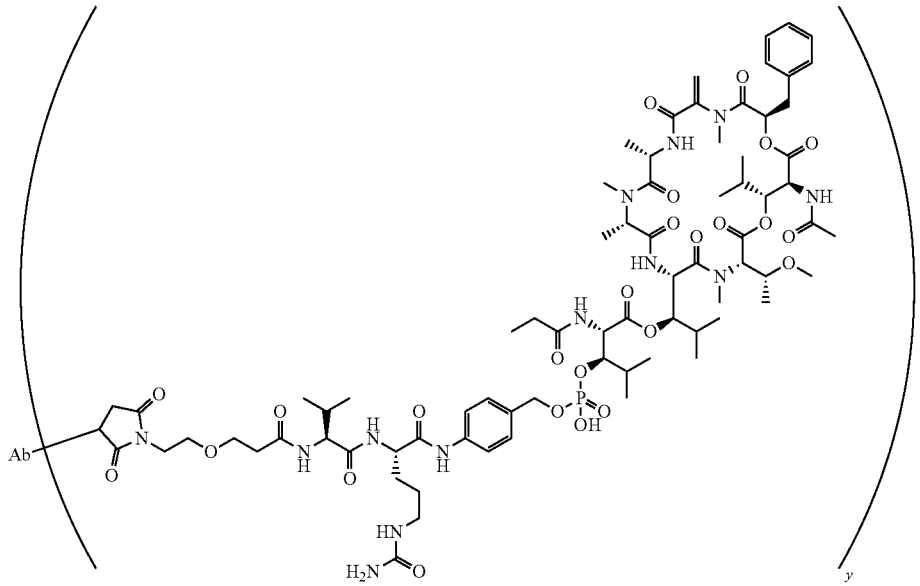

y is 2 or 4 and
Ab is an antibody or antigen binding fragment thereof that binds to human PMEL17 protein.

Embodiment 82

The conjugate of Formula (C), Formula (C-1) or Formula (C-2) having the structure:

wherein:
y is 2 or 4 and
Ab is an antibody or antigen binding fragment thereof that binds to human PMEL17 protein.

Embodiment 83

The conjugate of Formula (C), Formula (C-1) or Formula (C-2) having the structure:

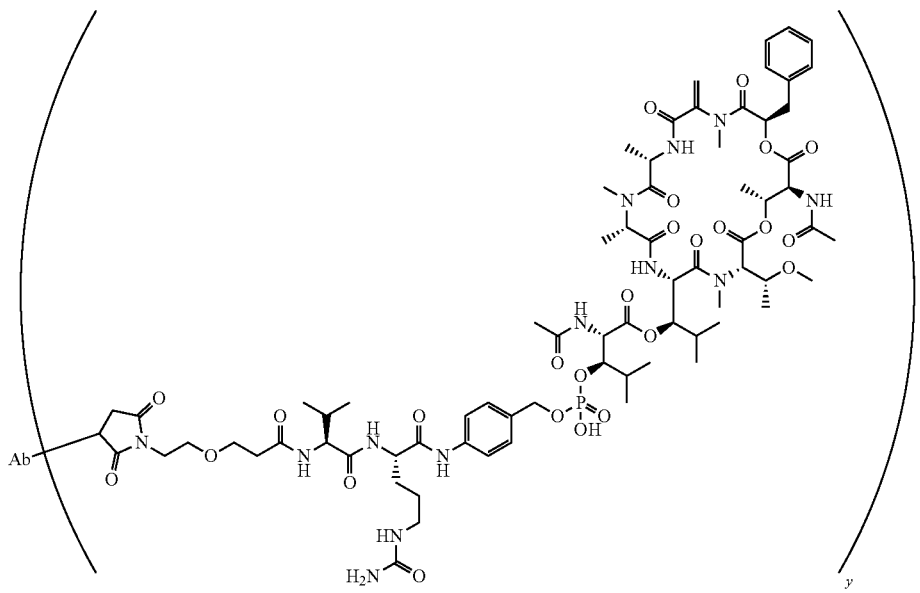

wherein:
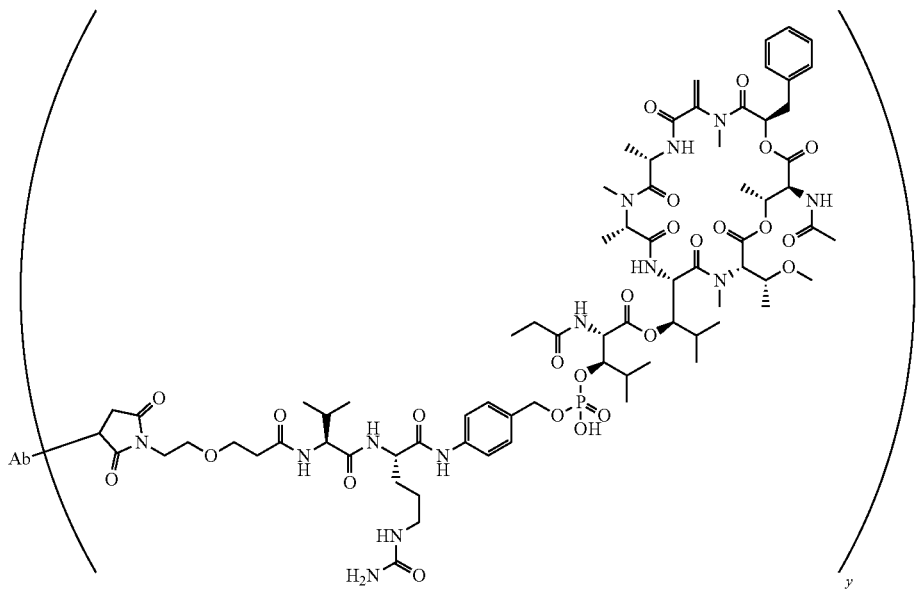
y is 2 or 4 and
Ab is an antibody or antigen binding fragment thereof that binds to human PMEL17 protein.
Embodiment 84
The conjugate of Formula (C), Formula (C-1) or Formula (C-2) having the structure:
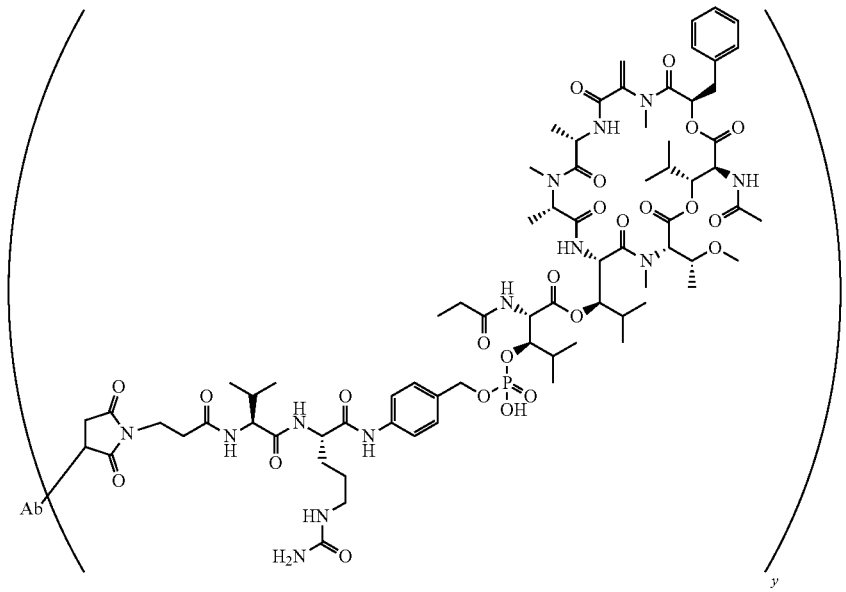
wherein:
y is 2 or 4 and
Ab is an antibody or antigen binding fragment thereof that binds to human PMEL17 protein.

Embodiment 85

The conjugate of Formula (C), Formula (C-1) or Formula (C-2) having the structure:

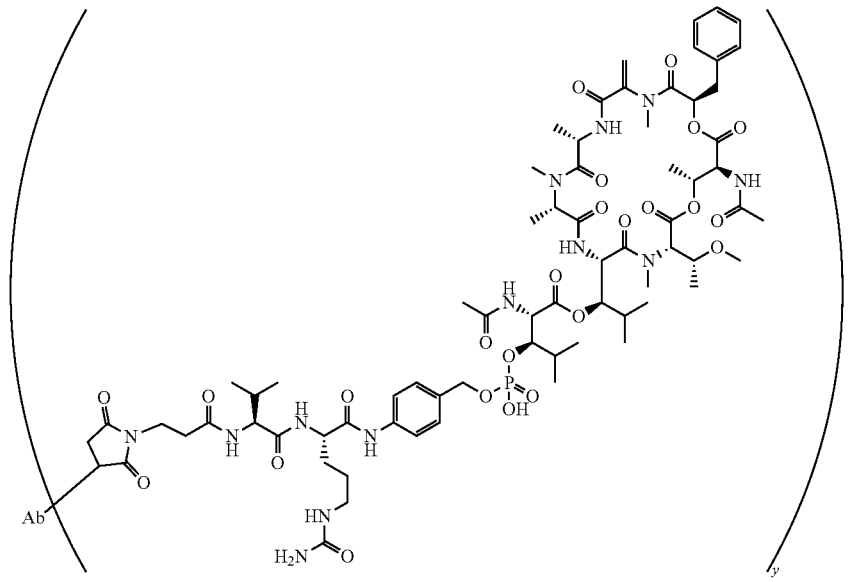

wherein:
y is 2 or 4 and
Ab is an antibody or antigen binding fragment thereof that binds to human PMEL17 protein.

Embodiment 86

The conjugate of Formula (C), Formula (C-1) or Formula (C-2) having the structure:

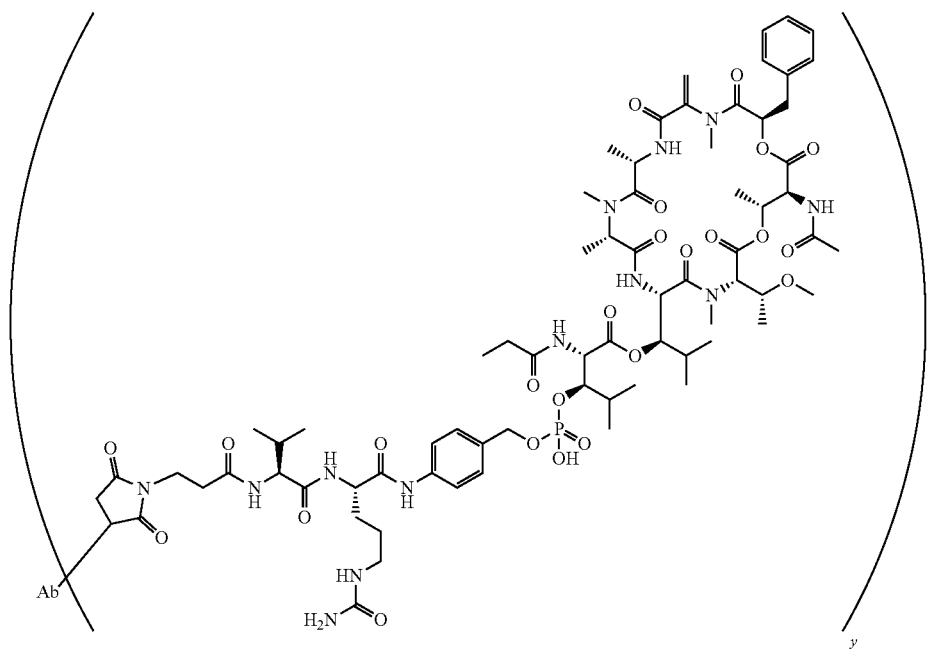

wherein:
y is 2 or 4 and
Ab is an antibody or antigen binding fragment thereof that binds to human PMEL17 protein.

Embodiment 87

The conjugate of Formula (C), Formula (C-1) or Formula (C-3) having the structure:

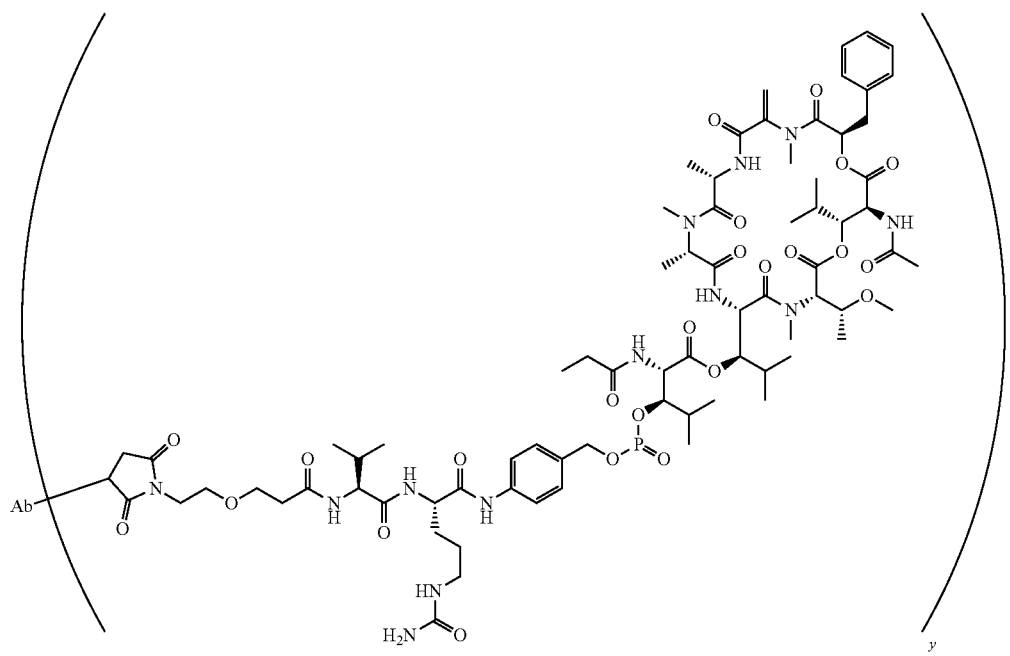

wherein:
y is 2 or 4 and
Ab is an antibody or antigen binding fragment thereof that binds to human PMEL17 protein.

Embodiment 88

The conjugate of Formula (C), Formula (C-1) or Formula (C-3) having the structure:

wherein:
y is 2 or 4 and
Ab is an antibody or antigen binding fragment thereof that binds to human PMEL17 protein.

Embodiment 89

The conjugate of Formula (C), Formula (C-1) or Formula (C-3) having the structure:

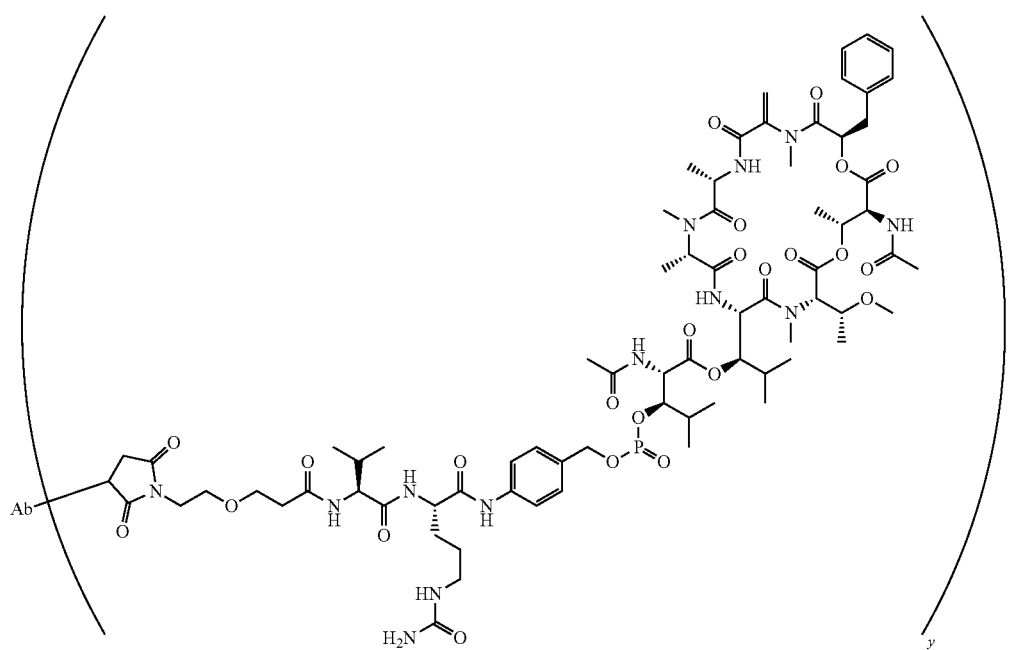

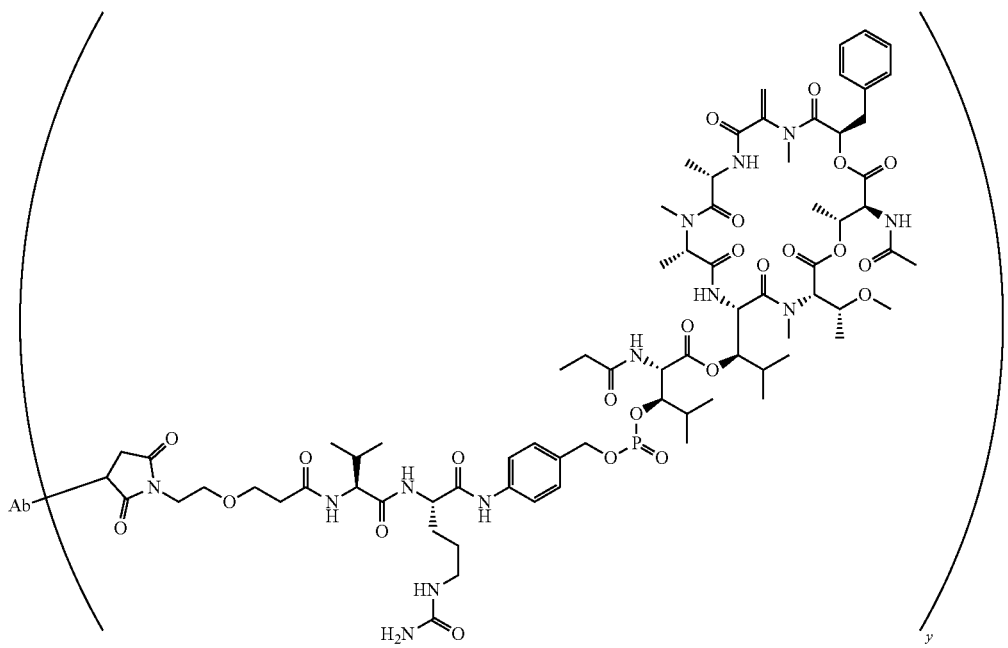

wherein:
y is 2 or 4 and
Ab is an antibody or antigen binding fragment thereof that binds to human PMEL17 protein.

Embodiment 90

The conjugate of Formula (C), Formula (C-1) or Formula (C-3) having the structure:

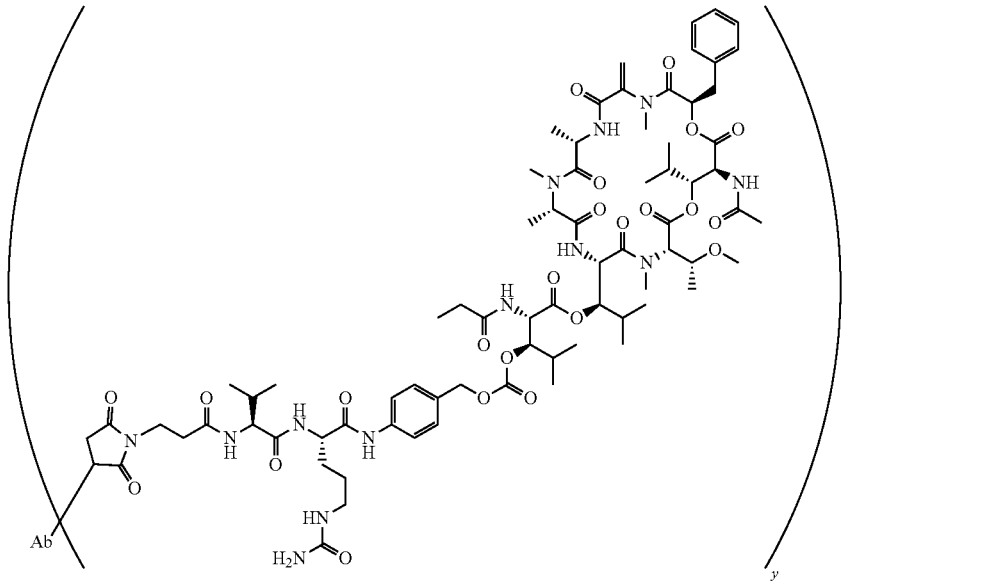

wherein:
y is 2 or 4 and
Ab is an antibody or antigen binding fragment thereof that binds to human PMEL17 protein.

Embodiment 91

The conjugate of Formula (C), Formula (C-1) or Formula (C-3) having the structure:

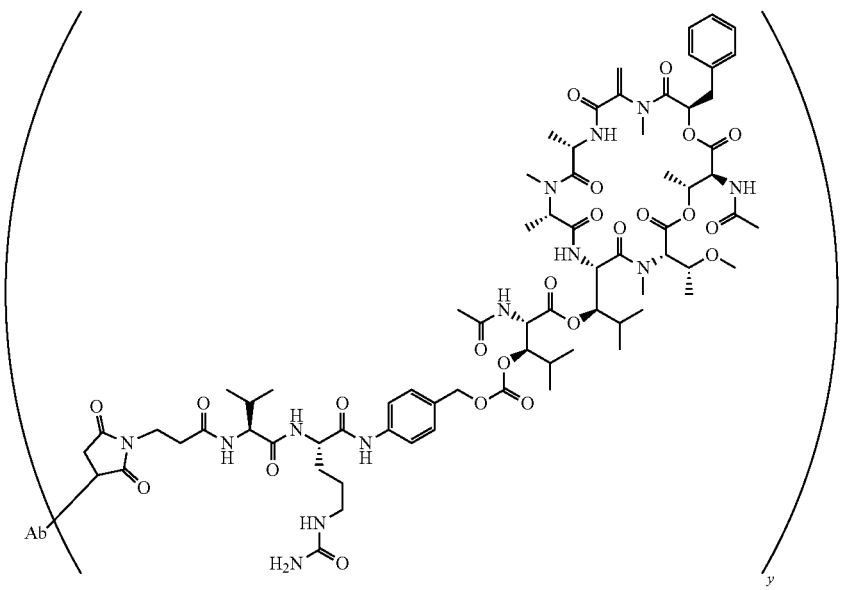

wherein:
y is 2 or 4 and
Ab is an antibody or antigen binding fragment thereof that binds to human PMEL17 protein.

Embodiment 92

The conjugate of Formula (C), Formula (C-1) or Formula (C-3) having the structure:

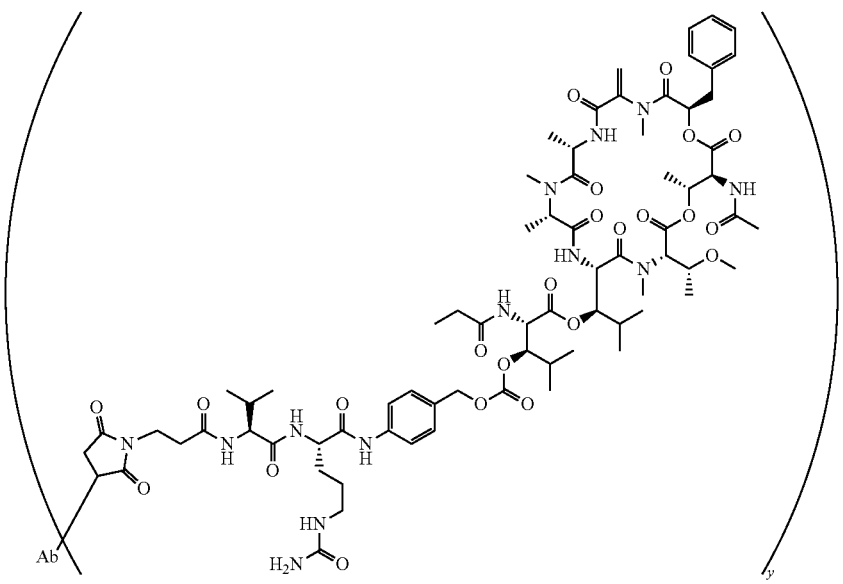

wherein:
y is 2 or 4 and
Ab is an antibody or antigen binding fragment thereof that binds to human PMEL17 protein.

Further, the antibodies, antibody fragments (e.g., antigen binding fragments) or functional equivalents of the present invention may be conjugated to a drug moiety that modifies a given biological response. Drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin, a protein such as tumor necrosis factor, α-interferon, β-interferon, nerve growth factor, platelet derived growth factor, tissue plasminogen activator, a cytokine, an apoptotic agent, an anti-angiogenic agent, or, a biological response modifier such as, for example, a lymphokine.

In one embodiment, the antibodies, antibody fragments (e.g., antigen binding fragments) or functional equivalents of the present invention are conjugated to a drug moiety, such as a cytotoxin, a drug (e.g., an immunosuppressant) or a radiotoxin. Examples of cytotoxins include but are not limited to, taxanes (see, e.g., International (PCT) Patent Application Nos. WO 01/38318 and PCT/US03/02675), DNA-alkylating agents (e.g., CC-1065 analogs), anthracyclines, tubulysin analogs, duocarmycin analogs, auristatin E, auristatin F, maytansinoids, pyrrolobenzodiazipines (PBDs), and cytotoxic agents comprising a reactive polyethylene glycol moiety (see, e.g., Sasse et al., J. Antibiot. (Tokyo), 53, 879-85 (2000), Suzawa et al., Bioorg. Med. Chem., 8, 2175-84 (2000), Ichimura et al., J. Antibiot. (Tokyo), 44, 1045-53 (1991), Francisco et al., Blood (2003) (electronic publication prior to print publication), U.S. Pat. Nos. 5,475, 092, 6,340,701, 6,372,738, and 6,436,931, U.S. Patent Application Publication No. 2001/0036923 A1, Pending U.S. patent application Ser. Nos. 10/024,290 and 10/116, 053, and International (PCT) Patent Application No. WO 01/49698), taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, anti-metabolites (e.g., methotrexate, 6-mercaptopurine, 6-thioguanine, cytarabine, 5-fluorouracil decarbazine), ablating agents (e.g., mechlorethamine, thiotepa chlorambucil, meiphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). (See e.g., Seattle Genetics US20090304721).

Other examples of cytotoxins that can be conjugated to the antibodies, antibody fragments (antigen binding fragments) or functional equivalents of the invention include duocarmycins, calicheamicins, maytansines and auristatins, and derivatives thereof.

Various types of cytotoxins, linkers and methods for conjugating therapeutic agents to antibodies are known in the art, see, e.g., Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Curr. Opin. Investig. Drugs 3:1089-1091; Senter and Springer, (2001) Adv. Drug Deliv. Rev. 53:247-264.

The antibodies, antibody fragments (e.g., antigen binding fragments) or functional equivalents of the present invention can also be conjugated to a radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine-131, indium-111, yttrium-90, and lutetium-177. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., (1998) Clin Cancer Res. 4(10):2483-90; Peterson et al., (1999) Bioconjug. Chem. 10(4):553-7; and Zimmerman et al., (1999) Nucl. Med. Biol. 26(8):943-50, each incorporated by reference in their entireties.

The antibodies, antibody fragments (e.g., antigen binding fragments) or functional equivalents of the present invention can also conjugated to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antibody fragment (e.g., antigen binding fragment) described herein (e.g., a Fab fragment, Fd fragment, Fv fragment, F(ab)$_2$ fragment, a VH domain, a VH CDR, a VL domain or a VL CDR) and a heterologous protein, polypeptide, or peptide.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama, (1998) Trends Biotechnol. 16(2):76-82; Hansson et al., (1999) J. Mol. Biol. 287:265-76; and Lorenzo and Blasco, (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an antigen may be recombined with one or more components, motifs, sections, parts, domains, fragments, etc. of one or more heterologous molecules.

Moreover, the antibodies, antibody fragments (e.g., antigen binding fragments) or functional equivalents of the present invention can be conjugated to marker sequences, such as a peptide, to facilitate purification. In preferred embodiments, the marker amino acid sequence is a hexahistidine peptide (SEQ ID NO: 267), such as the tag provided in a pQE vector (QIAGEN, Inc., 9259 Eton Avenue, Chatsworth, CA, 91311), among others, many of which are commercially available. As described in Gentz et al., (1989) Proc. Natl. Acad. Sci. USA 86:821-824, for instance, hexahistidine (SEQ ID NO: 267) provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "FLAG" tag (A. Einhauer et al., J. Biochem. Biophys. Methods 49: 455-465, 2001). According to the present invention, antibodies or antigen binding fragments can also be conjugated to tumor-penetrating peptides in order to enhance their efficacy.

In other embodiments, the antibodies, antibody fragments (e.g., antigen binding fragments) or functional equivalents of the present invention are conjugated to a diagnostic or detectable agent. Such immunoconjugates can be useful for monitoring or prognosing the onset, development, progression and/or severity of a disease or disorder as part of a clinical testing procedure, such as determining the efficacy of a particular therapy. Such diagnosis and detection can be accomplished by coupling the antibody to detectable substances including, but not limited to, various enzymes, such as, but not limited to, horseradish peroxidase, alkaline phosphatase, beta-galactosidase, or acetylcholinesterase;

prosthetic groups, such as, but not limited to, streptavidin/biotin and avidin/biotin; fluorescent materials, such as, but not limited to, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, umbelliferone, fluorescein, fluorescein isothiocyanate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}I$, $^{125}I$, $^{123}I$, and $^{121}I$), carbon ($^{14}C$), sulfur ($^{35}S$), tritium ($^{3}H$), indium ($^{115}In$, $^{113}In$, $^{112}In$, and $^{111}In$), technetium ($^{99}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$, $^{68}Ge$, $^{57}Co$, $^{65}Zn$, $^{85}Sr$, $^{32}P$, $^{153}Gd$, $^{169}Yb$, $^{51}Cr$, $^{54}Mn$, $^{75}Se$, $^{64}Cu$, $^{113}Sn$, and $^{117}Sn$; and positron emitting metals using various positron emission tomographies, and non-radioactive paramagnetic metal ions.

The antibodies, antibody fragments (e.g., antigen binding fragments) or functional equivalents of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

3. Conjugation and Preparation of ADCs

Processes for Making Antibody Conjugates of Formula (C), Formula (C-1) and Formula (C-2)

A general reaction scheme for the formation of conjugates of Formula (C) is shown in Scheme 1 below:

Scheme 1

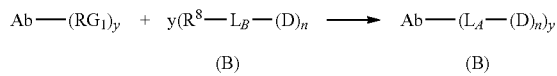

(B)     (B)

where: $RG_1$ is a reactive group on the antibody or antigen binding fragment thereof, Ab, by way of example only a thiol, amine or ketone, which reacts with a compatible reactive group, $R^8$, attached to the linker-drug compound thereby covalently linking antibody or antigen binding fragment thereof, Ab, to one or more linker-drug moieties. Non-limiting examples of such reactions of $RG_1$ and $R^8$ groups are a maleimide ($R^8$) reacting with a thiol ($RG_1$) to give a succinimide ring, or a hydroxylamine ($R^8$) reacting with a ketone ($RG_1$) to give an oxime.

In one embodiment, D is a GNAQ inhibitor, a GNA11 inhibitor, or an inhibitor of GNAQ and GNA11 (GNAQ/GNA11 inhibitor), $L_a$ is a linker further comprising a bivalent coupling group formed when $RG_1$ and $R^8$ react, n is 1, 2, 3 or 4, and y is 1, 2, 3 or 4.

A general reaction scheme for the formation of conjugates of Formula (C-1) is shown in Scheme 2 below:

Scheme 2

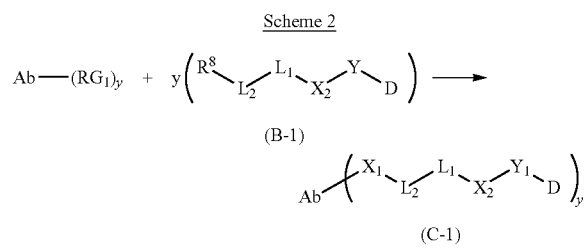

(B-1)

(C-1)

where: $RG_1$ is a reactive group on the antibody or antigen binding fragment thereof, Ab, by way of example only a thiol, amine or ketone, which reacts with a compatible reactive group, $R^8$, attached to the linker-drug moiety thereby covalently linking antibody or antigen binding fragment thereof, Ab, to one or more linker-drug moieties. Non-limiting examples of such reactions of $RG_1$ and $R^8$ groups are a maleimide ($R^8$) reacting with a thiol ($RG_1$) to give a succinimide ring, or a hydroxylamine ($R^8$) reacting with a ketone ($RG_1$) to give an oxime.

In one embodiment, D is a GNAQ inhibitor, a GNA11 inhibitor, or an inhibitor of GNAQ and GNA11 (GNAQ/GNA11 inhibitor), $X_1$ is a bivalent coupling group formed when $RG_1$ and $R^8$ react (e.g. a succinimide ring or an oxime), $Y_1$ is a phosphate group, $X_2$ is a self-immolative spacer, $L_1$ is a bivalent peptide linker, $L_2$ is a bond or a linker, and y is 1, 2, 3 or 4.

A general reaction scheme for the formation of conjugates of Formula (C-2) is shown in Scheme 3 below:

Scheme 3

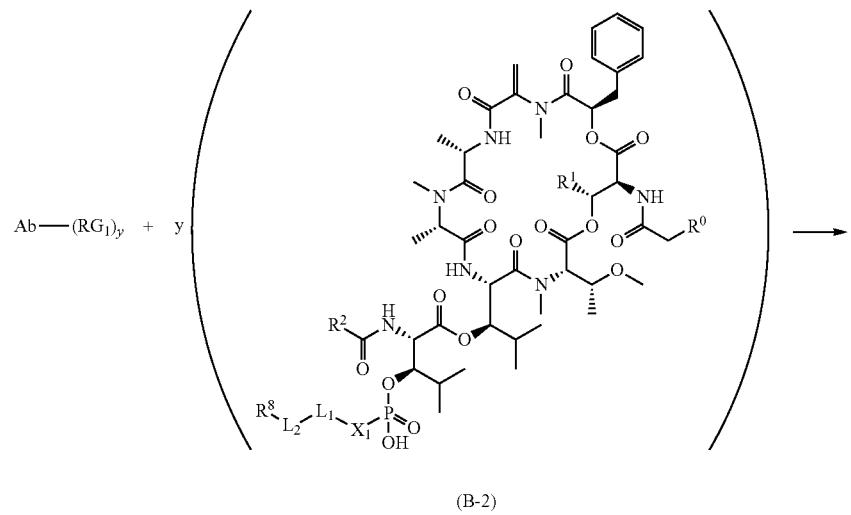

(B-2)

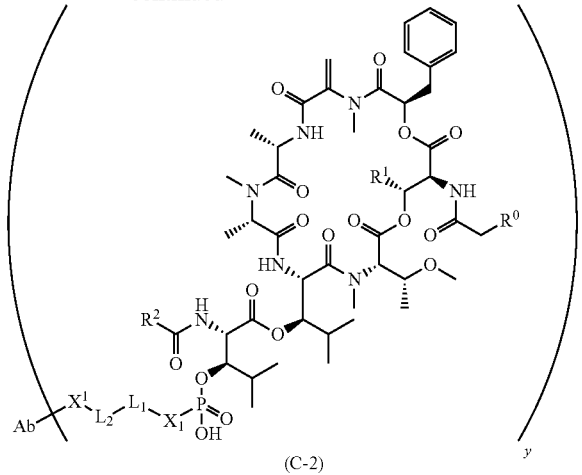

(C-2)

where: $RG_1$ is a reactive group on the antibody or antigen binding fragment thereof, Ab, by way of example only a thiol, amine or ketone, which reacts with a compatible reactive group, $R^8$, attached to the linker-drug moiety thereby covalently linking antibody or antigen binding fragment thereof, Ab, to one or more linker-drug moieties. Non-limiting examples of such reactions of $RG_1$ and $R^8$ groups are a maleimide ($R^8$) reacting with a thiol ($RG_1$) to give a succinimide ring, or a hydroxylamine ($R^8$) reacting with a ketone ($RG_1$) to give an oxime.

Here $R^0$ is methyl or ethyl, $R^1$ is methyl or isopropyl, $R^2$ is methyl or ethyl, $X_1$ is a bivalent coupling group formed when $RG_1$ and $R^8$ react (e.g. a succinimide ring or an oxime), $X_2$ is a self-immolative spacer, $L_1$ is a bivalent peptide linker, $L_2$ is a bond or a linker, and y is 1, 2, 3 or 4.

A general reaction scheme for the formation of conjugates of Formula (C-2) is shown in Scheme 4 below:

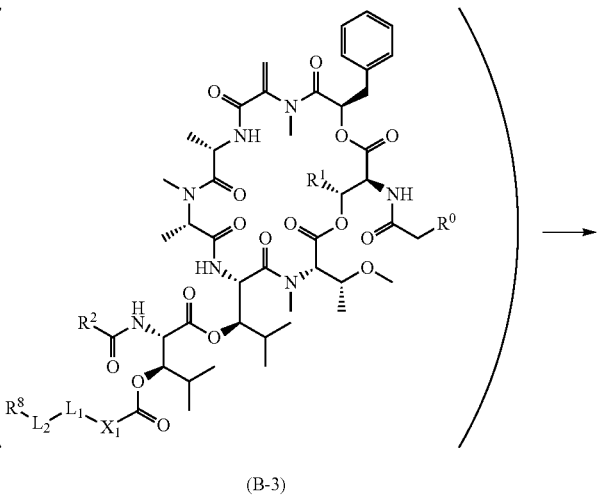

(B-3)

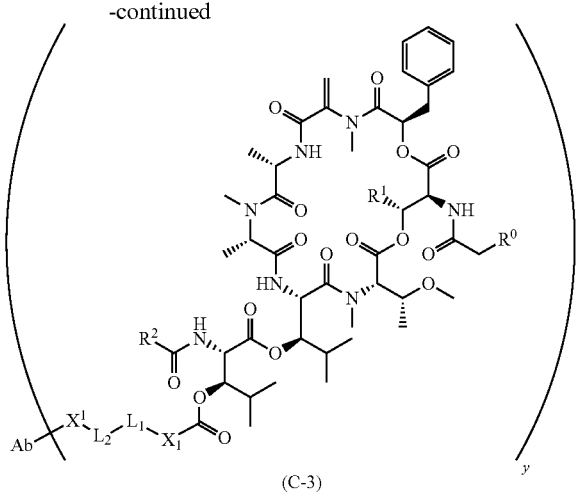

(C-3)

where: $RG_1$ is a reactive group on the antibody or antigen binding fragment thereof, Ab, by way of example only a thiol, amine or ketone, which reacts with a compatible reactive group, $R^8$, attached to the linker-drug moiety thereby covalently linking antibody or antigen binding fragment thereof, Ab, to one or more linker-drug moieties. Non-limiting examples of such reactions of $RG_1$ and $R^8$ groups are a maleimide ($R^8$) reacting with a thiol ($RG_1$) to give a succinimide ring, or a hydroxylamine ($R^6$) reacting with a ketone ($RG_1$) to give an oxime.

Here $R^0$ is methyl or ethyl, $R^1$ is methyl or isopropyl, $R^2$ is methyl or ethyl, $X_2$ is a bivalent coupling group formed when $RG_1$ and $R^8$ react (e.g. a succinimide ring or an oxime), $X_2$ is a self-immolative spacer, $L_1$ is a bivalent peptide linker, $L_2$ is a bond or a linker, and y is 1, 2, 3 or 4.

Process for Conjugation to Engineered Cysteine Antibody Residues

Conjugates of the invention can be prepared using cysteine residues engineered into an antibody by, for example, site-directed mutagenesis. Such site-specific conjugates are homogenous and have improved properties (Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925-932.)

Because engineered cysteines in antibodies expressed in mammalian cells are modified by adducts (disulfides) such as glutathione (GSH) and/or cysteine during their biosynthesis (Chen et al. 2009), the engineered cysteine residues in the product as initially expressed are unreactive to thiol reactive reagents such as maleimido or bromo- or iodoacetamide groups. To conjugate payload to an engineered cysteine after expression, glutathione or cysteine adducts need to be removed by reducing these disulfide adducts, which generally entails also reducing native disulfides in the expressed protein. Deprotection of adducted engineered cysteines can be accomplished by first exposing antibody to a reducing agent, e.g., dithiothreitol (DTT), TCEP, or reduced cysteine, followed by a procedure that allows for re-oxidation of all native disulfide bonds of an antibody to restore and/or stabilize the functional antibody structure.

Several methods can be employed to reduce and re-oxidize antibodies with engineered cysteine residues for preparation of antibody drug conjugates. Attempts to follow re-oxidation protocols previously described in the literature using high concentration of $CuSO_4$ resulted in protein precipitation (Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925). We have successfully prepared and obtained antibody drug conjugates with several different methods for reduction and antibody re-oxidation.

The following is a method to reduce and re-oxidize antibodies with engineered cysteine residues for preparation of antibody drug conjugates: Freshly prepared DTT is added to purified Cys mutant antibodies to a final concentration of 10 mM. After incubation with DTT at room temperature for 1 hour, mixture is dialyzed at 4° C. against PBS for three days with daily buffer exchange to remove DTT and re-oxidize native disulfide bonds of the antibody. An alternative method is to remove reducing reagents through a desalting column such as Sephadex G-25, equilibrated with PBS. Once protein is fully reduced, 1 mM oxidized ascorbate (dehydro-ascorbic acid) is optionally added to desalted samples and re-oxidation incubations are carried out for 20-24 hours.

In another exemplary method, deprotection of engineered Cys residues is accomplished by adding fully reduced cysteine at 20 mM concentration to antibodies bound to protein A-Sepharose resin. Reduction of the Cys adducts is achieved by incubation for approximately 30-60 minutes at room temperature, then reductant is rapidly removed by washing resin with 50 beds of PBS. Re-oxidation of the reduced antibody is achieved by incubating washed slurry at room temperature with or without addition of 50-2000 nM $CuCl_2$ as an accelerant. With the exception of use of copper sulfate, examples herein use each of the protocols described herein with similar results. Reoxidation restores intra-chain disulfides, while dialysis, desalting or protein A chromatography removes reducing agent as well as cysteines and glutathiones initially connected to engineered cysteine(s) of the antibody. HPLC reverse phase chromatography is typically used to monitor the reoxidation process: Antibodies are loaded onto a PLRP-S column (4000 Å, 50 mm×2.1 mm, Agilent) heated to 80° C. and eluted using a linear gradient of 30-45% CH₃CN in water containing 0.1% TFA at 1.5 mL/min. and peak detection at 215, 254, and 280 nm.

After re-oxidation, the antibody is conjugated to a linker-drug compound of, by way of example, compounds of Formula (B), Formula (B-1), Formula (B-2) or Formula (B-3) (see schemes 1-4). By way of example, a compound of Formula (B), Formula (B-1), Formula (B-2) or Formula (B-3) is added to re-oxidized Cys mutant antibody at 5-10 molar equivalents relative to antibody in PBS buffer (pH 7.2). Incubations are carried out for 1-2 hours. The conjugation process is monitored by reverse-phase HPLC, which is able to separate conjugated antibodies from non-conjugated ones. Conjugation reaction mixtures are analyzed on a PRLP-S column (4000 Å, 50 mm×2.1 mm, Agilent) heated to 80° C. and elution of the column are carried out by a linear gradient of 30-60% acetonitrile in water containing 0.1% TFA at a flow rate of 1.5 ml/min. Elution of proteins from the column is monitored at 280 nm, 254 nm and 215 nm.

Alternatively, for antibodies bound to a Protein A resin, once the antibody is re-oxidized, the resin is washed with 10 column volumes PBS and the resin is then resuspended in equal volume PBS and an 8× excess of a compound of Formula (B), Formula (B-1), Formula (B-2) or Formula (B-3) (in DMSO) is added and incubated at room temperature for 2 hours. The resin is then washed with 50 column volumes of PBS and the resulting antibody drug conjugate is eluted from the Protein A resin, neutralized with 1/10 volume 1 M Tris pH 9.0 and buffer exchanged into appropriate buffer to perform preparative size exclusion chromatography (if needed).

Immunoconjugates are also characterized in terms of average loading of a drug moiety to antibody binding moiety, generally referred to as drug-to-antibody ratio (DAR). The DAR value is extrapolated, for example, from LC-MS data for reduced and deglycosylated samples. LC/MS allows quantitation of the average number of molecules of payload (drug moiety) attached to an antibody in an ADC. HPLC separates an antibody into light and heavy chains, and also separates heavy chain (HC) and light chain (LC) according to the number of Linker-Payload groups per chain. Mass spectral data enables identification of the component species in the mixture, e.g., LC, LC+1, LC+2, HC, HC+1, HC+2, etc. From average loading of LC and HC chains, the average DAR can be calculated for an ADC. The DAR for a given immunoconjugate sample represents the average number of drug (payload) molecules attached to a tetrameric antibody containing two light chains and two heavy chains.

Throughout the text of this application, should there be a discrepancy between the text of the specification and the sequence listing, the text of the specification shall prevail.

TABLE 2

Examples of Anti-PMEL17 Antibodies of the Present Invention

G1_E152C_S375C_wt LC

| | | | |
|---|---|---|---|
| SEQ ID NO: 1 | HCDR1 (Combined) | GGTFSDYAIT | |
| SEQ ID NO: 2 | HCDR2 (Combined) | GIIPIFGTANYAQKFQG | |
| SEQ ID NO: 3 | HCDR3 (Combined) | EGGLLTDISYSRYWFAY | |
| SEQ ID NO: 4 | HCDR1 (Kabat) | DYAIT | |
| SEQ ID NO: 2 | HCDR2 (Kabat) | GIIPIFGTANYAQKFQG | |
| SEQ ID NO: 3 | HCDR3 (Kabat) | EGGLLTDISYSRYWFAY | |
| SEQ ID NO: 5 | HCDR1 (Chothia) | GGTFSDY | |
| SEQ ID NO: 6 | HCDR2 (Chothia) | IPIFGT | |
| SEQ ID NO: 3 | HCDR3 (Chothia) | EGGLLTDISYSRYWFAY | |
| SEQ ID NO: 7 | HCDR1 (IMGT) | GGTFSDYA | |
| SEQ ID NO: 8 | HCDR2 (IMGT) | IIPIFGTA | |
| SEQ ID NO: 9 | HCDR3 (IMGT) | AREGGLLTDISYSRYWFAY | |
| SEQ ID NO: 10 | VH | QVQLVQSGAEVKKPGSSVKVSCKASGGTFSDYAITWVRQAPGQGL EWMGGIIPIFGTANYAQKFQGRVTITADESTSTAYMELSSLRSED TAVYYCAREGGLLTDISYSRYWFAYWGQGTLVTVSS | |

TABLE 2-continued

Examples of Anti-PMEL17 Antibodies of the Present Invention

| SEQ ID NO: 11 | DNA VH | CAGGTGCAATTGGTGCAGAGCGGTGCCGAAGTGAAAAAACCGGGC<br>AGCAGCGTGAAAGTTAGCTGCAAAGCATCCGGAGGGACGTTTTCT<br>GACTACGCTATCACTTGGGTGCGCCAGGCCCCGGGCCAGGGCCTC<br>GAGTGGATGGGCGGTATCATCCCGATCTTCGGCACTGCGAACTAC<br>GCCCAGAAATTTCAGGGCCGGGTGACCATTACCGCCGATGAAAGC<br>ACCAGCACCGCCTATATGGAACTGAGCAGCCTGCGCAGCGAAGAT<br>ACGGCCGTGTATTATTGCGCGCGTGAAGGTGGTCTGCTGACTGAC<br>ATCTCTTACTCTCGTTACTGGTTCGCTTACTGGGGCCAAGGCACC<br>CTGGTGACTGTTAGCTCA |
| SEQ ID NO: 12 | Heavy<br>Chain | QVQLVQSGAEVKKPGSSVKVSCKASGGTFSDYAITWVRQAPGQGL<br>EWMGGIIPIFGTANYAQKFQGRVTITADESTSTAYMELSSLRSED<br>TAVYYCAREGGLLTDISYSRYWFAYWGQGTLVTVSSASTKGPSVF<br>PLAPSSKSTSGGTAALGCLVKDYFPCPVTVSWNSGALTSGVHTFP<br>AVLQSSGLYSLSSVVTVPSSSLGTQTYICNVNHKPSNTKVDKRVE<br>PKSCDKTHTCPPCPAPELLGGPSVFLFPPKPKDTLMISRTPEVTC<br>VVVDVSHEDPEVKFNWYVDGVEVHNAKTKPREEQYNSTYRVVSVL<br>TVLHQDWLNGKEYKCKVSNKALPAPIEKTISKAKGQPREPQVYTL<br>PPSREEMTKNQVSLTCLVKGFYPCDIAVEWESNGQPENNYKTTPP<br>VLDSDGSFFLYSKLTVDKSRWQQGNVFSCSVMHEALHNHYTQKSL<br>SLSPGK |
| SEQ ID NO: 13 | DNA Heavy<br>Chain | CAGGTGCAATTGGTGCAGAGCGGTGCCGAAGTGAAAAAACCGGGC<br>AGCAGCGTGAAAGTTAGCTGCAAAGCATCCGGAGGGACGTTTTCT<br>GACTACGCTATCACTTGGGTGCGCCAGGCCCCGGGCCAGGGCCTC<br>GAGTGGATGGGCGGTATCATCCCGATCTTCGGCACTGCGAACTAC<br>GCCCAGAAATTTCAGGGCCGGGTGACCATTACCGCCGATGAAAGC<br>ACCAGCACCGCCTATATGGAACTGAGCAGCCTGCGCAGCGAAGAT<br>ACGGCCGTGTATTATTGCGCGCGTGAAGGTGGTCTGCTGACTGAC<br>ATCTCTTACTCTCGTTACTGGTTCGCTTACTGGGGCCAAGGCACC<br>CTGGTGACTGTTAGCTCAGCTAGCACCAAGGGCCCAAGTGTGTTT<br>CCCCTGGCCCCCAGCAGCAAGTCTACTTCCGGCGGAACTGCTGCC<br>CTGGGTTGCCTGGTGAAGGACTACTTCCCCTGTCCCGTGACAGTG<br>TCCTGGAACTCTGGGGCTCTGACTTCCGGCGTGCACACCTTCCCC<br>GCCGTGCTGCAGAGCAGCGGCCTGTACAGCCTGAGCAGCGTGGTG<br>ACAGTGCCCTCCAGCTCTCTGGGAACCCAGACCTATATCTGCAAC<br>GTGAACCACAAGCCCAGCAACACCAAGGTGGACAAGAGAGTGGAG<br>CCCAAGAGCTGCGACAAGACCCACACCTGCCCCCCCTGCCCAGCT<br>CCAGAACTGCTGGGAGGGCCTTCCGTGTTCCTGTTCCCCCCCAAG<br>CCCAAGGACACCCTGATGATCAGCAGGACCCCCGAGGTGACCTGC<br>GTGGTGGTGGACGTGTCCCACGAGGACCCAGAGGTGAAGTTCAAC<br>TGGTACGTGGACGGCGTGGAGGTGCACAACGCCAAGACCAAGCCC<br>AGAGAGGAGCAGTACAACAGCACCTACAGGGTGGTGTCCGTGCTG<br>ACCGTGCTGCACCAGGACTGGCTGAACGGCAAAGAATACAAGTGC<br>AAAGTCTCCAACAAGGCCCTGCCAGCCCCAATCGAAAAGACAATC<br>AGCAAGGCCAAGGGCCAGCCACGGGAGCCCCAGGTGTACACCCTG<br>CCCCCCAGCCGGGAGGAGATGACCAAGAACCAGGTGTCCCTGACC<br>TGTCTGGTGAAGGGCTTCTACCCCTGTGATATCGCCGTGGAGTGG<br>GAGAGCAACGGCCAGCCCGAGAACAACTACAAGACCACCCCCCCA<br>GTGCTGGACAGCGACGGCAGCTTCTTCCTGTACAGCAAGCTGACC<br>GTGGACAAGTCCAGGTGGCAGCAGGGCAACGTGTTCAGCTGCAGC<br>GTGATGCACGAGGCCCTGCACAACCACTACACCCAGAAGTCCCTG<br>AGCCTGAGCCCCGGCAAG |
| SEQ ID NO: 14 | LCDR1<br>(Combined) | SGDALRDKFVY |
| SEQ ID NO: 15 | LCDR2<br>(Combined) | DDNNRPS |
| SEQ ID NO: 16 | LCDR3<br>(Combined) | QSWDHSYSLVV |
| SEQ ID NO: 14 | LCDR1<br>(Kabat) | SGDALRDKFVY |
| SEQ ID NO: 15 | LCDR2<br>(Kabat) | DDNNRPS |
| SEQ ID NO: 16 | LCDR3<br>(Kabat) | QSWDHSYSLVV |
| SEQ ID NO: 17 | LCDR1<br>(Chothia) | DALRDKF |
| SEQ ID NO: 18 | LCDR2<br>(Chothia) | DDN |

TABLE 2-continued

Examples of Anti-PMEL17 Antibodies of the Present Invention

| SEQ ID NO: 19 | LCDR3 (Chothia) | WDHSYSLV |
|---|---|---|
| SEQ ID NO: 20 | LCDR1 (IMGT) | ALRDKF |
| SEQ ID NO: 18 | LCDR2 (IMGT) | DDN |
| SEQ ID NO: 16 | LCDR3 (IMGT) | QSWDHSYSLVV |
| SEQ ID NO: 21 | VL | DIELTQPPSVSVSPGQTASITCSGDALRDKFVYWYQQKPGQAPVL VIYDDNNRPSGIPERFSGSNSGNTATLTISGTQAEDEADYYCQSW DHSYSLVVFGGGTKLTVL |
| SEQ ID NO: 22 | DNA VL | GATATCGAACTGACCCAGCCGCCGAGCGTGAGCGTGAGCCCGGGC CAGACCGCGAGCATTACCTGTAGCGGCGATGCTCTGCGTGACAAA TTCGTTTACTGGTACCAGCAGAAACCGGGCCAGGCGCCGGTGCTG GTGATCTACGACGACAACAACCGTCCGAGCGGCATCCCGGAACGT TTTAGCGGATCCAACAGCGGCAACACCGCGACCCTGACCATTAGC GGCACCCAGGCGGAAGACGAAGCGGATTATTACTGCCAGTCTTGG GACCATTCTTACTCTCTGGTTGTGTTTGGCGGCGGCACGAAGTTA ACTGTCCTG |
| SEQ ID NO: 23 | Light Chain | DIELTQPPSVSVSPGQTASITCSGDALRDKFVYWYQQKPGQAPVL VIYDDNNRPSGIPERFSGSNSGNTATLTISGTQAEDEADYYCQSW DHSYSLVVFGGGTKLTVLGQPKAAPSVTLFPPSSEELQANKATLV CLISDFYPGAVTVAWKADSSPVKAGVETTTPSKQSNNKYAASSYL SLTPEQWKSHRSYSCQVTHEGSTVEKTVAPTECS |
| SEQ ID NO: 24 | DNA Light Chain | GATATCGAACTGACCCAGCCGCCGAGCGTGAGCGTGAGCCCGGGC CAGACCGCGAGCATTACCTGTAGCGGCGATGCTCTGCGTGACAAA TTCGTTTACTGGTACCAGCAGAAACCGGGCCAGGCGCCGGTGCTG GTGATCTACGACGACAACAACCGTCCGAGCGGCATCCCGGAACGT TTTAGCGGATCCAACAGCGGCAACACCGCGACCCTGACCATTAGC GGCACCCAGGCGGAAGACGAAGCGGATTATTACTGCCAGTCTTGG GACCATTCTTACTCTCTGGTTGTGTTTGGCGGCGGCACGAAGTTA ACTGTCCTGGGACAACCTAAGGCCGCTCCCTCCGTGACCCTGTTC CCCCCCAGCTCCGAGGAACTGCAGGCCAACAAGGCCACCCTGGTG TGCCTGATCAGCGACTTCTACCCTGGCGCCGTGACCGTGGCCTGG AAGGCCGACAGCAGCCCCGTGAAGGCCGGCGTGGAGACAACCACC CCCAGCAAGCAGAGCAACAACAAGTACGCCGCCAGCAGCTACCTG AGCCTGACCCCCGAGCAGTGGAAGAGCCACAGAAGCTACAGCTGC CAGGTCACCCACGAGGGCAGCACCGTGGAGAAAACCGTGGCCCCC ACCGAGTGCAGC |

G1_E152C_S375C_3J_LC

| SEQ ID NO: 1 | HCDR1 (Combined) | GGTFSDYAIT |
|---|---|---|
| SEQ ID NO: 2 | HCDR2 (Combined) | GIIPIFGTANYAQKFQG |
| SEQ ID NO: 3 | HCDR3 (Combined) | EGGLLTDISYSRYWFAY |
| SEQ ID NO: 4 | HCDR1 (Kabat) | DYAIT |
| SEQ ID NO: 2 | HCDR2 (Kabat) | GIIPIFGTANYAQKFQG |
| SEQ ID NO: 3 | HCDR3 (Kabat) | EGGLLTDISYSRYWFAY |
| SEQ ID NO: 5 | HCDR1 (Chothia) | GGTFSDY |
| SEQ ID NO: 6 | HCDR2 (Chothia) | IPIFGT |
| SEQ ID NO: 3 | HCDR3 (Chothia) | EGGLLTDISYSRYWFAY |
| SEQ ID NO: 7 | HCDR1 (IMGT) | GGTFSDYA |

TABLE 2-continued

Examples of Anti-PMEL17 Antibodies of the Present Invention

| SEQ ID NO: 8 | HCDR2 (IMGT) | IIPIFGTA |
|---|---|---|
| SEQ ID NO: 9 | HCDR3 (IMGT) | AREGGLLTDISYSRYWFAY |
| SEQ ID NO: 10 | VH | QVQLVQSGAEVKKPGSSVKVSCKASGGTFSDYAITWVRQAPGQGL EWMGGIIPIFGTANYAQKFQGRVTITADESTSTAYMELSSLRSED TAVYYCAREGGLLTDISYSRYWFAYWGQGTLVTVSS |
| SEQ ID NO: 11 | DNA VH | CAGGTGCAATTGGTGCAGAGCGGTGCCGAAGTGAAAAAACCGGGC AGCAGCGTGAAAGTTAGCTGCAAAGCATCCGGAGGGACGTTTTCT GACTACGCTATCACTTGGGTGCGCCAGGCCCCGGGCCAGGGCCTC GAGTGGATGGGCGGTATCATCCCGATCTTCGGCACTGCGAACTAC GCCCAGAAATTTCAGGGCCGGGTGACCATTACCGCCGATGAAAGC ACCAGCACCGCCTATATGGAACTGAGCAGCCTGCGCAGCGAAGAT ACGGCCGTGTATTATTGCGCGCGTGAAGGTGGTCTGCTGACTGAC ATCTCTTACTCTCGTTACTGGTTCGCTTACTGGGGCCAAGGCACC CTGGTGACTGTTAGCTCA |
| SEQ ID NO: 12 | Heavy Chain | QVQLVQSGAEVKKPGSSVKVSCKASGGTFSDYAITWVRQAPGQGL EWMGGIIPIFGTANYAQKFQGRVTITADESTSTAYMELSSLRSED TAVYYCAREGGLLTDISYSRYWFAYWGQGTLVTVSSASTKGPSVF PLAPSSKSTSGGTAALGCLVKDYFPCPVTVSWNSGALTSGVHTPP AVLQSSGLYSLSSVVTVPSSSLGTQTYICNVNHKPSNTKVDKRVE PKSCDKTHTCPPCPAPELLGGPSVFLFPPKPKDTLMISRTPEVTC VVVDVSHEDPEVKFNWYVDGVEVHNAKTKPREEQYNSTYRVVSVL TVLHQDWLNGKEYKCKVSNKALPAPIEKTISKAKGQPREPQVYTL PPSREEMTKNQVSLTCLVKGFYPCDIAVEWESNGQPENNYKTTPP VLDSDGSFFLYSKLTVDKSRWQQGNVFSCSVMHEALHNHYTQKSL SLSPGK |
| SEQ ID NO: 13 | DNA Heavy | CAGGTGCAATTGGTGCAGAGCGGTGCCGAAGTGAAAAAACCGGGC AGCAGCGTGAAAGTTAGCTGCAAAGCATCCGGAGGGACGTTTTCT GACTACGCTATCACTTGGGTGCGCCAGGCCCCGGGCCAGGGCCTC GAGTGGATGGGCGGTATCATCCCGATCTTCGGCACTGCGAACTAC GCCCAGAAATTTCAGGGCCGGGTGACCATTACCGCCGATGAAAGC ACCAGCACCGCCTATATGGAACTGAGCAGCCTGCGCAGCGAAGAT ACGGCCGTGTATTATTGCGCGCGTGAAGGTGGTCTGCTGACTGAC ATCTCTTACTCTCGTTACTGGTTCGCTTACTGGGGCCAAGGCACC CTGGTGACTGTTAGCTCAGCTAGCACCAAGGGCCCAAGTGTGTTT CCCCTGGCCCCAGCAGCAAGTCTACTTCCGGCGGAACTGCTGCC CTGGGTTGCCTGGTGAAGGACTACTTCCCCTGTCCCGTGACAGTG TCCTGGAACTCTGGGGCTCTGACTTCCGGCGTGCACACCTTCCCC GCCGTGCTGCAGAGCAGCGGCCTGTACAGCCTGAGCAGCGTGGTG ACAGTGCCCTCCAGCTCTCTGGGAACCCAGACCTATATCTGCAAC GTGAACCACAAGCCCAGCAACACCAAGGTGGACAAGAGAGTGGAG CCCAAGAGCTGCGACAAGACCCACACCTGCCCCCCCTGCCCAGCT CCAGAACTGCTGGGAGGGCCTTCCGTGTTCCTGTTCCCCCCCAAG CCCAAGGACACCCTGATGATCAGCAGGACCCCCGAGGTGACCTGC GTGGTGGTGGACGTGTCCCACGAGGACCCAGAGGTGAAGTTCAAC TGGTACGTGGACGGCGTGGAGGTGCACAACGCCAAGACCAAGCCC AGAGAGGAGCAGTACAACAGCACCTACAGGGTGGTGTCCGTGCTG ACCGTGCTGCACCAGGACTGGCTGAACGGCAAAGAATACAAGTGC AAAGTCTCCAACAAGGCCCTGCCAGCCCCAATCGAAAAGACAATC AGCAAGGCCAAGGGCCAGCCACGGGAGCCCCAGGTGTACACCCTG CCCCCCAGCCGGGAGGAGATGACCAAGAACCAGGTGTCCCTGACC TGTCTGGTGAAGGGCTTCTACCCCTGTGATATCGCCGTGGAGTGG GAGAGCAACGGCCAGCCCGAGAACAACTACAAGACCACCCCCCCA GTGCTGGACAGCGACGGCAGCTTCTTCCTGTACAGCAAGCTGACC GTGGACAAGTCCAGGTGGCAGCAGGGCAACGTGTTCAGCTGCAGC GTGATGCACGAGGCCCTGCACAACCACTACACCCAGAAGTCCCTG AGCCTGAGCCCCGGCAAG |
| SEQ ID NO: 14 | LCDR1 (Combined) | SGDALRDKFVY |
| SEQ ID NO: 15 | LCDR2 (Combined) | DDNNRPS |
| SEQ ID NO: 16 | LCDR3 (Combined) | QSWDHSYSLVV |
| SEQ ID NO: 14 | LCDR1 (Kabat) | SGDALRDKFVY |

TABLE 2-continued

Examples of Anti-PMEL17 Antibodies of the Present Invention

| SEQ ID NO: 15 | LCDR2 (Kabat) | DDNNRPS |
|---|---|---|
| SEQ ID NO: 16 | LCDR3 (Kabat) | QSWDHSYSLVV |
| SEQ ID NO: 17 | LCDR1 (Chothia) | DALRDKF |
| SEQ ID NO: 18 | LCDR2 (Chothia) | DDN |
| SEQ ID NO: 19 | LCDR3 (Chothia) | WDHSYSLV |
| SEQ ID NO: 20 | LCDR1 (IMGT) | ALRDKF |
| SEQ ID NO: 18 | LCDR2 (IMGT) | DDN |
| SEQ ID NO: 16 | LCDR3 (IMGT) | QSWDHSYSLVV |
| SEQ ID NO: 25 | VL | SYELTQPLSVSVALGQTARITCSGDALRDKFVYWYQQKPGQAPVL VIYDDNNRPSGIPERFSGSNSGNTATLTISRAQAGDEADYYCQSW DHSYSLVVFGGGTKLTVL |
| SEQ ID NO: 26 | DNA VL | AGCTACGAGCTGACCCAGCCGCTGTCGGTGTCAGTCGCCCTGGGA CAAACTGCCAGGATCACTTGTTCCGGGGACGCATTGCGGGACAAG TTCGTGTACTGGTACCAGCAGAAGCCGGGTCAAGCCCCAGTGCTC GTGATCTACGACGACAACAACCGGCCTTCCGGTATCCCCGAACGC TTCTCCGGATCCAATAGCGGAAACACCGCCACCCTGACCATTTCG AGAGCTCAGGCCGGGGATGAAGCGGACTACTACTGCCAGTCATGG GATCACTCGTACTCCCTCGTCGTGTTTGGAGGCGGCACGAAGCTT ACTGTGCTG |
| SEQ ID NO: 27 | Light Chain | SYELTQPLSVSVALGQTARITCSGDALRDKFVYWYQQKPGQAPVL VIYDDNNRPSGIPERFSGSNSGNTATLTISRAQAGDEADYYCQSW DHSYSLVVFGGGTKLTVLGQPKAAPSVTLFPPSSEELQANKATLV CLISDFYPGAVTVAWKADSSPVKAGVETTTPSKQSNNKYAASSYL SLTPEQWKSHRSYSCQVTHEGSTVEKTVAPTECS |
| SEQ ID NO: 28 | DNA Light | AGCTACGAGCTGACCCAGCCGCTGTCGGTGTCAGTCGCCCTGGGA CAAACTGCCAGGATCACTTGTTCCGGGGACGCATTGCGGGACAAG TTCGTGTACTGGTACCAGCAGAAGCCGGGTCAAGCCCCAGTGCTC GTGATCTACGACGACAACAACCGGCCTTCCGGTATCCCCGAACGC TTCTCCGGATCCAATAGCGGAAACACCGCCACCCTGACCATTTCG AGAGCTCAGGCCGGGGATGAAGCGGACTACTACTGCCAGTCATGG GATCACTCGTACTCCCTCGTCGTGTTTGGAGGCGGCACGAAGCTT ACTGTGCTGGGCCAGCCTAAGGCCGCTCCCTCCGTGACCCTGTTC CCCCCCAGCTCCGAGGAACTGCAGGCCAACAAGGCCACCCTGGTG TGCCTGATCAGCGACTTCTACCCTGGCGCCGTGACCGTGGCCTGG AAGGCCGACAGCAGCCCCGTGAAGGCCGGCGTGGAGACAACCACC CCCAGCAAGCAGAGCAACAACAAGTACGCCGCCAGCAGCTACCTG AGCCTGACCCCCGAGCAGTGGAAGAGCCACAGAAGCTACAGCTGC CAGGTCACCCACGAGGGCAGCACCGTGGAGAAACCGTGGCCCCC ACCGAGTGCAGC |

G1_E152C_S375C_3RLC

| SEQ ID NO: 1 | HCDR1 (Combined) | GGTFSDYAIT |
|---|---|---|
| SEQ ID NO: 2 | HCDR2 (Combined) | GIIPIFGTANYAQKFQG |
| SEQ ID NO: 3 | HCDR3 (Combined) | EGGLLTDISYSRYWFAY |
| SEQ ID NO: 4 | HCDR1 (Kabat) | DYAIT |
| SEQ ID NO: 2 | HCDR2 (Kabat) | GIIPIFGTANYAQKFQG |
| SEQ ID NO: 3 | HCDR3 (Kabat) | EGGLLTDISYSRYWFAY |

TABLE 2-continued

Examples of Anti-PMEL17 Antibodies of the Present Invention

| SEQ ID NO: 5 | HCDR1 (Chothia) | GGTFSDY |
|---|---|---|
| SEQ ID NO: 6 | HCDR2 (Chothia) | IPIFGT |
| SEQ ID NO: 3 | HCDR3 (Chothia) | EGGLLTDISYSRYWFAY |
| SEQ ID NO: 7 | HCDR1 (IMGT) | GGTFSDYA |
| SEQ ID NO: 8 | HCDR2 (IMGT) | IIPIFGTA |
| SEQ ID NO: 9 | HCDR3 (IMGT) | AREGGLLTDISYSRYWFAY |
| SEQ ID NO: 10 | VH | QVQLVQSGAEVKKPGSSVKVSCKASGGTFSDYAITWVRQAPGQGL EWMGGIIPIFGTANYAQKFQGRVTITADESTSTAYMELSSLRSED TAVYYCAREGGLLTDISYSRYWFAYWGQGTLVTVSS |
| SEQ ID NO: 11 | DNA VH | CAGGTGCAATTGGTGCAGAGCGGTGCCGAAGTGAAAAAACCGGGC AGCAGCGTGAAAGTTAGCTGCAAAGCATCCGGAGGGACGTTTTCT GACTACGCTATCACTTGGGTGCGCCAGGCCCCGGGCCAGGGCCTC GAGTGGATGGGCGGTATCATCCCGATCTTCGGCACTGCGAACTAC GCCCAGAAATTTCAGGGCCGGGTGACCATTACCGCCGATGAAAGC ACCAGCACCGCCTATATGGAACTGAGCAGCCTGCGCAGCGAAGAT ACGGCCGTGTATTATTGCGCGCGTGAAGGTGGTCTGCTGACTGAC ATCTCTTACTCTCGTTACTGGTTCGCTTACTGGGGCCAAGGCACC CTGGTGACTGTTAGCTCA |
| SEQ ID NO: 12 | Heavy Chain | QVQLVQSGAEVKKPGSSVKVSCKASGGTFSDYAITWVRQAPGQGL EWMGGIIPIFGTANYAQKFQGRVTITADESTSTAYMELSSLRSED TAVYYCAREGGLLTDISYSRYWFAYWGQGTLVTVSSASTKGPSVF PLAPSSKSTSGGTAALGCLVKDYFPCPVTVSWNSGALTSGVHTFP AVLQSSGLYSLSSVVTVPSSSLGTQTYICNVNHKPSNTKVDKRVE PKSCDKTHTCPPCPAPELLGGPSVFLFPPKPKDTLMISRTPEVTC VVVDVSHEDPEVKFNWYVDGVEVHNAKTKPREEQYNSTYRVVSVL TVLHQDWLNGKEYKCKVSNKALPAPIEKTISKAKGQPREPQVYTL PPSREEMTKNQVSLTCLVKGFYPCDIAVEWESNGQPENNYKTTPP VLDSDGSFFLYSKLTVDKSRWQQGNVFSCSVMHEALHNHYTQKSL SLSPGK |
| SEQ ID NO: 13 | DNA Heavy Chain | CAGGTGCAATTGGTGCAGAGCGGTGCCGAAGTGAAAAAACCGGGC AGCAGCGTGAAAGTTAGCTGCAAAGCATCCGGAGGGACGTTTTCT GACTACGCTATCACTTGGGTGCGCCAGGCCCCGGGCCAGGGCCTC GAGTGGATGGGCGGTATCATCCCGATCTTCGGCACTGCGAACTAC GCCCAGAAATTTCAGGGCCGGGTGACCATTACCGCCGATGAAAGC ACCAGCACCGCCTATATGGAACTGAGCAGCCTGCGCAGCGAAGAT ACGGCCGTGTATTATTGCGCGCGTGAAGGTGGTCTGCTGACTGAC ATCTCTTACTCTCGTTACTGGTTCGCTTACTGGGGCCAAGGCACC CTGGTGACTGTTAGCTCAGCTAGCACCAAGGGCCCAAGTGTGTTT CCCCTGGCCCCCAGCAGCAAGTCTACTTCCGGCGGAACTGCTGCC CTGGGTTGCCTGGTGAAGGACTACTTCCCCTGTCCCGTGACAGTG TCCTGGAACTCTGGGGCTCTGACTTCCGGCGTGCACACCTTCCCC GCCGTGCTGCAGAGCAGCGGCCTGTACAGCCTGAGCAGCGTGGTG ACAGTGCCCTCCAGCTCTCTGGGAACCCAGACCTATATCTGCAAC GTGAACCACAAGCCCAGCAACACCAAGGTGGACAAGAGAGTGGAG CCCAAGAGCTGCGACAAGACCCACACCTGCCCCCCCTGCCCAGCT CCAGAACTGCTGGGAGGGCCTTCCGTGTTCCTGTTCCCCCCCAAG CCCAAGGACACCCTGATGATCAGCAGGACCCCCGAGGTGACCTGC GTGGTGGTGGACGTGTCCCACGAGGACCCAGAGGTGAAGTTCAAC TGGTACGTGGACGGCGTGGAGGTGCACAACGCCAAGACCAAGCCC AGAGAGGAGCAGTACAACAGCACCTACAGGGTGGTGTCCGTGCTG ACCGTGCTGCACCAGGACTGGCTGAACGGCAAAGAATACAAGTGC AAAGTCTCCAACAAGGCCCTGCCAGCCCCAATCGAAAAGACAATC AGCAAGGCCAAGGGCCAGCCACGGGAGCCCCAGGTGTACACCCTG CCCCCCAGCCGGGAGGAGATGACCAAGAACCAGGTGTCCCTGACC TGTCTGGTGAAGGGCTTCTACCCCTGTGATATCGCCGTGGAGTGG GAGAGCAACGGCCAGCCCGAGAACAACTACAAGACCACCCCCCCA GTGCTGGACAGCGACGGCAGCTTCTTCCTGTACAGCAAGCTGACC GTGGACAAGTCCAGGTGGCAGCAGGGCAACGTGTTCAGCTGCAGC GTGATGCACGAGGCCCTGCACAACCACTACACCCAGAAGTCCCTG AGCCTGAGCCCCGGCAAG |

TABLE 2-continued

Examples of Anti-PMEL17 Antibodies of the Present Invention

| SEQ ID NO: 14 | LCDR1 (Combined) | SGDALRDKFVY |
|---|---|---|
| SEQ ID NO: 15 | LCDR2 (Combined) | DDNNRPS |
| SEQ ID NO: 16 | LCDR3 (Combined) | QSWDHSYSLVV |
| SEQ ID NO: 14 | LCDR1 (Kabat) | SGDALRDKFVY |
| SEQ ID NO: 15 | LCDR2 (Kabat) | DDNNRPS |
| SEQ ID NO: 16 | LCDR3 (Kabat) | QSWDHSYSLVV |
| SEQ ID NO: 17 | LCDR1 (Chothia) | DALRDKF |
| SEQ ID NO: 18 | LCDR2 (Chothia) | DDN |
| SEQ ID NO: 19 | LCDR3 (Chothia) | WDHSYSLV |
| SEQ ID NO: 20 | LCDR1 (IMGT) | ALRDKF |
| SEQ ID NO: 18 | LCDR2 (IMGT) | DDN |
| SEQ ID NO: 16 | LCDR3 (IMGT) | QSWDHSYSLVV |
| SEQ ID NO: 29 | VL | SYELTQPPSVSVSPGQTASITCSGDALRDKFVYWYQQKPGQSPVL VIYDDNNRPSGIPERFSGSNSGNTATLTISGTQAMDEADYYCQSW DHSYSLVVFGGGTKLTVL |
| SEQ ID NO: 30 | DNA VL | TCGTACGAGCTCACTCAACCGCCTTCTGTGTCCGTGTCACCCGGG CAGACTGCCTCCATTACCTGTTCGGGAGATGCCCTGCGCGACAAG TTTGTGTACTGGTACCAGCAGAAGCCCGGACAGTCGCCAGTGCTC GTCATCTATGACGACAACAACAGACCTTCCGGTATCCCGGAACGG TTCAGCGGAAGCAATTCCGGCAACACCGCTACCCTGACCATTAGC GGCACTCAGGCCATGGACGAAGCGGATTACTACTGCCAATCCTGG GACCACTCATACTCCCTTGTGGTGTTCGGTGGCGGAACGAAGCTG ACCGTCCTG |
| SEQ ID NO: 31 | Light Chain | SYELTQPPSVSVSPGQTASITCSGDALRDKFVYWYQQKPGQSPVL VIYDDNNRPSGIPERFSGSNSGNTATLTISGTQAMDEADYYCQSW DHSYSLVVFGGGTKLTVLGQPKAAPSVTLFPPSSEELQANKATLV CLISDFYPGAVTVAWKADSSPVKAGVETTTPSKQSNNKYAASSYL SLTPEQWKSHRSYSCQVTHEGSTVEKTVAPTECS |
| SEQ ID NO: 32 | DNA Light Chain | TCGTACGAGCTCACTCAACCGCCTTCTGTGTCCGTGTCACCCGGG CAGACTGCCTCCATTACCTGTTCGGGAGATGCCCTGCGCGACAAG TTTGTGTACTGGTACCAGCAGAAGCCCGGACAGTCGCCAGTGCTC GTCATCTATGACGACAACAACAGACCTTCCGGTATCCCGGAACGG TTCAGCGGAAGCAATTCCGGCAACACCGCTACCCTGACCATTAGC GGCACTCAGGCCATGGACGAAGCGGATTACTACTGCCAATCCTGG GACCACTCATACTCCCTTGTGGTGTTCGGTGGCGGAACGAAGCTG ACCGTCCTGGGCCAGCCTAAGGCCGCTCCCTCCGTGACCCTGTTC CCCCCCAGCTCCGAGGAACTGCAGGCCAACAAGGCCACCCTGGTG TGCCTGATCAGCGACTTCTACCCTGGCGCCGTGACCGTGGCCTGG AAGGCCGACAGCAGCCCCGTGAAGGCCGGCGTGGAGACAACCACC CCCAGCAAGCAGAGCAACAACAAGTACGCCGCCAGCAGCTACCTG AGCCTGACCCCCGAGCAGTGGAAGAGCCACAGAAGCTACAGCTGC CAGGTCACCCACGAGGGCAGCACCGTGGAGAAACCGTGGCCCCC ACCGAGTGCAGC |
| G4 E152_S375C | | |
| SEQ ID NO: 33 | HCDR1 (Combined) | GGTFSTYAIS |
| SEQ ID NO: 34 | HCDR2 (Combined) | RIIPILGIANYAQKFQG |

TABLE 2-continued

Examples of Anti-PMEL17 Antibodies of the Present Invention

| SEQ ID NO: 35 | HCDR3 (Combined) | EVRMIFDY |
|---|---|---|
| SEQ ID NO: 36 | HCDR1 (Kabat) | TYAIS |
| SEQ ID NO: 34 | HCDR2 (Kabat) | RIIPILGIANYAQKFQG |
| SEQ ID NO: 35 | HCDR3 (Kabat) | EVRMIFDY |
| SEQ ID NO: 37 | HCDR1 (Chothia) | GGTFSTY |
| SEQ ID NO: 38 | HCDR2 (Chothia) | IPILGI |
| SEQ ID NO: 35 | HCDR3 (Chothia) | EVRMIFDY |
| SEQ ID NO: 39 | HCDR1 (IMGT) | GGTFSTYA |
| SEQ ID NO: 40 | HCDR2 (IMGT) | IIPILGIA |
| SEQ ID NO: 41 | HCDR3 (IMGT) | AREVRMIFDY |
| SEQ ID NO: 42 | VH | QVQLVQSGAEVKKPGSSVKVSCKASGGTFSTYAISWVRQAPGQGL EWMGRIIPILGIANYAQKFQGRVTITADESTSTAYMELSSLRSED TAVYYCAREVRMIFDYWGQGTLVTVSS |
| SEQ ID NO: 43 | DNA VH | CAGGTGCAATTGGTGCAGAGCGGTGCCGAAGTGAAAAAACCGGGC AGCAGCGTGAAAGTTAGCTGCAAAGCATCCGGAGGGACGTTTTCT ACTTACGCTATCTCTTGGGTGCGCCAGGCCCCGGGCCAGGGCCTC GAGTGGATGGGCCGTATCATCCCGATCCTGGGCATCGCGAACTAC GCCCAGAAATTTCAGGGCCGGGTGACCATTACCGCCGATGAAAGC ACCAGCACCGCCTATATGGAACTGAGCAGCCTGCGCAGCGAAGAT ACGGCCGTGTATTATTGCGCGCGTGAAGTTCGTATGATCTTCGAT TACTGGGGCCAAGGCACCCTGGTGACTGTTAGCTCA |
| SEQ ID NO: 44 | Heavy Chain | QVQLVQSGAEVKKPGSSVKVSCKASGGTFSTYAISWVRQAPGQGL EWMGRIIPILGIANYAQKFQGRVTITADESTSTAYMELSSLRSED TAVYYCAREVRMIFDYWGQGTLVTVSSASTKGPSVFPLAPSSKST SGGTAALGCLVKDYFPCPVTVSWNSGALTSGVHTFPAVLQSSGLY SLSSVVTVPSSSLGTQTYICNVNHKPSNTKVDKRVEPKSCDKTHT CPPCPAPELLGGPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPCDIAVEWESNGQPENNYKTTPPVLDSDGSFF LYSKLTVDKSRWQQGNVFSCSVMHEALHNHYTQKSLSLSPGK |
| SEQ ID NO: 45 | DNA Heavy Chain | CAGGTGCAATTGGTGCAGAGCGGTGCCGAAGTGAAAAAACCGGGC AGCAGCGTGAAAGTTAGCTGCAAAGCATCCGGAGGGACGTTTTCT ACTTACGCTATCTCTTGGGTGCGCCAGGCCCCGGGCCAGGGCCTC GAGTGGATGGGCCGTATCATCCCGATCCTGGGCATCGCGAACTAC GCCCAGAAATTTCAGGGCCGGGTGACCATTACCGCCGATGAAAGC ACCAGCACCGCCTATATGGAACTGAGCAGCCTGCGCAGCGAAGAT ACGGCCGTGTATTATTGCGCGCGTGAAGTTCGTATGATCTTCGAT TACTGGGGCCAAGGCACCCTGGTGACTGTTAGCTCAGCCTCTACG AAAGGCCCAAGCGTATTTCCCCTGGCTCCTTCTAGTAAATCAACC TCAGGTGGTACAGCAGCCCTTGGCTGCCTGGTCAAAGACTATTTC CCCTGTCCGGTGACCGTCTCATGGAACTCAGGTGCTTTGACATCT GGTGTGCATACATTCCCAGCTGTGCTGCAAAGTAGTGGACTGTAC AGCCTTTCCAGCGTGGTCACGGTGCCAAGTAGCTCCTTGGGTACT CAGACTTATATCTGCAATGTGAACCACAAGCCCTCTAACACGAAG GTGGACAAGCGCGTGGAGCCCAAATCTTGCGATAAGACGCATACT TGTCCCCCATGCCCTGCTCCTGAGCTGTTGGGAGGCCCGTCAGTG TTCTTGTTCCCTCCGAAGCCTAAGGACATTTGATGATAAGTAGG ACACCAGAGGTGACTTGCGTGGTGGTTGATGTGTCCCATGAAGAT CCCGAGGTCAAATTTAATTGGTACGTAGATGGTGTCGAAGTTCAC AATGCTAAGACTAAGCCAAGGGAAGAGCAGTACAACAGTACATAT AGGGTAGTCTCCGTGCTGACAGTCCTCCACCAGGACTGGTTGAAC GGCAAGGAATACAAATGTAAGGTGTCAAACAAAGCTCTGCCTGCT CCCATTGAGAAAACAATCTCTAAAGCCAAAGGCCAGCCGAGAGAG |

TABLE 2-continued

Examples of Anti-PMEL17 Antibodies of the Present Invention

|  |  |  |
|---|---|---|
|  |  | CCCCAAGTCTACACTTTGCCCCCGAGCAGGGAGGAAATGACCAAG<br>AATCAGGTGAGTCTGACGTGCCTCGTCAAAGGATTTTATCCATGC<br>GATATTGCAGTTGAATGGGAGAGCAATGGCCAGCCAGAGAACAAC<br>TATAAAACCACACCACCCGTGCTCGACTCTGATGGCAGCTTCTTC<br>CTCTATAGCAAGCTGACAGTCGATAAATCTCGCTGGCAGCAAGGC<br>AATGTGTTCTCCTGCTCCGTCATGCACGAGGCTTTGCATAACCAT<br>TATACTCAAAAATCTCTGTCCCTGTCACCTGGTAAA |
| SEQ ID NO: 46 | LCDR1<br>(Combined) | RASQSISSYLA |
| SEQ ID NO: 47 | LCDR2<br>(Combined) | AASSLQS |
| SEQ ID NO: 48 | LCDR3<br>(Combined) | QQSYDYYT |
| SEQ ID NO: 46 | LCDR1<br>(Kabat) | RASQSISSYLA |
| SEQ ID NO: 47 | LCDR2<br>(Kabat) | AASSLQS |
| SEQ ID NO: 48 | LCDR3<br>(Kabat) | QQSYDYYT |
| SEQ ID NO: 49 | LCDR1<br>(Chothia) | SQSISSY |
| SEQ ID NO: 50 | LCDR2<br>(Chothia) | AAS |
| SEQ ID NO: 51 | LCDR3<br>(Chothia) | SYDYY |
| SEQ ID NO: 52 | LCDR1<br>(IMGT) | QSISSY |
| SEQ ID NO: 50 | LCDR2<br>(IMGT) | AAS |
| SEQ ID NO: 48 | LCDR3<br>(IMGT) | QQSYDYYT |
| SEQ ID NO: 53 | VL | DIQMTQSPSSLSASVGDRVTITCRASQSISSYLAWYQQKPGKAPK<br>LLIYAASSLQSGVPSRFSGSGSGTDFTLTISSLQPEDFATYYCQQ<br>SYDYYTFGQGTKVEIK |
| SEQ ID NO: 54 | DNA VL | GATATCCAGATGACCCAGAGCCCGAGCAGCCTGAGCGCCAGCGTG<br>GGCGATCGCGTGACCATTACCTGCAGAGCCAGCCAGTCTATTTCT<br>TCTTACCTGGCTTGGTACCAGCAGAAACCGGGCAAAGCGCCGAAA<br>CTATTAATCTACGCTGCTTCTTCTCTGCAAAGCGGCGTGCCGAGC<br>CGCTTTAGCGGCAGCGGATCCGGCACCGATTTCACCCTGACCATT<br>AGCTCTCTGCAACCGGAAGACTTTGCGACCTATTATTGCCAGCAG<br>TCTTACGACTACTACACCTTTGGCCAGGGCACGAAAGTTGAAATT<br>AAA |
| SEQ ID NO: 55 | Light Chain | DIQMTQSPSSLSASVGDRVTITCRASQSISSYLAWYQQKPGKAPK<br>LLIYAASSLQSGVPSRFSGSGSGTDFTLTISSLQPEDFATYYCQQ<br>SYDYYTFGQGTKVEIKRTVAAPSVFIFPPSDEQLKSGTASVVCLL<br>NNFYPREAKVQWKVDNALQSGNSQESVTEQDSKDSTYSLSSTLTL<br>SKADYEKHKVYACEVTHQGLSSPVTKSFNRGEC |
| SEQ ID NO: 56 | DNA Light<br>Chain | GATATCCAGATGACCCAGAGCCCGAGCAGCCTGAGCGCCAGCGTG<br>GGCGATCGCGTGACCATTACCTGCAGAGCCAGCCAGTCTATTTCT<br>TCTTACCTGGCTTGGTACCAGCAGAAACCGGGCAAAGCGCCGAAA<br>CTATTAATCTACGCTGCTTCTTCTCTGCAAAGCGGCGTGCCGAGC<br>CGCTTTAGCGGCAGCGGATCCGGCACCGATTTCACCCTGACCATT<br>AGCTCTCTGCAACCGGAAGACTTTGCGACCTATTATTGCCAGCAG<br>TCTTACGACTACTACACCTTTGGCCAGGGCACGAAAGTTGAAATT<br>AAACGTACGGTGGCAGCTCCGTCTGTTTTCATCTTTCCACCTAGC<br>GACGAGCAACTCAAAAGTGGTACAGCATCCGTGGTTTGTCTGCTG<br>AACAATTTTTACCCCAGGGAGGCTAAGGTCCAGTGGAAAGTCGAT<br>AACGCTCTTCAGTCTGGCAACAGTCAGGAGAGCGTCACAGAGCAG<br>GACTCTAAGGATAGCACTTATAGTCTGTCCTCCACGCTGACACTG<br>TCTAAAGCGGATTATGAGAAGCACAAGGTTTACGCCTGTGAGGTA<br>ACGCACCAAGGACTCTCCTCCCCAGTTACCAAATCTTTCAACAGA<br>GGAGAATGT |

TABLE 2-continued

Examples of Anti-PMEL17 Antibodies of the Present Invention

MOR024353
E152C_S375C

| | | |
|---|---|---|
| SEQ ID NO: 57 | HCDR1 (Combined) | GGTFSDYAIS |
| SEQ ID NO: 58 | HCDR2 (Combined) | GIIPIFGDANYAQKFQG |
| SEQ ID NO: 59 | HCDR3 (Combined) | EGSSYFYMAY |
| SEQ ID NO: 60 | HCDR1 (Kabat) | DYAIS |
| SEQ ID NO: 58 | HCDR2 (Kabat) | GIIPIFGDANYAQKFQG |
| SEQ ID NO: 59 | HCDR3 (Kabat) | EGSSYFYMAY |
| SEQ ID NO: 5 | HCDR1 (Chothia) | GGTFSDY |
| SEQ ID NO: 61 | HCDR2 (Chothia) | IPIFGD |
| SEQ ID NO: 59 | HCDR3 (Chothia) | EGSSYFYMAY |
| SEQ ID NO: 7 | HCDR1 (IMGT) | GGTFSDYA |
| SEQ ID NO: 62 | HCDR2 (IMGT) | IIPIFGDA |
| SEQ ID NO: 63 | HCDR3 (IMGT) | AREGSSYFYMAY |
| SEQ ID NO: 64 | VH | QVQLVQSGAEVKKPGSSVKVSCKASGGTFSDYAISWVRQAPGQGL EWMGGIIPIFGDANYAQKFQGRVTITADESTSTAYMELSSLRSED TAVYYCAREGSSYFYMAYWGQGTLVTVSS |
| SEQ ID NO: 65 | DNA VH | CAGGTTCAGCTGGTGCAGTCTGGCGCCGAAGTGAAGAAACCTGGC AGCAGCGTGAAGGTGTCCTGCAAAGCAAGCGGCGGCACCTTCAGC GATTACGCCATCTCTTGGGTCCGACAGGCCCCTGGACAAGGCTTG GAATGGATGGGCGGCATCATCCCCATCTTCGGCGACGCCAATTAC GCCCAGAAATTCCAGGGCAGAGTGACCATCACCGCCGACGAGTCT ACAAGCACCGCCTACATGGAACTGAGCAGCCTGAGAAGCGAGGAC ACCGCCGTGTACTACTGTGCCAGAGAGGGCAGCAGCTACTTCTAC ATGGCCTATTGGGGCCAGGGCACCCTGGTCACAGTTAGCTCT |
| SEQ ID NO: 66 | Heavy Chain | QVQLVQSGAEVKKPGSSVKVSCKASGGTFSDYAISWVRQAPGQGL EWMGGIIPIFGDANYAQKFQGRVTITADESTSTAYMELSSLRSED TAVYYCAREGSSYFYMAYWGQGTLVTVSSASTKGPSVFPLAPSSK STSGGTAALGCLVKDYFPCPVTVSWNSGALTSGVHTFPAVLQSSG LYSLSSVVTVPSSSLGTQTYICNVNHKPSNTKVDKRVEPKSCDKT HTCPPCPAPELLGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSREEM TKNQVSLTCLVKGFYPCDIAVEWESNGQPENNYKTTPPVLDSDGS FFLYSKLTVDKSRWQQGNVFSCSVMHEALHNHYTQKSLSLSPGK |
| SEQ ID NO: 67 | DNA Heavy Chain | CAGGTTCAGCTGGTGCAGTCTGGCGCCGAAGTGAAGAAACCTGGC AGCAGCGTGAAGGTGTCCTGCAAAGCAAGCGGCGGCACCTTCAGC GATTACGCCATCTCTTGGGTCCGACAGGCCCCTGGACAAGGCTTG GAATGGATGGGCGGCATCATCCCCATCTTCGGCGACGCCAATTAC GCCCAGAAATTCCAGGGCAGAGTGACCATCACCGCCGACGAGTCT ACAAGCACCGCCTACATGGAACTGAGCAGCCTGAGAAGCGAGGAC ACCGCCGTGTACTACTGTGCCAGAGAGGGCAGCAGCTACTTCTAC ATGGCCTATTGGGGCCAGGGCACCCTGGTCACAGTTAGCTCTGCT AGCACCAAGGGCCCAAGTGTGTTTCCCCTGGCCCCCAGCAGCAAG TCTACTTCCGGCGGAACTGCTGCCCTGGGTTGCCTGGTGAAGGAC TACTTCCCCTGTCCCGTGACAGTGTCCTGGAACTCTGGGGCTCTG ACTTCCGGCGTGCACACCTTCCCCGCCGTGCTGCAGAGCAGCGGC CTGTACAGCCTGAGCAGCGTGGTGACAGTGCCCTCCAGCTCTCTG GGAACCCAGACCTATATCTGCAACGTGAACCACAAGCCCAGCAAC |

TABLE 2-continued

Examples of Anti-PMEL17 Antibodies of the Present Invention

|  |  |  |
|---|---|---|
|  |  | ACCAAGGTGGACAAGAGAGTGGAGCCCAAGAGCTGCGACAAGACC<br>CACACCTGCCCCCCCTGCCCAGCTCCAGAACTGCTGGGAGGGCCT<br>TCCGTGTTCCTGTTCCCCCCCAAGCCCAAGGACACCCTGATGATC<br>AGCAGGACCCCCGAGGTGACCTGCGTGGTGGTGGACGTGTCCCAC<br>GAGGACCCAGAGGTGAAGTTCAACTGGTACGTGGACGGCGTGGAG<br>GTGCACAACGCCAAGACCAAGCCCAGAGAGGAGCAGTACAACAGC<br>ACCTACAGGGTGGTGTCCGTGCTGACCGTGCTGCACCAGGACTGG<br>CTGAACGGCAAAGAATACAAGTGCAAAGTCTCCAACAAGGCCCTG<br>CCAGCCCCAATCGAAAAGACAATCAGCAAGGCCAAGGGCCAGCCA<br>CGGGAGCCCCAGGTGTACACCCTGCCCCCCAGCCGGGAGGAGATG<br>ACCAAGAACCAGGTGTCCCTGACCTGTCTGGTGAAGGGCTTCTAC<br>CCCTGTGATATCGCCGTGGAGTGGGAGAGCAACGGCCAGCCCGAG<br>AACAACTACAAGACCACCCCCCAGTGCTGGACAGCGACGGCAGC<br>TTCTTCCTGTACAGCAAGCTGACCGTGGACAAGTCCAGGTGGCAG<br>CAGGGCAACGTGTTCAGCTGCAGCGTGATGCACGAGGCCCTGCAC<br>AACCACTACACCCAGAAGTCCCTGAGCCTGAGCCCCGGCAAG |
| SEQ ID NO: 68 | LCDR1<br>(Combined) | SGDNIGSKLAS |
| SEQ ID NO: 69 | LCDR2<br>(Combined) | DDSNRPS |
| SEQ ID NO: 70 | LCDR3<br>(Combined) | AATAGDRWAYV |
| SEQ ID NO: 68 | LCDR1<br>(Kabat) | SGDNIGSKLAS |
| SEQ ID NO: 69 | LCDR2<br>(Kabat) | DDSNRPS |
| SEQ ID NO: 70 | LCDR3<br>(Kabat) | AATAGDRWAYV |
| SEQ ID NO: 71 | LCDR1<br>(Chothia) | DNIGSKL |
| SEQ ID NO: 72 | LCDR2<br>(Chothia) | DDS |
| SEQ ID NO: 73 | LCDR3<br>(Chothia) | TAGDRWAY |
| SEQ ID NO: 74 | LCDR1<br>(IMGT) | NIGSKL |
| SEQ ID NO: 72 | LCDR2<br>(IMGT) | DDS |
| SEQ ID NO: 70 | LCDR3<br>(IMGT) | AATAGDRWAYV |
| SEQ ID NO: 75 | VL | SYELTQPLSVSVALGQTARITCSGDNIGSKLASWYQQKPGQAPVL<br>VIYDDSNRPSGIPERFSGSNSGNTATLTISRAQAGDEADYYCAAT<br>AGDRWAYVFGGGTKLTVL |
| SEQ ID NO: 76 | DNA VL | AGCTATGAGCTGACACAGCCTCTGTCCGTGTCTGTGGCTCTGGGA<br>CAGACCGCCAGAATCACCTGTAGCGGCGACAACATCGGCAGCAAG<br>CTGGCCTCTTGGTATCAGCAGAAGCCTGGACAGGCCCCTGTGCTG<br>GTCATCTACGACGACAGCAATAGACCCAGCGGCATCCCCGAGAGA<br>TTCAGCGGCAGCAATAGCGGCAATACCGCCACACTGACCATCAGC<br>AGAGCACAGGCTGGCGACGAGGCCGATTACTATTGTGCTGCCACA<br>GCCGGCGACAGATGGGCCTATGTTTTGGCGGCGGAACAAAGCTG<br>ACCGTGCTG |
| SEQ ID NO: 77 | Light Chain | SYELTQPLSVSVALGQTARITCSGDNIGSKLASWYQQKPGQAPVL<br>VIYDDSNRPSGIPERFSGSNSGNTATLTISRAQAGDEADYYCAAT<br>AGDRWAYVFGGGTKLTVLGQPKAAPSVTLFPPSSEELQANKATLV<br>CLISDFYPGAVTVAWKADSSPVKAGVETTTPSKQSNNKYAASSYL<br>SLTPEQWKSHRSYSCQVTHEGSTVEKTVAPTECS |
| SEQ ID NO: 78 | DNA Light<br>Chain | AGCTATGAGCTGACACAGCCTCTGTCCGTGTCTGTGGCTCTGGGA<br>CAGACCGCCAGAATCACCTGTAGCGGCGACAACATCGGCAGCAAG<br>CTGGCCTCTTGGTATCAGCAGAAGCCTGGACAGGCCCCTGTGCTG<br>GTCATCTACGACGACAGCAATAGACCCAGCGGCATCCCCGAGAGA<br>TTCAGCGGCAGCAATAGCGGCAATACCGCCACACTGACCATCAGC<br>AGAGCACAGGCTGGCGACGAGGCCGATTACTATTGTGCTGCCACA |

TABLE 2-continued

Examples of Anti-PMEL17 Antibodies of the Present Invention

|  |  | GCCGGCGACAGATGGGCCTATGTTTTTGGCGGCGGAACAAAGCTG<br>ACCGTGCTGGGACAGCCTAAGGCCGCTCCCTCCGTGACCCTGTTC<br>CCCCCCAGCTCCGAGGAACTGCAGGCCAACAAGGCCACCCTGGTG<br>TGCCTGATCAGCGACTTCTACCCTGGCGCCGTGACCGTGGCCTGG<br>AAGGCCGACAGCAGCCCCGTGAAGGCCGGCGTGGAGACAACCACC<br>CCCAGCAAGCAGAGCAACAACAAGTACGCCGCCAGCAGCTACCTG<br>AGCCTGACCCCCGAGCAGTGGAAGAGCCACAGAAGCTACAGCTGC<br>CAGGTCACCCACGAGGGCAGCACCGTGGAGAAAACCGTGGCCCCC<br>ACCGAGTGCAGC |
|---|---|---|
| MOR024354<br>E152C_S375C |  |  |
| SEQ ID NO: 79 | HCDR1<br>(Combined) | GFTFSSFGMS |
| SEQ ID NO: 80 | HCDR2<br>(Combined) | AISYSGSDTYYADSVKG |
| SEQ ID NO: 81 | HCDR3<br>(Combined) | DVGVMDY |
| SEQ ID NO: 82 | HCDR1<br>(Kabat) | SFGMS |
| SEQ ID NO: 80 | HCDR2<br>(Kabat) | AISYSGSDTYYADSVKG |
| SEQ ID NO: 81 | HCDR3<br>(Kabat) | DVGVMDY |
| SEQ ID NO: 83 | HCDR1<br>(Chothia) | GFTFSSF |
| SEQ ID NO: 84 | HCDR2<br>(Chothia) | SYSGSD |
| SEQ ID NO: 81 | HCDR3<br>(Chothia) | DVGVMDY |
| SEQ ID NO: 85 | HCDR1<br>(IMGT) | GFTFSSFG |
| SEQ ID NO: 86 | HCDR2<br>(IMGT) | ISYSGSDT |
| SEQ ID NO: 87 | HCDR3<br>(IMGT) | ARDVGVMDY |
| SEQ ID NO: 88 | VH | QVQLLESGGGLVQPGGSLRLSCAASGFTFSSFGMSWVRQAPGKGL<br>EWVSAISYSGSDTYYADSVKGRFTISRDNSKNTLYLQMNSLRAED<br>TAVYYCARDVGVMDYWGQGTLVTVSS |
| SEQ ID NO: 89 | DNA VH | CAGGTTCAGCTGCTGGAATCTGGCGGAGGACTGGTTCAACCTGGC<br>GGCTCTCTGAGACTGTCTTGTGCCGCCAGCGGCTTCACCTTCAGC<br>AGCTTTGGCATGAGCTGGGTCCGACAGGCCCCTGGCAAAGGACTT<br>GAATGGGTGTCCGCCATCAGCTACAGCGGCAGCGATACCTACTAC<br>GCCGACAGCGTGAAGGGCAGATTCACCATCTCCAGAGACAACAGC<br>AAGAACACCCTGTACCTGCAGATGAACAGCCTGAGAGCCGAGGAC<br>ACCGCCGTGTACTACTGTGCCAGAGATGTGGGCGTGATGGACTAT<br>TGGGGCCAGGGCACACTGGTCACCGTTAGCTCT |
| SEQ ID NO: 90 | Heavy<br>Chain | QVQLLESGGGLVQPGGSLRLSCAASGFTFSSFGMSWVRQAPGKGL<br>EWVSAISYSGSDTYYADSVKGRFTISRDNSKNTLYLQMNSLRAED<br>TAVYYCARDVGVMDYWGQGTLVTVSSASTKGPSVFPLAPSSKSTS<br>GGTAALGCLVKDYFPCPVTVSWNSGALTSGVHTFPAVLQSSGLYS<br>LSSVVTVPSSSLGTQTYICNVNHKPSNTKVDKRVEPKSCDKTHTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDWLNG<br>KEYKCKVSNKALPAPIEKTISKAKGQPREPQVYTLPPSREEMTKN<br>QVSLTCLVKGFYPCDIAVEWESNGQPENNYKTTPPVLDSDGSFFL<br>YSKLTVDKSRWQQGNVFSCSVMHEALHNHYTQKSLSLSPGK |
| SEQ ID NO: 91 | DNA Heavy<br>Chain | CAGGTTCAGCTGCTGGAATCTGGCGGAGGACTGGTTCAACCTGGC<br>GGCTCTCTGAGACTGTCTTGTGCCGCCAGCGGCTTCACCTTCAGC<br>AGCTTTGGCATGAGCTGGGTCCGACAGGCCCCTGGCAAAGGACTT<br>GAATGGGTGTCCGCCATCAGCTACAGCGGCAGCGATACCTACTAC<br>GCCGACAGCGTGAAGGGCAGATTCACCATCTCCAGAGACAACAGC |

TABLE 2-continued

Examples of Anti-PMEL17 Antibodies of the Present Invention

|  |  |  |
|---|---|---|
|  |  | AAGAACACCCTGTACCTGCAGATGAACAGCCTGAGAGCCGAGGAC<br>ACCGCCGTGTACTACTGTGCCAGAGATGTGGGCGTGATGGACTAT<br>TGGGGCCAGGGCACACTGGTCACCGTTAGCTCTGCTAGCACCAAG<br>GGCCCAAGTGTGTTTCCCCTGGCCCCAGCAGCAAGTCTACTTCC<br>GGCGGAACTGCTGCCCTGGGTTGCCTGGTGAAGGACTACTTCCCC<br>TGTCCCGTGACAGTGTCCTGGAACTCTGGGGCTCTGACTTCCGGC<br>GTGCACACCTTCCCCGCCGTGCTGCAGAGCAGCGGCCTGTACAGC<br>CTGAGCAGCGTGGTGACAGTGCCCTCCAGCTCTCTGGGAACCCAG<br>ACCTATATCTGCAACGTGAACCACAAGCCCAGCAACACCAAGGTG<br>GACAAGAGAGTGGAGCCCAAGAGCTGCGACAAGACCCACACCTGC<br>CCCCCCTGCCCAGCTCCAGAACTGCTGGGAGGGCCTTCCGTGTTC<br>CTGTTCCCCCCCAAGCCCAAGGACACCCTGATGATCAGCAGGACC<br>CCCGAGGTGACCTGCGTGGTGGTGGACGTGTCCCACGAGGACCCA<br>GAGGTGAAGTTCAACTGGTACGTGGACGGCGTGGAGGTGCACAAC<br>GCCAAGACCAAGCCCAGAGAGGAGCAGTACAACAGCACCTACAGG<br>GTGGTGTCCGTGCTGACCGTGCTGCACCAGGACTGGCTGAACGGC<br>AAAGAATACAAGTGCAAAGTCTCCAACAAGGCCCTGCCAGCCCCA<br>ATCGAAAAGACAATCAGCAAGGCCAAGGGCCAGCCACGGGAGCCC<br>CAGGTGTACACCCTGCCCCCCAGCCGGGAGGAGATGACCAAGAAC<br>CAGGTGTCCCTGACCTGTCTGGTGAAGGGCTTCTACCCCTGTGAT<br>ATCGCCGTGGAGTGGGAGAGCAACGGCCAGCCCGAGAACAACTAC<br>AAGACCACCCCCCCAGTGCTGGACAGCGACGGCAGCTTCTTCCTG<br>TACAGCAAGCTGACCGTGGACAAGTCCAGGTGGCAGCAGGGCAAC<br>GTGTTCAGCTGCAGCGTGATGCACGAGGCCCTGCACAACCACTAC<br>ACCCAGAAGTCCCTGAGCCTGAGCCCCGGCAAG |
| SEQ ID NO: 92 | LCDR1<br>(Combined) | SGDNLGTYYAH |
| SEQ ID NO: 93 | LCDR2<br>(Combined) | SQSHRPS |
| SEQ ID NO: 94 | LCDR3<br>(Combined) | GAWDAPSPELV |
| SEQ ID NO: 92 | LCDR1<br>(Kabat) | SGDNLGTYYAH |
| SEQ ID NO: 93 | LCDR2<br>(Kabat) | SQSHRPS |
| SEQ ID NO: 94 | LCDR3<br>(Kabat) | GAWDAPSPELV |
| SEQ ID NO: 95 | LCDR1<br>(Chothia) | DNLGTYY |
| SEQ ID NO: 96 | LCDR2<br>(Chothia) | SQS |
| SEQ ID NO: 97 | LCDR3<br>(Chothia) | WDAPSPEL |
| SEQ ID NO: 98 | LCDR1<br>(IMGT) | NLGTYY |
| SEQ ID NO: 96 | LCDR2<br>(IMGT) | SQS |
| SEQ ID NO: 94 | LCDR3<br>(IMGT) | GAWDAPSPELV |
| SEQ ID NO: 99 | VL | SYELTQPLSVSVALGQTARITCSGDNLGTYYAHWYQQKPGQAPVL<br>VIYSQSHRPSGIPERFSGSNSGNTATLTISRAQAGDEADYYCGAW<br>DAPSPELVFGGGTKLTVL |
| SEQ ID NO: 100 | DNA VL | AGCTATGAGCTGACACAGCCTCTGTCCGTGTCTGTGGCTCTGGGA<br>CAGACCGCCAGAATCACCTGTAGCGGCGATAACCTGGGCACCTAC<br>TACGCCCACTGGTATCAGCAGAAGCCTGGACAGGCTCCCGTGCTG<br>GTCATCTACAGCCAGTCTCACAGACCCAGCGGCATCCCCGAGAGA<br>TTCAGCGGCAGCAATAGCGGCAATACCGCCACACTGACCATCAGC<br>AGAGCACAGGCTGGCGACGAGGCCGATTACTATTGTGGCGCTTGG<br>GACGCCCCATCTCCTGAGCTTGTTTTTGGCGGAGGCACCAAGCTG<br>ACAGTGCTG |
| SEQ ID NO: 101 | Light Chain | SYELTQPLSVSVALGQTARITCSGDNLGTYYAHWYQQKPGQAPVL<br>VIYSQSHRPSGIPERFSGSNSGNTATLTISRAQAGDEADYYCGAW<br>DAPSPELVFGGGTKLTVLGQPKAAPSVTLFPPSSEELQANKATLV |

TABLE 2-continued

Examples of Anti-PMEL17 Antibodies of the Present Invention

| | | |
|---|---|---|
| | | CLISDFYPGAVTVAWKADSSPVKAGVETTTPSKQSNNKYAASSYL SLTPEQWKSHRSYSCQVTHEGSTVEKTVAPTECS |
| SEQ ID NO: 102 | DNA Light Chain | AGCTATGAGCTGACACAGCCTCTGTCCGTGTCTGTGGCTCTGGGA CAGACCGCCAGAATCACCTGTAGCGGCGATAACCTGGGCACCTAC TACGCCCACTGGTATCAGCAGAAGCCTGGACAGGCTCCCGTGCTG GTCATCTACAGCCAGTCTCACAGACCCAGCGGCATCCCCGAGAGA TTCAGCGGCAGCAATAGCGGCAATACCGCCACACTGACCATCAGC AGAGCACAGGCTGGCGACGAGGCCGATTACTATTGTGGCGCTTGG GACGCCCCATCTCCTGAGCTTGTTTTTGGCGGAGGCACCAAGCTG ACAGTGCTGGGACAGCCTAAGGCCGCTCCCTCCGTGACCCTGTTC CCCCCCAGCTCCGAGGAACTGCAGGCCAACAAGGCCACCCTGGTG TGCCTGATCAGCGACTTCTACCCTGGCGCCGTGACCGTGGCCTGG AAGGCCGACAGCAGCCCCGTGAAGGCCGGCGTGGAGACAACCACC CCCAGCAAGCAGAGCAACAACAAGTACGCCGCCAGCAGCTACCTG AGCCTGACCCCCGAGCAGTGGAAGAGCCACAGAAGCTACAGCTGC CAGGTCACCCACGAGGGCAGCACCGTGGAGAAAACCGTGGCCCCC ACCGAGTGCAGC |

Y010341_E152C_S375C

| | | |
|---|---|---|
| SEQ ID NO: 103 | HCDR1 (Combined) | GFTFSSYAMS |
| SEQ ID NO: 104 | HCDR2 (Combined) | AISGSGGSTYYADSVKG |
| SEQ ID NO: 105 | HCDR3 (Combined) | AFRLYWLDV |
| SEQ ID NO: 106 | HCDR1 (Kabat) | SYAMS |
| SEQ ID NO: 104 | HCDR2 (Kabat) | AISGSGGSTYYADSVKG |
| SEQ ID NO: 105 | HCDR3 (Kabat) | AFRLYWLDV |
| SEQ ID NO: 107 | HCDR1 (Chothia) | GFTFSSY |
| SEQ ID NO: 108 | HCDR2 (Chothia) | SGSGGS |
| SEQ ID NO: 105 | HCDR3 (Chothia) | AFRLYWLDV |
| SEQ ID NO: 109 | HCDR1 (IMGT) | GFTFSSYA |
| SEQ ID NO: 110 | HCDR2 (IMGT) | ISGSGGST |
| SEQ ID NO: 111 | HCDR3 (IMGT) | ARAFRLYWLDV |
| SEQ ID NO: 112 | VH | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCARAFRLYWLDVWGQGTLVTVSS |
| SEQ ID NO: 113 | DNA VH | GAAGTTCAGCTGCTGGAATCTGGCGGAGGACTGGTTCAACCTGGC GGCTCTCTGAGACTGTCTTGTGCCGCCAGCGGCTTCACCTTTAGC AGCTACGCCATGAGCTGGGTCCGACAGGCTCCTGGCAAAGGCCTT GAATGGGTGTCCGCCATCTCTGGCTCTGGCGGCAGCACATATTAC GCCGACTCTGTGAAGGGCAGATTCACCATCAGCCGGGACAACAGC AAGAACACCCTGTACCTGCAGATGAACAGCCTGAGAGCCGAGGAC ACCGCCGTGTACTATTGTGCCAGAGCCTTCCGGCTGTACTGGCTG GATGTTTGGGGACAGGGCACCCTGGTCACAGTGTCATCT |
| SEQ ID NO: 114 | Heavy Chain | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCARAFRLYWLDVWGQGTLVTVSSASTKGPSVFPLAPSSKS TSGGTAALGCLVKDYFPCPVTVSWNSGALTSGVHTFPAVLQSSGL YSLSSVVTVPSSSLGTQTYICNVNHKPSNTKVDKRVEPKSCDKTH TCPPCPAPELLGGPSVFLFPPKPKDTLMISRTPEVTCVVVDVSHE DPEVKFNWYVDGVEVHNAKTKPREEQYNSTYRVVSVLTVLHQDWL NGKEYKCKVSNKALPAPIEKTISKAKGQPREPQVYTLPPSREEMT |

TABLE 2-continued

Examples of Anti-PMEL17 Antibodies of the Present Invention

| | | |
|---|---|---|
| | | KNQVSLTCLVKGFYPCDIAVEWESNGQPENNYKTTPPVLDSDGSF<br>FLYSKLTVDKSRWQQGNVFSCSVMHEALHNHYTQKSLSLSPGK |
| SEQ ID NO: 115 | DNA Heavy<br>Chain | GAAGTTCAGCTGCTGGAATCTGGCGGAGGACTGGTTCAACCTGGC<br>GGCTCTCTGAGACTGTCTTGTGCCGCCAGCGGCTTCACCTTTAGC<br>AGCTACGCCATGAGCTGGGTCCGACAGGCTCCTGGCAAAGGCCTT<br>GAATGGGTGTCCGCCATCTCTGGCTCTGGCGGCAGCACATATTAC<br>GCCGACTCTGTGAAGGGCAGATTCACCATCAGCCGGGACAACAGC<br>AAGAACACCCTGTACCTGCAGATGAACAGCCTGAGAGCCGAGGAC<br>ACCGCCGTGTACTATTGTGCCAGAGCCTTCCGGCTGTACTGGCTG<br>GATGTTTGGGGACAGGGCACCCTGGTCACAGTGTCATCTGCTAGC<br>ACCAAGGGCCCAAGTGTGTTTCCCCTGGCCCCCAGCAGCAAGTCT<br>ACTTCCGGCGGAACTGCTGCCCTGGGTTGCCTGGTGAAGGACTAC<br>TTCCCCGTCCCGTGACAGTGTCCTGGAACTCTGGGGCTCTGACT<br>TCCGGCGTGCACACCTTCCCCGCCGTGCTGCAGAGCAGCGGCCTG<br>TACAGCCTGAGCAGCGTGGTGACAGTGCCCTCCAGCTCTCTGGGA<br>ACCCAGACCTATATCTGCAACGTGAACCACAAGCCCAGCAACACC<br>AAGGTGGACAAGAGAGTGGAGCCCAAGAGCTGCGACAAGACCCAC<br>ACCTGCCCCCCCTGCCCAGCTCCAGAACTGCTGGGAGGGCCTTCC<br>GTGTTCCTGTTCCCCCCCAAGCCCAAGGACACCCTGATGATCAGC<br>AGGACCCCCGAGGTGACCTGCGTGGTGGTGGACGTGTCCCACGAG<br>GACCCAGAGGTGAAGTTCAACTGGTACGTGGACGGCGTGGAGGTG<br>CACAACGCCAAGACCAAGCCCAGAGAGGAGCAGTACAACAGCACC<br>TACAGGGTGGTGTCCGTGCTGACCGTGCTGCACCAGGACTGGCTG<br>AACGGCAAAGAATACAAGTGCAAAGTCTCCAACAAGGCCCTGCCA<br>GCCCCAATCGAAAAGACAATCAGCAAGGCCAAGGGCCAGCCACGG<br>GAGCCCCAGGTGTACACCCTGCCCCCCAGCCGGGAGGAGATGACC<br>AAGAACCAGGTGTCCCTGACCTGTCTGGTGAAGGGCTTCTACCCC<br>TGTGATATCGCCGTGGAGTGGGAGAGCAACGGCCAGCCCGAGAAC<br>AACTACAAGACCACCCCCCCAGTGCTGGACAGCGACGGCAGCTTC<br>TTCCTGTACAGCAAGCTGACCGTGGACAAGTCCAGGTGGCAGCAG<br>GGCAACGTGTTCAGCTGCAGCGTGATGCACGAGGCCCTGCACAAC<br>CACTACACCCAGAAGTCCCTGAGCCTGAGCCCCGGCAAG |
| SEQ ID NO: 116 | LCDR1<br>(Combined) | RASQSISSYLN |
| SEQ ID NO: 47 | LCDR2<br>(Combined) | AASSLQS |
| SEQ ID NO: 117 | LCDR3<br>(Combined) | QQVYSAPVT |
| SEQ ID NO: 116 | LCDR1<br>(Kabat) | RASQSISSYLN |
| SEQ ID NO: 47 | LCDR2<br>(Kabat) | AASSLQS |
| SEQ ID NO: 117 | LCDR3<br>(Kabat) | QQVYSAPVT |
| SEQ ID NO: 49 | LCDR1<br>(Chothia) | SQSISSY |
| SEQ ID NO: 50 | LCDR2<br>(Chothia) | AAS |
| SEQ ID NO: 118 | LCDR3<br>(Chothia) | VYSAPV |
| SEQ ID NO: 52 | LCDR1<br>(IMGT) | QSISSY |
| SEQ ID NO: 50 | LCDR2<br>(IMGT) | AAS |
| SEQ ID NO: 117 | LCDR3<br>(IMGT) | QQVYSAPVT |
| SEQ ID NO: 119 | VL | DIQMTQSPSSLSASVGDRVTITCRASQSISSYLNWYQQKPGKAPK<br>LLIYAASSLQSGVPSRFSGSGSGTDFTLTISSLQPEDFATYYCQQ<br>VYSAPVTFGQGTKVEIK |
| SEQ ID NO: 120 | DNA VL | GACATCCAGATGACACAGAGCCCAGCAGCCTGTCTGCCAGCGTG<br>GGAGACAGAGTGACCATCACCTGTAGAGCCAGCCAGAGCATCAGC<br>AGCTACCTGAACTGGTATCAGCAGAAGCCCGGCAAGGCCCCTAAA<br>CTGCTGATCTATGCCGCCAGCTCTCTGCAGTCTGGCGTGCCAAGC |

TABLE 2-continued

Examples of Anti-PMEL17 Antibodies of the Present Invention

| | | |
|---|---|---|
| | | AGATTTTCTGGCAGCGGCTCTGGCACCGACTTCACCCTGACCATA<br>TCTAGCCTGCAGCCAGAGGACTTCGCCACCTACTACTGCCAGCAG<br>GTCTACAGCGCCCCTGTGACATTTGGCCAGGGCACCAAGGTGGAA<br>ATCAAG |
| SEQ ID NO: 121 | Light Chain | DIQMTQSPSSLSASVGDRVTITCRASQSISSYLNWYQQKPGKAPK<br>LLIYAASSLQSGVPSRFSGSGSGTDFTLTISSLQPEDFATYYCQQ<br>VYSAPVTFGQGTKVEIKRTVAAPSVFIFPPSDEQLKSGTASVVCL<br>LNNFYPREAKVQWKVDNALQSGNSQESVTEQDSKDSTYSLSSTLT<br>LSKADYEKHKVYACEVTHQGLSSPVTKSFNRGEC |
| SEQ ID NO: 122 | DNA Light<br>Chain | GACATCCAGATGACACAGAGCCCTAGCAGCCTGTCTGCCAGCGTG<br>GGAGACAGAGTGACCATCACCTGTAGAGCCAGCCAGAGCATCAGC<br>AGCTACCTGAACTGGTATCAGCAGAAGCCCGGCAAGGCCCCTAAA<br>CTGCTGATCTATGCCGCCAGCTCTCTGCAGTCTGGCGTGCCAAGC<br>AGATTTTCTGGCAGCGGCTCTGGCACCGACTTCACCCTGACCATA<br>TCTAGCCTGCAGCCAGAGGACTTCGCCACCTACTACTGCCAGCAG<br>GTCTACAGCGCCCCTGTGACATTTGGCCAGGGCACCAAGGTGGAA<br>ATCAAGCGTACGGTGGCCGCTCCCAGCGTGTTCATCTTCCCCCCC<br>AGCGACGAGCAGCTGAAGAGTGGCACCGCCAGCGTGGTGTGCCTG<br>CTGAACAACTTCTACCCCGGGAGGCCAAGGTGCAGTGGAAGGTG<br>GACAACGCCCTGCAGAGCGGCAACAGCCAGGAGAGCGTCACCGAG<br>CAGGACAGCAAGGACTCCACCTACAGCCTGAGCAGCACCCTGACC<br>CTGAGCAAGGCCGACTACGAGAAGCATAAGGTGTACGCCTGCGAG<br>GTGACCCACCAGGGCCTGTCCAGCCCCGTGACCAAGAGCTTCAAC<br>AGGGGCGAGTGC |

Y010355 E152C_S375C

| | | |
|---|---|---|
| SEQ ID NO: 123 | HCDR1<br>(Combined) | GFTFSNYWIS |
| SEQ ID NO: 124 | HCDR2<br>(Combined) | RIKSKTYGGTTDYAEPVKG |
| SEQ ID NO: 125 | HCDR3<br>(Combined) | TSRRSYAFDY |
| SEQ ID NO: 126 | HCDR1<br>(Kabat) | NYWIS |
| SEQ ID NO: 124 | HCDR2<br>(Kabat) | RIKSKTYGGTTDYAEPVKG |
| SEQ ID NO: 125 | HCDR3<br>(Kabat) | TSRRSYAFDY |
| SEQ ID NO: 127 | HCDR1<br>(Chothia) | GFTFSNY |
| SEQ ID NO: 128 | HCDR2<br>(Chothia) | KSKTYGGT |
| SEQ ID NO: 125 | HCDR3<br>(Chothia) | TSRRSYAFDY |
| SEQ ID NO: 129 | HCDR1<br>(IMGT) | GFTFSNYW |
| SEQ ID NO: 130 | HCDR2<br>(IMGT) | IKSKTYGGTT |
| SEQ ID NO: 131 | HCDR3<br>(IMGT) | ARTSRRSYAFDY |
| SEQ ID NO: 132 | VH | EVQLVESGGGLVKPGGSLRLSCAASGFTFSNYWISWVRQAPGKGL<br>EWVGRIKSKTYGGTTDYAEPVKGRFTISRDDSKNTLYLQMNSLKT<br>EDTAVYYCARTSRRSYAFDYWGQGTLVTVSS |
| SEQ ID NO: 133 | DNA VH | GAAGTGCAGCTGGTGGAATCTGGCGGCGGACTTGTGAAACCTGGC<br>GGCTCTCTGAGACTGAGCTGTGCCGCTTCCGGCTTCACCTTCAGC<br>AACTACTGGATCAGCTGGGTCCGACAGGCCCCTGGCAAAGGACTT<br>GAGTGGGTCGGACGGATCAAGAGCAAGACCTACGGCGGCACCACC<br>GATTATGCCGAGCCTGTGAAGGGCAGATTCACCATCAGCCGGGAC<br>GACAGCAAGAACACCCTGTACCTGCAGATGAACAGCCTGAAAACC<br>GAGGACACCGCCGTGTACTACTGCGCCAGAACCAGCAGAAGAAGC<br>TACGCCTTCGACTACTGGGGCCAGGGCACACTGGTTACCGTTAGC<br>TCT |

TABLE 2-continued

Examples of Anti-PMEL17 Antibodies of the Present Invention

| SEQ ID NO: 134 | Heavy Chain | EVQLVESGGGLVKPGGSLRLSCAASGFTFSNYWISWVRQAPGKGL EWVGRIKSKTYGGTTDYAEPVKGRFTISRDDSKNTLYLQMNSLKT EDTAVYYCARTSRRSYAFDYWGQGTLVTVSSASTKGPSVFPLAPS SKSTSGGTAALGCLVKDYFPCPVTVSWNSGALTSGVHTFPAVLQS SGLYSLSSVVTVPSSSLGTQTYICNVNHKPSNTKVDKRVEPKSCD KTHTCPPCPAPELLGGPSVFLFPPKPKDTLMISRTPEVTCVVVDV SHEDPEVKFNWYVDGVEVHNAKTKPREEQYNSTYRVVSVLTVLHQ DWLNGKEYKCKVSNKALPAPIEKTISKAKGQPREPQVYTLPPSRE EMTKNQVSLTCLVKGFYPCDIAVEWESNGQPENNYKTTPPVLDSD GSFFLYSKLTVDKSRWQQGNVFSCSVMHEALHNHYTQKSLSLSPG K |
|---|---|---|
| SEQ ID NO: 135 | DNA Heavy Chain | GAAGTGCAGCTGGTGGAATCTGGCGGCGGACTTGTGAAACCTGGC GGCTCTCTGAGACTGAGCTGTGCCGCTTCCGGCTTCACCTTCAGC AACTACTGGATCAGCTGGGTCCGACAGGCCCCTGGCAAAGGACTT GAGTGGGTCGGACGGATCAAGAGCAAGACCTACGGCGGCACCACC GATTATGCCGAGCCTGTGAAGGGCAGATTCACCATCAGCCGGGAC GACAGCAAGAACACCCTGTACCTGCAGATGAACAGCCTGAAAACC GAGGACACCGCCGTGTACTACTGCGCCAGAACCAGCAGAAGAAGC TACGCCTTCGACTACTGGGGCCAGGGCACACTGGTTACCGTTAGC TCTGCTAGCACCAAGGGCCCAAGTGTGTTTCCCCTGGCCCCCAGC AGCAAGTCTACTTCCGGCGGAACTGCTGCCCTGGGTTGCCTGGTG AAGGACTACTTCCCCTGTCCCGTGACAGTGTCCTGGAACTCTGGG GCTCTGACTTCCGGCGTGCACACCTTCCCCGCCGTGCTGCAGAGC AGCGGCCTGTACAGCCTGAGCAGCGTGGTGACAGTGCCCTCCAGC TCTCTGGGAACCCAGACCTATATCTGCAACGTGAACCACAAGCCC AGCAACACCAAGGTGGACAAGAGAGTGGAGCCCAAGAGCTGCGAC AAGACCCACACCTGCCCCCCCTGCCCAGCTCCAGAACTGCTGGGA GGGCCTTCCGTGTTCCTGTTCCCCCCCAAGCCCAAGGACACCCTG ATGATCAGCAGGACCCCCGAGGTGACCTGCGTGGTGGTGGACGTG TCCCACGAGGACCCAGAGGTGAAGTTCAACTGGTACGTGGACGGC GTGGAGGTGCACAACGCCAAGACCAAGCCCAGAGAGGAGCAGTAC AACAGCACCTACAGGGTGGTGTCCGTGCTGACCGTGCTGCACCAG GACTGGCTGAACGGCAAAGAATACAAGTGCAAAGTCTCCAACAAG GCCCTGCCAGCCCCAATCGAAAAGACAATCAGCAAGGCCAAGGGC CAGCCACGGGAGCCCCAGGTGTACACCCTGCCCCCCAGCCGGGAG GAGATGACCAAGAACCAGGTGTCCCTGACCTGTCTGGTGAAGGGC TTCTACCCCTGTGATATCGCCGTGGAGTGGGAGAGCAACGGCCAG CCCGAGAACAACTACAAGACCACCCCCCCAGTGCTGGACAGCGAT GGCAGCTTCTTCCTGTACAGCAAGCTGACCGTGGACAAGTCCAGG TGGCAGCAGGGCAACGTGTTCAGCTGCAGCGTGATGCACGAGGCC CTGCACAACCACTACACCCAGAAGTCCCTGAGCCTGAGCCCCGGC AAG |
| SEQ ID NO: 136 | LCDR1 (Combined) | RASQSISSWLA |
| SEQ ID NO: 137 | LCDR2 (Combined) | DASSLES |
| SEQ ID NO: 138 | LCDR3 (Combined) | QQITRYPVT |
| SEQ ID NO: 136 | LCDR1 (Kabat) | RASQSISSWLA |
| SEQ ID NO: 137 | LCDR2 (Kabat) | DASSLES |
| SEQ ID NO: 138 | LCDR3 (Kabat) | QQITRYPVT |
| SEQ ID NO: 139 | LCDR1 (Chothia) | SQSISSW |
| SEQ ID NO: 140 | LCDR2 (Chothia) | DAS |
| SEQ ID NO: 141 | LCDR3 (Chothia) | ITRYPV |
| SEQ ID NO: 142 | LCDR1 (IMGT) | QSISSW |
| SEQ ID NO: 140 | LCDR2 (IMGT) | DAS |

TABLE 2-continued

Examples of Anti-PMEL17 Antibodies of the Present Invention

| SEQ ID NO: 138 | LCDR3 (IMGT) | QQITRYPVT |
|---|---|---|
| SEQ ID NO: 143 | VL | DIQMTQSPSTLSASVGDRVTITCRASQSISSWLAWYQQKPGKAPK LLIYDASSLESGVPSRFSGSGSGTEFTLTISSLQPEDFATYYCQQ ITRYPVTFGQGTKVEIK |
| SEQ ID NO: 144 | DNA VL | GACATCCAGATGACACAGAGCCCCAGCACACTGTCTGCCAGCGTG GGAGACAGAGTGACCATCACCTGTAGAGCCAGCCAGAGCATCTCC TCTTGGCTGGCCTGGTATCAGCAGAAGCCTGGCAAGGCCCCTAAG CTGCTGATCTACGATGCCAGCAGCCTGGAAAGCGGCGTGCCAAGC AGATTTTCTGGCAGCGGCTCTGGCACCGAGTTCACCCTGACCATA TCTAGCCTGCAGCCAGAGGACTTCGCCACCTACTACTGCCAGCAG ATCACAAGATACCCCGTGACCTTTGGCCAGGGCACCAAGGTGGAA ATCAAG |
| SEQ ID NO: 145 | Light Chain | DIQMTQSPSTLSASVGDRVTITCRASQSISSWLAWYQQKPGKAPK LLIYDASSLESGVPSRFSGSGSGTEFTLTISSLQPEDFATYYCQQ ITRYPVTFGQGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| SEQ ID NO: 146 | DNA Light Chain | GACATCCAGATGACACAGAGCCCCAGCACACTGTCTGCCAGCGTG GGAGACAGAGTGACCATCACCTGTAGAGCCAGCCAGAGCATCTCC TCTTGGCTGGCCTGGTATCAGCAGAAGCCTGGCAAGGCCCCTAAG CTGCTGATCTACGATGCCAGCAGCCTGGAAAGCGGCGTGCCAAGC AGATTTTCTGGCAGCGGCTCTGGCACCGAGTTCACCCTGACCATA TCTAGCCTGCAGCCAGAGGACTTCGCCACCTACTACTGCCAGCAG ATCACAAGATACCCCGTGACCTTTGGCCAGGGCACCAAGGTGGAA ATCAAGCGTACGGTGGCCGCTCCCAGCGTGTTCATCTTCCCCCCC AGCGACGAGCAGCTGAAGAGTGGCACCGCCAGCGTGGTGTGCCTG CTGAACAACTTCTACCCCGGGAGGCCAAGGTGCAGTGGAAGGTG GACAACGCCCTGCAGAGCGGCAACAGCCAGGAGAGCGTCACCGAG CAGGACAGCAAGGACTCCACCTACAGCCTGAGCAGCACCCTGACC CTGAGCAAGGCCGACTACGAGAAGCATAAGGTGTACGCCTGCGAG GTGACCCACCAGGGCCTGTCCAGCCCCGTGACCAAGAGCTTCAAC AGGGGCGAGTGC |

Y010356_E152C_S375C

| SEQ ID NO: 123 | HCDR1 (Combined) | GFTFSNYWIS |
|---|---|---|
| SEQ ID NO: 124 | HCDR2 (Combined) | RIKSKTYGGTTDYAEPVKG |
| SEQ ID NO: 147 | HCDR3 (Combined) | VSGYYSHSGGFDV |
| SEQ ID NO: 126 | HCDR1 (Kabat) | NYWIS |
| SEQ ID NO: 124 | HCDR2 (Kabat) | RIKSKTYGGTTDYAEPVKG |
| SEQ ID NO: 147 | HCDR3 (Kabat) | VSGYYSHSGGFDV |
| SEQ ID NO: 127 | HCDR1 (Chothia) | GFTFSNY |
| SEQ ID NO: 128 | HCDR2 (Chothia) | KSKTYGGT |
| SEQ ID NO: 147 | HCDR3 (Chothia) | VSGYYSHSGGFDV |
| SEQ ID NO: 129 | HCDR1 (IMGT) | GFTFSNYW |
| SEQ ID NO: 130 | HCDR2 (IMGT) | IKSKTYGGTT |
| SEQ ID NO: 148 | HCDR3 (IMGT) | ARVSGYYSHSGGFDV |

TABLE 2-continued

Examples of Anti-PMEL17 Antibodies of the Present Invention

| SEQ ID NO: 149 | VH | EVQLVESGGGLVKPGGSLRLSCAASGFTFSNYWISWVRQAPGKGL
EWVGRIKSKTYGGTTDYAEPVKGRFTISRDDSKNTLYLQMNSLKT
EDTAVYYCARVSGYYSHSGGFDVWGQGTLVTVSS |
|---|---|---|
| SEQ ID NO: 150 | DNA VH | GAAGTGCAGCTGGTGGAATCTGGCGGCGGACTTGTGAAACCTGGC
GGCTCTCTGAGACTGAGCTGTGCCGCTTCCGGCTTCACCTTCAGC
AACTACTGGATCAGCTGGGTCCGACAGGCCCCTGGCAAAGGACTT
GAGTGGGTCGGACGGATCAAGAGCAAGACCTACGGCGGCACCACC
GATTATGCCGAGCCTGTGAAGGGCAGATTCACCATCAGCCGGGAC
GACAGCAAGAACACCCTGTACCTGCAGATGAACAGCCTGAAAACC
GAGGACACCGCCGTGTACTACTGCGCCAGAGTGTCTGGCTACTAC
TCTCACAGCGGCGGCTTTGATGTGTGGGGCCAGGGAACACTGGTC
ACCGTTAGTTCT |
| SEQ ID NO: 151 | Heavy
Chain | EVQLVESGGGLVKPGGSLRLSCAASGFTFSNYWISWVRQAPGKGL
EWVGRIKSKTYGGTTDYAEPVKGRFTISRDDSKNTLYLQMNSLKT
EDTAVYYCARVSGYYSHSGGFDVWGQGTLVTVSSASTKGPSVFPL
APSSKSTSGGTAALGCLVKDYFPCPVTVSWNSGALTSGVHTFPAV
LQSSGLYSLSSVVTVPSSSLGTQTYICNVNHKPSNTKVDKRVEPK
SCDKTHTCPPCPAPELLGGPSVFLFPPKPKDTLMISRTPEVTCVV
VDVSHEDPEVKFNWYVDGVEVHNAKTKPREEQYNSTYRVVSVLTV
LHQDWLNGKEYKCKVSNKALPAPIEKTISKAKGQPREPQVYTLPP
SREEMTKNQVSLTCLVKGFYPCDIAVEWESNGQPENNYKTTPPVL
DSDGSFFLYSKLTVDKSRWQQGNVFSCSVMHEALHNHYTQKSLSL
SPGK |
| SEQ ID NO: 152 | DNA Heavy
Chain | GAAGTGCAGCTGGTGGAATCTGGCGGCGGACTTGTGAAACCTGGC
GGCTCTCTGAGACTGAGCTGTGCCGCTTCCGGCTTCACCTTCAGC
AACTACTGGATCAGCTGGGTCCGACAGGCCCCTGGCAAAGGACTT
GAGTGGGTCGGACGGATCAAGAGCAAGACCTACGGCGGCACCACC
GATTATGCCGAGCCTGTGAAGGGCAGATTCACCATCAGCCGGGAC
GACAGCAAGAACACCCTGTACCTGCAGATGAACAGCCTGAAAACC
GAGGACACCGCCGTGTACTACTGCGCCAGAGTGTCTGGCTACTAC
TCTCACAGCGGCGGCTTTGATGTGTGGGGCCAGGGAACACTGGTC
ACCGTTAGTTCTGCTAGCACCAAGGGCCCAAGTGTGTTTCCCCTG
GCCCCCAGCAGCAAGTCTACTTCCGGCGAACTGCTGCCCTGGGT
TGCCTGGTGAAGGACTACTTCCCCTGTCCCGTGACAGTGTCCTGG
AACTCTGGGGCTCTGACTTCCGGCGTGCACACCTTCCCGGCCGTG
CTGCAGAGCAGCGGCCTGTACAGCCTGAGCAGCGTGGTGACAGTG
CCCTCCAGCTCTCTGGGAACCCAGACCTATATCTGCAACGTGAAC
CACAAGCCCAGCAACACCAAGGTGGACAAGAGAGTGGAGCCCAAG
AGCTGCGACAAGACCCACACCTGCCCCCCCTGCCCAGCTCCAGAA
CTGCTGGGAGGGCCTTCCGTGTTCCTGTTCCCCCCCAAGCCCAAG
GACACCCTGATGATCAGCAGGACCCCCGAGGTGACCTGCGTGGTG
GTGGACGTGTCCCACGAGGACCCAGAGGTGAAGTTCAACTGGTAC
GTGGACGGCGTGGAGGTGCACAACGCCAAGACCAAGCCCAGAGAG
GAGCAGTACAACAGCACCTACAGGGTGGTGTCCGTGCTGACCGTG
CTGCACCAGGACTGGCTGAACGGCAAGAATACAAGTGCAAAGTC
TCCAACAAGGCCCTGCCAGCCCCAATCGAAAAGACAATCAGCAAG
GCCAAGGGCCAGCCACGGGAGCCCCAGGTGTACACCCTGCCCCCC
AGCCGGGAGGAGATGACCAAGAACCAGGTGTCCCTGACCTGTCTG
GTGAAGGGCTTCTACCCCTGTGATATCGCCGTGGAGTGGGAGAGC
AACGGCCAGCCCGAGAACAACTACAAGACCACCCCCCCAGTGCTG
GACAGCGACGGCAGCTTCTTCCTGTACAGCAAGCTGACCGTGGAC
AAGTCCAGGTGGCAGCAGGGCAACGTGTTCAGCTGCAGCGTGATG
CACGAGGCCCTGCACAACCACTACACCCAGAAGTCCCTGAGCCTG
AGCCCCGGCAAG |
| SEQ ID NO: 153 | LCDR1
(Combined) | RASQGISNYLA |
| SEQ ID NO: 154 | LCDR2
(Combined) | AASTLQS |
| SEQ ID NO: 155 | LCDR3
(Combined) | QKTWRTPGT |
| SEQ ID NO: 153 | LCDR1
(Kabat) | RASQGISNYLA |
| SEQ ID NO: 154 | LCDR2
(Kabat) | AASTLQS |
| SEQ ID NO: 155 | LCDR3
(Kabat) | QKTWRTPGT |
| SEQ ID NO: 156 | LCDR1
(Chothia) | SQGISNY |

TABLE 2-continued

Examples of Anti-PMEL17 Antibodies of the Present Invention

| SEQ ID NO: 50 | LCDR2 (Chothia) | AAS |
|---|---|---|
| SEQ ID NO: 157 | LCDR3 (Chothia) | TWRTPG |
| SEQ ID NO: 158 | LCDR1 (IMGT) | QGISNY |
| SEQ ID NO: 50 | LCDR2 (IMGT) | AAS |
| SEQ ID NO: 155 | LCDR3 (IMGT) | QKTWRTPGT |
| SEQ ID NO: 159 | VL | DIQMTQSPSSLSASVGDRVTITCRASQGISNYLAWYQQKPGKVPK LLIYAASTLQSGVPSRFSGSGSGTDFTLTISSLQPEDVATYYCQK TWRTPGTFGQGTKVEIK |
| SEQ ID NO: 160 | DNA VL | GACATCCAGATGACACAGAGCCCTAGCAGCCTGTCTGCCAGCGTG GGAGACAGAGTGACCATCACCTGTAGAGCCAGCCAGGGCATCAGC AACTACCTGGCCTGGTATCAGCAGAAACCCGGCAAGGTGCCCAAG CTGCTGATCTACGCTGCCAGCACACTGCAGAGCGGAGTGCCTAGC AGATTTTCTGGCAGCGGCTCCGGCACCGATTTCACCCTGACCATA TCTAGCCTGCAGCCAGAGGACGTGGCCACCTACTACTGTCAGAAA ACCTGGCGGACCCCTGGCACATTTGGCCAGGGAACAAAGGTGGAA ATCAAG |
| SEQ ID NO: 161 | Light Chain | DIQMTQSPSSLSASVGDRVTITCRASQGISNYLAWYQQKPGKVPK LLIYAASTLQSGVPSRFSGSGSGTDFTLTISSLQPEDVATYYCQK TWRTPGTFGQGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| SEQ ID NO: 162 | DNA Light Chain | GACATCCAGATGACACAGAGCCCTAGCAGCCTGTCTGCCAGCGTG GGAGACAGAGTGACCATCACCTGTAGAGCCAGCCAGGGCATCAGC AACTACCTGGCCTGGTATCAGCAGAAACCCGGCAAGGTGCCCAAG CTGCTGATCTACGCTGCCAGCACACTGCAGAGCGGAGTGCCTAGC AGATTTTCTGGCAGCGGCTCCGGCACCGATTTCACCCTGACCATA TCTAGCCTGCAGCCAGAGGACGTGGCCACCTACTACTGTCAGAAA ACCTGGCGGACCCCTGGCACATTTGGCCAGGGAACAAAGGTGGAA ATCAAGCGTACGGTGGCCGCTCCCAGCGTGTTCATCTTCCCCCCC AGCGACGAGCAGCTGAAGAGTGGCACCGCCAGCGTGGTGTGCCTG CTGAACAACTTCTACCCCGGGAGGCCAAGGTGCAGTGGAAGGTG GACAACGCCCTGCAGAGCGGCAACAGCCAGGAGAGCGTCACCGAG CAGGACAGCAAGGACTCCACCTACAGCCTGAGCAGCACCCTGACC CTGAGCAAGGCCGACTACGAGAAGCATAAGGTGTACGCCTGCGAG GTGACCCACCAGGGCCTGTCCAGCCCCGTGACCAAGAGCTTCAAC AGGGGCGAGTGC |

Y010415_E152C_S375C

| SEQ ID NO: 103 | HCDR1 (Combined) | GFTFSSYAMS |
|---|---|---|
| SEQ ID NO: 104 | HCDR2 (Combined) | AISGSGGSTYYADSVKG |
| SEQ ID NO: 163 | HCDR3 (Combined) | SRLIAPWLDY |
| SEQ ID NO: 106 | HCDR1 (Kabat) | SYAMS |
| SEQ ID NO: 104 | HCDR2 (Kabat) | AISGSGGSTYYADSVKG |
| SEQ ID NO: 163 | HCDR3 (Kabat) | SRLIAPWLDY |
| SEQ ID NO: 107 | HCDR1 (Chothia) | GFTFSSY |

TABLE 2-continued

Examples of Anti-PMEL17 Antibodies of the Present Invention

| SEQ ID NO: 108 | HCDR2 (Chothia) | SGSGGS |
|---|---|---|
| SEQ ID NO: 163 | HCDR3 (Chothia) | SRLIAPWLDY |
| SEQ ID NO: 109 | HCDR1 (IMGT) | GFTFSSYA |
| SEQ ID NO: 110 | HCDR2 (IMGT) | ISGSGGST |
| SEQ ID NO: 164 | HCDR3 (IMGT) | ARSRLIAPWLDY |
| SEQ ID NO: 165 | VH | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCARSRLIAPWLDYWGQGTLVTVSS |
| SEQ ID NO: 166 | DNA VH | GAAGTTCAGCTGCTGGAATCTGGCGGAGGACTGGTTCAACCTGGC GGCTCTCTGAGACTGTCTTGTGCCGCCAGCGGCTTCACCTTTAGC AGCTACGCCATGAGCTGGGTCCGACAGGCTCCTGGCAAAGGCCTT GAATGGGTGTCCGCCATCTCTGGCTCTGGCGGCAGCACATATTAC GCCGACTCTGTGAAGGGCAGATTCACCATCAGCCGGGACAACAGC AAGAACACCCTGTACCTGCAGATGAACAGCCTGAGAGCCGAGGAC ACCGCCGTGTACTACTGTGCCAGAAGCAGACTGATCGCCCCTTGG CTGGATTATTGGGGCCAGGGCACACTGGTCACCGTGTCATCT |
| SEQ ID NO: 167 | Heavy Chain | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCARSRLIAPWLDYWGQGTLVTVSSASTKGPSVFPLAPSSK STSGGTAALGCLVKDYFPCPVTVSWNSGALTSGVHTFPAVLQSSG LYSLSSVVTVPSSSLGTQTYICNVNHKPSNTKVDKRVEPKSCDKT HTCPPCPAPELLGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSREEM TKNQVSLTCLVKGFYPCDIAVEWESNGQPENNYKTTPPVLDSDGS FFLYSKLTVDKSRWQQGNVFSCSVMHEALHNHYTQKSLSLSPGK |
| SEQ ID NO: 168 | DNA Heavy Chain | GAAGTTCAGCTGCTGGAATCTGGCGGAGGACTGGTTCAACCTGGC GGCTCTCTGAGACTGTCTTGTGCCGCCAGCGGCTTCACCTTTAGC AGCTACGCCATGAGCTGGGTCCGACAGGCTCCTGGCAAAGGCCTT GAATGGGTGTCCGCCATCTCTGGCTCTGGCGGCAGCACATATTAC GCCGACTCTGTGAAGGGCAGATTCACCATCAGCCGGGACAACAGC AAGAACACCCTGTACCTGCAGATGAACAGCCTGAGAGCCGAGGAC ACCGCCGTGTACTACTGTGCCAGAAGCAGACTGATCGCCCCTTGG CTGGATTATTGGGGCCAGGGCACACTGGTCACCGTGTCATCTGCT AGCACCAAGGGCCCAAGTGTGTTTCCCCTGGCCCCCAGCAGCAAG TCTACTTCCGGCGGAACTGCTGCCCTGGGTTGCCTGGTGAAGGAC TACTTCCCCTGTCCCGTGACAGTGTCCTGGAACTCTGGGGCTCTG ACTTCCGGCGTGCACACCTTCCCCGCCGTGCTGCAGAGCAGCGGC CTGTACAGCCTGAGCAGCGTGGTGACAGTGCCCTCCAGCTCTCTG GGAACCCAGACCTATATCTGCAACGTGAACCACAAGCCCAGCAAC ACCAAGGTGGACAAGAGAGTGGAGCCCAAGAGCTGCGACAAGACC CACACCTGCCCCCCCTGCCCAGCTCCAGAACTGCTGGGAGGGCCT TCCGTGTTCCTGTTCCCCCCCAAGCCCAAGGACACCCTGATGATC AGCAGGACCCCCGAGGTGACCTGCGTGGTGGTGGACGTGTCCCAC GAGGACCCAGAGGTGAAGTTCAACTGGTACGTGGACGGCGTGGAG GTGCACAACGCCAAGACCAAGCCCAGAGAGGAGCAGTACAACAGC ACCTACAGGGTGGTGTCCGTGCTGACCGTGCTGCACCAGGACTGG CTGAACGGCAAAGAATACAAGTGCAAAGTCTCCAACAAGGCCCTG CCAGCCCCAATCGAAAAGACAATCAGCAAGGCCAAGGGCCAGCCA CGGGAGCCCCAGGTGTACACCCTGCCCCCCAGCCGGGAGGAGATG ACCAAGAACCAGGTGTCCCTGACCTGTCTGGTGAAGGGCTTCTAC CCCTGTGATATCGCCGTGGAGTGGGAGAGCAACGGCCAGCCCGAG AACAACTACAAGACCACCCCCCCAGTGCTGGACAGCGACGGCAGC TTCTTCCTGTACAGCAAGCTGACCGTGGACAAGTCCAGGTGGCAG CAGGGCAACGTGTTCAGCTGCAGCGTGATGCACGAGGCCCTGCAC AACCACTACACCCAGAAGTCCCTGAGCCTGAGCCCCGGCAAG |
| SEQ ID NO: 116 | LCDR1 (Combined) | RASQSISSYLN |
| SEQ ID NO: 47 | LCDR2 (Combined) | AASSLQS |
| SEQ ID NO: 169 | LCDR3 (Combined) | QQVYGSPPT |

TABLE 2-continued

Examples of Anti-PMEL17 Antibodies of the Present Invention

| SEQ ID NO: 116 | LCDR1 (Kabat) | RASQSISSYLN |
|---|---|---|
| SEQ ID NO: 47 | LCDR2 (Kabat) | AASSLQS |
| SEQ ID NO: 169 | LCDR3 (Kabat) | QQVYGSPPT |
| SEQ ID NO: 49 | LCDR1 (Chothia) | SQSISSY |
| SEQ ID NO: 50 | LCDR2 (Chothia) | AAS |
| SEQ ID NO: 170 | LCDR3 (Chothia) | VYGSPP |
| SEQ ID NO: 52 | LCDR1 (IMGT) | QSISSY |
| SEQ ID NO: 50 | LCDR2 (IMGT) | AAS |
| SEQ ID NO: 169 | LCDR3 (IMGT) | QQVYGSPPT |
| SEQ ID NO: 171 | VL | DIQMTQSPSSLSASVGDRVTITCRASQSISSYLNWYQQKPGKAPK LLIYAASSLQSGVPSRFSGSGSGTDFTLTISSLQPEDFATYYCQQ VYGSPPTFGQGTKVEIK |
| SEQ ID NO: 172 | DNA VL | GACATCCAGATGACACAGAGCCCTAGCAGCCTGTCTGCCAGCGTG GGAGACAGAGTGACCATCACCTGTAGAGCCAGCCAGAGCATCAGC AGCTACCTGAACTGGTATCAGCAGAAGCCCGGCAAGGCCCCTAAA CTGCTGATCTATGCCGCCAGCTCTCTGCAGTCTGGCGTGCCAAGC AGATTTTCTGGCAGCGGCTCTGGCACCGACTTCACCCTGACCATA TCTAGCCTGCAGCCAGAGGACTTCGCCACCTACTACTGCCAGCAG GTCTACGGCAGCCCTCCTACATTTGGCCAGGGCACCAAGGTGGAA ATCAAG |
| SEQ ID NO: 173 | Light Chain | DIQMTQSPSSLSASVGDRVTITCRASQSISSYLNWYQQKPGKAPK LLIYAASSLQSGVPSRFSGSGSGTDFTLTISSLQPEDFATYYCQQ VYGSPPTFGQGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| SEQ ID NO: 174 | DNA Light Chain | GACATCCAGATGACACAGAGCCCTAGCAGCCTGTCTGCCAGCGTG GGAGACAGAGTGACCATCACCTGTAGAGCCAGCCAGAGCATCAGC AGCTACCTGAACTGGTATCAGCAGAAGCCCGGCAAGGCCCCTAAA CTGCTGATCTATGCCGCCAGCTCTCTGCAGTCTGGCGTGCCAAGC AGATTTTCTGGCAGCGGCTCTGGCACCGACTTCACCCTGACCATA TCTAGCCTGCAGCCAGAGGACTTCGCCACCTACTACTGCCAGCAG GTCTACGGCAGCCCTCCTACATTTGGCCAGGGCACCAAGGTGGAA ATCAAGCGTACGGTGGCCGCTCCCAGCGTGTTCATCTTCCCCCCC AGCGACGAGCAGCTGAAGAGTGGCACCGCCAGCGTGGTGTGCCTG CTGAACAACTTCTACCCCCGGGAGGCCAAGGTGCAGTGGAAGGTG GACAACGCCCTGCAGAGCGGCAACAGCCAGGAGAGCGTCACCGAG CAGGACAGCAAGGACTCCACCTACAGCCTGAGCAGCACCCTGACC CTGAGCAAGGCCGACTACGAGAAGCATAAGGTGTACGCCTGCGAG GTGACCCACCAGGGCCTGTCCAGCCCCGTGACCAAGAGCTTCAAC AGGGGCGAGTGC |
| Y010417_E152C_S375C | | |
| SEQ ID NO: 175 | HCDR1 (Combined) | GYSFTSYWIG |
| SEQ ID NO: 176 | HCDR2 (Combined) | IIYPGDSDTRYSPSFQG |
| SEQ ID NO: 177 | HCDR3 (Combined) | GSSAASGLSGDL |
| SEQ ID NO: 178 | HCDR1 (Kabat) | SYWIG |

TABLE 2-continued

Examples of Anti-PMEL17 Antibodies of the Present Invention

| SEQ ID NO: 176 | HCDR2 (Kabat) | IIYPGDSDTRYSPSFQG |
| --- | --- | --- |
| SEQ ID NO: 177 | HCDR3 (Kabat) | GSSAASGLSGDL |
| SEQ ID NO: 179 | HCDR1 (Chothia) | GYSFTSY |
| SEQ ID NO: 180 | HCDR2 (Chothia) | YPGDSD |
| SEQ ID NO: 177 | HCDR3 (Chothia) | GSSAASGLSGDL |
| SEQ ID NO: 181 | HCDR1 (IMGT) | GYSFTSYW |
| SEQ ID NO: 182 | HCDR2 (IMGT) | IYPGDSDT |
| SEQ ID NO: 183 | HCDR3 (IMGT) | ARGSSAASGLSGDL |
| SEQ ID NO: 184 | VH | EVQLVQSGAEVKKPGESLKISCKGSGYSFTSYWIGWVRQMPGKGL EWMGIIYPGDSDTRYSPSFQGQVTISADKSISTAYLQWSSLKASD TAMYYCARGSSAASGLSGDLWGQGTLVTVSS |
| SEQ ID NO: 185 | DNA VH | GAAGTTCAGCTGGTGCAGTCTGGCGCCGAAGTGAAGAAGCCTGGC GAGAGCCTGAAGATCTCCTGCAAAGGCAGCGGCTACAGCTTCACC AGCTACTGGATCGGCTGGGTCCGACAGATGCCTGGCAAAGGCCTT GAGTGGATGGGCATCATCTACCCCGGCGACAGCGACACCAGATAC AGCCCTAGCTTTCAGGGCCAAGTGACCATCAGCGCCGACAAGAGC ATCAGCACAGCCTACCTGCAGTGGTCCAGCCTGAAGGCCTCTGAC ACCGCCATGTACTACTGTGCCAGAGGAAGCTCTGCCGCCTCTGGA CTGTCTGGCGATCTTTGGGGACAGGGCACACTGGTCACAGTGTCT AGT |
| SEQ ID NO: 186 | Heavy Chain | EVQLVQSGAEVKKPGESLKISCKGSGYSFTSYWIGWVRQMPGKGL EWMGIIYPGDSDTRYSPSFQGQVTISADKSISTAYLQWSSLKASD TAMYYCARGSSAASGLSGDLWGQGTLVTVSSASTKGPSVFPLAPS SKSTSGGTAALGCLVKDYFPCPVTVSWNSGALTSGVHTFPAVLQS SGLYSLSSVVTVPSSSLGTQTYICNVNHKPSNTKVDKRVEPKSCD KTHTCPPCPAPELLGGPSVFLFPPKPKDTLMISRTPEVTCVVVDV SHEDPEVKFNWYVDGVEVHNAKTKPREEQYNSTYRVVSVLTVLHQ DWLNGKEYKCKVSNKALPAPIEKTISKAKGQPREPQVYTLPPSRE EMTKNQVSLTCLVKGFYPCDIAVEWESNGQPENNYKTTPPVLDSD GSFFLYSKLTVDKSRWQQGNVFSCSVMHEALHNHYTQKSLSLSPG K |
| SEQ ID NO: 187 | DNA Heavy Chain | GAAGTTCAGCTGGTGCAGTCTGGCGCCGAAGTGAAGAAGCCTGGC GAGAGCCTGAAGATCTCCTGCAAAGGCAGCGGCTACAGCTTCACC AGCTACTGGATCGGCTGGGTCCGACAGATGCCTGGCAAAGGCCTT GAGTGGATGGGCATCATCTACCCCGGCGACAGCGACACCAGATAC AGCCCTAGCTTTCAGGGCCAAGTGACCATCAGCGCCGACAAGAGC ATCAGCACAGCCTACCTGCAGTGGTCCAGCCTGAAGGCCTCTGAC ACCGCCATGTACTACTGTGCCAGAGGAAGCTCTGCCGCCTCTGGA CTGTCTGGCGATCTTTGGGGACAGGGCACACTGGTCACAGTGTCT AGTGCTAGCACCAAGGGCCCAAGTGTGTTTCCCCTGGCCCCCAGC AGCAAGTCTACTTCCGGCGGAACTGCTGCCCTGGGTTGCCTGGTG AAGGACTACTTCCCCTGTCCCGTGACAGTGTCCTGGAACTCTGGG GCTCTGACTTCCGGCGTGCACACCTTCCCCGCCGTGCTGCAGAGC AGCGGCCTGTACAGCCTGAGCAGCGTGGTGACAGTGCCCTCCAGC TCTCTGGGAACCCAGACCTATATCTGCAACGTGAACCACAAGCCC AGCAACACCAAGGTGGACAAGAGAGTGGAGCCCAAGAGCTGCGAC AAGACCCACACCTGCCCCCCCTGCCCAGCTCCAGAACTGCTGGGA GGGCCTTCCGTGTTCCTGTTCCCCCCAAGCCCAAGGACACCCTG ATGATCAGCAGGACCCCCGAGGTGACCTGCGTGGTGGTGGACGTG TCCCACGAGGACCCCGAGGTGAAGTTCAACTGGTACGTGGACGGC GTGGAGGTGCACAACGCCAAGACCAAGCCCAGAGAGGAGCAGTAC AACAGCACCTACAGGGTGGTGTCCGTGCTGACCGTGCTGCACCAG GACTGGCTGAACGGCAAAGAATACAAGTGCAAAGTCTCCAACAAG GCCCTGCCAGCCCCAATCGAAAAGACAATCAGCAAGGCCAAGGGC CAGCCACGGGAGCCCCAGGTGTACACCCTGCCCCCCAGCCGGGAG GAGATGACCAAGAACCAGGTGTCCCTGACCTGTCTGGTGAAGGGC TTCTACCCCTGTGATATCGCCGTGGAGTGGGAGAGCAACGGCCAG CCCGAGAACAACTACAAGACCACCCCCCCAGTGCTGGACAGCGAC GGCAGCTTCTTCCTGTACAGCAAGCTGACCGTGGACAAGTCCAGG |

TABLE 2-continued

Examples of Anti-PMEL17 Antibodies of the Present Invention

| | | |
|---|---|---|
| | | TGGCAGCAGGGCAACGTGTTCAGCTGCAGCGTGATGCACGAGGCC CTGCACAACCACTACACCCAGAAGTCCCTGAGCCTGAGCCCCGGC AAG |
| SEQ ID NO: 116 | LCDR1 (Combined) | RASQSISSYLN |
| SEQ ID NO: 47 | LCDR2 (Combined) | AASSLQS |
| SEQ ID NO: 188 | LCDR3 (Combined) | QQDYYSPFT |
| SEQ ID NO: 116 | LCDR1 (Kabat) | RASQSISSYLN |
| SEQ ID NO: 47 | LCDR2 (Kabat) | AASSLQS |
| SEQ ID NO: 188 | LCDR3 (Kabat) | QQDYYSPFT |
| SEQ ID NO: 49 | LCDR1 (Chothia) | SQSISSY |
| SEQ ID NO: 50 | LCDR2 (Chothia) | AAS |
| SEQ ID NO: 189 | LCDR3 (Chothia) | DYYSPF |
| SEQ ID NO: 52 | LCDR1 (IMGT) | QSISSY |
| SEQ ID NO: 50 | LCDR2 (IMGT) | AAS |
| SEQ ID NO: 188 | LCDR3 (IMGT) | QQDYYSPFT |
| SEQ ID NO: 190 | VL | DIQMTQSPSSLSASVGDRVTITCRASQSISSYLNWYQQKPGKAPK LLIYAASSLQSGVPSRFSGSGSGTDFTLTISSLQPEDFATYYCQQ DYYSPFTFGQGTKVEIK |
| SEQ ID NO: 191 | DNA VL | GACATCCAGATGACACAGAGCCCTAGCAGCCTGTCTGCCAGCGTG GGAGACAGAGTGACCATCACCTGTAGAGCCAGCCAGAGCATCAGC AGCTACCTGAACTGGTATCAGCAGAAGCCCGGCAAGGCCCCTAAA CTGCTGATCTATGCCGCCAGCTCTCTGCAGTCTGGCGTGCCAAGC AGATTTTCTGGCAGCGGCTCTGGCACCGACTTCACCCTGACCATA TCTAGCCTGCAGCCAGAGGACTTCGCCACCTACTACTGCCAGCAG GACTACTACAGCCCCTTCACCTTTGGCCAGGGCACCAAGGTGGAA ATCAAG |
| SEQ ID NO: 192 | Light Chain | DIQMTQSPSSLSASVGDRVTITCRASQSISSYLNWYQQKPGKAPK LLIYAASSLQSGVPSRFSGSGSGTDFTLTISSLQPEDFATYYCQQ DYYSPFTFGQGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| SEQ ID NO: 193 | DNA Light Chain | GACATCCAGATGACACAGAGCCCTAGCAGCCTGTCTGCCAGCGTG GGAGACAGAGTGACCATCACCTGTAGAGCCAGCCAGAGCATCAGC AGCTACCTGAACTGGTATCAGCAGAAGCCCGGCAAGGCCCCTAAA CTGCTGATCTATGCCGCCAGCTCTCTGCAGTCTGGCGTGCCAAGC AGATTTTCTGGCAGCGGCTCTGGCACCGACTTCACCCTGACCATA TCTAGCCTGCAGCCAGAGGACTTCGCCACCTACTACTGCCAGCAG GACTACTACAGCCCCTTCACCTTTGGCCAGGGCACCAAGGTGGAA ATCAAGCGTACGGTGGCCGCTCCCAGCGTGTTCATCTTCCCCCCC AGCGACGAGCAGCTGAAGAGTGGCACCGCCAGCGTGGTGTGCCTG CTGAACAACTTCTACCCCCGGGAGGCCAAGGTGCAGTGGAAGGTG GACAACGCCCTGCAGAGCGGCAACAGCCAGGAGAGCGTCACCGAG CAGGACAGCAAGGACTCCACCTACAGCCTGAGCAGCACCCTGACC CTGAGCAAGGCCGACTACGAGAAGCATAAGGTGTACGCCTGCGAG GTGACCCACCAGGGCCTGTCCAGCCCCGTGACCAAGAGCTTCAAC AGGGGCGAGTGC |

TABLE 2-continued

Examples of Anti-PMEL17 Antibodies of the Present Invention

Y010429 E152C_S375C

| | | |
|---|---|---|
| SEQ ID NO: 103 | HCDR1 (Combined) | GFTFSSYAMS |
| SEQ ID NO: 104 | HCDR2 (Combined) | AISGSGGSTYYADSVKG |
| SEQ ID NO: 194 | HCDR3 (Combined) | AYKLSWLDL |
| SEQ ID NO: 106 | HCDR1 (Kabat) | SYAMS |
| SEQ ID NO: 104 | HCDR2 (Kabat) | AISGSGGSTYYADSVKG |
| SEQ ID NO: 194 | HCDR3 (Kabat) | AYKLSWLDL |
| SEQ ID NO: 107 | HCDR1 (Chothia) | GFTFSSY |
| SEQ ID NO: 108 | HCDR2 (Chothia) | SGSGGS |
| SEQ ID NO: 194 | HCDR3 (Chothia) | AYKLSWLDL |
| SEQ ID NO: 109 | HCDR1 (IMGT) | GFTFSSYA |
| SEQ ID NO: 110 | HCDR2 (IMGT) | ISGSGGST |
| SEQ ID NO: 195 | HCDR3 (IMGT) | ARAYKLSWLDL |
| SEQ ID NO: 196 | VH | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCARAYKLSWLDLWGQGTLVTVSS |
| SEQ ID NO: 197 | DNA VH | GAAGTTCAGCTGCTGGAATCTGGCGGAGGACTGGTTCAACCTGGC GGCTCTCTGAGACTGTCTTGTGCCGCCAGCGGCTTCACCTTTAGC AGCTACGCCATGAGCTGGGTCCGACAGGCTCCTGGCAAAGGCCTT GAATGGGTGTCCGCCATCTCTGGCTCTGGCGGCAGCACATATTAC GCCGACTCTGTGAAGGGCAGATTCACCATCAGCCGGGACAACAGC AAGAACACCCTGTACCTGCAGATGAACAGCCTGAGAGCCGAGGAC ACCGCCGTGTACTATTGTGCCAGAGCCTACAAGCTGAGCTGGCTG GATCTTTGGGGCCAGGGCACACTGGTCACAGTGTCATCT |
| SEQ ID NO: 198 | Heavy Chain | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCARAYKLSWLDLWGQGTLVTVSSASTKGPSVFPLAPSSKS TSGGTAALGCLVKDYFPCPVTVSWNSGALTSGVHTFPAVLQSSGL YSLSSVVTVPSSSLGTQTYICNVNHKPSNTKVDKRVEPKSCDKTH TCPPCPAPELLGGPSVFLFPPKPKDTLMISRTPEVTCVVVDVSHE DPEVKFNWYVDGVEVHNAKTKPREEQYNSTYRVVSVLTVLHQDWL NGKEYKCKVSNKALPAPIEKTISKAKGQPREPQVYTLPPSREEMT KNQVSLTCLVKGFYPCDIAVEWESNGQPENNYKTTPPVLDSDGSF FLYSKLTVDKSRWQQGNVFSCSVMHEALHNHYTQKSLSLSPGK |
| SEQ ID NO: 199 | DNA Heavy | GAAGTTCAGCTGCTGGAATCTGGCGGAGGACTGGTTCAACCTGGC GGCTCTCTGAGACTGTCTTGTGCCGCCAGCGGCTTCACCTTTAGC AGCTACGCCATGAGCTGGGTCCGACAGGCTCCTGGCAAAGGCCTT GAATGGGTGTCCGCCATCTCTGGCTCTGGCGGCAGCACATATTAC GCCGACTCTGTGAAGGGCAGATTCACCATCAGCCGGGACAACAGC AAGAACACCCTGTACCTGCAGATGAACAGCCTGAGAGCCGAGGAC ACCGCCGTGTACTATTGTGCCAGAGCCTACAAGCTGAGCTGGCTG GATCTTTGGGGCCAGGGCACACTGGTCACAGTGTCATCTGCTAGC ACCAAGGGCCCAAGTGTGTTTCCCCTGGCCCCCAGCAGCAAGTCT ACTTCCGGCGGAACTGCTGCCCTGGGTTGCCTGGTGAAGGACTAC TTCCCCTGTCCCGTGACAGTGTCTGGAACTCTGGGGCTCTGACT TCCGGCGTGCACACCTTCCCGCCGTGCTGCAGAGCAGCGGCCTG TACAGCCTGAGCAGCGTGGTGACAGTGCCCTCCAGCTCTCTGGGA ACCCAGACCTATATCTGCAACGTGAACCACAAGCCCAGCAACACC AAGGTGGACAAGAGAGTGGAGCCCAAGAGCTGCGACAAGACCCAC ACCTGCCCCCCCTGCCCAGCTCCAGAACTGCTGGGAGGGCCTTCC |

TABLE 2-continued

Examples of Anti-PMEL17 Antibodies of the Present Invention

|  |  |  |
|---|---|---|
|  |  | GTGTTCCTGTTCCCCCCAAGCCCAAGGACACCCTGATGATCAGC<br>AGGACCCCCGAGGTGACCTGCGTGGTGGTGGACGTGTCCCACGAG<br>GACCCAGAGGTGAAGTTCAACTGGTACGTGGACGGCGTGGAGGTG<br>CACAACGCCAAGACCAAGCCCAGAGAGGAGCAGTACAACAGCACC<br>TACAGGGTGGTGTCCGTGCTGACCGTGCTGCACCAGGACTGGCTG<br>AACGGCAAAGAATACAAGTGCAAAGTCTCCAACAAGGCCCTGCCA<br>GCCCCAATCGAAAAGACAATCAGCAAGGCCAAGGGCCAGCCACGG<br>GAGCCCCAGGTGTACACCCTGCCCCCAGCCGGGAGGAGATGACC<br>AAGAACCAGGTGTCCCTGACCTGTCTGGTGAAGGGCTTCTACCCC<br>TGTGATATCGCCGTGGAGTGGGAGAGCAACGGCCAGCCCGAGAAC<br>AACTACAAGACCACCCCCCCAGTGCTGGACAGCGACGGCAGCTTC<br>TTCCTGTACAGCAAGCTGACCGTGGACAAGTCCAGGTGGCAGCAG<br>GGCAACGTGTTCAGCTGCAGCGTGATGCACGAGGCCCTGCACAAC<br>CACTACACCCAGAAGTCCCTGAGCCTGAGCCCCGGCAAG |
| SEQ ID NO: 116 | LCDR1<br>(Combined) | RASQSISSYLN |
| SEQ ID NO: 47 | LCDR2<br>(Combined) | AASSLQS |
| SEQ ID NO: 200 | LCDR3<br>(Combined) | QQVWYAPVT |
| SEQ ID NO: 116 | LCDR1<br>(Kabat) | RASQSISSYLN |
| SEQ ID NO: 47 | LCDR2<br>(Kabat) | AASSLQS |
| SEQ ID NO: 200 | LCDR3<br>(Kabat) | QQVWYAPVT |
| SEQ ID NO: 49 | LCDR1<br>(Chothia) | SQSISSY |
| SEQ ID NO: 50 | LCDR2<br>(Chothia) | AAS |
| SEQ ID NO: 201 | LCDR3<br>(Chothia) | VVVYAPV |
| SEQ ID NO: 52 | LCDR1<br>(IMGT) | QSISSY |
| SEQ ID NO: 50 | LCDR2<br>(IMGT) | AAS |
| SEQ ID NO: 200 | LCDR3<br>(IMGT) | QQVWYAPVT |
| SEQ ID NO: 202 | VL | DIQMTQSPSSLSASVGDRVTITCRASQSISSYLNWYQQKPGKAPK<br>LLIYAASSLQSGVPSRFSGSGSGTDFTLTISSLQPEDFATYYCQQ<br>VWYAPVTFGQGTKVEIK |
| SEQ ID NO: 203 | DNA VL | GACATCCAGATGACACAGAGCCCTAGCAGCCTGTCTGCCAGCGTG<br>GGAGACAGAGTGACCATCACCTGTAGAGCCAGCCAGAGCATCAGC<br>AGCTACCTGAACTGGTATCAGCAGAAGCCCGGCAAGGCCCCTAAA<br>CTGCTGATCTATGCCGCCAGCTCTCTGCAGTCTGGCGTGCCAAGC<br>AGATTTTCTGGCAGCGGCTCTGGCACCGACTTCACCCTGACCATA<br>TCTAGCCTGCAGCCAGAGGACTTCGCCACCTACTACTGCCAGCAA<br>GTTTGGTACGCCCCTGTGACCTTTGGCCAGGGCACCAAGGTGGAA<br>ATCAAG |
| SEQ ID NO: 204 | Light Chain | DIQMTQSPSSLSASVGDRVTITCRASQSISSYLNWYQQKPGKAPK<br>LLIYAASSLQSGVPSRFSGSGSGTDFTLTISSLQPEDFATYYCQQ<br>VWYAPVTFGQGTKVEIKRTVAAPSVFIFPPSDEQLKSGTASVVCL<br>LNNFYPREAKVQWKVDNALQSGNSQESVTEQDSKDSTYSLSSTLT<br>LSKADYEKHKVYACEVTHQGLSSPVTKSFNRGEC |
| SEQ ID NO: 205 | DNA Light<br>Chain | GACATCCAGATGACACAGAGCCCTAGCAGCCTGTCTGCCAGCGTG<br>GGAGACAGAGTGACCATCACCTGTAGAGCCAGCCAGAGCATCAGC<br>AGCTACCTGAACTGGTATCAGCAGAAGCCCGGCAAGGCCCCTAAA<br>CTGCTGATCTATGCCGCCAGCTCTCTGCAGTCTGGCGTGCCAAGC<br>AGATTTTCTGGCAGCGGCTCTGGCACCGACTTCACCCTGACCATA<br>TCTAGCCTGCAGCCAGAGGACTTCGCCACCTACTACTGCCAGCAA<br>GTTTGGTACGCCCCTGTGACCTTTGGCCAGGGCACCAAGGTGGAA<br>ATCAAGCGTACGGTGGCCGCTCCCAGCGTGTTCATCTTCCCCCCC |

TABLE 2-continued

Examples of Anti-PMEL17 Antibodies of the Present Invention

|  |  |  |
|---|---|---|
|  |  | AGCGACGAGCAGCTGAAGAGTGGCACCGCCAGCGTGGTGTGCCTG<br>CTGAACAACTTCTACCCCCGGGAGGCCAAGGTGCAGTGGAAGGTG<br>GACAACGCCCTGCAGAGCGGCAACAGCCAGGAGAGCGTCACCGAG<br>CAGGACAGCAAGGACTCCACCTACAGCCTGAGCAGCACCCTGACC<br>CTGAGCAAGGCCGACTACGAGAAGCATAAGGTGTACGCCTGCGAG<br>GTGACCCACCAGGGCCTGTCCAGCCCCGTGACCAAGAGCTTCAAC<br>AGGGGCGAGTGC |
| Y010900 E152C_S375C |  |  |
| SEQ ID NO: 206 | HCDR1<br>(Combined) | GFTFSNAWMS |
| SEQ ID NO: 207 | HCDR2<br>(Combined) | RIKSKTDAGTTDYAAPVKG |
| SEQ ID NO: 208 | HCDR3<br>(Combined) | TIYPSAPSSSLDY |
| SEQ ID NO: 209 | HCDR1<br>(Kabat) | NAWMS |
| SEQ ID NO: 207 | HCDR2<br>(Kabat) | RIKSKTDAGTTDYAAPVKG |
| SEQ ID NO: 208 | HCDR3<br>(Kabat) | TIYPSAPSSSLDY |
| SEQ ID NO: 210 | HCDR1<br>(Chothia) | GFTFSNA |
| SEQ ID NO: 211 | HCDR2<br>(Chothia) | KSKTDAGT |
| SEQ ID NO: 208 | HCDR3<br>(Chothia) | TIYPSAPSSSLDY |
| SEQ ID NO: 212 | HCDR1<br>(IMGT) | GFTFSNAW |
| SEQ ID NO: 213 | HCDR2<br>(IMGT) | IKSKTDAGTT |
| SEQ ID NO: 214 | HCDR3<br>(IMGT) | ARTIYPSAPSSSLDY |
| SEQ ID NO: 215 | VH | EVQLVESGGGLVKPGGSLRLSCAASGFTFSNAWMSWVRQAPGKGL<br>EWVGRIKSKTDAGTTDYAAPVKGRFTISRDDSKNTLYLQMNSLKT<br>EDTAVYYCARTIYPSAPSSSLDYWGQGTLVTVSS |
| SEQ ID NO: 216 | DNA VH | GAAGTGCAGCTGGTGGAATCTGGCGGCGGACTTGTGAAACCTGGC<br>GGCTCTCTGAGACTGAGCTGTGCCGCTTCCGGCTTCACCTTCAGC<br>AATGCCTGGATGAGCTGGGTCCGACAGGCCCCTGGAAAAGGCCTT<br>GAGTGGGTCGGACGGATCAAGAGCAAGACCGATGCCGGCACCACC<br>GATTATGCTGCCCCTGTGAAGGGCAGATTCACCATCAGCAGGGAC<br>GACAGCAAGAACACCCTGTACCTGCAGATGAACAGCCTGAAAACC<br>GAGGACACCGCCGTGTACTACTGCGCCAGAACAATCTACCCCAGC<br>GCTCCTAGCAGCAGCCTGGATTATTGGGGCCAGGGCACACTGGTC<br>ACCGTGTCATCT |
| SEQ ID NO: 217 | Heavy<br>Chain | EVQLVESGGGLVKPGGSLRLSCAASGFTFSNAWMSWVRQAPGKGL<br>EWVGRIKSKTDAGTTDYAAPVKGRFTISRDDSKNTLYLQMNSLKT<br>EDTAVYYCARTIYPSAPSSSLDYWGQGTLVTVSSASTKGPSVFPL<br>APSSKSTSGGTAALGCLVKDYFPCPVTVSWNSGALTSGVHTFPAV<br>LQSSGLYSLSSVVTVPSSSLGTQTYICNVNHKPSNTKVDKRVEPK<br>SCDKTHTCPPCPAPELLGGPSVFLFPPKPKDTLMISRTPEVTCVV<br>VDVSHEDPEVKFNWYVDGVEVHNAKTKPREEQYNSTYRVVSVLTV<br>LHQDWLNGKEYKCKVSNKALPAPIEKTISKAKGQPREPQVYTLPP<br>SREEMTKNQVSLTCLVKGFYPCDIAVEWESNGQPENNYKTTPPVL<br>DSDGSFFLYSKLTVDKSRWQQGNVFSCSVMHEALHNHYTQKSLSL<br>SPGK |
| SEQ ID NO: 218 | DNA Heavy<br>Chain | GAAGTGCAGCTGGTGGAATCTGGCGGCGGACTTGTGAAACCTGGC<br>GGCTCTCTGAGACTGAGCTGTGCCGCTTCCGGCTTCACCTTCAGC<br>AATGCCTGGATGAGCTGGGTCCGACAGGCCCCTGGAAAAGGCCTT<br>GAGTGGGTCGGACGGATCAAGAGCAAGACCGATGCCGGCACCACC<br>GATTATGCTGCCCCTGTGAAGGGCAGATTCACCATCAGCAGGGAC<br>GACAGCAAGAACACCCTGTACCTGCAGATGAACAGCCTGAAAACC |

TABLE 2-continued

Examples of Anti-PMEL17 Antibodies of the Present Invention

|  |  |  |
|---|---|---|
|  |  | GAGGACACCGCCGTGTACTACTGCGCCAGAACAATCTACCCCAGC<br>GCTCCTAGCAGCAGCCTGGATTATTGGGGCCAGGGCACACTGGTC<br>ACCGTGTCATCTGCTAGCACCAAGGGCCCAAGTGTGTTTCCCCTG<br>GCCCCCAGCAGCAAGTCTACTTCCGGCGAACTGCTGCCCTGGGT<br>TGCCTGGTGAAGGACTACTTCCCCTGTCCCGTGACAGTGTCCTGG<br>AACTCTGGGGCTCTGACTTCCGGCGTGCACACCTTCCCCGCCGTG<br>CTGCAGAGCAGCGGCCTGTACAGCCTGAGCAGCGTGGTGACAGTG<br>CCCTCCAGCTCTCTGGGAACCCAGACCTATATCTGCAACGTGAAC<br>CACAAGCCCAGCAACACCAAGGTGGACAAGAGAGTGGAGCCCAAG<br>AGCTGCGACAAGACCCACACCTGCCCCCCCTGCCCAGCTCCAGAA<br>CTGCTGGGAGGGCTTCCGTGTTCCTGTTCCCCCCAAGCCCAAG<br>GACACCCTGATGATCAGCAGGACCCCCGAGGTGACCTGCGTGGTG<br>GTGGACGTGTCCCACGAGGACCCAGAGGTGAAGTTCAACTGGTAC<br>GTGGACGGCGTGGAGGTGCACAACGCCAAGACCAAGCCCAGAGAG<br>GAGCAGTACAACAGCACCTACAGGGTGGTGTCCGTGCTGACCGTG<br>CTGCACCAGGACTGGCTGAACGGCAAGAATACAAGTGCAAAGTC<br>TCCAACAAGGCCCTGCCAGCCCCAATCGAAAAGACAATCAGCAAG<br>GCCAAGGGCCAGCCACGGGAGCCCCAGGTGTACACCCTGCCCCCC<br>AGCCGGGAGGAGATGACCAAGAACCAGGTGTCCCTGACCTGTCTG<br>GTGAAGGGCTTCTACCCCTGTGATATCGCCGTGGAGTGGGAGAGC<br>AACGGCCAGCCCGAGAACAACTACAAGACCACCCCCCCAGTGCTG<br>GACAGCGACGGCAGCTTCTTCCTGTACAGCAAGCTGACCGTGGAC<br>AAGTCCAGGTGGCAGCAGGGCAACGTGTTCAGCTGCAGCGTGATG<br>CACGAGGCCCTGCACAACCACTACACCCAGAAGTCCCTGAGCCTG<br>AGCCCCGGCAAG |
| SEQ ID NO: 153 | LCDR1<br>(Combined) | RASQGISNYLA |
| SEQ ID NO: 154 | LCDR2<br>(Combined) | AASTLQS |
| SEQ ID NO: 219 | LCDR3<br>(Combined) | QQLIFFPLT |
| SEQ ID NO: 153 | LCDR1<br>(Kabat) | RASQGISNYLA |
| SEQ ID NO: 154 | LCDR2<br>(Kabat) | AASTLQS |
| SEQ ID NO: 219 | LCDR3<br>(Kabat) | QQLIFFPLT |
| SEQ ID NO: 156 | LCDR1<br>(Chothia) | SQGISNY |
| SEQ ID NO: 50 | LCDR2<br>(Chothia) | AAS |
| SEQ ID NO: 220 | LCDR3<br>(Chothia) | LIFFPL |
| SEQ ID NO: 158 | LCDR1<br>(IMGT) | QGISNY |
| SEQ ID NO: 50 | LCDR2<br>(IMGT) | AAS |
| SEQ ID NO: 219 | LCDR3<br>(IMGT) | QQLIFFPLT |
| SEQ ID NO: 221 | VL | DIQMTQSPSSLSASVGDRVTITCRASQGISNYLAWYQQKPGKVPK<br>LLIYAASTLQSGVPSRFSGSGSGTDFTLTISSLQPEDVATYYCQQ<br>LIFFPLTFGQGTKVEIK |
| SEQ ID NO: 222 | DNA VL | GACATCCAGATGACACAGAGCCCAGCAGCCTGTCTGCCAGCGTG<br>GGAGACAGAGTGACCATCACCTGTAGAGCCAGCCAGGGCATCAGC<br>AACTACCTGGCCTGGTATCAGCAGAAACCCGGCAAGGTGCCCAAG<br>CTGCTGATCTACGCTGCCAGCACACTGCAGAGCGGAGTGCCTAGC<br>AGATTTTCTGGCAGCGGCTCCGGCACCGATTTCACCCTGACCATA<br>TCTAGCCTGCAGCCAGAGGACGTGGCCACCTACTATTGCCAGCAG<br>CTGATCTTCTTCCCTCTGACCTTTGGCCAGGGCACCAAGGTGGAA<br>ATCAAG |
| SEQ ID NO: 223 | Light Chain | DIQMTQSPSSLSASVGDRVTITCRASQGISNYLAWYQQKPGKVPK<br>LLIYAASTLQSGVPSRFSGSGSGTDFTLTISSLQPEDVATYYCQQ<br>LIFFPLTFGQGTKVEIKRTVAAPSVFIFPPSDEQLKSGTASVVCL |

TABLE 2-continued

Examples of Anti-PMEL17 Antibodies of the Present Invention

| | | |
|---|---|---|
| | | LNNFYPREAKVQWKVDNALQSGNSQESVTEQDSKDSTYSLSSTLT<br>LSKADYEKHKVYACEVTHQGLSSPVTKSFNRGEC |
| SEQ ID NO: 224 | DNA Light<br>Chain | GACATCCAGATGACACAGAGCCCTAGCAGCCTGTCTGCCAGCGTG<br>GGAGACAGAGTGACCATCACCTGTAGAGCCAGCCAGGGCATCAGC<br>AACTACCTGGCCTGGTATCAGCAGAAACCCGGCAAGGTGCCCAAG<br>CTGCTGATCTACGCTGCCAGCACACTGCAGAGCGGAGTGCCTAGC<br>AGATTTTCTGGCAGCGGCTCCGGCACCGATTTCACCCTGACCATA<br>TCTAGCCTGCAGCCAGAGGACGTGGCCACCTACTATTGCCAGCAG<br>CTGATCTTCTTCCCTCTGACCTTTGGCCAGGGCACCAAGGTGGAA<br>ATCAAGCGTACGGTGGCCGCTCCCAGCGTGTTCATCTTCCCCCCC<br>AGCGACGAGCAGCTGAAGAGTGGCACCGCCAGCGTGGTGTGCCTG<br>CTGAACAACTTCTACCCCGGGAGGCCAAGGTGCAGTGGAAGGTG<br>GACAACGCCCTGCAGAGCGGCAACAGCCAGGAGAGCGTCACCGAG<br>CAGGACAGCAAGGACTCCACCTACAGCCTGAGCAGCACCCTGACC<br>CTGAGCAAGGCCGACTACGAGAAGCATAAGGTGTACGCCTGCGAG<br>GTGACCCACCAGGGCCTGTCCAGCCCCGTGACCAAGAGCTTCAAC<br>AGGGGCGAGTGC |

Y010903_E152C_S375C

| | | |
|---|---|---|
| SEQ ID NO: 206 | HCDR1<br>(Combined) | GFTFSNAWMS |
| SEQ ID NO: 207 | HCDR2<br>(Combined) | RIKSKTDAGTTDYAAPVKG |
| SEQ ID NO: 225 | HCDR3<br>(Combined) | ASHRLHSLFDV |
| SEQ ID NO: 209 | HCDR1<br>(Kabat) | NAVVMS |
| SEQ ID NO: 207 | HCDR2<br>(Kabat) | RIKSKTDAGTTDYAAPVKG |
| SEQ ID NO: 225 | HCDR3<br>(Kabat) | ASHRLHSLFDV |
| SEQ ID NO: 210 | HCDR1<br>(Chothia) | GFTFSNA |
| SEQ ID NO: 211 | HCDR2<br>(Chothia) | KSKTDAGT |
| SEQ ID NO: 225 | HCDR3<br>(Chothia) | ASHRLHSLFDV |
| SEQ ID NO: 212 | HCDR1<br>(IMGT) | GFTFSNAW |
| SEQ ID NO: 213 | HCDR2<br>(IMGT) | IKSKTDAGTT |
| SEQ ID NO: 226 | HCDR3<br>(IMGT) | ARASHRLHSLFDV |
| SEQ ID NO: 227 | VH | EVQLVESGGGLVKPGGSLRLSCAASGFTFSNAWMSWVRQAPGKGL<br>EWVGRIKSKTDAGTTDYAAPVKGRFTISRDDSKNTLYLQMNSLKT<br>EDTAVYYCARASHRLHSLFDVWGQGTLVTVSS |
| SEQ ID NO: 228 | DNA VH | GAAGTGCAGCTGGTGGAATCTGGCGGCGGACTTGTGAAACCTGGC<br>GGCTCTCTGAGACTGAGCTGTGCCGCTTCCGGCTTCACCTTCAGC<br>AATGCCTGGATGAGCTGGGTCCGACAGGCCCCTGGAAAAGGCCTT<br>GAGTGGGTCGGACGGATCAAGAGCAAGACCGATGCCGGCACCACC<br>GATTATGCTGCCCCTGTGAAGGGCAGATTCACCATCAGCAGGGAC<br>GACAGCAAGAACACCCTGTACCTGCAGATGAACAGCCTGAAAACC<br>GAGGACACCGCCGTGTACTACTGTGCCAGAGCCTCTCACAGACTG<br>CACAGCCTGTTTGACGTGTGGGGCCAGGGAACACTGGTCACCGTT<br>AGTTCT |
| SEQ ID NO: 229 | Heavy<br>Chain | EVQLVESGGGLVKPGGSLRLSCAASGFTFSNAWMSWVRQAPGKGL<br>EWVGRIKSKTDAGTTDYAAPVKGRFTISRDDSKNTLYLQMNSLKT<br>EDTAVYYCARASHRLHSLFDVWGQGTLVTVSSASTKGPSVFPLAP<br>SSKSTSGGTAALGCLVKDYFPCPVTVSWNSGALTSGVHTFPAVLQ<br>SSGLYSLSSVVTVPSSSLGTQTYICNVNHKPSNTKVDKRVEPKSC<br>DKTHTCPPCPAPELLGGPSVFLFPPKPKDTLMISRTPEVTCVVVD<br>VSHEDPEVKFNWYVDGVEVHNAKTKPREEQYNSTYRVVSVLTVLH |

TABLE 2-continued

Examples of Anti-PMEL17 Antibodies of the Present Invention

| | | |
|---|---|---|
| | | QDWLNGKEYKCKVSNKALPAPIEKTISKAKGQPREPQVYTLPPSR EEMTKNQVSLTCLVKGFYPCDIAVEWESNGQPENNYKTTPPVLDS DGSFFLYSKLTVDKSRWQQGNVFSCSVMHEALHNHYTQKSLSLSP GK |
| SEQ ID NO: 230 | DNA Heavy Chain | GAAGTGCAGCTGGTGGAATCTGGCGGCGGACTTGTGAAACCTGGC GGCTCTCTGAGACTGAGCTGTGCCGCTTCCGGCTTCACCTTCAGC AATGCCTGGATGAGCTGGGTCCGACAGGCCCCTGGAAAAGGCCTT GAGTGGGTCGGACGGATCAAGAGCAAGACCGATGCCGGCACCACC GATTATGCTGCCCCTGTGAAGGGCAGATTCACCATCAGCAGGGAC GACAGCAAGAACACCCTGTACCTGCAGATGAACAGCCTGAAAACC GAGGACACCGCCGTGTACTACTGTGCCAGAGCCTCTCACAGACTG CACAGCCTGTTTGACGTGTGGGGCCAGGGAACACTGGTCACCGTT AGTTCTGCTAGCACCAAGGGCCCAAGTGTGTTTCCCCTGGCCCCC AGCAGCAAGTCTACTTCCGGCGGAACTGCTGCCCTGGGTTGCCTG GTGAAGGACTACTTCCCCTGTCCCGTGACAGTGTCCTGGAACTCT GGGGCTCTGACTTCCGGCGTGCACACCTTCCCCGCCGTGCTGCAG AGCAGCGGCCTGTACAGCCTGAGCAGCGTGGTGACAGTGCCCTCC AGCTCTCTGGGAACCCAGACCTATATCTGCAACGTGAACCACAAG CCCAGCAACACCAAGGTGGACAAGAGAGTGGAGCCCAAGAGCTGC GACAAGACCCACACCTGCCCCCCCTGCCCAGCTCCAGAACTGCTG GGAGGGCCTTCCGTGTTCCTGTTCCCCCCCAAGCCCAAGGACACC CTGATGATCAGCAGGACCCCCGAGGTGACCTGCGTGGTGGTGGAC GTGTCCCACGAGGACCCAGAGGTGAAGTTCAACTGGTACGTGGAC GGCGTGGAGGTGCACAACGCCAAGACCAAGCCCAGAGAGGAGCAG TACAACAGCACCTACAGGGTGGTGTCCGTGCTGACCGTGCTGCAC CAGGACTGGCTGAACGGCAAAGAATACAAGTGCAAAGTCTCCAAC AAGGCCCTGCCAGCCCCAATCGAAAAGACAATCAGCAAGGCCAAG GGCCAGCCACGGGAGCCCAGGTGTACACCCTGCCCCCCAGCCGG GAGGAGATGACCAAGAACCAGGTGTCCCTGACCTGTCTGGTGAAG GGCTTCTACCCCTGTGATATCGCCGTGGAGTGGGAGAGCAACGGC CAGCCCGAGAACAACTACAAGACCACCCCCCCAGTGCTGGACAGC GACGGCAGCTTCTTCCTGTACAGCAAGCTGACCGTGGACAAGTCC AGGTGGCAGCAGGGCAACGTGTTCAGCTGCAGCGTGATGCACGAG GCCCTGCACAACCACTACACCCAGAAGTCCCTGAGCCTGAGCCCC GGCAAG |
| SEQ ID NO: 136 | LCDR1 (Combined) | RASQSISSWLA |
| SEQ ID NO: 137 | LCDR2 (Combined) | DASSLES |
| SEQ ID NO: 231 | LCDR3 (Combined) | QQGLFYPHT |
| SEQ ID NO: 136 | LCDR1 (Kabat) | RASQSISSWLA |
| SEQ ID NO: 137 | LCDR2 (Kabat) | DASSLES |
| SEQ ID NO: 231 | LCDR3 (Kabat) | QQGLFYPHT |
| SEQ ID NO: 139 | LCDR1 (Chothia) | SQSISSW |
| SEQ ID NO: 140 | LCDR2 (Chothia) | DAS |
| SEQ ID NO: 232 | LCDR3 (Chothia) | GLFYPH |
| SEQ ID NO: 142 | LCDR1 (IMGT) | QSISSW |
| SEQ ID NO: 140 | LCDR2 (IMGT) | DAS |
| SEQ ID NO: 231 | LCDR3 (IMGT) | QQGLFYPHT |
| SEQ ID NO: 233 | VL | DIQMTQSPSTLSASVGDRVTITCRASQSISSWLAWYQQKPGKAPK LLIYDASSLESGVPSRFSGSGSGTEFTLTISSLQPEDFATYYCQQ GLFYPHTFGQGTKVEIK |

TABLE 2-continued

Examples of Anti-PMEL17 Antibodies of the Present Invention

| SEQ ID NO: 234 | DNA VL | GACATCCAGATGACACAGAGCCCCAGCACACTGTCTGCCAGCGTG<br>GGAGACAGAGTGACCATCACCTGTAGAGCCAGCCAGAGCATCTCC<br>TCTTGGCTGGCCTGGTATCAGCAGAAGCCTGGCAAGGCCCCTAAG<br>CTGCTGATCTACGATGCCAGCAGCCTGGAAAGCGGCGTGCCAAGC<br>AGATTTTCTGGCAGCGGCTCTGGCACCGAGTTCACCCTGACCATA<br>TCTAGCCTGCAGCCAGAGGACTTCGCCACCTACTATTGTCAGCAG<br>GGCCTGTTCTACCCTCACACCTTTGGCCAGGGCACCAAGGTGGAA<br>ATCAAG |
| --- | --- | --- |
| SEQ ID NO: 235 | Light Chain | DIQMTQSPSTLSASVGDRVTITCRASQSISSWLAWYQQKPGKAPK<br>LLIYDASSLESGVPSRFSGSGSGTEFTLTISSLQPEDFATYYCQQ<br>GLFYPHTFGQGTKVEIKRTVAAPSVFIFPPSDEQLKSGTASVVCL<br>LNNFYPREAKVQWKVDNALQSGNSQESVTEQDSKDSTYSLSSTLT<br>LSKADYEKHKVYACEVTHQGLSSPVTKSFNRGEC |
| SEQ ID NO: 236 | DNA Light Chain | GACATCCAGATGACACAGAGCCCCAGCACACTGTCTGCCAGCGTG<br>GGAGACAGAGTGACCATCACCTGTAGAGCCAGCCAGAGCATCTCC<br>TCTTGGCTGGCCTGGTATCAGCAGAAGCCTGGCAAGGCCCCTAAG<br>CTGCTGATCTACGATGCCAGCAGCCTGGAAAGCGGCGTGCCAAGC<br>AGATTTTCTGGCAGCGGCTCTGGCACCGAGTTCACCCTGACCATA<br>TCTAGCCTGCAGCCAGAGGACTTCGCCACCTACTATTGTCAGCAG<br>GGCCTGTTCTACCCTCACACCTTTGGCCAGGGCACCAAGGTGGAA<br>ATCAAGCGTACGGTGGCCGCTCCCAGCGTGTTCATCTTCCCCCCC<br>AGCGACGAGCAGCTGAAGAGTGGCACCGCCAGCGTGGTGTGCCTG<br>CTGAACAACTTCTACCCCGGGAGGCCAAGGTGCAGTGGAAGGTG<br>GACAACGCCCTGCAGAGCGGCAACAGCCAGGAGAGCGTCACCGAG<br>CAGGACAGCAAGGACTCCACCTACAGCCTGAGCAGCACCCTGACC<br>CTGAGCAAGGCCGACTACGAGAAGCATAAGGTGTACGCCTGCGAG<br>GTGACCCACCAGGGCCTGTCCAGCCCCGTGACCAAGAGCTTCAAC<br>AGGGGCGAGTGC |

Y010906 E252C_S375C

| SEQ ID NO: 206 | HCDR1 (Combined) | GFTFSNAWMS |
| --- | --- | --- |
| SEQ ID NO: 207 | HCDR2 (Combined) | RIKSKTDAGTTDYAAPVKG |
| SEQ ID NO: 237 | HCDR3 (Combined) | DEYPWGWFDV |
| SEQ ID NO: 209 | HCDR1 (Kabat) | NAWMS |
| SEQ ID NO: 207 | HCDR2 (Kabat) | RIKSKTDAGTTDYAAPVKG |
| SEQ ID NO: 237 | HCDR3 (Kabat) | DEYPWGWFDV |
| SEQ ID NO: 210 | HCDR1 (Chothia) | GFTFSNA |
| SEQ ID NO: 211 | HCDR2 (Chothia) | KSKTDAGT |
| SEQ ID NO: 237 | HCDR3 (Chothia) | DEYPWGWFDV |
| SEQ ID NO: 212 | HCDR1 (IMGT) | GFTFSNAW |
| SEQ ID NO: 213 | HCDR2 (IMGT) | IKSKTDAGTT |
| SEQ ID NO: 238 | HCDR3 (IMGT) | ARDEYPWGWFDV |
| SEQ ID NO: 239 | VH | EVQLVESGGGLVKPGGSLRLSCAASGFTFSNAWMSWVRQAPGKGL<br>EWVGRIKSKTDAGTTDYAAPVKGRFTISRDDSKNTLYLQMNSLKT<br>EDTAVYYCARDEYPWGWFDVWGQGTLVTVSS |
| SEQ ID NO: 240 | DNA VH | GAAGTGCAGCTGGTGGAATCTGGCGGCGGACTTGTGAAACCTGGC<br>GGCTCTCTGAGACTGAGCTGTGCCGCTTCCGGCTTCACCTTCAGC<br>AATGCCTGGATGAGCTGGGTCCGACAGGCCCCTGGAAAAGGCCTT<br>GAGTGGGTCGGACGGATCAAGAGCAAGACCGATGCCGGCACCACC<br>GATTATGCTGCCCCTGTGAAGGGCAGATTCACCATCAGCAGGGAC |

TABLE 2-continued

Examples of Anti-PMEL17 Antibodies of the Present Invention

| | | |
|---|---|---|
| | | GACAGCAAGAACACCCTGTACCTGCAGATGAACAGCCTGAAAACC<br>GAGGACACCGCCGTGTACTACTGCGCCAGAGATGAGTACCCCTGG<br>GGATGGTTCGATGTGTGGGGACAGGGAACCCTGGTCACCGTTAGT<br>TCT |
| SEQ ID NO: 241 | Heavy<br>Chain | EVQLVESGGGLVKPGGSLRLSCAASGFTFSNAWMSWVRQAPGKGL<br>EWVGRIKSKTDAGTTDYAAPVKGRFTISRDDSKNTLYLQMNSLKT<br>EDTAVYYCARDEYPWGWFDVWGQGTLVTVSSASTKGPSVFPLAPS<br>SKSTSGGTAALGCLVKDYFPCPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPCDIAVEWESNGQPENNYKTTPPVLDSD<br>GSFFLYSKLTVDKSRWQQGNVFSCSVMHEALHNHYTQKSLSLSPG<br>K |
| SEQ ID NO: 242 | DNA Heavy<br>Chain | GAAGTGCAGCTGGTGGAATCTGGCGGCGGACTTGTGAAACCTGGC<br>GGCTCTCTGAGACTGAGCTGTGCCGCTTCCGGCTTCACCTTCAGC<br>AATGCCTGGATGAGCTGGGTCCGACAGGCCCCTGGAAAAGGCCTT<br>GAGTGGGTCGGACGGATCAAGAGCAAGACCGATGCCGGCACCACC<br>GATTATGCTGCCCCTGTGAAGGGCAGATTCACCATCAGCAGGGAC<br>GACAGCAAGAACACCCTGTACCTGCAGATGAACAGCCTGAAAACC<br>GAGGACACCGCCGTGTACTACTGCGCCAGAGATGAGTACCCCTGG<br>GGATGGTTCGATGTGTGGGGACAGGGAACCCTGGTCACCGTTAGT<br>TCTGCTAGCACCAAGGGCCCAAGTGTGTTTCCCCTGGCCCCCAGC<br>AGCAAGTCTACTTCCGGCGGAACTGCTGCCCTGGGTTGCCTGGTG<br>AAGGACTACTTCCCCTGTCCCGTGACAGTGTCCTGGAACTCTGGG<br>GCTCTGACTTCCGGCGTGCACACCTTCCCCGCCGTGCTGCAGAGC<br>AGCGGCCTGTACAGCCTGAGCAGCGTGGTGACAGTGCCCTCCAGC<br>TCTCTGGGAACCCAGACCTATATCTGCAACGTGAACCACAAGCCC<br>AGCAACACCAAGGTGGACAAGAGAGTGGAGCCCAAGAGCTGCGAC<br>AAGACCCACACCTGCCCCCCCTGCCCAGCTCCAGAACTGCTGGGA<br>GGGCCTTCCGTGTTCCTGTTCCCCCCCAAGCCCAAGGACACCCTG<br>ATGATCAGCAGGACCCCCGAGGTGACCTGCGTGGTGGTGGACGTG<br>TCCCACGAGGACCCAGAGGTGAAGTTCAACTGGTACGTGGACGGC<br>GTGGAGGTGCACAACGCCAAGACCAAGCCCAGAGAGGAGCAGTAC<br>AACAGCACCTACAGGGTGGTGTCCGTGCTGACCGTGCTGCACCAG<br>GACTGGCTGAACGGCAAAGAATACAAGTGCAAAGTCTCCAACAAG<br>GCCCCTGCCAGCCCCAATCGAAAAGACAATCAGCAAGGCCAAGGGC<br>CAGCCACGGGAGCCCCAGGTGTACACCCTGCCCCCCAGCCGGGAG<br>GAGATGACCAAGAACCAGGTGTCCCTGACCTGTCTGGTGAAGGGC<br>TTCTACCCCTGTGATATCGCCGTGGAGTGGGAGAGCAACGGCCAG<br>CCCGAGAACAACTACAAGACCACCCCCCAGTGCTGGACAGCGAC<br>GGCAGCTTCTTCCTGTACAGCAAGCTGACCGTGGACAAGTCCAGG<br>TGGCAGCAGGGCAACGTGTTCAGCTGCAGCGTGATGCACGAGGCC<br>CTGCACAACCACTACACCCAGAAGTCCCTGAGCCTGAGCCCCGGC<br>AAG |
| SEQ ID NO: 243 | LCDR1<br>(Combined) | RASQGISSWLA |
| SEQ ID NO: 47 | LCDR2<br>(Combined) | AASSLQS |
| SEQ ID NO: 244 | LCDR3<br>(Combined) | QQYIFYPLT |
| SEQ ID NO: 243 | LCDR1<br>(Kabat) | RASQGISSWLA |
| SEQ ID NO: 47 | LCDR2<br>(Kabat) | AASSLQS |
| SEQ ID NO: 244 | LCDR3<br>(Kabat) | QQYIFYPLT |
| SEQ ID NO: 245 | LCDR1<br>(Chothia) | SQGISSW |
| SEQ ID NO: 50 | LCDR2<br>(Chothia) | AAS |
| SEQ ID NO: 246 | LCDR3<br>(Chothia) | YIFYPL |
| SEQ ID NO: 247 | LCDR1<br>(IMGT) | QGISSW |

TABLE 2-continued

Examples of Anti-PMEL17 Antibodies of the Present Invention

| SEQ ID NO: 50 | LCDR2 (IMGT) | AAS |
|---|---|---|
| SEQ ID NO: 244 | LCDR3 (IMGT) | QQYIFYPLT |
| SEQ ID NO: 248 | VL | DIQMTQSPSSVSASVGDRVTITCRASQGISSWLAWYQQKPGKAPK LLIYAASSLQSGVPSRFSGSGSGTDFTLTISSLQPEDFATYYCQQ YIFYPLTFGQGTKVEIK |
| SEQ ID NO: 249 | DNA VL | GACATCCAGATGACACAGAGCCCTAGCTCCGTGTCTGCCAGCGTG GGAGACAGAGTGACCATCACCTGTAGAGCCAGCCAGGGCATCTCT TCTTGGCTGGCCTGGTATCAGCAGAAGCCTGGCAAGGCCCCTAAG CTGCTGATCTATGCCGCTTCCAGTCTGCAGAGCGGCGTGCCAAGC AGATTTTCTGGCAGCGGCTCTGGCACCGACTTCACCCTGACCATA TCTAGCCTGCAGCCAGAGGACTTCGCCACCTACTACTGCCAGCAG TACATCTTCTACCCTCTGACCTTCGGCCAGGGCACCAAGGTGGAA ATCAAG |
| SEQ ID NO: 250 | Light Chain | DIQMTQSPSSVSASVGDRVTITCRASQGISSWLAWYQQKPGKAPK LLIYAASSLQSGVPSRFSGSGSGTDFTLTISSLQPEDFATYYCQQ YIFYPLTFGQGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| SEQ ID NO: 251 | DNA Light Chain | GACATCCAGATGACACAGAGCCCTAGCTCCGTGTCTGCCAGCGTG GGAGACAGAGTGACCATCACCTGTAGAGCCAGCCAGGGCATCTCT TCTTGGCTGGCCTGGTATCAGCAGAAGCCTGGCAAGGCCCCTAAG CTGCTGATCTATGCCGCTTCCAGTCTGCAGAGCGGCGTGCCAAGC AGATTTTCTGGCAGCGGCTCTGGCACCGACTTCACCCTGACCATA TCTAGCCTGCAGCCAGAGGACTTCGCCACCTACTACTGCCAGCAG TACATCTTCTACCCTCTGACCTTCGGCCAGGGCACCAAGGTGGAA ATCAAGCGTACGGTGGCCGCTCCCAGCGTGTTCATCTTCCCCCCC AGCGACGAGCAGCTGAAGAGTGGCACCGCCAGCGTGGTGTGCCTG CTGAACAACTTCTACCCCCGGGAGGCCAAGGTGCAGTGGAAGGTG GACAACGCCCTGCAGAGCGGCAACAGCCAGGAGAGCGTCACCGAG CAGGACAGCAAGGACTCCACCTACAGCCTGAGCAGCACCCTGACC CTGAGCAAGGCCGACTACGAGAAGCATAAGGTGTACGCCTGCGAG GTGACCCACCAGGGCCTGTCCAGCCCCGTGACCAAGAGCTTCAAC AGGGGCGAGTGC |
| Y010910 E152C_S375C | | |
| SEQ ID NO: 206 | HCDR1 (Combined) | GFTFSNAWMS |
| SEQ ID NO: 207 | HCDR2 (Combined) | RIKSKTDAGTTDYAAPVKG |
| SEQ ID NO: 252 | HCDR3 (Combined) | VASPSAPGGFDY |
| SEQ ID NO: 209 | HCDR1 (Kabat) | NAWMS |
| SEQ ID NO: 207 | HCDR2 (Kabat) | RIKSKTDAGTTDYAAPVKG |
| SEQ ID NO: 252 | HCDR3 (Kabat) | VASPSAPGGFDY |
| SEQ ID NO: 210 | HCDR1 (Chothia) | GFTFSNA |
| SEQ ID NO: 211 | HCDR2 (Chothia) | KSKTDAGT |
| SEQ ID NO: 252 | HCDR3 (Chothia) | VASPSAPGGFDY |
| SEQ ID NO: 212 | HCDR1 (IMGT) | GFTFSNAW |
| SEQ ID NO: 213 | HCDR2 (IMGT) | IKSKTDAGTT |
| SEQ ID NO: 253 | HCDR3 (IMGT) | ARVASPSAPGGFDY |

TABLE 2-continued

Examples of Anti-PMEL17 Antibodies of the Present Invention

| SEQ ID NO: 254 | VH | EVQLVESGGGLVKPGGSLRLSCAASGFTFSNAWMSWVRQAPGKGL
EWVGRIKSKTDAGTTDYAAPVKGRFTISRDDSKNTLYLQMNSLKT
EDTAVYYCARVASPSAPGGFDYWGQGTLVTVSS |
|---|---|---|
| SEQ ID NO: 255 | DNA VH | GAAGTGCAGCTGGTGGAATCTGGCGGCGGACTTGTGAAACCTGGC
GGCTCTCTGAGACTGAGCTGTGCCGCTTCCGGCTTCACCTTCAGC
AATGCCTGGATGAGCTGGGTCCGACAGGCCCCTGGAAAAGGCCTT
GAGTGGGTCGGACGGATCAAGAGCAAGACCGATGCCGGCACCACC
GATTATGCTGCCCCTGTGAAGGGCAGATTCACCATCAGCAGGGAC
GACAGCAAGAACACCCTGTACCTGCAGATGAACAGCCTGAAAACC
GAGGACACCGCCGTGTACTACTGCGCCAGAGTGGCTTCTCCTTCT
GCTCCCGGCGGATTCGATTATTGGGGCCAGGGAACACTGGTCACC
GTGTCTAGT |
| SEQ ID NO: 256 | Heavy Chain | EVQLVESGGGLVKPGGSLRLSCAASGFTFSNAWMSWVRQAPGKGL
EWVGRIKSKTDAGTTDYAAPVKGRFTISRDDSKNTLYLQMNSLKT
EDTAVYYCARVASPSAPGGFDYWGQGTLVTVSSASTKGPSVFPLA
PSSKSTSGGTAALGCLVKDYFPCPVTVSWNSGALTSGVHTFPAVL
QSSGLYSLSSVVTVPSSSLGTQTYICNVNHKPSNTKVDKRVEPKS
CDKTHTCPPCPAPELLGGPSVFLFPPKPKDTLMISRTPEVTCVVV
DVSHEDPEVKFNWYVDGVEVHNAKTKPREEQYNSTYRVVSVLTVL
HQDWLNGKEYKCKVSNKALPAPIEKTISKAKGQPREPQVYTLPPS
REEMTKNQVSLTCLVKGFYPCDIAVEWESNGQPENNYKTTPPVLD
SDGSFFLYSKLTVDKSRWQQGNVFSCSVMHEALHNHYTQKSLSLS
PGK |
| SEQ ID NO: 257 | DNA Heavy Chain | GAAGTGCAGCTGGTGGAATCTGGCGGCGGACTTGTGAAACCTGGC
GGCTCTCTGAGACTGAGCTGTGCCGCTTCCGGCTTCACCTTCAGC
AATGCCTGGATGAGCTGGGTCCGACAGGCCCCTGGAAAAGGCCTT
GAGTGGGTCGGACGGATCAAGAGCAAGACCGATGCCGGCACCACC
GATTATGCTGCCCCTGTGAAGGGCAGATTCACCATCAGCAGGGAC
GACAGCAAGAACACCCTGTACCTGCAGATGAACAGCCTGAAAACC
GAGGACACCGCCGTGTACTACTGCGCCAGAGTGGCTTCTCCTTCT
GCTCCCGGCGGATTCGATTATTGGGGCCAGGGAACACTGGTCACC
GTGTCTAGTGCTAGCACCAAGGGCCCAAGTGTGTTTCCCCTGGCC
CCCAGCAGCAAGTCTACTTCCGGCGGAACTGCTGCCCTGGGTTGC
CTGGTGAAGGACTACTTCCCCTGTCCCGTGACAGTGTCCTGGAAC
TCTGGGGCTCTGACTTCCGGCGTGCACACCTTCCCCGCCGTGCTG
CAGAGCAGCGGCCTGTACAGCCTGAGCAGCGTGGTGACAGTGCCC
TCCAGCTCTCTGGGAACCCAGACCTATATCTGCAACGTGAACCAC
AAGCCCAGCAACACCAAGGTGGACAAGAGAGTGGAGCCCAAGAGC
TGCGACAAGACCCACACCTGCCCCCCCTGCCCAGCTCCAGAACTG
CTGGGAGGGCCTTCCGTGTTCCTGTTCCCCCCCAAGCCCAAGGAC
ACCCTGATGATCAGCAGGACCCCCGAGGTGACCTGCGTGGTGGTG
GACGTGTCCCACGAGGACCCAGAGGTGAAGTTCAACTGGTACGTG
GACGGCGTGGAGGTGCACAACGCCAAGACCAAGCCCAGAGAGGAG
CAGTACAACAGCACCTACAGGGTGGTGTCCGTGCTGACCGTGCTG
CACCAGGACTGGCTGAACGGCAAAGAATACAAGTGCAAAGTCTCC
AACAAGGCCCTGCCAGCCCCAATCGAAAAGACAATCAGCAAGGCC
AAGGGCCAGCCACGGGAGCCCCAGGTGTACACCCTGCCCCCCAGC
CGGGAGGAGATGACCAAGAACCAGGTGTCCCTGACCTGTCTGGTG
AAGGGCTTCTACCCCTGTGATATCGCCGTGGAGTGGGAGAGCAAT
GGCCAGCCCGAGAACAACTACAAGACCACCCCCCCAGTGCTGGAC
AGCGACGGCAGCTTCTTCCTGTACAGCAAGCTGACCGTGGACAAG
TCCAGGTGGCAGCAGGGCAACGTGTTCAGCTGCAGCGTGATGCAC
GAGGCCCTGCACAACCACTACACCCAGAAGTCCCTGAGCCTGAGC
CCCGGCAAG |
| SEQ ID NO: 153 | LCDR1 (Combined) | RASQGISNYLA |
| SEQ ID NO: 154 | LCDR2 (Combined) | AASTLQS |
| SEQ ID NO: 258 | LCDR3 (Combined) | QQSLFAPFT |
| SEQ ID NO: 153 | LCDR1 (Kabat) | RASQGISNYLA |
| SEQ ID NO: 154 | LCDR2 (Kabat) | AASTLQS |
| SEQ ID NO: 258 | LCDR3 (Kabat) | QQSLFAPFT |
| SEQ ID NO: 156 | LCDR1 (Chothia) | SQGISNY |

TABLE 2-continued

Examples of Anti-PMEL17 Antibodies of the Present Invention

| | | |
|---|---|---|
| SEQ ID NO: 50 | LCDR2 (Chothia) | AAS |
| SEQ ID NO: 259 | LCDR3 (Chothia) | SLFAPF |
| SEQ ID NO: 158 | LCDR1 (IMGT) | QGISNY |
| SEQ ID NO: 50 | LCDR2 (IMGT) | AAS |
| SEQ ID NO: 258 | LCDR3 (IMGT) | QQSLFAPFT |
| SEQ ID NO: 260 | VL | DIQMTQSPSSLSASVGDRVTITCRASQGISNYLAWYQQKPGKVPK LLIYAASTLQSGVPSRFSGSGSGTDFTLTISSLQPEDVATYYCQQ SLFAPFTFGQGTKVEIK |
| SEQ ID NO: 261 | DNA VL | GACATCCAGATGACACAGAGCCCTAGCAGCCTGTCTGCCAGCGTG GGAGACAGAGTGACCATCACCTGTAGAGCCAGCCAGGGCATCAGC AACTACCTGGCCTGGTATCAGCAGAAACCCGGCAAGGTGCCCAAG CTGCTGATCTACGCTGCCAGCACACTGCAGAGCGGAGTGCCTAGC AGATTTTCTGGCAGCGGCTCCGGCACCGATTTCACCCTGACCATA TCTAGCCTGCAGCCAGAGGACGTGGCCACCTACTACTGTCAGCAG AGCCTGTTCGCCCCTTTCACCTTTGGCCAGGGCACCAAGGTGGAA ATCAAG |
| SEQ ID NO: 262 | Light Chain | DIQMTQSPSSLSASVGDRVTITCRASQGISNYLAWYQQKPGKVPK LLIYAASTLQSGVPSRFSGSGSGTDFTLTISSLQPEDVATYYCQQ SLFAPFTFGQGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| SEQ ID NO: 263 | DNA Light Chain | GACATCCAGATGACACAGAGCCCTAGCAGCCTGTCTGCCAGCGTG GGAGACAGAGTGACCATCACCTGTAGAGCCAGCCAGGGCATCAGC AACTACCTGGCCTGGTATCAGCAGAAACCCGGCAAGGTGCCCAAG CTGCTGATCTACGCTGCCAGCACACTGCAGAGCGGAGTGCCTAGC AGATTTTCTGGCAGCGGCTCCGGCACCGATTTCACCCTGACCATA TCTAGCCTGCAGCCAGAGGACGTGGCCACCTACTACTGTCAGCAG AGCCTGTTCGCCCCTTTCACCTTTGGCCAGGGCACCAAGGTGGAA ATCAAGCGTACGGTGGCCGCTCCCAGCGTGTTCATCTTCCCCCCC AGCGACGAGCAGCTGAAGAGTGGCACCGCCAGCGTGGTGTGCCTG CTGAACAACTTCTACCCCCGGGAGGCCAAGGTGCAGTGGAAGGTG GACAACGCCCTGCAGAGCGGCAACAGCCAGGAGAGCGTCACCGAG CAGGACAGCAAGGACTCCACCTACAGCCTGAGCAGCACCCTGACC CTGAGCAAGGCCGACTACGAGAAGCATAAGGTGTACGCCTGCGAG GTGACCCACCAGGGCCTGTCCAGCCCCGTGACCAAGAGCTTCAAC AGGGGCGAGTGC |

Other antibodies of the invention include those where the amino acids or nucleic acids encoding the amino acids have been mutated, yet have at least 60, 70, 80, 90 or 95 percent identity to the sequences described in Table 2. In some embodiments, 1, 2, 3, 4 or 5 amino acids have been mutated in the variable regions when compared with the variable regions depicted in the sequence described in Table 2, while retaining substantially the same therapeutic activity as the antibodies listed in Table 2.

Since each of these antibodies can bind to PMEL17, the VH, VL, full length light chain, and full length heavy chain sequences (amino acid sequences and the nucleotide sequences encoding the amino acid sequences) can be "mixed and matched" to create other PMEL17-binding antibodies of the invention. Such "mixed and matched" PMEL17-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence. Accordingly, in one aspect, the invention provides an isolated monoclonal antibody or antigen binding region thereof having: a heavy chain variable region comprising an amino acid sequence selected from the group consisting of SEQ ID NOs: 10, 42, 64, 88, 112, 132, 149, 165, 184, 196, 215, 227, 239 or 254; and a light chain variable region comprising an amino acid sequence selected from the group consisting of SEQ ID NOs: 21, 25, 29, 53, 75, 99, 119, 143, 159, 171, 190, 202, 221, 233, 248 or 260; wherein the antibody specifically binds to PMEL17.

In another aspect, the invention provides (i) an isolated monoclonal antibody having: a full length heavy chain comprising an amino acid sequence that has been optimized for expression in the cell of a mammalian expression system selected from the group consisting of SEQ ID NOs: 12, 44, 66, 90, 114, 134, 151, 167, 186, 198, 217, 229, 241 or 256; and a full length light chain comprising an amino acid sequence that has been optimized for expression in the cell of a mammalian selected from the group consisting of SEQ ID NOs: 23, 27, 31, 55, 77, 101, 121, 145, 161, 173, 192, 204, 223, 235, 250 or 262; or (ii) a functional protein comprising an antigen binding portion thereof.

In another aspect, the present invention provides PMEL17-binding antibodies that comprise the heavy chain and light chain CDR1s, CDR2s and CDR3s as described in Table 2, or combinations thereof. The amino acid sequences of the VH CDR1s of the antibodies are shown, for example, in SEQ ID NOs: 1, 4, 5, 7, 33, 36, 37, 39, 57, 60, 79, 82, 83, 85, 103, 106, 107, 109, 123, 126, 127, 129, 175, 178, 179, 181, 206, 209, 210, and 212. The amino acid sequences of the VH CDR2s of the antibodies and are shown, for example, in SEQ ID NOs: 2, 6, 8, 34, 38, 40, 58, 61, 62, 80, 84, 86, 104, 108, 110, 124, 128, 130, 176, 180, 182, 207, 211, and 213. The amino acid sequences of the VH CDR3s of the antibodies are shown, for example, in SEQ ID NOs: 3, 9, 35, 41, 59, 63, 81, 87, 105, 111, 125, 131, 147, 148, 163, 164, 177, 183, 194, 195, 208, 214, 225, 226, 237, 238, 252, and 253. The amino acid sequences of the VL CDR1s of the antibodies are shown, for example, in SEQ ID NOs: 14, 17, 20, 46, 49, 52, 68, 71, 74, 92, 95, 98, 116, 136, 139, 142, 153, 156, 158, 243, 245, and 247. The amino acid sequences of the VL CDR2s of the antibodies are shown, for example, in SEQ ID Nos: 15, 18, 47, 50, 69, 72, 93, 96, 137, 140, and 154. The amino acid sequences of the VL CDR3s of the antibodies are shown, for example, in SEQ ID NOs: 16, 19, 48, 51, 70, 73, 94, 97, 117, 118, 138, 141, 155, 157, 169, 170188, 189, 200, 201, 219, 220, 231, 232, 244, 246, 258, and 259.

Given that each of these antibodies can bind to PMEL17 and that antigen-binding specificity is provided primarily by the CDR1, 2 and 3 regions, the VH CDR1, CDR2 and CDR3 sequences and VL CDR1, CDR2 and CDR3 sequences can be "mixed and matched" (i.e., CDRs from different antibodies can be mixed and matched. Such "mixed and matched" PMEL17-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention.

Accordingly, in some embodiments, the present invention provides an isolated monoclonal antibody or antigen binding region thereof comprising a heavy chain CDR1 comprising an amino acid sequence selected from the group consisting of SEQ ID NOs: 1, 4, 5, 7, 33, 36, 37, 39, 57, 60, 79, 82, 83, 85, 103, 106, 107, 109, 123, 126, 127, 129, 175, 178, 179, 181, 206, 209, 210, and 212; a heavy chain CDR2 comprising an amino acid sequence selected from the group consisting of SEQ ID NOs: 2, 6, 8, 34, 38, 40, 58, 61, 62, 80, 84, 86, 104, 108, 110, 124, 128, 130, 176, 180, 182, 207, 211, and 213; a heavy chain CDR3 comprising an amino acid sequence selected from the group consisting of SEQ ID NOs: 3, 9, 35, 41, 59, 63, 81, 87, 105, 111, 125, 131, 147, 148, 163, 164, 177, 183, 194, 195, 208, 214, 225, 226, 237, 238, 252, and 253; a light chain CDR1 comprising an amino acid sequence selected from the group consisting of SEQ ID NOs: 14, 17, 20, 46, 49, 52, 68, 71, 74, 92, 95, 98, 116, 136, 139, 142, 153, 156, 158, 243, 245, and 247; a light chain CDR2 comprising an amino acid sequence selected from the group consisting of SEQ ID NOs: 15, 18, 47, 50, 69, 72, 93, 96, 137, 140, and 154; and a light chain CDR3 comprising an amino acid sequence selected from the group consisting of SEQ ID NOs: 16, 19, 48, 51, 70, 73, 94, 97, 117, 118, 138, 141, 155, 157, 169, 170, 188, 189, 200, 201, 219, 220, 231, 232, 244, 246, 258, and 259; wherein the antibody specifically binds PMEL17.

In a specific embodiment, an antibody or antibody fragment (e.g., antigen binding fragments) that specifically binds to PMEL17 comprises a heavy chain CDR1 of SEQ ID NO:1, 4, 5 or 7, a heavy chain CDR2 of SEQ ID NO:2, 6 or 8; a heavy chain CDR3 of SEQ ID NO:3 or 9; a light chain CDR1 of SEQ ID NO:14, 17 or 20; a light chain CDR2 of SEQ ID NO:15 or 18; and a light chain CDR3 of SEQ ID NO:16 or 19.

In a specific embodiment, an antibody or antibody fragment (e.g., antigen binding fragments) that specifically binds to PMEL17 comprises a heavy chain CDR1 of SEQ ID NO:33, 36, 37 or 39, a heavy chain CDR2 of SEQ ID NO:34, 38 or 40; a heavy chain CDR3 of SEQ ID NO:35 or 41; a light chain CDR1 of SEQ ID NO:46, 49 or 52; a light chain CDR2 of SEQ ID NO:47 or 50; and a light chain CDR3 of SEQ ID NO:48 or 51.

In a specific embodiment, an antibody or antibody fragment (e.g., antigen binding fragments) that specifically binds to PMEL17 comprises a heavy chain CDR1 of SEQ ID NO:5, 7, 57 or 60, a heavy chain CDR2 of SEQ ID NO:58, 61 or 62; a heavy chain CDR3 of SEQ ID NO:59 or 63; a light chain CDR1 of SEQ ID NO:68, 71 or 74; a light chain CDR2 of SEQ ID NO:69 or 72; and a light chain CDR3 of SEQ ID NO:70 or 73.

In a specific embodiment, an antibody or antibody fragment (e.g., antigen binding fragments) that specifically binds to PMEL17 comprises a heavy chain CDR1 of SEQ ID NO:79, 82, 83 or 85, a heavy chain CDR2 of SEQ ID NO:80, 84 or 86; a heavy chain CDR3 of SEQ ID NO:81 or 87; a light chain CDR1 of SEQ ID NO:92, 95 or 98; a light chain CDR2 of SEQ ID NO:93 or 96; and a light chain CDR3 of SEQ ID NO:94 or 97.

In a specific embodiment, an antibody or antibody fragment (e.g., antigen binding fragments) that specifically binds to PMEL17 comprises a heavy chain CDR1 of SEQ ID NO:103, 106, 107 or 109, a heavy chain CDR2 of SEQ ID NO:104, 108 or 110; a heavy chain CDR3 of SEQ ID NO:105 or 111; a light chain CDR1 of SEQ ID NO:49, 52 or 116; a light chain CDR2 of SEQ ID NO:47 or 50; and a light chain CDR3 of SEQ ID NO:117 or 118.

In a specific embodiment, an antibody or antibody fragment (e.g., antigen binding fragments) that specifically binds to PMEL17 comprises a heavy chain CDR1 of SEQ ID NO:123, 126, 127 or 129, a heavy chain CDR2 of SEQ ID NO:124, 128 or 130; a heavy chain CDR3 of SEQ ID NO:125 or 131; a light chain CDR1 of SEQ ID NO:136, 139 or 142; a light chain CDR2 of SEQ ID NO:137 or 140; and a light chain CDR3 of SEQ ID NO:138 or 141.

In a specific embodiment, an antibody or antibody fragment (e.g., antigen binding fragments) that specifically binds to PMEL17 comprises a heavy chain CDR1 of SEQ ID NO:123, 126, 127 or 129, a heavy chain CDR2 of SEQ ID NO:124, 128 or 130; a heavy chain CDR3 of SEQ ID NO:147 or 148; a light chain CDR1 of SEQ ID NO:153, 156 or 158; a light chain CDR2 of SEQ ID NO:50 or 154; and a light chain CDR3 of SEQ ID NO:155 or 157.

In a specific embodiment, an antibody or antibody fragment (e.g., antigen binding fragments) that specifically binds to PMEL17 comprises a heavy chain CDR1 of SEQ ID NO:103, 106, 107 or 109, a heavy chain CDR2 of SEQ ID NO:104, 108 or 110; a heavy chain CDR3 of SEQ ID NO:163 or 164; a light chain CDR1 of SEQ ID NO:49, 52 or 116; a light chain CDR2 of SEQ ID NO:47 or 50; and a light chain CDR3 of SEQ ID NO:169 or 170.

In a specific embodiment, an antibody or antibody fragment (e.g., antigen binding fragments) that specifically binds to PMEL17 comprises a heavy chain CDR1 of SEQ ID NO:175, 178, 179 or 181, a heavy chain CDR2 of SEQ ID NO:176, 180 or 182; a heavy chain CDR3 of SEQ ID NO:177 or 183; a light chain CDR1 of SEQ ID NO:49, 52 or 116; a light chain CDR2 of SEQ ID NO:47 or 50; and a light chain CDR3 of SEQ ID NO:188 or 189.

In a specific embodiment, an antibody or antibody fragment (e.g., antigen binding fragments) that specifically binds to PMEL17 comprises a heavy chain CDR1 of SEQ ID NO: 103, 106, 107 or 109, a heavy chain CDR2 of SEQ ID NO: 104, 108 or 110; a heavy chain CDR3 of SEQ ID NO:194 or 195; a light chain CDR1 of SEQ ID NO: 49, 52 or 116; a light chain CDR2 of SEQ ID NO: 47 or 50; and a light chain CDR3 of SEQ ID NO:200 or 201.

In a specific embodiment, an antibody or antibody fragment (e.g., antigen binding fragments) that specifically binds to PMEL17 comprises a heavy chain CDR1 of SEQ ID NO:206, 209, 210 or 212, a heavy chain CDR2 of SEQ ID NO:207, 211 or 213; a heavy chain CDR3 of SEQ ID NO:208 or 214; a light chain CDR1 of SEQ ID NO:153, 156 or 158; a light chain CDR2 of SEQ ID NO:50 or 154; and a light chain CDR3 of SEQ ID NO:219 or 220.

In a specific embodiment, an antibody or antibody fragment (e.g., antigen binding fragments) that specifically binds to PMEL17 comprises a heavy chain CDR1 of SEQ ID NO: 206, 209, 210 or 212, a heavy chain CDR2 of SEQ ID NO: 207, 211 or 213; a heavy chain CDR3 of SEQ ID NO:225 or 226; a light chain CDR1 of SEQ ID NO:136, 139 or 142; a light chain CDR2 of SEQ ID NO:137 or 140; and a light chain CDR3 of SEQ ID NO:231 or 232.

In a specific embodiment, an antibody or antibody fragment (e.g., antigen binding fragments) that specifically binds to PMEL17 comprises a heavy chain variable region that comprises an HCDR1 of SEQ ID NO: 206, 209, 210 or 212, an HCDR2 of SEQ ID NO: 207, 211 or 213, and an HCDR3 of SEQ ID NO:237 or 238; and a light chain variable region that comprises an LCDR1 of SEQ ID NO:243, 245 or 247, an LCDR2 of SEQ ID NO:47 or 50, and an LCDR3 of SEQ ID NO:244 or 246.

In a specific embodiment, an antibody or antibody fragment (e.g., antigen binding fragments) that specifically binds to PMEL17 comprises a heavy chain variable region that comprises an HCDR1 of SEQ ID NO: 206, 209, 210 or 212, an HCDR2 of SEQ ID NO: 207, 211 or 213, and an HCDR3 of SEQ ID NO:252 or 253; and a light chain variable region that comprises an LCDR1 of SEQ ID NO:153, 156 or 158, an LCDR2 of SEQ ID NO:50 or 154, and an LCDR3 of SEQ ID NO:258 or 259.

In a specific embodiment, an antibody or antibody fragment (e.g., antigen binding fragments) that specifically binds to PMEL17 comprises CDR sequences selected from:
a) a heavy chain CDR1 of SEQ ID NO:1, a heavy chain CDR2 of SEQ ID NO:2, a heavy chain CDR3 of SEQ ID NO:3, a light chain CDR1 of SEQ ID NO:14, a light chain CDR2 of SEQ ID NO:15, and a light chain CDR3 of SEQ ID NO:16;
b) a heavy chain CDR1 of SEQ ID NO: 4, a heavy chain CDR2 of SEQ ID NO:2, a heavy chain CDR3 of SEQ ID NO:3, a light chain CDR1 of SEQ ID NO:14, a light chain CDR2 of SEQ ID NO:15, and a light chain CDR3 of SEQ ID NO:16;
c) a heavy chain CDR1 of SEQ ID NO:5, a heavy chain CDR2 of SEQ ID NO:6, a heavy chain CDR3 of SEQ ID NO:3, a light chain CDR1 of SEQ ID NO:17, a light chain CDR2 of SEQ ID NO: 18, and a light chain CDR3 of SEQ ID NO: 19; or
d) a heavy chain CDR1 of SEQ ID NO:7, a heavy chain CDR2 of SEQ ID NO:8, a heavy chain CDR3 of SEQ ID NO:9, a light chain CDR1 of SEQ ID NO:20, a light chain CDR2 of SEQ ID NO:18, and a light chain CDR3 of SEQ ID NO:16.

In a specific embodiment, an antibody or antibody fragment (e.g., antigen binding fragments) that specifically binds to PMEL17 comprises CDR sequences selected from:
a) a heavy chain CDR1 of SEQ ID NO:33, a heavy chain CDR2 of SEQ ID NO:34, a heavy chain CDR3 of SEQ ID NO:35, a light chain CDR1 of SEQ ID NO:46, a light chain CDR2 of SEQ ID NO:47, and a light chain CDR3 of SEQ ID NO:48;
b) a heavy chain CDR1 of SEQ ID NO:36, a heavy chain CDR2 of SEQ ID NO:34, a heavy chain CDR3 of SEQ ID NO:35, a light chain CDR1 of SEQ ID NO:46, a light chain CDR2 of SEQ ID NO:47, and a light chain CDR3 of SEQ ID NO:48;
c) a heavy chain CDR1 of SEQ ID NO:37, a heavy chain CDR2 of SEQ ID NO:38, a heavy chain CDR3 of SEQ ID NO:35, a light chain CDR1 of SEQ ID NO:49, a light chain CDR2 of SEQ ID NO:50, and a light chain CDR3 of SEQ ID NO:51; or
d) a heavy chain CDR1 of SEQ ID NO: 39, a heavy chain CDR2 of SEQ ID NO:40, a heavy chain CDR3 of SEQ ID NO:41, a light chain CDR1 of SEQ ID NO:52, a light chain CDR2 of SEQ ID NO:50, and a light chain CDR3 of SEQ ID NO:48.

In a specific embodiment, an antibody or antibody fragment (e.g., antigen binding fragments) that specifically binds to PMEL17 comprises CDR sequences selected from:
a) a heavy chain CDR1 of SEQ ID NO:57, a heavy chain CDR2 of SEQ ID NO:58, a heavy chain CDR3 of SEQ ID NO:59, a light chain CDR1 of SEQ ID NO:68, a light chain CDR2 of SEQ ID NO:69, and a light chain CDR3 of SEQ ID NO:70;
b) a heavy chain CDR1 of SEQ ID NO:60, a heavy chain CDR2 of SEQ ID NO:58, a heavy chain CDR3 of SEQ ID NO:59, a light chain CDR1 of SEQ ID NO:68, a light chain CDR2 of SEQ ID NO:69, and a light chain CDR3 of SEQ ID NO:70;
c) a heavy chain CDR1 of SEQ ID NO:5, a heavy chain CDR2 of SEQ ID NO:61, a heavy chain CDR3 of SEQ ID NO:59, a light chain CDR1 of SEQ ID NO:71, a light chain CDR2 of SEQ ID NO:72, and a light chain CDR3 of SEQ ID NO:73; or
d) a heavy chain CDR1 of SEQ ID NO:7, a heavy chain CDR2 of SEQ ID NO:62, a heavy chain CDR3 of SEQ ID NO:63, a light chain CDR1 of SEQ ID NO:74, a light chain CDR2 of SEQ ID NO:72, and a light chain CDR3 of SEQ ID NO:70.

In a specific embodiment, an antibody or antibody fragment (e.g., antigen binding fragments) that specifically binds to PMEL17 comprises CDR sequences selected from:

a) a heavy chain CDR1 of SEQ ID NO:79, a heavy chain CDR2 of SEQ ID NO:80, a heavy chain CDR3 of SEQ ID NO:81, a light chain CDR1 of SEQ ID NO:92, a light chain CDR2 of SEQ ID NO:93, and a light chain CDR3 of SEQ ID NO:94;

b) a heavy chain CDR1 of SEQ ID NO:82, a heavy chain CDR2 of SEQ ID NO:80, a heavy chain CDR3 of SEQ ID NO:81, a light chain CDR1 of SEQ ID NO:92, a light chain CDR2 of SEQ ID NO:93, and a light chain CDR3 of SEQ ID NO:94;

c) a heavy chain CDR1 of SEQ ID NO:83, a heavy chain CDR2 of SEQ ID NO:84, a heavy chain CDR3 of SEQ ID NO:81, a light chain CDR1 of SEQ ID NO:95, a light chain CDR2 of SEQ ID NO:96, and a light chain CDR3 of SEQ ID NO: 97; or d) a heavy chain CDR1 of SEQ ID NO: 85, a heavy chain CDR2 of SEQ ID NO:86, a heavy chain CDR3 of SEQ ID NO:87, a light chain CDR1 of SEQ ID NO:98, a light chain CDR2 of SEQ ID NO:96, and a light chain CDR3 of SEQ ID NO:94.

In a specific embodiment, an antibody or antibody fragment (e.g., antigen binding fragments) that specifically binds to PMEL17 comprises CDR sequences selected from:

a) a heavy chain CDR1 of SEQ ID NO:103, a heavy chain CDR2 of SEQ ID NO:104, a heavy chain CDR3 of SEQ ID NO:105, a light chain CDR1 of SEQ ID NO: 116; a light chain CDR2 of SEQ ID NO:47; and a light chain CDR3 of SEQ ID NO:117;

b) a heavy chain CDR1 of SEQ ID NO:106, a heavy chain CDR2 of SEQ ID NO:104, a heavy chain CDR3 of SEQ ID NO:105, a light chain CDR1 of SEQ ID NO: 116, a light chain CDR2 of SEQ ID NO:47, and a light chain CDR3 of SEQ ID NO:117;

c) a heavy chain CDR1 of SEQ ID NO:107, a heavy chain CDR2 of SEQ ID NO:108, a heavy chain CDR3 of SEQ ID NO:105, a light chain CDR1 of SEQ ID NO:49, a light chain CDR2 of SEQ ID NO:50, and a light chain CDR3 of SEQ ID NO:118; or d) a heavy chain CDR1 of SEQ ID NO:109, a heavy chain CDR2 of SEQ ID NO:110, a heavy chain CDR3 of SEQ ID NO:111, a light chain CDR1 of SEQ ID NO:52 a light chain CDR2 of SEQ ID NO:50, and a light chain CDR3 of SEQ ID NO:117.

In a specific embodiment, an antibody or antibody fragment (e.g., antigen binding fragments) that specifically binds to PMEL17 comprises CDR sequences selected from:

a) a heavy chain CDR1 of SEQ ID NO:123, a heavy chain CDR2 of SEQ ID NO:124, a heavy chain CDR3 of SEQ ID NO:125, a light chain CDR1 of SEQ ID NO:136, a light chain CDR2 of SEQ ID NO:137, and a light chain CDR3 of SEQ ID NO:138;

b) a heavy chain CDR1 of SEQ ID NO:126, a heavy chain CDR2 of SEQ ID NO:124, a heavy chain CDR3 of SEQ ID NO:125, a light chain CDR1 of SEQ ID NO:136, a light chain CDR2 of SEQ ID NO:137, and a light chain CDR3 of SEQ ID NO:138;

c) a heavy chain CDR1 of SEQ ID NO:127, a heavy chain CDR2 of SEQ ID NO:128, a heavy chain CDR3 of SEQ ID NO:125, a light chain CDR1 of SEQ ID NO:139, a light chain CDR2 of SEQ ID NO:140, and a light chain CDR3 of SEQ ID NO: 141; or d) a heavy chain CDR1 of SEQ ID NO: 129, a heavy chain CDR2 of SEQ ID NO:130, a heavy chain CDR3 of SEQ ID NO:131, a light chain CDR1 of SEQ ID NO:142, a light chain CDR2 of SEQ ID NO:140, and a light chain CDR3 of SEQ ID NO:138.

In a specific embodiment, an antibody or antibody fragment (e.g., antigen binding fragments) that specifically binds to PMEL17 comprises CDR sequences selected from:

a) a heavy chain CDR1 of SEQ ID NO:123, a heavy chain CDR2 of SEQ ID NO:124, a heavy chain CDR3 of SEQ ID NO:147, a light chain CDR1 of SEQ ID NO:153, a light chain CDR2 of SEQ ID NO:154, and a light chain CDR3 of SEQ ID NO:155;

b) a heavy chain CDR1 of SEQ ID NO:126, a heavy chain CDR2 of SEQ ID NO:124, a heavy chain CDR3 of SEQ ID NO:147, a light chain CDR1 of SEQ ID NO:153, a light chain CDR2 of SEQ ID NO: 154, and a light chain CDR3 of SEQ ID NO:155;

c) a heavy chain CDR1 of SEQ ID NO:127, a heavy chain CDR2 of SEQ ID NO:128, a heavy chain CDR3 of SEQ ID NO:147, a light chain CDR1 of SEQ ID NO:156, a light chain CDR2 of SEQ ID NO:50, and a light chain CDR3 of SEQ ID NO:157; or d) a heavy chain CDR1 of SEQ ID NO: 129, a heavy chain CDR2 of SEQ ID NO:130, a heavy chain CDR3 of SEQ ID NO:148, a light chain CDR1 of SEQ ID NO:158, a light chain CDR2 of SEQ ID NO:50, and a light chain CDR3 of SEQ ID NO:155.

In a specific embodiment, an antibody or antibody fragment (e.g., antigen binding fragments) that specifically binds to PMEL17 comprises CDR sequences selected from:

a) a heavy chain CDR1 of SEQ ID NO:103, a heavy chain CDR2 of SEQ ID NO:104, a heavy chain CDR3 of SEQ ID NO:163, a light chain CDR1 of SEQ ID NO: 116, a light chain CDR2 of SEQ ID NO:47, and a light chain CDR3 of SEQ ID NO:169;

b) a heavy chain CDR1 of SEQ ID NO:106, a heavy chain CDR2 of SEQ ID NO:104, a heavy chain CDR3 of SEQ ID NO:163, a light chain CDR1 of SEQ ID NO:116, a light chain CDR2 of SEQ ID NO:47, and a light chain CDR3 of SEQ ID NO:169;

c) a heavy chain CDR1 of SEQ ID NO:107, a heavy chain CDR2 of SEQ ID NO:108, a heavy chain CDR3 of SEQ ID NO:163, a light chain CDR1 of SEQ ID NO:49, a light chain CDR2 of SEQ ID NO:50, and a light chain CDR3 of SEQ ID NO:170; or d) a heavy chain CDR1 of SEQ ID NO: 109, a heavy chain CDR2 of SEQ ID NO:110, a heavy chain CDR3 of SEQ ID NO:164, a light chain CDR1 of SEQ ID NO:52, a light chain CDR2 of SEQ ID NO:50, and a light chain CDR3 of SEQ ID NO:169.

In a specific embodiment, an antibody or antibody fragment (e.g., antigen binding fragments) that specifically binds to PMEL17 comprises CDR sequences selection from:

a) a heavy chain CDR1 of SEQ ID NO:175, a heavy chain CDR2 of SEQ ID NO:176, a heavy chain CDR3 of SEQ ID NO:177, a light chain CDR1 of SEQ ID NO:116, a light chain CDR2 of SEQ ID NO:47, and a light chain CDR3 of SEQ ID NO:188;

b) a heavy chain CDR1 of SEQ ID NO:178, a heavy chain CDR2 of SEQ ID NO:176, a heavy chain CDR3 of SEQ ID NO:177, a light chain CDR1 of SEQ ID NO:116, a light chain CDR2 of SEQ ID NO:47, and a light chain CDR3 of SEQ ID NO:188;

c) a heavy chain CDR1 of SEQ ID NO:179, a heavy chain CDR2 of SEQ ID NO:180, a heavy chain CDR3 of SEQ ID NO:177, a light chain CDR1 of SEQ ID NO:49, a light chain CDR2 of SEQ ID NO:50, and a light chain CDR3 of SEQ ID NO:189; or d) a heavy chain CDR1 of SEQ ID NO: 181, a heavy chain CDR2 of SEQ ID NO:182; a heavy chain CDR3 of SEQ ID NO:183, a light chain CDR1 of SEQ ID NO:52, a light chain CDR2 of SEQ ID NO:50, and a light chain CDR3 of SEQ ID NO:188.

In a specific embodiment, an antibody or antibody fragment (e.g., antigen binding fragments) that specifically binds to PMEL17 comprises CDR sequences selected from:
- a) a heavy chain CDR1 of SEQ ID NO: 103, a heavy chain CDR2 of SEQ ID NO: 104, a heavy chain CDR3 of SEQ ID NO:194, a light chain CDR1 of SEQ ID NO: 116, a light chain CDR2 of SEQ ID NO: 47, and a light chain CDR3 of SEQ ID NO:200;
- b) a heavy chain CDR1 of SEQ ID NO: 106, a heavy chain CDR2 of SEQ ID NO: 104, a heavy chain CDR3 of SEQ ID NO:194, a light chain CDR1 of SEQ ID NO: 116, a light chain CDR2 of SEQ ID NO: 47, and a light chain CDR3 of SEQ ID NO:200;
- c) a heavy chain CDR1 of SEQ ID NO: 107, a heavy chain CDR2 of SEQ ID NO: 108, a heavy chain CDR3 of SEQ ID NO:194, a light chain CDR1 of SEQ ID NO: 49, a light chain CDR2 of SEQ ID NO: 50, and a light chain CDR3 of SEQ ID NO: 201; or
- d) a heavy chain CDR1 of SEQ ID NO: 109, a heavy chain CDR2 of SEQ ID NO: 110, a heavy chain CDR3 of SEQ ID NO:195, a light chain CDR1 of SEQ ID NO: 52, a light chain CDR2 of SEQ ID NO: 50, and a light chain CDR3 of SEQ ID NO:200.

In a specific embodiment, an antibody or antibody fragment (e.g., antigen binding fragments) that specifically binds to PMEL17 comprises CDR sequences selected from:
- a) a heavy chain CDR1 of SEQ ID NO:206, a heavy chain CDR2 of SEQ ID NO:207, a heavy chain CDR3 of SEQ ID NO:208, a light chain CDR1 of SEQ ID NO:153, a light chain CDR2 of SEQ ID NO:154, and a light chain CDR3 of SEQ ID NO:219;
- b) a heavy chain CDR1 of SEQ ID NO:209, a heavy chain CDR2 of SEQ ID NO:207, a heavy chain CDR3 of SEQ ID NO:208, a light chain CDR1 of SEQ ID NO:153, a light chain CDR2 of SEQ ID NO: 154, and a light chain CDR3 of SEQ ID NO:219;
- c) a heavy chain CDR1 of SEQ ID NO:210, a heavy chain CDR2 of SEQ ID NO:211, a heavy chain CDR3 of SEQ ID NO:208, a light chain CDR1 of SEQ ID NO:156, a light chain CDR2 of SEQ ID NO:50, and a light chain CDR3 of SEQ ID NO:220; or
- d) a heavy chain CDR1 of SEQ ID NO: 212, a heavy chain CDR2 of SEQ ID NO:213, a heavy chain CDR3 of SEQ ID NO:214, a light chain CDR1 of SEQ ID NO:158, a light chain CDR2 of SEQ ID NO:50, and a light chain CDR3 of SEQ ID NO:219.

In a specific embodiment, an antibody or antibody fragment (e.g., antigen binding fragments) that specifically binds to PMEL17 comprises CDR sequences selected from:
- a) a heavy chain CDR1 of SEQ ID NO: 206, a heavy chain CDR2 of SEQ ID NO: 207, a heavy chain CDR3 of SEQ ID NO:225, a light chain CDR1 of SEQ ID NO:136, a light chain CDR2 of SEQ ID NO:137, and a light chain CDR3 of SEQ ID NO:231;
- b) a heavy chain CDR1 of SEQ ID NO: 209, a heavy chain CDR2 of SEQ ID NO: 207, a heavy chain CDR3 of SEQ ID NO:225, a light chain CDR1 of SEQ ID NO:136, a light chain CDR2 of SEQ ID NO:137, and a light chain CDR3 of SEQ ID NO:231;
- c) a heavy chain CDR1 of SEQ ID NO: 210, a heavy chain CDR2 of SEQ ID NO: 211, a heavy chain CDR3 of SEQ ID NO:225, a light chain CDR1 of SEQ ID NO:139, a light chain CDR2 of SEQ ID NO:140, and a light chain CDR3 of SEQ ID NO: 232; or
- d) a heavy chain CDR1 of SEQ ID NO: 212, a heavy chain CDR2 of SEQ ID NO: 213, a heavy chain CDR3 of SEQ ID NO: 226, a light chain CDR1 of SEQ ID NO:142; a light chain CDR2 of SEQ ID NO: 140; and a light chain CDR3 of SEQ ID NO:231.

In a specific embodiment, an antibody or antibody fragment (e.g., antigen binding fragments) that specifically binds to PMEL17 comprises CDR sequences selected from:
- a) a heavy chain variable region that comprises an HCDR1 of SEQ ID NO: 206, an HCDR2 of SEQ ID NO: 207, and an HCDR3 of SEQ ID NO:237, and a light chain variable region that comprises an LCDR1 of SEQ ID NO:243, an LCDR2 of SEQ ID NO:47, and an LCDR3 of SEQ ID NO:244;
- b) a heavy chain variable region that comprises an HCDR1 of SEQ ID NO: 209, an HCDR2 of SEQ ID NO: 207, and an HCDR3 of SEQ ID NO:237, and a light chain variable region that comprises an LCDR1 of SEQ ID NO:243, an LCDR2 of SEQ ID NO:47, and an LCDR3 of SEQ ID NO:244;
- c) a heavy chain variable region that comprises an HCDR1 of SEQ ID NO: 210, an HCDR2 of SEQ ID NO: 211, and an HCDR3 of SEQ ID NO:237, and a light chain variable region that comprises an LCDR1 of SEQ ID NO:245, an LCDR2 of SEQ ID NO:50, and an LCDR3 of SEQ ID NO:246; or
- d) a heavy chain variable region that comprises an HCDR1 of SEQ ID NO: 212, an HCDR2 of SEQ ID NO: 213, and an HCDR3 of SEQ ID NO:238; and a light chain variable region that comprises an LCDR1 of SEQ ID NO:247, an LCDR2 of SEQ ID NO: 50, and an LCDR3 of SEQ ID NO:244.

In a specific embodiment, an antibody or antibody fragment (e.g., antigen binding fragments) that specifically binds to PMEL17 comprises CDR sequences selected from:
- a) a heavy chain variable region that comprises an HCDR1 of SEQ ID NO: 206, an HCDR2 of SEQ ID NO: 207, and an HCDR3 of SEQ ID NO:252, and a light chain variable region that comprises an LCDR1 of SEQ ID NO:153, an LCDR2 of SEQ ID NO: 154, and an LCDR3 of SEQ ID NO:258;
- b) a heavy chain variable region that comprises an HCDR1 of SEQ ID NO: 209, an HCDR2 of SEQ ID NO: 207, and an HCDR3 of SEQ ID NO:252, and a light chain variable region that comprises an LCDR1 of SEQ ID NO:153, an LCDR2 of SEQ ID NO:154, and an LCDR3 of SEQ ID NO:258;
- c) a heavy chain variable region that comprises an HCDR1 of SEQ ID NO: 210, an HCDR2 of SEQ ID NO: 211, and an HCDR3 of SEQ ID NO:252, and a light chain variable region that comprises an LCDR1 of SEQ ID NO:156, an LCDR2 of SEQ ID NO:50, and an LCDR3 of SEQ ID NO:259; or
- d) a heavy chain variable region that comprises an HCDR1 of SEQ ID NO: 212, an HCDR2 of SEQ ID NO: 213, and an HCDR3 of SEQ ID NO: 253; and a light chain variable region that comprises an LCDR1 of SEQ ID NO:158, an LCDR2 of SEQ ID NO:50, and an LCDR3 of SEQ ID NO:258.

In a specific embodiment, an antibody or antibody fragment (e.g., antigen binding fragments) that specifically binds to PMEL17 comprises a heavy chain variable region (VH) comprising the amino acid sequence of SEQ ID NO:10, and a light chain variable region (VL) comprising the amino acid sequence of SEQ ID NO:21.

In a specific embodiment, an antibody or antibody fragment (e.g., antigen binding fragments) that specifically binds to PMEL17 comprises a heavy chain variable region (VH) comprising the amino acid sequence of SEQ ID NO:10, and a light chain variable region (VL) comprising the amino acid sequence of SEQ ID NO:25.

In a specific embodiment, an antibody or antibody fragment (e.g., antigen binding fragments) that specifically binds to PMEL17 comprises a heavy chain variable region (VH) comprising the amino acid sequence of SEQ ID NO:10, and a light chain variable region (VL) comprising the amino acid sequence of SEQ ID NO:29.

In a specific embodiment, an antibody or antibody fragment (e.g., antigen binding fragments) that specifically binds to PMEL17 comprises a heavy chain variable region (VH) comprising the amino acid sequence of SEQ ID NO:42, and a light chain variable region (VL) comprising the amino acid sequence of SEQ ID NO:53.

In a specific embodiment, an antibody or antibody fragment (e.g., antigen binding fragments) that specifically binds to PMEL17 comprises a heavy chain variable region (VH) comprising the amino acid sequence of SEQ ID NO:64, and a light chain variable region (VL) comprising the amino acid sequence of SEQ ID NO:75.

In a specific embodiment, an antibody or antibody fragment (e.g., antigen binding fragments) that specifically binds to PMEL17 comprises a heavy chain variable region (VH) comprising the amino acid sequence of SEQ ID NO:88, and a light chain variable region (VL) comprising the amino acid sequence of SEQ ID NO:99.

In a specific embodiment, an antibody or antibody fragment (e.g., antigen binding fragments) that specifically binds to PMEL17 comprises a heavy chain variable region (VH) comprising the amino acid sequence of SEQ ID NO:112, and a light chain variable region (VL) comprising the amino acid sequence of SEQ ID NO:119.

In a specific embodiment, an antibody or antibody fragment (e.g., antigen binding fragments) that specifically binds to PMEL17 comprises a heavy chain variable region (VH) comprising the amino acid sequence of SEQ ID NO:132, and a light chain variable region (VL) comprising the amino acid sequence of SEQ ID NO:143.

In a specific embodiment, an antibody or antibody fragment (e.g., antigen binding fragments) that specifically binds to PMEL17 comprises a heavy chain variable region (VH) comprising the amino acid sequence of SEQ ID NO:149, and a light chain variable region (VL) comprising the amino acid sequence of SEQ ID NO:159.

In a specific embodiment, an antibody or antibody fragment (e.g., antigen binding fragments) that specifically binds to PMEL17 comprises a heavy chain variable region (VH) comprising the amino acid sequence of SEQ ID NO:165, and a light chain variable region (VL) comprising the amino acid sequence of SEQ ID NO:171.

In a specific embodiment, an antibody or antibody fragment (e.g., antigen binding fragments) that specifically binds to PMEL17 comprises a heavy chain variable region (VH) comprising the amino acid sequence of SEQ ID NO:184, and a light chain variable region (VL) comprising the amino acid sequence of SEQ ID NO:190.

In a specific embodiment, an antibody or antibody fragment (e.g., antigen binding fragments) that specifically binds to PMEL17 comprises a heavy chain variable region (VH) comprising the amino acid sequence of SEQ ID NO:196, and a light chain variable region (VL) comprising the amino acid sequence of SEQ ID NO:202.

In a specific embodiment, an antibody or antibody fragment (e.g., antigen binding fragments) that specifically binds to PMEL17 comprises a heavy chain variable region (VH) comprising the amino acid sequence of SEQ ID NO:215, and a light chain variable region (VL) comprising the amino acid sequence of SEQ ID NO:221.

In a specific embodiment, an antibody or antibody fragment (e.g., antigen binding fragments) that specifically binds to PMEL17 comprises a heavy chain variable region (VH) comprising the amino acid sequence of SEQ ID NO:227, and a light chain variable region (VL) comprising the amino acid sequence of SEQ ID NO:233.

In a specific embodiment, an antibody or antibody fragment (e.g., antigen binding fragments) that specifically binds to PMEL17 comprises a heavy chain variable region (VH) comprising the amino acid sequence of SEQ ID NO:239, and a light chain variable region (VL) comprising the amino acid sequence of SEQ ID NO:248.

In a specific embodiment, an antibody or antibody fragment (e.g., antigen binding fragments) that specifically binds to PMEL17 comprises a heavy chain variable region (VH) comprising the amino acid sequence of SEQ ID NO:254, and a light chain variable region (VL) comprising the amino acid sequence of SEQ ID NO:260.

In a specific embodiment, an antibody or antibody fragment (e.g., antigen binding fragments) that specifically binds to PMEL17 comprises a heavy chain comprising the amino acid sequence of SEQ ID NO:12, and a light chain comprising the amino acid sequence of SEQ ID NO:23.

In a specific embodiment, an antibody or antibody fragment (e.g., antigen binding fragments) that specifically binds to PMEL17 comprises a heavy chain comprising the amino acid sequence of SEQ ID NO:12, and a light chain comprising the amino acid sequence of SEQ ID NO:27.

In a specific embodiment, an antibody or antibody fragment (e.g., antigen binding fragments) that specifically binds to PMEL17 comprises a heavy chain comprising the amino acid sequence of SEQ ID NO:12, and a light chain comprising the amino acid sequence of SEQ ID NO:31.

In a specific embodiment, an antibody or antibody fragment (e.g., antigen binding fragments) that specifically binds to PMEL17 comprises a heavy chain comprising the amino acid sequence of SEQ ID NO:44, and a light chain comprising the amino acid sequence of SEQ ID NO:55.

In a specific embodiment, an antibody or antibody fragment (e.g., antigen binding fragments) that specifically binds to PMEL17 comprises a heavy chain comprising the amino acid sequence of SEQ ID NO:66, and a light chain comprising the amino acid sequence of SEQ ID NO:77.

In a specific embodiment, an antibody or antibody fragment (e.g., antigen binding fragments) that specifically binds to PMEL17 comprises a heavy chain comprising the amino acid sequence of SEQ ID NO:90, and a light chain comprising the amino acid sequence of SEQ ID NO:101.

In a specific embodiment, an antibody or antibody fragment (e.g., antigen binding fragments) that specifically binds to PMEL17 comprises a heavy chain comprising the amino acid sequence of SEQ ID NO:114, and a light chain comprising the amino acid sequence of SEQ ID NO:121.

In a specific embodiment, an antibody or antibody fragment (e.g., antigen binding fragments) that specifically binds to PMEL17 comprises a heavy chain comprising the amino acid sequence of SEQ ID NO:134, and a light chain comprising the amino acid sequence of SEQ ID NO:145.

In a specific embodiment, an antibody or antibody fragment (e.g., antigen binding fragments) that specifically binds to PMEL17 comprises a heavy chain comprising the amino acid sequence of SEQ ID NO:151, and a light chain comprising the amino acid sequence of SEQ ID NO:161.

In a specific embodiment, an antibody or antibody fragment (e.g., antigen binding fragments) that specifically binds to PMEL17 comprises a heavy chain comprising the amino acid sequence of SEQ ID NO:167, and a light chain comprising the amino acid sequence of SEQ ID NO:173.

In a specific embodiment, an antibody or antibody fragment (e.g., antigen binding fragments) that specifically binds to PMEL17 comprises a heavy chain comprising the amino acid sequence of SEQ ID NO:186, and a light chain comprising the amino acid sequence of SEQ ID NO:192.

In a specific embodiment, an antibody or antibody fragment (e.g., antigen binding fragments) that specifically binds to PMEL17 comprises a heavy chain comprising the amino acid sequence of SEQ ID NO:198, and a light chain comprising the amino acid sequence of SEQ ID NO:204.

In a specific embodiment, an antibody or antibody fragment (e.g., antigen binding fragments) that specifically binds to PMEL17 comprises a heavy chain comprising the amino acid sequence of SEQ ID NO:217, and a light chain comprising the amino acid sequence of SEQ ID NO:223.

In a specific embodiment, an antibody or antibody fragment (e.g., antigen binding fragments) that specifically binds to PMEL17 comprises a heavy chain comprising the amino acid sequence of SEQ ID NO:229, and a light chain comprising the amino acid sequence of SEQ ID NO:235.

In a specific embodiment, an antibody or antibody fragment (e.g., antigen binding fragments) that specifically binds to PMEL17 comprises a heavy chain comprising the amino acid sequence of SEQ ID NO:241, and a light chain comprising the amino acid sequence of SEQ ID NO:250.

In a specific embodiment, an antibody or antibody fragment (e.g., antigen binding fragments) that specifically binds to PMEL17 comprises a heavy chain comprising the amino acid sequence of SEQ ID NO:256, and a light chain comprising the amino acid sequence of SEQ ID NO:262.

In certain embodiments, an antibody that specifically binds to PMEL17 is an antibody or antibody fragment (e.g., antigen binding fragment) that is described in Table 2.

1. Identification of Epitopes and Antibodies that Bind to the Same Epitope

The present invention also provides antibodies and antibody fragments (e.g., antigen binding fragments) that specifically bind to the same epitope as the anti-PMEL17 antibodies described in Table 2, or cross compete with the antibodies described in Table 2. Additional antibodies and antibody fragments (e.g., antigen binding fragments) can therefore be identified based on their ability to cross-compete (e.g., to competitively inhibit the binding of, in a statistically significant manner) with other antibodies of the invention in PMEL17 binding assays, for example, via BIACORE or assays known to persons skilled in the art for measuring binding. The ability of a test antibody to inhibit the binding of antibodies and antibody fragments (e.g., antigen binding fragments) of the present invention to a PMEL17 (e.g., human PMEL17) demonstrates that the test antibody can compete with that antibody or antibody fragment (e.g., antigen binding fragments) for binding to PMEL17; such an antibody may, according to non-limiting theory, bind to the same or a related (e.g., a structurally similar or spatially proximal or overlapping) epitope on the PMEL17 protein as the antibody or antibody fragment (e.g., antigen binding fragments) with which it competes. In certain embodiments, the antibodies that bind to the same epitope on PMEL17 as the antibodies or antibody fragments (e.g., antigen binding fragments) described in Table 2 are human or humanized monoclonal antibodies. Such human or humanized monoclonal antibodies can be prepared and isolated as described herein.

2. Further Alteration of the Framework of Fc Region

The immunoconjugates of the invention may comprise modified antibodies or antigen binding fragments thereof that further comprise modifications to framework residues within VH and/or VL, e.g. to improve the properties of the antibody. In some embodiments, the framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 20030153043 by Carr et al.

In addition or in the alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity (ADCC). Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below.

In one embodiment, the hinge region of $CH_1$ is modified such that the number of cysteine residues in the hinge region is altered, e.g., increased or decreased. This approach is described further in U.S. Pat. No. 5,677,425 by Bodmer et al. The number of cysteine residues in the hinge region of $CH_1$ is altered to, for example, facilitate assembly of the light and heavy chains or to increase or decrease the stability of the antibody.

In some embodiments, the antibody or antibody fragment disclosed herein include modified or engineered amino acid residues, e.g., one or more cysteine residues, as sites for conjugation to a drug moiety (Junutula J R, et al., Nat Biotechnol 2008, 26:925-932). In one embodiment, the invention provides a modified antibody or antibody fragment comprising a substitution of one or more amino acids with cysteine at the positions described herein. Sites for cysteine substitution are in the constant regions of the antibody or antibody fragment and are thus applicable to a variety of antibody or antibody fragment, and the sites are selected to provide stable and homogeneous conjugates. A modified antibody or fragment can have one, two or more cysteine substitutions, and these substitutions can be used in combination with other modification and conjugation methods as described herein. Methods for inserting cysteine at specific locations of an antibody are known in the art, see, e.g., Lyons et al., (1990) Protein Eng., 3:703-708, WO 2011/005481, WO2014/124316, WO 2015/138615. In certain embodiments, a modified antibody comprises a substitution of one or more amino acids with cysteine on its constant region selected from positions 117, 119, 121, 124, 139, 152, 153, 155, 157, 164, 169, 171, 174, 189, 191, 195, 197, 205, 207, 246, 258, 269, 274, 286, 288, 290, 292, 293, 320, 322, 326, 333, 334, 335, 337, 344, 355, 360, 375, 382, 390, 392, 398, 400 and 422 of a heavy chain of the antibody, and wherein the positions are numbered according to the EU system. In some embodiments a modified antibody or antibody fragment comprises a substitution of one or more amino acids with cysteine on its constant region selected from positions 107, 108, 109, 114, 129, 142, 143, 145, 152, 154, 156, 159, 161, 165, 168, 169, 170, 182, 183, 197, 199, and 203 of a light chain of the antibody or antibody fragment, wherein the positions are numbered according to the EU system, and wherein the light chain is a human kappa light chain. In certain embodiments a modified antibody or antibody fragment thereof comprises a combination of substitution of two or more amino acids with cysteine on its constant regions wherein the combinations comprise substitutions at positions 375 of an antibody heavy chain, position 152 of an antibody heavy chain, position 360 of an antibody heavy chain, or position 107 of an antibody light chain and wherein the positions are numbered according to the EU system. In certain embodiments a modified antibody or antibody fragment thereof comprises a substitution of one amino acid with cysteine on its constant regions wherein the substitution is position 375 of an antibody heavy chain, position 152 of an antibody heavy chain, position 360 of an antibody heavy chain, position 107 of an antibody light chain, position 165 of an antibody light chain or position 159 of an antibody light chain and wherein the positions are numbered according to the EU system, and wherein the light chain is a kappa chain. In particular embodiments a modified antibody or antibody fragment thereof comprises a combination of substitution of two amino acids with cysteine on its constant regions wherein the combinations comprise substitutions at positions 375 of an antibody heavy chain and position 152 of an antibody heavy chain, wherein the positions are numbered according to the EU system. In particular embodiments a modified antibody or antibody fragment thereof comprises a substitution of one amino acid with cysteine at position 360 of an antibody heavy chain, wherein the positions are numbered according to the EU system. In other particular embodiments a modified antibody or antibody fragment thereof comprises a substitution of one amino acid with cysteine at position 107 of an antibody light chain and wherein the positions are numbered according to the EU system, and wherein the light chain is a kappa chain.

In additional embodiments antibodies or antibody fragments (e.g., antigen binding fragment) useful in immunoconjugates of the invention include modified or engineered antibodies, such as an antibody modified to introduce one or more other reactive amino acid (other than cysteine), including Pcl, pyrrolysine, peptide tags (such as S6, A1 and ybbR tags), and non-natural amino acids, in place of at least one amino acid of the native sequence, thus providing a reactive site on the antibody or antigen binding fragment for conjugation to a drug moiety or a linker-drug moiety with complementary reactivity. For example, the antibodies or antibody fragments can be modified to incorporate Pcl or pyrrolysine (W. Ou, et al., (2011) PNAS 108 (26), 10437-10442; WO2014124258) or unnatural amino acids (J. Y. Axup, et al., Proc Natl Acad Sci USA, 109 (2012), pp. 16101-16106; for review, see C. C. Liu and P. G. Schultz (2010) Annu Rev Biochem 79, 413-444; C. H. Kim, et al., (2013) Curr Opin Chem Biol. 17, 412-419) as sites for conjugation to a drug. Similarly, peptide tags for enzymatic conjugation methods can be introduced into an antibody (Strop P., et al., Chem Biol. 2013, 20(2):161-7; Rabuka D., Curr Opin Chem Biol. 2010 December; 14(6):790-6; Rabuka D, et al., Nat Protoc. 2012, 7(6):1052-67). One other example is the use of 4'-phosphopantetheinyl transferases (PPTase) for the conjugation of Co-enzyme A analogs (WO2013184514), and (Grunewald et al., (2015) Bioconjugate Chem. 26 (12), 2554-62). Methods for conjugating such modified or engineered antibodies with payloads or linker-payload combinations are known in the art.

In another embodiment, the Fc hinge region of an antibody is mutated to decrease the biological half-life of the antibody. More specifically, one or more amino acid mutations are introduced into the $CH_2$—$CH_3$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another embodiment, one or more amino acid residues are altered to thereby alter the ability of the antibody to fix complement. This approach is described in, e.g., the PCT Publication WO 94/29351 by Bodmer et al. Allotypic amino acid residues include, but are not limited to, constant region of a heavy chain of the IgG1, IgG2, and IgG3 subclasses as well as constant region of a light chain of the kappa isotype as described by Jefferis et al., MAbs. 1:332-338 (2009).

Antibody fusion protein complexes containing such mutations mediate reduced or no antibody-dependent cellular cytotoxicity (ADCC) or complement-dependent cytotoxicity (CDC). In some embodiments, amino acid residues L234 and L235 of the IgG1 constant region are substituted to A234 and A235. In some embodiments, amino acid residue N267 of the IgG1 constant region is substituted to A267. In some embodiments, amino acid residues D265 and P329 of the IgG1 constant region are substituted to A265 and A329. Other antibody Fc silencing mutations may also be used.

In another embodiment, one or more amino acid residues are altered to thereby alter the ability of the antibody to fix complement. This approach is described in, e.g., the PCT Publication WO 94/29351 by Bodmer et al. In a specific embodiment, one or more amino acids of an antibody or antigen binding fragment thereof of the present invention are replaced by one or more allotypic amino acid residues. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In still another embodiment, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the $CH_1$ or CL region to contain a salvage receptor binding epitope taken from two loops of a $CH_2$ domain of an Fc region of an IgG, as described in U.S. Pat. Nos. 5,869,046 and 6,121,022 by Presta et al.

3. Production of the Anti-PMEL17 Antibodies

Anti-PMEL17 antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The invention further provides polynucleotides encoding the antibodies described herein, e.g., polynucleotides encoding heavy or light chain variable regions or segments comprising the complementarity determining regions as described herein. In some embodiments, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 11, 43, 65, 89, 113, 133, 150, 166, 185, 197, 216, 228, 240, and 255. In some embodiments, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 22, 26, 30, 54, 76, 100, 120, 144, 160, 172, 191, 203, 222, 234, 249, and 261.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 13, 45, 67, 91, 115, 135, 152, 168, 187, 199, 218, 230, 242, and 257. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO: 24, 28, 32, 56, 78, 102, 122, 146, 162, 174, 193, 205, 224, 236, 251, and 263.

The polynucleotides of the invention can encode only the variable region sequence of an anti-PMEL17 antibody. They can also encode both a variable region and a constant region of the antibody. Some of the polynucleotide sequences encode a polypeptide that comprises variable regions of both the heavy chain and the light chain of one of the exemplified mouse anti-PMEL17 antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence (e.g., sequences as described in the Examples below) encoding an anti-PMEL17 antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, CA, 1990; Mattila et al., Nucleic Acids Res. 19:967, 1991; and Eckert et al., PCR Methods and Applications 1:17, 1991.

Also provided in the invention are expression vectors and host cells for producing the anti-PMEL17 antibodies described above. Various expression vectors can be employed to express the polynucleotides encoding the anti-PMEL17 antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-PMEL17 polynucleotides and polypeptides in mammalian (e.g., human) cells include pThioHis A, B & C, pcDNA™3.1/His, pEBVHis A, B & C (Invitrogen, San Diego, CA), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-PMEL17 antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti- PMEL17 antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-PMEL17 antibody sequences. More often, the inserted anti-PMEL17 antibody sequences are linked to a signal sequences before inclusion in the vector. Vectors to be used to receive sequences encoding anti-PMEL17 antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-PMEL17 antibody chains can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-PMEL17 polypeptides of the invention. Insect cells in combination with baculovirus vectors can also be used.

In some preferred embodiments, mammalian host cells are used to express and produce the anti-PMEL17 polypeptides of the present invention. For example, they can be either a hybridoma cell line expressing endogenous immunoglobulin genes (e.g., the myeloma hybridoma clones as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., Molecular Cloning: A Laboratory Manual, $4^{th}$ ed.). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-PMEL17 antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Therapeutic Uses

The antibodies, antibody fragments (e.g., antigen binding fragments), and antibody drug conjugates of the invention are useful in a variety of applications including, but not limited to, treatment or prevention of cancer, such as solid cancers or heme malignancies. In certain embodiments, the antibodies, antibody fragments (e.g., antigen binding fragments), and antibody drug conjugates of the invention are useful for inhibiting tumor growth, inducing differentiation, reducing tumor volume, and/or reducing the tumorigenicity of a tumor. The methods of use can be in vitro, ex vivo, or in vivo methods.

In one aspect, the antibodies, antibody fragments (e.g., antigen binding fragments), and antibody drug conjugates of the invention are useful for detecting the presence of PMEL17 in a biological sample. The term "detecting" as used herein encompasses quantitative or qualitative detection. In certain embodiments, a biological sample comprises a cell or tissue. In certain embodiments, such tissues include normal and/or cancerous tissues that express PMEL17 at higher levels relative to other tissues.

In one aspect, the invention provides a method of detecting the presence of PMEL17 in a biological sample. In certain embodiments, the method comprises contacting the biological sample with an anti-PMEL17 antibody under conditions permissive for binding of the antibody to the antigen, and detecting whether a complex is formed between the antibody and the antigen.

In one aspect, the invention provides a method of diagnosing a disorder associated with increased expression of PMEL17. In certain embodiments, the method comprises contacting a test cell with an anti-PMEL17 antibody; determining the level of expression (either quantitatively or qualitatively) of PMEL17 on the test cell by detecting binding of the anti-PMEL17 antibody to the PMEL17 antigen; and comparing the level of expression of PMEL17 in the test cell with the level of expression of PMEL17 on a control cell (e.g., a normal cell of the same tissue origin as the test cell or a cell that expresses PMEL17 at levels comparable to such a normal cell), wherein a higher level of expression of PMEL17 on the test cell as compared to the control cell indicates the presence of a disorder associated with increased expression of PMEL17. In certain embodiments, the test cell is obtained from an individual suspected of having a disorder associated with increased expression of PMEL17. In certain embodiments, the disorder is a cell proliferative disorder, such as a cancer or a tumor. In certain embodiments, the method comprises measuring the copy number of the PMEL17 gene in a test cell.

In certain embodiments, a method of diagnosis or detection, such as those described above, comprises detecting binding of an anti-PMEL17 antibody to PMEL17 expressed on the surface of a cell or in a membrane preparation obtained from a cell expressing PMEL17 on its surface. An exemplary assay for detecting binding of an anti-PMEL17 antibody to PMEL17 expressed on the surface of a cell is a "FACS" assay.

Certain other methods can be used to detect binding of anti-PMEL17 antibodies to PMEL17. Such methods include, but are not limited to, antigen-binding assays that are well known in the art, such as Western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-PMEL17 antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain embodiments, anti-PMEL17 antibodies are immobilized on an insoluble matrix. Immobilization entails separating the anti-PMEL17 antibody from any PMEL17 protein that remains free in solution. This conventionally is accomplished by either insolubilizing the anti-PMEL17 antibody before the assay procedure, as by adsorption to a water-insoluble matrix or surface (Bennich et al, U.S. Pat. No. 3,720,760), or by covalent coupling (for example, using glutaraldehyde cross-linking), or by insolubilizing the anti-PMEL17 antibody after formation of a complex between the anti-PMEL17 antibody and PMEL17 protein, e.g., by immunoprecipitation.

Any of the above embodiments of diagnosis or detection can be carried out using an immunoconjugate of the invention in place of or in addition to an anti-PMEL17 antibody.

In one embodiment, the invention provides a method of treating or preventing a disease comprising administering the antibodies, antibody fragments (e.g., antigen binding fragments), or antibody drug conjugates of the invention to a patient. The invention also provides use of the antibodies, antibody fragments (e.g., antigen binding fragments), or antibody drug conjugates of the invention to treat or prevent disease in a patient. In some embodiments, the invention provides antibodies, antibody fragments (e.g., antigen binding fragments), or antibody drug conjugates of the invention for use in the treatment or prevention of disease in a patient. In further embodiments, the invention provides use of the antibodies, antibody fragments (e.g., antigen binding fragments), or antibody drug conjugates of the invention in the manufacture of a medicament for treatment or prevention of disease in a patient.

In certain embodiments, the disease treated with the antibodies, antibody fragments (e.g., antigen binding fragments), and antibody drug conjugates of the invention is a cancer. In certain embodiments, the cancer is characterized by PMEL17 expressing cells to which the antibodies, antibody fragments (e.g., antigen binding fragments), and antibody drug conjugates of the invention binds. In certain embodiments, the cancer is characterized by an increase in expression of PMEL17 relative to a healthy patient. In some embodiments, the expression of PMEL17 may be measured by an increase in PMEL17 RNA. In other embodiments, the cancer is characterized by an increase in DNA copy number of PMEL17. Other methods of measuring or determining levels of PMEL17 expression are known to persons skilled in the art. In certain embodiments, the cancer is characterized by a mutation, e.g., an activating mutation affecting Q209 or R183, in the GNAQ and/or the GNA11 gene. Examples of diseases which can be treated and/or prevented include, but are not limited to, melanoma, uveal melanoma, hepatocellular carcinoma, and a metastatic cancer thereof.

The present invention provides for methods of treating or preventing cancer comprising administering a therapeutically effective amount of the antibodies, antibody fragments (e.g., antigen binding fragments), or antibody drug conjugates of the invention. In certain embodiments, the cancer is a solid cancer such as melanoma, uveal melanoma, uveal melanoma, hepatocellular carcinoma, or a metastatic cancer thereof. In certain embodiments, the subject is a human. In certain embodiments, the cancer is a resistant cancer and/or relapsed cancer.

In certain embodiments, the invention provides for methods of inhibiting tumor growth comprising administering to a subject a therapeutically effective amount of the antibodies, antibody fragments (e.g., antigen binding fragments), or antibody drug conjugates of the invention. In certain embodiments, the tumor is of a solid cancer such as melanoma, uveal melanoma, hepatocellular carcinoma, or a metastatic cancer thereof. In certain embodiments, the subject is a human. In certain embodiments, the subject has a tumor or has had a tumor removed.

In certain embodiments, the tumor expresses the PMEL17 to which the anti-PMEL17 antibody binds. In certain embodiments, the tumor overexpresses the human PMEL17. In certain embodiments, the tumor has an increase copy number of the PMEL17 gene. In certain embodiments, the tumor is characterized by a mutation, e.g., an activating mutation affecting Q209 or R183, in the GNAQ and/or the GNA11 gene.

The present invention also provides for methods of selecting patients for treatment with antibodies, antibody fragments (e.g., antigen binding fragments), or antibody drug conjugates of the invention comprising administering a therapeutically effective amount of said antibodies, antibody fragments (e.g., antigen binding fragments), or antibody drug conjugates. In certain aspects of the invention the methods comprise selecting a patient by measuring for expression of PMEL17. In certain aspects of the invention the methods comprise selecting a patient by identifying a mutation, e.g., an activating mutation affecting Q209 or R183, in the GNAQ or the GNA11 gene. In certain embodiments, the methods comprise measuring the level of PMEL17 expression in the patient as well as detecting for the GNAQ and/or GNA11 gene.

For the treatment or prevention of the disease, the appropriate dosage of the antibodies, antibody fragments (e.g., antigen binding fragments), or antibody drug conjugates of the present invention depends on various factors, such as the type of disease to be treated, the severity and course of the disease, the responsiveness of the disease, previous therapy, patient's clinical history, and so on. The antibody or agent can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody, antibody fragment (e.g., antigen binding fragment), or antibody drug conjugates. The treating physician can estimate repetition rates for dosing based on measured residence times and concentrations of the drug in bodily fluids or tissues.

Combination Therapy

In certain instances, an antibody, antibody fragment (e.g., antigen binding fragment), or antibody drug conjugate of the present invention is combined with other therapeutic treatments, such as surgery and radiation therapy, therapeutic agents, such as other anti-cancer agents, anti-allergic agents, anti-nausea agents (or anti-emetics), pain relievers, cytoprotective agents, and combinations thereof.

In one embodiment, an antibody, antibody fragment (e.g., antigen binding fragment), or antibody drug conjugate of the present invention is combined in a pharmaceutical combination formulation, or dosing regimen as combination therapy, with a second compound having anti-cancer properties. The second compound of the pharmaceutical combination formulation or dosing regimen can have complementary activities to the antibody or immunoconjugate of the combination such that they do not adversely affect each other. For example, an antibody, antibody fragment (e.g., antigen binding fragment), or antibody drug conjugate of the present invention can be administered in combination with, but not limited to, a chemotherapeutic agent, immunomodulatory agents, a tyrosine kinase inhibitor, a GNAQ/GNA11 downstream signaling pathway inhibitor, IAP inhibitors, Bcl2 inhibitors, Mcl1 inhibitors, and other GNAQ/GNA11 inhibitors.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g., synergistic effect.

The term "combination therapy" refers to the administration of two or more therapeutic agents to treat or prevent a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating or preventing the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), and pemetrexed.

In one aspect, the present invention provides a method of treating or preventing cancer by administering to a subject in need thereof an antibody drug conjugate of the present invention in combination with one or more MDM2 inhibitors, PKC inhibitors, PRC2 inhibitors, MAPK inhibitors, GPCR inhibitors, tyrosine kinase inhibitors, including but not limited to, BTK inhibitors, EGFR inhibitors, Her2 inhibitors, Her3 inhibitors, IGFR inhibitors, and Met inhibitors.

For example, MDM2 inhibitors include but are not limited to, RG7112 (RO5045337); RG7388 (RO5503781, Idasanutlin); MI-77301 (SAR405838); MK-8242 (SCH-900242); AMG232; CGM097; DS3032b; HDM201; and ALRN-6924.

For example, PKC inhibitors include but are not limited to, Balanol; Riluzole; Staurosporin; Enzastaurin; 6V1-1 (KAI-9803 or Delcasertib); EV1-2 (KAI-1678); Aprinocarsen; Midostaurin (PKC412); UCN-01 (7-hydroxystaurosporin); Rottlerin (5, 7, dihydroxy-2,2-dimethyl-6-(2,4,6-trihydroxy-3-methyl-5-acetlybenzyl)-8-cinnamoyl-1,2-chromene); and Bryostatin 1.

For example, PRC2 inhibitors include but are not limited to, EI1; EPZ011989; EPZ005687; Tetramethylpiperidinyl Benzamides; UNC1999; and GSK126.

For example, MAPK inhibitors include but are not limited to, Vemurafenib (Zelboraf); dabrafenib (Tafinlar); encorafenib (Braftovi); trametinib (Mekinist); cobimetinib (Cotellic); binimetinib (Mektovi); and ulixertinib.

For example, tyrosine kinase inhibitors include but are not limited to, Ibrutinib (PCI-32765); Erlotinib hydrochloride (Tarceva®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); and Imatinib or Imatinib mesylate (Gilvec® and Gleevec®).

Epidermal growth factor receptor (EGFR) inhibitors include but are not limited to, Erlotinib hydrochloride (Tarceva®), Gefitinib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4).

EGFR antibodies include but are not limited to, Cetuximab (Erbitux®); Panitumumab (Vectibix®); Matuzumab (EMD-72000); Nimotuzumab (hR3); Zalutumumab; TheraCIM h-R3; MDX0447 (CAS 339151-96-1); and ch806 (mAb-806, CAS 946414-09-1).

Human Epidermal Growth Factor Receptor 2 (Her2 receptor) (also known as Neu, ErbB-2, CD340, or p185) inhibitors include but are not limited to, Trastuzumab (Herceptin®); Pertuzumab (Omnitarg®); trastuzumab emtansine (Kadcyla®); Neratinib (HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443); Lapatinib or Lapatinib ditosylate (Tykerb®); (3R,4R)-4-amino-1-((4-((3-methoxyphenyl)amino)pyrrolo[2,1-f][1,2,4]triazin-5-yl)methyl)piperidin-3-ol (BMS690514); (2E)-N-[4-[(3-Chloro-4-fluorophenyl)amino]-7-[[(3S)-tetrahydro-3-furanyl]oxy]-6-qui nazolinyl]-4-(dimethylamino)-2-butenamide (BIBW-2992, CAS 850140-72-6); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS 599626, CAS 714971-09-2); Canertinib dihydrochloride (PD183805 or CI-1033); and N-(3,4-Dichloro-2-fluorophenyl)-6-methoxy-7-[[(3aα,5βaα)-octahydro-2-methylcyclopenta[c]pyrrol-5-yl]methoxy]-4-quinazolinamine (XL647, CAS 781613-23-8).

Her3 inhibitors include but are not limited to, LJM716, MM-121, AMG-888, RG7116, REGN-1400, AV-203, MP-RM-1, MM-111, and MEHD-7945A.

MET inhibitors include but are not limited to, Cabozantinib (XL184, CAS 849217-68-1); Foretinib (GSK1363089, formerly XL880, CAS 849217-64-7); Tivantinib (ARQ197, CAS 1000873-98-2); 1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458); Cryzotinib (Xalkori®, PF-02341066); (3Z)-5-(2,3-Dihydro-1H-indol-1-ylsulfonyl)-3-({3,5-dimethyl-4-[(4-methylpiperazin-1-yl)carbonyl]-1H-pyrrol-2-yl}methylene)-1,3-dihydro-2H-indol-2-one (SU11271); (3Z)—N-(3-Chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide (SU 11274); (3Z)—N-(3-Chlorophenyl)-3-{[3,5-dimethyl-4-(3-morpholin-4-ylpropyl)-1H-pyrrol-2-yl]methylene}-N-methyl-2-oxoindoline-5-sulfonamide (SU11606); 6-[Difluoro[6-(1-methyl-1H-pyrazol-4-yl)-1,2,4-triazolo[4,3-b]pyridazin-3-yl]methyl]-quinoline (JNJ38877605, CAS 943540-75-8); 2-[4-[1-(Quinolin-6-ylmethyl)-1H-[1,2,3]triazolo[4,5-b]pyrazin-6-yl]-1H-pyrazol-1-yl]ethanol (PF04217903, CAS 956905-27-4); N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide (M K2461, CAS 917879-39-1); 6-[[6-(1-Methyl-1H-pyrazol-4-yl)-1,2,4-triazolo[4,3-b]pyridazin-3-yl]thio]-quinoline (SGX523, CAS 1022150-57-7); and (3Z)-5-[[(2,6-Dichlorophenyl)methyl]sulfonyl]-3-[[3,5-dimethyl-4-[[(2R)-2-(1-pyrrolidinylmethyl)-1-pyrrolidinyl]carbonyl]-1H-pyrrol-2-yl]methylene]-1,3-dihydro-2H-indol-2-one (PHA665752, CAS 477575-56-7).

IGF1R inhibitors include but are not limited to, BMS-754807, XL-228, OSI-906, GSK0904529A, A-928605, AXL1717, KW-2450, MK0646, AMG479, IMCA12, MEDI-573, and B1836845. See e.g., Yee, JNCI, 104; 975 (2012) for review.

In another aspect, the present invention provides a method of treating or preventing cancer by administering to a subject in need thereof an antibody drug conjugate of the present invention in combination with one or more GNAQ/GNA11 downstream signaling pathway inhibitors, including but not limited to, β-arrestin inhibitors, GRK inhibitors, MAPK inhibitors, PI3K inhibitors, JAK inhibitors, etc.

For example, phosphoinositide 3-kinase (PI3K) inhibitors include but are not limited to, Idelalisib (Zydelig, GS-1101, Cal-101), 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran- 2,7,10(1H)-trione (PX866, CAS 502632-66-8); and 8-Phenyl-2-(morpholin-4-yl)-chromen-4-one (LY294002, CAS 154447-36-6).

In yet another aspect, the present invention provides a method of treating or preventing cancer by administering to a subject in need thereof an antibody drug conjugate of the present invention in combination with one or more pro-apoptosis, including but not limited to, IAP inhibitors, Bcl2 inhibitors, MCl1 inhibitors, Trail agents, Chk inhibitors.

For examples, IAP inhibitors include but are not limited to, LCL161, GDC-0917, AEG-35156, AT406, and TL32711. Other examples of IAP inhibitors include but are not limited to those disclosed in WO04/005284, WO 04/007529, WO05/097791, WO 05/069894, WO 05/069888, WO 05/094818, US2006/0014700, US2006/0025347, WO 06/069063, WO 06/010118, WO 06/017295, and WO08/134679, all of which are incorporated herein by reference.

BCL-2 inhibitors include but are not limited to, Venetoclax (also known as GDC-0199, ABT-199, RG7601); 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386); Tetrocarcin A; Antimycin; Gossypol ((−)BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (−)-Gossypol acetic acid (AT-101); 4-[4-[(4'-Chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]-benzamide (ABT-737, CAS 852808-04-9); and Navitoclax (ABT-263, CAS 923564-51-6).

Proapoptotic receptor agonists (PARAs) including DR4 (TRAILR1) and DR5 (TRAILR2), including but are not limited to, Dulanermin (AMG-951, RhApo2L/TRAIL); Mapatumumab (HRS-ETR1, CAS 658052-09-6); Lexatumumab (HGS-ETR2, CAS 845816-02-6); Apomab (Apomab®); Conatumumab (AMG655, CAS 896731-82-1); and Tigatuzumab (CS1008, CAS 946415-34-5, available from Daiichi Sankyo).

Checkpoint Kinase (CHK) inhibitors include but are not limited to, 7-Hydroxystaurosporine (UCN-01); 6-Bromo-3-(1-methyl-1H-pyrazol-4-yl)-5-(3R)-3-piperidinyl-pyrazolo[1,5-a]pyrimidin-7-amine (SCH900776, CAS 891494-63-6); 5-(3-Fluorophenyl)-3-ureidothiophene-2-carboxylic acid N—[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-k/]pyrrolo[3,4-i][1,6]benzodiazocine-1,3(2H)-dione (SB-218078, CAS 135897-06-2); and TAT-S216A (YGRKKRRQRRRLYRSPAMPENL (SEQ ID NO: 282)), and CBP501 ((d-Bpa)sws(d-Phe-F5)(d-Cha)rrrqrr).

In a further embodiment, the present invention provides a method of treating or preventing cancer by administering to a subject in need thereof an antibody drug conjugate of the present invention in combination with one or more immunomodulators (e.g., one or more of: an activator of a costimulatory molecule or an inhibitor of an immune checkpoint molecule).

In certain embodiments, the immunomodulator is an activator of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, STING, or CD83 ligand.

In certain embodiments, the immunomodulator is an inhibitor of an immune checkpoint molecule. In one embodiment, the immunomodulator is an inhibitor of PD-1, PD-L1, PD-L2, CTLA4, TIM3, LAG3, VISTA, BTLA, TIGIT, LAIR1, CD160, 2B4 and/or TGFR beta. In one embodiment, the inhibitor of an immune checkpoint molecule inhibits PD-1, PD-L1, LAG-3, TIM-3 or CTLA4, or any combination thereof. The term "inhibition" or "inhibitor" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40%, 50% or more is included by this term. Thus, inhibition need not be 100%.

Inhibition of an inhibitory molecule can be performed at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof (also referred to herein as "an antibody molecule") that binds to PD-1, PD-L1, PD-L2, CTLA4, TIM3, LAG3, VISTA, BTLA, TIGIT, LAIR1, CD160, 2B4 and/or TGFR beta, or a combination thereof.

In one embodiment, the antibody molecule is a full antibody or fragment thereof (e.g., a Fab, F(ab')$_2$, Fv, or a single chain Fv fragment (scFv)). In yet other embodiments, the antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG4 (e.g., human IgG1 or IgG4). In one embodiment, the heavy chain constant region is human IgG1 or human IgG4. In one embodiment, the constant region is altered, e.g., mutated, to modify the properties of the antibody molecule (e.g., to increase or decrease one or more of: Fc receptor binding, antibody glycosylation, the number of cysteine residues, effector cell function, or complement function).

In certain embodiments, the antibody molecule is in the form of a bispecific or multispecific antibody molecule. In one embodiment, the bispecific antibody molecule has a first binding specificity to PD-1 or PD-L1 and a second binding specificity, e.g., a second binding specificity to TIM-3, LAG-3, or PD-L2. In one embodiment, the bispecific antibody molecule binds to PD-1 or PD-L1 and TIM-3. In another embodiment, the bispecific antibody molecule binds to PD-1 or PD-L1 and LAG-3. In another embodiment, the bispecific antibody molecule binds to PD-1 and PD-L1. In yet another embodiment, the bispecific antibody molecule binds to PD-1 and PD-L2. In another embodiment, the bispecific antibody molecule binds to TIM-3 and LAG-3. Any combination of the aforesaid molecules can be made in a multispecific antibody molecule, e.g., a trispecific antibody that includes a first binding specificity to PD-1 or PD-1, and a second and third binding specificities to two or more of: TIM-3, LAG-3, or PD-L2.

In certain embodiments, the immunomodulator is an inhibitor of PD-1, e.g., human PD-1. In another embodiment, the immunomodulator is an inhibitor of PD-L1, e.g., human PD-L1. In one embodiment, the inhibitor of PD-1 or PD-L1 is an antibody molecule to PD-1 or PD-L1. The PD-1 or PD-L1 inhibitor can be administered alone, or in combination with other immunomodulators, e.g., in combination with an inhibitor of LAG-3, TIM-3 or CTLA4. In an exemplary embodiment, the inhibitor of PD-1 or PD-L1, e.g., the anti-PD-1 or PD-L1 antibody molecule, is administered in combination with a LAG-3 inhibitor, e.g., an anti-LAG-3 antibody molecule. In another embodiment, the inhibitor of PD-1 or PD-L1, e.g., the anti-PD-1 or PD-L1 antibody molecule, is administered in combination with a TIM-3 inhibitor, e.g., an anti-TIM-3 antibody molecule. In yet other embodiments, the inhibitor of PD-1 or PD-L1, e.g., the anti-PD-1 antibody molecule, is administered in combination with a LAG-3 inhibitor, e.g., an anti-LAG-3 antibody molecule, and a TIM-3 inhibitor, e.g., an anti-TIM-3 antibody molecule. Other combinations of immunomodulators with a PD-1 inhibitor (e.g., one or more of PD-L2, CTLA4, TIM3, LAG3, VISTA, BTLA, TIGIT, LAIR1, CD160, 2B4 and/or TGFR) are also within the present invention. Any of the antibody molecules known in the art or disclosed herein can be used in the aforesaid combinations of inhibitors of checkpoint molecule.

In one embodiment, the PD-1 inhibitor is an anti-PD-1 antibody chosen from Nivolumab, Pembrolizumab or Pidilizumab. In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and PCT Publication No. WO2006/121168.

In other embodiments, the anti-PD-1 antibody is Pembrolizumab. Pembrolizumab (Trade name KEYTRUDA formerly Lambrolizumab, also known as Merck 3745, MK-3475 or SCH-900475) is a humanized IgG4 monoclonal antibody that binds to PD1. Pembrolizumab is disclosed, e.g., in Hamid, O. et al. (2013) New England Journal of Medicine 369 (2): 134-44, PCT Publication No. WO2009/114335, and U.S. Pat. No. 8,354,509.

In some embodiments, the anti-PD-1 antibody is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in PCT Publication No. WO2009/101611. Other anti-PD1 antibodies are disclosed in U.S. Pat. No. 8,609,089, US Publication No. 2010028330, and/or US Publication No. 20120114649. Other anti-PD1 antibodies include AMP 514 (Amplimmune).

In some embodiments, the PD-1 inhibitor is PDR001, also known as spartalizumab, or any other anti-PD-1 antibody disclosed in WO2015/112900.

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224.

In some embodiments, the PD-LI inhibitor is anti-PD-LI antibody. In some embodiments, the anti-PD-LI inhibitor is chosen from YW243.55.S70, MPDL3280A, MEDI-4736, or MDX-1105MSB-0010718C (also referred to as A09-246-2) disclosed in, e.g., WO 2013/0179174, and having a sequence disclosed herein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-LI antibody described in PCT Publication No. WO2007/005874.

In one embodiment, the PD-L1 inhibitor is YW243.55.S70. The YW243.55.S70 antibody is an anti-PD-LI described in PCT Publication No. WO 2010/077634 (heavy and light chain variable region sequences shown in SEQ ID Nos. 20 and 21, respectively).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in PCT Publication Nos. WO2010/027827 and WO2011/066342).

In one embodiment, the LAG-3 inhibitor is an anti-LAG-3 antibody molecule. In one embodiment, the LAG-3 inhibitor is BMS-986016. In one embodiment, the LAG-3 inhibitor is LAG525 or any anti-LAG3 antibody disclosed in WO2015/138920.

In one embodiment, the TIM-3 inhibitor is an anti-TIM3 antibody molecule. In one embodiment, the TIM-3 inhibitor is MBG453 or any anti-TIM3 antibody disclosed in WO2015/117002.

Pharmaceutical Compositions

To prepare pharmaceutical or sterile compositions including immunoconjugates, the immunoconjugates of the invention are mixed with a pharmaceutically acceptable carrier or excipient. The compositions can additionally contain one or more other therapeutic agents that are suitable for treating or preventing a PMEL17 expressing cancer (including, but not limited to subcutaneous melanoma, uveal melanoma, hepatocellular carcinoma, and a metastatic cancer thereof).

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, NY, 1993; Lieberman, et al. (eds.), Pharmaceutical Dosage Forms: tablets, Marcel Dekker, NY, 1990; Lieberman, et al. (eds.) Pharmaceutical Dosage Forms: Disperse Systems, Marcel Dekker, NY, 1990; Weiner and Kotkoskie, Excipient Toxicity and Safety, Marcel Dekker, Inc., New York, N.Y., 2000).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, U K, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or prevention or predicted to affect treatment or prevention. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof of the invention can be provided by continuous infusion, or by doses at intervals of, e.g., one day, one week, or 1-7 times per week, once every other week, once every three weeks, once every four weeks, once every five weeks, once every six weeks, once every seven weeks, or once very eight weeks. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the immunoconjugates of the invention, the dosage administered to a patient may be 0.0001 mg/kg to 100 mg/kg of the patient's body weight. The dosage may be between 0.0001 mg/kg and 30 mg/kg, 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof of the invention may be calculated using the patient's weight in kilograms (kg) multiplied by the dose to be administered in mg/kg.

Doses of the immunoconjugates the invention may be repeated and the administrations may be separated by less than 1 day, at least 1 day, 2 days, 3 days, 5 days, 10 days, 15 days, 30 days, 45 days, 2 months, 75 days, 3 months, 4 months, 5 months, or at least 6 months. In some embodiments, the immunoconjugates of the invention may be given twice weekly, once weekly, once every two weeks, once every three weeks, once every four weeks, or less frequently. In a specific embodiment, doses of the immunoconjugates of the invention are repeated every 2 weeks.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, U K, 2001).

The route of administration may be by, e.g., topical or cutaneous application, injection or infusion by subcutaneous, intravenous, intraperitoneal, intracerebral, intramuscular, intraocular, intraarterial, intracerebrospinal, intralesional administration, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present invention may also be administered via one or more routes of administration using one or more of a variety of methods known in the art. As will be appreciated by the skilled artisan, the route and/or mode of administration will vary depending upon the desired results. Selected routes of administration for the immunoconjugates of the invention include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the invention can be administered via a non-parenteral route, such as a topical, epidermal or mucosal route of administration, for example, intranasally, orally, vaginally, rectally, sublingually or topically. In one embodiment, the immunoconjugates of the invention is administered by infusion. In another embodiment, the immunoconjugates of the invention is administered subcutaneously.

If the immunoconjugates of the invention are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the invention (see, e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During et al., Ann. Neurol. 25:351, 1989; Howard et al., J. Neurosurg. 7 1:105, 1989; U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly (methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more immunoconjugates of the invention. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rel. Bioact. Mater. 24:853-854, 1997; and Lam et al., Proc. Int'l. Symp. Control Rel. Bioact. Mater. 24:759-760, 1997, each of which is incorporated herein by reference in their entirety.

If the immunoconjugates of the invention are administered topically, they can be formulated in the form of an ointment, cream, transdermal patch, lotion, gel, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the immunoconjugates are administered intranasally, it can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, $10^{th}$ ed., McGraw-Hill, New York, N.Y.; Poole and Peterson (eds.) (2001) Pharmacotherapeutics for Advanced Practice:A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the immunoconjugates of the invention may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the immunoconjugates of the invention. The two or more therapies may be administered within one same patient visit.

In certain embodiments, the immunoconjugates of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al., (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The invention provides protocols for the administration of pharmaceutical composition comprising immunoconjugates of the invention alone or in combination with other therapies to a subject in need thereof. The therapies (e.g., prophylactic or therapeutic agents) of the combination therapies of the present invention can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the invention can be administered to a subject concurrently.

The term "concurrently" is not limited to the administration of therapies (e.g., prophylactic or therapeutic agents) at exactly the same time, but rather it is meant that a pharmaceutical composition comprising antibodies or fragments thereof the invention are administered to a subject in a sequence and within a time interval such that the antibody drug conjugates of the invention can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 5 minutes apart, less than 15 minutes apart, less than 30 minutes apart, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration. The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

Example 1: Synthesis of Exemplary Linker-Drug Compounds

Example 1-1: Synthesis of (R)-1-((3S,6S,9S,12S, 18R,21S,22R)-21-acetamido-18-benzyl-22-isopropyl-3-((R)-1-methoxyethyl)-4,9,10,12,16-pentamethyl-15-methylene-2,5,8,11,14,17,20-heptaoxo-1, 19-dioxa-4,7,10,13,16-pentaazacyclodocosan-6-yl)-2-methylpropyl (2S,3R)-3-((((4-((S)-2-((S)-2-(3-(2-(2,5-dioxo-2,5-dihydro-1H-pyrrol-1-yl)ethoxy) propanamido)-3-methylbutanamido)-5-ureidopentanamido)benzyl)oxy)(hydroxy) phosphoryl)oxy)-4-methyl-2-propionamidopentanoate (B1)

Step 1: Synthesis of (R)-1-((3S,6S,9S,12S,18R,21S, 22R)-21-acetamido-18-benzyl-22-isopropyl-3-((R)-1-methoxyethyl)-4,9,10,12,16-pentamethyl-15-methylene-2,5,8,11,14,17,20-heptaoxo-1,19-dioxa-4,7,10, 13,16-pentaazacyclodocosan-6-yl)-2-methylpropyl (2S,3R)-3-((hydroxyhydrophosphoryl)oxy)-4-methyl-2-propionamidopentanoate (1-1)

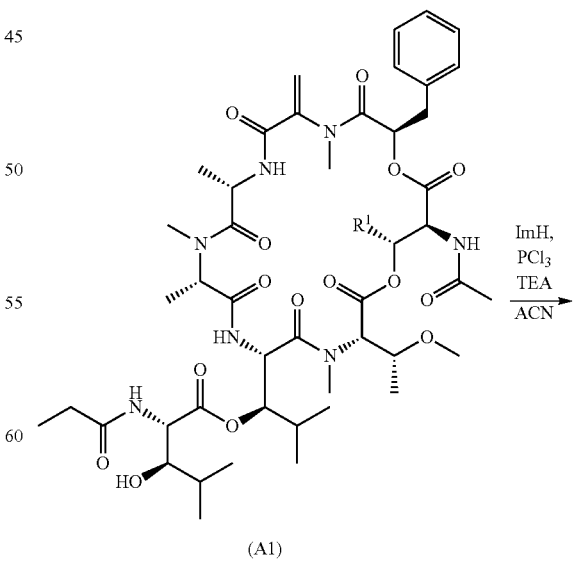

(A1)

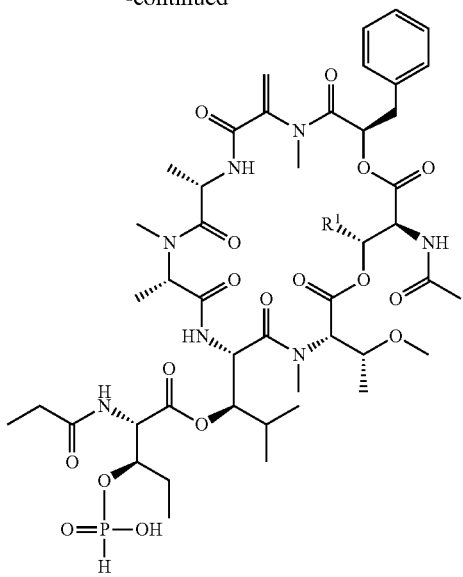

(1-1)

Imidazole (102 mg, 1.49 mmol, 15 equiv.) was dissolved in acetonitrile (ACN) (1.4 mL) and cooled in an ice-bath (crashing of ImH is observed and the mixture was raised from the ice-bath to solubilize ImH) while still cold. Then, phosphorus trichloride (1.0 M in ACN) (499 μl, 0.499 mmol, 5 equiv.) was added dropwise (which results in a white suspension) and the mixture was agitated for 10 min. Then triethylamine (250 μl, 1.796 mmol, 18 equiv.) was added and the mixture agitated for 40 min after which (R)-1-((3S,6S, 9S,12S,18R,21S,22R)-21-acetamido-18-benzyl-22-isopropyl-3-((R)-1-methoxyethyl)-4,9,10,12,16-pentamethyl-15-methylene-2,5,8,11,14,17,20-heptaoxo-1,19-dioxa-4,7,10, 13,16-pentaazacyclodocosan-6-yl)-2-methylpropyl (2S, 3R)-3-hydroxy-4-methyl-2-propionamidopentanoate (A1) (100 mg, 0.100 mmol, 1.0 equiv., compound (A1) was obtained using the method described in Example 3-1) in ACN (1.7 mL) was added. The yellowish-orange heterogenous mixture was warmed to room temperature and agitiated for a total of 60 minutes. The mixture was treated with water (0.2 mL) and the material purified by reverse-phase flash chromatography (0-100% ACN/Water, 40 gram C18 column, neutral mobile phase) and the product fractions collected and lyophillized to afford the H-phosphonate (1-1) as a yellowish-white amorphous powder. LCMS: MH+=1066.3, 0.78 min (Acquity UPLC BEH C18 1.7 um Column, 2-98% 2 min run with Water/MeCN+0.1% NH₄OH, basic method).

Step 2: Synthesis of (R)-1-((3S,6S,9S,12S,18R,21S, 22R)-21-acetamido-18-benzyl-22-isopropyl-3-((R)-1-methoxyethyl)-4,9,10,12,16-pentamethyl-15-methylene-2,5,8,11,14,17,20-heptaoxo-1,19-dioxa-4,7,10, 13,16-pentaazacyclodocosan-6-yl)-2-methylpropyl (2S,3R)-3-((((4-((S)-2-((S)-2-(3-(2-(2,5-dioxo-2,5-dihydro-1H-pyrrol-1-yl)ethoxy)propanamido)-3-methylbutanamido)-5-ureidopentanamido)benzyl) oxy)(hydroxy)phosphoryl)oxy)-4-methyl-2-propionamidopentanoate (B1)

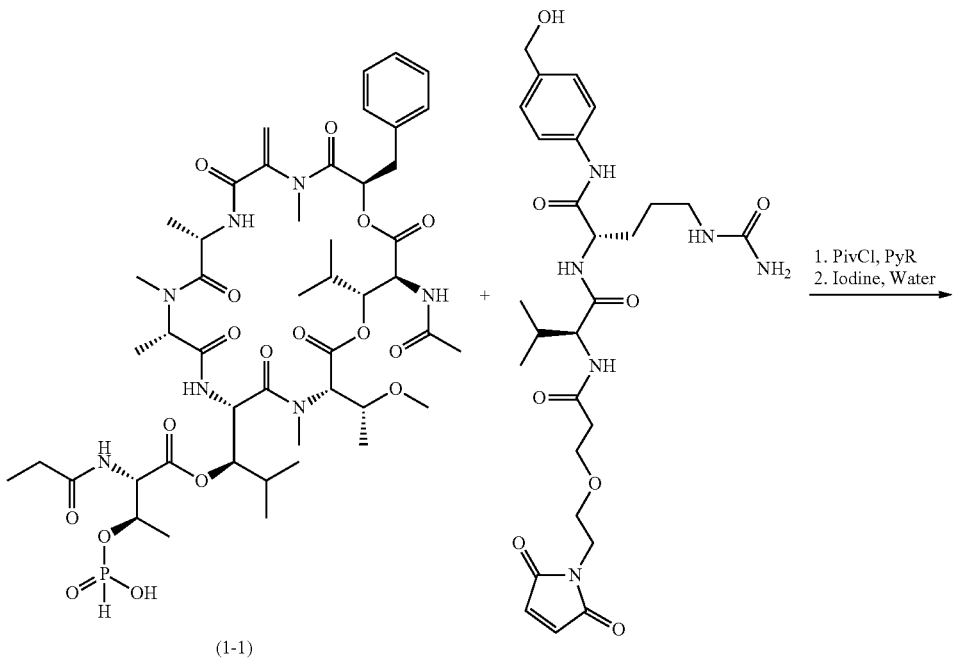

(1-1)

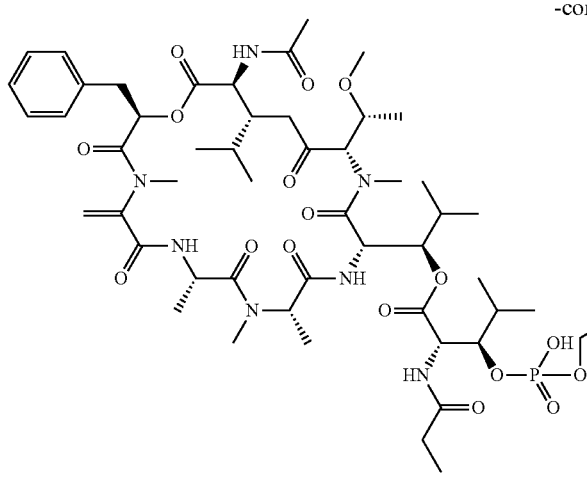

(B1)

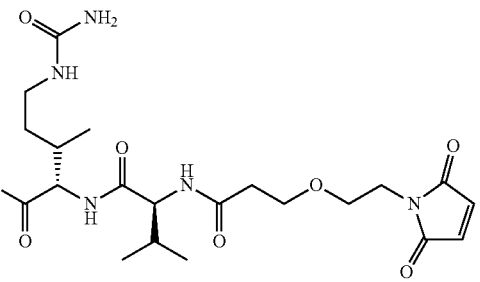

(R)-1-((3S,6S,9S,12S,18R,21S,22R)-21-acetamido-18-benzyl-22-isopropyl-3-((R)-1-methoxyethyl)-4,9,10,12,16-pentamethyl-15-methylene-2,5,8,11,14,17,20-heptaoxo-1,19-dioxa-4,7,10,13,16-pentaazacyclodocosan-6-yl)-2-methylpropyl (2S,3R)-3-((hydroxyhydrophosphoryl)oxy)-4-methyl-2-propionamidopentanoate (1-1) (100 mg, 0.094 mmol, 1.0 equiv.) and (S)-2-((S)-2-(3-(2-(2,5-dihydro-1H-pyrrol-1-yl)ethoxy) propanamido)-3-methylbutanamido)-N-(4-(hydroxymethyl) phenyl)-5-ureidopentanamide (108 mg, 0.188 mmol, 2.0 equiv., CAS #is 2055041-37-5) (both lyophilized powders were transferred into a 10 mL vial) and dissolved in pyridine (4 mL). Then, pivaloyl chloride (0.058 mL, 0.469 mmol, 5 equiv.) was added dropwise to give a faint yellow solution. The mixture was agitiated at room temperature for 10 minutes and then 1.0 equiv. additional pivaloyl chloride was added. A freshly prepared solution of iodine (47.6 mg, 0.188 mmol, 2.0 equiv.) in pyridine-water (14:1, 750 uL) was added to give a dark-brown clear solution. The mixture was agitated for 25 minutes and directly purified by reverse-phase flash chromatography (40 g C-18 column, 0% Ac/MeCN 3 minutes, then 0-60% ACN/Water over 15 minutes, neutral method) to afford (R)-1-((3S,6S,9S,12S,18R,21S,22R)-21-acetamido-18-benzyl-22-isopropyl-3-((R)-1-methoxyethyl)-4,9,10,12,16-pentamethyl-15-methylene-2,5,8,11,14,17,20-heptaoxo-1,19-dioxa-4,7,10,13,16-pentaazacyclodocosan-6-yl)-2-methylpropyl (2S,3R)-3-((((4-((S)-2-((S)-2-(3-(2-(2,5-dioxo-2,5-dihydro-1H-pyrrol-1-yl)ethoxy) propanamido)-3-methylbutanamido)-5-ureidopentanamido)benzyl)oxy)(hydroxy)phosphoryl)oxy)-4-methyl-2-propionamidopentanoate (B-1). HRMS; MH+=1638.7700, 2.84 min.

Example 1-2: Synthesis of (R)-1-((3S,6S,9S,12S,18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4,7,10,13,16-pentaazacyclodocosan-6-yl)-2-methylpropyl (2S,3R)-2-acetamido-3-((((4-((S)-2-((S)-2-(3-(2-(2,5-dioxo-2,5-dihydro-1H-pyrrol-1-yl)ethoxy)propanamido)-3-methylbutanamido)-5-ureidopentanamido)benzyl)oxy)(hydroxy)phosphoryl)oxy)-4-methylpentanoate (B2)

Step 1: Synthesis of (R)-1-((3S,6S,9S,12S,18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4,7,10,13,16-pentaazacyclodocosan-6-yl)-2-methylpropyl (2S,3R)-2-acetamido-3-((hydroxyhydrophosphoryl)oxy)-4-methylpentanoate (1-2)

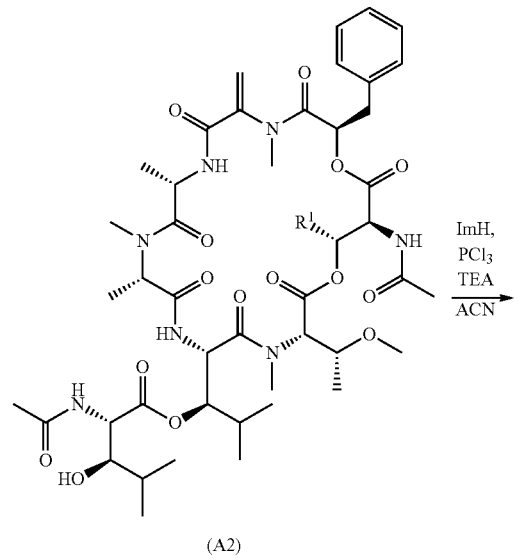

(A2)

-continued

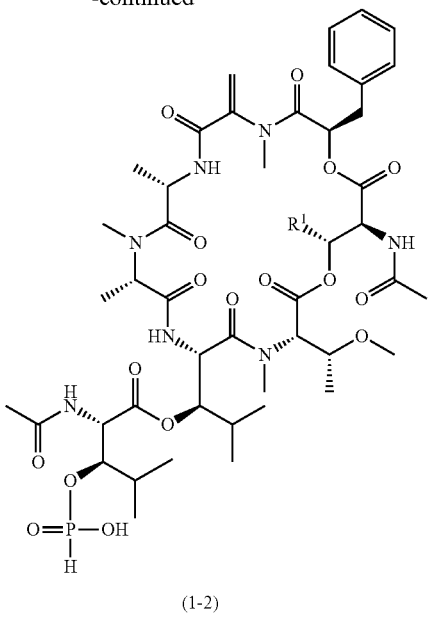

(1-2)

Imidazole (85 mg, 1.25 mmol, 15 equiv.) was dissolved in acetonitrile (ACN) (2.5 mL) and cooled in an ice-bath (crashing of ImH is observed and the mixture was raised from the ice-bath to solubilize ImH) while still cold. Then, phosphorus trichloride (36.4 µl dissolved in 0.5 mL MeCN, 0.417 mmol, 5 equiv.) was added dropwise (which results in a white suspension) and the mixture was agitated for 10 min. Then triethylamine (174 µl, 1.25 mmol, 15 equiv.) was added and the mixture agitated for 40 min after which (R)-1-((3S,6S,9S,12S,18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4,7,10,13,16-pentaazacyclodocosan-6-yl)-2-methylpropyl (2S,3R)-2-acetamido-3-hydroxy-4-methylpentanoate (A2) (80 mg, 0.084 mmol, 1.0 equiv., compound (A2) was obtained using the method described in Example 3-2) in ACN (1.7 mL) was added. The yellowish-orange heterogenous mixture was warmed to room temperature and agitated for a total of 30 minutes. The mixture was treated with water (1 mL) and the material purified by reverse-phase flash chromatography (0-100% ACN/Water, 40 gram C18 column, neutral mobile phase) and the product fractions collected and lyophillized to afford the H-phosphonate (1-2) as a yellowish-white amorphous powder. LCMS: MH+=1024.3, 0.78 min (Acquity UPLC BEH C18 1.7 um Column, 2-98% 2 min run with Water/MeCN+0.1% NH$_4$OH, basic method).

Step 2: Synthesis of (R)-1-((3S,6S,9S,12S,18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4,7,10,13,16-pentaazacyclodocosan-6-yl)-2-methylpropyl (2S,3R)-2-acetamido-3-((((4-((S)-2-((S)-2-(3-(2-(2,5-dioxo-2,5-dihydro-1H-pyrrol-1-yl)ethoxy)propanamido)-3-methylbutanamido)-5-ureidopentanamido)benzyl)oxy)(hydroxy)phosphoryl)oxy)-4-methylpentanoate

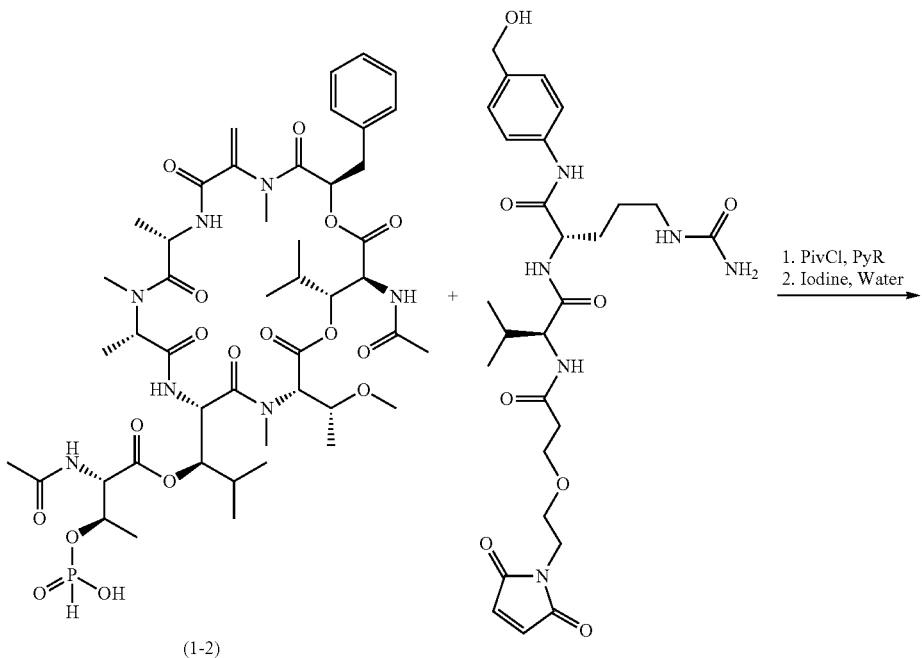

(1-2)

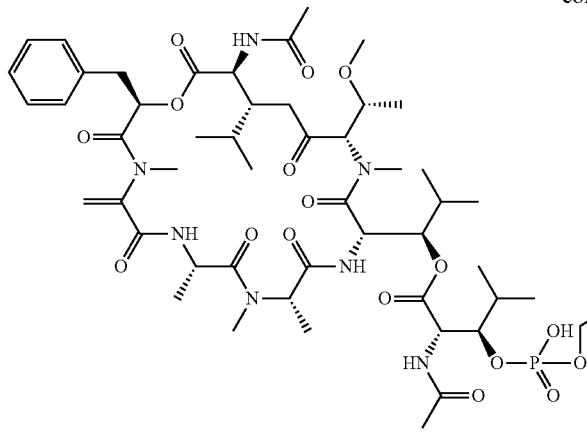

(B2)

(R)-1-((3S,6S,9S,12S,18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4,7,10,13,16-pentaazacyclodocosan-6-yl)-2-methylpropyl (2S,3R)-2-acetamido-3-((hydroxyhydrophosphoryl)oxy)-4-methylpentanoate (1-2) (50 mg, 0.049 mmol, 1.0 equiv.) and (S)-2-((S)-2-(3-(2-(2,5-dioxo-2,5-dihydro-1H-pyrrol-1-yl)ethoxy)propanamido)-3-methylbutanamido)-N-(4-(hydroxymethyl)phenyl)-5-ureidopentanamide (CAS #2055041-37-5) (33.7 mg, 0.059 mmol, 1.2 equiv.) (both lyophilized powders were transferred into a 10 mL vial) and dissolved in pyridine (1 mL). Then, pivaloyl chloride (0.042 mL, 0.342 mmol, 7 equiv.) was added dropwise to give a faint yellow solution. The mixture was agitiated at room temperature for 30 minutes. A freshly prepared solution of iodine (49.6 mg, 0.195 mmol, 4 equiv.) in pyridine-water (20:1, 500 uL) was added to give a dark-brown clear solution. The mixture was agitated for 30 minutes and directly purified by reverse-phase flash chromatography (40 g C-18 column, 0% Ac/MeCN 3 minutes, then 0-70% ACN/Water over 15 minutes, neutral method) to afford (R)-1-((3S,6S,9S,12S,18R,21S,22R)-21-acetamido-18-benzyl-22-isopropyl-3-((R)-1-methoxyethyl)-4,9,10,12,16-pentamethyl-15-methylene-2,5,8,11,14,17,20-heptaoxo-1,19-dioxa-4,7,10,13,16-pentaazacyclodocosan-6-yl)-2-methylpropyl (2S,3R)-3-((((4-((S)-2-((S)-2-(3-(2-(2,5-dioxo-2,5-dihydro-1H-pyrrol-1-yl)ethoxy)propanamido)-3-methylbutanamido)-5-ureidopentanamido)benzyl)oxy)(hydroxy)phosphoryl)oxy)-4-methyl-2-propionamidopentanoate (B2). HRMS; MH+=1595.7200, 2.25 min.

Example 1-3: Synthesis of (R)-1-((3S,6S,9S,12S,18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4,7,10,13,16-pentaazacyclodocosan-6-yl)-2-methylpropyl (2S,3R)-3-((((4-((S)-2-((S)-2-(3-(2-(2,5-dioxo-2,5-dihydro-1H-pyrrol-1-yl)ethoxy)propanamido)-3-methylbutanamido)-5-ureidopentanamido)benzyl)oxy)(hydroxy)phosphoryl)oxy)-4-methyl-2-propionamidopentanoate (B3)

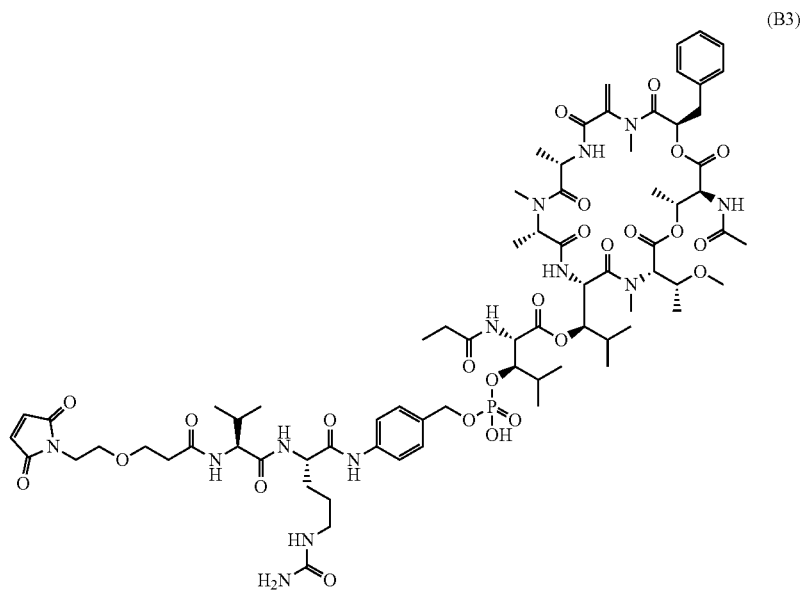 [SMILES: C=C1C(=O)N[C@@H](C)C(=O)N(C)[C@@H](C)C(=O)N[C@@H]([C@H](OC(=O)[C@@H](NC(=O)CC)[C@H](OP(=O)(O)OCc2ccc(NC(=O)[C@H](CCCNC(N)=O)NC(=O)[C@@H](NC(=O)CCOCCN3C(=O)C=CC3=O)C(C)C)cc2)C(C)C)C(C)C)C(=O)N(C)[C@@H]([C@@H](C)OC)C(=O)O[C@H](C)[C@H](NC(C)=O)C(=O)O[C@H](Cc2ccccc2)C(=O)N1C]

(B3)

Compound (B3) can be obtained using procedures similar to the methods described in Example 1-1, except in step 1 where compound (A3) (from Example 3-3) is used in place of compound (A1).

Example 1-4: Synthesis of (R)-1-((3S,6S,9S,12S,18R,21S,22R)-21-acetamido-18-benzyl-22-isopropyl-3-((R)-1-methoxyethyl)-4,9,10,12,16-pentamethyl-15-methylene-2,5,8,11,14,17,20-heptaoxo-1,19-dioxa-4,7,10,13,16-pentaazacyclodocosan-6-yl)-2-methylpropyl (2S,3R)-3-((((4-((S)-2-((S)-2-(3-(2,5-dioxo-2,5-dihydro-1H-pyrrol-1-yl)propanamido)-3-methylbutanamido)-5-ureidopentanamido)benzyl)oxy)(hydroxy)phosphoryl)oxy)-4-methyl-2-propionamidopentanoate (B4)

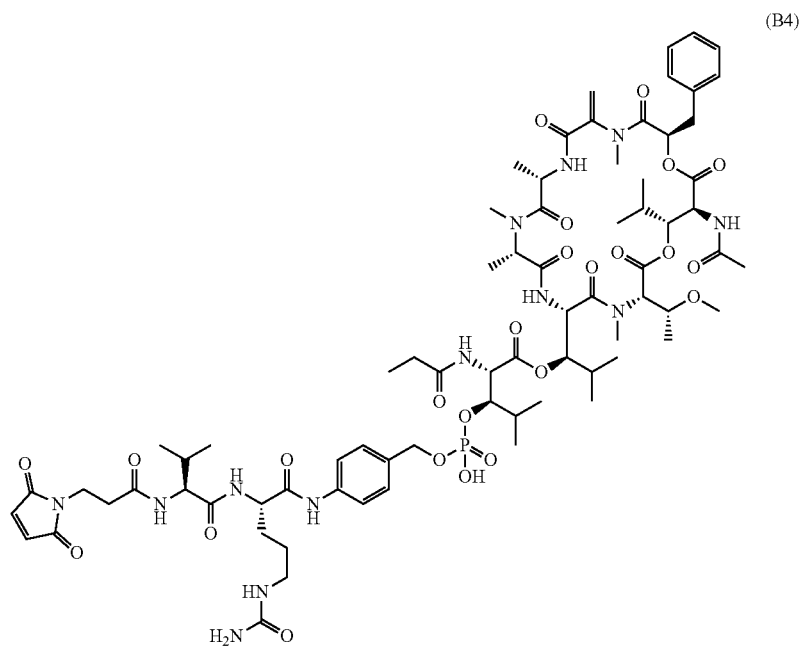 [SMILES: C=C1C(=O)N[C@@H](C)C(=O)N(C)[C@@H](C)C(=O)N[C@@H]([C@H](OC(=O)[C@@H](NC(=O)CC)[C@H](OP(=O)(O)OCc2ccc(NC(=O)[C@H](CCCNC(N)=O)NC(=O)[C@@H](NC(=O)CCN3C(=O)C=CC3=O)C(C)C)cc2)C(C)C)C(C)C)C(=O)N(C)[C@@H]([C@@H](C)OC)C(=O)O[C@H](C(C)C)[C@H](NC(C)=O)C(=O)O[C@H](Cc2ccccc2)C(=O)N1C]

(B4)

Compound (B4) was obtained using procedures similar to the methods described in Example 1-1, except in step 2 where (S)-2-((S)-2-(3-(2,5-dioxo-2,5-dihydro-1H-pyrrol-1-yl)propanamido)-3-methylbutanamido)-N-(4-(hydroxymethyl)phenyl)-5-ureidopentanamide (CAS #1949793-46-7) was used in place of (S)-2-((S)-2-(3-(2-(2,5-dioxo-2,5-dihydro-1H-pyrrol-1-yl)ethoxy)propanamido)-3-methylbutanamido)-N-(4-(hydroxymethyl)phenyl)-5-ureidopentanamide (CAS #is 2055041-37-5). HRMS; MH+=1594.5400, 2.88 min.

Example 1-5: Synthesis of (R)-1-((3S,6S,9S,12S, 18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4,7,10,13,16-pentaazacyclodocosan-6-yl)-2-methylpropyl (2S,3R)-2-acetamido-3-((((4-((S)-2-((S)-2-(3-(2,5-dioxo-2,5-dihydro-1H-pyrrol-1-yl)propanamido)-3-methylbutanamido)-5-ureidopentanamido)benzyl)oxy)(hydroxy)phosphoryl)oxy)-4-methylpentanoate (B5)

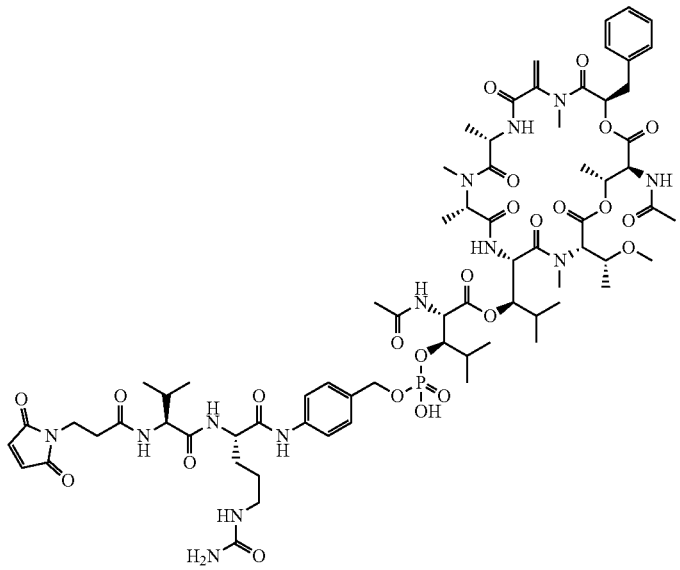

(B5)

Compound (B5) can be obtained using procedures similar to the methods described in Example 1-1, except in step 1 where compound (A2) (from Example 3-2) was used in place of compound (A1), and in step 2 where (S)-2-((S)-2-(3-(2,5-dioxo-2,5-dihydro-1H-pyrrol-1-yl)propanamido)-3-methylbutanamido)-N-(4-(hydroxymethyl)phenyl)-5-ureidopentanamide (CAS #1949793-46-7) is used in place of (S)-2-((S)-2-(3-(2-(2,5-dioxo-2,5-dihydro-1H-pyrrol-1-yl)ethoxy)propanamido)-3-methylbutanamido)-N-(4-(hydroxymethyl)phenyl)-5-ureidopentanamide (CAS #is 2055041-37-5).

Example 1-6: Synthesis of (R)-1-((3S,6S,9S,12S, 18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4, 7,10,13,16-pentaazacyclodocosan-6-yl)-2-methylpropyl (2S,3R)-3-(((((4-((S)-2-((S)-2-(3-(2,5-dioxo-2,5-dihydro-1H-pyrrol-1-yl)propanamido)-3-methylbutanamido)-5-ureidopentanamido)benzyl)oxy)(hydroxy)phosphoryl)oxy)-4-methyl-2-propionamidopentanoate (B6)

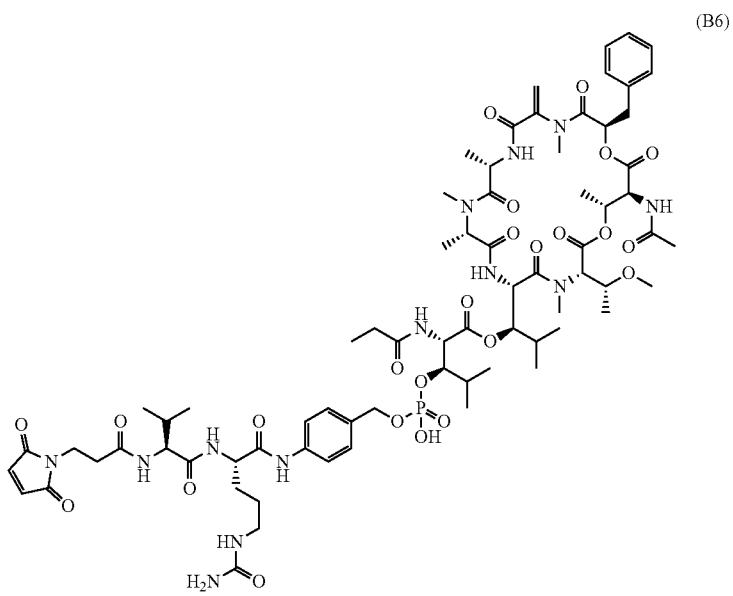 [SMILES: C=C1C(=O)N[C@@H](C)C(=O)N(C)[C@@H](C)C(=O)N[C@@H]([C@H](OC(=O)[C@@H](NC(=O)CC)[C@H](OP(=O)(O)OCc2ccc(NC(=O)[C@H](CCCNC(N)=O)NC(=O)[C@@H](NC(=O)CCN3C(=O)C=CC3=O)C(C)C)cc2)C(C)C)C(C)C)C(=O)N(C)[C@@H]([C@@H](C)OC)C(=O)O[C@H](C)[C@H](NC(C)=O)C(=O)O[C@H](Cc2ccccc2)C(=O)N1C]

(B6)

Compound (B6) can be obtained using procedures similar to the methods described in Example 1-1, except in step 1 where compound (A3) (from Example 3-3) was used in place of compound (A1), and in step 2 where (S)-2-((S)-2-(3-(2,5-dioxo-2,5-dihydro-1H-pyrrol-1-yl)propanamido)-3-methylbutanamido)-N-(4-(hydroxymethyl)phenyl)-5-ureidopentanamide (CAS #1949793-46-7) is used in place of (S)-2-((S)-2-(3-(2-(2,5-dioxo-2,5-dihydro-1H-pyrrol-1-yl)ethoxy)propanamido)-3-methylbutanamido)-N-(4-(hydroxymethyl)phenyl)-5-ureidopentanamide (CAS #is 2055041-37-5).

Example 1-7: Synthesis of (R)-1-((3S,6S,9S,12S, 18R,21S,22R)-21-acetamido-18-benzyl-22-isopropyl-3-((R)-1-methoxyethyl)-4,9,10,12,16-pentamethyl-15-methylene-2,5,8,11,14,17,20-heptaoxo-1, 19-dioxa-4,7,10,13,16-pentaazacyclodocosan-6-yl)-2-methylpropyl (2S,3R)-3-((((4-((S)-2-((S)-2-(3-(2-(2,5-dioxo-2,5-dihydro-1H-pyrrol-1-yl)ethoxy) propanamido)-3-methylbutanamido)-5-ureidopentanamido)benzyl)oxy)carbonyl)oxy)-4-methyl-2-propionamidopentanoate (B7)
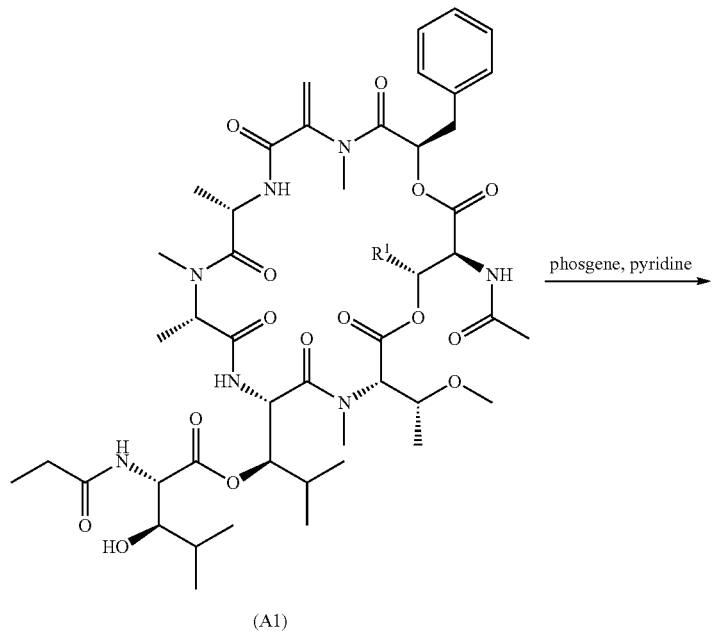
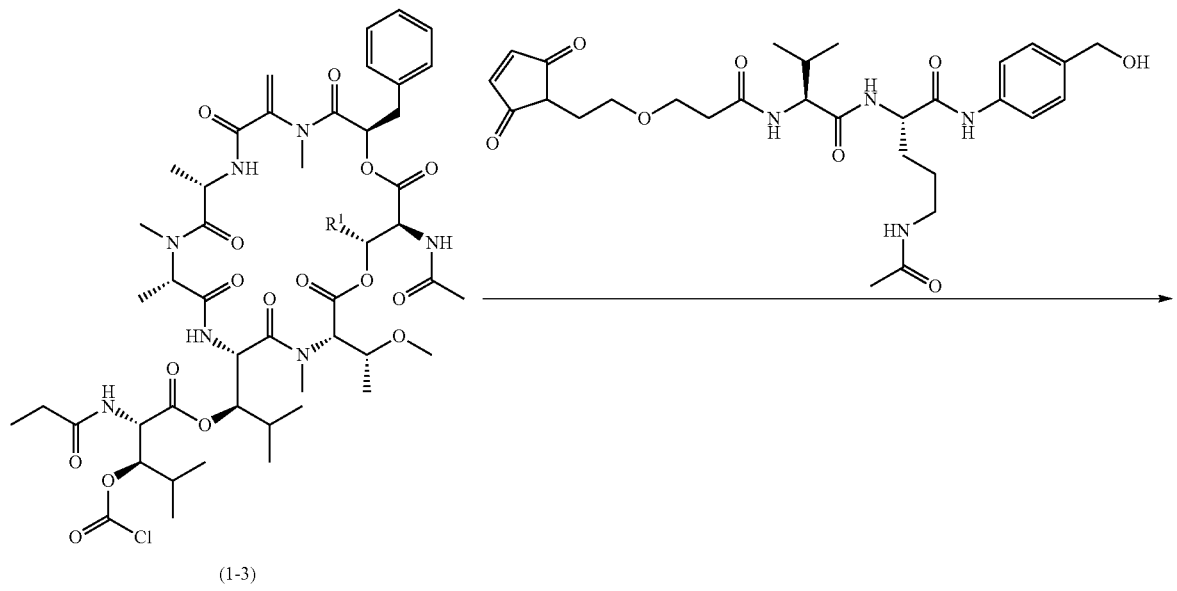

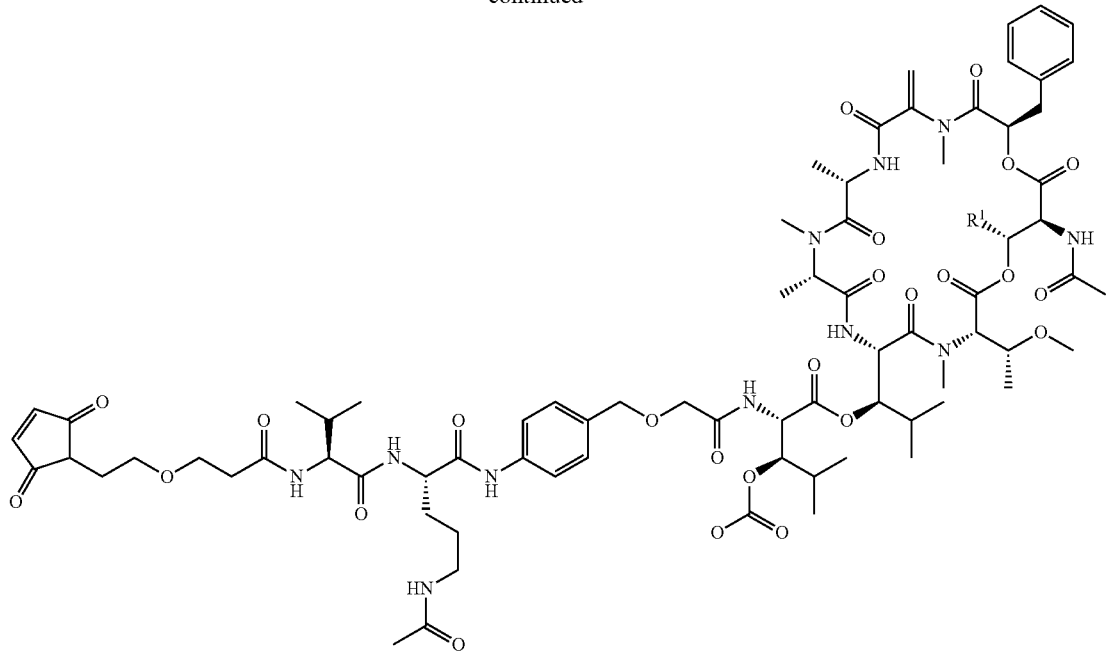

(B7)

Compound (B7) may be obtained by reacting chloroformate (1-3) with (S)-2-((S)-2-(3-(2-(2,5-dioxo-2,5-dihydro-1H-pyrrol-1-yl)ethoxy)propanamido)-3-methylbutanamido)-N-(4-(hydroxymethyl)phenyl)-5-ureidopentanamide (CAS #is 2055041-37-5). Chloroformate (1-3) may be obtained by reacting Compound (A1) with phosgene.

Example 1-8: Synthesis of (R)-1-((3S,6S,9S,12S,18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4,7,10,13,16-pentaazacyclodocosan-6-yl)-2-methylpropyl (2S,3R)-2-acetamido-3-((((4-((S)-2-((S)-2-(3-(2-(2,5-dioxo-2,5-dihydro-1H-pyrrol-1-yl)ethoxy)propanamido)-3-methylbutanamido)-5-ureidopentanamido)benzyl)oxy)carbonyl)oxy)-4-methylpentanoate (B8)

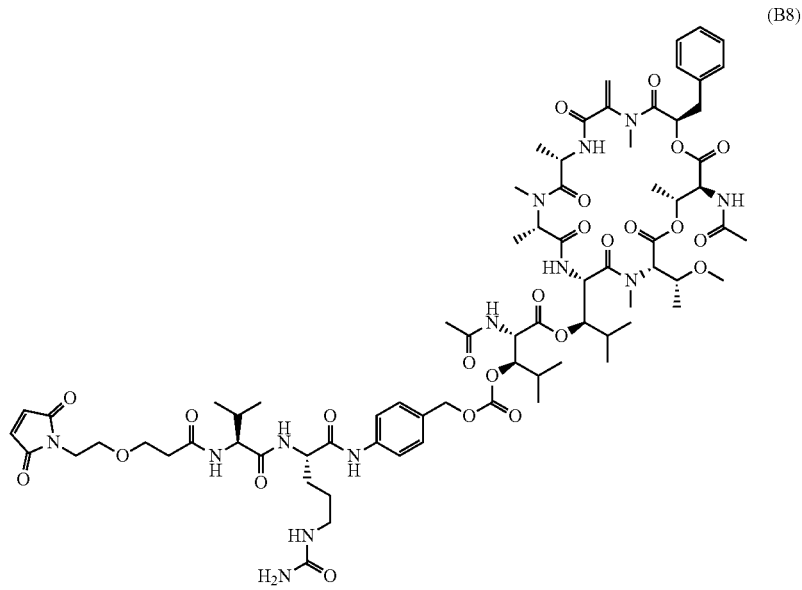 [SMILES: C=C1C(=O)N[C@@H](C)C(=O)N(C)[C@@H](C)C(=O)N[C@@H]([C@H](OC(=O)[C@@H](NC(C)=O)[C@H](OC(=O)OCc2ccc(NC(=O)[C@H](CCCNC(N)=O)NC(=O)[C@@H](NC(=O)CCOCCN3C(=O)C=CC3=O)C(C)C)cc2)C(C)C)C(C)C)C(=O)N(C)[C@@H]([C@@H](C)OC)C(=O)O[C@H](C)[C@H](NC(C)=O)C(=O)O[C@H](Cc2ccccc2)C(=O)N1C]

(B8)

Compound (B8) may be obtained using the method described in Example 1-7, except Compound (A2) is used in place of Compound (A1).

Example 1-9: Synthesis of (R)-1-((3S,6S,9S,12S,18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4,7,10,13,16-pentaazacyclodocosan-6-yl)-2-methylpropyl (2S,3R)-3-((((4-((S)-2-((S)-2-(3-(2-(2,5-dioxo-2,5-dihydro-1H-pyrrol-1-yl)ethoxy)propanamido)-3-methylbutanamido)-5-ureidopentanamido)benzyl)oxy)carbonyl)oxy)-4-methyl-2-propionamidopentanoate (B9)

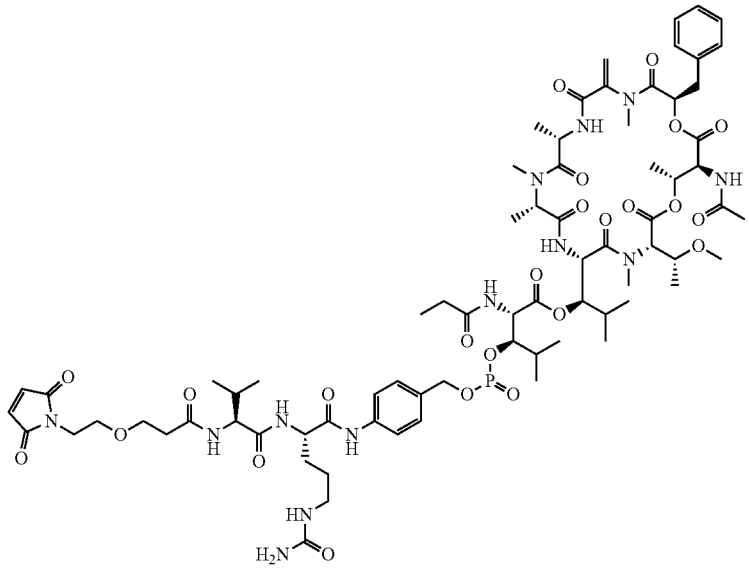

(B9)

Compound (B9) may be obtained using the method described in Example 1-7, except Compound (A3) is used in place of Compound (A1).

Example 1-10: Synthesis of (R)-1-((3S,6S,9S,12S,18R,21S,22R)-21-acetamido-18-benzyl-22-isopropyl-3-((R)-1-methoxyethyl)-4,9,10,12,16-pentamethyl-15-methylene-2,5,8,11,14,17,20-heptaoxo-1,19-dioxa-4,7,10,13,16-pentaazacyclodocosan-6-yl)-2-methylpropyl (2S,3R)-3-((((4-((S)-2-((S)-2-(3-(2,5-dioxo-2,5-dihydro-1H-pyrrol-1-yl)propanamido)-3-methylbutanamido)-5-ureidopentanamido)benzyl)oxy)carbonyl)oxy)-4-methyl-2-propionamidopentanoate (B10)

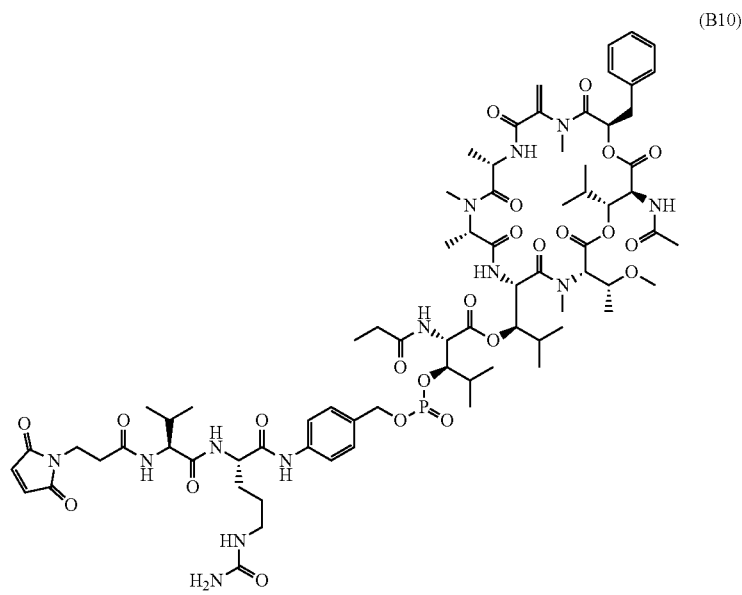

(B10)

Compound (B10) may be obtained using the method described in Example 1-7, except (S)-2-((S)-2-(3-(2,5-dioxo-2,5-dihydro-1H-pyrrol-1-yl)propanamido)-3-methylbutanamido)-N-(4-(hydroxymethyl) phenyl)-5-ureidopentanamide (CAS #1949793-46-7) is used in place of (S)-2-((S)-2-(3-(2-(2,5-dioxo-2,5-dihydro-1H-pyrrol-1-yl)ethoxy)propanamido)-3-methylbutanamido)-N-(4-(hydroxymethyl)phenyl)-5-ureidopentanamide (CAS #is 2055041-37-5).

Example 1-11: Synthesis of (R)-1-((3S,6S,9S,12S,18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4,7,10,13,16-pentaazacyclodocosan-6-yl)-2-methylpropyl (2S,3R)-2-acetamido-3-((((4-((S)-2-((S)-2-(3-(2,5-dioxo-2,5-dihydro-1H-pyrrol-1-yl)propanamido)-3-methylbutanamido)-5-ureidopentanamido)benzyl)oxy)carbonyl)oxy)-4-methylpentanoate (B11)

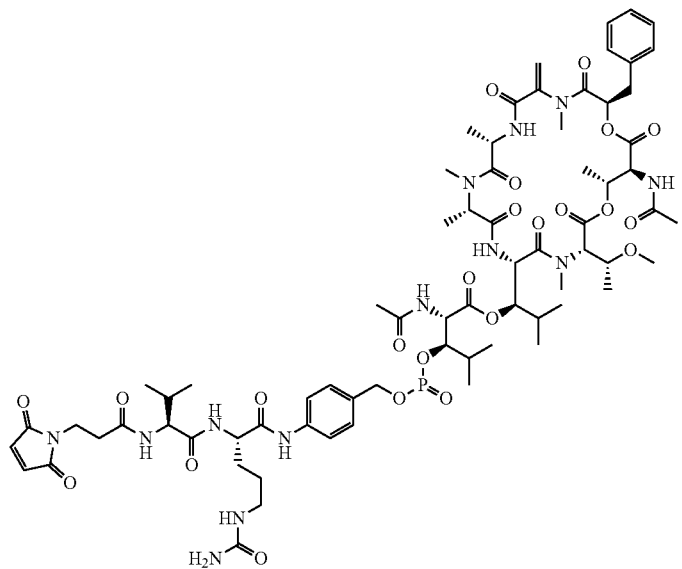

(B11)

Compound (E11) may be obtained using the method described in Example 1-10, except Compound (A2) is used in place of Compound (A1).

Example 1-12: Synthesis of (R)-1-((3S,6S,9S,12S, 18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4, 7,10,13,16-pentaazacyclodocosan-6-yl)-2-methylpropyl (2S,3R)-3-(((((4-((S)-2-((S)-2-(3-(2,5-dioxo-2,5-dihydro-1H-pyrrol-1-yl)propanamido)-3-methylbutanamido)-5-ureidopentanamido benzyl) oxy)carbonyl)oxy)-4-methyl 2-propionamidopentanoate (B12)

(B12)

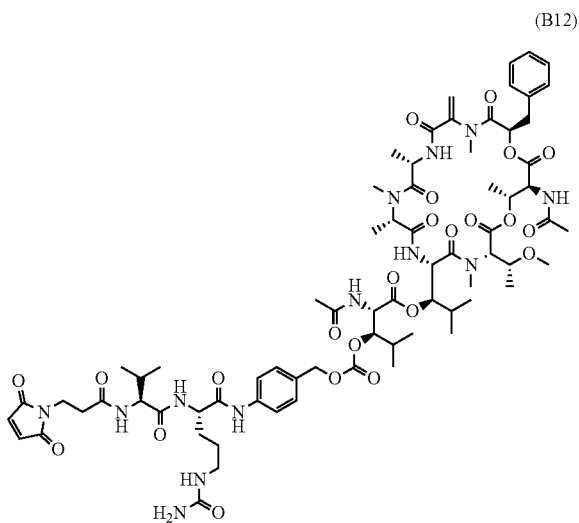 [SMILES: C=C1C(=O)N[C@@H](C)C(=O)N(C)[C@@H](C)C(=O)N[C@@H]([C@H](OC(=O)[C@@H](NC(C)=O)[C@H](OC(=O)OCc2ccc(NC(=O)[C@H](CCCNC(N)=O)NC(=O)[C@@H](NC(=O)CCN3C(=O)C=CC3=O)C(C)C)cc2)C(C)C)C(C)C)C(=O)N(C)[C@@H]([C@@H](C)OC)C(=O)O[C@H](C)[C@H](NC(C)=O)C(=O)O[C@H](Cc2ccccc2)C(=O)N1C]

Compound (B12) may be obtained using the method described in Example 1-10, except Compound (A3) is used in place of Compound (A1).

Example 2: Generation of Anti-PM ELI 7 Antibodies

Example 2-1: Preparation of Cell Lines Expressing PMEL17

Full length human, cyno and rat PMEL17 genes were synthesized based on amino acid sequences from the GenBank or Uniprot databases. All synthesized DNA fragments were cloned into appropriate expression vectors.

Engineered stable PMEL17-expressing cell lines were generated and cultured under appropriate selection conditions to produce stable PMEL17-expressing cell lines.

Example 2-2: Whole Cell Panning Against PMEL17

The phagemid libraries are based on the HuCAL PLATINUM® (Knappik et al., 2000) and Ylanthia concepts (Tiller et al., 2013) and employ the CysDisplay™ technology for displaying the Fab on the phage surface (Lohning, 2001).

For each panning, about $4 \times 10^{13}$ HuCAL PLATINUM® or about $1 \times 10^{14}$ Ylanthia® phage-antibodies phage-antibodies were blocked in PBS/5% FCS. In parallel, $0.5-1.0 \times 10^7$ target cells expressing antigen PMEL17 and $0.5-1.0 \times 10^7$ adsorption cells without expression of antigen PMEL17 per phage pool were resuspended in 1 ml PBS/5% FCS for blocking on ice. The blocked target cells were spun down, resuspended in the pre-blocked phage particles and incubated for 2 h at 4° C. on a rotator. The phage-cell complexes were washed three times in PBS/5% FCS. Elution of specifically bound phage from target cells was performed by 10 min acidic elution with 0.1 M glycine-HCl/0.5 M NaCl, pH 2.2. After centrifugation, the supernatant (eluate) was neutralized by adding 2 M unbuffered Tris. For removal of phage binding to cell surface molecules other than the target antigen, post-adsorption was performed three times with $0.5-1.0 \times 10^7$ adsorption cells each. The final supernatant was used for infection of 14 ml E. coli TG1 culture grown to an OD600 of 0.6-0.8. The culture was incubated for 45 min in a water bath at 37° C. for phage infection. The bacterial pellets were resuspended in 2×YT medium, plated on $L_B$/Cam agar plates and incubated o/n at 30° C. Colonies were scraped off the plates and were used for phage rescue and phage amplification. Amplified phage were used for the next panning round. The second and third round of the whole cell panning was performed according to the protocol of the first round.

Example 2-3: Subcloning, Expression and Screening of Fab Fragments

To facilitate rapid expression of soluble Fab, the Fab encoding inserts of the selected HuCAL PLATINUM® phage were subcloned from pMORPH®30 display vector into pMORPH®x11_FH expression vector. Subcloning was performed by triple digest via EcoRI, Xbal and Bmtl. After transformation of E. coli TG1-F-single clone expression and preparation of periplasmic extracts containing HuCAL®-Fab fragments were performed as described previously (Rauchenberger et al., 2003).

The Fab encoding inserts of the selected Ylanthia® phage were subcloned from pYPdis10 display vector into pYBex10_Fab_FH expression vector. Subcloning was performed by triple digest via Xbal, EcoRI-HF and Pstl-HF. After transformation of E. coli TG1-F-single clone expression and preparation of periplasmic extracts containing Ylanthia®-Fab fragments were performed as described previously (Rauchenberger et al., 2003).

Expression of Fab fragments encoded by pMORPH®x11_Fab_FH and pYBex10_Fab_FH in E. coli TG1 F-cells was carried out in shake flask cultures using 500 ml of 2×YT medium supplemented with 0.1% glucose and 34 µg/ml chloramphenicol. Cultures were shaken at 30° C. until the $OD_{600}$ reached a value of 0.5. Fab expression was induced by addition IPTG (isopropyl-β-D-thiogalactopyranoside) at a final concentration of 0.75 mM and further cultivation for 20 h at 30° C. Cells were harvested and disrupted using lysozyme. $His_6$-tagged (SEQ ID NO: 267) Fab fragments were isolated via IMAC (Bio-Rad, Germany) and eluted using imidazole. Buffer exchange to 1×Dulbecco's PBS (pH 7.2) was performed using PD10 columns (GE Healthcare, Germany). Samples were sterile filtered (0.2 µm). Protein concentrations were determined by UV-spectrophotometry. The purity of the samples was analyzed in denaturing, reducing 15% SDS-PAGE. The homogeneity of Fab preparations was determined in native state by size exclusion chromatography (HP-SEC) with calibration standards.

In FACS screening, purified Fabs were titrated on a variety of PMEL17 expressing and PMEL17 non expressing cell lines (for control). Cells were harvested using Accutase, adjusted to $4 \times 10^6$ cells/ml into FACS buffer (PBS, 3% FCS and 0.02% Na-Azide) and kept on ice to avoid internalization. 15 µl of cell suspension/well were transferred into 384 well V-bottom plates (Greiner, Cat #781280) and incubated with 15 µl of Fab at different concentrations (most commonly from 200 to 3.5×10⁻³ nm) for 1 hour at 4° C., gently shaking. Following incubation, cells were washed three times with FACS buffer. After each washing step, cells were centrifuged (250×g, 4 min, 4° C.) and carefully resuspended. 15 µl of detection antibody conjugated to PE (PE-conjugated goat anti-human IgG, F(ab')2 fragment specific, 1:150 in FACS buffer; Jackson Immuno Research, #109-116-097) or Alexa Fluor (Alexa Fluor-conjugated goat anti-human IgG, F(ab')2 fragment specific, 1:150 in FACS buffer; Jackson Immuno Research, #109-606-097) were added and samples were incubated for 45 minutes to 1 hour on ice in the dark, gently shaking. After 3 washing steps, cells were resuspended in 30 µl of FACS buffer and samples were measured using the IntelliCyt HTFC device.

In order additionally verify the specificity of the identified antibodies, the antigen was immuno-captured from cell lysate and used as coating material for ELISA based screenings. PMEL17 expressing and PMEL17 non expressing cells (used as negative control) were centrifugated (250 g, 5 min) and resuspended in lysis buffer (MSD Tris Lysis Buffer, Meso Scale Discovery, R60TX-2) containing protease inhibitors (Complete EDTA free Protease Inhibitor Cocktail, Roche, 11 873 580 001) at 1×10⁷ to 1×10⁸ cells/mL and incubated 30 min at 4° C. Lysate was spinned down at 13000 rpm for 5 minutes to discard cell debris and the supernatant was aliquotted and stored at −80° C. Preliminary testing demonstrated that the lysate could be freezed and thawed 3 times without major loss of signal in ELISA.

So as to perform the screening ELISA anti-His IgGs were coated overnight on a maxisorb 384 wells plate (R&D systems, MAB050, 10 µg/ml, 20 µl per well). Plates were blocked with 3% BSA and 20 µl of purified Fab were transferred at different concentrations (most commonly from 400 to 0.2 nM) to each well for 1 hour. The plate was washed 3 times and 20 µl PMEL17 containing cell lysate was added at a concentration of 2×105 lysed cells/well for 1 hour. After 3 additional washing, the presence of PMEL17 was revealed using the tool antibody PMEL17 biotinylated (5 µg/ml, 20 µl per well) and streptavidin-ECL (Dianova, 13MSA37, 1:1500, 20 µl per well). 20 µl per well of MSD read buffer 1× (Meso Scale Discovery, R92TC-2) were added to the plate and signals were detected via the MSD Sector Imager 6000.

Example 2-4: Conversion into IgG

Conversion of selected Fabs into IgGs was achieved by a PCR-based method in 96-well format. The Fab bacterial expression vectors pMORPH®x11_FH and pYBex10_Fab_FH were converted into the IgG mammalian expression vector pMORPH®4 and pYMex10 (for HuCAL and Ylanthia clones, respectively).

pMORPHx11_FH plasmid DNA was first amplified by PCR using a biotinylated primer specific to the phoA leader region and a non biotinylated primer specific to the bacterial CL domain. The amplified product was captured on streptavidin beads, digested with BsiWI or HpaI (for VLkappa or VLlambda clones, respectively), washed and then digested again with MfeI. This procedure resulted in the release of the purified vector backbone into the supernatant, now lacking the bacterial constant light chain region (CL) and the phoA heavy chain leader. A kappa or lambda specific mammalian pIN expression cassette was then cloned into the vector backbone carrying the mammalian CL, polyA site, CMV promotor and mammalian heavy chain leader sequence. In a second PCR step, the newly generated Fab insert was amplified again using a biotinylated primer specific to the CH1 region and a non-biotinylated primer binding within the bacterial ompA leader. The PCR product was captured on streptavidin beads, digested with EcoRV, washed and digested with BlpI resulting in the release of the purified insert into the supernatant. Inserts were finally cloned into the Fab_Cys acceptor vector for expression in mammalian cells.

pYBex10_Fab_FH plasmid DNA was first amplified by PCR using a biotinylated primer specific to the phoA leader region and a non biotinylated primer specific to the bacterial CL domain. The amplified product was captured on streptavidin beads, digested with NheI, washed and then digested again with KpnI. This procedure resulted in the release of the purified vector backbone into the supernatant, now lacking the bacterial constant light chain region (CL) and the phoA heavy chain leader. A kappa or lambda specific mammalian pIN expression cassette was then cloned into the vector backbone carrying the mammalian CL, polyA site, CMV promotor and mammalian heavy chain leader sequence. In a second PCR step, the newly generated Fab insert was amplified again using a biotinylated primer specific to the CH₁ region and a non-biotinylated primer binding within the bacterial ompA leader. The PCR product was captured on streptavidin beads, digested with XhoI, washed and digested with NdeI resulting in the release of the purified insert into the supernatant. Inserts were finally cloned into the Fab_Cys acceptor vector for expression in mammalian cells.

After transformation of E. coli XL-1 blue cells, single clones were controlled via colony PCR and sequencing of the whole insert region.

Example 2-5: Confirmatory Screening of Human IgG

DNA preparations of single colonies were prepared by using an appropriate DNA preparation kit in combination with the BioRobot®8000 device. Individual DNA concentrations were determined by UV-spectrophotometry. Eukaryotic HEK293 c18 cells (ATCC #CRL-10852) were used in a 96-well expression system for the generation of conditioned cell culture supernatants containing full-length IgG. Eukaryotic HEK293 c18 cells were seeded in a 96-well flat-bottom plate to a density of ~4×10⁴ cells/50p1/well the day before and transfected with equal amounts of Ig expression vector DNA. After incubation for 40-50 h at 37° C. and 6% CO2 the culture supernatants were transferred to a 96-well U-bottom plate and cleared by centrifugation. The resulting Ig supernatants were tested by an anti-Fd capture ELISA for calculation of Ig concentration in reference to known standards and stored at −20° C. for later use in specificity and/or functional screening assays.

DNA of clones of interest were subjected to sequencing with primer CMV_HC_for (CTC TAG CGC CAC CAT GAA ACA (SEQ ID NO: 264)) for VH domain and IgG_const_for (AGC CCA GCA ACA CCA AGG (SEQ ID NO: 265)) for Fc domain followed by light chain sequencing with T7 promoter primer (TAA TAC GAC TCA CTA TAG GG (SEQ ID NO: 266)) to obtain complete IgG sequence information.

FACS screening was performed in the 384-well plate format using the HTFC screening platform from IntelliCyt. Cells were harvested using Accutase, adjusted to ~4×10⁶ cells/ml into FACS buffer (PBS, 3% FCS and 0.02% Na-Azide) and kept on ice to avoid internalization. 15 µl of cell suspension/well were transferred into 384 well V-bottom plates (Greiner, Cat #781280) and incubated with 15 µl of IgG containing supernatant (or diluted purified control antibodies) for 1 hour at 4° C., gently shaking. Following incubation, cells were washed three times with FACS buffer. After each washing step, cells were centrifuged (250×g, 4 min, 4° C.) and carefully resuspended. 15 µl of detection antibody conjugated to PE (PE-conjugated goat anti-human IgG, F(ab')2 fragment specific, 1:150 in FACS buffer; Jackson Immuno Research, #109-116-097) were added and samples were incubated for 45 minutes to 1 hour on ice in the dark, gently shaking. After 3 washing steps, cells were resuspended in 30 µl of FACS buffer and samples were measured using the IntelliCyt HTFC device.

Example 2-6: Production of Human IgG and Human Fab_Cys

Eukaryotic HKB11 cells were transfected with pMORPH®4 or pYMex10 expression vector DNA encoding both heavy and light chains of IgGs. Cell culture supernatant was harvested on day 3 or 7 post transfection. The cell culture supernatant was subjected to standard Protein A affinity chromatography (MabSelect SURE, GE Healthcare) and Capture Select IgG-CH1 (BAC) for human IgG and human Fab_Cys, respectively. If not stated otherwise, buffer exchange was performed to 1×Dulbcecco's PBS (pH 7.2, Invitrogen) and samples were sterile filtered (0.2 µm pore size). Purity of IgG was analyzed under denaturing, reducing and non-reducing conditions using a Labchip System (GXII, Perkin Elmer, USA) or on SDS-PAGE. Protein concentrations were determined by UV-spectrophotometry and HP-SEC was performed to analyze IgG preparations in native state.

Example 2-7: Production of Anti-PMEL17 G1 and G4 Antibodies

For the first panning round, about $4 \times 10^{13}$ HuCAL PLATINUM® phage were blocked with PBS/5% FBS. In parallel, $1.0 \times 10^7$ target cells expressing antigen PMEL17 and 1.5-$3.0 \times 10^7$ adsorption cells without expression of antigen PMEL17 per phage pool were resuspended in 1 ml PBS/5% FCS for blocking on ice. To preclear non-specific binding, phage were incubated with $0.5 \times 10^7$ adsorption cells without expression of antigen PMEL17 per phage pool for 30 minutes on ice. After incubation, the cells were pelleted by centrifugation and the supernatant was added to a fresh sample of with $0.5 \times 10^7$ adsorption cells without expression of antigen PMEL17. The same incubation conditions were applied and pre-absorption was again applied to a fresh sample of $0.5 \times 10^7$ adsorption cells without expression of antigen PMEL17 for a total of three pre-absorption rounds. After the final pre-absorption, the supernatant was added to $1.0 \times 10^7$ target cells expressing antigen PMEL17 and incubated on ice for 2 hours with occasional mixing. The phage-cell complexes were washed three times in PBS/5% FCS. Elution of specifically bound phage from target cells was performed by 10 minute acidic elution with 0.1 M glycine-HCl/0.5 M NaCl, pH 2.5. After centrifugation, the supernatant (eluate) was neutralized by adding 2 M unbuffered Tris and this eluate was used to infect 14 ml E. coli TG1 F' culture grown to an $OD_{600}$ of 0.6-0.8. The culture was incubated for 20 minutes at 37° C. and then an addition 25 minutes at 37° C. with shaking at 200 rpm for phage infection. The bacterial pellets were resuspended in 2×YT medium, plated on LB/Chloroamphenicol agar plates and incubated overnight at 30° C. Colonies were scraped off the plates and were used for phage rescue and phage amplification. Amplified phage were used for the next panning round. The second and third rounds of panning were performed similarly except that only about $1 \times 10^{12}$ HuCAL phage was used to reduce background and improve the effectiveness of preclearing. After the final round of panning, plasmid DNA was prepared from each phage output and the Fab-containing inserts were cloned into a bacterial expression vector. After ligation and transformation, individual colonies were picked into 2XT/chloramphenicol and cultured. Fab expression was induced by addition of 0.25 mM IPTG in cultures grown overnight in 96 well microtiter plates at 25° C. Cell pellets were lysed with 0.1% lysozyme in PBS and then blocked by the addition of BSA to a final concentration of 1%. FACS staining was performed on PMEL17-expressing and control cells.

Example 2-8: Apparent Affinities of Anti-PMEL17 Antibodies

Purified IgGs were titrated on a variety of PMEL17 expressing and PMEL17 non expressing cell lines (for control) to determine EC50 values. Cells were harvested using Accutase, adjusted to ~4×106 cells/ml into FACS buffer (PBS, 3% FCS and 0.02% Na-Azide) and kept on ice to avoid internalization. 15 µl of cell suspension/well were transferred into 384 well V-bottom plates (Greiner, Cat #781280) and incubated with 15 µl of IgGs at different concentrations (most commonly from 200 to 3.5×10−3 nM) for 1 hour at 4° C., gently shaking. Following incubation, cells were washed three times with FACS buffer. After each washing step, cells were centrifuged (250×g, 5 min, 4° C.) and carefully resuspended. 15 µl of detection antibody conjugated to PE (PE-conjugated goat anti-human IgG, F(ab')2 fragment specific, 1:150 in FACS buffer; Jackson Immuno Research, #109-116-097) or Alexa Fluor (Alexa Fluor-conjugated goat anti-human IgG, F(ab')2 fragment specific, 1:150 in FACS buffer; Jackson Immuno Research, #109-606-097) were added and samples were incubated for 45 minutes to 1 hour on ice in the dark, gently shaking. After 3 washing steps, cells were resuspended in 30 µl of FACS buffer and samples were measured using the IntelliCyt HTFC device. EC50 values were calculated using the Graphpad Prism software. G-361 melanoma cell line expresses human PMEL17 at a lower level compared to the HKB11-human PMEL17 overexpressing cell line, and therefore allows a more precise ranking of the clones depending on their apparent affinity on cells. As illustrated in Table 3, a variety of EC50 ranging from ~200 pM to ~70 nM was reached.

TABLE 3

Apparent affinities (FACS EC50 (nM)) and cross-reactivity of anti-PMEL17 antibodies.

|  | G-361 (PE) | G-361 (Alexa Fluor) | HKB11-cyno (Alexa Fluor) | HKB11-rat (Alexa Fluor) | B16-F10 (mouse) (Alexa Fluor) | UACC-62 (PE) | Cross spe profile (based on C14 detection ab) |
|---|---|---|---|---|---|---|---|
| Y101341 | 0.4 |  | 2.6 | 1.8 | 1.2 | Negative | h/c/r/m |
| Y010906 | — | 2.0 | 2.0 | 21.7 | 139.8 | Negative | h/c/r/m |
| Y010900 | — | 1.3 | 1.2 | 9.3 | >100 | Negative | h/c/r/m |
| Y010355 | 0.5 |  | 3.9 | 0.8 | 0.8 | Negative | h/c/r/m |
| Y010356 | 1.6 |  | 4.5 | 1.4 | 1.4 | Negative | h/c/r/m |

TABLE 3-continued

Apparent affinities (FACS EC50 (nM)) and cross-reactivity of anti-PMEL17 antibodies.

|  | G-361 (PE) | G-361 (Alexa Fluor) | HKB11-cyno (Alexa Fluor) | HKB11-rat (Alexa Fluor) | B16-F10 (mouse) (Alexa Fluor) | UACC-62 (PE) | Cross spe profile (based on C14 detection ab) |
|---|---|---|---|---|---|---|---|
| Y010429 | 2.5 | — | 10.7 | 1.5 | 60.2 | Negative | h/c/r |
| MOR024354 | — | 1.7 | 2.1 | 2.4 | >100 | Negative | h/c/r |
| Y010415 | 0.3 | — | 5.4 | 0.4 | >100 | Negative | h/c/r |
| Y010903 | — | 3.2 | 2.0 | 5.6 | 927.5 | Negative | h/c/(m) |
| Y010910 | — | 10.0 | 3.5 | 13.7 | 41.1 | Negative | h/c/(m) |
| MOR024353 | — | 62.8 | 1.6 | 7.5 | >100 | Negative | h/c |
| Y010417 | 2.8 | — | 6.3 | >100 | >100 | Negative | h/c |

Example 2-9: Cross-Reactivity of Anti-PMEL17 Antibodies

The cross-specificity of the IgGs was evaluated in does response FACS on G-361 (human melanoma), HKB11-cyno-PMEL17, HKB11-rat PMEL17 and B16-F10 (mouse PMEL17 expressing melanoma) (Table 3). Testing on G-361 was performed using a detection antibody labelled to PE. In contrast, an Alexa-Fluor labelled detection antibody had to be used for testing the candidates on the other cell lines so as to reach detectable signals.

IgGs were classified into several epitope groups according to their cross-specificity profiles. The various cross-reactive profiles of the IgGs nevertheless suggest that their target at least 4 epitopes (human/cyno/rat/mouse, human/cyno/rat, human/cyno/mouse and human/cyno).

Example 2-10: ADC Assays

IgGs were tested in dose response for their ability to internalize and induce the killing of various PMEL17 expressing cells in both piggyback ADC assay and after direct conjugation.

For piggyback ADC assay, the Fab-ZAP (goat anti-humAb-saporin-coupled; ATS Biotechnology, Cat #IT-51) compound was used which specifically binds to human Fc and is coupled to a cytotoxin element, the saporin. Cells were harvested using Accutase and adjusted to $5 \times 10^4$ cells/ml. 50 µl of the cell suspension were transferred per well into a 96-well flat clear bottom white plate (Corning, 3610) and incubated overnight at 37° C., 5% CO2. On the following day, antibody candidates were incubated at different concentrations (most commonly from 44 to $7 \times 10^{-3}$ nM) with the Fab-ZAP compound at 8 nM for 30 minutes at 37° C. 50 µl per well of the IgG—Fab-ZAP complexes were then added to the target cells. For controls, wells with cells only, cells only incubated with candidate IgGs (=100% viability control) and cells only incubated with Fab-ZAP (to check for unspecific killing of the secondary reagent) were prepared. Final concentration of IgGs were 22 to $3.5 \times 10^{-3}$ nM and Fab-ZAP 4 nM. Plates were incubated for 72 h at 37° C. and 5% CO2. The amount of viable cells was evaluated using CellTiter-Glo (Promega #G7571) and the luminescence detected with the Tecan Infinite 500. Viability was then normalized to the cells+IgG only control.

Almost all IgGs could efficiently kill G-361 melanoma (>80% maximum killing) and showed limited killing on the non PMEL17 expressing 293T cells (<30% maximum killing). G-361 killing was also achieved with a range of EC50s which may be affinity or epitope related. Cross-specificity could also be confirmed for most of the IgGs reactive to human/cyno/rat/mouse, human/cyno/rat and human/cyno/mouse, i.e. IgGs specific to mouse PMEL17 could also kill B16-F10 (mouse melanoma).

Example 2-11: Engineering of Anti-PMEL17 Antibodies

Generally, all engineering processes, were performed using PCR-based strategies. Engineering processes involved the following aspects: Germlining, Removal of PTM sites, pI engineering, and Codon optimization. After synthesis and assembly by overlap extension PCR the re-engineered VH and VL fragments were subcloned into the appropriate vector backbones for subsequent IgG expressions.

Example 3: Synthesis of Compounds A1-A3

Example 3-1: Isolation Process of (R)-1-((3S,6S,9S,12S,18R,21S,22R)-21-acetamido-18-benzyl-22-isopropyl-3-((R)-1-methoxyethyl)-4,9,10,12,16-pentamethyl-15-methylene-2,5,8,11,14,17,20-heptaoxo-1,19-dioxa-4,7,10,13,16-pentaazacyclodocosan-6-yl)-2-methylpropyl (2S,3R)-3-hydroxy-4-methyl-2-propionamidopentanoate (A1) from Dried Leaves of *Ardisia crenata*

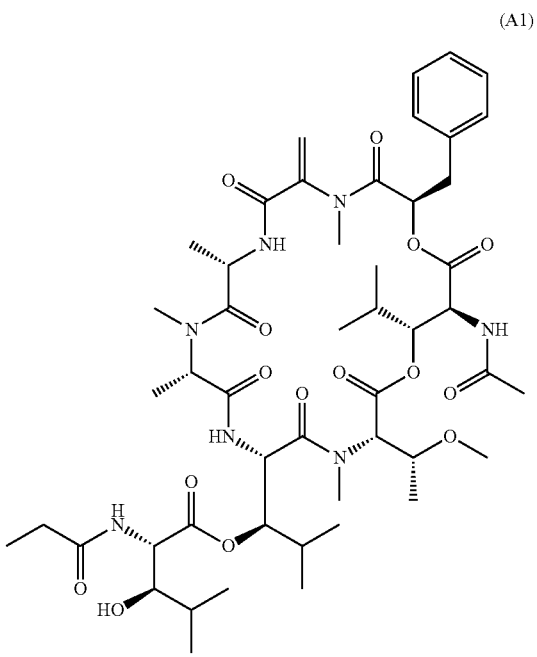 [SMILES: C=C1C(=O)N[C@@H](C)C(=O)N(C)[C@@H](C)C(=O)N[C@@H]([C@H](OC(=O)[C@@H](NC(=O)CC)[C@H](O)C(C)C)C(C)C)C(=O)N(C)[C@@H]([C@@H](C)OC)C(=O)O[C@H](C(C)C)[C@H](NC(C)=O)C(=O)O[C@H](Cc2ccccc2)C(=O)N1C]

(A1)

Compound A1 was isolated based on methods described in Japanese Patent Publication No. JP62283999. Step 1: Extraction: 25 kg dried leaves of *Ardisia crenata* were milled into fine powder and extracted with 500 L methanol. After filtration the extract was evaporated to dryness. The residue was dissolved in 100 L ethyl acetate and extracted five times with 100 L deionized water (sodium chloride was added in order to improve phase separation. The organic layer was evaporated to dryness. The residue was dissolved in 50 L acetonitrile/water (9/1) and extracted with 50 L heptane. The acetonitrile/water layer was evaporated until only water was left. This was then extracted with 50 L ethyl acetate. The ethyl acetate layer was evaporated to dryness yielding 109 g of crude extract.

Step 2: Defatting: The crude extract was dissolved in 25 L acetonitrile/water (9/1) and extracted three times with 25 L heptane. The acetonitrile/water layer was evaporated until only water was left. This was then extracted with 25 L ethyl acetate. The ethyl acetate layer was evaporated to dryness yielding 40 g of crude extract.

Step 3: Flash chromatography: The crude extract was dissolved in acetone/methanol (1/1), adsorbed onto 100 g Isolute (diatomaceous earth) and evaporated to dryness. Flash chromatography on silica gel with a ternary solvent system with cyclohexane (eluent A), ethyl acetate (eluent B) and methanol (eluent C) was performed (experimental details: column: RediSep Rf 120 g; flow rate: 85 mL/min; gradient: 0 min: 75% A, 25% B, 0% C; 3 min: 75% A, 25% B, 0% C; 10 min: 0% A, 100% B, 0% C; 17.5 min: 0% A, 90% B 10% C; 25 min: 0% A, 50% B, 50% C; 30 min: 0% A, 50% B, 50% C; the different segments of the gradient are connected by linear changes over time). Four runs with 10 g extract each were performed. Time based fractionation was applied and the collected fractions were analyzed by UPLC-UV-MS for presence of Compound (A1). Fractions containing Compound (A1) were pooled and evaporated to dryness resulting in a fraction of 25 g.

Step 4: Size-exclusion chromatography (SEC): The 25 g fraction was dissolved in 400 mL methanol and further fractionated by SEC on a column (length 25 cm, diameter 12.5 cm) packed with Sephadex LH20 and methanol as eluent. Fractions of 200 mL each were collected and the collected fractions were analyzed by UPLC-UV-MS for presence of Compound (A1). Fractions containing Compound (A1) were pooled and evaporated to dryness resulting in an enriched fraction of 6.2 g.

Step 5: 1st preparative HPLC: The enriched fraction of 6.2 g was dissolved in 12 mL methanol/dimethylsulfoxide (1/1) and further fractionated by preparative HPLC (experimental details: column: Sunfire C18, 30×150 mm, 5 µm particle size; eluent A: deionized water with 0.1% formic acid, eluent B: methanol with 0.1% formic acid; flow rate 60 mL/min; gradient: 0 min: 35% A, 65% B; 0.5 min: 35% A, 65% B; 17 min: 15% A, 85% B; 15.0 min: 0% A, 100% B; 19 min: 0% A, 100% B; 19.1 min: 35% A, 65% B; 20 min: 35% A, 65% B; the different segments of the gradient are connected by linear changes over time). Fractionation was triggered by mass spectrometry. 15 runs with 410 mg enriched fraction each were performed. Fractions containing Compound (A1) were pooled and evaporated to dryness resulting in a semi-pure fraction of 488 mg with an estimated content of 70% Compound (A1).

Step 6: 2$^{nd}$ preparative HPLC: The semi-pure fraction of 488 mg was dissolved in 4 mL methanol and further fractionated by preparative HPLC (experimental details: column: X-Select PFP, 19×250 mm, 5 µm particle size; eluent A: deionized water with 0.1% formic acid, eluent B: acetonitrile with 0.1% formic acid; flow rate 30 mL/min; gradient: 0 min: 45% A, 55% B; 0.5 min: 45% A, 55% B; 24 min: 25% A, 75% B; 24.0 min: 0% A, 100% B; 27.5 min: 0% A, 100% B; 27.6 min: 45% A, 55% B; 30.5 min: 45% A, 55% B; the different segments of the gradient are connected by linear changes over time). Fractionation was triggered by mass spectrometry. Five runs witch 98 mg semi-pure fraction each were performed. Fractions containing Compound (A1) were pooled and evaporated to dryness resulting in 287 mg Compound (A1) with a purity >95%.

Compound (A1): Retention time: 4.73 min, molecular formula [M+H]+: C49H76N7O15+, calculated monoisotopic mass [M+H]+: 1002.5394 Da, observed mass: 1002.5391 Da. Experimental details: column: ACQUITY UPLC BEH C18, 2.1×100 mm, 1.7 µm particle size; eluent A: deionized water with 0.1% formic acid, eluent B: acetonitrile with 0.1% formic acid; flow rate 0.9 mL/min; linear gradient: 0 min: 95% A, 5% B to 6.4 min: 0% A, 100% B. $^1$H NMR (600 MHz, Acetonitrile-d$_3$) δ 8.36 (d, J=9.4 Hz, 1H), 7.50 (d, J=10.0 Hz, 1H), 7.38-7.22 (m, 6H), 6.94 (d, J=4.4 Hz, 1H), 6.77 (d, J=9.9 Hz, 1H), 5.39 (d, J=9.8 Hz, 1H), 5.34 (dd, J=8.8, 3.8 Hz, 1H), 5.31-5.25 (m, 2H), 5.21-5.15 (m, 2H), 5.11 (dd, J=9.9, 1.9 Hz, 1H), 4.90-4.84 (m, 1H), 4.70 (q, J=6.9 Hz, 1H), 4.39 (dd, J=7.7, 2.1 Hz, 1H), 4.10 (d, J=9.8 Hz, 1H), 3.82-3.74 (m, 1H), 3.60 (ddd, J=9.8, 4.4, 2.0 Hz, 1H), 3.38 (s, 3H), 3.23 (s, 3H), 3.16-3.11 (m, 1H), 2.94-2.85 (m, 1H), 2.84 (s, 3H), 2.66 (s, 3H), 2.55-2.43 (m, 2H), 2.16 (s, 3H), 1.96-1.90 (m, 1H), 1.89-1.74 (m, 2H), 1.37 (d, J=7.0 Hz, 3H), 1.32 (d, J=6.6 Hz, 3H), 1.19 (d, J=6.5 Hz, 3H), 1.17 (d, J=6.0 Hz, 3H), 1.12 (d, J=7.7 Hz, 3H), 1.06 (d, J=6.8 Hz, 3H), 0.96 (d, J=6.6 Hz, 3H), 0.88 (d, J=6.6 Hz, 3H), 0.85 (d, J=7.0 Hz, 3H), 0.77 (d, J=6.5 Hz, 3H).

Example 3-2: Generation Process for (R)-1-((3S,6S, 9S,12S,18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4,7,10,13,16-pentaazacyclodocosan-6-yl)-2-methylpropyl (2S,3R)-2-acetamido-3-hydroxy-4-methylpentanoate (A2)

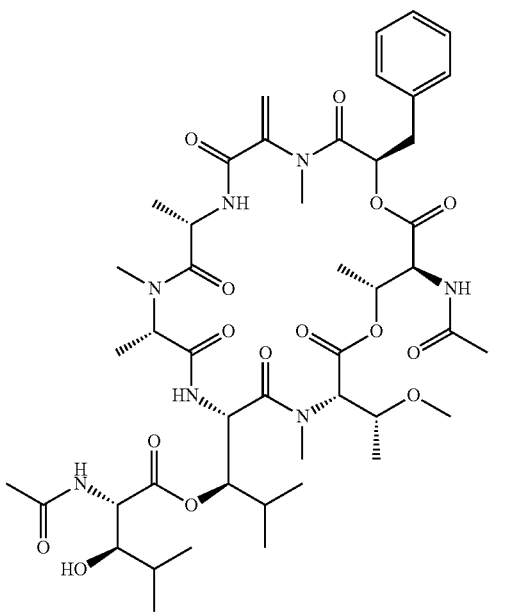

(A2)

Compound (A2) was obtained using the methods described in [M. Taniguchi et al., Tetrahedron 59 (2003)

4533-4538]. Isolation was performed using the methods described for Compound (A1) in Example 3-1 The material was then characterized by UPLC-UV-HRMS, 1D-NMR- and 2D-NMR-experiments. Compound (A2): Retention time: 4.20 min, molecular formula [M+H]+: $C_{46}H_{70}N_{7}O_{15}$+, calculated monoisotopic mass [M+H]+: 960.4924 Da, observed mass: 960.4914 Da. $^{1}$H NMR (600 MHz, $_{1,4}$-Dioxane-d$_{8}$) δ 8.36 (d, J=9.2 Hz, 1H), 7.37 (d, J=10.0 Hz, 1H), 7.31-7.21 (m, 4H), 7.21-7.16 (m, 2H), 6.79-6.72 (m, 2H), 5.40-5.37 (m, 1H), 5.36-5.33 (m, 1H), 5.30-5.28 (m, 2H), 5.20 (dd, J=9.0, 3.7 Hz, 1H), 5.13 (d, J=1.9 Hz, 1H), 5.04 (dd, J=9.9, 1.4 Hz, 1H), 4.89-4.82 (m, 1H), 4.73 (q, J=6.9 Hz, 1H), 4.39 (dd, J=8.0, 2.0 Hz, 1H), 4.04 (d, J=9.9 Hz, 1H), 3.80-3.73 (m, 1H), 3.65 (ddd, J=9.8, 4.3, 1.9 Hz, 1H), 3.37 (s, 3H), 3.21 (s, 3H), 3.11 (dd, J=14.7, 3.7 Hz, 1H), 2.89 (dd, J=14.7, 8.9 Hz, 1H), 2.84 (s, 3H), 2.62 (s, 3H), 2.14 (s, 3H), 2.12 (s, 3H), 1.99-1.90 (m, 1H), 1.75-1.69 (m, 1H), 1.35 (d, J=6.8 Hz, 3H), 1.30 (d, J=6.5 Hz, 3H), 1.18-1.14 (m, 6H), 1.11 (d, J=6.5 Hz, 3H), 1.04 (d, J=6.7 Hz, 3H), 0.86 (d, J=6.8 Hz, 3H), 0.78 (d, J=6.6 Hz, 4H).

Example 3-3: Generation Process for (R)-1-((3S,6S, 9S,12S,18R,21S,22R)-21-acetamido-18-benzyl-3-((R)-1-methoxyethyl)-4,9,10,12,16,22-hexamethyl-15-methylene-2,5,8,11,14,17,20-heptaoxo-1,19-dioxa-4,7,10,13,16-pentaazacyclodocosan-6-yl)-2-methylpropyl (2S,3R)-3-hydroxy-4-methyl-2-propionamidopentanoate (A3)

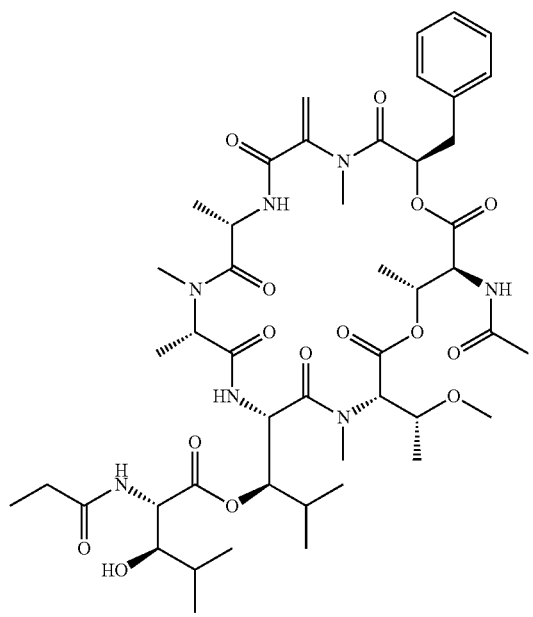

(A3)

Compound (A3) was obtained using the methods described in [M. Taniguchi et al. Tetrahedron 59 (2003) 4533-4538]. Isolation was performed using the methods described for Compound (A1) in Example 3-1. The material was then characterized by UPLC-UV-HRMS, 1D-NMR- and 2D-NMR-experiments. Compound (A3): Retention time: 4.42 min, molecular formula [M+H]+: $C_{47}H_{72}N_{7}O_{15}$+, calculated monoisotopic mass [M+H]+: 974.5081 Da, observed mass: 974.5098 Da. $^{1}$H NMR (600 MHz, $_{1,4}$-Dioxane-d$_{8}$) δ 8.37 (d, J=9.1 Hz, 1H), 7.38 (d, J=9.9 Hz, 1H), 7.31-7.23 (m, 4H), 7.22-7.16 (m, 1H), 7.12 (d, J=7.7 Hz, 1H), 6.78-6.72 (m, 2H), 5.41-5.33 (m, 2H), 5.32-5.26 (m, 2H), 5.20 (dd, J=8.8, 3.7 Hz, 1H), 5.12 (d, J=2.2 Hz, 1H), 5.04 (dd, J=9.9, 1.7 Hz, 1H), 4.89-4.81 (m, 1H), 4.72 (q, J=7.0 Hz, 1H), 4.40 (dd, J=7.8, 2.1 Hz, 1H), 4.04 (d, J=9.8 Hz, 1H), 3.81-3.73 (m, 1H), 3.68-3.64 (m, 1H), 3.38 (s, 3H), 3.21 (s, 3H), 3.11 (dd, J=14.6, 3.7 Hz, 1H), 2.89 (dd, J=14.7, 8.9 Hz, 1H), 2.83 (s, 3H), 2.62 (s, 3H), 2.51-2.41 (m, 2H), 2.14 (s, 3H), 1.99-1.89 (m, 1H), 1.78-1.68 (m, 1H), 1.34 (d, J=6.9 Hz, 3H), 1.30 (d, J=6.5 Hz, 3H), 1.18-1.14 (m, 6H), 1.13-1.08 (m, 6H), 1.04 (d, J=6.7 Hz, 3H), 0.86 (d, J=6.8 Hz, 3H), 0.78 (d, J=6.6 Hz, 3H).

Example 4: Process for the Production of Anti-PMEL17 Antibody Drug Conjugates

Antibody was incubated with RMP Protein A resin (GE) at a ratio of 10 mg Ab to 1 ml resin in PBS for 15 minutes with mixing in an appropriately sized disposable column. Cysteine HCl was added to a final concentration of 20 mM and incubated with agitation for 30 min at room temperature to allow the reactive cysteines to be deblocked. The resin was quickly washed with 50 column volumes PBS on a vacuum manifold. The resin was then resuspeneded in an equal volume PBS containing 250 nM CuCl$_{2}$. Reformation of antibody interchain disulfides was monitored by taking time points. At each time point, 25 µL of resin slurry was removed, 1 µL of 20 mM of Compound (B1) or Compound (B2) was added, and the tube flicked several times. The resin was spun down, supernatant removed, and then eluted with 50 µL Antibody elution buffer (Thermo). The resin was pelleted and the supernatant analyzed by reverse phase chromatography using an Agilent PLRP-S 4000A 5 um, 4.6×50 mm column (Buffer A is water, 0.1% TFA, Buffer B Acetonitrile, 0.1% TFA, column held at 80 C, Flowrate 1.5 ml/min).

Once it was determined that the antibody has reformed its interchain disulfide bonds, the resin was washed with 10 column volumes PBS and the resin was resuspended in an equal volume PBS and 8 equivalents of linker-payload (20 mM) in DMSO was added and then incubated at room temperature for 2 hours. The resin was then washed with 50 column volumes PBS. The ADC was eluted from the protein A resin with Antibody elution buffer and neutralized with 1/10 volume 1 M Tris pH 9.0. The ADC was then buffer exchanged into PBS or other suitable buffer and preparative size exclusion chromatography to remove aggregates was performed (S200 Increase; GE), if needed. The following analyses were performed—analytical SEC to determine percent monomer, mass spectroscopy to determine DAR, LAL test to determine endotoxin load and protein concentration was determined by A280 utilizing extinction coefficient and molecular weight of antibody.

Example 5: In Vitro Anti-Uveal Melanoma Activity of GNAQ/11 Inhibitors Compound (A1) and Compound (A2)

92.1 uveal melanoma and MIAPACA pancreatic ductal adenocarcinoma cells were seeded at low cell density in 96-well plates and treated with increasing concentrations of Compound (A1) or Compound (A2) as indicated. Following drug treatment for 96 or 120 hours, cell viability and proliferation were determined using a resazurin-based viability assay. Briefly, cells were incubated with a resazurin-based solution and color change was detected by absorbance with a spectrophotometer and used as a readout of cell viability. Data presented as mean of 3 independent replicates and relative to PBS-treated cells (control). Table 4 shows the growth inhibition 50% (GI$_{50}$) for Compound (A2) and Compound (A1). Compound (A2) and Compound (A1) displayed potent target-dependent anti-UM activity (FIG. 1).

TABLE 4

Growth inhibitory activity of Compound (A1) and Compound (A2) in UM cells

| Cell line | Mutation | Compound (A1) GI$_{50}$ nM | Compound (A2) GI$_{50}$ nM |
|---|---|---|---|
| 92.1 | GNAQ$^{Q209L}$ | 0.18 | 7.7 |
| MIAPACA | WT | >10 μM | >10 μM |

Figure 2:
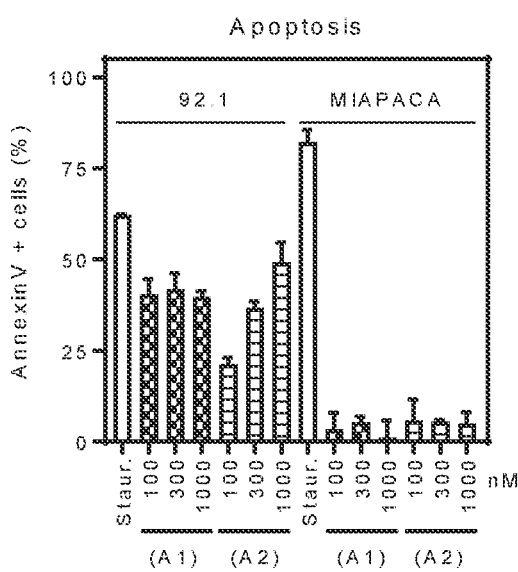
FIG. 2 shows exemplary data on activity of GNAQ/11 inhibitors Compound (A1) and Compound (A2) to induce apoptosis in uveal melanoma cells.

Example 6: Compound (A1) and Compound (A2) Induce Apoptosis in Uveal Melanoma Cells 92.1 and MIAPACA cells were seeded in 96-well plates (5000 cells per well) and treated with increasing concentrations of Compound (A1), Compound (A2), and a fixed dose of Staurosporine (100 nM, positive control) as indicated. Following drug treatment for 96, cells were subjected to fluorescence-activated flow cytometry using an Annexin V antibody conjugated to a fluorescent dye. Data presented as mean of 3 independent replicates. Compound (A2) and Compound (A1) induced apoptosis in UM cells in GNAQ/11 dependent manner (FIG. 2).

Example 7: Analysis of GNAQ/11 Inhibition by Compound (A1) and Compound (A2) in Uveal Melanoma Cells 92.1 uveal melanoma were treated with increasing concentrations of Compound (A1) or Compound (A2) as indicated. Following drug treatment overnight, cells were processed for determination of IP1 levels using TR-FRET (time-resolved fluorescent resonance energy transfer) or protein levels by western-blotting. FIG. 3A shows IP1 levels (nM) in 92.1 cells treated with DMSO (control), Compound (A2) or Compound (A1). FIG. 3B shows correlation between IP1 levels and relative proliferation in Compound (A1)-treated 92.1 cells. FIG. 3C shows immunoblots of 92.1 cells treated with Compound (A1) and Compound (A2) to determine the effect on ERK signaling.

Example 8: Metabolic Stability and PK Properties of Compound (A1)

The plasma stability of Compound (A1) was investigated in mouse, rat, monkey and human plasma and compared to buffer. Both disappearance of Compound (A1) (FIG. 4A) as well as appearance of the ring-opened form of Compound (A1) having the structure of Compound (A4)

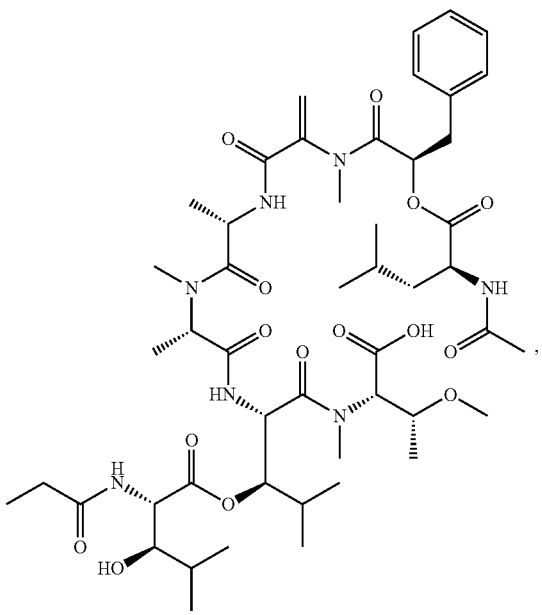

Compound (A6)

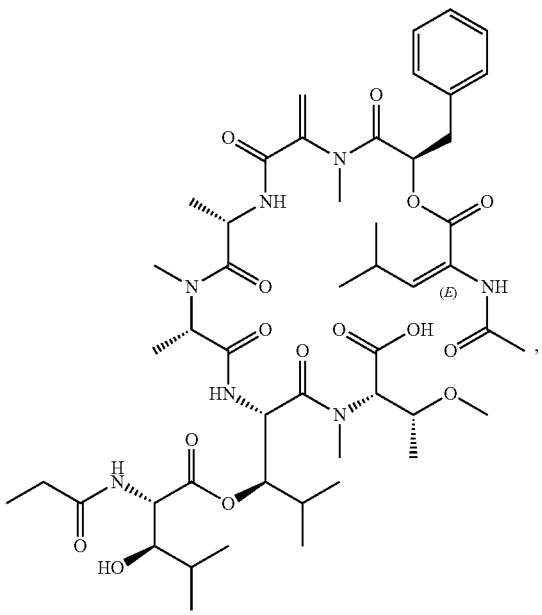 [SMILES: C=C(C(=O)N[C@@H](C)C(=O)N(C)[C@@H](C)C(=O)N[C@H](C(=O)N(C)[C@H](C(=O)O)[C@@H](C)OC)[C@H](OC(=O)[C@@H](NC(=O)CC)[C@H](O)C(C)C)C(C)C)N(C)C(=O)[C@@H](Cc1ccccc1)OC(=O)/C(=C\C(C)C)NC(C)=O]

or Compound (A8)

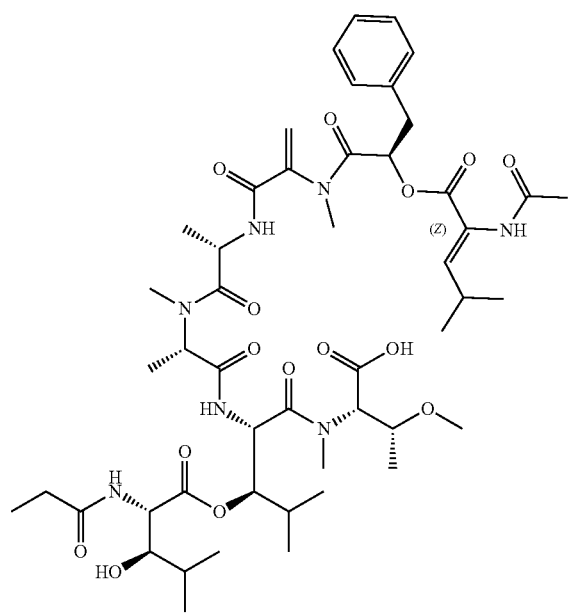

(FIG. 4B) were monitored over 24 h. The transformation seem to be slightly faster in human plasma when compared to the other species. With the exception of the rat, adding the % remaining Compound (A1) and % formed Compound (A8) shows stoichiometry over 24 h, indicating that no other transformation seem to play a significant role (FIG. 4C).

The PK of Compound (A1) after intravenous dosing in mouse was characterized by a very high clearance and moderate to high volume of distribution. A slightly over-proportional increase of exposure with dose was observed in the range of 0.2-0.8 mg/kg (FIG. 4D). Table 5 summarizing all PK values is shown below.

TABLE 5

PK properties of Compound (A1)

| | Dose (mg/kg) | | |
|---|---|---|---|
| | 0.2 | 0.4 | 0.8 |
| Cmax (nM) | 31 | 83 | 240 |
| Cmax/D (nM/(mg/kg)) | 156 | 208 | 300 |
| AUCinf (nM*h) | 16 | 47 | 137 |
| AUCinf/D (nM*h/(mg/kg)) | 82 | 118 | 171 |
| C0 (nM) | 43 | 108 | 380 |
| C0/D (nM/(mg/kg)) | 217 | 270 | 475 |
| CL [mL/min/kg] | 204 | 141 | 97 |
| Vss [L/kg] | 8.6 | 4.9 | 4.6 |

Example 9: Metabolic Stability and PK Properties of Compound (A2)

In vitro stability of Compound (A2) was tested in plasma and blood from different species (FIG. 5A). Compound (A2) showed good chemical stability in three different systems (FIG. 5B). PK of Compound (A2) in female balb/c mice showed high clearance and a short elimination half-life (FIG. 5C). Table 6 summarizes some PK values. Compound (A2) showed high intrinsic clearance in liver microsomes from mouse, rat and human, but low clearance in hepatocytes, probably due to limited membrane permeability (Table 7). Incubations of Compound (A2) in hepatic S9 fraction and in plasma showed similar half-lives. Compound (A2) and Compound (A1) were stable in buffer at pH 5.6 and in lysosomes over 4 h (FIG. 5D).

TABLE 6

PK properties of Compound (A2) in female balb/c mice (1 mg/kg iv)

| | |
|---|---|
| CL (mL · min$^{-1}$ · kg$^{-1}$) | 175 ± 29 |
| t$_{1/2}$ (h) | 0.4 ± 0.01 |
| AUC i.v. d.n. (nM · h) | 101 ± 16 |

TABLE 7

Stability of Compound (A2)

| | mouse | rat | human |
|---|---|---|---|
| Hepatic microsomes (ul/min/kg) | 107 | 33 | 44 |
| Hepatocytes (ul/min/10$^6$ cells) | — | 8 | <4 |
| Hepatic S9 (+/−NADPH) t$^{1/2}$ (h) | 1.9/>2 | >2/>2 | 1.9/>2 |
| Plasma t$^{1/2}$ (h) | 2.1 | 4.1 | 2.0 |

Example 10: In Vitro Anti-Uveal Melanoma Activity of Anti-PMEL17-(B1) ADCs

Parental and non-targeting control (NT)- or PMEL17-shRNA transduced 92.1 cells were seeded at low cell density in 96-well plates and treated with increasing concentrations of 3207-(B1) (Isotype control), G4-(B1), and G1-(B1) in the presence or absence of doxycycline as indicated. Following drug treatment for 96 or 120 hours, cell viability and proliferation were determined using a resazurin-based viability assay. Briefly, cells were incubated with a resazurin-based solution and color change was detected by absorbance with a spectrophotometer and used as a readout of cell viability. Data presented as mean of 3 independent replicates and relative to PBS-treated cells (control) (FIG. 6). Anti-PMEL17-(B1) ADCs inhibit the proliferation of uveal melanoma cells in a PMEL17- and dose-dependent manner.

Example 11: Anti-PMEL17-(B1) ADCs Induce Apoptosis in Uveal Melanoma Cells 92.1 cells were seeded in 96-well plates (5000 cells per well) and treated with increasing concentrations of Compound (A1), 3207-(B1) (Isotype control), G4-(B1), and G1-(B1) as indicated. Following drug treatment for 96, cells were subjected to fluorescence-activated flow cytometry using an Annexin V antibody conjugated to a fluorescent dye. Data presented as mean of 3 independent replicates. Both G4-(B1) and G1-(B1) induced apoptosis in 92.1 cells in a dose-dependent manner (FIG. 7).

Example 12: In Vitro Anti-Uveal Melanoma Activity of Anti-PMEL17-(B2) ADCs and Anti-PMEL17 mAbs 92.1 uveal melanoma cells were seeded at low cell density in 96-well plates and treated with increasing concentrations of 3207-(B2) (Isotype control), G4-(B2), and G1-(B2), and anti-PMEL17-B1 and -G4 mAbs as indicated. Following drug treatment for 96 or 120 hours, cell viability and proliferation were determined using a resazurin-based viability assay. Data presented as mean of 3 independent replicates and relative to PBS-treated cells (control) (FIG. 8). Anti-PMEL17-(B2) ADCs and anti-PMEL17 mAbs exhibit minimal anti-proliferative effect in uveal melanoma cells.

Example 13: Analysis of GNAQ/11 Inhibition by Anti-PMEL17-(B1) and Anti-PMEL17-(B2) ADCs in Uveal Melanoma Cells 92.1 uveal melanoma were treated with DMSO, Compound (A1) (8 nM) and increasing concentrations of Isotype-(B1), anti-PMEL17-(B1) and anti-PMEL17-(B2) ADCs as indicated. Following drug treatment for 2 days, cells were processed for determination of IP1 levels using TR-FRET (time-resolved fluorescent resonance energy transfer). IP1 levels (nM) are presented as mean of 3 independent replicates. As indicated by reduced levels of IP1, both G1-(B1) and G1-(B2) inhibit mutant GNAQ and GNA11 in a dose-dependent manner (FIG. 9).

Figure 10:
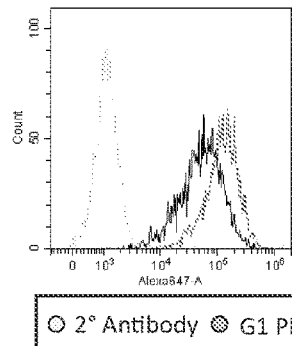
FIGS. 10A-10D show exemplary data on binding activity of anti-PMEL17 antibodies to intact platelets and uveal melanoma cells.
Figure 10:
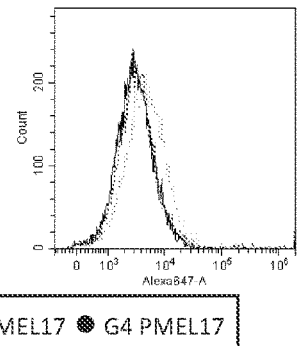
Figure 10:
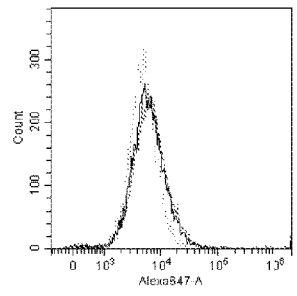
Figure 10:
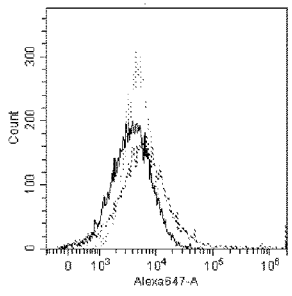

Example 14: Binding Analysis of Anti-PMEL17 Antibodies to Intact Platelets and Uveal Melanoma Cells The uveal melanoma cell line 92.1 and platelets isolated from Human Platelet Rich Plasma (PRP from 3 human donors) were subjected to fluorescence-activated flow cytometry using anti-PMEL17 antibodies G1 (black line) and G4 (grey line), and anti-human IgG secondary antibody conjugated to a fluorescent dye, or the conjugated secondary antibody only (light grey line) (FIG. 10). In contrast to 92.1 uveal melanoma cells, human platelets do not show cell surface expression of PMEL17.

Figure 11:
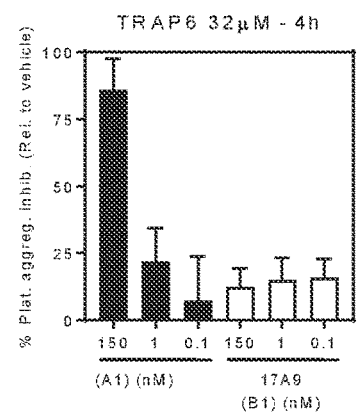
FIGS. 11A-11C show exemplary data on impact of Compound (A1) and anti-PMEL17-(B1) ADCs on human platelet aggregation.
Figure 11:
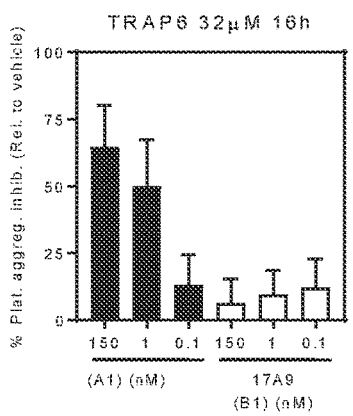
Figure 11:
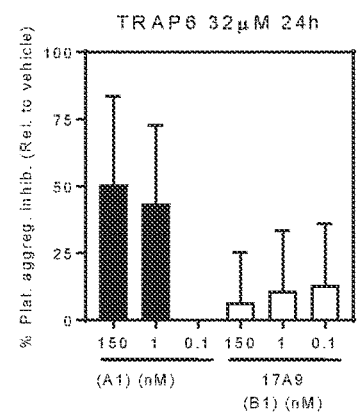

Example 15: Impact of Compound (A1) and Anti-PMEL17-(B1) ADCs on Human Platelet Aggregation Human Platelet Rich Plasma (PRP) was incubated with ADC 17A9-(B1), an anti-PMEL Ab conjugated to B1, or Compound (A1) (0.1, 1, and 150 nM) for 4, 16 or 24 h. Platelet aggregation was then measured following treatment with Thrombin Receptor Activating Peptide 6 (TRAP6) at 32 uM. While Compound (A1) induced platelet aggregation, anti-PMEL17-(B1) did not induce platelet aggregation up to 24 hours (FIG. 11).

Example 16: Anti-PMEL17-(B1) ADCs Inhibit Tumor Growth in Mouse Model

Figure 12:
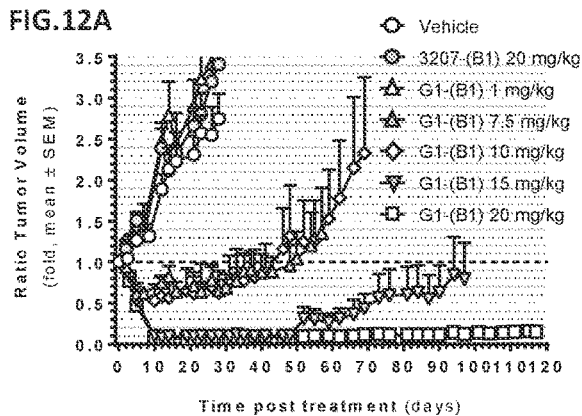
FIGS. 12A-12E show exemplary data on in vivo anti-tumor activity of anti-PMEL17-(B1) ADCs. G1-(B1) inhibited tumor growth in a dose-dependent manner (FIG. 12A). Values are mean±SEM; sample size, (n=5-12 mice per group). Initial tumor volume at day 0 was approximately 200-250 mm³. No body weight loss was observed for up to 14 days after treatment (FIG. 12B). Values are mean±SEM; sample size, (n=4 mice per group). G1-(B1) treatment resulted in GNAQ signaling inhibition and inhibition of tumor cell proliferation as indicated by reduced levels of pERK and Ki67, respectively (FIG. 12C). In addition, G1-(B1) induced cell apoptosis compared to vehicle- and isotype control 3207-(B1)-treated mice, which correlated with tumor cell accumulation of G1-(B1) ADC as detected by IgG staining (FIG. 12C). No changes were observed in MITF and PMEL17 levels following GNAQ inhibition (FIG. 12C). No platelet aggregation inhibition was observed in G1-(B1) treated mice for up to 7 days (FIGS. 12D & E).
Figure 12:
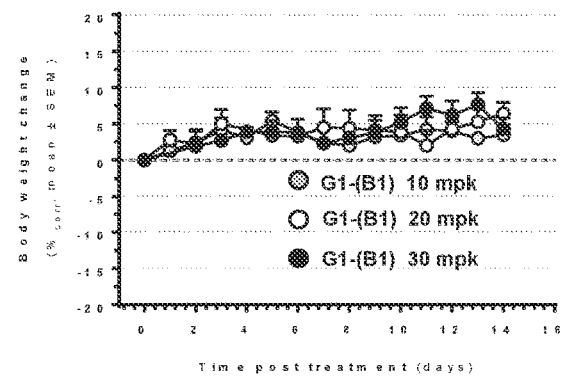
Figure 12:
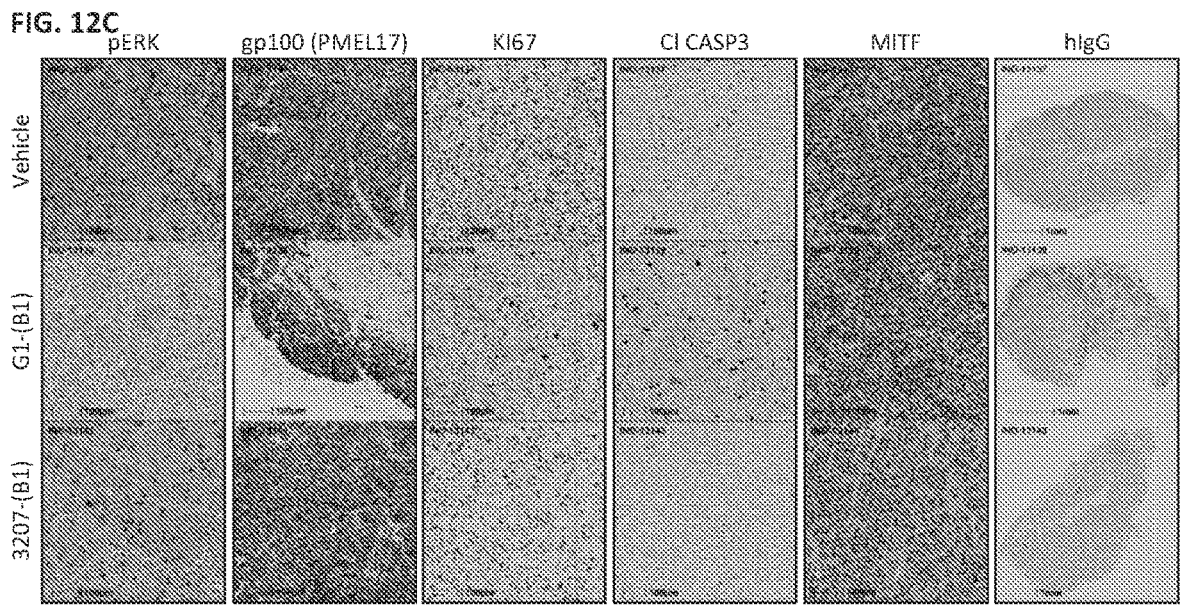
Figure 12:
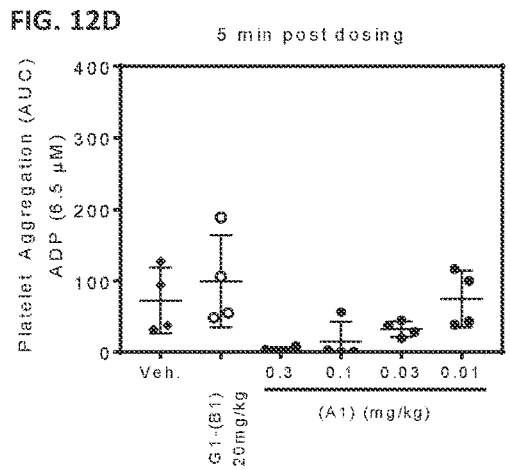
Figure 12:
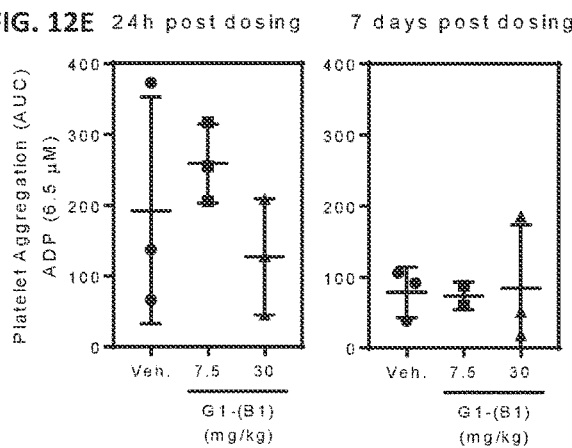

Female nude mice bearing 92.1-luciferase subcutaneous xenografts were treated with a single i.v. injection of 3207-(B1), G1-(B1) or vehicle at the indicated doses. Treatment (single dose i.v. injection) was performed 17 days post tumor inoculation. Values are mean±SEM; sample size, (n=5-12 mice per group). Initial tumor volume at day 0 was approximately 200-250 mm$^3$. G1-(B1) inhibited tumor growth in a dose-dependent manner (FIG. 12A).

Body weight change of female naive nude mice after treatment with G1-(B1) was monitored at the indicated doses. Treatments (single dose i.v. injection) were performed at day 0. Values are mean±SEM; sample size, (n=4 mice per group). Initial body weight at day 0 was approximately 24 g. Body weight was measured every day for 14 days following drug treatment. No body weight loss was observed for up to 14 days after treatment (FIG. 12B).

Immunohistochemical analysis of tumour tissue from 92.1-luciferase subcutaneous xenografts treated with vehicle, 3207-(B1) (7.5 mg/kg body weight), or G1-(B1) (7.5 mg/kg body weight) was performed. Tumors were fixed in 10% (vol/vol) neutral buffered formalin for 24 h at room temperature, then rinsed in PBS, processed for dehydration, cleared, and embedded in paraffin. 3 µm sections were prepared and processed for hematoxylin and eosin (H&E) staining and for immunohistochemistry. Immunohistochemical staining was performed on formalin-fixed, paraffin-embedded tissue sections using a Bond-RX (Leica) fully automated system for anti-hIgG (ThermoFischer) and anti-gp100 (PMEL17) (clone EP4863; Abcam) staining, and a Discovery XT (Ventana Medical System) fully automated system for anti-Ki67 (clone Sp6; NeoMarkers), anti-pERK1/2 (clone D13.14.4E; Cell Signaling), anti-MITF (Sigma) and anti-cleaved Caspase-3 (Cell Signaling) staining. Briefly, G1-(B1) treatment resulted in GNAQ signaling inhibition and inhibition of tumor cell proliferation as indicated by reduced levels of pERK and Ki67, respectively (FIG. 12C). In addition, G1-(B1) induced cell apoptosis compared to vehicle- and 3207-(B1)-treated mice, which correlated with tumor cell accumulation of G1-(B1) ADC as detected by IgG staining (FIG. 12C). No changes were observed in MITF and PMEL17 levels following G1-(A1) treatment (FIG. 12C).

Whole blood platelet aggregation of naive mice treated with vehicle, G1-(B1) (20 mg/kg body weight), or Compound (A1) (0.01, 0.03, 0.1, and 0.3 mg/kg body weight) was tested. Animals were euthanized 5 min post single i.v. dosing and blood was collected via vena cava. After 1 h, whole blood aggregation was measured following platelet activation with ADP at 6.5 uM (FIG. 12D). In contrast to Compound (A1) G1-(B1) did not have any significant effect on ADP-induced platelet aggregation in vivo.

Whole blood platelet aggregation of naive mice treated with vehicle and G1-(B1) (7.5 and 30 mg/kg body weight) at 24 h or 7 d post dosing was measured. Mice were euthanized 24 h or 7 d post single i.v. dosing and blood was collected via vena cava. After 1 h, whole blood aggregation was measured following platelet activation with ADP at 6.5 uM. No platelet aggregation inhibition was observed in G1-(B1) treated mice for up to 7 days (FIG. 12E).

Figure 13:
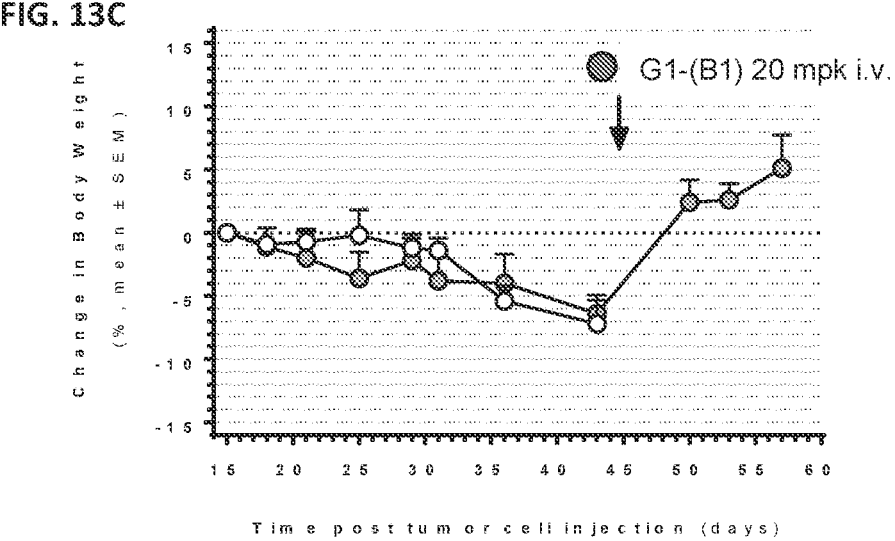
FIGS. 13A-13C show exemplary data on effect of G1-(B1) ADC on a liver and lung metastasis mouse model of uveal melanoma. Individual pictures from each mice are presented at day 45 following i.v. injection of 92.1-luciferase cells (just before the initiation of treatment) and 12 days post treatment (FIGS. 13A and 13B); sample size, (n=6 mice per group). Initial BLI for liver metastasis at day 0 was approximately 2.8*109 p/sec/cm2. Lung tumors (bioluminescence signal) in FIG. 13B are indicated by a black arrow. Corresponding body weight modulation (% vs day 15) was assessed 2-3 times per week prior and post treatment with G1-(B1) 20 mg/kg (grey circles). Values in FIG. 13C are mean±SEM; sample size, (n=5-6 mice per group). Initial body weight at day 15 was approximately 21 g.

Example 17: Effect of G1-(B1) on a Liver and Lung Metastasis Mouse Model of Uveal Melanoma Female NOD-Scid mice were intravenously injected with 92.1-luciferase cells (approximately 2 million cells per animal) and bioluminescence was measured twice a week to evaluate tumor formation. After 45 days all injected mice developed liver and lung metastases as detected by bioluminescence signal (BLI) (FIGS. 13A and 13B). Tumor bearing mice were treated with a single i.v. injection of G1-(B1) (20 mg/kg body weight) and bioluminescence was monitored over time as a readout of tumor progression. Individual pictures from each mice are presented at day 45 following i.v. injection of 92.1-luciferase cells (just before the initiation of treatment) and 12 days post treatment (FIGS. 13A and 13B); sample size, (n=6 mice per group). Initial BLI for liver metastasis at day 0 was approximately 2.8*10$^9$ p/sec/cm$^2$. Lung tumors (bioluminescence signal) in FIG. 13B are indicated by a black arrow. As indicated by reduced in vivo and ex vivo bioluminescence, G1-(B1) induced regression of liver and lung metastases following a single i.v. dose of 20 mg/kg.

Corresponding body weight modulation (% vs day 15) was assessed 2-3 times per week prior and post treatment with G1-(B1) 20 mg/kg (grey circles). Values are mean±SEM; sample size, (n=5-6 mice per group). Initial body weight at day 15 was approximately 21 g. G1-(B1) treatment resulted in body weight restoration in a liver and lung metastasis model of uveal melanoma.

Example 18: PK Properties of G1-(B1) ADCs

The pharmacokinetic profile of G1-(B1) showed a slightly over-proportional increase of exposure with dose between 7.5 and 30 mg/kg in nude mice (FIG. 14A). Clearance, volume of distribution and half-life are in the typical range for ADCs. Table 8 summarizes some PK values.

In tumor bearing mice, free payload concentrations were measured after dosing either target binding G1-(B1) or isotype control 3207-(B1). A clear (>4-fold) increase in tumor delivery of Compound (A1) payload could be observed using the targeted ADC (FIG. 14B). The conversion of Compound (A1) (open circles) into its ring-opened form of Compound (A1) having the structure of Compound (A4)

Compound (A6)

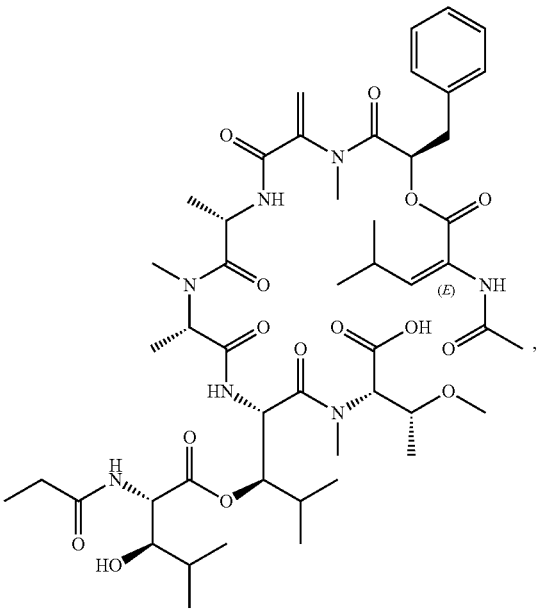 [SMILES: C=C(C(=O)N[C@@H](C)C(=O)N(C)[C@@H](C)C(=O)N[C@H](C(=O)N(C)[C@H](C(=O)O)[C@@H](C)OC)[C@H](OC(=O)[C@@H](NC(=O)CC)[C@H](O)C(C)C)C(C)C)N(C)C(=O)[C@@H](Cc1ccccc1)OC(=O)/C(=C\C(C)C)NC(C)=O]

or Compound (A8)

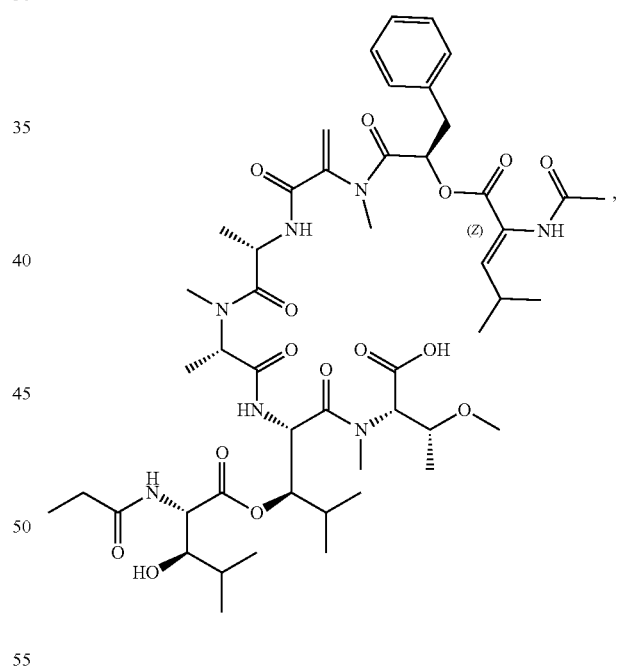

(filled circles) while being conjugated to the antibody was shown in vivo in mice (FIG. 14C). The exposures in an in vivo efficacy study, comparing two different DAR2 formats with the DAR4 format of G1-(B1) and with the DAR4 Fc-silent format, showed lowest clearance for the DAR2 (E152C) and the DAR4 Fc-silent ADCs, whereas the DAR2 (S375C) exposure decreases faster (FIG. 14D). From comparing the PK of the non-targeted 3207-ADCs (FIG. 14E) one can deduce that the Fc-silencing has a significant effect on lowering the clearance of the DAR4 format.

TABLE 8

| PK properties of G1-(B1) ADCs | | |
|---|---|---|
| Nude mice - dose (mg/kg) | 7.5 | 30 |
| $AUC_{last}$ (ug/mL*h) | 6'779 ± 1'061 | 45'346 ± 3'785 |
| $AUC_{last}$ (ug/mL*h) dose normaliz. | 904 | 1'511 |
| $AUC_{inf}$ (ug/mL*h) | 9'211 ± 2'337 | 73'680 ± 9'867 |
| AUC extrap (%) | 25 ± 9 | 38 ± 3 |
| CL (mL/h/kg) | 0.9 ± 0.3 | 0.4 ± 0.05 |
| Vz (L/kg) | 0.21 ± 0.01 | 0.15 ± 0.01 |
| app. $t_{elim}$ (h) | 176 ± 37 | 259 ± 25 |

Example 19: In Vitro Stability of Anti-PMEL17-GNAQ/11i ADCs in Buffer, Mouse, Rat, and Human Plasma and In Vivo Stability of Anti-PMEL17-GNAQ/11i ADCs in Mouse Anti-PMEL17G1_E152C_S375C_(B2) (G1-(B2)) was spiked at 100 μg/mL into respective matrix and incubated at 37° C. Samples were collected at 0, 1, 2, and 4 h by flash freezing at −70° C. Aliquots of each sample were immunoprecipitated using Capture Select FcXL beads and were incubated with buffer containing papain to release the payload from the bead captured ADC. Released payload was then analyzed by HPLC MS to determine relative levels of Compound (A2)-PO$_4$ (i.e.

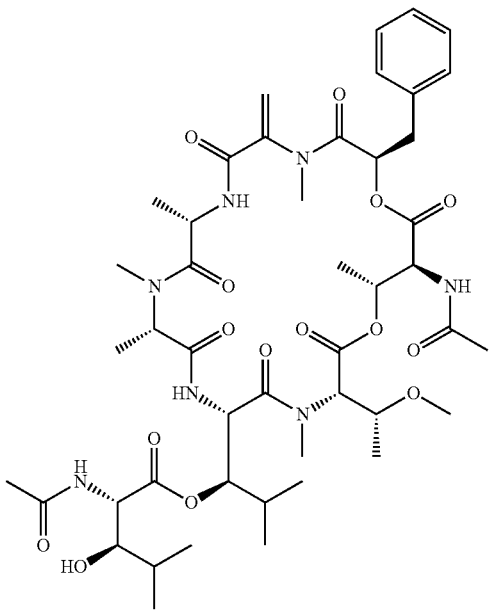 [SMILES: C=C1C(=O)N[C@@H](C)C(=O)N(C)[C@@H](C)C(=O)N[C@@H]([C@H](OC(=O)[C@@H](NC(C)=O)[C@H](O)C(C)C)C(C)C)C(=O)N(C)[C@@H]([C@@H](C)OC)C(=O)O[C@H](C)[C@H](NC(C)=O)C(=O)O[C@H](Cc2ccccc2)C(=O)N1C]

from see Example 1.2), and ring opened Compound (A2)-PO$_4$ having the structure of Compound (A5)-PO$_4$ (i.e. Compound (A5)-PO$_4$

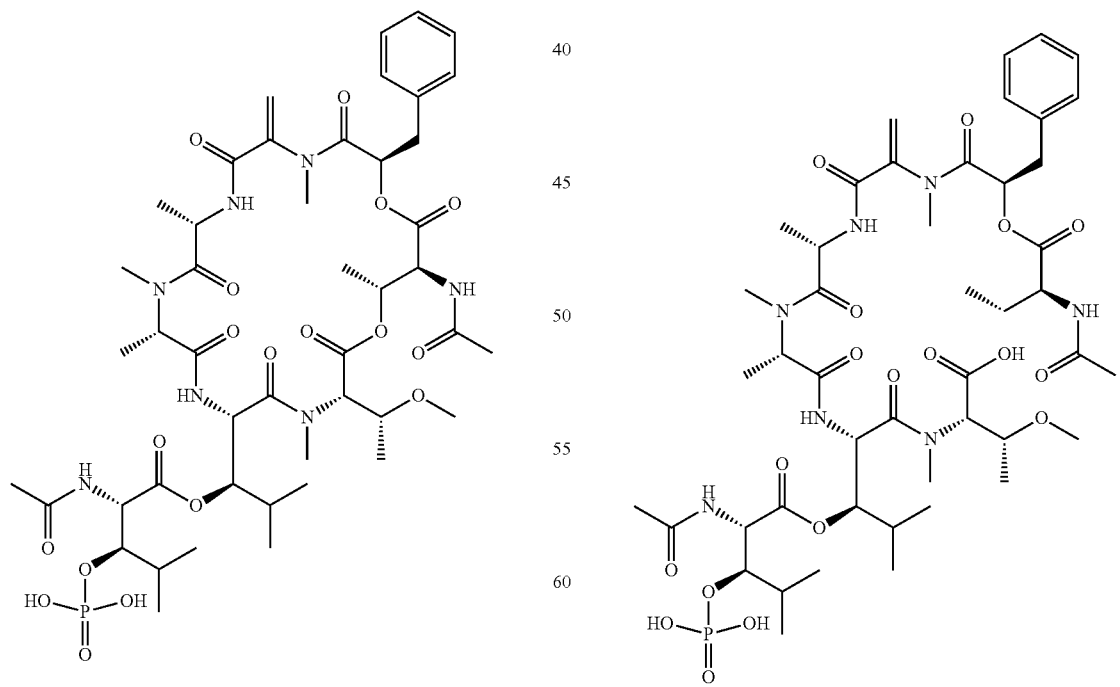

from

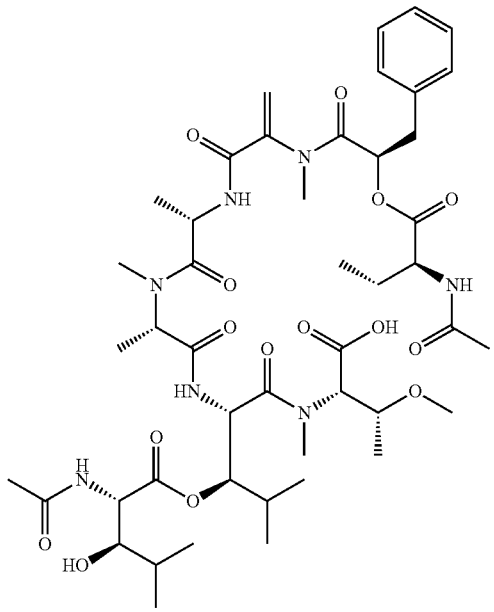

Compound (A7)-PO$_4$,

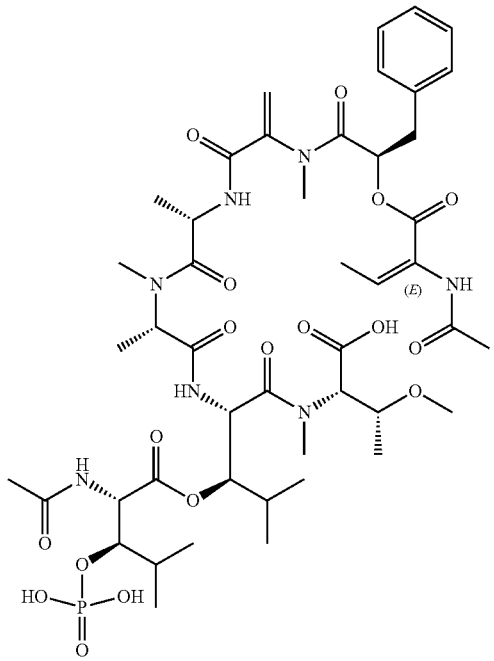 [SMILES: C=C(C(=O)N[C@@H](C)C(=O)N(C)[C@@H](C)C(=O)N[C@H](C(=O)N(C)[C@H](C(=O)O)[C@@H](C)OC)[C@H](OC(=O)[C@@H](NC(C)=O)[C@H](OP(=O)(O)O)C(C)C)C(C)C)N(C)C(=O)[C@@H](Cc1ccccc1)OC(=O)/C(=C\C)NC(C)=O]

or Compound (A9)-PO$_4$,

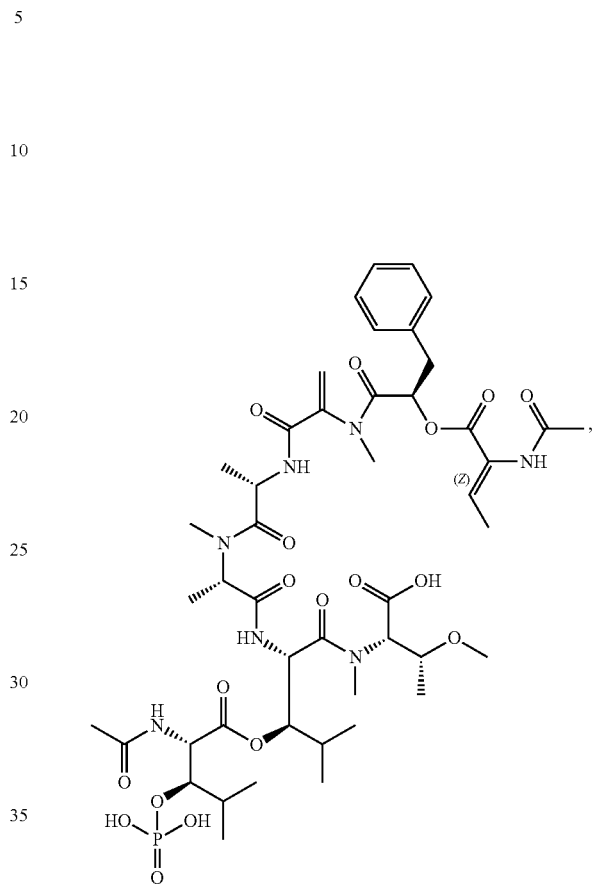

(where ring opened Compound (A2)-PO$_4$— inactive payload). Graph depicts the percent of released payload that was present as Compound (A2)-PO$_4$ over the time course of the experiment (FIG. 15A).

Anti-PMEL17G1_E152C_S375C_(B1) (G1-(B1)), Anti-PMEL17G1_E152C_(B1) (G1-E152C-DAR2-(B1)), Anti-PMEL17G1_S375C_(B1) (G1-S375C-DAR2-(B1)), and Fc-silent Anti-PMEL17G1_E152C_S375C_(B1) (Fc-silent G1-(B1)) were spiked at 100 μg/mL into respective matrix and incubated at 37° C. Samples were collected at 0, 2, 4, and 6 h by flash freezing at −70° C. Aliquots of each sample were immuno-precipitated using Capture Select FcXL beads and were incubated with buffer containing papain to release the payload from the bead captured ADC. Released payloads were then analyzed by HPLC MS to determine relative levels of Compound (A1)-PO$_4$, Compound (A6)-PO$_4$,
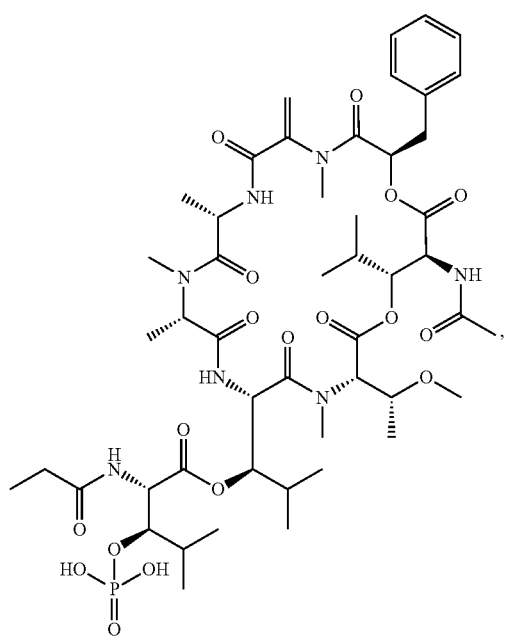 [SMILES: C=C1C(=O)N[C@@H](C)C(=O)N(C)[C@@H](C)C(=O)N[C@@H]([C@H](OC(=O)[C@@H](NC(=O)CC)[C@H](OP(=O)(O)O)C(C)C)C(C)C)C(=O)N(C)[C@@H]([C@@H](C)OC)C(=O)O[C@H](C(C)C)[C@H](NC(C)=O)C(=O)O[C@H](Cc2ccccc2)C(=O)N1C]
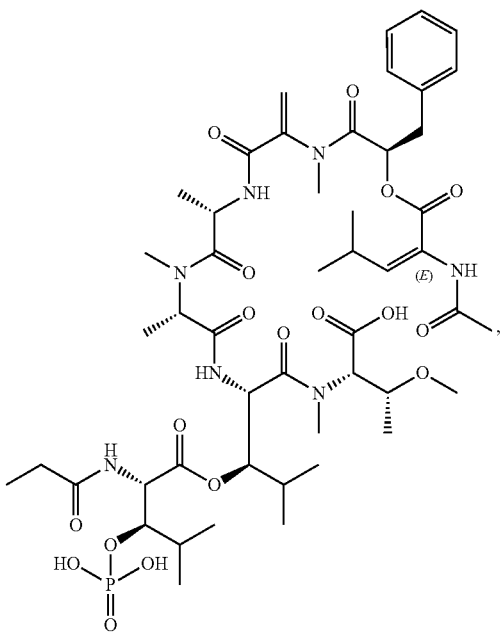 [SMILES: C=C(C(=O)N[C@@H](C)C(=O)N(C)[C@@H](C)C(=O)N[C@H](C(=O)N(C)[C@H](C(=O)O)[C@@H](C)OC)[C@H](OC(=O)[C@@H](NC(=O)CC)[C@H](OP(=O)(O)O)C(C)C)C(C)C)N(C)C(=O)[C@@H](Cc1ccccc1)OC(=O)/C(=C\C(C)C)NC(C)=O]
and ring opened Compound (A1)-PO$_4$ having the structure of Compound (A4)-PO$_4$,
or Compound (A8)-PO$_4$,
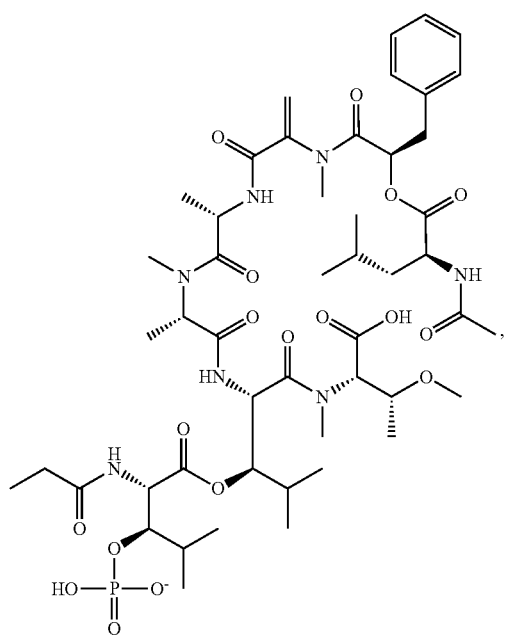
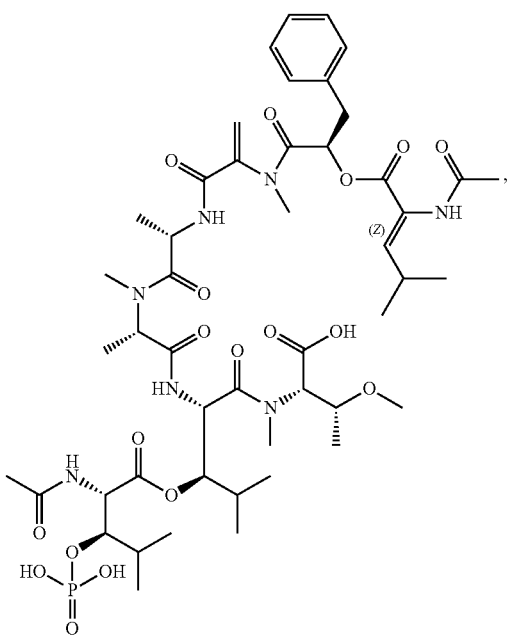 [SMILES: C=C(C(=O)N[C@@H](C)C(=O)N(C)[C@@H](C)C(=O)N[C@H](C(=O)N(C)[C@H](C(=O)O)[C@@H](C)OC)[C@H](OC(=O)[C@@H](NC(C)=O)[C@H](OP(=O)(O)O)C(C)C)C(C)C)N(C)C(=O)[C@@H](Cc1ccccc1)OC(=O)/C(=C/C(C)C)NC(C)=O]

(where ring opened compounds of Compound (A1)-PO$_4$,

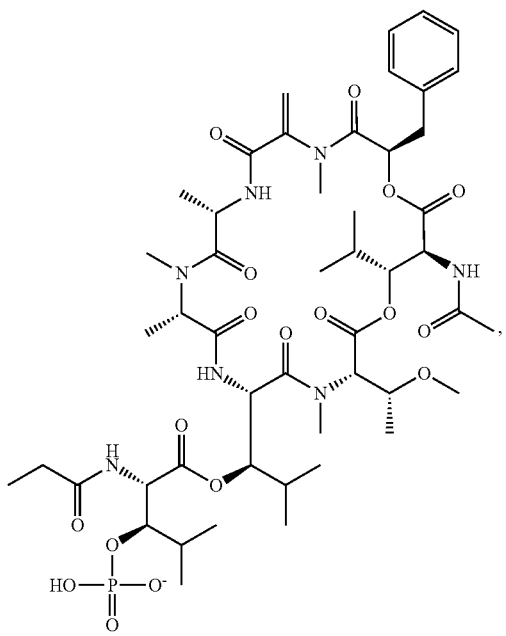 [SMILES: C=C1C(=O)N[C@@H](C)C(=O)N(C)[C@@H](C)C(=O)N[C@@H]([C@H](OC(=O)[C@@H](NC(=O)CC)[C@H](OP(=O)([O-])O)C(C)C)C(C)C)C(=O)N(C)[C@@H]([C@@H](C)OC)C(=O)O[C@H](C(C)C)[C@H](NC(C)=O)C(=O)O[C@H](Cc2ccccc2)C(=O)N1C]

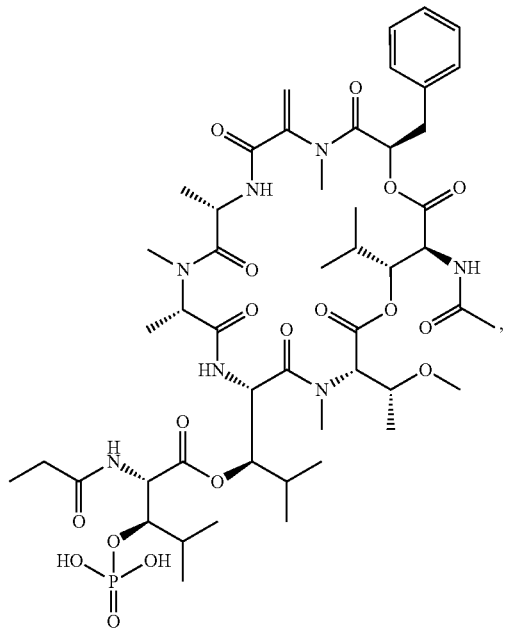 [SMILES: C=C1C(=O)N[C@@H](C)C(=O)N(C)[C@@H](C)C(=O)N[C@@H]([C@H](OC(=O)[C@@H](NC(=O)CC)[C@H](OP(=O)(O)O)C(C)C)C(C)C)C(=O)N(C)[C@@H]([C@@H](C)OC)C(=O)O[C@H](C(C)C)[C@H](NC(C)=O)C(=O)O[C@H](Cc2ccccc2)C(=O)N1C]

and ring opened Compound (A1)-PO$_4$ having the structure of Compound (A4)-PO$_4$, are—inactive payload). Graph depicts the percent of released payload that was present as Compound (A1)-PO$_4$ over the time course of the experiment for each of the different ADC constructs (FIG. 15B).

Anti-PMEL17G1_E152C_S375C_(B1) (G1-(B1)), Anti-PMEL17G1_E152C_(B1) (G1-E152C-DAR2-(B1)), Anti-PMEL17G1_S375C_(B1) (G1-S375C-DAR2-(B1)), and Fc-silent Anti-PMEL17G1_E152C_S375C_(B1) (Fc-silent G1-(B1)) were each intravenously injected in nude mice at 20 mg/kg (body weight). Nine mice were dosed with each of the ADC constructs described above. Three animals per group (ADC construct) were terminally bled to collect serum samples for analysis at 24 h, day 7, and day 14 post dose. Aliquots of each sample were immuno-precipitated using Capture Select FcXL beads and were incubated with buffer containing papain to release the payload from the bead captured ADC. Released payloads were then analyzed by HPLC MS to determine relative levels of Compound (A1)-PO$_4$,

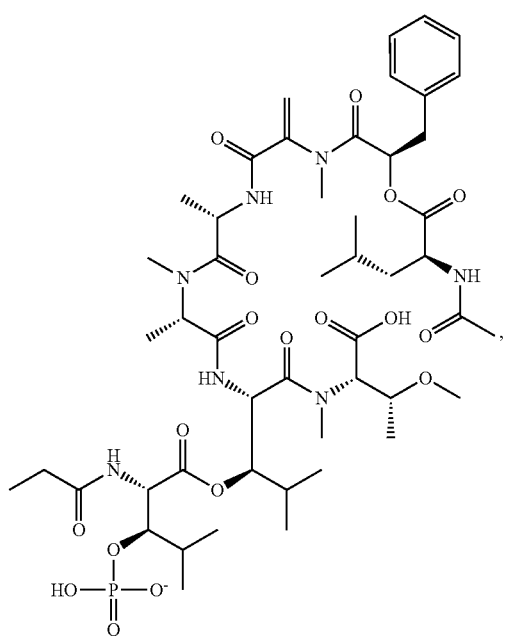

Compound (A6)-PO$_4$,

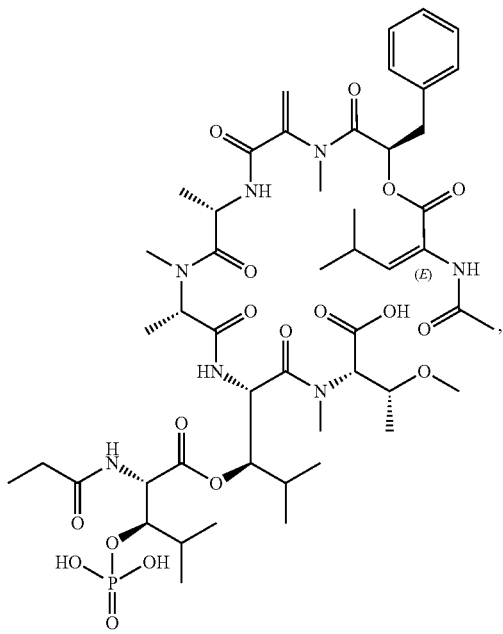 [SMILES: C=C(C(=O)N[C@@H](C)C(=O)N(C)[C@@H](C)C(=O)N[C@H](C(=O)N(C)[C@H](C(=O)O)[C@@H](C)OC)[C@H](OC(=O)[C@@H](NC(=O)CC)[C@H](OP(=O)(O)O)C(C)C)C(C)C)N(C)C(=O)[C@@H](Cc1ccccc1)OC(=O)/C(=C\C(C)C)NC(C)=O]

or Compound (A8)-PO$_4$,

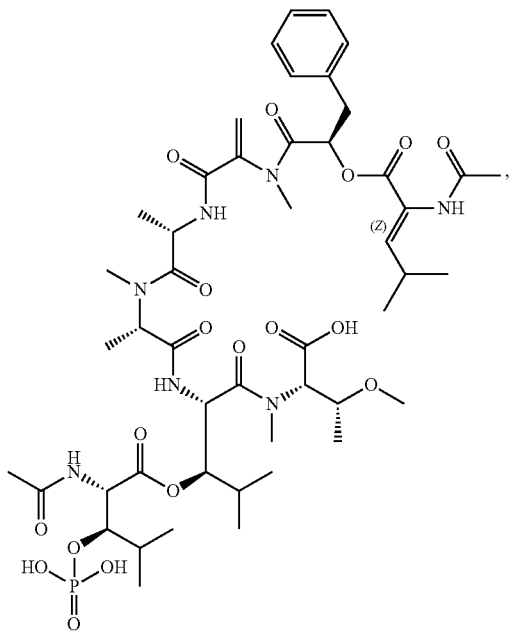 [SMILES: C=C(C(=O)N[C@@H](C)C(=O)N(C)[C@@H](C)C(=O)N[C@H](C(=O)N(C)[C@H](C(=O)O)[C@@H](C)OC)[C@H](OC(=O)[C@@H](NC(C)=O)[C@H](OP(=O)(O)O)C(C)C)C(C)C)N(C)C(=O)[C@@H](Cc1ccccc1)OC(=O)/C(=C/C(C)C)NC(C)=O]

(where ring opened compounds of Compound (A1)-PO$_4$— are inactive payload). Graph shows the percent of payload present on the ADCs in the active form of Compound (A1)-PO$_4$ (assuming Compound (A1)-PO$_4$+Compound (A8)-PO$_4$=100%) (FIG. 15C). Initial values were estimated based on in vitro experimental results.

Example 20: In Vivo Efficacy of G1-E152C-DAR2-(B1), G1-S375C-DAR2-(B1), Fc-Silent G1-(B1) in a Xenograft Model of Uveal Melanoma Female nude mice bearing 92.1-luciferase subcutaneous xenografts were treated with 3207-E152C_S375C-DAR4-(B1), G1-E152C_S375C-DAR4-(B1), G1-E152C-DAR2-(B1), G1-S375C-DAR2-(B1), Fc-silent 3207-(B1), and Fc-silent G1-DAR4 at 7.5 mg/kg. Treatments (single dose i.v. injection) were performed 17 days post tumor inoculation. Values represent mean±SEM; sample size, (n=5-6 mice per group). Initial tumor volume at day 0 was approximately 300-325 mm$^3$. (FIG. 16). G1-E152C-DAR2-(B1), Fc-silent G1-DAR4, and G1-E152C_S375C-DAR4-(B1) exhibit comparable antitumor activity in the 92.1 xenograft model of uveal melanoma, while G1-S375C-DAR2-(B1) and non-targeted 3207-ADCs have no effect on tumor growth.

Example 21: In Vitro Activity of G1-3J-DAR4-(B1), G1-3R-DAR4-(B1), G1-DAR4-(B1), G1-3J-DAR2 (E152C)-(B1), Fc Silent G1-3J-DAR2 (E152C)-(B1), 3207-DAR2 (E152C)-(B1), and G1-DAR2 (E152C)-(B1)

In FIG. 17A, 92.1 (left panel) and MP41 (right panel) cells were seeded at low cell density in 96-well plates and treated with increasing concentrations of G1-3J-DAR4-(B1), G1-3R-DAR4-(B1), G1-DAR4-(B1) as indicated. Following drug treatment for 96 or 120 hours, cell viability and proliferation were determined using a resazurin-based viability assay. Briefly, cells were incubated with a resazurin-based solution and color change was detected by absorbance with a spectrophotometer and used as a readout of cell viability. Data presented as mean of 3 independent replicates and relative to PBS-treated cells (control). G150 (is the concentration for 50% of maximal inhibition of cell proliferation) value for each ADC and cell line is depicted in Table 9. Anti-PMEL17-(B1) ADCs inhibit the proliferation of uveal melanoma cells in a PMEL17- and dose-dependent manner.

TABLE 9

Growth inhibitory activity of G1-3J-DAR4-(B1), G1-3R-DAR4-(B1), G1-DAR4-(B1) in UM cells

| Cell line | G1-3J-DAR4-(B1) GI$_{50}$ nM | G1-3R-DAR4-(B1) GI$_{50}$ nM | G1-DAR4-(B1) GI$_{50}$ nM |
|---|---|---|---|
| 92.1 | 0.850 | 0.811 | 0.722 |
| MP41 | 0.582 | 0.654 | 0.563 |

FIG. 17B depicts results of a cell proliferation assay in 92.1 cell line with G1-3J-DAR2 (E152C)-(B1), Fc Silent G1-3J-DAR2 (E152C)-(B1), 3207-DAR2 (E152C)-(B1), and G1-DAR2 (E152C)-(B1) as described in FIG. 17A. G150 is depicted in Table 10.

TABLE 10

Growth inhibitory activity of G1-3J-DAR2 (E152C)-(B1), Fc Silent G1-3J -DAR2 (E152C)-(B1), 3207-DAR2 (E152C)-(B1), and G1-DAR2 (E152C)-(B1) in UM cells

| Cell line | G1-3J-DAR2 (E152C)-(B1) GI50 nM | Fc Silent G1-3J -DAR2 (E152C)-(B1) GI50 nM | 3207-DAR2 (E152C)-(B1) GI50 nM | G1-DAR2 (E152C)-(B1) GI50 nM |
|---|---|---|---|---|
| 92.1 | 0.309 | 0.278 | >150 | 0.365 |

Example 22: Anti-PMEL17-(B1) ADCs Inhibit Tumor Growth in Mouse Model

Figure 18:
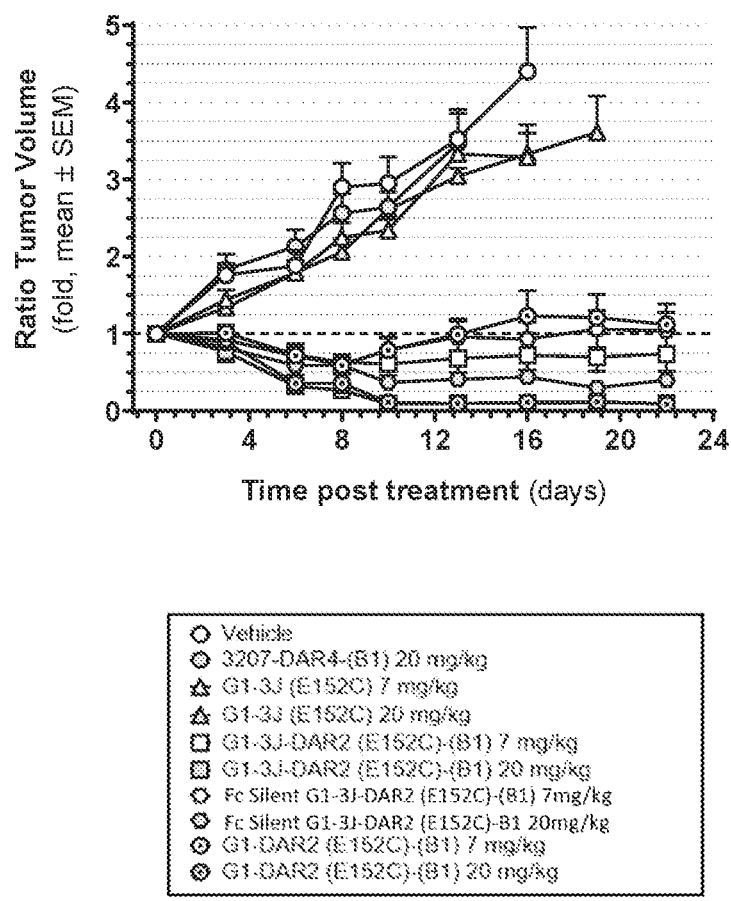
FIG. 18 shows exemplary data show exemplary data on in vivo anti-tumor activity of anti-PMEL17-(B1) ADCs.

Female nude mice bearing 92.1-luciferase subcutaneous xenografts were treated with a single i.v. injection of 3207-(B1), G1-3J(E152C), G1-3J-DAR2 (E152C)-(B1), Fc Silent G1-3J-DAR2 (E152C)-(B1), G1-DAR2 (E152C)-(B1) or vehicle at the indicated doses. Treatment (single dose i.v. injection) was performed 14-17 days post tumor inoculation. Values are mean±SEM; sample size, (n=5-12 mice per group). Initial tumor volume at day 0 was approximately 200-250 mm3. G1-3J-DAR2 (E152C)-(B1) and Fc Silent G1-3J-DAR2 (E152C)-(B1) inhibited tumor growth in a dose-dependent manner (FIG. 18).

Example 23: Immunohistochemical Analysis of Tumor Biopsies from Metastatic Uveal Melanoma Patients Tumours were fixed in 10% (vol/vol) neutral buffered formalin for 24 h at room temperature, then rinsed in PBS, processed for dehydration, cleared, and embedded in paraffin. 3 µm sections were prepared and processed for immunohistochemistry. Immunohistochemical staining was performed on formalin-fixed, paraffin-embedded tissue sections using a Bond-RX (Leica) fully automated system for anti-gp100 (PMEL17) (mouse monoclonal HMB45) staining. Metastatic uveal melanoma samples exhibit high and relatively homogenous expression of PMEL17 (FIG. 19A). Quantification of PMEL17 expression levels and proportion of PMEL17 positive cells in metastatic uveal melanoma patient samples (FIG. 19B, FIG. 19C).

Example 24: Competitive Binding Assay

SPR was used to assess epitope binning for anti-PMEL antibodies on a T200 Biacore instrument (catalog #28975001, GE Healthcare Life Sciences).

Surface Plasmon Resonance (SPR) is a technique to measure bimolecular interactions in real-time in a label free environment. Molecules are immobilized on a sensor surface over which a sample solution flows. The interaction between the immobilized molecule and the flowing sample causes a refractive index change. The refractive index change is an altering of the angle at which reduced intensity polarized light is reflected from the supporting glass plane. This angle change is caused by binding or dissociation of molecules from the sensor surface and is proportional to the mass of bound material and is recorded by the instrument in a sensorgram. The sensorgram shows increasing response as molecules interact, the response remains constant if the interaction reaches equilibrium, and the response decreases as the sample is replaced by buffer and the interaction partners dissociate. From the association and dissociation event responses, an association rate (ka), a dissociation rate (kd) and an overall affinity (KD) are determined. For epitope binning, KDs are not determined.

In the first step, G1 LC 3J and 17A9 antibodies were directly immobilized onto a CM5 chip surface via Amine Coupling to achieve approximately 2000RU respectively on Fc2 and Fc3. Flow cell 1 did not have an antibody immobilized onto it and served as the reference Fc. The immobilized antibodies on Fc2 and Fc3 are the base antibodies in the experiment After immobilization, human PMEL flowed over in the second step at 20 nM over all flow cells for 60 seconds at 30 ul/min.

The third and final step has the G1 LC 3J antibody alone or G1 LC 3J antibody plus 17A9 antibody flowing over Fc2 or the 17A9 antibody alone or 17A9 antibody plus G1 LC 3J antibody flowing over Fc3 (FIG. 20A). The antibodies flowed over at 500 nM total concentration over both flow cells for 120 seconds at 30 ul/min for association followed by a dissociation phase of 120 seconds at 30 ul/min with running buffer.

As expected, when G1 LC 3J was the base antibody, no binging signal was observed when G13J flowed over. 100RU binding was observed when 17A9 was flowed over, suggestive it binds to a different epitope than G1 LC 3J (FIG. 20B). Similar trends observed when 17A9 was the base antibody. In step 3, no binding observed with itself but binding observed when G1 LC 3J flowed over (FIG. 20C). This indicated that G1 LC 3J and 17A9 bind to different epitopes.

Regeneration was performed at the end of each cycle on all flow cells. The regeneration buffer was Glycine 2.0 which flowed at 30p1/min for 30 seconds.

The data was analyzed using the Biacore T200 Evaluation Software version 3.0.

It is understood that the examples and embodiments described herein are for illustrative purposes only and that various modifications or changes in light thereof will be suggested to persons skilled in the art and are to be included within the spirit and purview of this application and the scope of the appended claims.

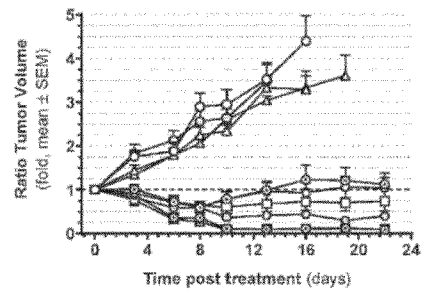

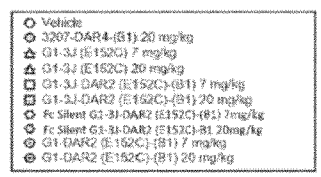

We claim:

1. An antibody or antigen binding fragment thereof that binds human PMEL17 comprising:
   a. a heavy chain variable region that comprises a heavy chain CDR1 (Complementarity Determining Region 1) of SEQ ID NO:1, 4, 5 or 7, a heavy chain CDR2 (Complementarity Determining Region 2) of SEQ ID NO:2, 6 or 8, and a heavy chain CDR3 (Complementarity Determining Region 3) of SEQ ID NO:3 or 9; and a light chain variable region that comprises a light chain CDR1 (Complementarity Determining Region 1) of SEQ ID NO:14, 17 or 20, a light chain CDR2 (Complementarity Determining Region 2) of SEQ ID NO:15 or 18, and a light chain CDR3 (Complementarity Determining Region 3) of SEQ ID NO:16 or 19;
   b. a heavy chain variable region that comprises a heavy chain CDR1 of SEQ ID NO:33, 36, 37 or 39, a heavy chain CDR2 of SEQ ID NO:34, 38 or 40; a heavy chain CDR3 of SEQ ID NO:35 or 41; and a light chain variable region that comprises a light chain CDR1 of SEQ ID NO:46, 49 or 52; a light chain CDR2 of SEQ ID NO:47 or 50; and a light chain CDR3 of SEQ ID NO:48 or 51;
   c. a heavy chain variable region that comprises a heavy chain CDR1 of SEQ ID NO:5, 7, 57 or 60, a heavy chain CDR2 of SEQ ID NO:58, 61 or 62; a heavy chain CDR3 of SEQ ID NO:59 or 63; and a light chain variable region that comprises a light chain CDR1 of SEQ ID NO:68, 71 or 74; a light chain CDR2 of SEQ ID NO:69 or 72; and a light chain CDR3 of SEQ ID NO:70 or 73;
   d. a heavy chain variable region that comprises a heavy chain CDR1 of SEQ ID NO:79, 82, 83 or 85, a heavy chain CDR2 of SEQ ID NO:80, 84 or 86; a heavy chain CDR3 of SEQ ID NO:81 or 87; and a light chain variable region that comprises a light chain CDR1 of SEQ ID NO:92, 95 or 98; a light chain CDR2 of SEQ ID NO:93 or 96; and a light chain CDR3 of SEQ ID NO:94 or 97;

e. a heavy chain variable region that comprises a heavy chain CDR1 of SEQ ID NO:103, 106, 107 or 109, a heavy chain CDR2 of SEQ ID NO:104, 108 or 110; a heavy chain CDR3 of SEQ ID NO:105 or 111; and a light chain variable region that comprises a light chain CDR1 of SEQ ID NO:49, 52 or 116; a light chain CDR2 of SEQ ID NO:47 or 50; and a light chain CDR3 of SEQ ID NO:117 or 118;

f. a heavy chain variable region that comprises a heavy chain CDR1 of SEQ ID NO:123, 126, 127 or 129, a heavy chain CDR2 of SEQ ID NO:124, 128 or 130; a heavy chain CDR3 of SEQ ID NO:125 or 131; and a light chain variable region that comprises a light chain CDR1 of SEQ ID NO:136, 139 or 142; a light chain CDR2 of SEQ ID NO:137 or 140; and a light chain CDR3 of SEQ ID NO:138 or 141;

g. a heavy chain variable region that comprises a heavy chain CDR1 of SEQ ID NO:123, 126, 127 or 129, a heavy chain CDR2 of SEQ ID NO:124, 128 or 130; a heavy chain CDR3 of SEQ ID NO:147 or 148; and a light chain variable region that comprises a light chain CDR1 of SEQ ID NO:153, 156 or 158; a light chain CDR2 of SEQ ID NO:50 or 154; and a light chain CDR3 of SEQ ID NO:155 or 157;

h. a heavy chain variable region that comprises a heavy chain CDR1 of SEQ ID NO:103, 106, 107 or 109, a heavy chain CDR2 of SEQ ID NO:104, 108 or 110; a heavy chain CDR3 of SEQ ID NO:163 or 164; and a light chain variable region that comprises a light chain CDR1 of SEQ ID NO:49, 52 or 116; a light chain CDR2 of SEQ ID NO:47 or 50; and a light chain CDR3 of SEQ ID NO:169 or 170;

i. a heavy chain variable region that comprises a heavy chain CDR1 of SEQ ID NO:175, 178, 179 or 181, a heavy chain CDR2 of SEQ ID NO:176, 180 or 182; a heavy chain CDR3 of SEQ ID NO:177 or 183; and a light chain variable region that comprises a light chain CDR1 of SEQ ID NO:49, 52 or 116; a light chain CDR2 of SEQ ID NO:47 or 50; and a light chain CDR3 of SEQ ID NO:188 or 189;

j. a heavy chain variable region that comprises a heavy chain CDR1 of SEQ ID NO: 103, 106, 107 or 109, a heavy chain CDR2 of SEQ ID NO: 104, 108 or 110; a heavy chain CDR3 of SEQ ID NO:194 or 195; and a light chain variable region that comprises a light chain CDR1 of SEQ ID NO: 49, 52 or 116; a light chain CDR2 of SEQ ID NO: 47 or 50; and a light chain CDR3 of SEQ ID NO:200 or 201;

k. a heavy chain variable region that comprises a heavy chain CDR1 of SEQ ID NO:206, 209, 210 or 212, a heavy chain CDR2 of SEQ ID NO:207, 211 or 213; a heavy chain CDR3 of SEQ ID NO:208 or 214; and a light chain variable region that comprises a light chain CDR1 of SEQ ID NO:153, 156 or 158; a light chain CDR2 of SEQ ID NO:50 or 154; and a light chain CDR3 of SEQ ID NO:219 or 220;

l. A heavy chain variable region that comprises a heavy chain CDR1 of SEQ ID NO: 206, 209, 210 or 212, a heavy chain CDR2 of SEQ ID NO: 207, 211 or 213; a heavy chain CDR3 of SEQ ID NO:225 or 226; and a light chain variable region that comprises a light chain CDR1 of SEQ ID NO:136, 139 or 142; a light chain CDR2 of SEQ ID NO:137 or 140; and a light chain CDR3 of SEQ ID NO:231 or 232;

m. a heavy chain variable region that comprises a heavy chain CDR1 of SEQ ID NO: 206, 209, 210 or 212, a heavy chain CDR2 of SEQ ID NO: 207, 211 or 213, and a heavy chain CDR3 of SEQ ID NO:237 or 238; and a light chain variable region that comprises a light chain CDR1 of SEQ ID NO:243, 245 or 247, a light chain CDR2 of SEQ ID NO:47 or 50, and a light chain CDR3 of SEQ ID NO:244 or 246;

n. a heavy chain variable region that comprises a heavy chain CDR1 of SEQ ID NO: 206, 209, 210 or 212, a heavy chain CDR2 of SEQ ID NO: 207, 211 or 213, and a heavy chain CDR3 of SEQ ID NO:252 or 253; and a light chain variable region that comprises a light chain CDR1 of SEQ ID NO:153, 156 or 158, a light chain CDR2 of SEQ ID NO:50 or 154, and a light chain CDR3 of SEQ ID NO:258 or 259;

o. a heavy chain CDR1 of SEQ ID NO:1, a heavy chain CDR2 of SEQ ID NO:2, a heavy chain CDR3 of SEQ ID NO:3, a light chain CDR1 of SEQ ID NO:14, a light chain CDR2 of SEQ ID NO:15, and a light chain CDR3 of SEQ ID NO:16;

p. a heavy chain CDR1 of SEQ ID NO: 4, a heavy chain CDR2 of SEQ ID NO:2, a heavy chain CDR3 of SEQ ID NO:3, a light chain CDR1 of SEQ ID NO:14, a light chain CDR2 of SEQ ID NO:15, and a light chain CDR3 of SEQ ID NO:16;

q. a heavy chain CDR1 of SEQ ID NO:5, a heavy chain CDR2 of SEQ ID NO:6, a heavy chain CDR3 of SEQ ID NO:3, a light chain CDR1 of SEQ ID NO:17, a light chain CDR2 of SEQ ID NO: 18, and a light chain CDR3 of SEQ ID NO: 19;

r. a heavy chain CDR1 of SEQ ID NO:7, a heavy chain CDR2 of SEQ ID NO:8, a heavy chain CDR3 of SEQ ID NO:9, a light chain CDR1 of SEQ ID NO:20, a light chain CDR2 of SEQ ID NO:18, and a light chain CDR3 of SEQ ID NO:16;

s. a heavy chain CDR1 of SEQ ID NO:33, a heavy chain CDR2 of SEQ ID NO:34, a heavy chain CDR3 of SEQ ID NO:35, a light chain CDR1 of SEQ ID NO:46, a light chain CDR2 of SEQ ID NO:47, and a light chain CDR3 of SEQ ID NO:48;

t. a heavy chain CDR1 of SEQ ID NO:36, a heavy chain CDR2 of SEQ ID NO:34, a heavy chain CDR3 of SEQ ID NO:35, a light chain CDR1 of SEQ ID NO:46, a light chain CDR2 of SEQ ID NO:47, and a light chain CDR3 of SEQ ID NO:48;

u. a heavy chain CDR1 of SEQ ID NO:37, a heavy chain CDR2 of SEQ ID NO:38, a heavy chain CDR3 of SEQ ID NO:35, a light chain CDR1 of SEQ ID NO:49, a light chain CDR2 of SEQ ID NO:50, and a light chain CDR3 of SEQ ID NO:51;

v. a heavy chain CDR1 of SEQ ID NO: 39, a heavy chain CDR2 of SEQ ID NO:40, a heavy chain CDR3 of SEQ ID NO:41, a light chain CDR1 of SEQ ID NO:52, a light chain CDR2 of SEQ ID NO:50, and a light chain CDR3 of SEQ ID NO:48;

w. a heavy chain CDR1 of SEQ ID NO:57, a heavy chain CDR2 of SEQ ID NO:58, a heavy chain CDR3 of SEQ ID NO:59, a light chain CDR1 of SEQ ID NO:68, a light chain CDR2 of SEQ ID NO:69, and a light chain CDR3 of SEQ ID NO:70;

x. a heavy chain CDR1 of SEQ ID NO:60, a heavy chain CDR2 of SEQ ID NO:58, a heavy chain CDR3 of SEQ ID NO:59, a light chain CDR1 of SEQ ID NO:68, a light chain CDR2 of SEQ ID NO:69, and a light chain CDR3 of SEQ ID NO:70;
y. a heavy chain CDR1 of SEQ ID NO:5, a heavy chain CDR2 of SEQ ID NO:61, a heavy chain CDR3 of SEQ ID NO:59, a light chain CDR1 of SEQ ID NO:71, a light chain CDR2 of SEQ ID NO:72, and a light chain CDR3 of SEQ ID NO:73;
z. a heavy chain CDR1 of SEQ ID NO:7, a heavy chain CDR2 of SEQ ID NO:62, a heavy chain CDR3 of SEQ ID NO:63, a light chain CDR1 of SEQ ID NO:74, a light chain CDR2 of SEQ ID NO:72, and a light chain CDR3 of SEQ ID NO:70;
aa. a heavy chain CDR1 of SEQ ID NO:79, a heavy chain CDR2 of SEQ ID NO:80, a heavy chain CDR3 of SEQ ID NO:81, a light chain CDR1 of SEQ ID NO:92, a light chain CDR2 of SEQ ID NO:93, and a light chain CDR3 of SEQ ID NO:94;
bb. a heavy chain CDR1 of SEQ ID NO:82, a heavy chain CDR2 of SEQ ID NO:80, a heavy chain CDR3 of SEQ ID NO:81, a light chain CDR1 of SEQ ID NO:92, a light chain CDR2 of SEQ ID NO:93, and a light chain CDR3 of SEQ ID NO:94;
cc. a heavy chain CDR1 of SEQ ID NO:83, a heavy chain CDR2 of SEQ ID NO:84, a heavy chain CDR3 of SEQ ID NO:81, a light chain CDR1 of SEQ ID NO:95, a light chain CDR2 of SEQ ID NO:96, and a light chain CDR3 of SEQ ID NO: 97;
dd. a heavy chain CDR1 of SEQ ID NO: 85, a heavy chain CDR2 of SEQ ID NO:86, a heavy chain CDR3 of SEQ ID NO:87, a light chain CDR1 of SEQ ID NO:98, a light chain CDR2 of SEQ ID NO:96, and a light chain CDR3 of SEQ ID NO:94;
ee. a heavy chain CDR1 of SEQ ID NO:103, a heavy chain CDR2 of SEQ ID NO:104, a heavy chain CDR3 of SEQ ID NO:105, a light chain CDR1 of SEQ ID NO: 116; a light chain CDR2 of SEQ ID NO:47; and a light chain CDR3 of SEQ ID NO:117;
ff. a heavy chain CDR1 of SEQ ID NO:106, a heavy chain CDR2 of SEQ ID NO:104, a heavy chain CDR3 of SEQ ID NO:105, a light chain CDR1 of SEQ ID NO: 116, a light chain CDR2 of SEQ ID NO:47, and a light chain CDR3 of SEQ ID NO:117;
gg. a heavy chain CDR1 of SEQ ID NO:107, a heavy chain CDR2 of SEQ ID NO:108, a heavy chain CDR3 of SEQ ID NO:105, a light chain CDR1 of SEQ ID NO:49, a light chain CDR2 of SEQ ID NO:50, and a light chain CDR3 of SEQ ID NO:118;
hh. a heavy chain CDR1 of SEQ ID NO:109, a heavy chain CDR2 of SEQ ID NO:110, a heavy chain CDR3 of SEQ ID NO:111, a light chain CDR1 of SEQ ID NO:52, a light chain CDR2 of SEQ ID NO:50, and a light chain CDR3 of SEQ ID NO:117;
ii. a heavy chain CDR1 of SEQ ID NO:123, a heavy chain CDR2 of SEQ ID NO:124, a heavy chain CDR3 of SEQ ID NO:125, a light chain CDR1 of SEQ ID NO:136, a light chain CDR2 of SEQ ID NO:137, and a light chain CDR3 of SEQ ID NO:138;
jj. a heavy chain CDR1 of SEQ ID NO:126, a heavy chain CDR2 of SEQ ID NO:124, a heavy chain CDR3 of SEQ ID NO:125, a light chain CDR1 of SEQ ID NO:136, a light chain CDR2 of SEQ ID NO:137, and a light chain CDR3 of SEQ ID NO:138;
kk. a heavy chain CDR1 of SEQ ID NO:127, a heavy chain CDR2 of SEQ ID NO:128, a heavy chain CDR3 of SEQ ID NO:125, a light chain CDR1 of SEQ ID NO:139, a light chain CDR2 of SEQ ID NO:140, and a light chain CDR3 of SEQ ID NO: 141;
ll. A heavy chain CDR1 of SEQ ID NO: 129, a heavy chain CDR2 of SEQ ID NO:130, a heavy chain CDR3 of SEQ ID NO:131, a light chain CDR1 of SEQ ID NO:142, a light chain CDR2 of SEQ ID NO:140, and a light chain CDR3 of SEQ ID NO:138;
mm. a heavy chain CDR1 of SEQ ID NO:123, a heavy chain CDR2 of SEQ ID NO:124, a heavy chain CDR3 of SEQ ID NO:147, a light chain CDR1 of SEQ ID NO:153, a light chain CDR2 of SEQ ID NO:154, and a light chain CDR3 of SEQ ID NO:155;
nn. a heavy chain CDR1 of SEQ ID NO:126, a heavy chain CDR2 of SEQ ID NO:124, a heavy chain CDR3 of SEQ ID NO:147, a light chain CDR1 of SEQ ID NO:153, a light chain CDR2 of SEQ ID NO: 154, and a light chain CDR3 of SEQ ID NO:155;
oo. a heavy chain CDR1 of SEQ ID NO:127, a heavy chain CDR2 of SEQ ID NO:128, a heavy chain CDR3 of SEQ ID NO:147, a light chain CDR1 of SEQ ID NO:156, a light chain CDR2 of SEQ ID NO:50, and a light chain CDR3 of SEQ ID NO:157;
pp. a heavy chain CDR1 of SEQ ID NO: 129, a heavy chain CDR2 of SEQ ID NO:130, a heavy chain CDR3 of SEQ ID NO:148, a light chain CDR1 of SEQ ID NO:158, a light chain CDR2 of SEQ ID NO:50, and a light chain CDR3 of SEQ ID NO:155;
qq. a heavy chain CDR1 of SEQ ID NO:103, a heavy chain CDR2 of SEQ ID NO:104, a heavy chain CDR3 of SEQ ID NO:163, a light chain CDR1 of SEQ ID NO: 116, a light chain CDR2 of SEQ ID NO:47, and a light chain CDR3 of SEQ ID NO:169;
rr. a heavy chain CDR1 of SEQ ID NO:106, a heavy chain CDR2 of SEQ ID NO:104, a heavy chain CDR3 of SEQ ID NO:163, a light chain CDR1 of SEQ ID NO:116, a light chain CDR2 of SEQ ID NO:47, and a light chain CDR3 of SEQ ID NO:169;
ss. a heavy chain CDR1 of SEQ ID NO:107, a heavy chain CDR2 of SEQ ID NO:108, a heavy chain CDR3 of SEQ ID NO:163, a light chain CDR1 of SEQ ID NO:49, a light chain CDR2 of SEQ ID NO:50, and a light chain CDR3 of SEQ ID NO:170;
tt. a heavy chain CDR1 of SEQ ID NO: 109, a heavy chain CDR2 of SEQ ID NO:110, a heavy chain CDR3 of SEQ ID NO:164, a light chain CDR1 of SEQ ID NO:52, a light chain CDR2 of SEQ ID NO:50, and a light chain CDR3 of SEQ ID NO:169;
uu. a heavy chain CDR1 of SEQ ID NO:175, a heavy chain CDR2 of SEQ ID NO:176, a heavy chain CDR3 of SEQ ID NO:177, a light chain CDR1 of SEQ ID NO:116, a light chain CDR2 of SEQ ID NO:47, and a light chain CDR3 of SEQ ID NO:188;
vv. a heavy chain CDR1 of SEQ ID NO:178, a heavy chain CDR2 of SEQ ID NO:176, a heavy chain CDR3 of SEQ ID NO:177, a light chain CDR1 of SEQ ID NO:116, a light chain CDR2 of SEQ ID NO:47, and a light chain CDR3 of SEQ ID NO:188;
ww. a heavy chain CDR1 of SEQ ID NO:179, a heavy chain CDR2 of SEQ ID NO:180, a heavy chain CDR3 of SEQ ID NO:177, a light chain CDR1 of SEQ ID NO:49, a light chain CDR2 of SEQ ID NO:50, and a light chain CDR3 of SEQ ID NO:189;
xx. a heavy chain CDR1 of SEQ ID NO: 181, a heavy chain CDR2 of SEQ ID NO:182; a heavy chain CDR3 of SEQ ID NO:183, a light chain CDR1 of SEQ ID NO:52, a light chain CDR2 of SEQ ID NO:50, and a light chain CDR3 of SEQ ID NO:188;

yy. a heavy chain CDR1 of SEQ ID NO: 103, a heavy chain CDR2 of SEQ ID NO: 104, a heavy chain CDR3 of SEQ ID NO:194, a light chain CDR1 of SEQ ID NO: 116, a light chain CDR2 of SEQ ID NO: 47, and a light chain CDR3 of SEQ ID NO:200;

zz. a heavy chain CDR1 of SEQ ID NO: 106, a heavy chain CDR2 of SEQ ID NO: 104, a heavy chain CDR3 of SEQ ID NO:194, a light chain CDR1 of SEQ ID NO: 116, a light chain CDR2 of SEQ ID NO: 47, and a light chain CDR3 of SEQ ID NO:200;

aaa. a heavy chain CDR1 of SEQ ID NO: 107, a heavy chain CDR2 of SEQ ID NO: 108, a heavy chain CDR3 of SEQ ID NO:194, a light chain CDR1 of SEQ ID NO: 49, a light chain CDR2 of SEQ ID NO: 50, and a light chain CDR3 of SEQ ID NO: 201;

bbb. a heavy chain CDR1 of SEQ ID NO: 109, a heavy chain CDR2 of SEQ ID NO: 110, a heavy chain CDR3 of SEQ ID NO:195, a light chain CDR1 of SEQ ID NO: 52, a light chain CDR2 of SEQ ID NO: 50, and a light chain CDR3 of SEQ ID NO:200;

ccc. a heavy chain CDR1 of SEQ ID NO:206, a heavy chain CDR2 of SEQ ID NO:207, a heavy chain CDR3 of SEQ ID NO:208, a light chain CDR1 of SEQ ID NO:153, a light chain CDR2 of SEQ ID NO:154, and a light chain CDR3 of SEQ ID NO:219;

ddd. a heavy chain CDR1 of SEQ ID NO:209, a heavy chain CDR2 of SEQ ID NO:207, a heavy chain CDR3 of SEQ ID NO:208, a light chain CDR1 of SEQ ID NO:153, a light chain CDR2 of SEQ ID NO: 154, and a light chain CDR3 of SEQ ID NO:219;

eee. a heavy chain CDR1 of SEQ ID NO:210, a heavy chain CDR2 of SEQ ID NO:211, a heavy chain CDR3 of SEQ ID NO:208, a light chain CDR1 of SEQ ID NO:156, a light chain CDR2 of SEQ ID NO:50, and a light chain CDR3 of SEQ ID NO:220;

fff. a heavy chain CDR1 of SEQ ID NO: 212, a heavy chain CDR2 of SEQ ID NO:213, a heavy chain CDR3 of SEQ ID NO:214, a light chain CDR1 of SEQ ID NO:158, a light chain CDR2 of SEQ ID NO:50, and a light chain CDR3 of SEQ ID NO:219;

ggg. a heavy chain CDR1 of SEQ ID NO: 206, a heavy chain CDR2 of SEQ ID NO: 207, a heavy chain CDR3 of SEQ ID NO:225, a light chain CDR1 of SEQ ID NO:136, a light chain CDR2 of SEQ ID NO:137, and a light chain CDR3 of SEQ ID NO:231;

hhh. a heavy chain CDR1 of SEQ ID NO: 209, a heavy chain CDR2 of SEQ ID NO: 207, a heavy chain CDR3 of SEQ ID NO:225, a light chain CDR1 of SEQ ID NO:136, a light chain CDR2 of SEQ ID NO:137, and a light chain CDR3 of SEQ ID NO:231;

iii. a heavy chain CDR1 of SEQ ID NO: 210, a heavy chain CDR2 of SEQ ID NO: 211, a heavy chain CDR3 of SEQ ID NO:225, a light chain CDR1 of SEQ ID NO:139, a light chain CDR2 of SEQ ID NO:140, and a light chain CDR3 of SEQ ID NO: 232;

jjj. a heavy chain CDR1 of SEQ ID NO: 212, a heavy chain CDR2 of SEQ ID NO: 213, a heavy chain CDR3 of SEQ ID NO: 226, a light chain CDR1 of SEQ ID NO:142; a light chain CDR2 of SEQ ID NO: 140; and a light chain CDR3 of SEQ ID NO:231;

kkk. a heavy chain variable region that comprises a heavy chain CDR1 of SEQ ID NO: 206, a heavy chain CDR2 of SEQ ID NO: 207, and a heavy chain CDR3 of SEQ ID NO:237, and a light chain variable region that comprises a light chain CDR1 of SEQ ID NO:243, a light chain CDR2 of SEQ ID NO:47, and a light chain CDR3 of SEQ ID NO:244;

lll. a heavy chain variable region that comprises a heavy chain CDR1 of SEQ ID NO: 209, a heavy chain CDR2 of SEQ ID NO: 207, and a heavy chain CDR3 of SEQ ID NO:237, and a light chain variable region that comprises a light chain CDR1 of SEQ ID NO:243, a light chain CDR2 of SEQ ID NO:47, and a light chain CDR3 of SEQ ID NO:244;

mmm. a heavy chain variable region that comprises a heavy chain CDR1 of SEQ ID NO: 210, a heavy chain CDR2 of SEQ ID NO: 211, and a heavy chain CDR3 of SEQ ID NO:237, and a light chain variable region that comprises a light chain CDR1 of SEQ ID NO:245, a light chain CDR2 of SEQ ID NO:50, and a light chain CDR3 of SEQ ID NO:246;

nnn. a heavy chain variable region that comprises a heavy chain CDR1 of SEQ ID NO: 212, a heavy chain CDR2 of SEQ ID NO: 213, and a heavy chain CDR3 of SEQ ID NO:238; and a light chain variable region that comprises a light chain CDR1 of SEQ ID NO:247, a light chain CDR2 of SEQ ID NO: 50, and a light chain CDR3 of SEQ ID NO:244;

ooo. a heavy chain variable region that comprises a heavy chain CDR1 of SEQ ID NO: 206, a heavy chain CDR2 of SEQ ID NO: 207, and a heavy chain CDR3 of SEQ ID NO:252, and a light chain variable region that comprises a light chain CDR1 of SEQ ID NO:153, a light chain CDR2 of SEQ ID NO: 154, and a light chain CDR3 of SEQ ID NO:258;

ppp. a heavy chain variable region that comprises a heavy chain CDR1 of SEQ ID NO: 209, a heavy chain CDR2 of SEQ ID NO: 207, and a heavy chain CDR3 of SEQ ID NO:252, and a light chain variable region that comprises a light chain CDR1 of SEQ ID NO:153, a light chain CDR2 of SEQ ID NO:154, and a light chain CDR3 of SEQ ID NO:258;

qqq. a heavy chain variable region that comprises a heavy chain CDR1 of SEQ ID NO: 210, a heavy chain CDR2 of SEQ ID NO: 211, and a heavy chain CDR3 of SEQ ID NO:252, and a light chain variable region that comprises a light chain CDR1 of SEQ ID NO:156, a light chain CDR2 of SEQ ID NO:50, and a light chain CDR3 of SEQ ID NO:259; or rrr. a heavy chain variable region that comprises a heavy chain CDR1 of SEQ ID NO: 212, a heavy chain CDR2 of SEQ ID NO: 213, and a heavy chain CDR3 of SEQ ID NO: 253; and a light chain variable region that comprises a light chain CDR1 of SEQ ID NO:158, a light chain CDR2 of SEQ ID NO:50, and a light chain CDR3 of SEQ ID NO:258.

2. The antibody or antigen binding fragment thereof of claim 1 comprising:

a. A heavy chain variable region (VH) comprising the amino acid sequence of SEQ ID NO:10, and a light chain variable region (VL) comprising the amino acid sequence of SEQ ID NO:21;

b. A heavy chain variable region (VH) comprising the amino acid sequence of SEQ ID NO:10, and a light chain variable region (VL) comprising the amino acid sequence of SEQ ID NO:25;

c. A heavy chain variable region (VH) comprising the amino acid sequence of SEQ ID NO:10, and a light chain variable region (VL) comprising the amino acid sequence of SEQ ID NO:29;

d. A heavy chain variable region (VH) comprising the amino acid sequence of SEQ ID NO:42, and a light chain variable region (VL) comprising the amino acid sequence of SEQ ID NO:53;

e. A heavy chain variable region (VH) comprising the amino acid sequence of SEQ ID NO:64, and a light chain variable region (VL) comprising the amino acid sequence of SEQ ID NO:75;
f. A heavy chain variable region (VH) comprising the amino acid sequence of SEQ ID NO:88, and a light chain variable region (VL) comprising the amino acid sequence of SEQ ID NO:99;
g. A heavy chain variable region (VH) comprising the amino acid sequence of SEQ ID NO:112, and a light chain variable region (VL) comprising the amino acid sequence of SEQ ID NO:119;
h. A heavy chain variable region (VH) comprising the amino acid sequence of SEQ ID NO:132, and a light chain variable region (VL) comprising the amino acid sequence of SEQ ID NO:143;
i. A heavy chain variable region (VH) comprising the amino acid sequence of SEQ ID NO:149, and a light chain variable region (VL) comprising the amino acid sequence of SEQ ID NO:159;
j. A heavy chain variable region (VH) comprising the amino acid sequence of SEQ ID NO:165, and a light chain variable region (VL) comprising the amino acid sequence of SEQ ID NO:171;
k. A heavy chain variable region (VH) comprising the amino acid sequence of SEQ ID NO:184, and a light chain variable region (VL) comprising the amino acid sequence of SEQ ID NO:190;
l. A heavy chain variable region (VH) comprising the amino acid sequence of SEQ ID NO:196, and a light chain variable region (VL) comprising the amino acid sequence of SEQ ID NO:202;
m. A heavy chain variable region (VH) comprising the amino acid sequence of SEQ ID NO:215, and a light chain variable region (VL) comprising the amino acid sequence of SEQ ID NO:221;
n. A heavy chain variable region (VH) comprising the amino acid sequence of SEQ ID NO:227, and a light chain variable region (VL) comprising the amino acid sequence of SEQ ID NO:233;
o. A heavy chain variable region (VH) comprising the amino acid sequence of SEQ ID NO:239, and a light chain variable region (VL) comprising the amino acid sequence of SEQ ID NO:248; or
p. A heavy chain variable region (VH) comprising the amino acid sequence of SEQ ID NO:254, and a light chain variable region (VL) comprising the amino acid sequence of SEQ ID NO:260.

3. The antibody or antigen binding fragment thereof of claim 1 comprising:
a. A heavy chain comprising the amino acid sequence of SEQ ID NO:12, and a light chain comprising the amino acid sequence of SEQ ID NO:23;
b. A heavy chain comprising the amino acid sequence of SEQ ID NO:12, and a light chain comprising the amino acid sequence of SEQ ID NO:27;
c. A heavy chain comprising the amino acid sequence of SEQ ID NO:12, and a light chain comprising the amino acid sequence of SEQ ID NO:31;
d. A heavy chain comprising the amino acid sequence of SEQ ID NO:44, and a light chain comprising the amino acid sequence of SEQ ID NO:55;
e. A heavy chain comprising the amino acid sequence of SEQ ID NO:66, and a light chain comprising the amino acid sequence of SEQ ID NO:77;
f. A heavy chain comprising the amino acid sequence of SEQ ID NO:90, and a light chain comprising the amino acid sequence of SEQ ID NO:101;
g. A heavy chain comprising the amino acid sequence of SEQ ID NO:114, and a light chain comprising the amino acid sequence of SEQ ID NO:121;
h. A heavy chain comprising the amino acid sequence of SEQ ID NO:134, and a light chain comprising the amino acid sequence of SEQ ID NO:145;
i. A heavy chain comprising the amino acid sequence of SEQ ID NO:151, and a light chain comprising the amino acid sequence of SEQ ID NO:161;
j. A heavy chain comprising the amino acid sequence of SEQ ID NO:167, and a light chain comprising the amino acid sequence of SEQ ID NO:173;
k. A heavy chain comprising the amino acid sequence of SEQ ID NO:186, and a light chain comprising the amino acid sequence of SEQ ID NO:192;
l. A heavy chain comprising the amino acid sequence of SEQ ID NO:198, and a light chain comprising the amino acid sequence of SEQ ID NO:204;
m. A heavy chain comprising the amino acid sequence of SEQ ID NO:217, and a light chain comprising the amino acid sequence of SEQ ID NO:223;
n. A heavy chain comprising the amino acid sequence of SEQ ID NO:229, and a light chain comprising the amino acid sequence of SEQ ID NO:235;
o. A heavy chain comprising the amino acid sequence of SEQ ID NO:241, and a light chain comprising the amino acid sequence of SEQ ID NO:250; or
p. A heavy chain comprising the amino acid sequence of SEQ ID NO:256, and a light chain comprising the amino acid sequence of SEQ ID NO:262.

4. The antibody or antigen binding fragment thereof of claim 1, wherein the antibody or antigen binding fragment thereof comprises one or more cysteine substitutions.

5. The antibody or antigen binding fragment thereof of claim 4, wherein the antibody or antigen binding fragment thereof comprises one or more cysteine substitutions selected from E152C, S375C, or both E152C and S375C of the heavy chain of the antibody or antigen binding fragment thereof, wherein the position is numbered according to the EU system.

6. The antibody or antigen binding fragment thereof of claim 1, wherein said antibody is a monoclonal antibody.

7. A pharmaceutical composition comprising the antibody, or antigen binding fragment thereof, of claim 1 and a pharmaceutically acceptable carrier.

8. A nucleic acid that encodes the antibody or antigen binding fragment of claim 1.

9. The nucleic acid of claim 8, wherein the nucleic acid comprises the nucleotide sequence of SEQ ID NOs: 13, 24, 28, 32, 45, 56, 67, 78, 91, 102, 115, 122, 135, 146, 152, 162, 168, 174, 187, 193, 199, 205, 218, 224, 230, 236, 242, 251, 257, or 263.

10. A vector comprising the nucleic acid of claim 8.

11. A host cell comprising the nucleic acid of claim 8.

12. A process for producing an antibody or antigen binding fragment comprising cultivating the host cell of claim 11 and recovering the antibody from cell culture.

13. The process of claim 12 wherein recovering the antibody from cell culture comprises the steps of:
a) removing cells and filtering the culture;
b) purifying the culture by affinity chromatography;
c) inactivating any viruses in the culture by adjusting the pH to 3.4-3.6, then readjusting the pH to 5.8-6.2 and filtering the culture;

d) purifying the culture by cation exchange chromatography and performing on-column reduction of the culture;
e) performing anion exchange chromatography on the culture;
f) removing viruses by nanofiltration;
g) filtering the culture containing the antibody; and
h) obtaining purified antibody.

14. A diagnostic reagent comprising the antibody or antigen binding fragment thereof of claim 1.

15. The diagnostic reagent of claim 14, wherein the antibody or antigen binding fragment thereof is labeled with a radiolabel, a fluorophore, a chromophore, an imaging agent, or a metal ion.

16. An antibody drug conjugate comprising the formula (C)

$$Ab\text{-}(L_A\text{-}(D)_n)_y \qquad (C)$$

wherein:
D is a GNAQ inhibitor, a GNA11 inhibitor or an inhibitor of GNAQ and GNA11;
Ab is an antibody or antigen binding fragment thereof that binds to human PMEL17 protein;
$L_A$ is a linker;
n is 1, 2, 3 or 4, and
y is 1, 2, 3 or 4,
wherein the antibody or antigen binding fragment thereof comprises:

a. a heavy chain variable region that comprises a heavy chain CDR1 (Complementarity Determining Region 1) of SEQ ID NO:1, 4, 5 or 7, a heavy chain CDR2 (Complementarity Determining Region 2) of SEQ ID NO:2, 6 or 8, and a heavy chain CDR3 (Complementarity Determining Region 3) of SEQ ID NO:3 or 9; and a light chain variable region that comprises a light chain CDR1 (Complementarity Determining Region 1) of SEQ ID NO:14, 17 or 20, a light chain CDR2 (Complementarity Determining Region 2) of SEQ ID NO:15 or 18, and a light chain CDR3 (Complementarity Determining Region 3) of SEQ ID NO:16 or 19;

b. a heavy chain variable region that comprises a heavy chain CDR1 of SEQ ID NO:33, 36, 37 or 39, a heavy chain CDR2 of SEQ ID NO:34, 38 or 40; a heavy chain CDR3 of SEQ ID NO:35 or 41; and a light chain variable region that comprises a light chain CDR1 of SEQ ID NO:46, 49 or 52; a light chain CDR2 of SEQ ID NO:47 or 50; and a light chain CDR3 of SEQ ID NO:48 or 51;

c. a heavy chain variable region that comprises a heavy chain CDR1 of SEQ ID NO:5, 7, 57 or 60, a heavy chain CDR2 of SEQ ID NO:58, 61 or 62; a heavy chain CDR3 of SEQ ID NO:59 or 63; and a light chain variable region that comprises a light chain CDR1 of SEQ ID NO:68, 71 or 74; a light chain CDR2 of SEQ ID NO:69 or 72; and a light chain CDR3 of SEQ ID NO:70 or 73;

d. a heavy chain variable region that comprises a heavy chain CDR1 of SEQ ID NO:79, 82, 83 or 85, a heavy chain CDR2 of SEQ ID NO:80, 84 or 86; a heavy chain CDR3 of SEQ ID NO:81 or 87; and a light chain variable region that comprises a light chain CDR1 of SEQ ID NO:92, 95 or 98; a light chain CDR2 of SEQ ID NO:93 or 96; and a light chain CDR3 of SEQ ID NO:94 or 97;

e. a heavy chain variable region that comprises a heavy chain CDR1 of SEQ ID NO:103, 106, 107 or 109, a heavy chain CDR2 of SEQ ID NO:104, 108 or 110; a heavy chain CDR3 of SEQ ID NO:105 or 111; and a light chain variable region that comprises a light chain CDR1 of SEQ ID NO:49, 52 or 116; a light chain CDR2 of SEQ ID NO:47 or 50; and a light chain CDR3 of SEQ ID NO:117 or 118;

f. a heavy chain variable region that comprises a heavy chain CDR1 of SEQ ID NO:123, 126, 127 or 129, a heavy chain CDR2 of SEQ ID NO:124, 128 or 130; a heavy chain CDR3 of SEQ ID NO:125 or 131; and a light chain variable region that comprises a light chain CDR1 of SEQ ID NO:136, 139 or 142; a light chain CDR2 of SEQ ID NO:137 or 140; and a light chain CDR3 of SEQ ID NO:138 or 141;

g. a heavy chain variable region that comprises a heavy chain CDR1 of SEQ ID NO:123, 126, 127 or 129, a heavy chain CDR2 of SEQ ID NO:124, 128 or 130; a heavy chain CDR3 of SEQ ID NO:147 or 148; and a light chain variable region that comprises a light chain CDR1 of SEQ ID NO:153, 156 or 158; a light chain CDR2 of SEQ ID NO:50 or 154; and a light chain CDR3 of SEQ ID NO:155 or 157;

h. a heavy chain variable region that comprises a heavy chain CDR1 of SEQ ID NO:103, 106, 107 or 109, a heavy chain CDR2 of SEQ ID NO:104, 108 or 110; a heavy chain CDR3 of SEQ ID NO:163 or 164; and a light chain variable region that comprises a light chain CDR1 of SEQ ID NO:49, 52 or 116; a light chain CDR2 of SEQ ID NO:47 or 50; and a light chain CDR3 of SEQ ID NO:169 or 170;

i. a heavy chain variable region that comprises a heavy chain CDR1 of SEQ ID NO:175, 178, 179 or 181, a heavy chain CDR2 of SEQ ID NO:176, 180 or 182; a heavy chain CDR3 of SEQ ID NO:177 or 183; and a light chain variable region that comprises a light chain CDR1 of SEQ ID NO:49, 52 or 116; a light chain CDR2 of SEQ ID NO:47 or 50; and a light chain CDR3 of SEQ ID NO:188 or 189;

j. a heavy chain variable region that comprises a heavy chain CDR1 of SEQ ID NO: 103, 106, 107 or 109, a heavy chain CDR2 of SEQ ID NO: 104, 108 or 110; a heavy chain CDR3 of SEQ ID NO:194 or 195; and a light chain variable region that comprises a light chain CDR1 of SEQ ID NO: 49, 52 or 116; a light chain CDR2 of SEQ ID NO: 47 or 50; and a light chain CDR3 of SEQ ID NO:200 or 201;

k. a heavy chain variable region that comprises a heavy chain CDR1 of SEQ ID NO:206, 209, 210 or 212, a heavy chain CDR2 of SEQ ID NO:207, 211 or 213; a heavy chain CDR3 of SEQ ID NO:208 or 214; and a light chain variable region that comprises a light chain CDR1 of SEQ ID NO:153, 156 or 158; a light chain CDR2 of SEQ ID NO:50 or 154; and a light chain CDR3 of SEQ ID NO:219 or 220;

l. A heavy chain variable region that comprises a heavy chain CDR1 of SEQ ID NO: 206, 209, 210 or 212, a heavy chain CDR2 of SEQ ID NO: 207, 211 or 213; a heavy chain CDR3 of SEQ ID NO:225 or 226; and a light chain variable region that comprises a light chain CDR1 of SEQ ID NO:136, 139 or 142; a light chain CDR2 of SEQ ID NO:137 or 140; and a light chain CDR3 of SEQ ID NO:231 or 232;

m. a heavy chain variable region that comprises a heavy chain CDR1 of SEQ ID NO: 206, 209, 210 or 212, a heavy chain CDR2 of SEQ ID NO: 207, 211 or 213, and a heavy chain CDR3 of SEQ ID NO:237 or 238; and a light chain variable region that comprises a light chain CDR1 of SEQ ID NO:243, 245 or 247, a light chain CDR2 of SEQ ID NO:47 or 50, and a light chain CDR3 of SEQ ID NO:244 or 246;
n. a heavy chain variable region that comprises a heavy chain CDR1 of SEQ ID NO: 206, 209, 210 or 212, a heavy chain CDR2 of SEQ ID NO: 207, 211 or 213, and a heavy chain CDR3 of SEQ ID NO:252 or 253; and a light chain variable region that comprises a light chain CDR1 of SEQ ID NO:153, 156 or 158, a light chain CDR2 of SEQ ID NO:50 or 154, and a light chain CDR3 of SEQ ID NO:258 or 259;
o. a heavy chain CDR1 of SEQ ID NO:1, a heavy chain CDR2 of SEQ ID NO:2, a heavy chain CDR3 of SEQ ID NO:3, a light chain CDR1 of SEQ ID NO:14, a light chain CDR2 of SEQ ID NO:15, and a light chain CDR3 of SEQ ID NO:16;
p. a heavy chain CDR1 of SEQ ID NO: 4, a heavy chain CDR2 of SEQ ID NO:2, a heavy chain CDR3 of SEQ ID NO:3, a light chain CDR1 of SEQ ID NO:14, a light chain CDR2 of SEQ ID NO:15, and a light chain CDR3 of SEQ ID NO:16;
q. a heavy chain CDR1 of SEQ ID NO:5, a heavy chain CDR2 of SEQ ID NO:6, a heavy chain CDR3 of SEQ ID NO:3, a light chain CDR1 of SEQ ID NO:17, a light chain CDR2 of SEQ ID NO: 18, and a light chain CDR3 of SEQ ID NO: 19;
r. a heavy chain CDR1 of SEQ ID NO:7, a heavy chain CDR2 of SEQ ID NO:8, a heavy chain CDR3 of SEQ ID NO:9, a light chain CDR1 of SEQ ID NO:20, a light chain CDR2 of SEQ ID NO:18, and a light chain CDR3 of SEQ ID NO:16;
s. a heavy chain CDR1 of SEQ ID NO:33, a heavy chain CDR2 of SEQ ID NO:34, a heavy chain CDR3 of SEQ ID NO:35, a light chain CDR1 of SEQ ID NO:46, a light chain CDR2 of SEQ ID NO:47, and a light chain CDR3 of SEQ ID NO:48;
t. a heavy chain CDR1 of SEQ ID NO:36, a heavy chain CDR2 of SEQ ID NO:34, a heavy chain CDR3 of SEQ ID NO:35, a light chain CDR1 of SEQ ID NO:46, a light chain CDR2 of SEQ ID NO:47, and a light chain CDR3 of SEQ ID NO:48;
u. a heavy chain CDR1 of SEQ ID NO:37, a heavy chain CDR2 of SEQ ID NO:38, a heavy chain CDR3 of SEQ ID NO:35, a light chain CDR1 of SEQ ID NO:49, a light chain CDR2 of SEQ ID NO:50, and a light chain CDR3 of SEQ ID NO:51;
v. a heavy chain CDR1 of SEQ ID NO: 39, a heavy chain CDR2 of SEQ ID NO:40, a heavy chain CDR3 of SEQ ID NO:41, a light chain CDR1 of SEQ ID NO:52, a light chain CDR2 of SEQ ID NO:50, and a light chain CDR3 of SEQ ID NO:48;
w. a heavy chain CDR1 of SEQ ID NO:57, a heavy chain CDR2 of SEQ ID NO:58, a heavy chain CDR3 of SEQ ID NO:59, a light chain CDR1 of SEQ ID NO:68, a light chain CDR2 of SEQ ID NO:69, and a light chain CDR3 of SEQ ID NO:70;
x. a heavy chain CDR1 of SEQ ID NO:60, a heavy chain CDR2 of SEQ ID NO:58, a heavy chain CDR3 of SEQ ID NO:59, a light chain CDR1 of SEQ ID NO:68, a light chain CDR2 of SEQ ID NO:69, and a light chain CDR3 of SEQ ID NO:70;
y. a heavy chain CDR1 of SEQ ID NO:5, a heavy chain CDR2 of SEQ ID NO:61, a heavy chain CDR3 of SEQ ID NO:59, a light chain CDR1 of SEQ ID NO:71, a light chain CDR2 of SEQ ID NO:72, and a light chain CDR3 of SEQ ID NO:73;
z. a heavy chain CDR1 of SEQ ID NO:7, a heavy chain CDR2 of SEQ ID NO:62, a heavy chain CDR3 of SEQ ID NO:63, a light chain CDR1 of SEQ ID NO:74, a light chain CDR2 of SEQ ID NO:72, and a light chain CDR3 of SEQ ID NO:70;
aa. a heavy chain CDR1 of SEQ ID NO:79, a heavy chain CDR2 of SEQ ID NO:80, a heavy chain CDR3 of SEQ ID NO:81, a light chain CDR1 of SEQ ID NO:92, a light chain CDR2 of SEQ ID NO:93, and a light chain CDR3 of SEQ ID NO:94;
bb. a heavy chain CDR1 of SEQ ID NO:82, a heavy chain CDR2 of SEQ ID NO:80, a heavy chain CDR3 of SEQ ID NO:81, a light chain CDR1 of SEQ ID NO:92, a light chain CDR2 of SEQ ID NO:93, and a light chain CDR3 of SEQ ID NO:94;
cc. a heavy chain CDR1 of SEQ ID NO:83, a heavy chain CDR2 of SEQ ID NO:84, a heavy chain CDR3 of SEQ ID NO:81, a light chain CDR1 of SEQ ID NO:95, a light chain CDR2 of SEQ ID NO:96, and a light chain CDR3 of SEQ ID NO: 97;
dd. a heavy chain CDR1 of SEQ ID NO: 85, a heavy chain CDR2 of SEQ ID NO:86, a heavy chain CDR3 of SEQ ID NO:87, a light chain CDR1 of SEQ ID NO:98, a light chain CDR2 of SEQ ID NO:96, and a light chain CDR3 of SEQ ID NO:94;
ee. a heavy chain CDR1 of SEQ ID NO:103, a heavy chain CDR2 of SEQ ID NO:104, a heavy chain CDR3 of SEQ ID NO:105, a light chain CDR1 of SEQ ID NO: 116; a light chain CDR2 of SEQ ID NO:47; and a light chain CDR3 of SEQ ID NO:117;
ff. a heavy chain CDR1 of SEQ ID NO:106, a heavy chain CDR2 of SEQ ID NO:104, a heavy chain CDR3 of SEQ ID NO:105, a light chain CDR1 of SEQ ID NO: 116, a light chain CDR2 of SEQ ID NO:47, and a light chain CDR3 of SEQ ID NO:117;
gg. a heavy chain CDR1 of SEQ ID NO:107, a heavy chain CDR2 of SEQ ID NO:108, a heavy chain CDR3 of SEQ ID NO:105, a light chain CDR1 of SEQ ID NO:49, a light chain CDR2 of SEQ ID NO:50, and a light chain CDR3 of SEQ ID NO:118;
hh. a heavy chain CDR1 of SEQ ID NO:109, a heavy chain CDR2 of SEQ ID NO:110, a heavy chain CDR3 of SEQ ID NO:111, a light chain CDR1 of SEQ ID NO:52, a light chain CDR2 of SEQ ID NO:50, and a light chain CDR3 of SEQ ID NO:117;
ii. a heavy chain CDR1 of SEQ ID NO:123, a heavy chain CDR2 of SEQ ID NO:124, a heavy chain CDR3 of SEQ ID NO:125, a light chain CDR1 of SEQ ID NO:136, a light chain CDR2 of SEQ ID NO:137, and a light chain CDR3 of SEQ ID NO:138;
jj. a heavy chain CDR1 of SEQ ID NO:126, a heavy chain CDR2 of SEQ ID NO:124, a heavy chain CDR3 of SEQ ID NO:125, a light chain CDR1 of SEQ ID NO:136, a light chain CDR2 of SEQ ID NO:137, and a light chain CDR3 of SEQ ID NO:138;
kk. a heavy chain CDR1 of SEQ ID NO:127, a heavy chain CDR2 of SEQ ID NO:128, a heavy chain CDR3 of SEQ ID NO:125, a light chain CDR1 of SEQ ID NO:139, a light chain CDR2 of SEQ ID NO:140, and a light chain CDR3 of SEQ ID NO: 141;
ll. A heavy chain CDR1 of SEQ ID NO: 129, a heavy chain CDR2 of SEQ ID NO:130, a heavy chain CDR3 of SEQ ID NO:131, a light chain CDR1 of SEQ ID NO:142, a light chain CDR2 of SEQ ID NO:140, and a light chain CDR3 of SEQ ID NO:138;
mm. a heavy chain CDR1 of SEQ ID NO:123, a heavy chain CDR2 of SEQ ID NO:124, a heavy chain CDR3 of SEQ ID NO:147, a light chain CDR1 of SEQ ID NO:153, a light chain CDR2 of SEQ ID NO:154, and a light chain CDR3 of SEQ ID NO:155;
nn. a heavy chain CDR1 of SEQ ID NO:126, a heavy chain CDR2 of SEQ ID NO:124, a heavy chain CDR3 of SEQ ID NO:147, a light chain CDR1 of SEQ ID NO:153, a light chain CDR2 of SEQ ID NO: 154, and a light chain CDR3 of SEQ ID NO:155;
oo. a heavy chain CDR1 of SEQ ID NO:127, a heavy chain CDR2 of SEQ ID NO:128, a heavy chain CDR3 of SEQ ID NO:147, a light chain CDR1 of SEQ ID NO:156, a light chain CDR2 of SEQ ID NO:50, and a light chain CDR3 of SEQ ID NO:157;
pp. a heavy chain CDR1 of SEQ ID NO: 129, a heavy chain CDR2 of SEQ ID NO:130, a heavy chain CDR3 of SEQ ID NO:148, a light chain CDR1 of SEQ ID NO:158, a light chain CDR2 of SEQ ID NO:50, and a light chain CDR3 of SEQ ID NO:155;
qq. a heavy chain CDR1 of SEQ ID NO:103, a heavy chain CDR2 of SEQ ID NO:104, a heavy chain CDR3 of SEQ ID NO:163, a light chain CDR1 of SEQ ID NO: 116, a light chain CDR2 of SEQ ID NO:47, and a light chain CDR3 of SEQ ID NO:169;
rr. a heavy chain CDR1 of SEQ ID NO:106, a heavy chain CDR2 of SEQ ID NO:104, a heavy chain CDR3 of SEQ ID NO:163, a light chain CDR1 of SEQ ID NO:116, a light chain CDR2 of SEQ ID NO:47, and a light chain CDR3 of SEQ ID NO:169;
ss. a heavy chain CDR1 of SEQ ID NO:107, a heavy chain CDR2 of SEQ ID NO:108, a heavy chain CDR3 of SEQ ID NO:163, a light chain CDR1 of SEQ ID NO:49, a light chain CDR2 of SEQ ID NO:50, and a light chain CDR3 of SEQ ID NO:170;
tt. a heavy chain CDR1 of SEQ ID NO: 109, a heavy chain CDR2 of SEQ ID NO:110, a heavy chain CDR3 of SEQ ID NO:164, a light chain CDR1 of SEQ ID NO:52, a light chain CDR2 of SEQ ID NO:50, and a light chain CDR3 of SEQ ID NO:169;
uu. a heavy chain CDR1 of SEQ ID NO:175, a heavy chain CDR2 of SEQ ID NO:176, a heavy chain CDR3 of SEQ ID NO:177, a light chain CDR1 of SEQ ID NO:116, a light chain CDR2 of SEQ ID NO:47, and a light chain CDR3 of SEQ ID NO:188;
vv. a heavy chain CDR1 of SEQ ID NO:178, a heavy chain CDR2 of SEQ ID NO:176, a heavy chain CDR3 of SEQ ID NO:177, a light chain CDR1 of SEQ ID NO:116, a light chain CDR2 of SEQ ID NO:47, and a light chain CDR3 of SEQ ID NO:188;
ww. a heavy chain CDR1 of SEQ ID NO:179, a heavy chain CDR2 of SEQ ID NO:180, a heavy chain CDR3 of SEQ ID NO:177, a light chain CDR1 of SEQ ID NO:49, a light chain CDR2 of SEQ ID NO:50, and a light chain CDR3 of SEQ ID NO:189;
xx. a heavy chain CDR1 of SEQ ID NO: 181, a heavy chain CDR2 of SEQ ID NO:182; a heavy chain CDR3 of SEQ ID NO:183, a light chain CDR1 of SEQ ID NO:52, a light chain CDR2 of SEQ ID NO:50, and a light chain CDR3 of SEQ ID NO:188;
yy. a heavy chain CDR1 of SEQ ID NO: 103, a heavy chain CDR2 of SEQ ID NO: 104, a heavy chain CDR3 of SEQ ID NO:194, a light chain CDR1 of SEQ ID NO: 116, a light chain CDR2 of SEQ ID NO: 47, and a light chain CDR3 of SEQ ID NO:200;
zz. a heavy chain CDR1 of SEQ ID NO: 106, a heavy chain CDR2 of SEQ ID NO: 104, a heavy chain CDR3 of SEQ ID NO:194, a light chain CDR1 of SEQ ID NO: 116, a light chain CDR2 of SEQ ID NO: 47, and a light chain CDR3 of SEQ ID NO:200;
aaa. a heavy chain CDR1 of SEQ ID NO: 107, a heavy chain CDR2 of SEQ ID NO: 108, a heavy chain CDR3 of SEQ ID NO:194, a light chain CDR1 of SEQ ID NO: 49, a light chain CDR2 of SEQ ID NO: 50, and a light chain CDR3 of SEQ ID NO: 201;
bbb. a heavy chain CDR1 of SEQ ID NO: 109, a heavy chain CDR2 of SEQ ID NO: 110, a heavy chain CDR3 of SEQ ID NO:195, a light chain CDR1 of SEQ ID NO: 52, a light chain CDR2 of SEQ ID NO: 50, and a light chain CDR3 of SEQ ID NO:200;
ccc. a heavy chain CDR1 of SEQ ID NO:206, a heavy chain CDR2 of SEQ ID NO:207, a heavy chain CDR3 of SEQ ID NO:208, a light chain CDR1 of SEQ ID NO:153, a light chain CDR2 of SEQ ID NO:154, and a light chain CDR3 of SEQ ID NO:219;
ddd. a heavy chain CDR1 of SEQ ID NO:209, a heavy chain CDR2 of SEQ ID NO:207, a heavy chain CDR3 of SEQ ID NO:208, a light chain CDR1 of SEQ ID NO:153, a light chain CDR2 of SEQ ID NO: 154, and a light chain CDR3 of SEQ ID NO:219;
eee. a heavy chain CDR1 of SEQ ID NO:210, a heavy chain CDR2 of SEQ ID NO:211, a heavy chain CDR3 of SEQ ID NO:208, a light chain CDR1 of SEQ ID NO:156, a light chain CDR2 of SEQ ID NO:50, and a light chain CDR3 of SEQ ID NO:220;
fff. a heavy chain CDR1 of SEQ ID NO: 212, a heavy chain CDR2 of SEQ ID NO:213, a heavy chain CDR3 of SEQ ID NO:214, a light chain CDR1 of SEQ ID NO:158, a light chain CDR2 of SEQ ID NO:50, and a light chain CDR3 of SEQ ID NO:219;
ggg. a heavy chain CDR1 of SEQ ID NO: 206, a heavy chain CDR2 of SEQ ID NO: 207, a heavy chain CDR3 of SEQ ID NO:225, a light chain CDR1 of SEQ ID NO:136, a light chain CDR2 of SEQ ID NO:137, and a light chain CDR3 of SEQ ID NO:231;
hhh. a heavy chain CDR1 of SEQ ID NO: 209, a heavy chain CDR2 of SEQ ID NO: 207, a heavy chain CDR3 of SEQ ID NO:225, a light chain CDR1 of SEQ ID NO:136, a light chain CDR2 of SEQ ID NO:137, and a light chain CDR3 of SEQ ID NO:231;
iii. a heavy chain CDR1 of SEQ ID NO: 210, a heavy chain CDR2 of SEQ ID NO: 211, a heavy chain CDR3 of SEQ ID NO:225, a light chain CDR1 of SEQ ID NO:139, a light chain CDR2 of SEQ ID NO:140, and a light chain CDR3 of SEQ ID NO: 232;

jjj. a heavy chain CDR1 of SEQ ID NO: 212, a heavy chain CDR2 of SEQ ID NO: 213, a heavy chain CDR3 of SEQ ID NO: 226, a light chain CDR1 of SEQ ID NO:142; a light chain CDR2 of SEQ ID NO: 140; and a light chain CDR3 of SEQ ID NO:231;

kkk. a heavy chain variable region that comprises a heavy chain CDR1 of SEQ ID NO: 206, a heavy chain CDR2 of SEQ ID NO: 207, and a heavy chain CDR3 of SEQ ID NO:237, and a light chain variable region that comprises a light chain CDR1 of SEQ ID NO:243, a light chain CDR2 of SEQ ID NO:47, and a light chain CDR3 of SEQ ID NO:244;

lll. a heavy chain variable region that comprises a heavy chain CDR1 of SEQ ID NO: 209, a heavy chain CDR2 of SEQ ID NO: 207, and a heavy chain CDR3 of SEQ ID NO:237, and a light chain variable region that comprises a light chain CDR1 of SEQ ID NO:243, a light chain CDR2 of SEQ ID NO:47, and a light chain CDR3 of SEQ ID NO:244;

mmm. a heavy chain variable region that comprises a heavy chain CDR1 of SEQ ID NO: 210, a heavy chain CDR2 of SEQ ID NO: 211, and a heavy chain CDR3 of SEQ ID NO:237, and a light chain variable region that comprises a light chain CDR1 of SEQ ID NO:245, a light chain CDR2 of SEQ ID NO:50, and a light chain CDR3 of SEQ ID NO:246;

nnn. a heavy chain variable region that comprises a heavy chain CDR1 of SEQ ID NO: 212, a heavy chain CDR2 of SEQ ID NO: 213, and a heavy chain CDR3 of SEQ ID NO:238; and a light chain variable region that comprises a light chain CDR1 of SEQ ID NO:247, a light chain CDR2 of SEQ ID NO: 50, and a light chain CDR3 of SEQ ID NO:244;

ooo. a heavy chain variable region that comprises a heavy chain CDR1 of SEQ ID NO: 206, a heavy chain CDR2 of SEQ ID NO: 207, and a heavy chain CDR3 of SEQ ID NO:252, and a light chain variable region that comprises a light chain CDR1 of SEQ ID NO:153, a light chain CDR2 of SEQ ID NO: 154, and a light chain CDR3 of SEQ ID NO:258;

ppp a heavy chain variable region that comprises a heavy chain CDR1 of SEQ ID NO: 209, a heavy chain CDR2 of SEQ ID NO: 207, and a heavy chain CDR3 of SEQ ID NO:252, and a light chain variable region that comprises a light chain CDR1 of SEQ ID NO:153, a light chain CDR2 of SEQ ID NO:154, and a light chain CDR3 of SEQ ID NO:258;

qqq. a heavy chain variable region that comprises a heavy chain CDR1 of SEQ ID NO: 210, a heavy chain CDR2 of SEQ ID NO: 211, and a heavy chain CDR3 of SEQ ID NO:252, and a light chain variable region that comprises a light chain CDR1 of SEQ ID NO:156, a light chain CDR2 of SEQ ID NO:50, and a light chain CDR3 of SEQ ID NO:259; or rrr. a heavy chain variable region that comprises a heavy chain CDR1 of SEQ ID NO: 212, a heavy chain CDR2 of SEQ ID NO: 213, and a heavy chain CDR3 of SEQ ID NO: 253; and a light chain variable region that comprises a light chain CDR1 of SEQ ID NO:158, a light chain CDR2 of SEQ ID NO:50, and a light chain CDR3 of SEQ ID NO:258.

17. The antibody drug conjugate of claim 16, wherein said n is 1.

18. The antibody drug conjugate of claim 16, wherein said y is 2.

19. The antibody drug conjugate of claim 16, wherein said linker is a cleavable linker or a non-cleavable linker.

20. The antibody drug conjugate of claim 19, wherein the linker comprises a ValCit peptide linker.

21. The antibody drug conjugate of claim 16, wherein D is an inhibitor of GNAQ and GNA11.

22. The antibody drug conjugate of claim 16, wherein D is

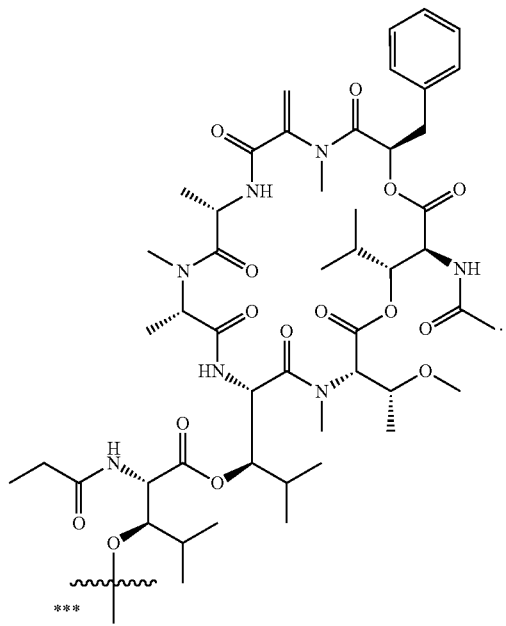 [SMILES: *O[C@H](C(C)C)[C@H](NC(=O)CC)C(=O)O[C@H](C(C)C)[C@@H]1NC(=O)[C@H](C)N(C)C(=O)[C@H](C)NC(=O)C(=C)N(C)C(=O)[C@@H](Cc2ccccc2)OC(=O)[C@@H](NC(C)=O)[C@@H](C(C)C)OC(=O)[C@H]([C@@H](C)OC)N(C)C1=O]

23. The antibody drug conjugate of claim 16, wherein D is

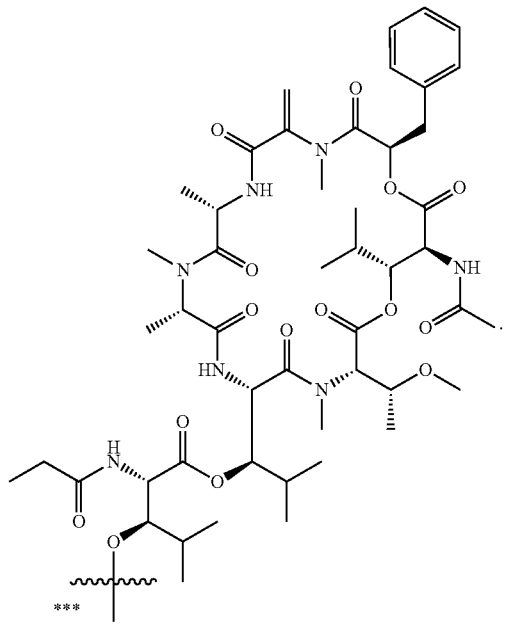 [SMILES: *O[C@H](C(C)C)[C@H](NC(=O)CC)C(=O)O[C@H](C(C)C)[C@@H]1NC(=O)[C@H](C)N(C)C(=O)[C@H](C)NC(=O)C(=C)N(C)C(=O)[C@@H](Cc2ccccc2)OC(=O)[C@@H](NC(C)=O)[C@@H](C(C)C)OC(=O)[C@H]([C@@H](C)OC)N(C)C1=O]

24. The antibody drug conjugate of claim 16 comprising the following structure,

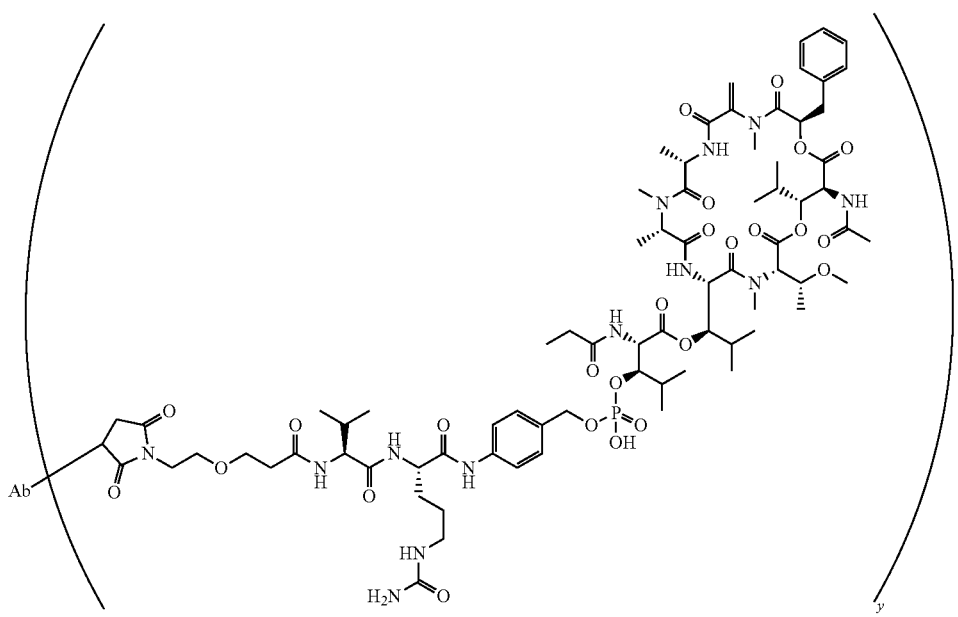
25. The antibody drug conjugate of claim 16 comprising the following structure,
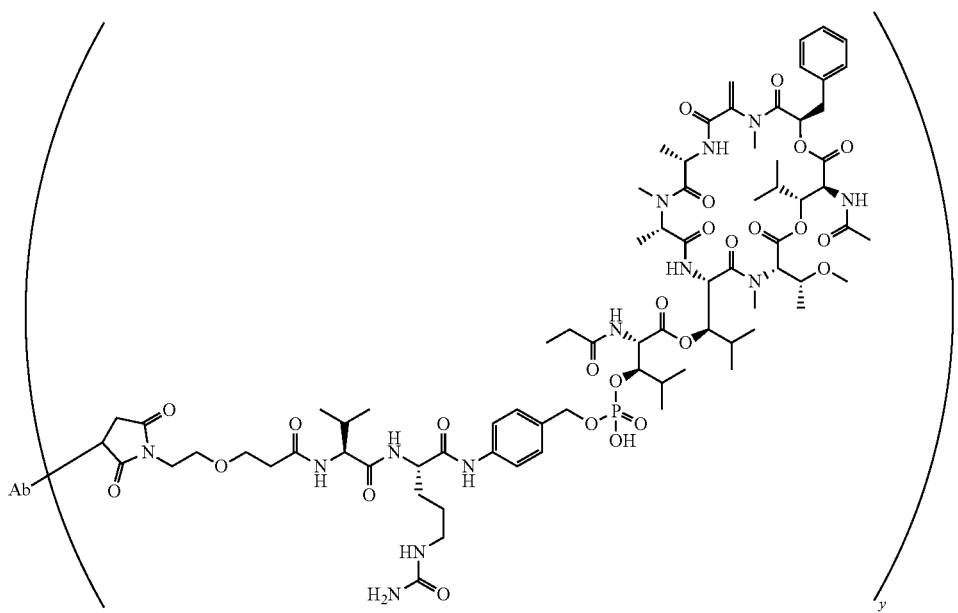
26. An antibody drug conjugate having the following Formula (C-2):

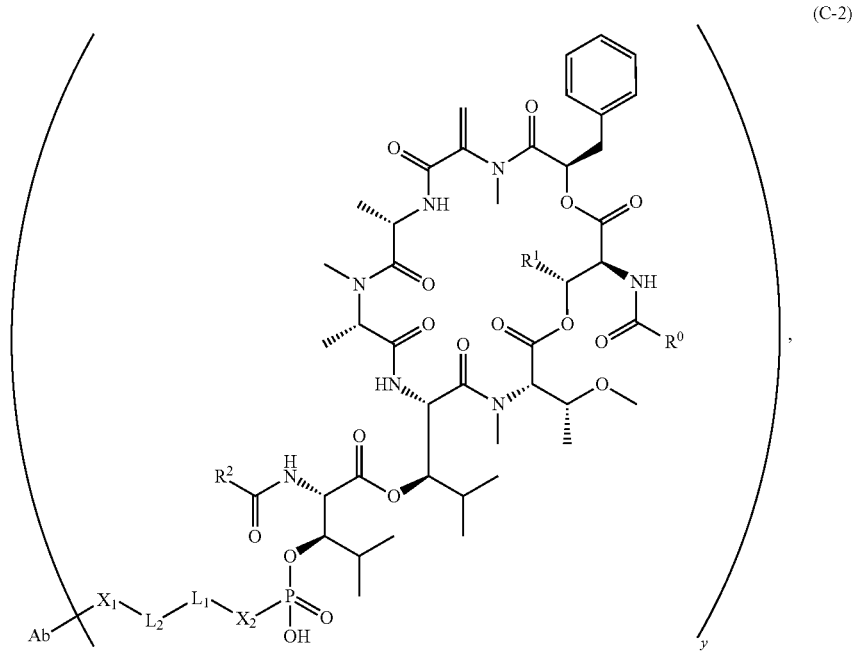

wherein:
R⁰ is methyl or ethyl;
R¹ is methyl or isopropyl;
R² is methyl or ethyl;
Ab is an antibody or antigen binding fragment thereof that binds to human PMEL17 protein of claim 1;
X₁ is a bivalent coupling group;
X₂ is a self-immolative spacer;
L₁ is a bivalent peptide linker;
L₂ is a bond or a linker, and
y is 1, 2, 3 or 4.

27. A pharmaceutical composition comprising the antibody drug conjugate of claim 16 and a pharmaceutically acceptable carrier.

28. A method of treating cancer in a patient in need thereof, comprising administering to said patient the antibody drug conjugate of claim 16, wherein the cancer expresses PMEL17, the cancer contains a mutation of the GNAQ or GNA11 gene, or the cancer expresses PMEL17 and contains a mutation of the GNAQ gene, the GNA11 gene, or both.

29. The method of claim 28, wherein the antibody drug conjugate is administered to the patient in combination with one or more additional therapeutic compounds.

30. The method of claim 29, wherein the one or more additional therapeutic compounds is selected from a standard of care chemotherapeutic, an MDM2 inhibitor, an MRC2 inhibitor, a PKC inhibitor, a MAPK inhibitor, a costimulatory molecule, or a checkpoint inhibitor.

31. The method of claim 30, wherein the costimulatory molecule is selected from an agonist of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, STING, or CD83 ligand.

32. The method of claim 30, wherein the checkpoint inhibitor is selected from an inhibitor of PD-1, PD-L1, PD-L2, CTLA4, TIM3, LAG3, VISTA, BTLA, TIGIT, LAIR1, CD160, 2B4 and/or TGFR beta.

33. The method of claim 28 wherein the cancer is uveal melanoma, subcutaneous melanoma, hepatocellular carcinoma, or a metastatic cancer thereof.

34. A method of treating cancer in a patient in need thereof, comprising administering to said patient the pharmaceutical composition of claim 27, wherein the cancer expresses PMEL17, the cancer contains a mutation of the GNAQ or GNA11 gene, or the cancer expresses PMEL17 and contains a mutation of the GNAQ gene, the GNA11 gene, or both.

35. The method of claim 34, wherein the pharmaceutical composition is administered to the patient in combination with one or more additional therapeutic compounds.

36. The method of claim 35, wherein the one or more additional therapeutic compounds is selected from a standard of care chemotherapeutic, an MDM2 inhibitor, an MRC2 inhibitor, a PKC inhibitor, a MAPK inhibitor, a costimulatory molecule, or a checkpoint inhibitor.

37. The method of claim 36, wherein the costimulatory molecule is selected from an agonist of OX40, CO2, CD27, CD S, ICAM-1, LFA-1 (CD11a/CD18), ICOS (CD278), 4-1 BB (CD137), GITR, CD30, CD40, BAFFR, HVEM, CD7, LIGHT, NKG2C, SLAMF7, NKp80, CD160, B7-H3, STING, or CD83 ligand.

38. The method of claim 36, wherein the checkpoint inhibitor is selected from an inhibitor of PD-1, PD-L1, PD-L2, CTLA4, TIM3, LAG3, VISTA, BTLA, TIGIT, LAIR1, CD160, 2B4 and/or TGFR beta.

39. The method of claim 34, wherein the cancer is uveal melanoma, subcutaneous melanoma, hepatocellular carcinoma, or a metastatic cancer thereof.

40. The antibody drug conjugate of claim 16, wherein Ab is an antibody or antigen binding fragment thereof that binds human PMEL17 comprising:
a. A heavy chain variable region (VH) comprising the amino acid sequence of SEQ ID NO:10, and a light chain variable region (VL) comprising the amino acid sequence of SEQ ID NO:21;

A heavy chain variable region (VH) comprising the amino acid sequence of SEQ ID NO:10, and a light chain variable region (VL) comprising the amino acid sequence of SEQ ID NO:25;
c. A heavy chain variable region (VH) comprising the amino acid sequence of SEQ ID NO:10, and a light chain variable region (VL) comprising the amino acid sequence of SEQ ID NO:29;
d. A heavy chain variable region (VH) comprising the amino acid sequence of SEQ ID NO:42, and a light chain variable region (VL) comprising the amino acid sequence of SEQ ID NO:53;
e. A heavy chain variable region (VH) comprising the amino acid sequence of SEQ ID NO:64, and a light chain variable region (VL) comprising the amino acid sequence of SEQ ID NO:75;
f. A heavy chain variable region (VH) comprising the amino acid sequence of SEQ ID NO:88, and a light chain variable region (VL) comprising the amino acid sequence of SEQ ID NO:99;
g. A heavy chain variable region (VH) comprising the amino acid sequence of SEQ ID NO:112, and a light chain variable region (VL) comprising the amino acid sequence of SEQ ID NO:119;
h. A heavy chain variable region (VH) comprising the amino acid sequence of SEQ ID NO: 132, and a light chain variable region (VL) comprising the amino acid sequence of SEQ ID NO:143;
i. A heavy chain variable region (VH) comprising the amino acid sequence of SEQ ID NO:149, and a light chain variable region (VL) comprising the amino acid sequence of SEQ ID NO:159;
j. A heavy chain variable region (VH) comprising the amino acid sequence of SEQ ID NO:165, and a light chain variable region (VL) comprising the amino acid sequence of SEQ ID NO:171;
k. A heavy chain variable region (VH) comprising the amino acid sequence of SEQ ID NO: 184, and a light chain variable region (VL) comprising the amino acid sequence of SEQ ID NO:190;
l. A heavy chain variable region (VH) comprising the amino acid sequence of SEQ ID NO: 196, and a light chain variable region (VL) comprising the amino acid sequence of SEQ ID NO:202;
m. A heavy chain variable region (VH) comprising the amino acid sequence of SEQ ID NO:215, and a light chain variable region (VL) comprising the amino acid sequence of SEQ ID NO:221;
n. A heavy chain variable region (VH) comprising the amino acid sequence of SEQ ID NO:227, and a light chain variable region (VL) comprising the amino acid sequence of SEQ ID NO:233;
o. A heavy chain variable region (VH) comprising the amino acid sequence of SEQ ID NO:239, and a light chain variable region (VL) comprising the amino acid sequence of SEQ ID NO:248;
p. A heavy chain variable region (VH) comprising the amino acid sequence of SEQ ID NO:254, and a light chain variable region (VL) comprising the amino acid sequence of SEQ ID NO:260;
q. A heavy chain comprising the amino acid sequence of SEQ ID NO:12, and a light chain comprising the amino acid sequence of SEQ ID NO:23;
r. A heavy chain comprising the amino acid sequence of SEQ ID NO:12, and a light chain comprising the amino acid sequence of SEQ ID NO:27;
s. A heavy chain comprising the amino acid sequence of SEQ ID NO:12, and a light chain comprising the amino acid sequence of SEQ ID NO:31;
t. A heavy chain comprising the amino acid sequence of SEQ ID NO:44, and a light chain comprising the amino acid sequence of SEQ ID NO:55;
u. A heavy chain comprising the amino acid sequence of SEQ ID NO:66, and a light chain comprising the amino acid sequence of SEQ ID NO:77;
v. A heavy chain comprising the amino acid sequence of SEQ ID NO:90, and a light chain comprising the amino acid sequence of SEQ ID NO: 101;
w. A heavy chain comprising the amino acid sequence of SEQ ID NO:114, and a light chain comprising the amino acid sequence of SEQ ID NO:121;
x. A heavy chain comprising the amino acid sequence of SEQ ID NO:134, and a light chain comprising the amino acid sequence of SEQ ID NO:145;
y. A heavy chain comprising the amino acid sequence of SEQ ID NO: 151, and a light chain comprising the amino acid sequence of SEQ ID NO:161;
z. A heavy chain comprising the amino acid sequence of SEQ ID NO:167, and a light chain comprising the amino acid sequence of SEQ ID NO: 173;
aa. A heavy chain comprising the amino acid sequence of SEQ ID NO: 186, and a light chain comprising the amino acid sequence of SEQ ID NO: 192;
bb. A heavy chain comprising the amino acid sequence of SEQ ID NO: 198, and a light chain comprising the amino acid sequence of SEQ ID NO:204;
cc. A heavy chain comprising the amino acid sequence of SEQ ID NO:217, and a light chain comprising the amino acid sequence of SEQ ID NO:223;
dd. A heavy chain comprising the amino acid sequence of SEQ ID NO:229, and a light chain comprising the amino acid sequence of SEQ ID NO:235;
ee. A heavy chain comprising the amino acid sequence of SEQ ID NO:241, and a light chain comprising the amino acid sequence of SEQ ID NO:250; or
ff. A heavy chain comprising the amino acid sequence of SEQ ID NO:256, and a light chain comprising the amino acid sequence of SEQ ID NO:262.

41. The antibody drug conjugate of claim 40, wherein the antibody or antigen binding fragment thereof comprises one or more cysteine substitutions selected from E152C, S375C, or both E152C and S375C of the heavy chain of the antibody or antigen binding fragment thereof, wherein the position is numbered according to the EU system.

42. An antibody drug conjugate of comprising the following structure,

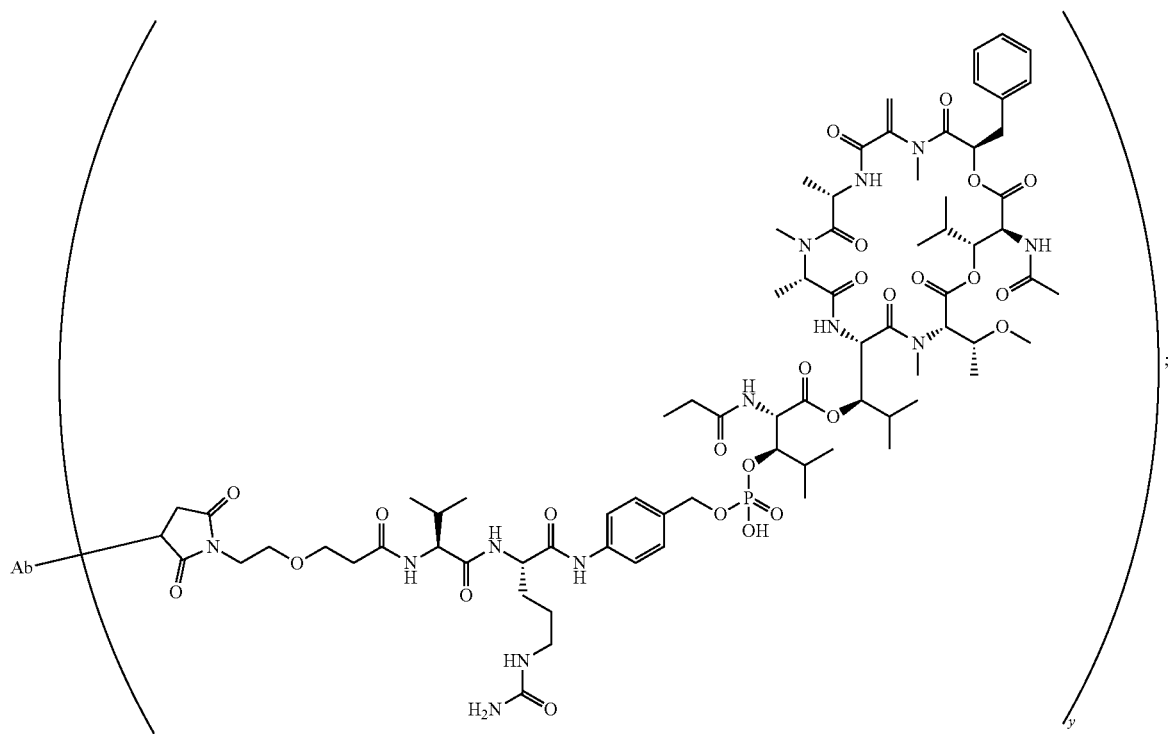

wherein Ab is an antibody or antigen binding fragment thereof that binds to human PMEL17 protein comprising:

a. A heavy chain variable region (VH) comprising the amino acid sequence of SEQ ID NO:10, and a light chain variable region (VL) comprising the amino acid sequence of SEQ ID NO:21;
b. A heavy chain variable region (VH) comprising the amino acid sequence of SEQ ID NO:10, and a light chain variable region (VL) comprising the amino acid sequence of SEQ ID NO:25;
c. A heavy chain variable region (VH) comprising the amino acid sequence of SEQ ID NO:10, and a light chain variable region (VL) comprising the amino acid sequence of SEQ ID NO:29;
d. A heavy chain variable region (VH) comprising the amino acid sequence of SEQ ID NO:42, and a light chain variable region (VL) comprising the amino acid sequence of SEQ ID NO:53;
e. A heavy chain variable region (VH) comprising the amino acid sequence of SEQ ID NO:64, and a light chain variable region (VL) comprising the amino acid sequence of SEQ ID NO:75;
f. A heavy chain variable region (VH) comprising the amino acid sequence of SEQ ID NO:88, and a light chain variable region (VL) comprising the amino acid sequence of SEQ ID NO:99;
g. A heavy chain variable region (VH) comprising the amino acid sequence of SEQ ID NO:112, and a light chain variable region (VL) comprising the amino acid sequence of SEQ ID NO:119;
h. A heavy chain variable region (VH) comprising the amino acid sequence of SEQ ID NO: 132, and a light chain variable region (VL) comprising the amino acid sequence of SEQ ID NO:143;
i. A heavy chain variable region (VH) comprising the amino acid sequence of SEQ ID NO:149, and a light chain variable region (VL) comprising the amino acid sequence of SEQ ID NO:159;
j. A heavy chain variable region (VH) comprising the amino acid sequence of SEQ ID NO:165, and a light chain variable region (VL) comprising the amino acid sequence of SEQ ID NO:171;
k. A heavy chain variable region (VH) comprising the amino acid sequence of SEQ ID NO: 184, and a light chain variable region (VL) comprising the amino acid sequence of SEQ ID NO:190;
l. A heavy chain variable region (VH) comprising the amino acid sequence of SEQ ID NO: 196, and a light chain variable region (VL) comprising the amino acid sequence of SEQ ID NO:202;
m. A heavy chain variable region (VH) comprising the amino acid sequence of SEQ ID NO:215, and a light chain variable region (VL) comprising the amino acid sequence of SEQ ID NO:221;
n. A heavy chain variable region (VH) comprising the amino acid sequence of SEQ ID NO:227, and a light chain variable region (VL) comprising the amino acid sequence of SEQ ID NO:233;
o. A heavy chain variable region (VH) comprising the amino acid sequence of SEQ ID NO:239, and a light chain variable region (VL) comprising the amino acid sequence of SEQ ID NO:248;
p. A heavy chain variable region (VH) comprising the amino acid sequence of SEQ ID NO:254, and a light chain variable region (VL) comprising the amino acid sequence of SEQ ID NO:260;
q. A heavy chain comprising the amino acid sequence of SEQ ID NO:12, and a light chain comprising the amino acid sequence of SEQ ID NO:23;

r. A heavy chain comprising the amino acid sequence of SEQ ID NO:12, and a light chain comprising the amino acid sequence of SEQ ID NO:27;
s. A heavy chain comprising the amino acid sequence of SEQ ID NO:12, and a light chain comprising the amino acid sequence of SEQ ID NO:31;
t. A heavy chain comprising the amino acid sequence of SEQ ID NO:44, and a light chain comprising the amino acid sequence of SEQ ID NO:55;
u. A heavy chain comprising the amino acid sequence of SEQ ID NO:66, and a light chain comprising the amino acid sequence of SEQ ID NO:77;
v. A heavy chain comprising the amino acid sequence of SEQ ID NO:90, and a light chain comprising the amino acid sequence of SEQ ID NO: 101;
w. A heavy chain comprising the amino acid sequence of SEQ ID NO:114, and a light chain comprising the amino acid sequence of SEQ ID NO:121;
x. A heavy chain comprising the amino acid sequence of SEQ ID NO:134, and a light chain comprising the amino acid sequence of SEQ ID NO:145;
y. A heavy chain comprising the amino acid sequence of SEQ ID NO: 151, and a light chain comprising the amino acid sequence of SEQ ID NO:161;
z. A heavy chain comprising the amino acid sequence of SEQ ID NO:167, and a light chain comprising the amino acid sequence of SEQ ID NO: 173;
aa. A heavy chain comprising the amino acid sequence of SEQ ID NO:186, and a light chain comprising the amino acid sequence of SEQ ID NO: 192;
bb. A heavy chain comprising the amino acid sequence of SEQ ID NO:198, and a light chain comprising the amino acid sequence of SEQ ID NO:204;
cc. A heavy chain comprising the amino acid sequence of SEQ ID NO:217, and a light chain comprising the amino acid sequence of SEQ ID NO:223;
dd. A heavy chain comprising the amino acid sequence of SEQ ID NO:229, and a light chain comprising the amino acid sequence of SEQ ID NO:235;
ee. A heavy chain comprising the amino acid sequence of SEQ ID NO:241, and a light chain comprising the amino acid sequence of SEQ ID NO:250; or
ff. A heavy chain comprising the amino acid sequence of SEQ ID NO:256, and a light chain comprising the amino acid sequence of SEQ ID NO:262; and
wherein y is 2.

43. The antibody drug conjugate of claim 42, wherein the antibody or antigen binding fragment thereof comprises one or more cysteine substitutions selected from E152C, S375C, or both E152C and S375C of the heavy chain of the antibody or antigen binding fragment thereof, wherein the position is numbered according to the EU system.

44. An antibody drug conjugate of comprising the following structure,

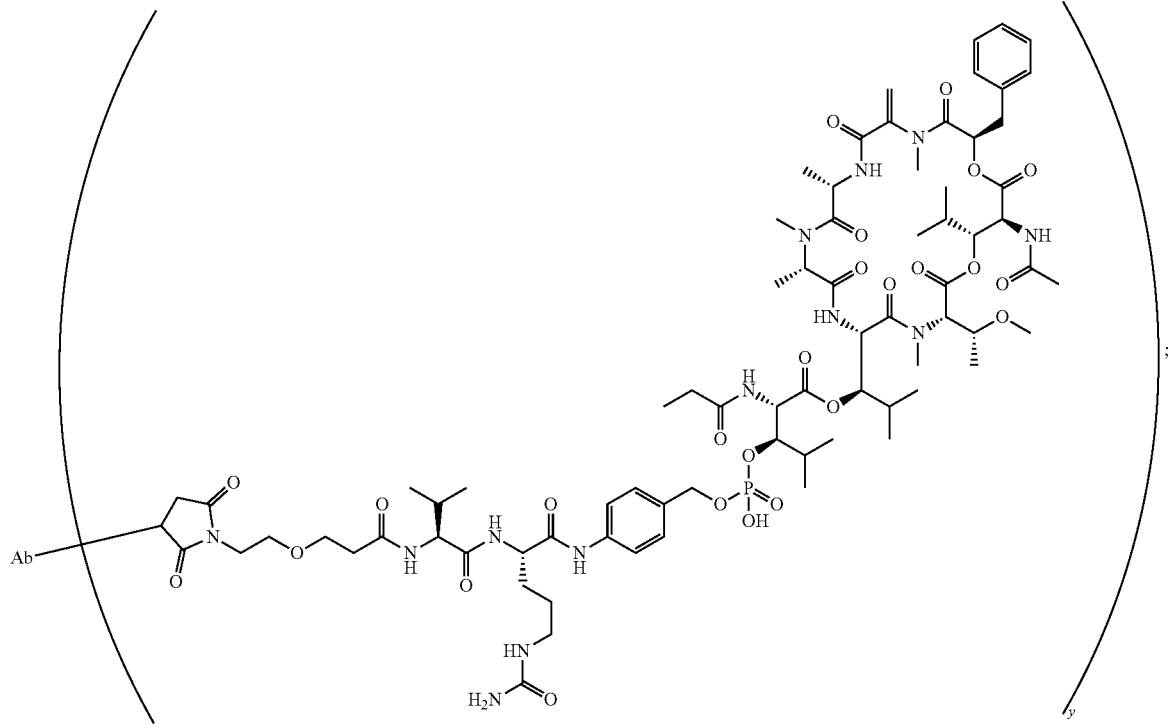

wherein Ab is an antibody or antigen binding fragment thereof that binds to human PMEL17 protein comprising:
a. A heavy chain variable region (VH) comprising the amino acid sequence of SEQ ID NO:10, and a light chain variable region (VL) comprising the amino acid sequence of SEQ ID NO:21;
b. A heavy chain variable region (VH) comprising the amino acid sequence of SEQ ID NO:10, and a light chain variable region (VL) comprising the amino acid sequence of SEQ ID NO:25;
c. A heavy chain variable region (VH) comprising the amino acid sequence of SEQ ID NO:10, and a light chain variable region (VL) comprising the amino acid sequence of SEQ ID NO:29;
d. A heavy chain variable region (VH) comprising the amino acid sequence of SEQ ID NO:42, and a light chain variable region (VL) comprising the amino acid sequence of SEQ ID NO:53;
e. A heavy chain variable region (VH) comprising the amino acid sequence of SEQ ID NO:64, and a light chain variable region (VL) comprising the amino acid sequence of SEQ ID NO:75;
f. A heavy chain variable region (VH) comprising the amino acid sequence of SEQ ID NO:88, and a light chain variable region (VL) comprising the amino acid sequence of SEQ ID NO:99;
g. A heavy chain variable region (VH) comprising the amino acid sequence of SEQ ID NO:112, and a light chain variable region (VL) comprising the amino acid sequence of SEQ ID NO:119;
h. A heavy chain variable region (VH) comprising the amino acid sequence of SEQ ID NO: 132, and a light chain variable region (VL) comprising the amino acid sequence of SEQ ID NO:143;
i. A heavy chain variable region (VH) comprising the amino acid sequence of SEQ ID NO:149, and a light chain variable region (VL) comprising the amino acid sequence of SEQ ID NO:159;
j. A heavy chain variable region (VH) comprising the amino acid sequence of SEQ ID NO:165, and a light chain variable region (VL) comprising the amino acid sequence of SEQ ID NO:171;
k. A heavy chain variable region (VH) comprising the amino acid sequence of SEQ ID NO: 184, and a light chain variable region (VL) comprising the amino acid sequence of SEQ ID NO:190;
l. A heavy chain variable region (VH) comprising the amino acid sequence of SEQ ID NO: 196, and a light chain variable region (VL) comprising the amino acid sequence of SEQ ID NO:202;
m. A heavy chain variable region (VH) comprising the amino acid sequence of SEQ ID NO:215, and a light chain variable region (VL) comprising the amino acid sequence of SEQ ID NO:221;
n. A heavy chain variable region (VH) comprising the amino acid sequence of SEQ ID NO:227, and a light chain variable region (VL) comprising the amino acid sequence of SEQ ID NO:233;
o. A heavy chain variable region (VH) comprising the amino acid sequence of SEQ ID NO:239, and a light chain variable region (VL) comprising the amino acid sequence of SEQ ID NO:248;
p. A heavy chain variable region (VH) comprising the amino acid sequence of SEQ ID NO:254, and a light chain variable region (VL) comprising the amino acid sequence of SEQ ID NO:260;
q. A heavy chain comprising the amino acid sequence of SEQ ID NO:12, and a light chain comprising the amino acid sequence of SEQ ID NO:23;
r. A heavy chain comprising the amino acid sequence of SEQ ID NO:12, and a light chain comprising the amino acid sequence of SEQ ID NO:27;
s. A heavy chain comprising the amino acid sequence of SEQ ID NO:12, and a light chain comprising the amino acid sequence of SEQ ID NO:31;
t. A heavy chain comprising the amino acid sequence of SEQ ID NO:44, and a light chain comprising the amino acid sequence of SEQ ID NO:55;
u. A heavy chain comprising the amino acid sequence of SEQ ID NO:66, and a light chain comprising the amino acid sequence of SEQ ID NO:77;
v. A heavy chain comprising the amino acid sequence of SEQ ID NO:90, and a light chain comprising the amino acid sequence of SEQ ID NO: 101;
w. A heavy chain comprising the amino acid sequence of SEQ ID NO:114, and a light chain comprising the amino acid sequence of SEQ ID NO:121;
x. A heavy chain comprising the amino acid sequence of SEQ ID NO:134, and a light chain comprising the amino acid sequence of SEQ ID NO:145;
y. A heavy chain comprising the amino acid sequence of SEQ ID NO: 151, and a light chain comprising the amino acid sequence of SEQ ID NO:161;
z. A heavy chain comprising the amino acid sequence of SEQ ID NO:167, and a light chain comprising the amino acid sequence of SEQ ID NO: 173;
aa. A heavy chain comprising the amino acid sequence of SEQ ID NO:186, and a light chain comprising the amino acid sequence of SEQ ID NO: 192;
bb. A heavy chain comprising the amino acid sequence of SEQ ID NO:198, and a light chain comprising the amino acid sequence of SEQ ID NO:204;
cc. A heavy chain comprising the amino acid sequence of SEQ ID NO:217, and a light chain comprising the amino acid sequence of SEQ ID NO:223;
dd. A heavy chain comprising the amino acid sequence of SEQ ID NO:229, and a light chain comprising the amino acid sequence of SEQ ID NO:235;
ee. A heavy chain comprising the amino acid sequence of SEQ ID NO:241, and a light chain comprising the amino acid sequence of SEQ ID NO:250; or
ff. A heavy chain comprising the amino acid sequence of SEQ ID NO:256, and a light chain comprising the amino acid sequence of SEQ ID NO:262; and wherein y is 2.

45. The antibody drug conjugate of claim 44, wherein the antibody or antigen binding fragment thereof comprises one or more cysteine substitutions selected from E152C, S375C, or both E152C and S375C of the heavy chain of the antibody or antigen binding fragment thereof, wherein the position is numbered according to the EU system.

46. An antibody drug conjugate of comprising the following structure,

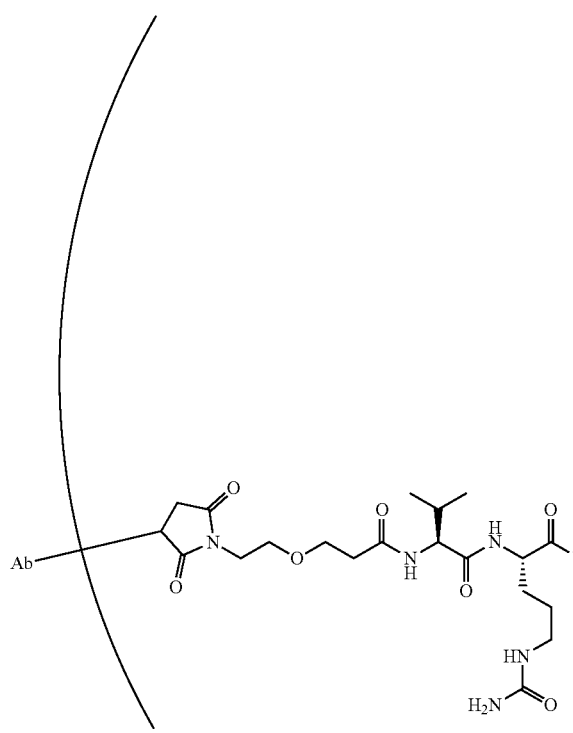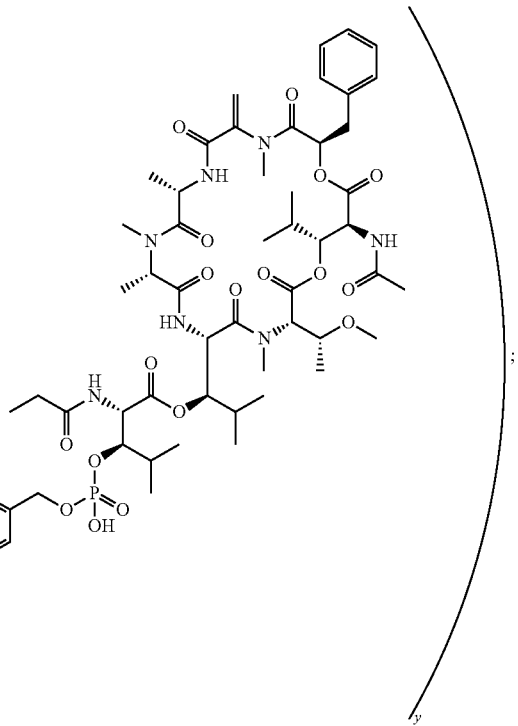

wherein Ab is an antibody or antigen binding fragment thereof that binds to human PMEL17 protein comprising:

a. a heavy chain CDR1 of SEQ ID NO:1, a heavy chain CDR2 of SEQ ID NO:2, a heavy chain CDR3 of SEQ ID NO:3, a light chain CDR1 of SEQ ID NO:14, a light chain CDR2 of SEQ ID NO:15, and a light chain CDR3 of SEQ ID NO:16;

b. a heavy chain CDR1 of SEQ ID NO: 4, a heavy chain CDR2 of SEQ ID NO:2, a heavy chain CDR3 of SEQ ID NO:3, a light chain CDR1 of SEQ ID NO:14, a light chain CDR2 of SEQ ID NO:15, and a light chain CDR3 of SEQ ID NO:16;

c. a heavy chain CDR1 of SEQ ID NO:5, a heavy chain CDR2 of SEQ ID NO:6, a heavy chain CDR3 of SEQ ID NO:3, a light chain CDR1 of SEQ ID NO:17, a light chain CDR2 of SEQ ID NO:18, and a light chain CDR3 of SEQ ID NO:19; or d. a heavy chain CDR1 of SEQ ID NO:7, a heavy chain CDR2 of SEQ ID NO:8, a heavy chain CDR3 of SEQ ID NO:9, a light chain CDR1 of SEQ ID NO:20, a light chain CDR2 of SEQ ID NO:18, and a light chain CDR3 of SEQ ID NO:16, and wherein y is 2.

47. An antibody drug conjugate of comprising the following structure,

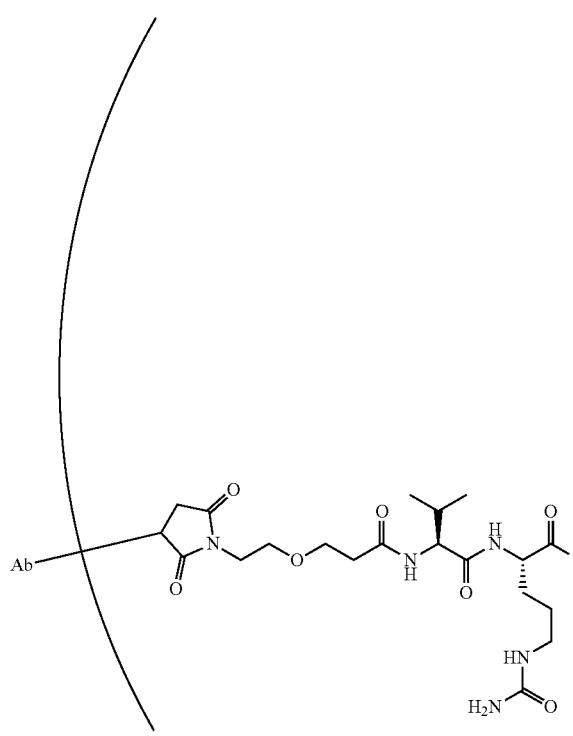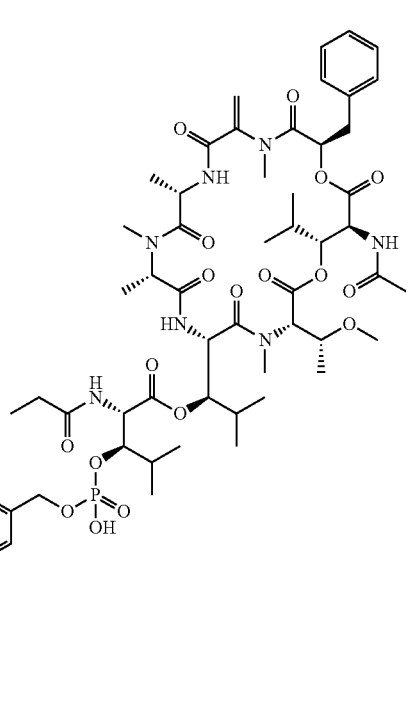
wherein Ab is an antibody or antigen binding fragment thereof comprising a heavy chain variable region (VH) comprising the amino acid sequence of SEQ ID NO:10 and a light chain variable region (VL) comprising the amino acid sequence of SEQ ID NO:25; and
wherein y is 2.
48. An antibody drug conjugate of comprising the following structure,
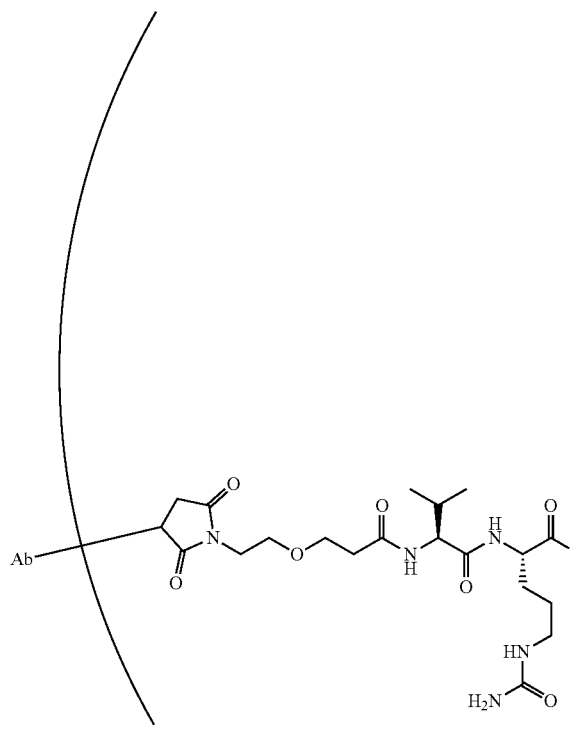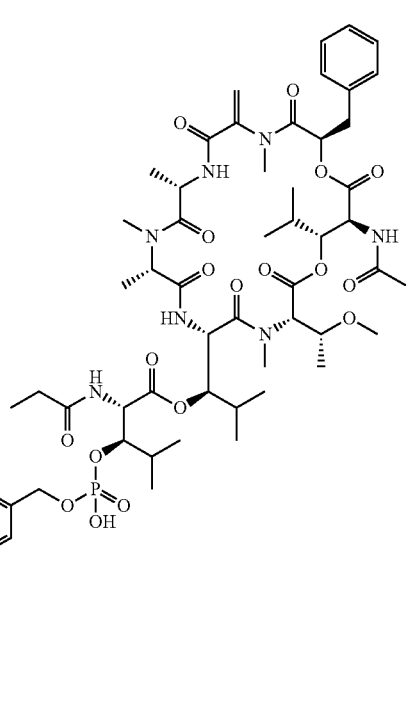

wherein Ab is an antibody or antigen binding fragment thereof comprising a heavy chain comprising the amino acid sequence of SEQ ID NO:12, except that the amino acid at position 375 is S, wherein the position is numbered according to the EU system, and a light chain comprising the amino acid sequence of SEQ ID NO:27; and wherein y is 2.

49. A pharmaceutical composition comprising the antibody drug conjugate of claim 46 and a pharmaceutically acceptable carrier.

50. A pharmaceutical composition comprising the antibody drug conjugate of claim 47 and a pharmaceutically acceptable carrier.

51. A pharmaceutical composition comprising the antibody drug conjugate of claim 48 and a pharmaceutically acceptable carrier.

52. A method of treating cancer in a patient in need thereof, comprising administering to said patient the antibody drug conjugate of claim 46, wherein the cancer expresses PMEL17, the cancer contains a mutation of the GNAQ or GNA11 gene, or the cancer expresses PMEL17 and contains a mutation of the GNAQ gene, the GNA11 gene, or both.

53. A method of treating cancer in a patient in need thereof, comprising administering to said patient the antibody drug conjugate of claim 47, wherein the cancer expresses PMEL17, the cancer contains a mutation of the GNAQ or GNA11 gene, or the cancer expresses PMEL17 and contains a mutation of the GNAQ gene, the GNA11 gene, or both.

54. A method of treating cancer in a patient in need thereof, comprising administering to said patient the antibody drug conjugate of claim 48, wherein the cancer expresses PMEL17, the cancer contains a mutation of the GNAQ or GNA11 gene, or the cancer expresses PMEL17 and contains a mutation of the GNAQ gene, the GNA11 gene, or both.

55. A process for producing an anti-PMEL17 antibody drug conjugate comprising:
(a) pre-forming a linker-drug moiety of the following Formula (B):

$$R^8\text{-}L_B\text{-}(D)_n \qquad (B)$$

wherein:
D is a GNAQ inhibitor, a GNA11 inhibitor or an inhibitor of GNAQ and GNA11;
$R^8$ is a reactive group;
$L_B$ is a cleavable or non-cleavable linker, and
n is 1, 2, 3 or 4;
(b) conjugating said linker-drug moiety to the antibody recovered from the cell culture of claim 35 to produce an antibody drug conjugate; and
(c) purifying the antibody drug conjugate.

* * * * *

UNITED STATES PATENT AND TRADEMARK OFFICE
CERTIFICATE OF CORRECTION

PATENT NO. : 11,779,649 B2
APPLICATION NO. : 16/718866
DATED : October 10, 2023
INVENTOR(S) : Matthew Burger et al.

Page 1 of 5

It is certified that error appears in the above-identified patent and that said Letters Patent is hereby corrected as shown below:

On the Title Page

Replace the title page with the attached title page, showing the corrected number of claims.

In the Claims

At Column 543, Claim number 16, Line number 43, delete "ppp" and insert --ppp.--.

At Column 544, Claim number 23, Line number 40 to Line number 64, delete

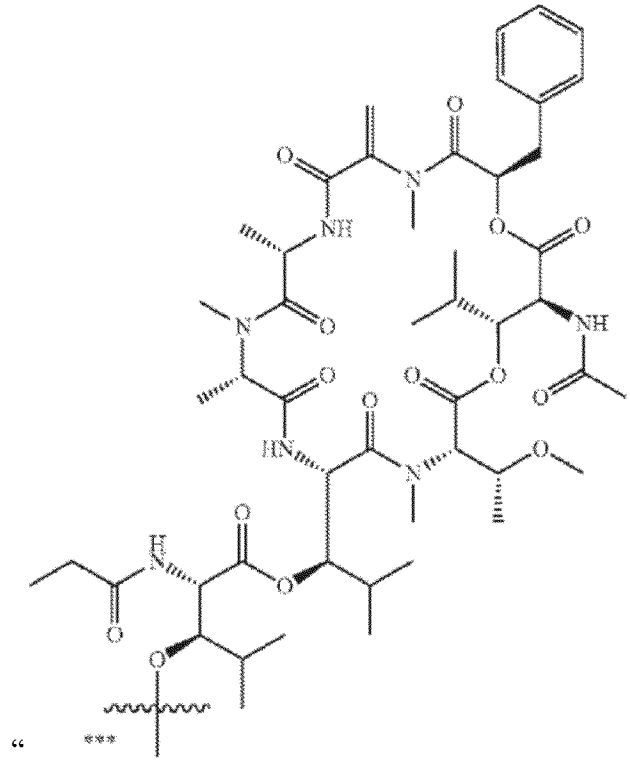

" and insert

Signed and Sealed this
Twenty-fifth Day of March, 2025

Coke Morgan Stewart
*Acting Director of the United States Patent and Trademark Office*

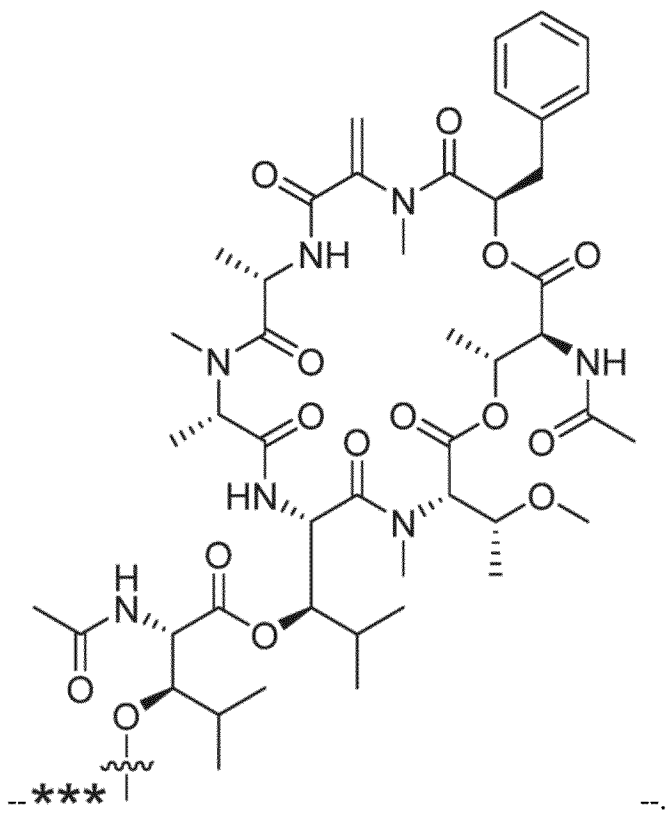
—***  --.
At Column 545-546, Claim number 25, delete
"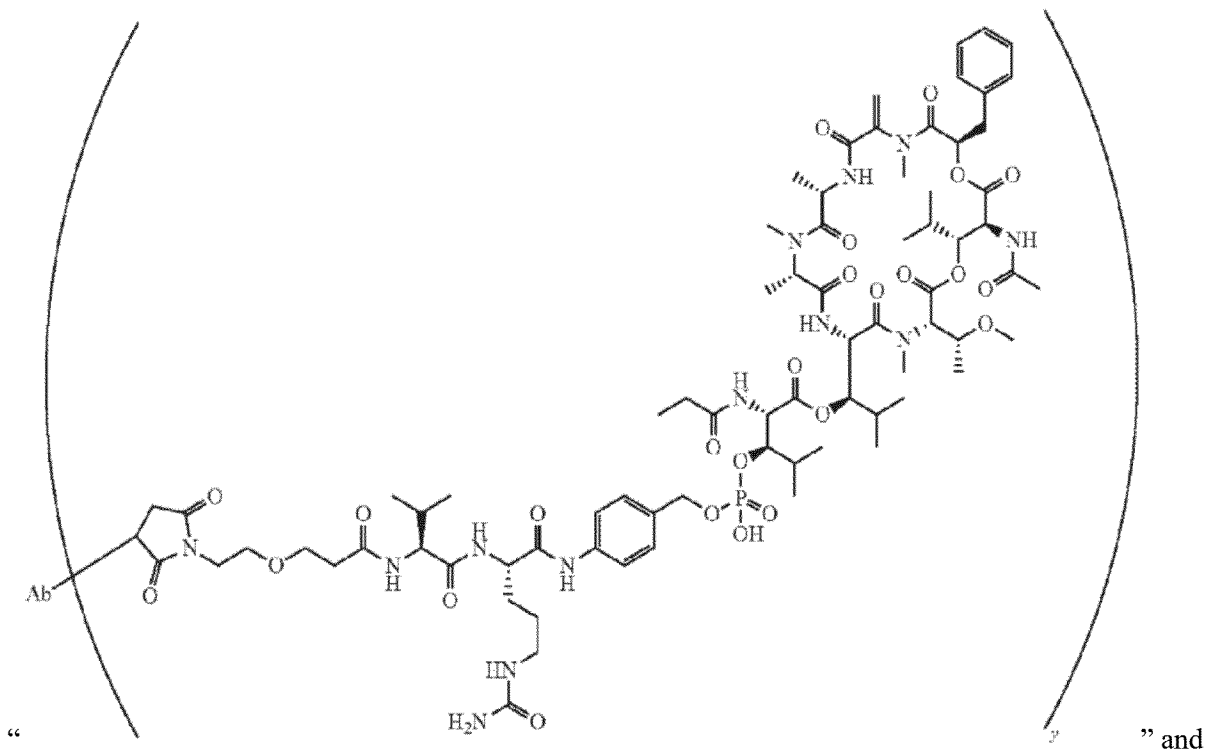" and insert --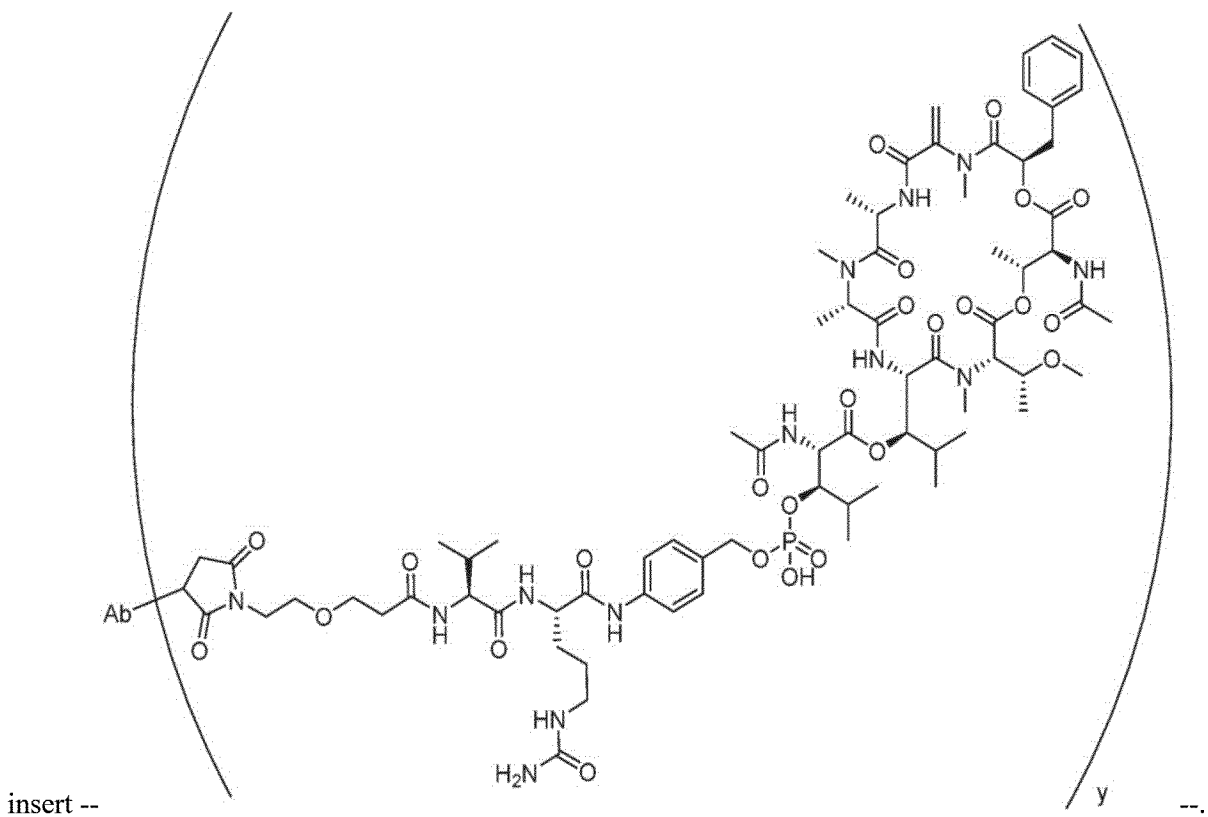--.

At Column 547, Claim number 31, Line number 60, delete "CDS,".

At Column 548, Claim number 37, Line number 50, delete "CD S,".

At Column 548, Claim number 37, Line numbers 50-51, delete "4-1 BB" and insert --4-1BB--.

At Column 549, Claim number 40, Line number 1, delete "A heavy chain variable region (VH)" and insert --b. A heavy chain variable region (VH)--.

At Column 550, Claim number 42, Line number 66, delete "An antibody drug conjugate of comprising" and insert --An antibody drug conjugate comprising--.

At Column 554, Line number 26 to Column 556, Line number 57, delete Claim number 44.

At Column 556, Line number 59 to Column 556, Line number 64, delete Claim number 45.

At Column 556, Claim number 46, Line number 66, delete "An antibody drug conjugate of comprising" and insert --An antibody drug conjugate comprising--.

At Column 557, Claim number 47, Line number 66, delete "An antibody drug conjugate of comprising" and insert --An antibody drug conjugate comprising--.

At Column 559, Claim number 48, Line number 37, delete "An antibody drug conjugate of comprising" and insert --An antibody drug conjugate comprising--.

At Column 562, Claim number 55, Line number 24, delete "recovered from the cell culture of claim 35" and insert --recovered from the cell culture of claim 13--.

CERTIFICATE OF CORRECTION (continued)

(12) United States Patent
Burger et al.

(10) Patent No.: US 11,779,649 B2
(45) Date of Patent: Oct. 10, 2023

(54) ANTIBODIES TO PMEL17 AND CONJUGATES THEREOF

(71) Applicant: Novartis AG, Basel (CH)

(72) Inventors: Matthew Burger, Belmont, MA (US); Joseph Anthony D'Alessio, Boston, MA (US); Tony Fleming, Stow, MA (US); Vivek Rauniyar, Cambridge, MA (US); Eusebio Manchado Robles, Basel (CH); Christian Kunz, Planegg (DE); Markus Waldhuber, Munich (DE)

(73) Assignee: Novartis AG, Basel (CH)

( * ) Notice: Subject to any disclaimer, the term of this patent is extended or adjusted under 35 U.S.C. 154(b) by 509 days.

(21) Appl. No.: 16/718,866

(22) Filed: Dec. 18, 2019

(65) Prior Publication Data
US 2020/0197528 A1   Jun. 25, 2020

Related U.S. Application Data

(60) Provisional application No. 62/803,110, filed on Feb. 8, 2019, provisional application No. 62/783,565, filed on Dec. 21, 2018.

(51) Int. Cl.
*A61K 47/68* (2017.01)
*A61P 35/00* (2006.01)
(Continued)

(52) U.S. Cl.
CPC ...... *A61K 47/6803* (2017.08); *A61K 31/4745* (2013.01); *A61P 35/00* (2018.01); *C07K 16/18* (2013.01); *A61K 45/06* (2013.01)

(58) Field of Classification Search
CPC ............ A61K 47/6803; A61K 31/4745; A61K 45/06; A61K 2039/505; A61P 35/00
See application file for complete search history.

(56) References Cited

U.S. PATENT DOCUMENTS

| | | | |
|---|---|---|---|
| 9,056,910 | B2 | 6/2015 | Chen et al. |
| 9,597,411 | B2 | 3/2017 | Chen et al. |

(Continued)

FOREIGN PATENT DOCUMENTS

| | | |
|---|---|---|
| EP | 3465221 B1 | 7/2020 |
| JP | S62283999 A | 12/1987 |

(Continued)

OTHER PUBLICATIONS

Gerber et al. ("Combining antibody-drug conjugates and immune-mediated cancer therapy: What to expect?", Biochemical Pharmacology, vol. 102, 2016, pp. 1-6) (Year: 2016).*
(Continued)

*Primary Examiner* — Scarlett Y Goon
*Assistant Examiner* — Jessica Soto-Rodriguez
(74) *Attorney, Agent, or Firm* — K&L Gates LLP

(57) ABSTRACT

This application discloses anti-PMEL17 antibodies, antigen binding fragments thereof, and antibody drug conjugates comprising antibodies or antigen binding fragments conjugated to a GNAQ/GNA11 inhibitor. The application also discloses methods of treating or preventing cancer using the antibodies, antigen binding fragments, and antibody drug conjugates. Also disclosed herein are methods of making the antibodies, antigen binding fragments, and antibody drug conjugates, and methods of using the antibodies and antigen binding fragments as diagnostic reagents.

53 Claims, 16 Drawing Sheets

Specification includes a Sequence Listing.